United States Patent
Jin et al.

(10) Patent No.: US 12,274,697 B2
(45) Date of Patent: Apr. 15, 2025

(54) COMPOSITIONS AND METHODS FOR TREATING EZH2-MEDIATED CANCER

(71) Applicant: Icahn School of Medicine at Mount Sinai, New York, NY (US)

(72) Inventors: Jian Jin, New York, NY (US); Ramon Parsons, Manhasset, NY (US); Ilias Stratikopoulos, New York, NY (US); Xiaobao Yang, New York, NY (US); Anqi Ma, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 17/978,696

(22) Filed: Nov. 1, 2022

(65) Prior Publication Data

US 2023/0114294 A1  Apr. 13, 2023

Related U.S. Application Data

(60) Division of application No. 16/926,418, filed on Jul. 10, 2020, now Pat. No. 11,510,920, which is a continuation of application No. 16/345,591, filed as application No. PCT/US2017/058718 on Oct. 27, 2017, now abandoned.

(60) Provisional application No. 62/414,195, filed on Oct. 28, 2016.

(51) Int. Cl.
| | |
|---|---|
| C07D 401/14 | (2006.01) |
| A61K 31/437 | (2006.01) |
| A61K 31/444 | (2006.01) |
| A61K 31/496 | (2006.01) |
| A61P 35/00 | (2006.01) |
| A61P 35/02 | (2006.01) |
| A61P 43/00 | (2006.01) |
| C07D 405/12 | (2006.01) |
| C07D 405/14 | (2006.01) |
| C07D 417/14 | (2006.01) |
| C07D 471/04 | (2006.01) |

(52) U.S. Cl.
CPC .......... *A61K 31/496* (2013.01); *A61K 31/444* (2013.01); *C07D 401/14* (2013.01); *C07D 405/12* (2013.01); *C07D 405/14* (2013.01); *C07D 417/14* (2013.01)

(58) Field of Classification Search
CPC .. C07D 401/14; C07D 471/04; A61K 31/437; A61P 35/00; A61P 35/02; A61P 43/00
See application file for complete search history.

(56) References Cited

U.S. PATENT DOCUMENTS

| | | | |
|---|---|---|---|
| 5,691,147 A | 10/1997 | Draetta et al. | |
| 8,377,937 B2 | 2/2013 | Bencsik et al. | |
| 8,648,096 B2 | 2/2014 | Muller et al. | |
| 9,809,603 B1 | 11/2017 | Jacques | |
| 9,822,094 B2 | 11/2017 | Man et al. | |
| 11,472,799 B2 | 10/2022 | Jin et al. | |
| 2002/0098161 A1 | 7/2002 | Uhrich | |
| 2004/0063773 A1 | 4/2004 | Tang et al. | |
| 2011/0172107 A1 | 7/2011 | Katz et al. | |
| 2011/0196150 A1 | 8/2011 | Man et al. | |
| 2014/0031325 A1 | 1/2014 | Bartlett et al. | |
| 2014/0356322 A1 | 12/2014 | Crews et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0045504 A1 | 2/2016 | Grembecka et al. | |
| 2017/0008904 A1 | 1/2017 | Crew et al. | |
| 2017/0114098 A1 | 4/2017 | Aivado et al. | |
| 2017/0121321 A1 | 5/2017 | Crews et al. | |
| 2017/0224685 A1 | 8/2017 | Duncan et al. | |
| 2017/0283807 A1 | 10/2017 | Mounir et al. | |
| 2018/0072741 A1 | 3/2018 | Vechorkin et al. | |
| 2018/0086767 A1 | 3/2018 | Fesik et al. | |
| 2018/0134684 A1 | 5/2018 | Bradner et al. | |
| 2018/0186800 A1 | 7/2018 | Yamamoto et al. | |
| 2019/0092768 A1 | 3/2019 | Gray et al. | |
| 2019/0255041 A1 | 8/2019 | Jin et al. | |
| 2019/0336503 A1 | 11/2019 | Jin et al. | |
| 2019/0367525 A1 | 12/2019 | Ioannidis et al. | |
| 2020/0338070 A1 | 10/2020 | Jin et al. | |
| 2020/0399266 A1 | 12/2020 | Jin et al. | |
| 2021/0261538 A1 | 8/2021 | Jin et al. | |
| 2021/0283261 A1 | 9/2021 | Jin et al. | |
| 2021/0355140 A1 | 11/2021 | Shunatona et al. | |
| 2021/0395244 A1 | 12/2021 | Jin et al. | |
| 2022/0054488 A1 | 2/2022 | Jin et al. | |
| 2022/0348580 A1 | 11/2022 | Jin et al. | |
| 2023/0022524 A1 | 1/2023 | Jin et al. | |
| 2023/0070613 A1 | 3/2023 | Jin et al. | |

(Continued)

FOREIGN PATENT DOCUMENTS

| | | |
|---|---|---|
| CN | 102822165 | 12/2012 |
| CN | 103189067 | 7/2013 |
| CN | 104736569 | 6/2015 |

(Continued)

OTHER PUBLICATIONS

Office Action in U.S. Appl. No. 16/970,305, mailed on Sep. 8, 2023, 22 pages.

(Continued)

*Primary Examiner* — Brenda L Coleman

(74) *Attorney, Agent, or Firm* — Fish & Richardson P.C.

(57) ABSTRACT

Methods for designing bivalent compounds which selectively degrade/disrupt EZH2 and compositions and methods of using such degraders/disruptors to treat EZH2-mediated cancer are provided.

12 Claims, 31 Drawing Sheets

(56) References Cited

U.S. PATENT DOCUMENTS

| | | | |
|---|---|---|---|
| 2023/0167106 | A1 | 6/2023 | Jin et al. |
| 2023/0391765 | A1 | 12/2023 | Jin et al. |

FOREIGN PATENT DOCUMENTS

| | | |
|---|---|---|
| CN | 105085620 | 11/2015 |
| CN | 105175284 | 12/2015 |
| CN | 108137507 | 6/2018 |
| CN | 109071552 | 12/2018 |
| CN | 109790143 | 5/2019 |
| CN | 112778303 | 5/2021 |
| JP | 2007-512364 | 5/2007 |
| JP | 2008-525526 | 7/2008 |
| JP | 2009-542721 | 12/2009 |
| JP | 2009-542723 | 12/2009 |
| JP | 2010-532386 | 10/2010 |
| JP | 2010-532387 | 10/2010 |
| JP | 2015-508414 | 3/2015 |
| JP | 2016-540811 | 12/2016 |
| JP | 2017-513862 | 6/2017 |
| JP | 2018-502097 | 1/2018 |
| JP | 2018-526430 | 9/2018 |
| JP | 2019-514883 | 5/2020 |
| JP | 2021-511342 | 5/2021 |
| MX | 2018000471 | 4/2018 |
| MX | 2018000360 | 6/2018 |
| WO | WO 2008/109104 | 9/2008 |
| WO | WO 2014/100719 | 6/2014 |
| WO | WO 2015/101293 | 7/2015 |
| WO | WO 2015/104677 | 7/2015 |
| WO | WO 2015/192123 | 12/2015 |
| WO | WO 2016/073956 | 5/2016 |
| WO | WO 2016/105518 | 6/2016 |
| WO | WO 2016/106518 | 7/2016 |
| WO | WO 2016/115480 | 7/2016 |
| WO | WO 2016/149668 | 9/2016 |
| WO | WO 2016/168992 | 10/2016 |
| WO | WO 2016/174130 | 11/2016 |
| WO | WO 2016/197032 | 12/2016 |
| WO | WO 2016/208595 | 12/2016 |
| WO | WO 2017/011371 | 1/2017 |
| WO | WO 2017/011590 | 1/2017 |
| WO | WO 2017/024317 | 2/2017 |
| WO | WO 2017/024319 | 2/2017 |
| WO | WO 2017/079267 | 5/2017 |
| WO | WO 2017/147700 | 9/2017 |
| WO | WO 2017/147701 | 9/2017 |
| WO | WO 2017/185031 | 10/2017 |
| WO | WO 2017/197051 | 11/2017 |
| WO | WO 2017/197055 | 11/2017 |
| WO | WO 2018/049200 | 3/2018 |
| WO | WO 2018/098280 | 5/2018 |
| WO | WO 2018/106870 | 6/2018 |
| WO | WO 2018/117177 | 6/2018 |
| WO | WO 2018/119441 | 6/2018 |
| WO | WO 2018/144649 | 8/2018 |
| WO | WO 2019/084030 | 5/2019 |
| WO | WO 2019/222380 | 11/2019 |
| WO | WO 2019/246570 | 12/2019 |
| WO | WO 2020/252043 | 12/2020 |
| WO | WO 2021/021904 | 2/2021 |
| WO | WO 2021/057872 | 4/2021 |
| WO | WO 2023/006063 | 2/2023 |

OTHER PUBLICATIONS

CN Office Action in Chinese Appln. No. 201780081246.8, dated Mar. 4, 2023, 16 pages (with English Translation).
EP Office Action in European Appln. No. 17877800.7, Apr. 13, 2023, 7 pages.
EP Office Action in European Appln. No. 19763958.6, dated May 10, 2023, 4 pages.
EP Office Action in European Appln. No. 19821826.5, dated Apr. 12, 2023, 4 pages.
JP Office Action in Japanese Appln. No. 2020-546159, dated May 9, 2023, 14 pages (with English Translation).
JP Office Action in Japanese Appln. No. 2020-570728, dated Jun. 27, 2023, 11 pages (with English Translation).
JP Office Action in Japanese Appln. No. 2021-500187, dated Jul. 4, 2023, 12 pages (with English Translation).
PCT International Preliminary Report on Patentability in International Appln. No. PCT/US2021/055574, dated May 4, 2023, 8 pages.
PCT International Search Report and Written Opinion in International Appln. No. PCT/US2022/050929, dated Apr. 7, 2023, 13 pages.
Popow et al., "Highly selective PTK2 proteolysis targeting chimeras to probe focal adhesion kinase scaffolding functions," Journal of Medicinal Chemistry, 2019, 62(5):2508-2520.
Wang et al., "Discovery of potent 2-Aryl-6,7-dihydro-5$H$-pyrrolo[1,2-$a$] imidazoles as WDR5-WIN-site inhibitors using fragment-based methods and structure-based design," Journal of Medicinal Chemistry, 2018, 61(13):5623-5642.
Wei et al., "Discovery of a first-in-class mitogen-activated protein kinase kinase 1/2 degrader," Journal of Medicinal Chemistry, 2019, 62(23):10897-10911.
Xue et al., "Protein degradation through covalent inhibitor-based Protacs," Chemical Communications, 2020, 56(10):1521-1524.
U.S. Appl. No. 18/032,758, filed Apr. 19, 2023, Jian Jin.
Office Action in Chinese Appln. No. 201980054694.8, mailed on Sep. 1, 2023, 21 pages (with Machine translation).
AU Office Action in Australian Appln. No. 2022201488, dated Feb. 14, 2023, 6 pages.
CN Office Action in Chinese Appln. No. 201980030599.4, dated Jan. 5, 2023, 13 pages (with English Translation).
EP Extended European Search Report in European Appln. No. 20802303.6, dated Dec. 23, 2022, 6 pages.
EP Office Action in European Appln. No. 17863645.2, dated Nov. 11, 2022, 6 pages.
Fioravanti et al., "Six years (2012-2018) of researches on catalytic EZH2 inhibitors: The boom of the 2-pyridone compounds," Manuscript, The Chemical Record, 2018, 18(12):1818-1832.
Kumar et al., "EZH2 Inhibitor GSK126 for Cancer Treatment: Metabolism, drug transporter and rat pharmacokinetic studies," Medical Research Archives, 2015, Issue 3, 31 pages.
PCT Invitation to Pay Additional Fees in International Appln. No. PCT/US2022/050929, dated Feb. 6, 2023, 3 pages.
Stazi et al., "EZH2 inhibitors: a patent review (2014-2016)," Expert Opinion on Therapeutic Patents, 2017, 27(7):797-813.
Abramovich et al., "Hox regulation of normal and leukemic hematopoietic stem cells," Curr. Opin. Hematol., May 2005, 12(3):210-216.
Addie et al., "Discovery of 4-Amino-$N$-[(1$S$)-1-(4-chlorophenyl)-3-hydroxypropyl]-1-(7$H$-pyrrolo[2,3-$d$]pyrimidin-4-yl)piperidine-4-carboxamide (AZD5363), an Orally Bioavailable, Potent Inhibitor of Akt Kinases," J. Med. Chem., Mar. 2013, 56(5):2059-2073.
Aguilar et al., "Discovery of 4-((3'$R$,4'$S$,5'$R$)-6"-Chloro-4'-(3-chloro-2-fluorophenyl)l'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development," Journal of Medicinal Chemistry, Mar. 2017, 60(7):2819-2839.
Alinari et al., "Selective inhibition of protein arginine methyltransferase 5 blocks initiation and maintenance of B-cell transformation, " Blood, Apr. 2015, 125(16):2530-2543.
Alzabin et al., "Hematopoietic progenitor kinase 1 is a critical component of prostaglandin E2-mediated suppression of the antitumor immune response," Cancer Immunol. Immunother., 2010, 59:419-429.
Alzabin et al., "Hematopoietic Progenitor Kinase 1 is a Negative Regulator of Dendritic Cell Activation," J Immunol, 2009, 182:6187-6194.
Anders et al., "Differential expression analysis for sequence count data," Genome Biol., 2010 11:R106.
Armstrong et al., "MLL translocations specify a distinct gene expression profile that distinguishes a unique leukemia, " Nat Genet., Jan. 2002, 30:41-47.

(56) References Cited

OTHER PUBLICATIONS

Artinger et al., "An MLL-dependent network sustains hematopoiesis," Proc. Natl. Acad. Sci. USA, Jul. 2013, 110(29):12000-12005.
Asiaban et al., "Cell-Based Ligand Discovery for the ENL Yeats Domain," ACS Chem. Biol., Apr. 2020, 15(4):895-903.
AU Notice of Allowance in Australian Appln. No. 2017348322, dated Dec. 14, 2021, 3 pages.
AU Office Action in Australian Appln. No. 2017348322, dated Dec. 10, 2020, 7 pages.
AU Office Action in Australian Appln. No. 2017348322, dated Sep. 27, 2021, 2 pages.
Ayton et al., "Molecular mechanisms of leukemogenesis mediated by MLL fusion proteins," Oncogene, Oct. 2001, 20:5695-5707.
Bachman et al., "EZH2 Expression is Associated With High Proliferation Rate and Aggressive Tumor Subgroups in Cutaneous Melanoma and Cancers of the Endometrium, Prostate, and Breast," J. Clin. Oncol., 2006, 24(2):268-273.
Bai et al., "Targeted degradation of BET proteins in triple-negative breast cancer," Cancer Res., May 1, 2017, 77(9):2476-2487.
Basiorka et al. "Lenalidomide Stabilizes the Erythropoietin Receptor by Inhibiting the E3 Ubiquitin Ligase RNF41," Cancer Res., Apr. 2016, 76:3531-3540.
Bennett et al., "The Role of Nuclear Receptor-Binding SET Domain Family Histone Lysine Methyltransferases in Cancer," Cold Spring Harb. Perspect. Med., Jun. 2017, 7(6):a026708.
Berge et al., "Pharmaceutical Salts," Journal of Pharmaceutical Science, 1997, 66:1-19.
Bilsland et al., "Behavioral and neurochemical alterations in mice deficient in anaplastic lymphoma kinase suggest therapeutic potential for psychiatric indications," Neuropsychopharmacology, 2008, 33:685-700.
Biondi et al., "Biological and therapeutic aspects of infant leukemia.," Blood, Jul. 2000, 96:24-33.
Biswas et al., "Function of leukemogenic mixed lineage leukemia 1 (MLL) fusion proteins through distinct partner protein complexes," Proc. Natl. Acad. Sci. USA, Sep. 2011, 108(38):15751-15756.
Bitoun et al., "The mixed-lineage leukemia fusion partner 10 AF4 stimulates RNA polymerase II transcriptional elongation and mediates coordinated chromatin remodeling," Human Molecular Genetics, Jan. 2007, 16:92-106.
Blake et al., "Discovery and preclinical pharmacology of a selective ATP-competitive Akt inhibitor (GDC-0068) for the treatment of human tumors," J. Med. Chem., Sep. 2012, 55(18):8110-8127.
Bolshan et al., "Synthesis, optimization, and evaluation of novel small molecules as antagonists of WDR5-MLL interaction," ACS Medicinal Chemistry Letters, Mar. 2013, 4(3):353-357.
Bondeson et al., "Catalytic in vivo protein knockdown by small-molecule Protacs," Nature Chemical Biology, 2015, 11(8):611-617.
Bondeson et al., "Lessons in PROTAC design from selective degradation with a promiscuous warhead," Cell Chem. Biol., Jan. 2018, 25:78-87e5.
Bottcher et al., "Fragment-based discovery of a chemical probe for the PWWP1 domain of NSD3," Nat. Chem. Biol., Aug. 2019, 15:822-829.
Bourdi et al., "Safety Assessment of Metarrestin in Dogs: A Clinical Candidate Targeting a Subnuclear Structure Unique to Metastatic Cancer Cell," Regul. Toxicol. Pharmacol., Aug. 2020, 116:104716.
Bracken et al., "*EZH2* is downstream of the pRB-E2F pathway, essential for proliferation and amplified in cancer," EMBO J., 2003, 22(20)5323-5335.
Bradley et al., "EZH2 Inhibitor Efficacy in Non-Hodgkin's Lymphoma Does Not Require Suppression of H3K27 Monomethylation," Chem. Biol., 2014, 21(11):1463-1475.
Brand et al., "Homolog-selective degradation as a strategy to probe the function of CDK6 in AML," Cell Chem. Biol., Feb. 2019, 26(2):300-306e9.
Brauer et al., "Building a better understanding of the intracellular tyrosine kinase PTK6—BRK by BRK," Biochim. Biophys. Acta., Aug. 2010, 1806:66-73.

Braun et al., "Coordinated Splicing of Regulatory Detained Introns within Oncogenic Transcripts Creates an Exploitable Vulnerability in Malignant Glioma," Cancer Cell, Oct. 2017, 32(4):411-426.
Broom et al., "Polycomb repressive complex 2 structure with inhibitor reveals a mechanism of activation and drug resistance," Nat. Commun., Apr. 28, 2016, 7:11384, 12 pages.
Browne et al., "Regulation of peptide-chain elongation in mammalian cells," Eur. J. Biochem., Nov. 2002, 269:5360-5368.
Buckley et al., "HaloProtacs: use of small molecule Protacs to induce degradation of HaloTag fusion proteins," ACS Chemical Biology, Aug. 2015, 10(8):1831-1837.
Buckley et al., "Small-molecule control of intracellular protein levels through modulation of the ubiquitin proteasome system," Angew Chem. Int. Ed. Engl., 2014, 53(9):2312-2330.
Buckley et al., "Small-molecule inhibitors of the interaction between the E3 ligase VHL and HIFlα," Angew Chem Int. Ed. Engl., 2012, 51(46):11463-11467.
Buckley et al., "Targeting the von Hippel-Lindau E3 ubiquitin ligase using small molecules to disrupt the VHL/HIF-1α interaction," Journal of the American Chemical Society, 2012, 134(10):4465-4468.
Burkhart et al., "Cellular mechanisms of tumour suppression by the retinoblastoma gene," Nature Reviews Cancer, 2008, 8(9):671-682.
Burnet, "The concept of immunological surveillance," Progress Exp. Tumor Res., 1970, 13:1-27.
Burslem et al., "Small-molecule modulation of protein homeostasis," Chem. Rev., Aug. 2017, 117(17):11269-11301.
Burslem et al., "The advantages of targeted protein degradation over inhibition: An RTK case study," Cell Chem. Biol., Jan. 2018, 25:67-77e3.
Cai et al., "Subunit composition and substrate specificity of a MOF-containing histone acetyltransferase distinct from the male-specific lethal (MSL) complex," The Journal of Biological Chemistry, Feb. 2010, 285(7):4268-4272.
Cai et al., "ZFX Mediates Non-canonical Oncogenic Functions of the Androgen Receptor Splice Variant 7 in Castrate-Resistant Prostate Cancer," 2018, Mol. Cell 72, 341-354 e346.
Campbell et al., "EPZ011989, A Potent, Orally-Available EZH2 Inhibitor with Robust in Vivo Activity," ACS Med. Chem. Lett., 2015, 6(5):491-495.
Cao et al., "Regulation and functional role of eEF1A2 in pancreatic carcinoma," Biochem. Biophys. Res. Commun., 2009, 380(1):11-16.
Cao et al., "Role of Histone H3 Lysine 27 Methylation in Polycomb-Group Silencing," Science, 2002, 298(5595):1039-1043.
Cao et al., "Targeting MLL1 H3K4 methyltransferase activity in mixed-lineage leukemia," Molecular Cell, Jan. 2014, 53(2):247-261.
Cappuzzo et al., "Erlotinib as maintenance treatment in advanced non-small-cell lung cancer: a multicentre, randomised, placebo-controlled phase 3 study," Lancet Oncol., Jun. 2010, 11:521-529.
Cardenas et al., "Enantioselective Synthesis of Pyrrolopyrimidine Scaffolds through Cation-Directed Nucleophilic Aromatic Substitution," Org. Lett., Mar. 2018, 20:2037-2041.
Carugo et al., "In vivo functional platform targeting patient-derived xenografts identifies WDR5-Myc association as a critical determinant of pancreatic cancer," Cell Reports, Jun. 2016, 16(1):133-147.
Castro et al., "Breast tumor kinase and extracellular signal-regulated kinase 5 mediate Met receptor signaling to cell migration in breast cancer cells," Breast Cancer Research, 2010, 12:R60, 15 pages.
Chamberlain et al., "Structure of the human Cereblon-DDB1-lenalidomide complex reveals basis for responsiveness to thalidomide analogs," Nat. Struct. Mol. Biol., 2014, 21(9):803-809.
Chang et al., "EZH2 promotes expansion of breast tumor initiating cells through activation of RAF1-β-catenin signaling," Cancer Cell, 2011, 19(1):86-100.
Chan-Penebre et al., "A selective inhibitor of PRMT5 with in vivo and in vitro potency in MCL models," Nature Chemical Biology, Apr. 2015, 11:432-437.
Chau et al., "An Anatomical Site and Genetic-Base Prognostic Model for Patients With Nuclear Protein in Testis (NUT) Midline Carcinoma: Analysis of 124 Patients," JNCI Cancer Spectr 4, 2020, pkz094 2020.

(56) References Cited

OTHER PUBLICATIONS

Chawade et al., "Normalyzer: a tool for rapid evaluation of normalization methods for omics data sets," J. Proteome. Res., 2014, 13:3114-31202014.
Chen et al., "Design, synthesis, and initial evaluation of affinity-based small molecular probe for detection of WDR5," Bioorganic Chemistry, Feb. 2018, 76:380-385.
Chen et al., "Gene expression profiling of WDR5 regulated genes in bladder cancer," Genomics Data, Sep. 2015, 5:27-29.
Chen et al., "PTK6 promotes hepatocellular carcinoma cell proliferation and invasion," Am. J. Transl. Res., Oct. 2016, (10):4354-4361.
Chen et al., "Upregulated WDR5 promotes proliferation, self-renewal and chemoresistance in bladder cancer via mediating H3K4 trimethylation," Scientific Reports, Feb. 2015, 5: 12 pages.
Chi et al., "Covalent histone modifications—miswritten, misinterpreted and mis-erased in human cancers," Nat. Rev. Cancer, 2010, 10:457-469.
Choi et al., "EML4-ALK mutations in lung cancer that confer resistance to ALK inhibitors," N. Engl. J. Med., Oct. 2010, 363(18):1734-1739.
Choi et al., "Identification of novel isoforms of the EML4-ALK transforming gene in non-small cell lung cancer," Cancer Res., Jul. 2008, 68(13):4971-4976.
Christott et al., "Discovery of a Selective Inhibitor for the Yeats Domains of ENL/AF9.," SLAS Discov., 2019, 24:133-141.
Chung et al., "Cbx8 acts non-canonically with Wdr5 to promote mammary tumorigenesis," Cell Reports, Jul. 2016, 16(2):472-486.
Clinicaltrials.gov [online], "Metarrestin (ML-246) in Subjects with Metastatic Solid Tumors," Jan. 10, 2020, retrieved on Mar. 16, 2022, retrieved from URL<https://clinicaltrials.gov/ct2/show/NCT04222413>, 12 pages.
CN Office Action in Chinese Appln. No. 201780081246.8, dated Dec. 2, 2021, 18 pages (with English Translation).
CN Office Action in Chinese Appln. No. 201780081246.8, dated Jun. 4, 2021, 19 pages (with English Translation).
CN Office Action in Chinese Appln. No. 201780085879.6, dated Jan. 5, 2022, 18 pages (with English Translation).
CN Office Action in Chinese Appln. No. 201780085879.6, dated Jun. 27, 2022, 15 pages (with English Translation).
Corthay, "Does the immune system naturally protect against cancer?" Front. Immunol., May 2014, 5(197):1-8.
Cromm et al., "Addressing kinase-independent functions of Fak via Protac-mediated degradation," J. Am. Chem. Soc., Nov. 2018, 140(49):17019-17026.
Cromm et al., "Targeted protein degradation: from chemical biology to drug discovery," Cell Chem. Biol., Sep. 2017, 24(9):1181-1190.
Czermin et al., "*Drosophila* enhancer of Zeste/ESC complexes have a histone H3 methyltransferase activity that marks chromosomal Polycomb sites," Cell, 2002, 111(2):185-196.
Dai et al., "WDR5 expression is prognostic of breast cancer outcome," PLoS One, Sep. 2015, 10: 15 pages.
Davies et al., "Monoacidic Inhibitors of the Kelch-like ECH-Associated Protein 1: Nuclear Factor Erythroid 2-Related Factor 2 (KEAP1:NRF2) Protein-Protein Interaction with High Cell Potency Identified by Fragment-Based Discovery," Journal of Medicinal Chemistry, Apr. 2016, 59(8):3991-4006.
Dawson et al., "Inhibition of BET recruitment to chromatin as an effective treatment for MLL-fusion leukaemia," Nature, 2011, 478:529-15 533.
Deng et al., "Protein arginine methyltransferase 5 functions as an epigenetic activator of the androgen receptor to promote prostate cancer cell growth, " Oncogene, 2017, 36:1223-1231.
Derry et al., "Altered localization and activity of the intracellular tyrosine kinase BRK/Sik in prostate tumor cells," Oncogene, Jul. 2003, 22:4212-4220.
Deshpande et al., "Chromatin modifications as therapeutic targets in MLL-rearranged leukaemia," Trends Immunol., Nov. 2012, 33(11):563-570.

Dias et al., "Structural analysis of the KANSL1/WDR5/KANSL2 complex reveals that WDR5 is required for efficient assembly and chromatin targeting of the NSL complex," Genes & Development, May 2014, 28(9):929-942.
Douglass, Jr. et al., "A comprehensive mathematical model for three-body binding equilibria," J. Am. Chem. Soc., Apr. 2013, 135(16):6092-6099.
Du et al., "FOXC1, a target of polycomb, inhibits metastasis of breast cancer cells," Breast Cancer Res. Treat., 2012, 131(1):65-73.
Duanmin et al., "eEF1A2 protein expression correlates with lymph node metastasis and decreased survival in pancreatic ductal adenocarcinoma," Hepatogastroenterology, Jun. 2013, 60(124):870-875.
Dumble et al., "Discovery of novel AKT inhibitors with enhanced anti-tumor effects in combination with the MEK inhibitor," PloS One, Jun. 2014, 9(6), 11 pages.
EA Office Action in Eurasian Appln. No. 201991071, dated Jun. 10, 2020, 4 pages (with English translation).
Ee et al., "An embryonic stem cell-specific NuRD complex functions through interaction with WDR5," Stem Cell Reports, Jun. 2017, 8(6): 9 pages.
EP Extended European Search Report in European Appln. No. 17863645.2, dated Aug. 6, 2020, 10 pages.
EP Extended European Search Report in European Appln. No. 17877800.7, dated Feb. 19, 2021, 9 pages.
EP Extended European Search Report in European Appln. No. 19757825.5, dated Jan. 26, 2022, 14 pages.
EP Extended European Search Report in European Appln. No. 19763958.6, dated Dec. 8, 2021, 12 pages.
EP Extended European Search Report in European Appln. No. 19821826.5, dated May 3, 2022, 10 pages.
EP Extended European Search Report in European Appln. No. 19830269.7, dated Mar. 7, 2022, 6 pages.
EP Office Action in European Appln. No. 17863645.2, dated Apr. 6, 2021, 7 pages.
EP Office Action in European Appln. No. 17863645.2, dated Mar. 11, 2022, 5 pages.
EP Office Action in European Appln. No. 17877800.7, dated May 24, 2022, 6 pages.
EP Office Action in European Appln. No. 19821826.5, dated Jan. 13, 2022, 4 pages.
EP Partial Supplementary Search Report in European Appln. No. 19757825.5, dated Oct. 18, 2021, 16 pages.
Erb et al. (2017). Transcription control by the ENL Yeats domain in acute leukaemia. Nature 543, 270-274.
Fabian et al., "A small molecule-kinase interaction map for clinical kinase inhibitors," Nat. Biotechnol., Mar. 2005, 23(3):329-336.
Fan et al., "A Kinase Inhibitor Targeted to mTORC1 Drives Regression in Glioblastoma," Cancer Cell, Mar. 2017, 31(3):424-435.
Fan et al., "BAHCC1 binds H3K27me3 via a conserved BAH module to mediate gene silencing and oncogenesis," Nature genetics, 2020, 52:1384-1396.
fda.gov [online], "Data Standards Manual (Monographs)," Feb. 27, 2018, retrieved on Feb. 7, 2022, retrieved from URL <https://www.fda.gov/drugs/electronic-regulatory-submission-and-review/data-standards-manual-monographs>, 1 page.
fda.gov [online], "Development & Approval Process | Drugs," Oct. 28, 2019, retrieved on Feb. 4, 2022, retrieved from URL <https://www.fda.gov/drugs/development-approval-process-drugs>, 4 pages.
Fei et al., "Protac and its Application in the Treatment of Cancer," Chemistry of Life, Aug. 2014, 34(4):549-554 (with English abstract).
Ferguson et al., "Kinase inhibitors: the road ahead," Nat. Rev. Drug Discov., May 2018, 17:353-377.
Ferrando et al., "Gene expression signatures in *MLL*-rearranged T-lineage and B-precursor acute leukemias: dominance of *HOX* dysregulation," Blood, Jul. 2003, 102(1):262-268.
Finn et al., "The cyclin-dependent kinase 4/6 inhibitor palbociclib in combination with letrozole versus letrozole alone as first-line treatment of oestrogen receptor-positive, HER2-negative, advanced breast cancer (Paloma-1/Trio-18): a randomised phase 2 study," The Lancet Oncology, 2015, 16(1):25-35.

(56) References Cited

OTHER PUBLICATIONS

Fischer et al., "Structure of the DDB1-CRBN E3 ubiquitin ligase in complex with thalidomide," Nature, Aug. 2014, 512(7512):49-53.
Fisher et al., "Targeted protein degradation and the enzymology of degraders," Current Opinion in Chemical Biology, 2018, 44:47-55.
Frankowski et al., "Metarrestin, a perinucleolar compartment inhibitor, effectively suppresses metastasis," Science Translational Medicine, May 2018, 10(441), 13 pages.
Frost et al., "Potent and selective chemical probe of hypoxic signalling downstream of HIF-α hydroxylation via VHL inhibition," Nat. Commun., Nov. 2016, 7:13312, 12 pages.
Fujii et al., "Enhancer of Zeste Homologue 2 (EZH2) Down-regulates RUNX3 by Increasing Histone H3 Methylation," J. Biol. Chem., 2008, 283(25):17324-17332.
Fujii et al., "MEKERK pathway regulates EZH2 overexpression in association with aggressive breast cancer subtypes," Oncogene, 2011, 30(39):4118-4128.
Gadd et al., "A Children's Oncology Group and Target initiative exploring the genetic landscape of Wilms tumor," Nat. Genet., Oct. 2017, 49:1487-1494.
Galdeano et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities," J. Med. Chem., 2014, 57(20):8657-8663.
Gao et al., "ZLD1122, a novel EZH2 and EZH1 small molecular inhibitor, blocks H3K27 methylation and diffuse large B cell lymphoma cell growth," RSC Adv., 2016, 6:28512-28521.
Garapaty-Rao et al., "Identification of EZH2 and EZH1 small molecule inhibitors with selective impact on diffuse large B cell lymphoma cell growth," Chem. Biol., 2013, 20(11):1329-1339.
Garnar-Wortzel et al., "Chemical Inhibition of ENL/AF9 Yeats Domains in Acute Leukemia," ACS Central Science, Apr. 2021, 7(5):815-830.
Ge et al., "WDR5 high expression and its effect on tumorigenesis in leukemia," Oncotarget, Jun. 2016, 7(25):37740-37754.
Gehling et al., "Discovery, design, and synthesis of indole-based EZH2 inhibitors," Bioorg. Med. Chem. Lett., 2015, 25(17):3644-3649.
Genscript.com [online], "Gen Script Make Research Easy," available on or before Mar. 3, 2015, retrieved on Mar. 17, 2022, retrieved from URL<https://www.genscript.com/gRNAdatabase.html>.
Getlik et al., "Structure-based optimization of a small molecule antagonist of the interaction between WD repeat-containing protein 5 (WDR5) and mixed-lineage leukemia 1 (MLL1)," Journal of Medicinal Chemistry, Mar. 2016, 59(6):2478-2496.
Gillis et al., "Biochemical and biological characterization of lymphocyte regulatory molecules; V. Identification of an interleukin 2-producing human leukemia T cell line," The Journal of experimental medicine, Dec. 1980,152:1709-1719.
Github.com [online], "PreprocessCore," Oct. 26, 2021, retrieved on Mar. 17, 2022, retrieved from URL<Gihttps://github.com/bmbolstad/preprocessCore>, 1 pages.
Github.com [online], "ProteiNorm," Jul. 27, 2020, retrieved on Mar. 17, 2022, retrieved from URL <https://github.com/ByrumLab/proteiNorm>, 3 page.
Gluz et al., "Triplenegative breast cancer—current status and future directions," Ann. Oncol., 2009, 20(12):1913-1927.
Godin-Heymann et al., "The T790M 'gatekeeper' mutation in EGFR mediates resistance to low concentrations of an irreversible EGFR inhibitor," Mol. Cancer Ther., Apr. 2008, 7(4):874-879.
Gonzalez et al., "Downregulation of EZH2 decreases growth of estrogen receptor-negative invasive breast carcinoma and requires BRCAI," Oncogene, 2009, 28(6):843-853.
Gonzalez et al., "EZH2 expands breast stem cells through activation of Notch1 signaling," Proc. Natl. Acad. Sci. USA, 2014, 111(8):3098-3103.
Grabe et al., "C797S Resistance: The undruggable EGFR mutation in non-small cell lung cancer?" ACS Med. Chem. Lett., 2018, 9:779-782.
Grebien et al., "Pharmacological targeting of the Wdr5-MLL interaction in C/EBPα N-terminal leukemia," Nature Chemical Biology, Aug. 2015, 11(8): 11 pages.
Guarnaccia et al., "Moonlighting with WDR5: A cellular multitasker," Journal of Clinical Medicine, Feb. 2018, 7(2): 17 pages.
Gullà et al., "Protein arginine methyltransferase 5 has prognostic relevance and is a druggable target in multiple myeloma," Leukemia, 2018, 32:996-1002.
Haegebarth et al., "Protein tyrosine kinase 6 negatively regulates growth and promotes enterocyte differentiation in the small intestine," Mol. Cell Biol., Jul. 2006, 26:4949-4957.
Hallberg et al., "Mechanistic insight into ALK receptor tyrosine kinase in human cancer biology," Nature Reviews Cancer, Oct. 2013, 13:685-700.
Hamilton et al., "Targeting CDK4/6 in patients with cancer," Cancer Treatment Reviews, 2016, 45:129-138.
Han et al., "Discovery of ARD-69 as a Highly Potent Proteolysis Targeting Chimera (Protac) Degrader of Androgen Receptor (AR) for the Treatment of Prostate Cancer," Journal of Medicinal Chemistry, Jan. 2019, 62:941-964.
Harvey et al., "Brk protects breast cancer cells from autophagic cell death induced by loss of anchorage," The American Journal of Pathology, Sep. 2009, 175:1226-1234.
Harvey et al., "Use of RNA interference to validate Brk as a novel therapeutic target in breast cancer: Brk promotes breast carcinoma cell proliferation," Oncogene, Aug. 2003, 22:5006-5010.
He et al., "HIV-1 Tat and Host AFF4 Recruit Two Transcription Elongation Factors into a Bifunctional Complex for Coordinated Activation of HIV-I Transcription," Mol. Cell., May 2010, 38(3):428-438.
He et al., "Human Polymerase-Associated Factor complex (PAFc) connects the Super Elongation Complex (SEC) to RNA polymerase II on chromatin," Proc. Natl. Acad. Sci. USA, Sep. 2011, 108(36):E636-E645.
Heerding et al., "Identification of 4-(2-(4-amino-1,2,5-oxadiazol-3-yl)-1-ethyl-7-{[(3S)-3-piperidinylmethyl]oxy }-1H-imidazo[4,5-c]pyridin-4-yl)-2-methyl-3-butyn-2-ol (GSK690693), a novel inhibitor of AKT kinase," Journal of Medicinal Chemistry, Sep. 2008, 51(18):5663-5679.
Heidenreich et al., "Structure-Based Approach toward Identification of Inhibitory Fragments for Eleven-Nineteen-Leukemia Protein (ENL)," J. Med. Chem., Nov. 2018, 61(23):10929-10934.
Henning et al., "Degradation of Akt using protein-catalyzed capture agent," Journal of Peptide Science, 2016, 22:196-200.
Herbst et al., "Gefitinib—a novel targeted approach to treating cancer," Nat. Rev. Cancer, Dec. 2004, 4:956-965.
Hernandez et al., "The Kinase Activity of Hematopoietic Progenitor Kinase 1 is Essential for the Regulation of T Cell Function," Cell reports, Oct. 2018, 25:80-94.
Herrera-Abreu et al., "Early adaptation and acquired resistance to CDK4/6 inhibition in estrogen receptor-positive breast cancer," Cancer Research, 2016, 76(8):2301-2313.
Hess, "MLL: a histone methyltransferase disrupted in leukemia," Trends Mol. Med., Oct. 2004, 10(10):500-507.
Higa et al., "CUL4-DDB 1 ubiquitin ligase interacts with multiple WD40-repeat proteins and regulates histone methylation," Nature Cell Biology, Nov. 2006, 8(11):1277-1283.
Hirai et al., "MK-2206, an allosteric Akt inhibitor, enhances antitumor efficacy by standard chemotherapeutic agents or molecular targeted drugs in vitro and in vivo," Molecular Cancer Therapeutics, Jul. 2010, 9(7):1956-1967.
Hiroyuki et al., "The structure of bestatin," The Journal of Antibiotics, Jan. 1976, 29(1):100-101.
Hirsch et al., "Lung cancer: current therapies and new targeted treatments," Lancet, Jan. 2017, 389:299-311.
Holm et al., "Global H3K27 trimethylation and EZH2 abundance in breast tumor subtypes," Mol. Oncol., 2012, 6(5):494-506.
Hsu et al., "Recognition of histone acetylation by the GAS41 Yeats domain promotes H2A.Z deposition in non-small cell lung cancer," Genes Dev., 2018, 32:58-69.
Hu et al., "Human HPK1, a novel human hematopoietic progenitor kinase that activates the JNK/SAPK kinase cascade," Genes Dev., Sep. 1996, 10:225 1-2264.

(56) References Cited

OTHER PUBLICATIONS

Hu et al., "Small Molecule Inhibitors of Protein Arginine Methyltransferases," Expert Opinion Investigational Drugs, 2016, 25:335-358.

Huang et al., "A Chemoproteomic Approach to Query the Degradable Kinome Using a Multi-kinase Degrader," Cell Chemical Biology, Jan. 2018, 25(1):88-99.

Huang et al., "Covalent inhibition of NSD1 histone methyltransferase," Nat. Chem. Biol, 2020, 16:1403-1410.

Huber et al., "Variance stabilization applied to microarray data calibration and to the quantification of differential expression," Bioinformatics, 2002, 18 Suppl 1:S96-104.

IN Office Action in Indian Appln. No. 201917020814, dated Jun. 23, 2021, 6 pages (with English Translation).

Irie et al., "PTK6 regulates IGF-1-induced anchorage-independent survival," PLoS One, Jul. 2010, 5(7):e11729.

Ito et al., "Identification of a primary target of thalidomide teratogenicity," Science, Mar. 2010, 327(5971):1345-1350.

Ito et al., "PTK6 Inhibition Suppresses Metastases of Triple-Negative Breast Cancer via Snail-Dependent E-Cadherin regulation," Cancer Res., Aug. 2016, 76:4406-4417.

Ito et al., "PTK6 regulates growth and survival of endocrine therapy-resistant ER+ breast cancer cells," NPJ Breast Cancer, Nov. 2017, 3:45.

Iwahara et al., "Molecular characterization of ALK, a receptor tyrosine kinase expressed specifically in the nervous system," Oncogene, Jan. 30, 1997, 14:439-449.

Jakobsson et al., "The dual methyltransferase METTL13 targets N terminus and Lys55 of eEF1A and modulates codon-specific translation rates," Nature Communications, Aug. 2018, 15 pages.

Jiang et al., "Development of dual and selective degraders of cyclin-dependent kinases 4 and 6," Angew. Chem. Int. Ed. Engl., May 2019, 58(19):6321-6326.

Jiang et al., "Targeting BRK-Positive Breast Cancers with Small-Molecule Kinase Inhibitors," Cancer Res., Jan. 2017, 77:175-186.

Jiao et al., "Structural basis of histone H3K27 trimethylation by an active polycomb repressive complex 2," Science, 2015, 350(6258):aac4383.

Jin et al., "Targeting methyltransferase PRMT5 eliminates leukemia stem cells in chronic myelogenous leukemia," The Journal of Clinical Investigation, Oct. 2016, 126:3961-3980.

JP Office Action in Japanese Appln. No. 2019-522841, dated Jul. 12, 2022, 8 pages (with English Translation).

JP Office Action in Japanese Appln. No. 2019-522841, dated Oct. 5, 2021, 14 pages (with English Translation).

JP Office Action in Japanese Appln. No. 2019-530811, dated Dec. 14, 2021, 4 pages (with English Translation).

Jude et al., "Unique and independent roles for MLL in adult hematopoietic stem cells and progenitors," Cell Stem Cell, Sep. 2007, 1(3):324-337.

Justin et al., "Structural basis of oncogenic histone H3K27M inhibition of human polycomb repressive complex 2," Nat. Commun., 2016, 7:11316.

Kanda et al., "Protein arginine methyltransferase 5 is associated with malignant phenotype and peritoneal metastasis in gastric cancer," International Journal of Oncology, Jun. 2016, 49:1195-1202.

Kanis et al., "A small molecule inhibitor of the perinucleolar compartment, ML246, attenuates growth and spread of ovarian cancer," Gynecol. Oncol. Res. Pract., 2018, 5:7.

Kanis et al., "Metarrestin: A novel compound active against ovarian cancer," Gynecol Oncol., Oct. 2015, 139(1):190.

Kaniskan et al., "Inhibitors of Protein Methyltransferases and Demethylases," Chem. Rev., 2018, 118(3):989-1068.

Kaniskan et al., "Selective inhibitors of protein methyltransferases," Journal of Medicinal Chemistry, 2015, 58:1596-1629.

Karatas et al., "Discovery of a highly potent, cell-permeable macrocyclic peptidomimetic (MM-589) targeting the WD repeat domain 5 protein (WDR5)-mixed lineage leukemia (MLL) protein-protein interaction," Journal of Medicinal Chemistry, Jun. 2017, 60(12):4818-4839.

Khalyfa et al., "Characterization of elongation factor-1A (eEF1A-1) and eEF1A-2/S1 protein expression in normal and *wasted* mice," Journal of Biological Chemistry, 2001, 276:22915-22922.

Kiefer et al., "HPKI, a hematopoietic protein kinase activating the SAPK/JNK pathway," EMBO J., Dec. 1996, 15(24):7013-7025.

Kim et al., "Targeted disruption of the EZH2-EED complex inhibits EZH2-dependent cancer" Nature Chemical Biology, 2013, 9:643-650.

Kim et al., "Targeting EZH2 in cancer," Nat. Med., 2016, 22(2):128-134.

Kleer et al., "EZH2 is a marker of aggressive breast cancer and promotes neoplastic transformation of breast epithelial cells," PNAS, 2003, 100(20):11606-11611.

Klein et al., "Yaf9 subunit of the NuA4 and SWR1 complexes targets histone H3K27ac through its Yeats domain," Nucleic Acids Res., Jan. 2018, 46:421-430.

Knutson et al., "A selective inhibitor of EZH2 blocks H3K27 methylation and kills mutant lymphoma cells," Nat. Chem. Biol., 8(11):890-896, 2012.

Knutson et al., "Durable tumor regression in genetically altered malignant rhabdoid tumors by inhibition of methyltransferase EZH2," Proc. Natl. Acad. Sci. USA., 2013, 110(19):7922-7927.

Kobayashi et al., "EGFR mutation and resistance of non-small-cell lung cancer to gefitinib," N. Engl. J. Med., Feb. 2005, 352(8):786-792.

Koivunen et al., "*EML4-ALK* fusion gene and efficacy of an ALK kinase inhibitor in lung cancer," Clinical Cancer Research, Jul. 1, 2008, 14(13):4275-4283.

Konze et al., "An Orally Bioavailable Chemical Probe of the Lysine Methyltransferases EZH2 and EZHI," ACS Chem. Biol., 2013, 8(6):1324-1334.

Krause et al., "Tyrosine kinases as targets for cancer therapy," N. Engl. J. Med., Jul. 2005, 353(2):172-187.

Krivtsov et al., "*MLL* translocations, histone modifications and leukaemia stem-cell development," Nat. Rev. Cancer, Nov. 2007, 7:823-833.

Kryukov et al., "*MTAP* deletion confers enhanced dependency on the PRMT5 arginine methyltransferase in cancer cells," Science, 2016, 351(6278):1214-1218.

Kuenzi et al., "Polypharmacology-based ceritinib repurposing using integrated functional proteomics," Nat. Chem. Biol., Dec. 2017, 13(12):1222-1231.

Kung et al., "Design and Synthesis of Pyridone-Containing 3,4-Dihydroisoquinoline-1(2H)-ones as a Novel Class of Enhancer of Zeste Homolog 2 (EZH2) Inhibitors," J. Med. Chem., 2016, 59(18):8306-8325.

Kuzmichev et al., "Histone methyltransferase activity associated with a human multiprotein complex containing the Enhancer of Zeste protein," Genes Dev., 2002, 16(22):2893-2905.

Kwak et al., "Anaplastic lymphoma kinase inhibition in non-small-cell lung cancer," New England Journal of Medicine, Oct. 28, 2010, 363(18):1693-1703.

Lai et al., "Induced protein degradation: an emerging drug discovery paradigm," Nat. Rev. Drug Discov., Feb. 2017, 16(2):101-114.

Lai et al., "Modular Protac design for the degradation of oncogenic BCR-ABL," Angewandte Chemie International Edition English, Jan. 2016, 55(2):807-810.

Lapierre et al., "Discovery of 3-(3-(4-(1-Aminocyclobutyl)phenyl)-5-phenyl-3H-imidazo[4,5-b]pyridin-2-yl)pyridin-2-amine (ARQ 092): An orally bioavailable, selective, and potent allosteric AKT inhibitor," Journal of Medicinal Chemistry, 2016, 59:6455-6469.

Lebraud et al., "Protein Degradation by In-Cell Self-Assembly of Proteolysis Targeting Chimeras," ACS Central Science, 2016, 2:927-934.

Li et al., "AF9 Yeats domain links histone acetylation to DOTIL-mediated H3K79 methylation," Cell, Oct. 2014, 159(3):558-571.

Li et al., "Discovery of MD-224 as a first-in-class, highly potent, and efficacious proteolysis targeting chimera Murine Double Minute 2 degrader capable of achieving complete and durable tumor regression," J. Med. Chem., 2019, 62(2):448-466.

(56) References Cited

OTHER PUBLICATIONS

Li et al., "Discovery of potent and noncovalent reversible EGFR kinase inhibitors of EGFR$^{L858R/T790M/C797S}$," ACS Med. Chem. Lett., Jun. 2019, 10(6):869-873.

Li et al., "High-affinity small molecular blockers of mixed lineage leukemia 1 (MLL1)-WDR5 interaction inhibit MILL1 complex H3K4 methyltransferase activity," European Journal of Medicinal Chemistry, Nov. 2016, 124:480-489.

Li et al., "Molecular Coupling of Histone Crotonylation and Active Transcription by AF9 Yeats Domain," Mol. Cell., Apr. 2016, 62(2):181-193.

Li et al., "RSEM: accurate transcript quantification from RNA-Seq data with or without a reference genome," Bmc Bioinformatics, 2011, 12:323.

Li et al., "Structure-based design and synthesis of small molecular inhibitors disturbing the interaction of MLL1-WDR5," European Journal of Medicinal Chemistry, Aug. 2016, 118:1-8.

Li et al., "Structure-guided development of Yeats domain inhibitors by targeting π-π-π stacking," Nat. Chem. Biol., Dec. 2018, 14:1140-1149.

Li et al., "The OncoPPi network of cancer-focused protein-protein interactions to inform biological insights and therapeutic strategies," Nat. Commun., Feb. 2017, 8:14356.

Li et al., "Understanding histone H3 lysine 36 methylation and its deregulation in disease," Cell. Mol. Life Sci., Aug. 2019, 76(15):2899-2916.

Li et al., "ZMYND11-MBTD1 induces leukemogenesis through hijacking NuA4/TIP60 acetyltransferase complex and a PWWP-mediated chromatin association mechanism," Nat. Commun., 2021, 12(1), 18 pages.

Lim et al., "CDK4/6 inhibitors: promising opportunities beyond breast cancer," Cancer Discovery, 2016, 6(7):697-699.

Lin et al., "AFF4, a component of the ELL/PTEFb elongation complex and a shared subunit of MLL chimeras, can link transcription elongation to leukemia," Mol. Cell., Feb. 2010, 37(3):429-437.

Lin et al., "Clinicopathologic features, patterns of recurrence, and survival among women with triple-negative breast cancer in the National Comprehensive Cancer Network," Cancer, 2012, 118(22):5463-5472.

Lin et al., "Targeting ALK: Precision Medicine Takes on Drug Resistance," Cancer Discovery, Feb. 2017, 7(2):137-155.

Ling et al., "Involvement of hematopoietic progenitor kinase 1 in T cell receptor signaling," The Journal of biological chemistry, Jun. 2001, 276:18908-18914.

Liou et al., "HPK1 is activated by lymphocyte antigen receptors and negatively regulates AP-1," Immunity, Apr. 2000, 12(4):399-408.

Liu et al., "Calcineurin is a common target of cyclophilin-cyclosporin A and FKBP-FK506 complexes," Cell, Aug. 1991, 66(4):807-815.

Liu et al., "Critical role of kinase activity of hematopoietic progenitor kinase 1 in anti-tumor immune surveillance," PloS one, Mar. 2019, 14:e02 12670.

Liu et al., "METTL13 Methylation of eEF1A Increases Translational Output to Promote Tumorigenesis," Cell, Jan. 2019, 176:491-504.e421.

Liu et al., "Widening Synthesis Bottlenecks: Realization of Ultrafast and Continuous-Flow Synthesis of High-Silica Zeolite SSZ-13 for NOx Removal," Angew. Chem., May 4, 2015, 127(19):5775-5779.

Losada et al., "Binding of eEF1A2 to the RNA-dependent protein kinase PKR modulates its activity and promotes tumour cell survival," British Journal of Cancer, Nov. 2018, 119(11):1410-1420.

Lu et al., "Epigenetic Perturbations by Arg882-Mutated DNMT3A Potentiate Aberrant Stem Cell Gene-Expression Program and Acute Leukemia Development," Cancer Cell, 2016, 30:92-107.

Lu et al., "Hijacking the E3 ubiquitin ligase cereblon to efficiently target BRD4," Chemistry & Biology, Jun. 2015, 22(6):755-763.

Lu et al., "Targeting EGFR$^{L858R/T790M}$ and EGFR$^{L858R/T790M/C797S}$ resistance mutations in NSCLC: Current developments in medicinal chemistry," Med. Res. Rev., Jan. 2018, 38(5):1550-1581.

Mahara et al., "HIFI-α activation underlies a functional switch in the paradoxical role of Ezh2/PRC2 in breast cancer," PNAS, 2016, 113(26):E3735-E3744.

Mahmoud et al., "Discovery of 4-anilino α-carbolines as novel Brk inhibitors," Bioorganic & Medicinal Chemistry Letters, Apr. 2014, 24:1948-1951.

Majer et al., "A687V EZH2 is a gain-offunction mutation found in lymphoma patients," FEBS Lett., 2012, 586(19):3448-3451.

Maniaci et al., "Homo-Protacs: bivalent small-molecule dimerizers of the VHL E3 ubiquitin ligase to induce self-degradation," Nature Communication, Oct. 8, 2017, 14 pages.

Manning et al., "AKT/PKB signaling: navigating the network," Cell, Apr. 2017, 169(3):381-405.

Marjon et al., "*MTAP* Deletions in Cancer Create Vulnerability to Targeting of the MAT2A/PRMT5/RIOK1 Axis," Cell Reports, Apr. 2016, 15:574-587.

Marschalek, "MLL Leukemia and Future Treatment Strategies," Arch. Pharm. Chem. Life Sci., Apr. 2015, 348(4):221-228.

Matsushime et al., "Identification and properties of an atypical catalytic subunit (p34$^{PSK-J3}$/cdk4) for mammalian D type G1 cyclins," Cell, 1992, 71(2):323-334.

Mavrakis et al., "Disordered methionine metabolism in MTAP/CDKN2A-deleted cancers leads to dependence on PRMT5," Science, Feb. 2016, 351(6278):1208-1213.

Mcalpine et al., "Abstract 4857: Discovery of PF-06855800, a SAM competitive PRMT5 inhibitor with potent antitumor activity," American Association for Cancer Research Annual Meeting, 2018, 78(13 Supplement), 4 pages.

McCabe et al., "EZH2 inhibition as a therapeutic strategy for lymphoma with EZH2-activating mutations," Nature, 2012, 492(7427):108-112.

McCabe et al., "Mutation of A677 in histone methyltransferase EZH2 in human B-cell lymphoma promotes hypertrimethylation of histone H3 on lysine 27 (H3K27)," Proc. Natl. Acad. Sci. USA, 2012, 109(8):2989-2994.

Meyer et al., "New insights to the MLL recombinome of acute leukemias," Leukemia, Aug. 2009, 23:1490-1499.

Meyer et al., "The *MLL* recombinome of acute leukemias in 2013," Leukemia, Nov. 2013, 27:2165-2176.

Meyer et al., "The MLL recombinome of acute leukemias," Leukemia, May 2006, 20:777-784.

Meyerson et al., "Identification of G$_1$ kinase activity for cdk6, a novel cyclin D partner," Molecular and Cellular Biology. 1994, 14(3):2077-2086.

Mi et al., "Yeats2 links histone acetylation to tumorigenesis of non-small cell lung cancer," Nat. Commun., Oct. 2017, 8:1088, 14 pages.

Migliori et al., "Symmetric dimethylation of H3R2 is a newly identified histone mark that supports euchromatin maintenance," Nature Structural and Molecular Biology, Feb. 2012, 19(2):136-144.

Miller et al., "Compass: a complex of proteins associated with atrithorax-related SET domain protein," Proceedings of the National Academy of Sciences, Nov. 2001, 98(23):12902-12907.

Mitchell et al., "Cloning and characterisation of cDNAs encoding a novel non-receptor tyrosine kinase, brk, expressed in human breast tumours, " Oncogene, Aug. 1994, 9:2383-2390.

Mohan et al., "Licensed to elongate: a molecular mechanism for MLL-based leukaemogenesis," Nat. Rev. Cancer, Oct. 2010, 10:721-728.

Mohan et al., "Linking H3K79 trimethylation to Wnt signaling through a novel Dot1-containing complex (DotCom)," Genes Dev., 2010, 24:574-589.

Molander et al., "Efficient hydrolysis of organotrifluoroborates via silica gel and water," Journal of Organic Chemistry, Oct. 2009, 74(19):364-7369.

Morin et al., "Somatic mutations altering EZH2 (Y641) in follicular and diffuse large B-cell lymphomas of germinal-center origin," Nat. Genet., 2010, 42(2):181-185.

Morris et al., "*ALK*, the chromosome 2 gene locus altered by the t(2;5) in non-Hodgkin's lymphoma, encodes a novel neural receptor tyrosine kinase that is highly related to leukocyte tyrosine kinase (LTK)," Oncogene, Mar. 8, 1997, 14:2175-2188.

(56) References Cited

OTHER PUBLICATIONS

Morris et al., "Fusion of a kinase gene, *ALK*, to a nucleolar protein gene, *NPM*, in non-Hodgkin's lymphoma," Science, Mar. 4, 1994, 263(5151):1281-1284.
Moustakim et al., "Discovery of an MLLT1/3 Yeats Domain Chemical Probe," Angew. Chem. Int. Ed. Engl., Dec. 2018, 57(50):16302-16307.
Mueller et al., "A role for the MLL fusion partner ENL in transcriptional elongation and chromatin modification," Blood, Dec. 2007, 110(13):4445-4454.
Mueller et al., "Misguided Transcriptional Elongation Causes Mixed Lineage Leukemia," Plos Biol., Nov. 2009, 7(11):e1000249, 15 pages.
Müller et al., "Histone methyltransferase activity of a *Drosophila* Poly comb group repressor complex," Cell, 2002, 111(2):197-208.
MX Office Action in Mexican Appln. No. MX/a/2019/004950, dated Aug. 6, 2021, 6 pages (with English translation).
MX Office Action in Mexican Appln. No. MX/a/2019/004950, dated Nov. 23, 2021, 8 pages (with English Translation).
Nadeem Abbas et al., "Advances in targeting the epidermal growth factor receptor pathway by synthetic products and its regulation by epigenetic modulators as a therapy for glioblastoma," Cells, Apr. 2019, 8:350, 22 pages.
Neklesa et al., "Small-molecule hydrophobic tagging induced degradation of HaloTag fusion proteins," Nat. Chem. Biol., 2011, 7(8):538-543.
Ni et al., "Structural Insights into Interaction Mechanisms of Alternative Piperazine-urea Yeats Domain Binders in MLLTI," ACS Med. Chem. Lett., Dec. 2019, 10(12):1661-1666.
Nicholson et al., "EGFR and cancer prognosis," Eur. J. Cancer, Sep. 2001, 37(Supp. 4):9-15.
Noble et al., "Protein kinase inhibitors: insights into drug design from structure," Science, Mar. 2004, 303:1800-1805.
Odho et al., "Characterization of a novel WDR5-binding site that recruits RbBP5 through a conserved motif to enhance methylation of histone H3 lysine 4 by mixed lineage leukemia protein-1," Journal of Biological Chemistry, Oct. 2010, 285(43):32967-32976.
Ohoka et al., "In vivo knockdown of pathogenic proteins via specific and nongenetic inhibitor of apoptosis protein (IAP)-dependent protein erasers (Snipers)," Journal of Biological Chemistry, Mar. 2017, 292(11):4556-4570.
Okada et al., "hDOTIL links histone methylation to leukemogenesis," Cell, Apr. 2005, 121(2):167-178.
Okuhira et al., "Specific degradation of CRABP-II via cIAPI-mediated ubiquitylation induced by hybrid molecules that crosslink cIAP1 and the target protein," FEBS Lett., Apr. 2011, 585(8):1147-1152.
Olson et al., "Pharmacological perturbation of CDK9 using selective CDK9 inhibition or degradation," Nat. Chem. Biol., Feb. 2018, 14:163-170.
Ono et al., "PTK6 promotes cancer migration and invasion in pancreatic cancer cells dependent on ERK signaling," PLoS One, 2014, 9:e96060.
Ostrander et al., "Brk/PTK6 signaling in normal and cancer cell models," Curr. Opin. Phannacol., 2010, 10:662-669.
Ottis et al., "Proteolysis-targeting chimeras: induced protein degradation as a therapeutic strategy," ACS Chem. Biol., Mar. 2017, 12(4):892-898.
Paez et al., "*EGFR* mutations in lung cancer: correlation with clinical response to gefitinib therapy," Science, Jun. 2004, 304:1497-500.
Pao et al., "Acquired resistance of lung adenocarcinomas to gefitinib or erlotinib is associated with a second mutation in the EGFR kinase domain," PLoS Med., Feb. 2005, 2(3):e73.
Papazimas et al., "A General Strategy for the Preparation of Thalidomide-Conjugate Linkers," Synlett, Aug. 23, 2017, 28:2881-2885.
Park et al., "Discovery of EGF receptor inhibitors that are selective for the d746-750/T790M/C797S mutant through structure-based de novo design," Angew. Chem. Int. Ed., Jun. 2017, 56(26):7634-7638.

Park et al., "PTK6 inhibition promotes apoptosis of Lapatinib-resistant Her2$^+$breast cancer cells by inducing Bim," Breast Cancer Res, 2015, 17:86.
Patel et al., "A conserved arginine-containing motif crucial for the assembly and enzymatic activity of the mixed lineage leukemia protein-I core complex," The Journal of Biological Chemistry, Nov. 2008, 283(47):32162-32175.
Patel et al., "Recent updates on third generation EGFR inhibitors and emergence of fourth generation EGFR inhibitors to combat C797S resistance," Eur. J. Med. Chem., Dec. 2017, 142:32-47.
Patel et al., "Structure of WDR5 bound to mixed lineage leukemia protein-I peptide," The Journal of Biological Chemistry, Nov. 2008, 283(47):32158-32161.
PCT International Preliminary Report on Patentability in International Appln No. PCT/US2018/063847, dated Jun. 18, 2020, 8 pages.
PCT International Preliminary Report on Patentability in International Appln. No. PCT/US2019/019123, dated Aug. 27, 2020, 10 pages.
PCT International Preliminary Report on Patentability in International Appln. No. PCT/US2019/038560, dated Dec. 30, 2020, 9 pages.
PCT International Preliminary Report on Patentability in International Appln. No. PCT/US2019/040507, dated Jan. 5, 2021, 7 pages.
PCT International Preliminary Report on Patentability in International Appln. No. PCT/US2020/031527, dated Nov. 2, 2021, 8 pages.
PCT International Search Report and Written Opinion in International Appln. No. PCT/US2017/058718, dated Jan. 28, 2018, 8 pages.
PCT International Search Report and Written Opinion in International Appln. No. PCT/US2017/065027, dated Mar. 6, 2018, 8 pages.
PCT International Search Report and Written Opinion in International Appln. No. PCT/US2018/063847, dated Mar. 27, 2019, 11 pages.
PCT International Search Report and Written Opinion in International Appln. No. PCT/US2019/019123, dated Jun. 20, 2019, 15 pages.
PCT International Search Report and Written Opinion in International Appln. No. PCT/US2019/021014, dated Jun. 27, 2019, 11 pages.
PCT International Search Report and Written Opinion in International Appln. No. PCT/US2019/038560, dated Oct. 10, 2019, 12 pages.
PCT International Search Report and Written Opinion in International Appln. No. PCT/US2019/040507, dated Nov. 12, 2019, 10 pages.
PCT International Search Report and Written Opinion in International Appln. No. PCT/US2020/031527, dated Sep. 14, 2020, 11 pages.
PCT International Search Report and Written Opinion in International Appln. No. PCT/US2021/055574, dated Feb. 25, 2022, 11 pages.
PCT International Search Report and Written Opinion in International Appln. No. PCT/US2022/013225, dated Jun. 6, 2022, 24 pages.
PCT Invitation to Pay Additional Fees in International Appln. No. PCT/US2019/019123, dated Apr. 8, 2019, 3 pages.
PCT Invitation to Pay Additional Fees in International Appln. No. PCT/US2019/021014, dated Apr. 22, 2019, 2 pages.
PCT Invitation to Pay Additional Fees in International Appln. No. PCT/US2019/038560, dated Aug. 14, 2019, 2 pages.
PCT Invitation to Pay Additional Fees in International Appln. No. PCT/US2021/055574, dated Dec. 22, 2021, 2 pages.
Pellegrino et al., "EEF1A2 inactivates p53 by way of PI3K/AKT/mTOR-dependent stabilization of MDM4 in hepatocellular carcinoma," Hepatology, May 2014, 59(5):1886-1899.
Peng et al., "Protein tyrosine kinase 6 promotes ERBB2-induced mammary gland tumorigenesis in the mouse," Cell Death Dis., 2015, 6:e1848.

(56) References Cited

OTHER PUBLICATIONS

Perlman et al., "*MLLT1* Yeats domain mutations in clinically distinctive Favourable Histology Wilms tumours," Nat. Commun., Dec. 2015, 6:10013, 10 pages.
Peters et al., "Alectinib versus Crizotinib in Untreated ALK Positive Non-Small-Cell Lung Cancer," New England Journal of Medicine, Aug. 31, 2017, 377(9):829-838.
Pettersson et al., "PROteolysis TArgeting Chimeras (Protacs)—past, present and future," Drug Discov. Today Technol., Apr. 2019, 31:15-27.
Pieters et al., "A treatment protocol for infants younger than 1 year with acute lymphoblastic leukaemia (Interfant-99): an observational study and a multicentre randomised trial," Lancet, Jul. 2007, 370:240-250.
Prabhu et al., "Adapting AlphaLISA high throughput screen to discover a novel small-molecule inhibitor targeting protein arginine methyltransferase 5 in pancreatic and colorectal cancers," Oncotarget, May 2017, 8(25):39963-39977.
Prêtre et al., "Inhibition of Akt and other AGC kinases: A target for clinical cancer therapy?," Accepted Manuscript, Seminars in Cancer Biology, 2018, 48:70-77.
PubChem-CID-44631912, NIH, National Center for Biotechnology Information, Create Date: Mar. 8, 2010, 30 pages.
Pui et al., "Treating Childhood Acute Lymphoblastic Leukemia without Cranial Irradiation," N. Engl. J. Med., Jun. 2009, 360(26):2730-2741.
Pulford et al., "Detection of anaplastic lymphoma kinase (ALK) and nucleolar protein nucleophosmin (NPM)-ALK proteins in normal and neoplastic cells with the monoclonal antibody ALK1," Blood, Feb. 15, 1997, 89(4):1394-1404.
Qi et al., "Selective inhibition of Ezh2 by a small molecule inhibitor blocks tumor cells proliferation," Proc. Natl. Acad. Sci. USA, 2012, 109(52):21360-21365.
Quentmeier et al., "EZH2 Y641 mutations in follicular lymphoma," Leukemia, 2011, 25(4):726-729.
Raina et al., "Protacinduced BET protein degradation as a therapy for castration-resistant prostate cancer," Proceedings of the National Academy of Sciences of the United States of America, Jun. 2016, 113(26):7124-7129.
Rao et al., "Hijacked in cancer: the KMT2 (MLL) family of methyltransferases," Nat. Rev. Cancer, Jun. 2015, 15:334-346.
Ren et al., "PHF19 promotes multiple myeloma tumorigenicity through PRC2 activation and broad H3K27me3 domain formation," Blood, 2019, 134:1176-1189.
Ren et al., "Polycomb protein EZH2 regulates tumor invasion via the transcriptional repression of the metastasis suppressor RKIP in breast and prostate cancer," Cancer Res., 2012, 72(12):3091-3104.
Ribas et al., "Cancer immunotherapy using checkpoint blockade," Science (New York, NY), Mar. 2018, 359(6382):1350-1355.
Rikova et al., "Global survey of phosphotyrosine signaling identifies oncogenic kinases in lung cancer," Cell, Dec. 14, 2007, 131(6):1190-1203.
Ritchie et al., "*limma* powers differential expression analyses for RNA-sequencing and microarray studies," Nucleic Acids Res., 2015, 43(7):e47.
Rodrik-Outmezguine et al., "Overcoming mTOR resistance mutations with a new-generation mTOR inhibitor," Nature, Jun. 2016, 534:272-276.
Roguev et al., "The *Saccharomyces cerevisiae* Set1 complex includes an ash2 homologue and methylates histone 3 lysine, " The EMBO journal, Dec. 2001, 20(24):7137-7148.
Rosati et al., "*NUP98* is fused to the NSD3 gene in acute myeloid leukemia associated with t(8;11)(p11.2;p15)," Blood, 2002, 99:3857-3860.
Sakamoto et al., "Protacs: chimeric molecules that target proteins to the Skp1-Cullin-F box complex for ubiquitination and degradation," Proc. Natl. Acad. Sci. USA, Jul. 2001, 98(15):8554-8559.
Salami et al., "Waste disposal—An attractive strategy for cancer therapy," Science, Mar. 2017, 355:1163-1167.

Saura et al., "A first-in-human phase I study of the ATP-competitive AKT inhibitor ipatasertib demonstrates robust and safe targeting of AKT in patients with solid tumors," Cancer Discovery, Jan. 2017, 7(1):102-113.
Sauvageau et al., "Poly comb group proteins: multi-faceted regulators of somatic stem cells and cancer," Cell Stem Cell., 2010, 7(3):299-313.
Sawasdikosol et al., "Hematopoietic progenitor kinase 1 (HPK1) regulates prostaglandin E2-induced fos gene transcription," Blood, May 2003, 101(9):3687-3689.
Sawasdikosol et al., "HPK1 as a novel target for cancer immunotherapy," Immunologic Research, Dec. 2012, 54(1-3):262-265.
Sawasdikosol et al., "Prostaglandin E2 activates HPK 1 kinase activity via a PKA-dependent pathway," The Journal of biological chemistry, Nov. 2007, 282(48):34693-34699.
Schapira et al., "Targeted protein degradation: expanding the toolbox," Nat. Rev. Drug Discov., Dec. 2019, 18(12):949-963.
Schmandt et al., "The BRK tyrosine kinase is expressed in highgrade serous carcinoma of the ovary," Cancer Biol. Ther., 2006, 5:1136-1141.
Schneider et al. "Characterization of EBV-genome negative 'null ' and 'T' cell lines derived from children with acute lymphoblastic leukemia and leukemic transformed non-Hodgkin lymphoma," International Journal of Cancer, May 1977, 19(5): 621-626.
Schramm et al., "Novel BQCA- and TBPB-derived M1 receptor hybrid ligands: orthosteric carbachol differentially regulates partial agonism," ChemMedChem, Jul. 2019, 14(14):1349-1358.
Senisterra et al., "Small-molecule inhibition of MLL activity by disruption of its interaction with WDR5," Biochemical Journal, Jan. 2013, 449(1):151-159.
Seshacharyulu et al., "Targeting the EGFR signaling pathway in cancer therapy," Expert Opin. Ther. Targets, Jan. 2012, 16:15-31.
Shanle et al., "Association of Taf14 with acetylated histone H3 directs gene transcription and the DNA damage response," Genes Dev., 2015, 29:1795-1800.
Sharma et al., "Epidermal growth factor receptor mutations in lung cancer," Nat. Rev. Cancer, Mar. 2007, 7:169-181.
Shaw et al., "Ceritinib in *ALK*-rearranged non-small-cell lung cancer," New England Journal of Medicine, Mar. 27, 2014, 370(13):1189-1197.
Shen et al., "Identification of LEM-14 inhibitor of the oncoprotein NSD2," Biochem Biophys. Res. Commun., Jan. 2019, 508(1):102-108.
Shen et al., "NSD3-Short is an Adaptor Protein that Couples BRD4 to the CHD8 Chromatin Remodeler," Mol. Cell., Dec. 2015, 60(6):847-859.
Shen et al., "Structure-based design of 5-methylpyrimidopyridone derivatives as new wild-type sparing inhibitors of the epidermal growth factor receptor triple mutant (EGFR$^{L858R/T790M/C797S}$), " J. Med Chem., Jul. 2019, 62:7302-7308.
Sherr et al., "Targeting CDK4 and CDK6: from discovery to therapy," Cancer Discovery, 2016, 6(4):353-367.
Shibata et al., "Development of protein degradation inducers of oncogenic BCR-ABL protein by conjugation of ABL kinase inhibitors and IAP ligands," Cancer Science, Aug. 2017, 108(8):1657-1666.
Shimizu et al., "The protein arginine methyltransferase 5 promotes malignant phenotype of hepatocellular carcinoma cells and is associated with adverse patient outcomes after curative hepatectomy," International Journal of Oncology, Jan. 2017, 50(2):381-386.
Shiota et al., "Hyperphosphorylation of a novel 80 kDa proteintyrosine kinase similar to Ltk in a human 40 Ki-1 lymphoma cell line, AMS3," Oncogene, Jun. 1994, 9(6):1567-1574.
Shui et al., "Hematopoietic progenitor kinase 1 negatively regulates T-cell receptor signaling and T cell-mediated immune responses," Nature Immunology, Jan. 2007, 8(1):84-91.
Slany, "When epigenetics kills: MLL fusion proteins in leukemia," Hematol. Oncol., Mar. 2005, 23:1-9.
Sneeringer et al., "Coordinated activities of wild-type plus mutant EZH2 drive tumor-associated hypertrimethylation of lysine 27 on histone H3 (H3K27) in human B-cell lymphomas," Proc. Natl. Acad. Sci. USA, Dec. 7, 2010, 107(49): 20980-20985.

(56) References Cited

OTHER PUBLICATIONS

Soda et al., "Identification of the transforming EML4-ALK fusion gene in non-small-cell lung cancer," Nature, Aug. 2, 2007,448:561-566.

Solomon et al., "First-line crizotinib versus chemotherapy in *ALK*-positive lung cancer," New England Journal of Medicine, Dec. 4, 2014, 371(23):2167-2177.

Song et al., "Selective inhibition of EZH2 by ZLD1039 blocks H3K27methylation and leads to potent anti-tumor activity in breast cancer," Sci. Rep., 2016, 6:20864.

Song et al., "WDR5 interacts with mixed lineage leukemia (MLL) protein via the histone HJ-binding pocket," The Journal of Biological Chemistry, Dec. 2008, 283(50):35258-35264.

Soucy et al., "An inhibitor of NEDD8-activating enzyme as a new approach to treat cancer," Nature, Apr. 2009, 458:732-736.

Subramanian et al., "Gene set enrichment analysis: a knowledge-based approach for interpreting genome-wide expression profiles," Proc. Natl. Acad. Sci. USA, Sep. 2005, 102(43):15545-15550.

Suda et al., "The structure of bestatin," The Journal of Antibiotic, Jan. 1976, 29(1):100-101.

Sun et al., "Discovery of AMG 232, a potent, selective, and orally bioavailable MDM2-p53 inhibitor in clinical development," Journal of Medicinal Chemistry, Feb. 2014, 57(4):1454-1472.

Sun et al., "Protac-induced BTK degradation as a novel therapy for mutated Btk C481S induced ibrutinib-resistant B-cell malignancies," Cell Research, Jul. 2018, 28(7):779-781.

Sun et al., "Up-regulated WDR5 promotes gastric cancer formation by induced cyclin DI expression," Journal of Cellular Biochemistry, Apr. 2018, 119(4): 28 pages.

Sun et al., "WDR5 supports an N-Myc transcriptional complex that drives a protumorigenic gene expression signature in neuroblastoma," Cancer Research, Dec. 2015 75(23):5143-5154.

Tahirovic et al., "Discovery of *N-alkyl* piperazine side chain based CXCR4 antagonists with improved drug-like properties," ACS Med. Chem. Lett., May 2018, 9(5):446-451.

Takeuchi et al., "KIF5B-ALK, a novel fusion oncokinase identified by an immunohistochemistry-based diagnostic system for ALK-positive lung cancer," Clinical Cancer Research, May 1, 2009, 15(9):3143-3149.

Tan et al., "A kinase-independent role for EGF receptor in autophagy initiation," Cell, Jan. 2015, 160(1-2):145-160.

Tan et al., "Next-generation epidermal growth factor receptor tyrosine kinase inhibitors in epidermal growth factor receptor-mutant non-small cell lung cancer," Lung Cancer, Mar. 2016, 93:59-68.

Tan et al., "PBK/AKT-mediated upregulation of WDR5 promotes colorectal cancer metastasis by directly targeting ZNF407," Cell Death and Disease, Mar. 2017, 8(3): 12 pages.

Taniguchi et al., "Silencing of Kruppel-like factor 2 by the histone methyltransferase EZH2 in human cancer," Oncogene, 2012, 31(15):1988-1994.

Tarighat et al., "The dual epigenetic role of PRMT5 in acute myeloid leukemia: gene activation and repression via histone arginine methylation," Leukemia, Nov. 2016, 30:789-799.

Thomas et al., "Interaction with WDR5 promotes target gene recognition and tumorigenesis by MYC," Molecular Cell, May 2015, 58(3):440-452.

Thomas et al., "The MYC-WDR5 nexus and cancer," Cancer Research, Oct. 2015, 75(19):4012-4015.

Thress et al., "Acquired *EGFR* C797S mutation mediates resistance to AZD9291 in non-small cell lung cancer harboring *EGFR* T790M," Nat. Med., May 2015, 21:560-562.

Toure et al., "Small-Molecule Protacs: New Approaches to Protein Degradation," Angewandte Chemie-International Edition, Feb. 2016, 55(6):1966-1973.

Trievel et al., "WDR5, a complexed protein," Nature Structural & Molecular Biology, Jul. 2009, 16(7):678-680.

Turner et al., "Palbociclib in hormone-receptor-positive advanced breast cancer," New England Journal of Medicine, 2015, 373(3):209-219.

Turner-Ivey et al., "Development of mammary hyperplasia, dysplasia, and invasive ductal carcinoma in transgenic mice expressing the 8p11 amplicon oncogene NSD3," Breast Cancer Res. Treat., Jul. 2017, 164(2):349-358.

Varambally et al., "The polycomb group protein EZH2 is involved in progression of prostate cancer," Nature, 2002, 419(6907):624-629.

Varfolomeev et al., "IAP antagonists induce autoubiquitination of c-IAPs, NF-κB activation, and TNFα-dependent apoptosis," Cell, Nov. 2007, 131(4):669-681.

Vassilev et al., "In vivo activation of the p53 pathway by small-molecule antagonists of MDM2," Science, Feb. 2004, 303(5659):844-848.

Verma et al., "Identification of Potent, Selective, Cell-Active Inhibitors of the Histone Lysine Methyltransferase EZH2," ACS Med. Chem. Lett., 2012, 3(12):1091-1096.

Vivanco et al., "A kinase-independent function of AKT promotes cancer cell survival," eLIFE, 2014, 3:e03751.

Vu et al., "Discovery of RG7112: a small-molecule MDM2 inhibitor in clinical development," ACS Medicinal Chemistry Letters, May 2013, 4(5):466-469.

Wakeling, "Use of pure antioestrogens to elucidate the mode of action of oestrogens," Biochemical Pharmacology, May 1995, 49(11):1545-1549.

Wan et al., "ENL links histone acetylation to oncogenic gene expression in acute myeloid leukaemia," Nature, Mar. 2017, 543:265-269.

Wan et al., "Impaired cell fate through gain-of-function mutations in a chromatin reader," Nature, Jan. 2020, 577:121-126.

Wang et al., "EAI045: The fourth-generation EGFR inhibitor overcoming T790M and C797S resistance," Cancer Lett., Jan. 2017, 385:51-54.

Wang et al., "MapSplice: accurate mapping of RNA-seq reads for splice junction discovery," Nucleic Acids Res., 2010, 38:e178.

Wang et al., "NUP98-NSD1 links H3K36 methylation to Hox-A gene activation and leukaemogenesis," Nat. Cell. Biol., Jul. 2007, 9(7):804-812.

Wang et al., "Polycomb genes, miRNA, and their deregulation in B-cell malignancies," Blood, 2015, 125(8):1217-1225.

Wei et al., "Protein arginine methylation of non-histone proteins and its role in diseases," Cell Cycle, 2014, 13(1):32-41.

Weisberg et al., "Smac mimetics: implications for enhancement of targeted therapies in leukemia," Leukemia, Dec. 2010, 24:2100-2109.

Weiss et al., "Anaplastic lymphoma kinase and leukocyte tyrosine kinase: functions and genetic interactions in learning, memory and adult neurogenesis," Pharmacology, Biochemistry and Behavior, Jan. 2012, 100(3):566-574.

Weiss et al., "The role of T3 surface molecules in the activation of human T cells: a two-stimulus requirement for IL 2 production reflects events occurring at a pre-translational level," Journal of Immunology, Aug. 1984, 133(1):123-128.

Wieduwilt et al., "The epidermal growth factor receptor family: biology driving targeted therapeutics," Cell. Mol. Life Sci., May 2008, 65(10):1566-1584.

Winter et al., "Phthalimide conjugation as a strategy for in vivo target protein degradation," Science, May 2015, 348(6241):1376-1381.

Wood et al., "Lack of the t(2;5) or other mutations resulting in expression of anaplastic lymphoma kinase catalytic domain in CD30+primary cutaneous lymphoproliferative disorders and Hodgkin's disease," Blood, Sep. 1, 1996, 88(5):1765-1770.

Wu et al., "Overexpression of WD repeat domain 5 associates with aggressive clinicopathological features and unfavorable prognosis in head neck squamous cell carcinoma," International Association of Oral Pathologists and the American Academy of Oral Pathology, Apr. 2018, 47(5): 27 pages.

Xie et al., "Pharmacological targeting of the pseudokinase Her3," Nature Chemical Biology, Dec. 2014, 10(12):1006-1012.

Xie et al., "WDR5 positively regulates p53 stability by inhibiting p53 ubiquitination," Biochemical and Biophysical Research Communications, May 2017, 487(2):333-338.

(56) References Cited

OTHER PUBLICATIONS

Xu et al., "eEF1A2 promotes cell migration, invasion and metastasis in pancreatic cancer by upregulating MMP-9 expression through Akt activation," Clin. Exp. Metastasis, May 2013, 30(7):933-944.
Xu et al., "Selective inhibition of EZH2 and EZH1 enzymatic activity by a small molecule suppresses *MLL*-rearranged leukemia," Blood, Jan. 2015, 125:346-357.
Xu et al., "Targeting EZH2 and PRC2 dependence as novel anti-cancer therapy," Exp. Hematol., 2015, 43(8):698-712.
Yang et al., "Structure-Activity Relationship Studies for Enhancer of Zeste Homologue 2 (EZH2) and Enhancer of Zeste Homologue 1 (EZH1) Inhibitors," J. Med. Chem., 2016, 59(16):7617-7633.
Yokoyama et al., "A Higher-Order Complex Containing AF4 and ENL Family Proteins with P-TEFb Facilitates Oncogenic and Physiologic MLL-Dependent Transcription," Cancer Cell, Feb. 2010, 17(2):198-212.
You et al., "Discovery of an AKT degrader with prolonged inhibition of downstream signaling," Cell Chemical Biology, 2020, 27(1):66-73.
Yu et al., "Altered *Hox* Expression and Segmental Identity in *Mll*-Mutant Mice," Nature, Nov. 1995, 378:505-508.
Yu et al., "Requirement for CDK4 kinase function in breast cancer," Cancer Cell, 2006, 9(1):23-32.
Yu et al., "Targeting AKT1-E17K and the PI3K/AKT pathway with an allosteric AKT inhibitor, ARQ 092," PLOS One, Oct. 2015, 10(10):e0140479.
Yun et al., "The T790M mutation in EGFR kinase causes drug resistance by increasing the affinity for ATP," Proc. Natl. Acad. Sci. USA, Feb. 2008, 105(6):2070-2075.
Zeng et al., "Discovery of novel imidazo[1,2-a]pyrazin-8-amines as Brk/PTK6 inhibitors," Bioorg. Med. Chem. Lett., Oct. 2011, 21(19):5870-5875.
Zengerle et al., "Selective Small Molecule Induced Degradation of the BET Bromodomain Protein BRD4," ACS Chemical Biology, Jun. 2015, 10(8):1770-1777.
Zhang et al., "Proteolysis targeting chimeras (Protacs) of anaplastic lymphoma linase (ALK)," Eur. J. Med. Chem., May 2018, 151:304-314.
Zhang et al., "Structural Insights into Histone Crotonyl-Lysine Recognition by the AF9 Yeats Domain," Structure, Sep. 2016, 24(9):1606-1612.
Zhao et al., "Protacs suppression of CDK4/6, crucial kinases for cell cycle regulation in cancer," Chem. Commun. (Camb)., 2019, 55:2704-2707.
Zhao et al., "The language of chromatin modification in human cancers," Nat. Rev. Cancer, Jul. 2021, 21:413-430.
Zheng et al., "PTK6 activation at the membrane regulates epithelial-mesenchymal transition in prostate cancer," Cancer Res., Sep. 2013, 73(17):5426-5437.
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry, 2018, 61(2):462-481.
Zuber et al., "RNAi screen identifies Brd4 as a therapeutic target in acute myeloid leukaemia," Nature, 2011, 478:524-528.
U.S. Appl. No. 16/345,591, filed Apr. 26, 2019, Jian Jin.
U.S. Appl. No. 16/926,418, filed Jul. 10, 2020, Jian Jin.
U.S. Appl. No. 16/467,888, filed Jun. 7, 2019, Jian Jin.
U.S. Appl. No. 17/453,619, filed Nov. 4, 2021, Jian Jin.
U.S. Appl. No. 16/769,326, filed Jun. 3, 2020, Jian Jin.
U.S. Appl. No. 16/970,305, filed Aug. 14, 2020, Jian Jin.
U.S. Appl. No. 16/977,654, filed Sep. 2, 2020, Jian Jin.
U.S. Appl. No. 17/938,502, filed Oct. 6, 2022, Jian Jin.
U.S. Appl. No. 17/256,516, filed Dec. 28, 2020, Jian Jin.
U.S. Appl. No. 17/254,345, filed Dec. 21, 2020, Jian Jin.
U.S. Appl. No. 17/604,636, filed Oct. 18, 2021, Jian Jin.
U.S. Appl. No. 17/336,059, filed Jun. 1, 2021, Jian Jin.
Ishoey et al., "Translation Termination Factor GSPT1 is a Phenotypically Relevant Off-Target of Heterobifunctional Phthalimide Degraders," ACS Chemical Biology, Jan. 22, 2018, 13(3):553-560.
Office Action in Chinese Appln. No. 202080049386.9, mailed on Feb. 2, 2024, 23 pages (with Machine translation).
Herrera-Montavez et al., "MEK1/2-Targeting Protacs Promote the Collateral Degradation of CRAF in KRAS Mutant Cells," bioRxiv, Jun. 2023, retrieved from URL<https://doi.org/10.1101/2023.06.15.545136]>, 28 pages.
Karaman et al., "A quantitative analysis of kinase inhibitor selectivity," Nature biotechnology, Jan. 2008, 26(1):127-132.
Office Action in Australian Appln. No. 2019288740, mailed on Jun. 13, 2024, 4 pages.
Office Action in Japanese Appln. No. 2021-565854, mailed on May 7, 2024, 6 pages (with English translation).
Office Action in European Appln. No. 17877800.7, mailed Mar. 6, 2024, 6 pages.
International Preliminary Report on Patentability Chapter II in International Appln. No. PCT/US2022/050929, mailed on Jun. 21, 2024, 6 pages.

MDA-MB-468, 2 days

MDA-MB-468, 2 days

HCC1187

COMPOSITIONS AND METHODS FOR TREATING EZH2-MEDIATED CANCER

CROSS-REFERENCE TO RELATED APPLICATIONS

This application is a division of U.S. application Ser. No. 16/926,418, filed Jul. 10, 2020, which is a continuation of U.S. application Ser. No. 16/345,591, having a 371 completion date of Apr. 26, 2019, which is a U.S. National Stage application, and claims priority of International Application No. PCT/US2017/058718, filed Oct. 27, 2017, which claims priority of U.S. Provisional Application No. 62/414,195, filed Oct. 28, 2016. The contents of all of the prior applications are incorporated herein by reference in their entirety.

TECHNICAL FIELD

This disclosure relates to compositions and methods for administering one or more bivalent compounds which selectively degrade/disrupt enhancer of zeste homologue 2 (EZH2) to a subject for the treatment of EZH2-mediated cancer, and to methods for designing such degraders/disruptors.

BACKGROUND OF THE INVENTION

EZH2 (enhancer of zeste homolog 2) is the main catalytic subunit of the polycomb repressive complex 2 (PRC2) that catalyzes methylation of histone H3 lysine 27 (H3K27) (Cao et al., 2002: Czermin et al., 2002; Kuzmichev et al., 2002; Muller et al., 2002). The trimethylation of H3K27 (H3K27me3) is a transcriptionally repressive epigenetic mark that regulates gene expression, differentiation, and development. Dysregulation of EZH2, other PRC2 components (e.g., EED and SUZ12), and/or H3K27 trimethylation have been associated with a number of cancers. For example, EZH2 is overexpressed in a broad spectrum of cancers, including prostate cancer, breast cancer, myeloma, and lymphoma. High EZH2 expression correlates with poor prognosis (Bachmann et al., 2006; Bodor et al., 2011; Bracken et al., 2003; Kim and Roberts, 2016; Kleer et al., 2003; Morin et al., 2010; Sauvageau and Sauvageau, 2010: Varambally et al., 2002). Hyper-trimethylation of H3K27 catalyzed by PRC2 drives tumorigenesis and progression of cancers including diffused large B cell lymphoma (DLBCL) and malignant rhabdoid tumor (MRT) (Majer et al., 2012; McCabe et al., 2012a: Sneeringer et al., 2010). Thus, pharmacological inhibition of EZH2 has been pursued as a targeted therapy for treating these cancers. In fact, EZH2 inhibitors, which effectively inhibit the methyltransferase activity of EZH2, display robust antiproliferative activity in DLBCL and MRT cellular and animal models (Kaniskan et al., 2017: Wang et al., 2015; Xu et al., 2015). A number of EZH2 inhibitors including UNC1999, an orally bioavailable inhibitor developed by the inventors of the present application, have been reported (Bradley et al., 2014; Brooun et al., 2016; Campbell et al., 2015; Gao et al., 2016; Garapaty-Rao et al., 2013: Gehling et al., 2015; Kaniskan et al., 2017; Knutson et al., 2013; Knutson et al., 2012: Konze et al., 2013; Kung et al., 2016; McCabe et al., 2012b; Qi et al., 2012: Song et al., 2016; Verma et al., 2012: Yang et al., 2016). Among them, EPZ-6438, GSK126, CPI-1205, and PF-06821497 have entered Phase I/II clinical trials for the treatment of several subtypes of lymphoma and MRT.

Breast cancer (BC) has the highest incidence rate (43.3/100,000) and is one of the leading causes of cancer death among women (14.9%) in North America (Stewart and Wild, 2014). Triple-negative breast cancer (TNBC), a subtype of BC that lacks estrogen receptor (ER), progesterone receptor (PR), and human epidermal growth factor receptor 2 (HER2), represents ~12-20% of all BCs. TNBC has poor prognosis, high recurrence, and a low survival rate (Lin et al., 2012). Currently, there are no effective therapies for treating a substantial portion of TNBC patients, highlighting an unmet medical need (Gluz et al., 2009).

Overexpression of EZH2 has been identified as a major driver for breast cancer development and progression (Bachmann et al., 2006; Bracken et al., 2003: Chang et al., 2011: Holm et al., 2012: Fujii et al., 2011: Gonzalez et al., 2014; Kleer et al., 2003; Mahara et al., 2016). It has been shown that EZH2 downregulates the tumor and metastasis suppressor RKIP (Raf-1 kinase inhibitor protein) (Ren et al., 2012), tumor suppressor KLF2 (Kruppel-like factor) (Taniguchi et al., 2012), forkhead box transcription factor FOXC1 (Du et al., 2012), and tumor suppressor RUNX3 (Runt-related transcription factor 3) (Fujii et al., 2008). Knockdown of EZH2 via RNA interference blocks proliferation of breast cancer cells (Fujii et al., 2008; Gonzalez et al., 2008). However, current EZH2 inhibitors, which do not affect EZH2 protein levels, are ineffective at inhibiting growth of breast cancer cells with EZH2 overexpression even though they effectively inhibit the enzymatic activity of EZH2. Therefore, overexpression of EZH2, but not the catalytic activity of EZH2/PRC2, is critical for breast cancer progression.

SUMMARY

The present disclosure relates generally to bivalent compounds which selectively degrade/disrupt EZH2 ("EZH2 degraders/disruptors"), and to methods for the treatment of EZH2-mediated cancers, which include, but are not limited to, cancers that overexpress EZH2 relative to wild-type tissues of the same species and tissue types, with the EZH2 degraders/disruptors. Without wishing to be bound by theory, because the EZH2 degraders/disruptors disclosed herein have dual functions (enzyme inhibition plus protein degradation/disruption), the bivalent compounds disclosed/claimed here can be significantly more effective therapeutic agents than current EZH2 inhibitors, which inhibit the enzymatic activity of EZH2 but do not affect EZH2 protein levels. The present disclosure further provides methods for identifying EZH2 degraders/disruptors as described herein.

More specifically, the document provides a bivalent compound including an EZH2 ligand conjugated to a degradation/disruption tag. The EZH2 ligand can be an EZH2 inhibitor. The EZH2 ligand can, for example, include UNC1999, EPZ005687, EPZ-6438, GSK126, EI1, CPI-1205, GSK343, CPI-360, EPZ011989, N-((4,6-dimethyl-2-oxo-1,2-dihydropyridin-3-yl)methyl)-1-isopropyl-6-(6-(4-isopropylpiperazin-1-yl) pyridin-3-yl)-1H-indazole-4-carboxamide ("compound 24") (see, e.g., Yang et al., 2016), 3-chloro-4-(2-cyano-3-(pyridazin-4-yl)phenoxy)-N-(2,2,6,6-tetramethylpiperidin-4-yl)benzamide ("compound 3") (see, e.g., Garapaty-Rao et al., 2013), 5,8-dichloro-2-((4,6-dimethyl-2-oxo-1,2-dihydropyridin-3-yl)methyl)-7-(3,5-dimethylisoxazol-4-yl)-3,4-dihydroisoquinolin-1(2H)-one ("compound 31") (see, e.g., Kung et al., 2016), ZLD1039, PF-06821497, and JQEZ5, and analogs thereof. The degradation/disruption tag can bind to a ubiquitin ligase (e.g., an E3 ligase such as a cereblon E3 ligase or a VHL E3 ligase) and/or mimic EZH2 protein misfolding. The degradation/disruption tag can include a bulky and/or hydrophobic group. The degradation/disruption tag can, for example, include adamantane, 1-((4,4,5,5,5-pentafluoropentyl) sulfinyl) nonane, pomalidomide, thalidomide, lenalidomide, VHL-1, and analogs thereof.

In any of the above-described bivalent compounds, an EZH2 ligand can be conjugated to a degradation/disruption tag through a linker. The linker can, for example, include an acyclic or cyclic saturated or unsaturated carbon, ethylene glycol, amide, amino, ether, or carbonyl containing group. The linker can, for example, include one or more of Formulas I-XIV:

Formula I
m = 0-15
n = 0-15

Formula II
m = 0-15
n = 0-15

Formula III
n = 0-15

Formula IV
m = 0-15
n = 0-15

Formula V
n = 0-15

Formula VI
n = 0-15

Formula VII
n = 0-15

Formula VIII
n = 0-15

Formula IX
n = 0-15

Formula X
X = O, NR
R = H, $C_{1-6}$ alkyl
m = 0-15
n = 0-15

Formula XI
R = H, $C_{1-6}$ alkyl
m = 0-15
n = 0-15
* R, S and racemic

Formula XII
X = O or $H_2$
Y = O or $H_2$
n = 0-15

Formula XIII
X = O or $H_2$
Y = O or $H_2$
m = 0-15
n = 0-6
o = 0-15

Formula XIV
X = O or $H_2$
Y = O or $H_2$
m = 0-15
n = 0-15

R is independently —$CH_2$—; —$CF_2$—; —CH($C_{1-3}$ alkyl)-; —C($C_{1-3}$ alkyl) ($C_{1-3}$ alkyl)-; —CH=CH—; —C($C_{1-3}$ alkyl)=C($C_{1-3}$ alkyl)-; —C≡C—; —O—; —NH—; —N($C_{1-3}$ alkyl)-; —C(O)NH—; —C(O)N($C_{1-3}$ alkyl)-;

3-13 membered rings, fused rings, bridged rings, or spiro rings with or without heteroatoms (—NH—, —N($C_{1-3}$ alkyl)-, O).

A few examples of R group:

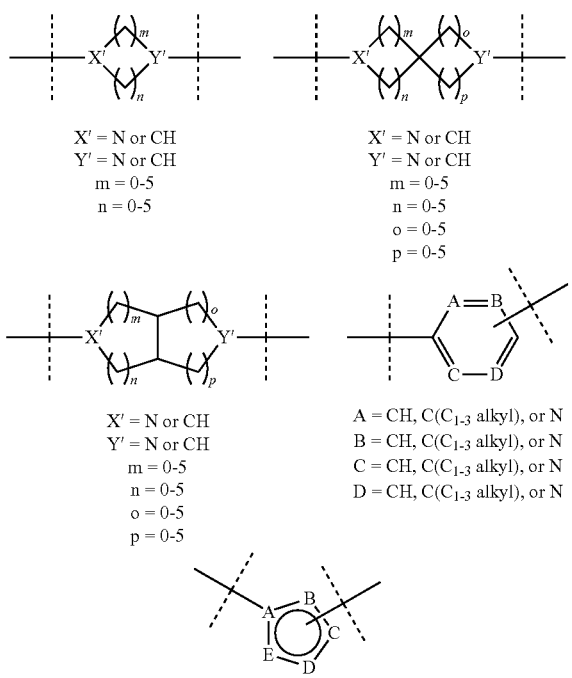

X' = N or CH
Y' = N or CH
m = 0-5
n = 0-5

X' = N or CH
Y' = N or CH
m = 0-5
n = 0-5
o = 0-5
p = 0-5

X' = N or CH
Y' = N or CH
m = 0-5
n = 0-5
o = 0-5
p = 0-5

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S Any of the above-described bivalent compounds can include, for example, AM16-10A, AM16-11A, AM16-37A, AM16-38A, XY019-43, XY019-44, XY019-079, XY019-080, AM16-91A, AM16-92A, AM16-93A, AM16-97A, AM16-100A, AM16-101A, AM16-102A, AM16-105A, AM16-106A, XY012-120, AM29-21A, AM29-22A, AM29-32A, AM29-33A, AM16-103A, AM29-182A, AM29-55A, AM29-151A, AM29-152A, AM29-137A, AM29-153A, AM29-138A, AM29-154A, AM29-139A, AM29-155A, AM29-170A, AM29-156A, AM29-171A, AM29-157A, AM29-172A, AM29-173A, AM16-79A, AM29-177A, AM29-141A, AM29-178A, AM29-142A, AM29-179A, AM29-143A, AM29-180A, AM29-144A, AM29-145A, AM29-181A, AM41-16A, AM41-17A, AM41-18A, XY012-157, XF034-164A, XF034-165A, XF034-166A, XF034-167A, XF034-168A, XY019-041, XF034-169A, XF034-170A, XF034-171A, CZ40-10, CZ40-09, CZ40-11, XY019-077, XY019-083, XY019-084, XF034-172A, XF034-173A, XF034-174A, XF034-175A, XF034-176A, XF034-177A, YS36-48, YS36-49, YS36-50, YS36-51, YS36-52, YS36-53, YS36-54, YS36-55, YS36-56, YS36-57, YS36-58, YS36-59, XY028-086, CZ40-72, CZ40-73, CZ40-75, CZ40)-149, CZ40-74, CZ40)-131. AM41-36A, AM41-37A. AM41-39A, AM41-41A, AM41-38A. AM41-40A, XF042-84, XF042-85, XF042-95, XF042-132, XF042-86, XF042-94, XF042-89. XF042-90, XF042-93, XF042-133, XF042-91, and XF042-92.

Another aspect of the document is a bivalent compound, which can include, for example, AM16-10A, AM16-11A, AM16-37A, AM16-38A, XY019-43, XY019-44, XY019-079, XY019-080, AM16-91A, AM16-92A, AM16-93A, AM16-97A, AM16-100A, AM16-101A, AM16-102A, AM16-105A, AM16-106A, XY012-120, AM29-21A, AM29-22A. AM29-32A, AM29-33A, AM16-103A, AM29-182A, AM29-55A, AM29-151A, AM29-152A, AM29-137A. AM29-153A. AM29-138A, AM29-154A, AM29-139A. AM29-155A. AM29-170A, AM29-156A, AM29-171A, AM29-157A, AM29-172A, AM29-173A, AM16-79A. AM29-177A, AM29-141A, AM29-178A, AM29-142A, AM29-179A, AM29-143A, AM29-180A, AM29-144A, AM29-145A, AM29-181A, AM41-16A. AM41-17A. AM41-18A, XY012-157, XF034-164A, XF034-165A. XF034-166A. XF034-167A. XF034-168A, XY019-041, XF034-169A, XF034-170A. XF034-171A, CZ40-10, CZ40-09, CZ40-11. XY019-077. XY019-083, XY019-084, XF034-172A, XF034-173A, XF034-174A, XF034-175A. XF034-176A, XF034-177A, YS36-48, YS36-49, YS36-50, YS36-51, YS36-52, YS36-53, YS36-54, YS36-55, YS36-56, YS36-57, YS36-58, YS36-59, XY028-086, CZ40-72, CZ40-73, CZ40-75, CZ40-149, CZ40-74, CZ40-131, AM41-36A, AM41-37A, AM41-39A. AM41-41A, AM41-38A, AM41-40A, XF042-84, XF042-85, XF042-95, XF042-132, XF042-86, XF042-94, XF042-89, XF042-90, XF042-93, XF042-133, XF042-91, and XF042-92.

Also provided by the document is a method of treating an EZH2-mediated cancer, which includes administering to a subject in a subject in need thereof with an EZH2-mediated cancer bivalent compound including an EZH2 ligand conjugated to a degradation/disruption tag. The EZH2-mediated cancer can overexpress EZH2 relative to a wild-type tissue of the same species and tissue type. The EZH2-mediated cancer can express hyper-trimethylated H3K27. The bivalent compound can include, for example, AM16-10A, AM16-11A, AM16-37A, AM16-38A, XY019-43, XY019-44, XY019-079, XY019-080, AM16-91A, AM16-92A, AM16-93A, AM16-97A, AM16-100A, AM16-101A, AM16-102A, AM16-105A, AM16-106A, XY012-120, AM29-21A, AM29-22A, AM29-32A, AM29-33A, AM16-103A, AM29-182A, AM29-55A, AM29-151A, AM29-152A, AM29-137A, AM29-153A, AM29-138A, AM29-154A, AM29-139A, AM29-155A, AM29-170A, AM29-156A, AM29-171A, AM29-157A. AM29-172A, AM29-173A, AM16-79A, AM29-177A, AM29-141A, AM29-178A, AM29-142A, AM29-179A, AM29-143A, AM29-180A. AM29-144A, AM29-145A, AM29-181A, AM41-16A, AM41-17A, AM41-18A, XY012-157, XF034-164A, XF034-165A. XF034-166A, XF034-167A, XF034-168A, XY019-041, XF034-169A, XF034-170A, XF034-171A, CZ40-10, CZ40-09, CZ40-11, XY019-077, XY019-083, XY019-084, XF034-172A, XF034-173A, XF034-174A, XF034-175A. XF034-176A. XF034-177A, YS36-48, YS36-49, YS36-50, YS36-51, YS36-52, YS36-53, YS36-54, YS36-55, YS36-56, YS36-57, YS36-58. YS36-59, XY028-086, CZ40-72, CZ40-73, CZ40-75, CZ40-149, CZ40-74, CZ40-131, AM41-36A, AM41-37A, AM41-39A, AM41-41A, AM41-38A, AM41-40A, XF042-84, XF042-85, XF042-95, XF042-132, XF042-86, XF042-94, XF042-89, XF042-90, XF042-93, XF042-133, XF042-91, and XF042-92.

In any of the above-described methods, the bivalent compound can be administered to the subject orally, parenterally, intradermally, subcutaneously, topically, or rectally.

Any of the above-described methods can further include treating the subject with one or more additional therapeutic regimens for treating cancer. The additional therapeutic regimens for treating cancer can include, for example, surgery, chemotherapy, radiation therapy (e.g., ionizing radiation or ultraviolet light), hormone therapy, or immunotherapy (e.g., antibody therapy). For example, one or more bivalent compounds can be administered to the subject in conjunction with an effective amount of at least one established chemotherapeutic agent (e.g., actinomycin D, cyclophosphamide, doxorubicin, etoposide, and/or paclitaxel).

In any of the above-described methods, the EZH2-mediated cancer can include breast cancer (e.g., triple-negative breast cancer), glioblastoma, prostate cancer, uterine cancer, ovarian cancer, pancreatic cancer, melanoma, renal cell carcinoma, bladder cancer, colorectal cancer, lymphoma, leukemia, malignant rhabdoid tumor, and oropharyngeal cancer.

In any of the above-described methods, the EZH2-mediated cancer can include a relapsed cancer.

In any of the above-described methods, the EZH2-mediated cancer can be (known, predicted, or determined to be) refractory to one or more previous treatments (e.g., surgery, chemotherapy, radiation therapy, hormone therapy, or immunotherapy).

Moreover, the document additionally provides identifying a bivalent compound which mediates degradation/disruption of EZH2, the method including:
  providing a bivalent test compound including an EZH2 ligand conjugated to a degradation/disruption tag;
  contacting the bivalent test compound with a cell including a ubiquitin ligase and EZH2;
  determining whether EZH2 levels decrease in the cell; and
  identifying the bivalent test compound as a bivalent compound which mediates reduction of EZH2 if EZH2 levels decrease in the cell. The cell can be a cancer cell (e.g., an EZH2-mediated cancer cell).

As used herein, the terms "about" and "approximately" are defined as being within plus or minus 10% of a given value or state, preferably within plus or minus 5% of said value or state.

Unless otherwise defined, all technical and scientific terms used herein have the same meaning as commonly understood by one of ordinary skill in the art to which this invention belongs. Methods and materials are described herein for use in the present invention: other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
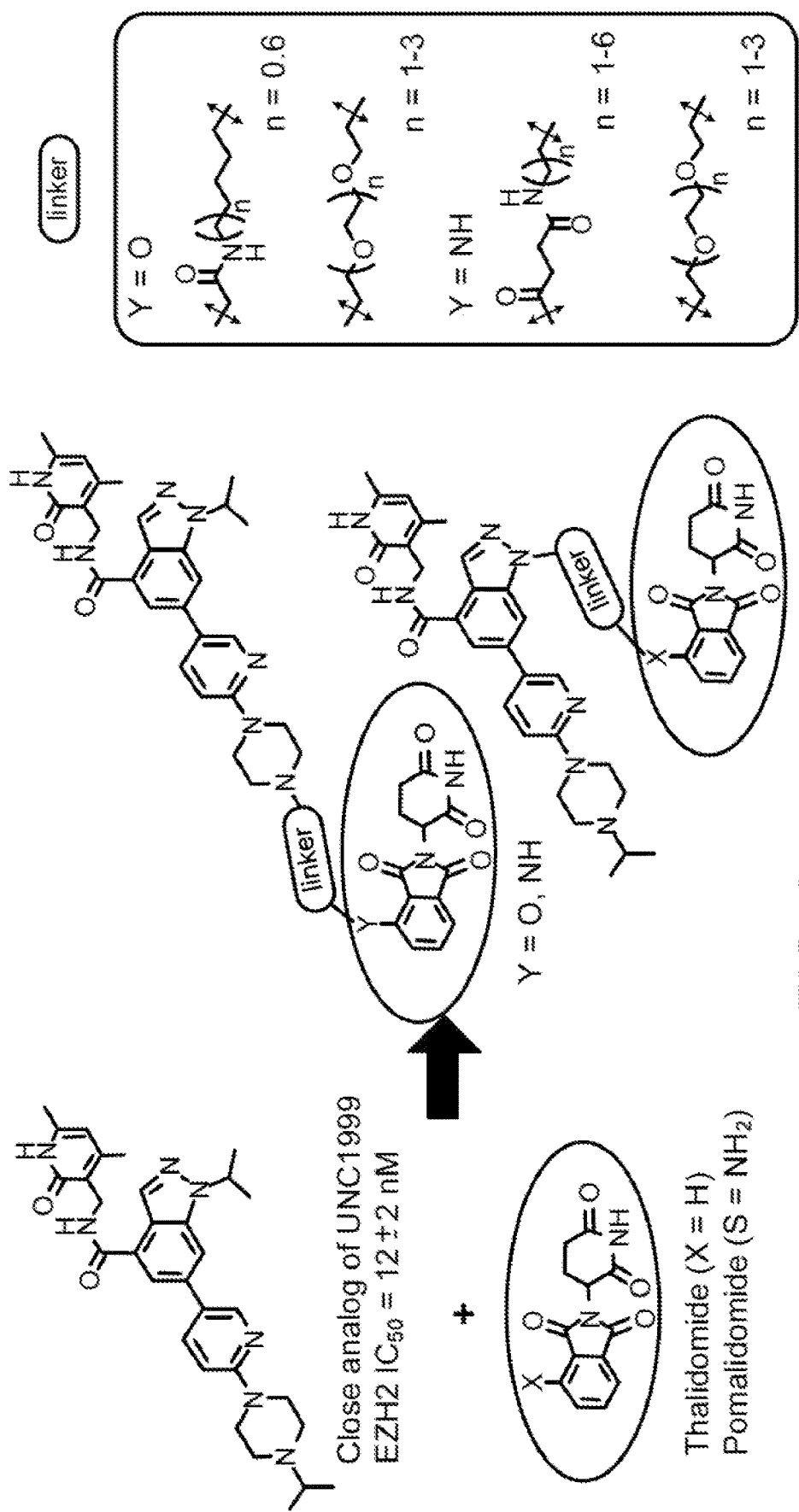
FIG. 1 depicts exemplary structures of bivalent compounds as described in the instant disclosure. Thalidomide/pomalidomide-based EZH2 degraders/disruptors and exemplary linkers 1-4.

The present disclosure is based, in part, on the discovery that novel bivalent compounds which selectively degrade/disrupt EZH2 ("EZH2 degraders/disruptors") are useful in the treatment of EZH2-mediated cancers, including but not limited to TNBC. As discussed in the following examples, this disclosure provides specific examples of novel EZH2 degraders/disruptors. The effect of exemplary degraders/disruptors on the proliferation of different tumor cell lines was examined. The effect of exemplary degraders/disruptors on EZH2 and H3K27me3 protein levels and the enzymatic activity of the PRC2-EZH2 complex were also evaluated. This novel therapeutic approach can be beneficial, particularly since the standard of care for TNBC is primarily chemotherapy and radiation. In addition, without wishing to be bound by theory, because the EZH2 degraders/disruptors disclosed herein have dual functions (enzyme inhibition plus protein degradation/disruption), they can be significantly more effective than current EZH2 inhibitors, which inhibit the enzymatic activity of EZH2 but do not affect EZH2 protein levels, for treating other EZH2-mediated cancers.

A number of selective EZH2 inhibitors, including UNC1999, EPZ005687, EPZ-6438, GSK126, EI1, CPI-1205, GSK343, CPI-360, EPZ011989, compound 24, compound 3, compound 31, ZLD1039, PF-06821497, and JQEZ5 have been discovered (Bradley et al., 2014; Broun et al., 2016; Campbell et al., 2015; Gao et al., 2016; Garapaty-Rao et al., 2013; Gehling et al., 2015; Kaniskan et al., 2017; Knutson et al., 2013; Knutson et al., 2012; Konze et al., 2013; Kung et al., 2016; McCabe et al., 2012b; Qi et al., 2012; Song et al., 2016; Verma et al., 2012; Yang et al., 2016). Some of these inhibitors (e.g., EPZ-6438, GSK126, CPI-1205, and PF-06821497) have been in clinical trials for treating diffused large B cell lymphoma (DLBCL), follicular lymphoma (FL), and malignant rhabdoid tumor (MRT). However, these inhibitors have exhibited very limited success in treating breast cancers and prostate cancers mainly because these compounds only inhibit the methyltransferase activity of EZH2, but do not change EZH2 protein levels. Representative examples of selective EZH2 inhibitors are provided below.

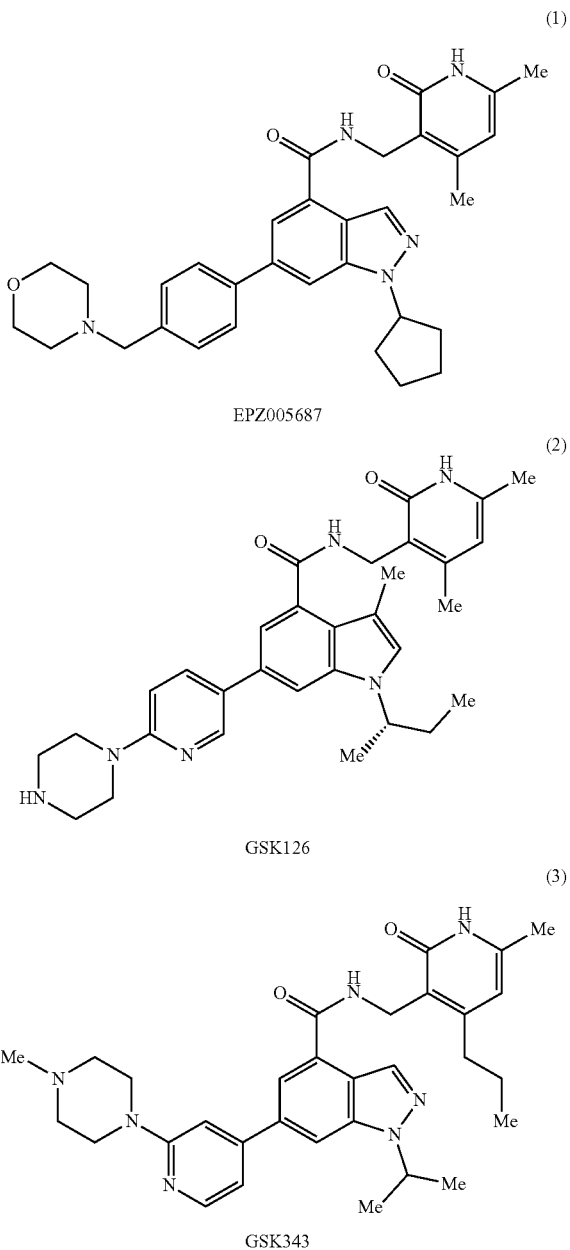

EPZ005687 (1)

GSK126 (2)

GSK343 (3)

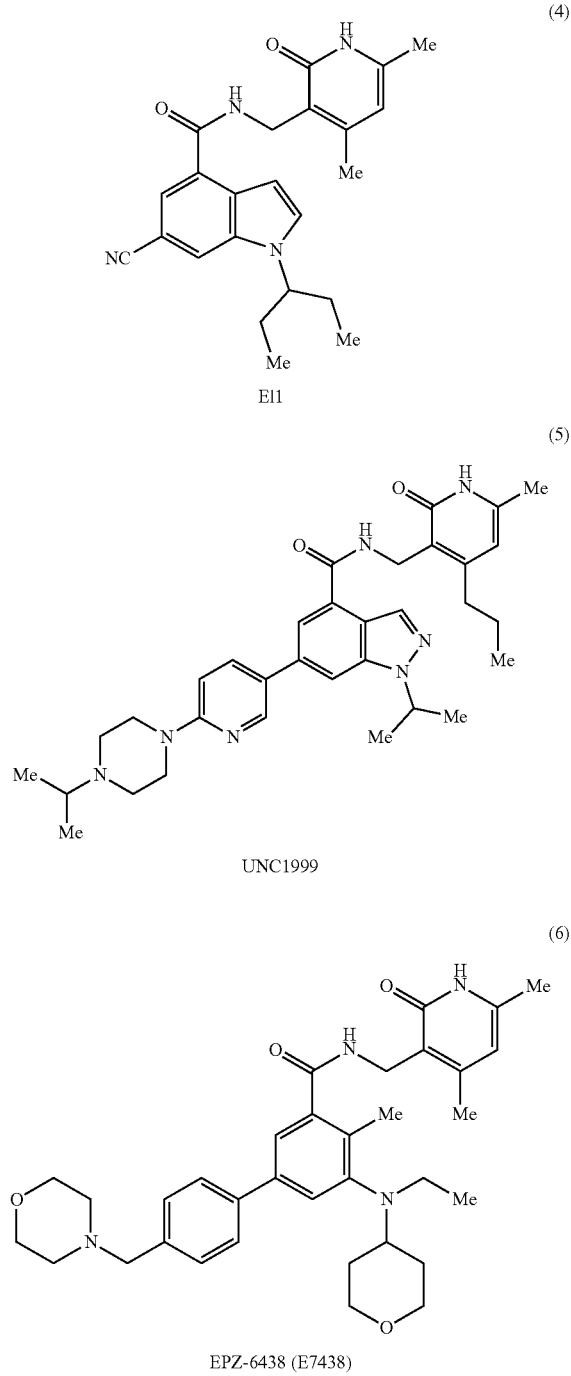
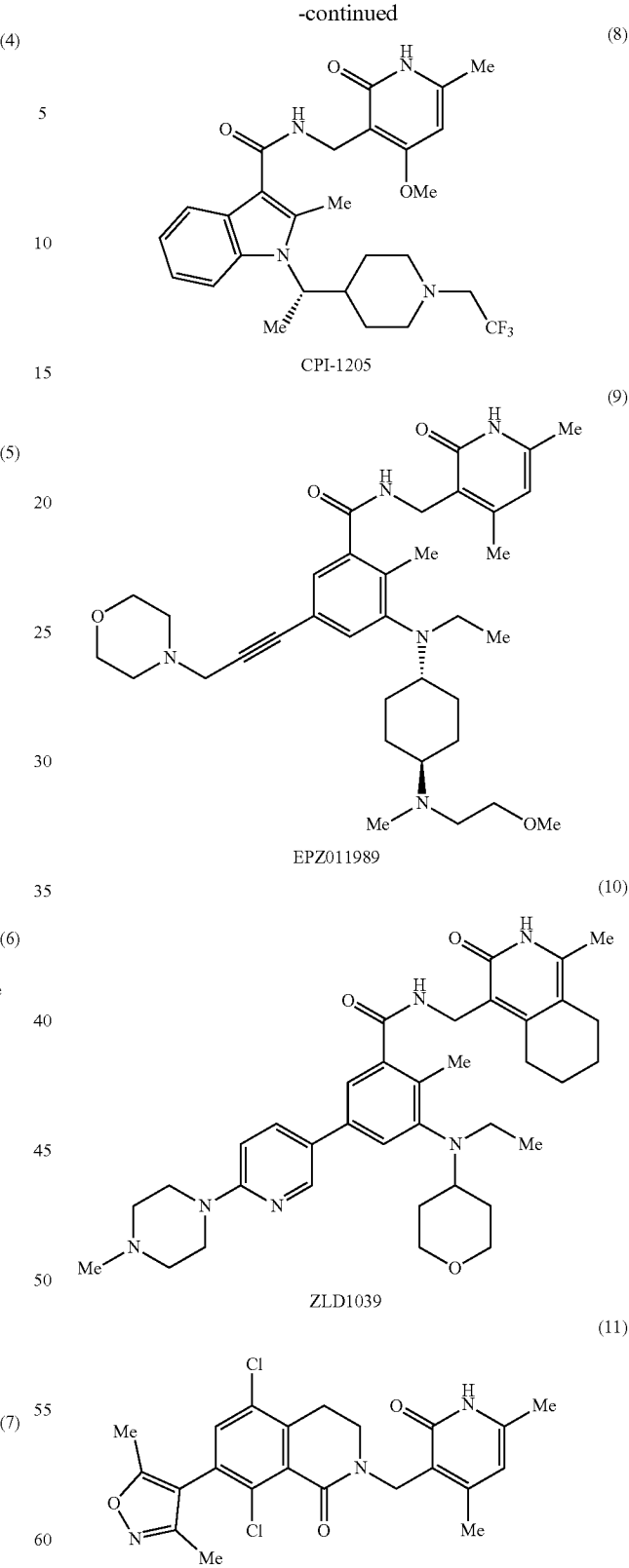
Representative Small-Molecule EZH2 Inhibitors
As described earlier, known EZH2 inhibitors (Bradley et al., 2014; Broonn et al., 2016; Campbell et al., 2015; Gao et al., 2016; Garapaty-Rao et al., 2013; Gehling et al., 2015; Kaniskan et al., 2017; Knutson et al., 2013; Knutson et al., 2012; Konze et al., 2013; Kung et al., 2016; McCabe et al., 2012b; Qi et al., 2012; Song et al., 2016; Verma et al., 2012; Yang et al., 2016) inhibit the catalytic activity of the PRC2-EZH2, but do not change EZH2 protein levels. Here, a different approach was taken: an EZH2 ligand or targeting moiety (e.g., an EZH2 inhibitor such as UNC1999 or compound 24) was linked with a ubiquitin ligase (e.g., an E3 ligase)-binding moiety (e.g., thalidomide or VHL-1) or a hydrophobic group (e.g., adamantane) to generate bivalent compounds. These bivalent inhibitors (EZH2 degraders/disruptors) recruit the ubiquitination machinery to EZH2, leading to selective degradation of EZH2 via the ubiquitin-proteasome pathway, and/or mimic EZH2 protein misfolding and subsequent degradation at the proteasome or loss of function. Therefore, these degraders/disruptors can be effective therapeutic agents for treating breast cancers (including TNBC), prostate cancers, and other cancers while current EZH2 inhibitors are ineffective. In addition, these EZH2 degraders/disruptors can be more effective than EZH2 inhibitors for the treatment of those EZH2-mediated cancers where EZH2 inhibitors are effective, including, e.g., DLBCB, FL, and MRT.

Accordingly, in some aspects, the present disclosure provides bivalent compounds, referred to herein as "EZH2 degraders/disruptors", comprising an enhancer of zeste homologue 2 (EZH2) ligand (or targeting moiety) conjugated to a degradation/disruption tag. Linkage of the EZH2 ligand to the degradation/disruption tag can be direct, or indirect via a linker.

As used herein, the term "enhancer of zeste homologue 2 ligand" or "EZH2 ligand" refers to compound that associates and/or binds to EZH2. The EZH2 ligand can be, e.g., a small-molecule compound (i.e., a molecule of molecular weight less than about 1.5 kilodaltons (kDa)), a peptide, or an antibody or fragment thereof which is capable of binding to EZH2 and/or interfering with the methyltransferase enzymatic activity of EZH2.

The EZH2 ligand can be an EZH2 inhibitor, which is capable of interfering with the methyltransferase enzymatic activity of EZH2. As used herein, an "inhibitor" refers to an agent that restrains, retards, or otherwise causes inhibition of a physiological, chemical or enzymatic action or function. An inhibitor may cause at least 5% decrease in enzyme activity. An inhibitor may also refer to a drug, compound or agent that prevents or reduces the expression, transcription or translation of a gene or protein. An inhibitor may reduce or prevent the function of a protein, for instance by binding to and/or activating/inactivating another protein or receptor. In some aspects, the EZH2 inhibitors of the present disclosure include, for example, UNC1999, EPZ005687, EPZ-6438, GSK126, EI1, CPI-1205, GSK343, CPI-360, EPZ011989, compound 24, compound 3, compound 31, ZLD1039, PF-06821497, JQEZ5, and analogs thereof.

Figure 2:
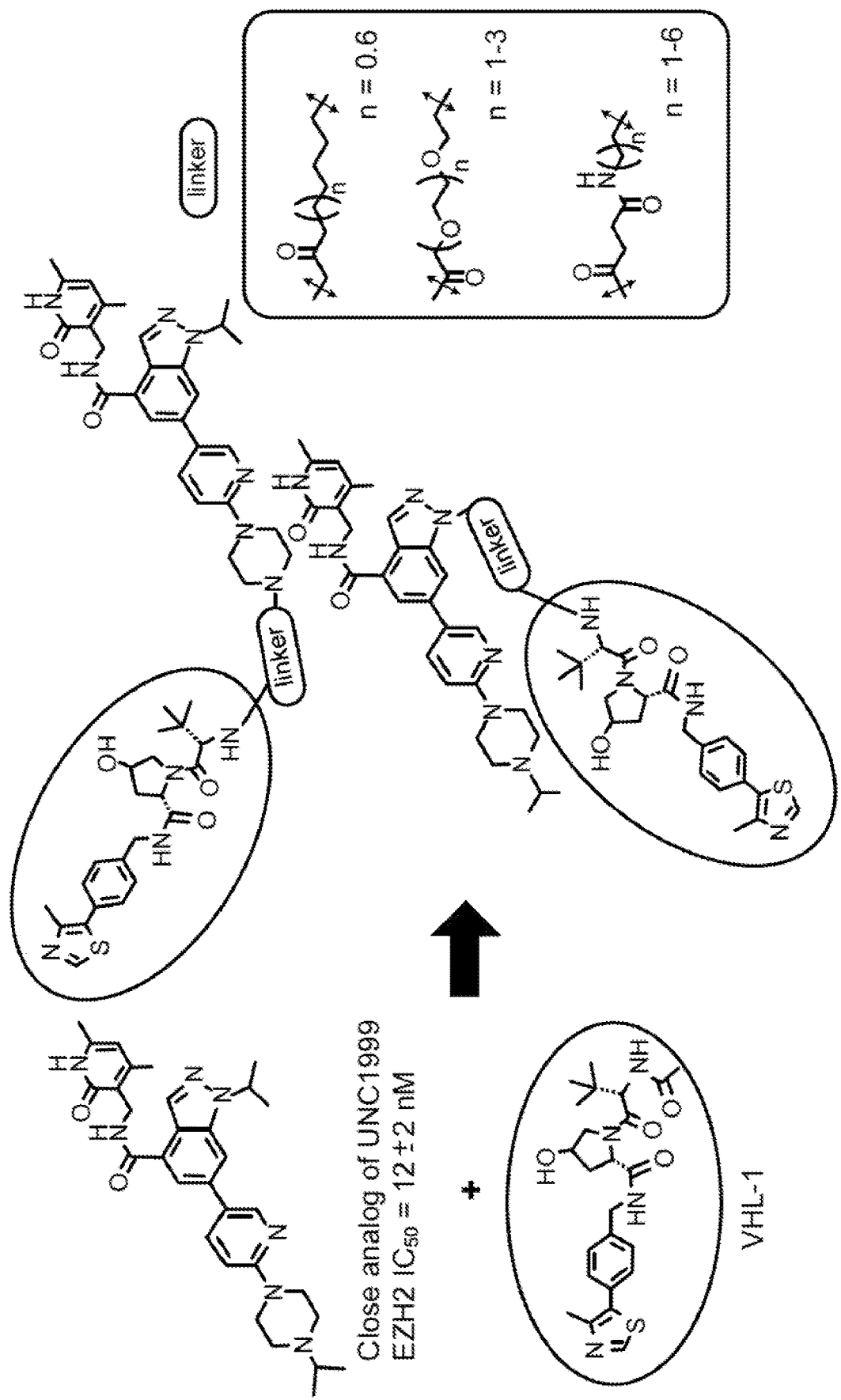
FIG. 2 depicts exemplary structures of VHL-1-based EZH2 degraders/disruptors and exemplary linkers 5-7.
Figure 3:
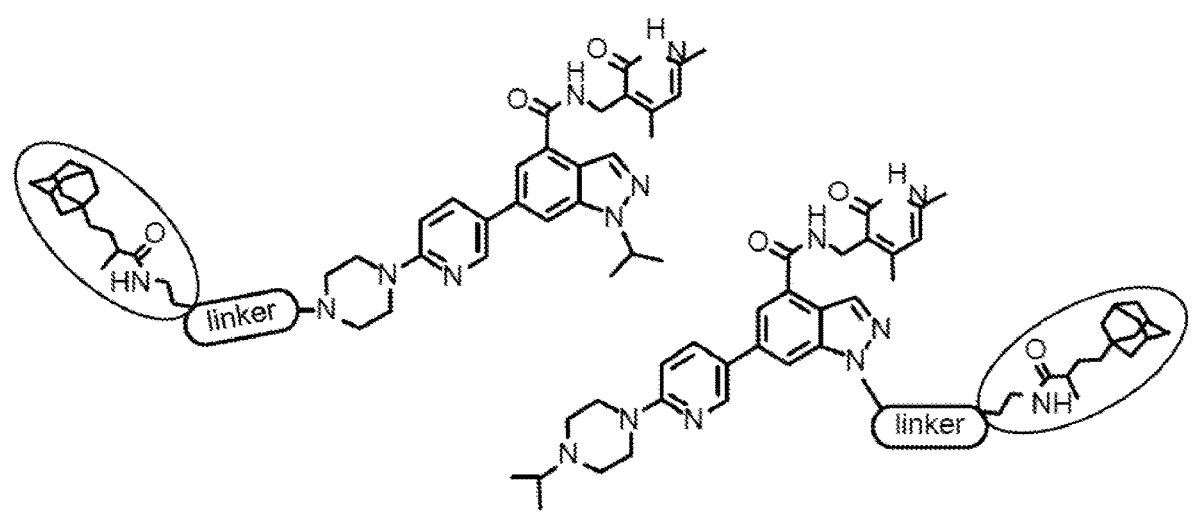
FIG. 3 depicts exemplary structures of adamantane-based EZH2 degraders/disruptors.
Figure 4:
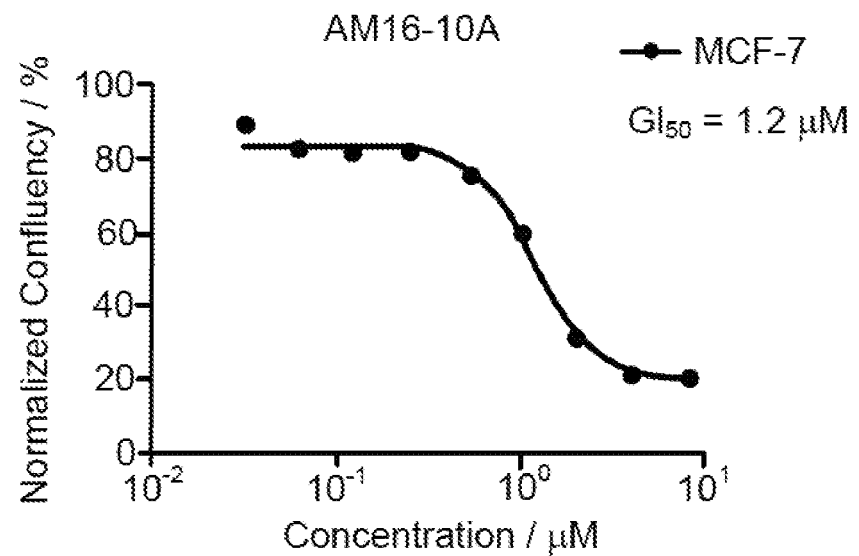
FIG. 4 is a graph depicting the $GI_{50}$ for AM16-10A for MCF-7 cells.
Figure 5:
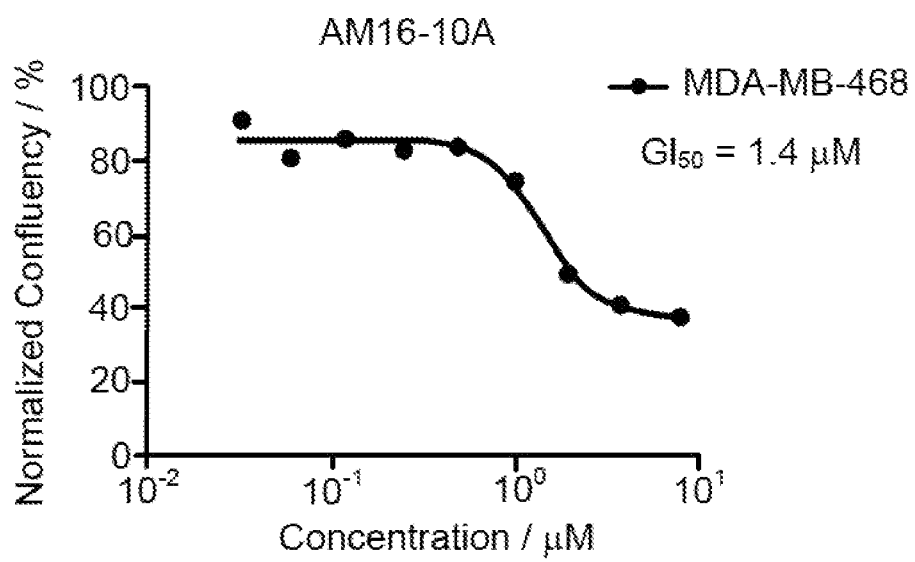
FIG. 5 is a graph depicting the $GI_{50}$ for AM16-10A for MDA-MB-468 cells.
Figure 6:
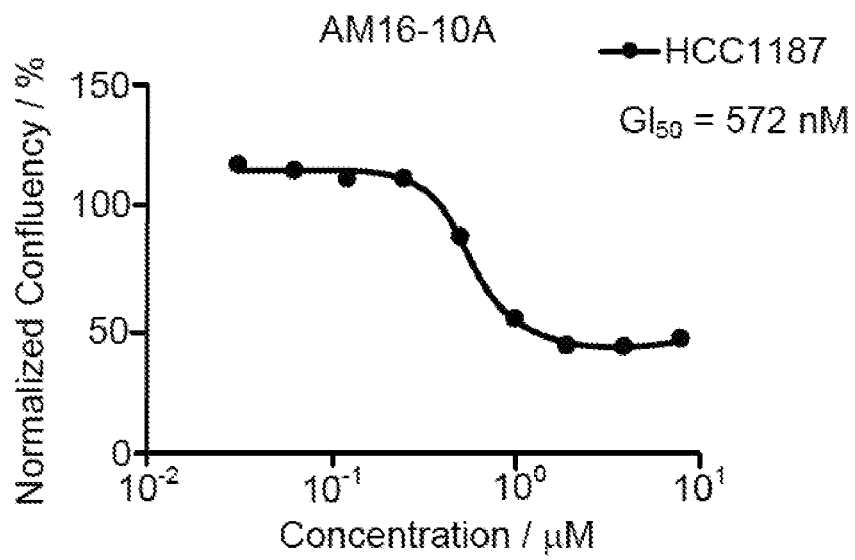
FIG. 6 is a graph depicting the $GI_{50}$ for AM16-10A for HCC1187 cells.
Figure 7:
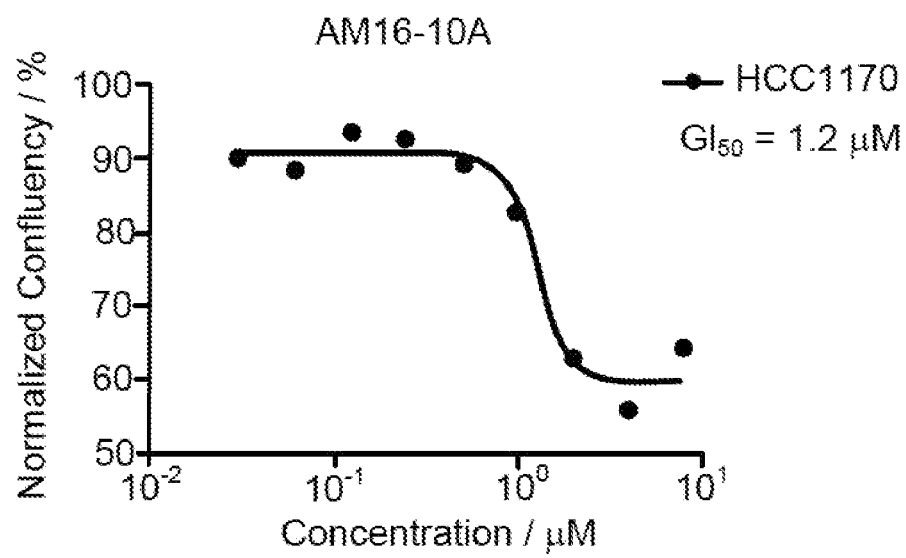
FIG. 7 is a graph depicting the $GI_{50}$ for AM16-10A for HCC1170 cells.
Figure 8:
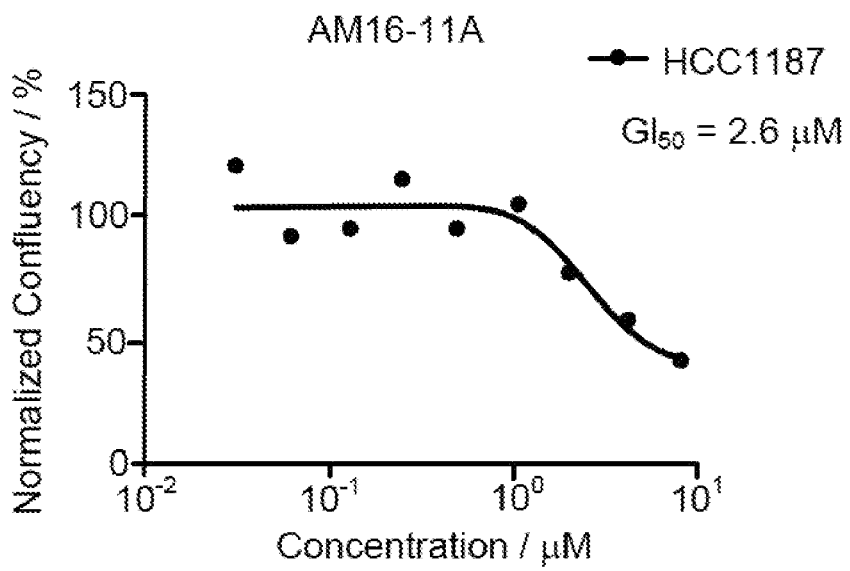
FIG. 8 is a graph depicting the $GI_{50}$ for AM16-11A for HCC1187 cells.
Figure 9:
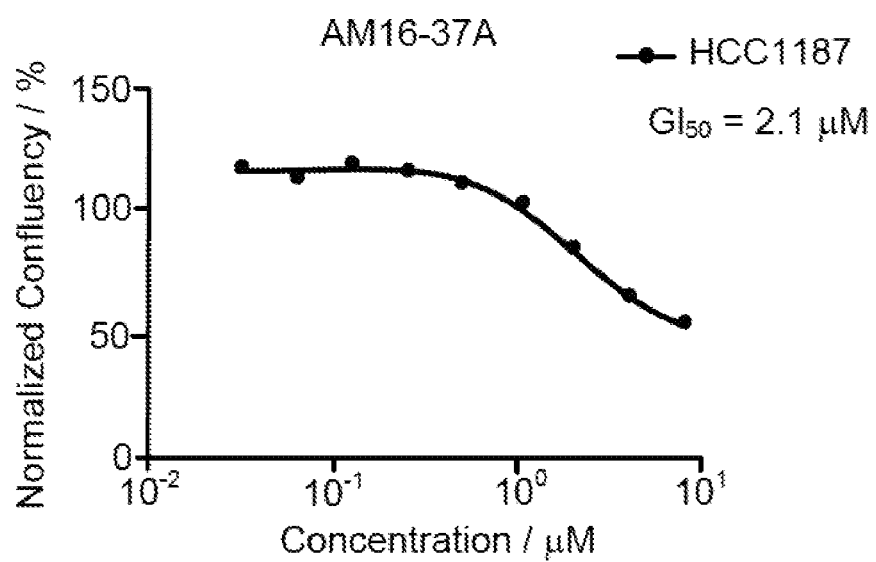
FIG. 9 is a graph depicting the $GI_{50}$ for AM16-37A for HCC1187 cells.
Figure 10:
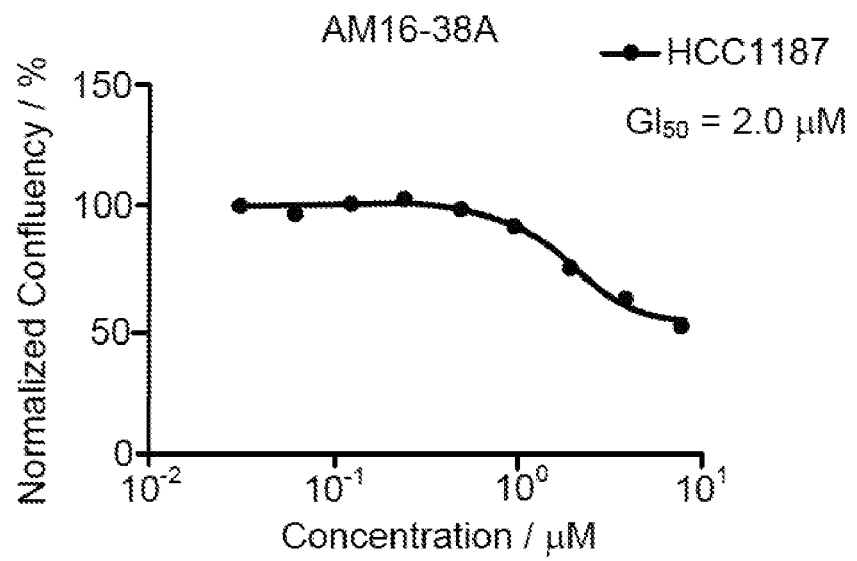
FIG. 10 is a graph depicting the $GI_{50}$ for AM16-38A for HCC1187 cells.
Figure 11:
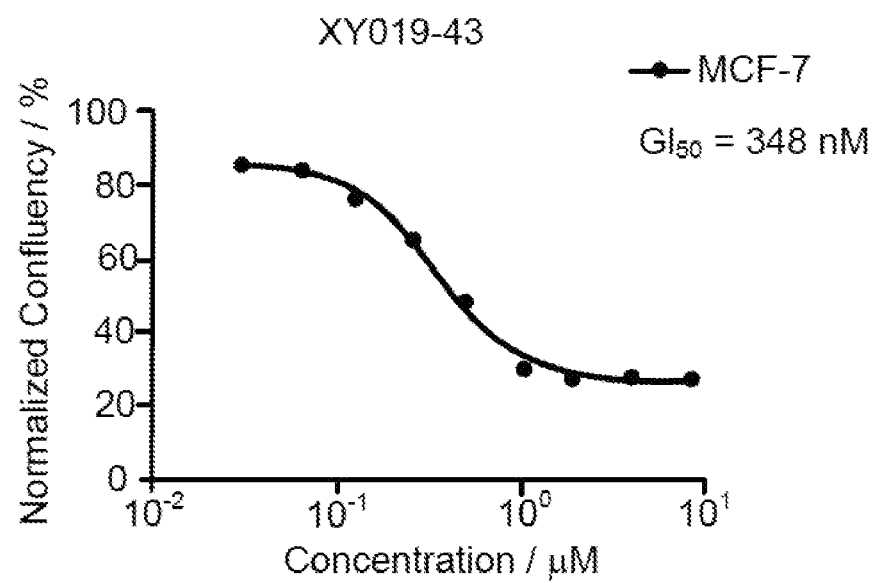
FIG. 11 is a graph depicting the $GI_{50}$ for XY019-43 for MCF-7 cells.
Figure 12:
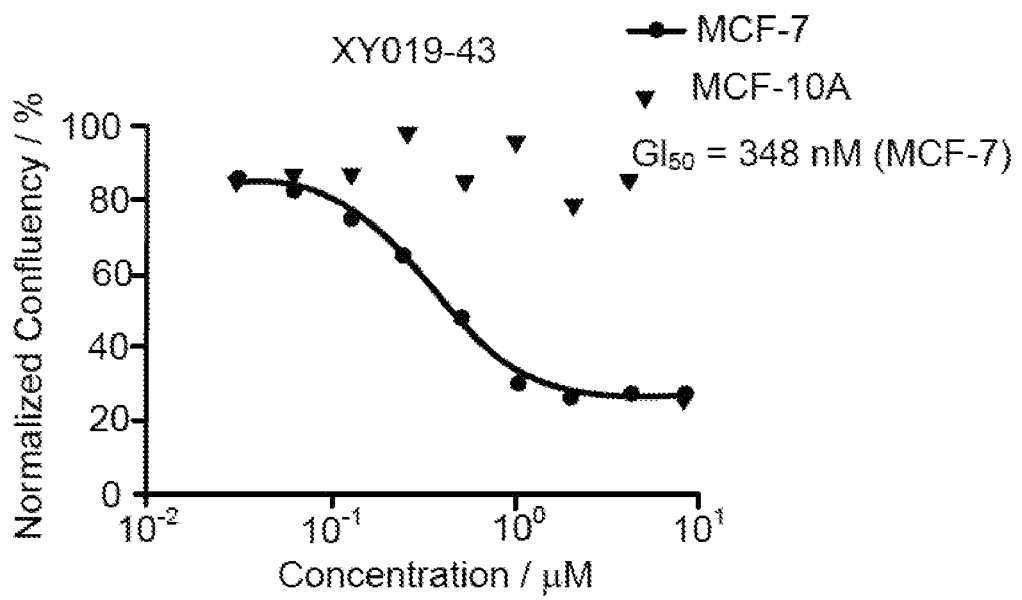
FIG. 12 is a graph depicting the $GI_{50}$ for XY019-43 for MCF-7 and MCF-10A (control) cells.
Figure 13:
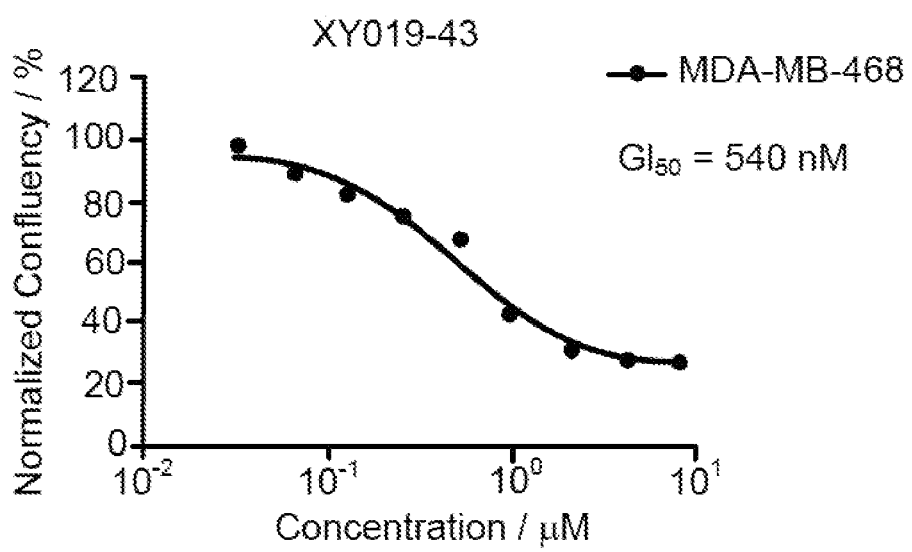
FIG. 13 is a graph depicting the $GI_{50}$ for XY019-43 for MDA-MB-468 cells.
Figure 14:
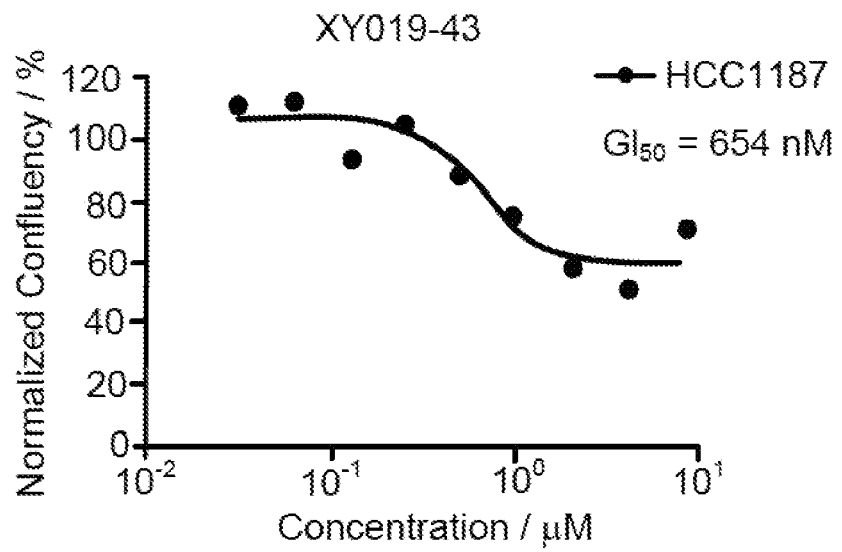
FIG. 14 is a graph depicting the $GI_{50}$ for XY019-43 for HCC1187 cells.
Figure 15:
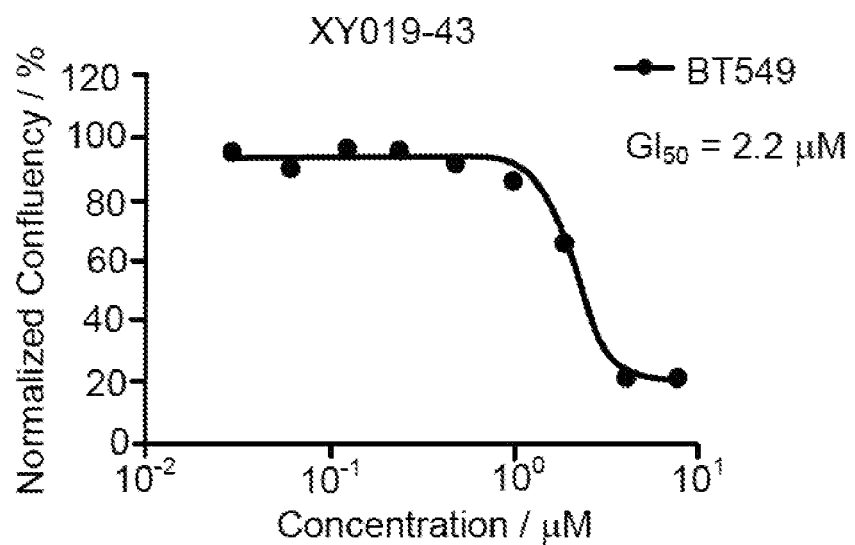
FIG. 15 is a graph depicting the $GI_{50}$ for XY019-43 for BT549 cells.
Figure 16:
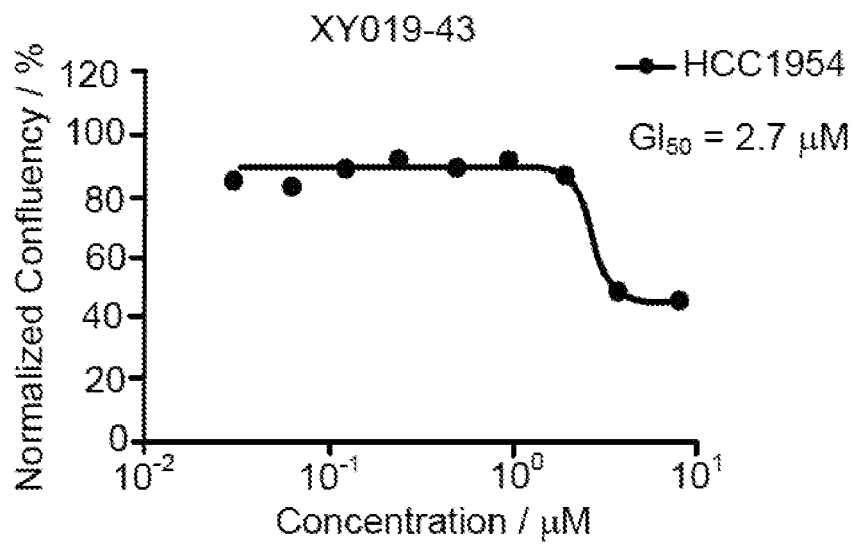
FIG. 16 is a graph depicting the $GI_{50}$ for XY019-43 for HCC1954 cells.
Figure 17:
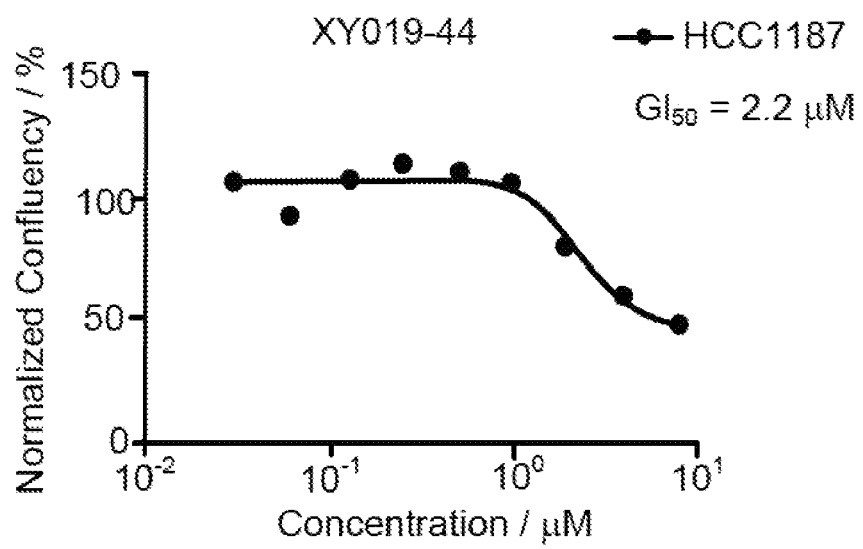
FIG. 17 is a graph depicting the $GI_{50}$ for XY019-44 for HCC1187 cells.
Figure 18:
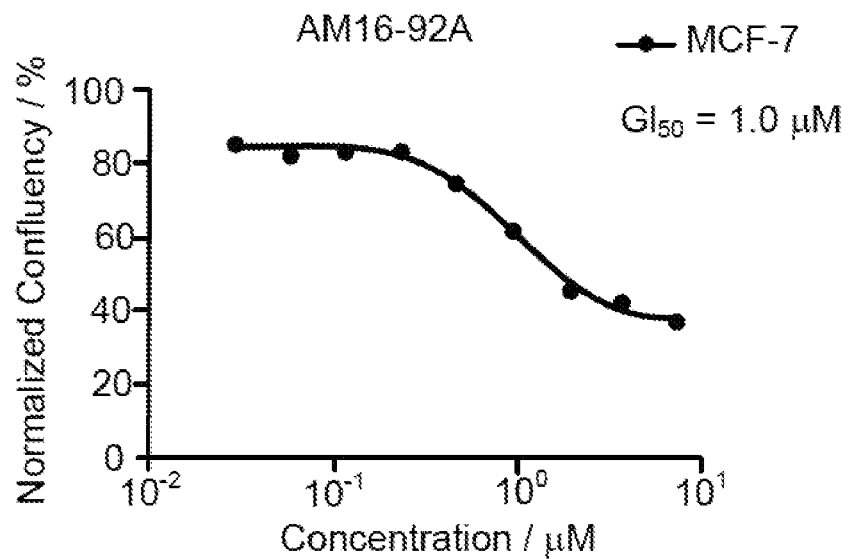
FIG. 18 is a graph depicting the $GI_{50}$ for AM16-92A for MCF-7 cells.
Figure 19:
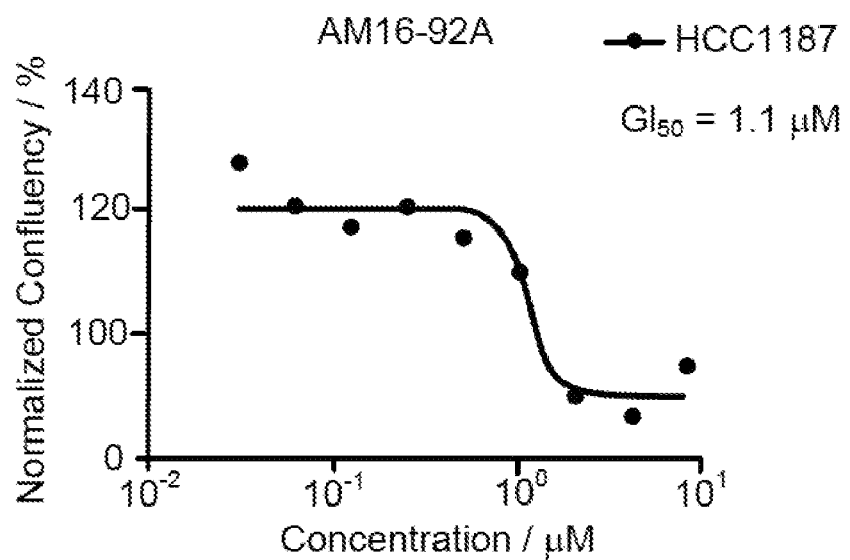
FIG. 19 is a graph depicting the $GI_{50}$ for AM16-92A for HCC1187 cells.
Figure 20:
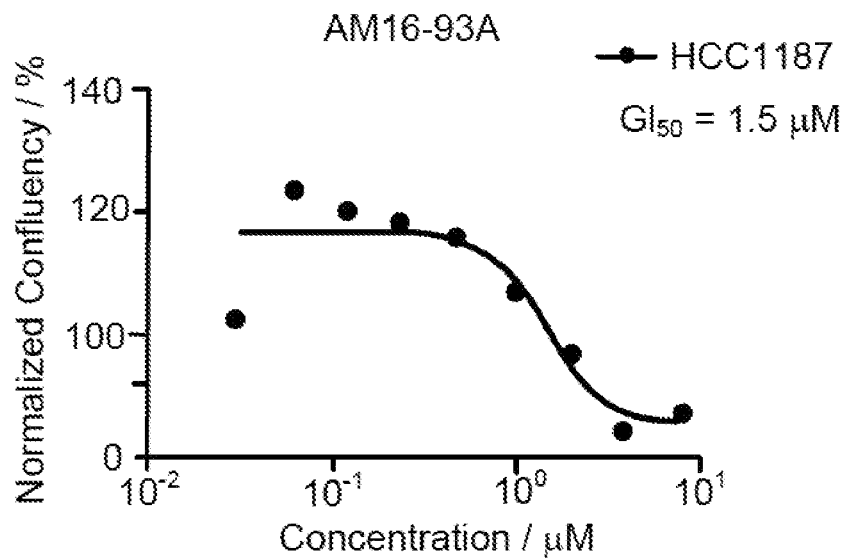
FIG. 20 is a graph depicting the $GI_{50}$ for AM16-93A for HCC1187 cells.
Figure 21:
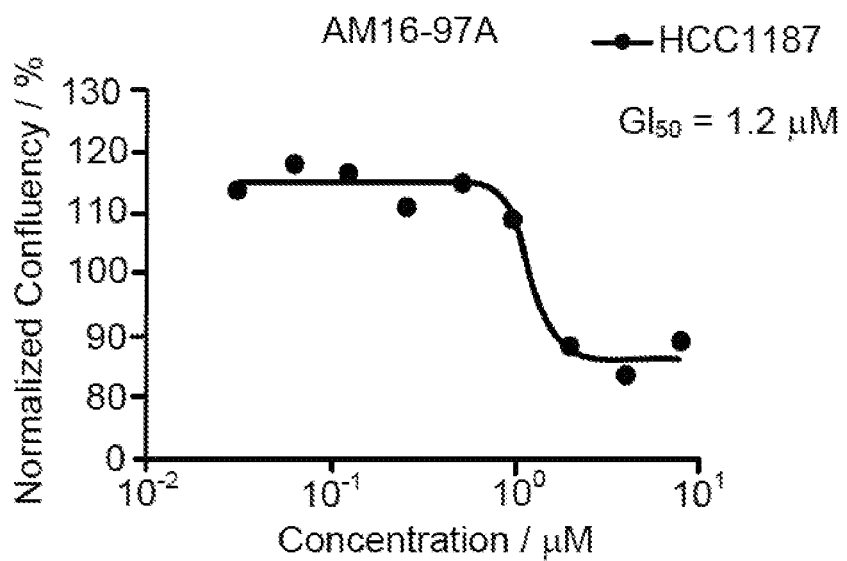
FIG. 21 is a graph depicting the $GI_{50}$ for AM16-97A for HCC1187 cells.
Figure 22:
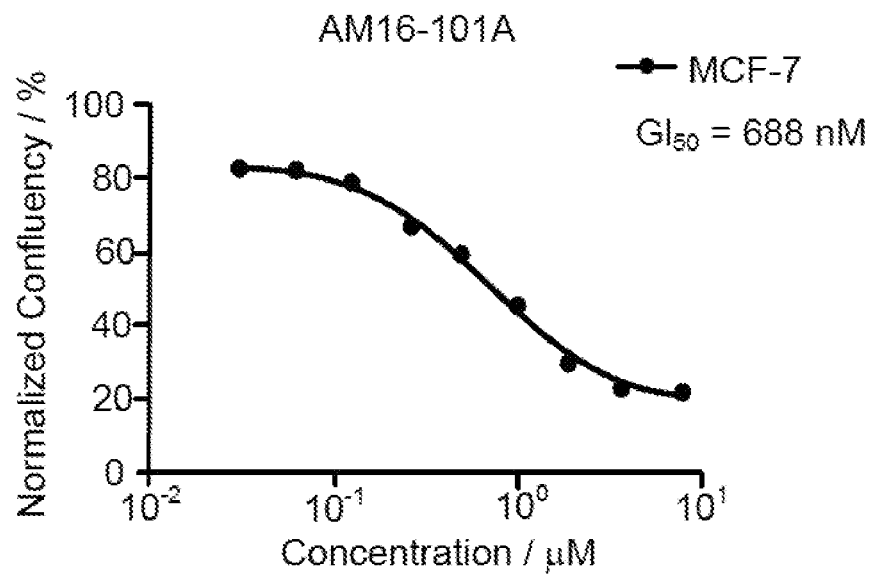
FIG. 22 is a graph depicting the $GI_{50}$ for AM16-101A for MCF-7 cells.
Figure 23:
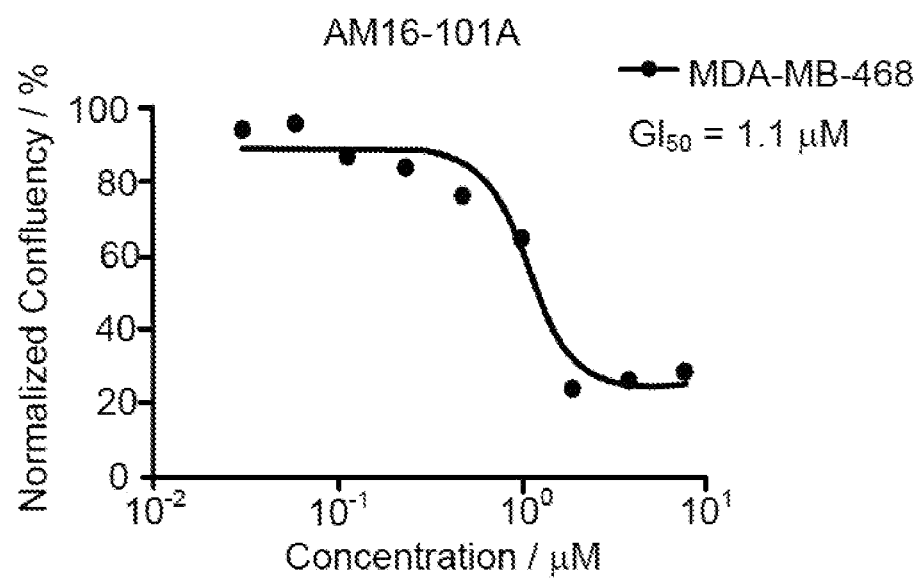
FIG. 23 is a graph depicting the $GI_{50}$ for AM16-101A for MDA-MB-468 cells.
Figure 24:
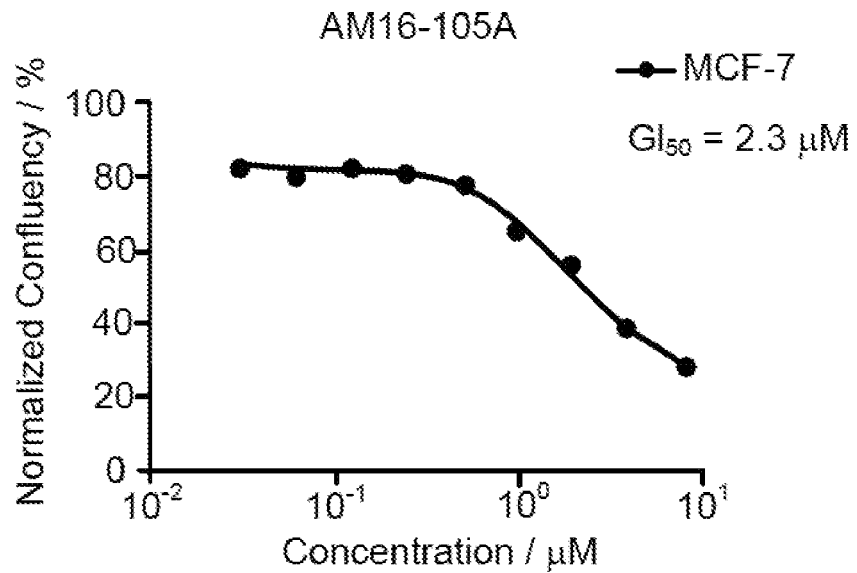
FIG. 24 is a graph depicting the $GI_{50}$ for AM16-105A for MCF-7 cells.
Figure 25:
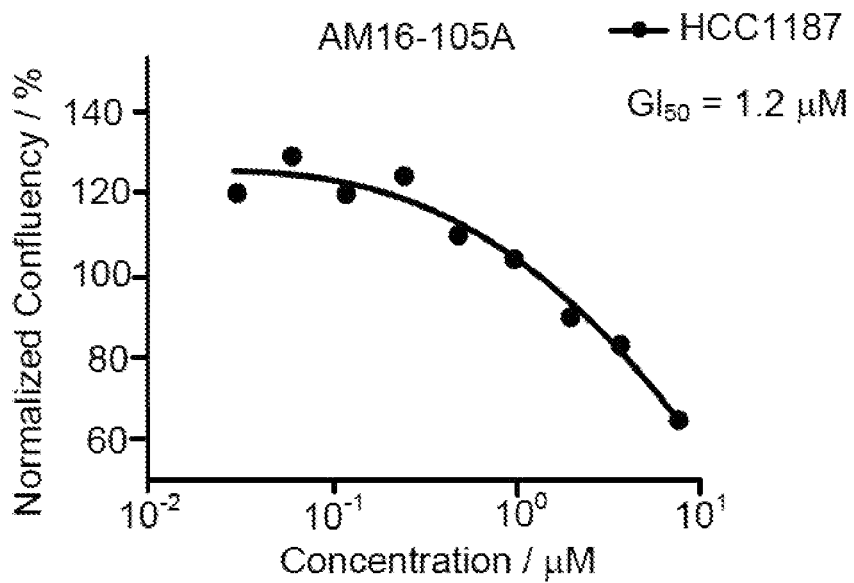
FIG. 25 is a graph depicting the $GI_{50}$ for AM16-105A for HCC1187 cells.
Figure 26:
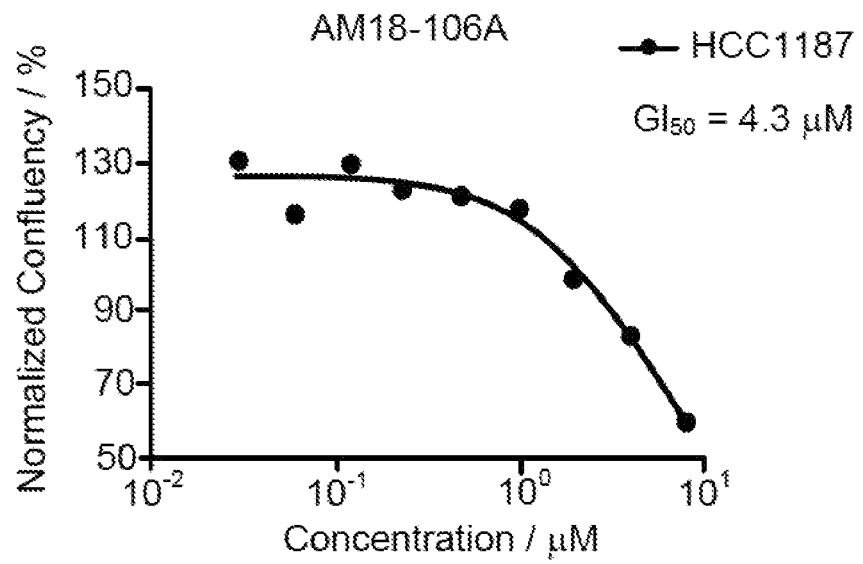
FIG. 26 is a graph depicting the $GI_{50}$ for AM16-106A for HCC1187 cells.
Figure 27:
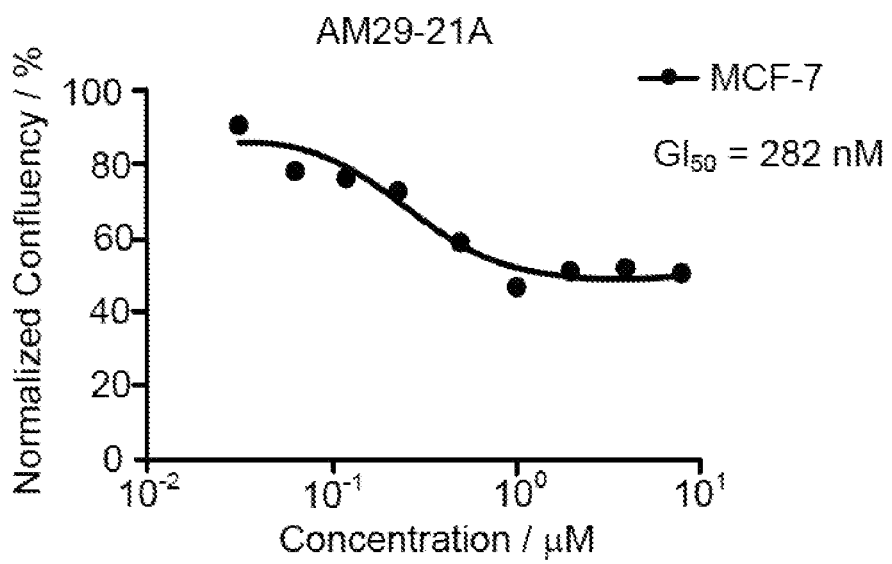
FIG. 27 is a graph depicting the $GI_{50}$ for AM29-21A for MCF-7 cells.
Figure 28:
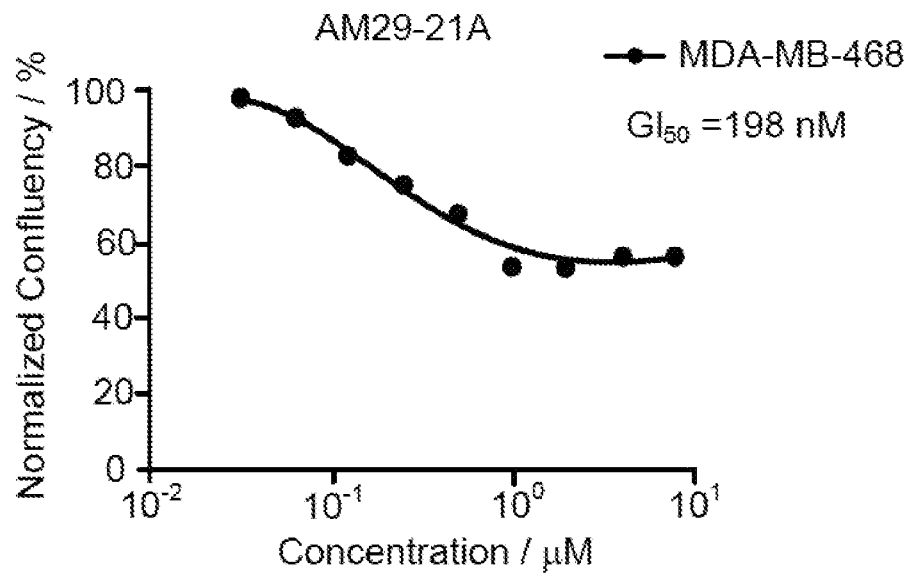
FIG. 28 is a graph depicting the $GI_{50}$ for AM29-21A for MDA-MB-468 cells.
Figure 29:
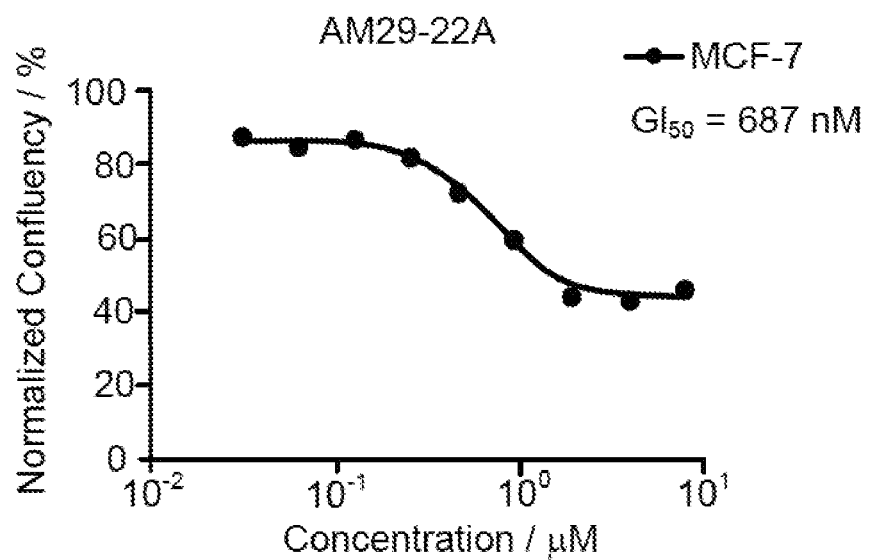
FIG. 29 is a graph depicting the $GI_{50}$ for AM29-22A for MCF-7 cells.
Figure 30:
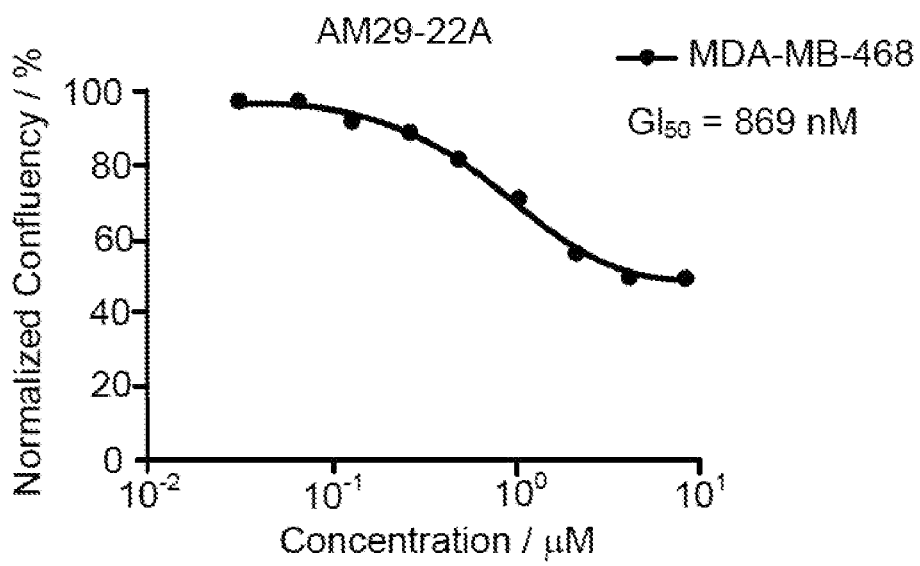
FIG. 30 is a graph depicting the $GI_{50}$ for AM29-22A for MDA-MB-468 cells.
Figure 31:
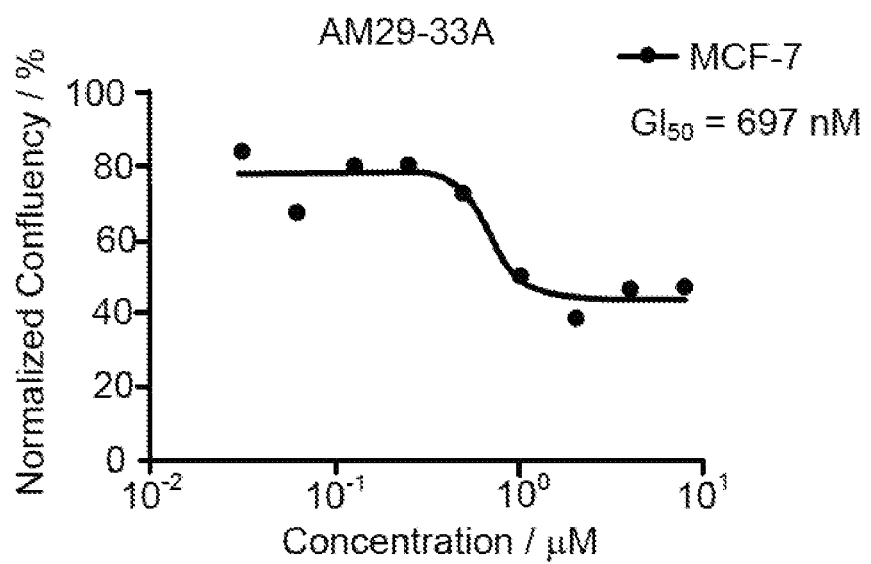
FIG. 31 is a graph depicting the $GI_{50}$ for AM29-33A for MCF-7 cells.
Figure 32:
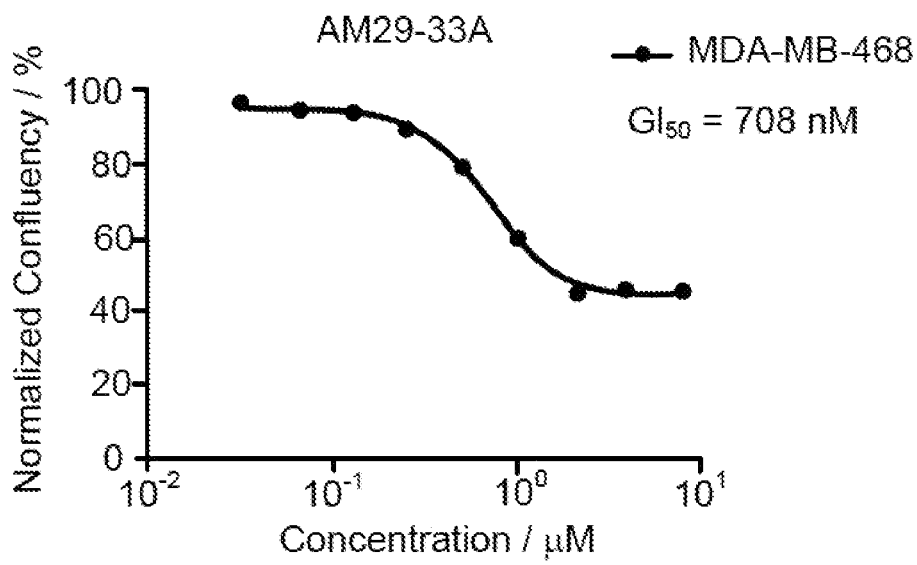
FIG. 32 is a graph depicting the $GI_{50}$ for AM29-33A for MDA-MB-468 cells.
Figure 33:
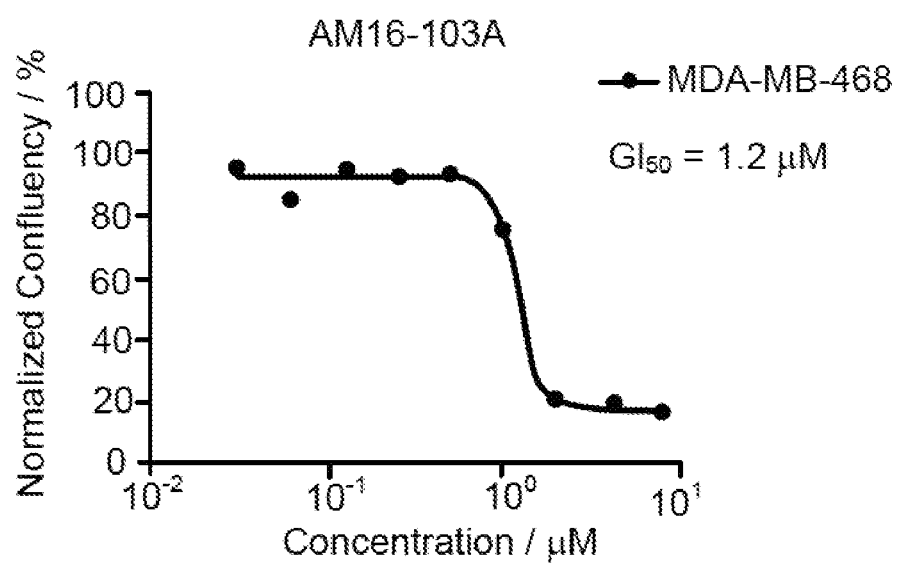
FIG. 33 is a graph depicting the $GI_{50}$ for AM16-103A for MDA-MB-468 cells.
Figure 34:
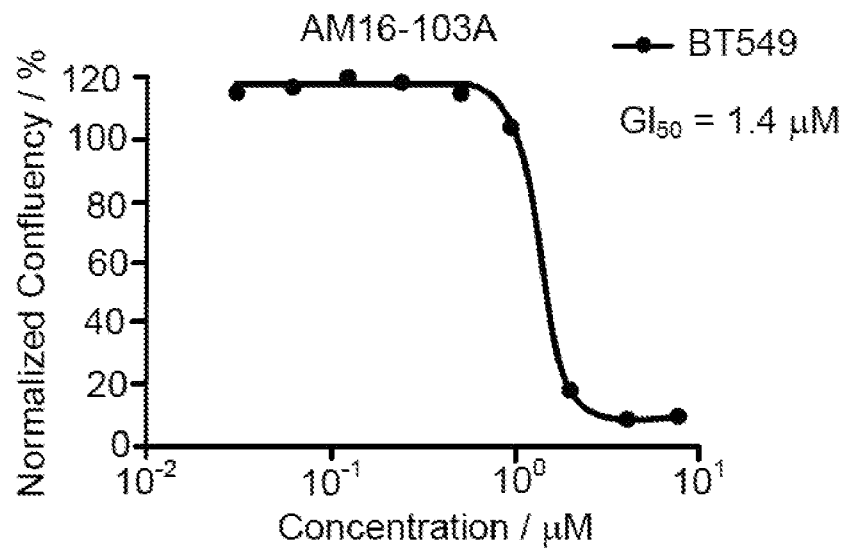
FIG. 34 is a graph depicting the $GI_{50}$ for AM16-103A for BT549 cells.
Figure 35:
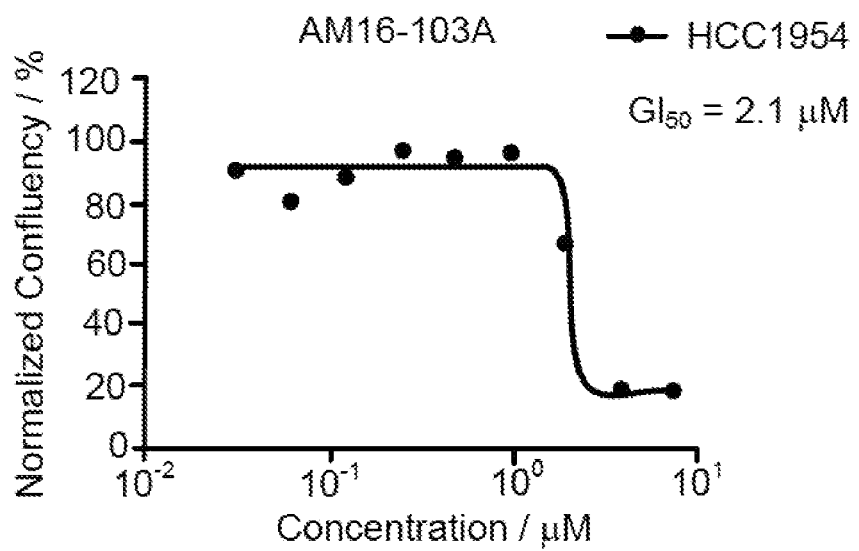
FIG. 35 is a graph depicting the $GI_{50}$ for AM16-103A for HCC1954 cells.
Figure 36:
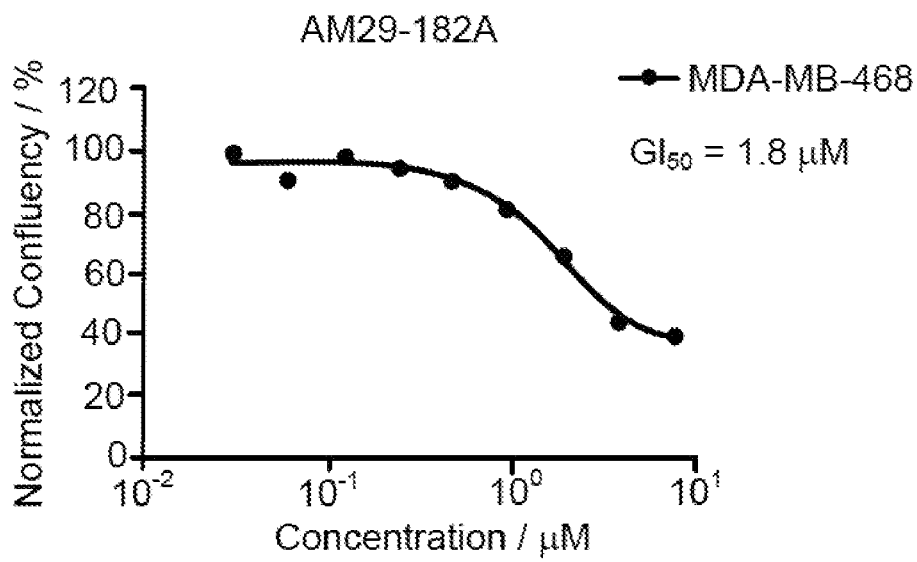
FIG. 36 is a graph depicting the $GI_{50}$ for AM29-182A for MDA-MB-468 cells.
Figure 37:
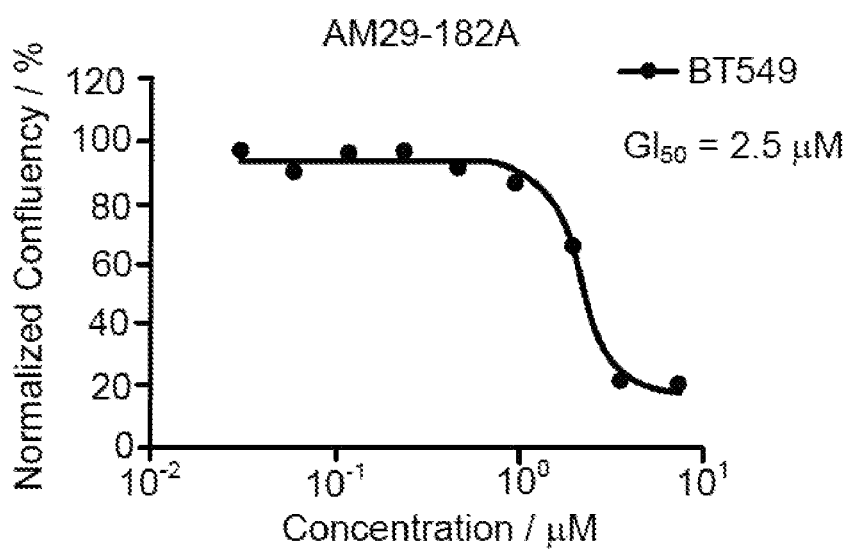
FIG. 37 is a graph depicting the $GI_{50}$ for AM29-182A for BT549 cells.
Figure 38:
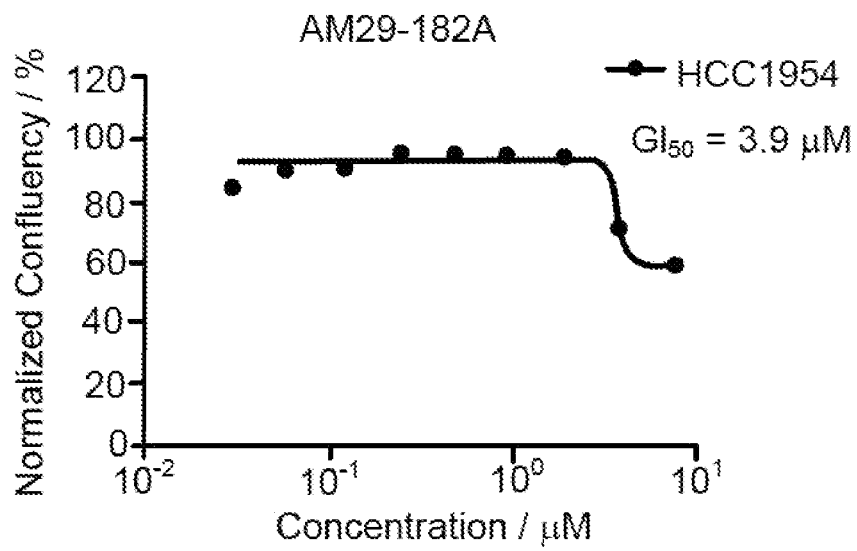
FIG. 38 is a graph depicting the $GI_{50}$ for AM29-182A for HCC1954 cells.
Figure 39:
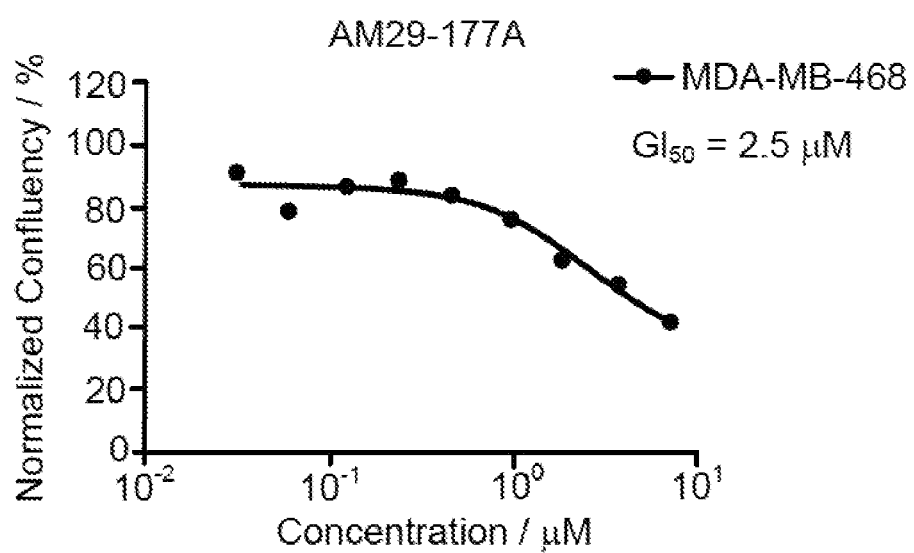
FIG. 39 is a graph depicting the $GI_{50}$ for AM29-177A for MDA-MB-468 cells.
Figure 40:
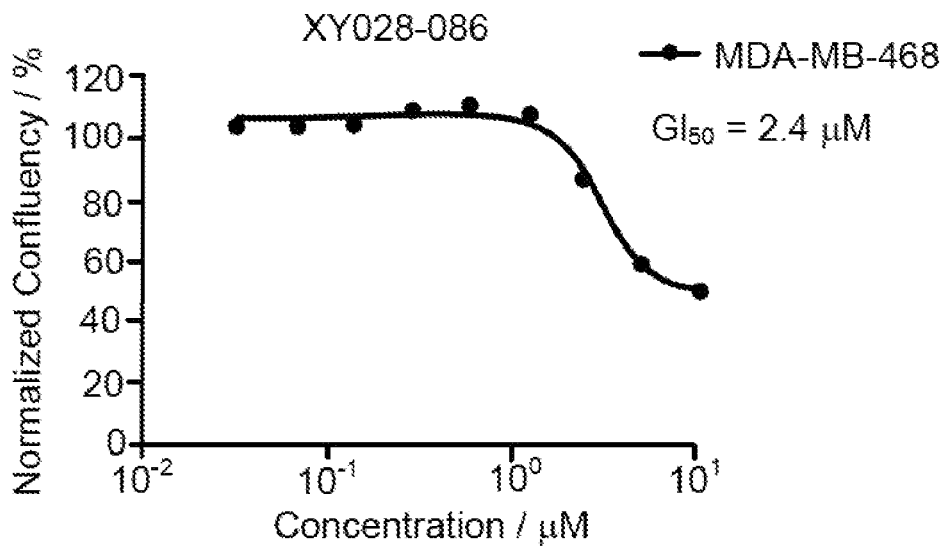
FIG. 40 is a graph depicting the $GI_{50}$ for XY028-086 for MDA-MB-468 cells.
Figure 41:
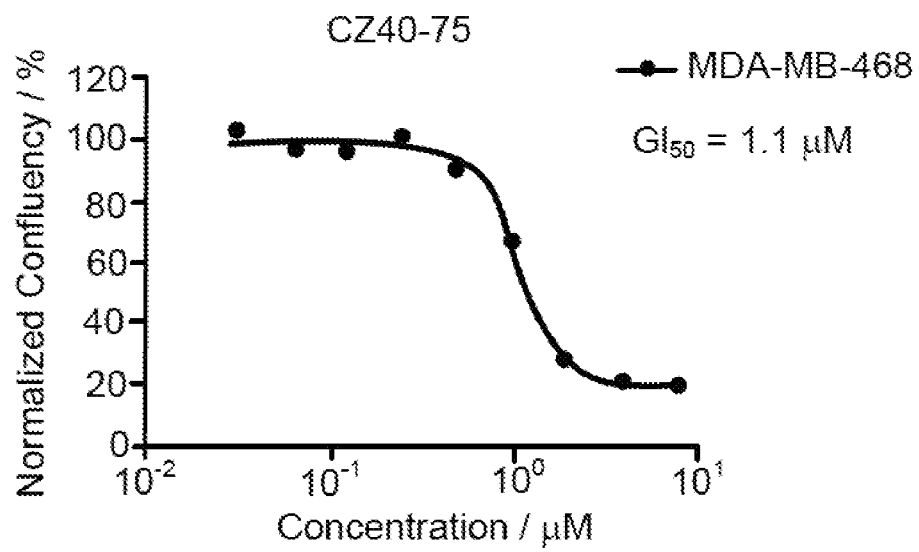
FIG. 41 is a graph depicting the $GI_{50}$ for CZ40-75 for MDA-MB-468 cells.
Figure 42:
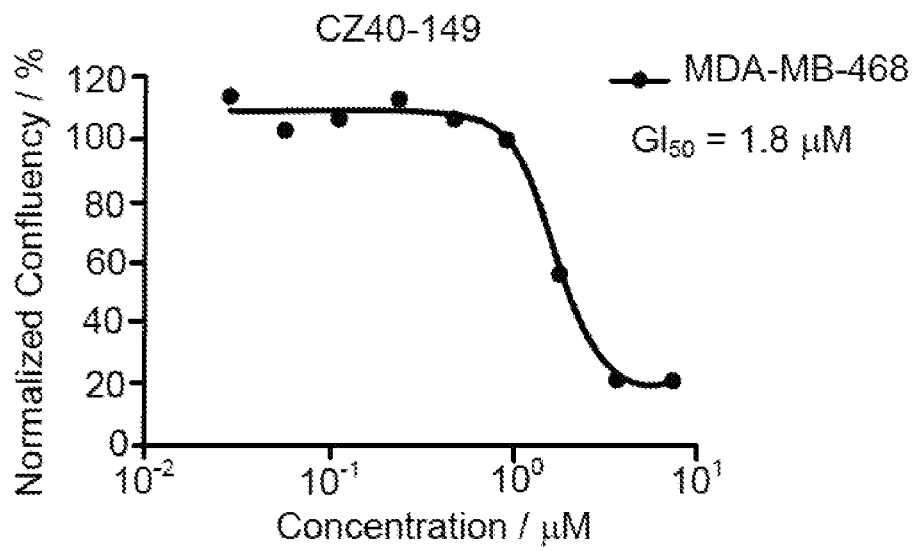
FIG. 42 is a graph depicting the $GI_{50}$ for CZ40-149 for MDA-MB-468 cells.
Figure 43:
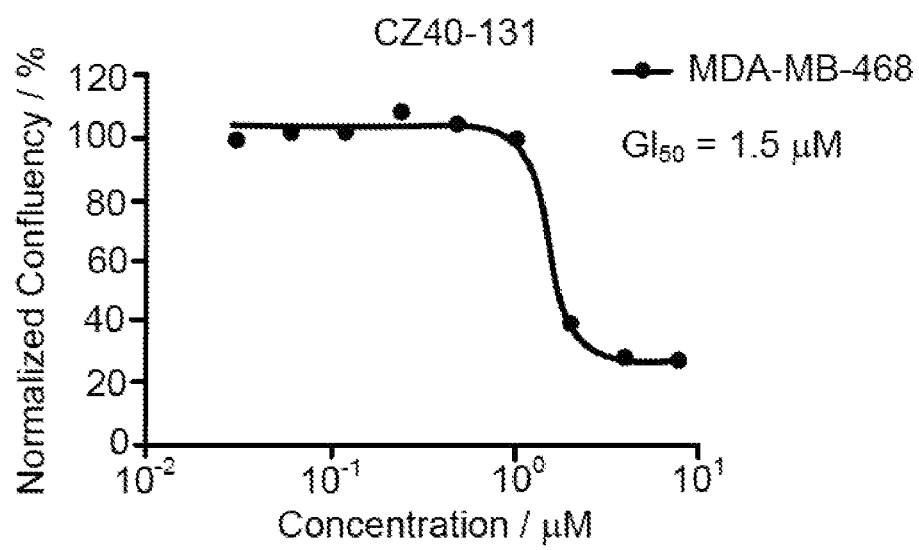
FIG. 43 is a graph depicting the $GI_{50}$ for CZ40-131 for MDA-MB-468 cells.
Figure 44:
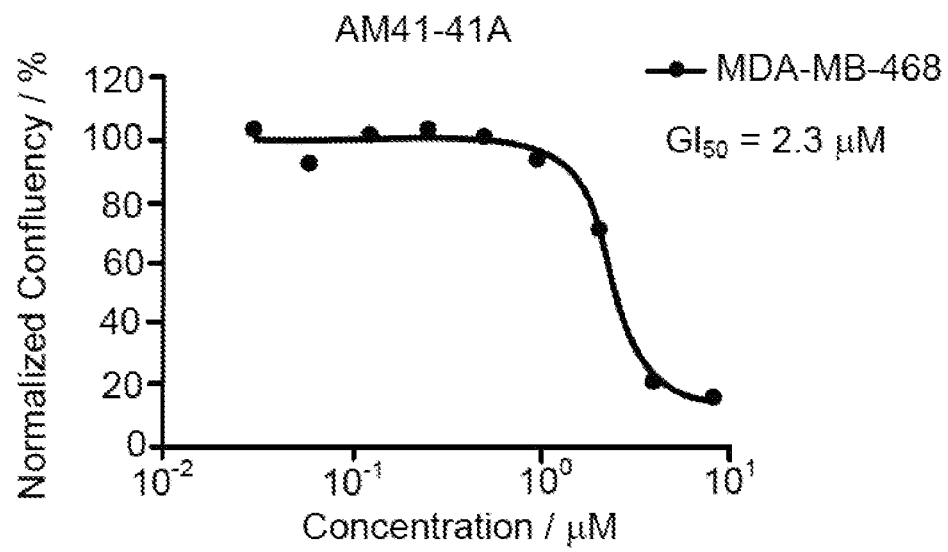
FIG. 44 is a graph depicting the $GI_{50}$ for AM41-41A for MDA-MB-468 cells.
Figure 45:
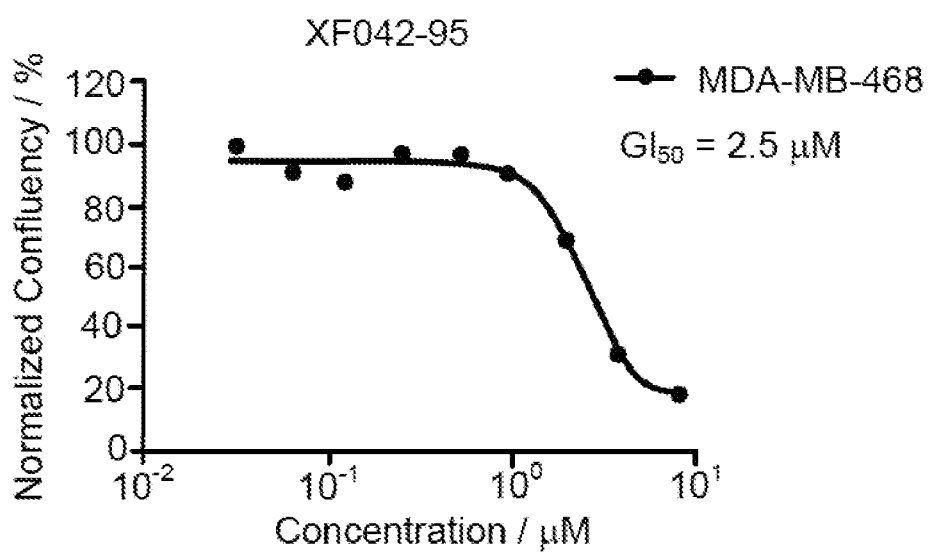
FIG. 45 is a graph depicting the $GI_{50}$ for XF042-95 for MDA-MB-468 cells.
Figure 46:
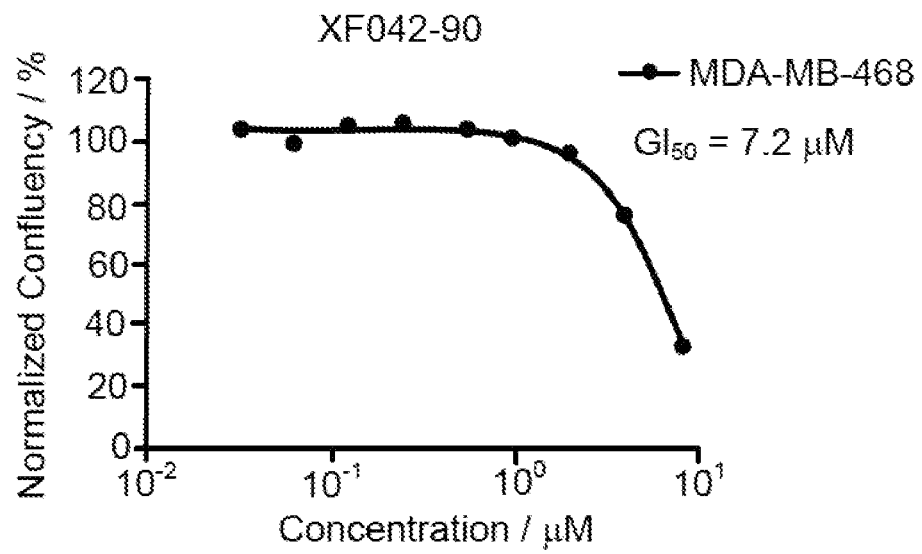
FIG. 46 is a graph depicting the $GI_{50}$ for XF042-90 for MDA-MB-468 cells.
Figure 47:
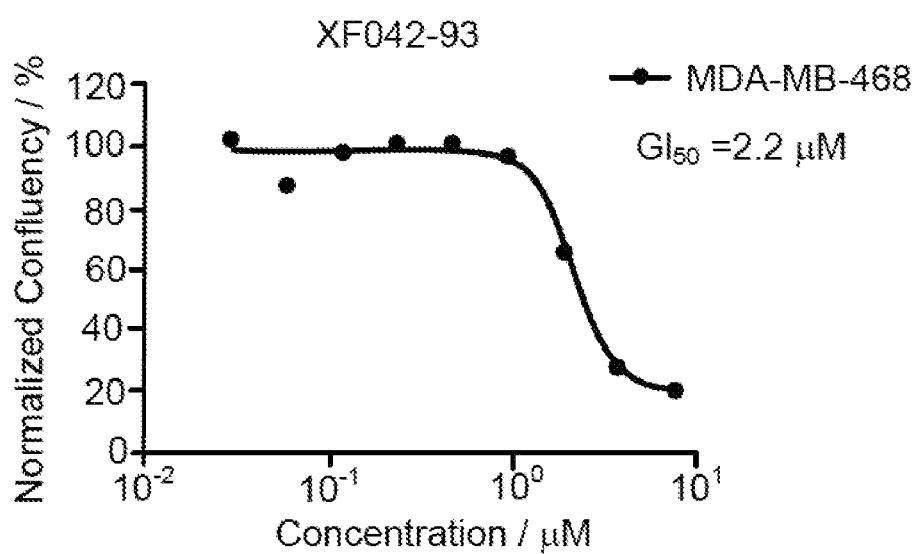
FIG. 47 is a graph depicting the $GI_{50}$ for XF042-93 for MDA-MB-468 cells.
Figure 48:
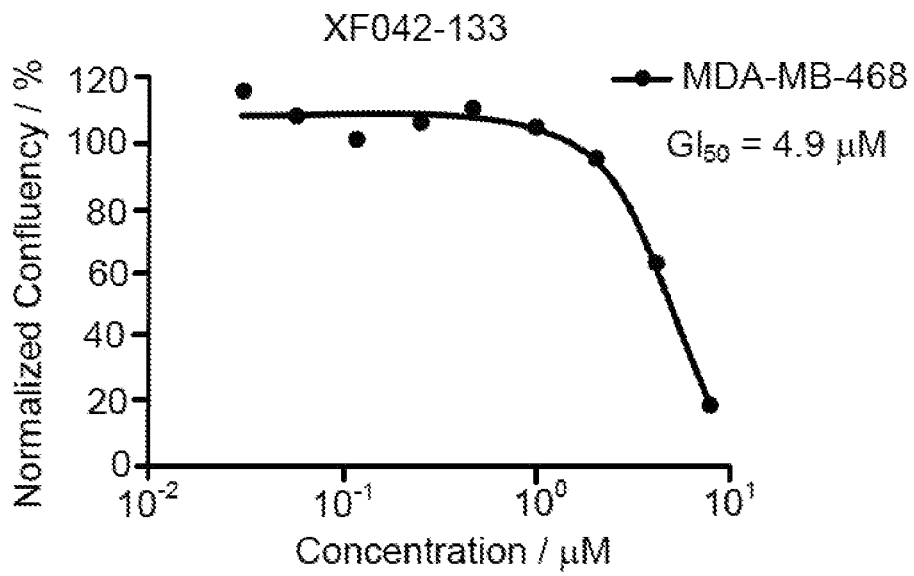
FIG. 48 is a graph depicting the $GI_{50}$ for XF042-133 for MDA-MB-468 cells.
Figure 49:
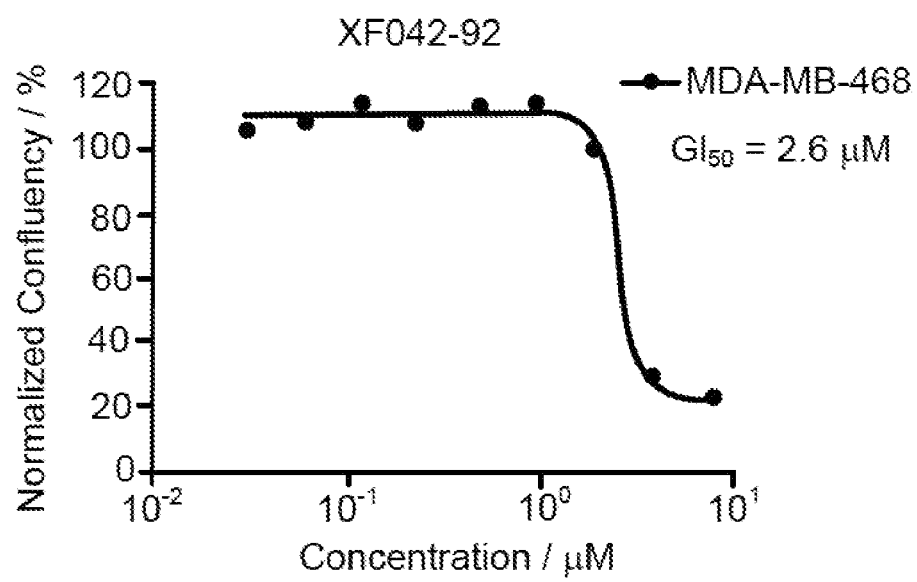
FIG. 49 is a graph depicting the $GI_{50}$ for XF042-92 for MDA-MB-468 cells.

As used herein, the term "degradation/disruption tag" refers to a moiety, which associates with/binds to a ubiquitin ligase for recruitment of the corresponding ubiquitination machinery to the EHZ2/PRC2 complex, or mimics EZH2 protein misfolding and subsequent degradation at the proteasome or loss of function. One or more degradation/disruption tags can be introduced to the solvent-exposed portion of an EZH2 ligand to create EZH2 degraders/disruptors. Exemplary structures of EZH2 degraders/disruptors containing such tags are illustrated in FIGS. 1-3.

For example, a docking model of UNC1999 and its close analogs in PRC2 crystal structures (Broroun et al., 2016; Jiao and Liu. 2015: Justin et al., 2016) shows that two regions of UNC1999 and its analogs are solvent-exposed, thus presenting suitable handles to introduce a degradation/disruption tag without interfering with the inhibitors' ability to bind to EZH2. These regions are the piperazine portion (marked in red in FIGS. 1-3) and isopropyl group (marked in blue in FIGS. 1-3). Structure-activity relationship (SAR) studies showed that modifying these two portions resulted in negligible effects on the molecule's potency towards EZH2 (Konze et al., 2013; Yang et al., 2016).

In some aspects, the degradation/disruption tags of the present disclosure include, for example, immunomodulatory drugs (e.g., thalidomide, pomalidomide, and lenalidomide), VHL-1, bulky hydrophobic groups (e.g., adamantane and 1-((4.4.5.5.5-pentafluoropentyl) sulfinyl) nonane), and their analogs. Immunomodulatory drugs such as 20) thalidomide and pomalidomide (structures shown in FIG. 1) bind cereblon (CRBN or CRL4[CRBN]), a component of a cullin-RING ubiquitin ligase (CRL) complex (Bondeson et al., 2015; Chamberlain et al., 2014; Fischer et al., 2014; Ito et al., 2010; Winter et al., 2015). VHL-1 (structure shown in FIG. 2), a hydroxyproline-containing ligand, binds van Hippel-Lindau protein (VHL or CRL2[VHL]), a component of another CRL complex (Bondeson et al., 2015; Buckley et al., 2012a; Buckley et al., 2012b; Galdeano et al., 2014; Zengerle et al., 2015). Bulky hydrophobic groups (e.g., adamantane) mimic protein misfolding, leading to the degradation of the target protein by proteasome (Buckley and Crews. 2014).

As used herein, a "linker" is a bond, molecule or group of molecules that binds (i.e., bridges) two separate entities to one another. A Linker can provide for optimal spacing of the two entities. The term "linker" in some aspects refers to any agent or molecule that bridges the EZH2 ligand to the degradation/disruption tag. One of ordinary skill in the art recognizes that sites on the EZH2 ligand and/or the degradation/disruption tag, which are not necessary for the function of the bivalent compound of the present disclosures, are ideal sites for attaching a linker, provided that the linker, once attached to the conjugate of the present disclosures, does not interfere with the function of the bivalent compound, i.e., the ability to target EZH2 and recruit a ubiquitin ligase or mimic protein misfolding. The length of the linker can be adjusted to minimize the molecular weight of the degrader/disruptor, avoid any steric interference of EZH2 with the E3 ligase, and/or enhance mimicry of EZH2 protein misfolding by the hydrophobic tag at the same time.

Exemplary linkers include, but are not limited to, the linkers of Formulas I-XIV below:

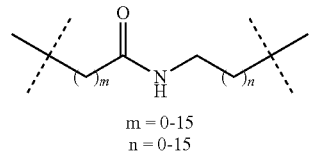

Formula I m = 0-15
n = 0-15

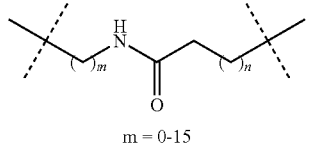

Formula II m = 0-15
n = 0-15

-continued

Formula III

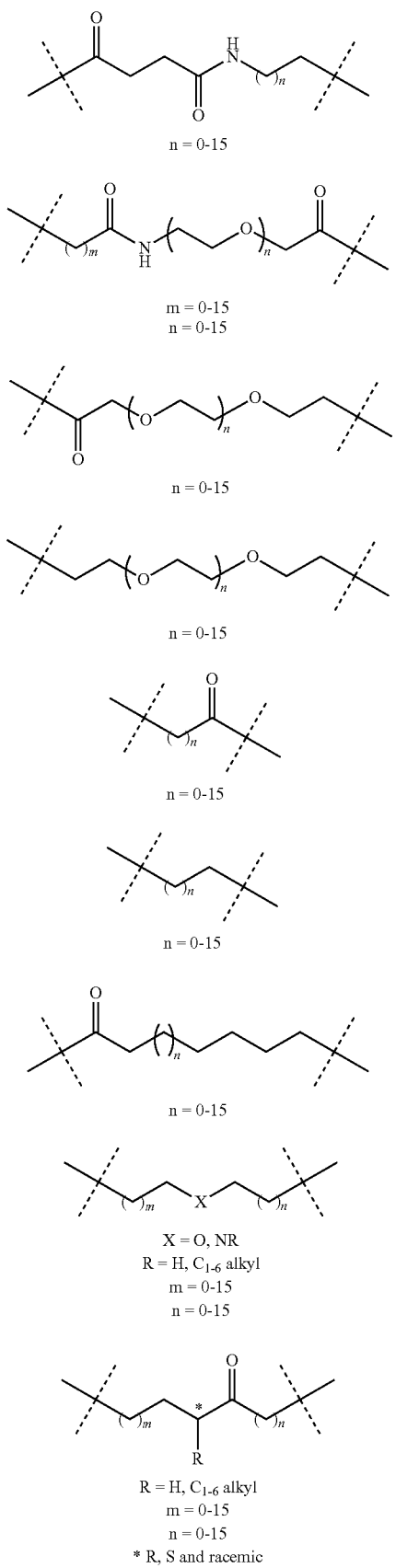

Formula IV

Formula V

Formula VI

Formula VII

Formula VIII

Formula IX

Formula X

Formula XI

-continued

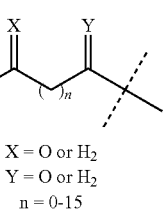

Formula XII

X = O or $H_2$
Y = O or $H_2$
n = 0-15

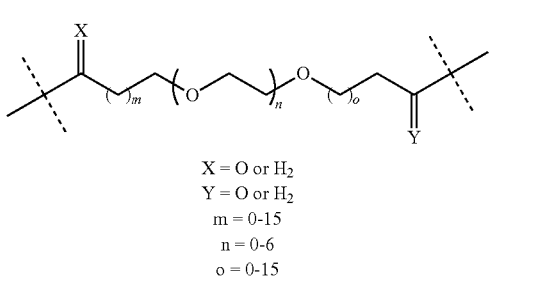

Formula XIII

X = O or $H_2$
Y = O or $H_2$
m = 0-15
n = 0-6
o = 0-15

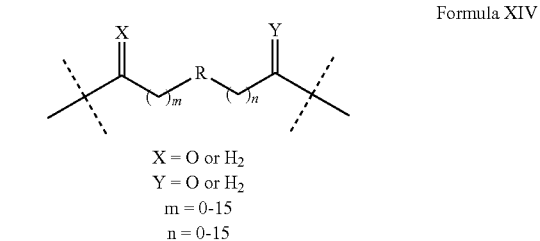

Formula XIV

X = O or $H_2$
Y = O or $H_2$
m = 0-15
n = 0-15

R is independently —$CH_2$—; —$CF_2$—; —CH($C_{1-3}$ alkyl)-; —C($C_{1-3}$ alkyl) ($C_{1-3}$ alkyl)-; —CH═CH—; —C($C_{1-3}$ alkyl)═C($C_{1-3}$ alkyl)-; —C≡C—; —O—; —NH—; —N($C_{1-3}$ alkyl)-; —C(O)NH—; —C(O)N($C_{1-3}$ alkyl)-;

3-13 membered rings, fused rings, bridged rings, or spiro rings with or without heteroatoms (—NH—, —N($C_{1-3}$ alkyl)-, O).

A few examples of R group:

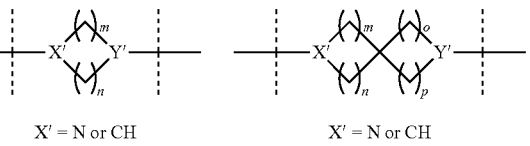

X' = N or CH
Y' = N or CH
m = 0-5
n = 0-5

X' = N or CH
Y' = N or CH
m = 0-5
n = 0-5
o = 0-5
p = 0-5

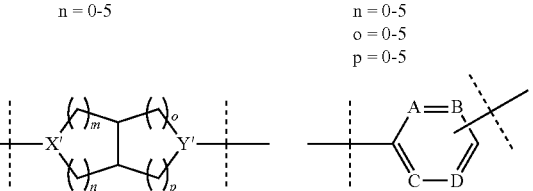

X' = N or CH
Y' = N or CH
m = 0-5
n = 0-5
o = 0-5
p = 0-5

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N -continued

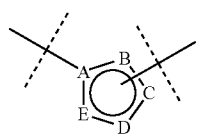

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S In some aspects, the EZH2 degraders/disruptors have the form "X-linker-Y", as shown below:

wherein X comprises a degradation/disruption tag (e.g., adamantane) and Y comprises an EZH2 ligand (e.g., an EZH2 inhibitor). Exemplary degradation/disruption tags (X) and exemplary EZH2 ligands (Y) are described above and are also illustrated below.

X includes but is not limited to

I

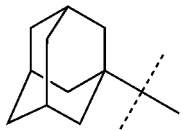

II

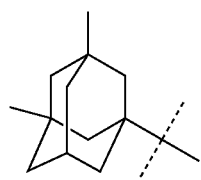

III

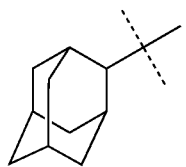

IV

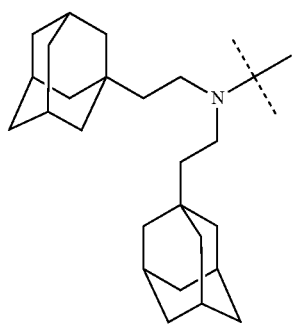

V

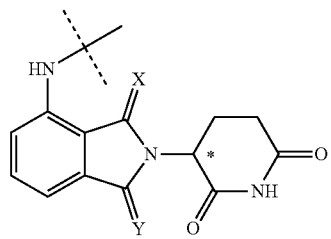

X = O or H$_2$
Y = O or H$_2$
* R, S and racemic

VI

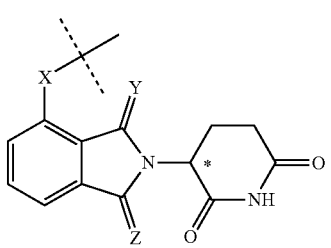

X = O, C$_{1-6}$ alkyl
Y = O or H$_2$
Z = O or H$_2$
* R, S and racemic

VII

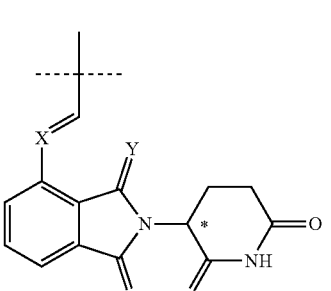

X = C$_{1-6}$ alkyl
Y = O or H$_2$
Z = O or H$_2$
* R, S and racemic

VIII

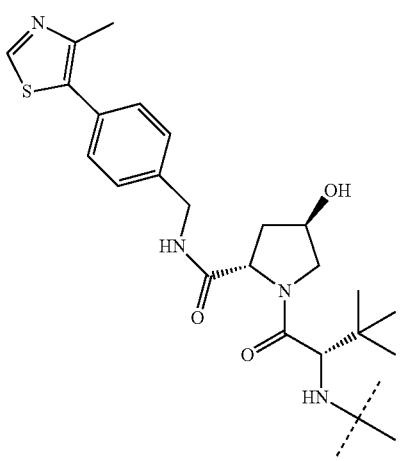

IX
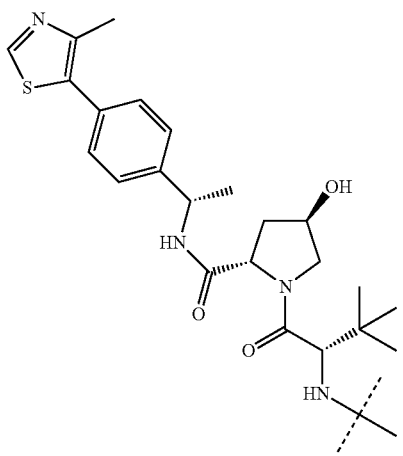
X
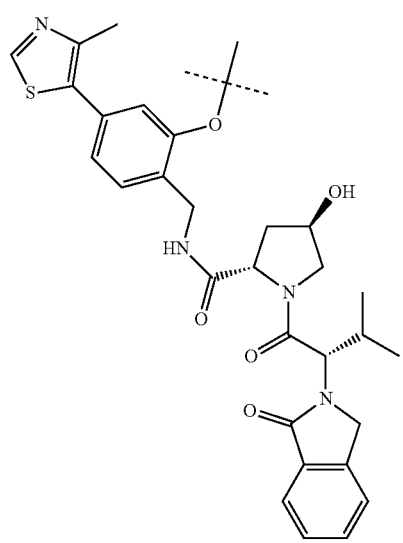
XI
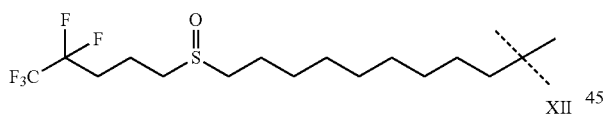
XII
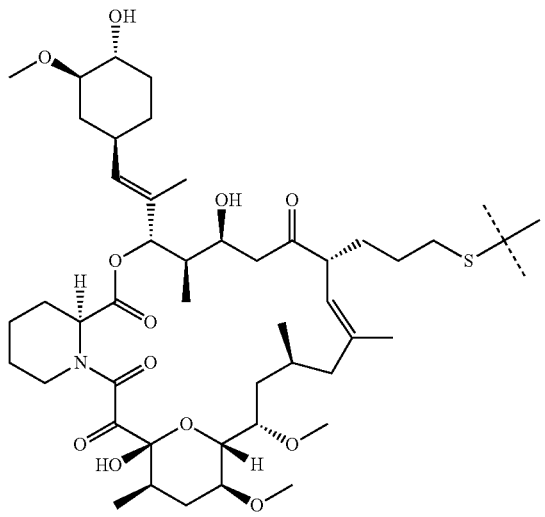
I
Y includes but is not limited to
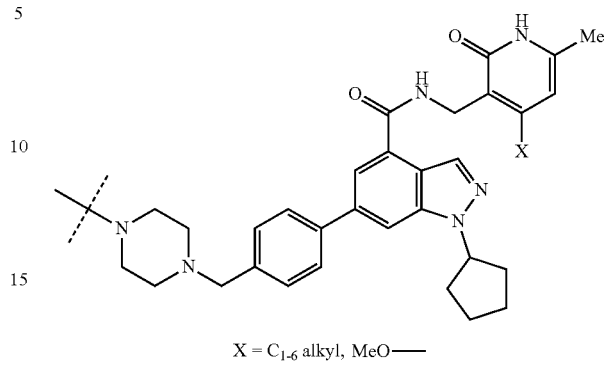
X = C$_{1-6}$ alkyl, MeO—
II
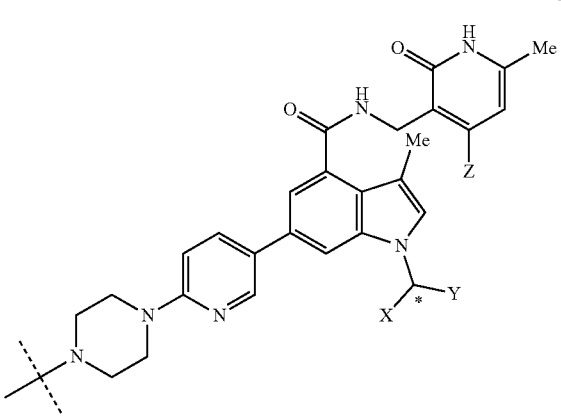
X = H, C$_{1-6}$ alkyl
Y = H, C$_{1-6}$ alkyl
Z = C$_{1-6}$ alkyl, MeO—
* R, S and racemic
III
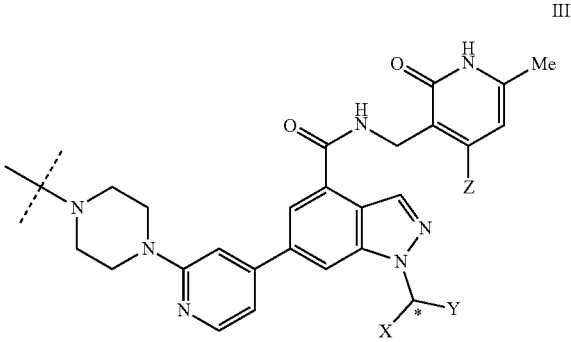
X = H, C$_{1-6}$ alkyl
Y = H, C$_{1-6}$ alkyl
Z = C$_{1-6}$ alkyl, MeO—
* R, S and racemic 21
-continued
IV
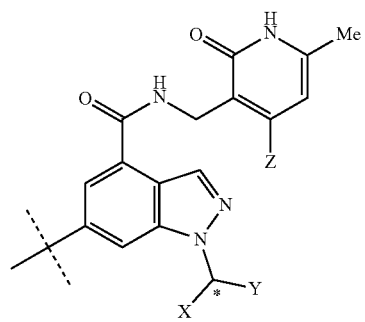
X = H, C$_{1-6}$ alkyl
Y = H, C$_{1-6}$ alkyl
Z = C$_{1-6}$ alkyl, MeO—
G = CH or N
*R, S and racemic
V
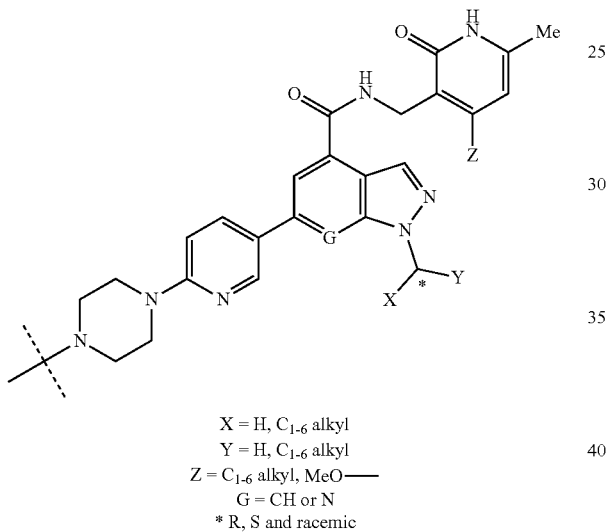
X = H, C$_{1-6}$ alkyl
Y = H, C$_{1-6}$ alkyl
Z = C$_{1-6}$ alkyl, MeO—
G = CH or N
* R, S and racemic
VI
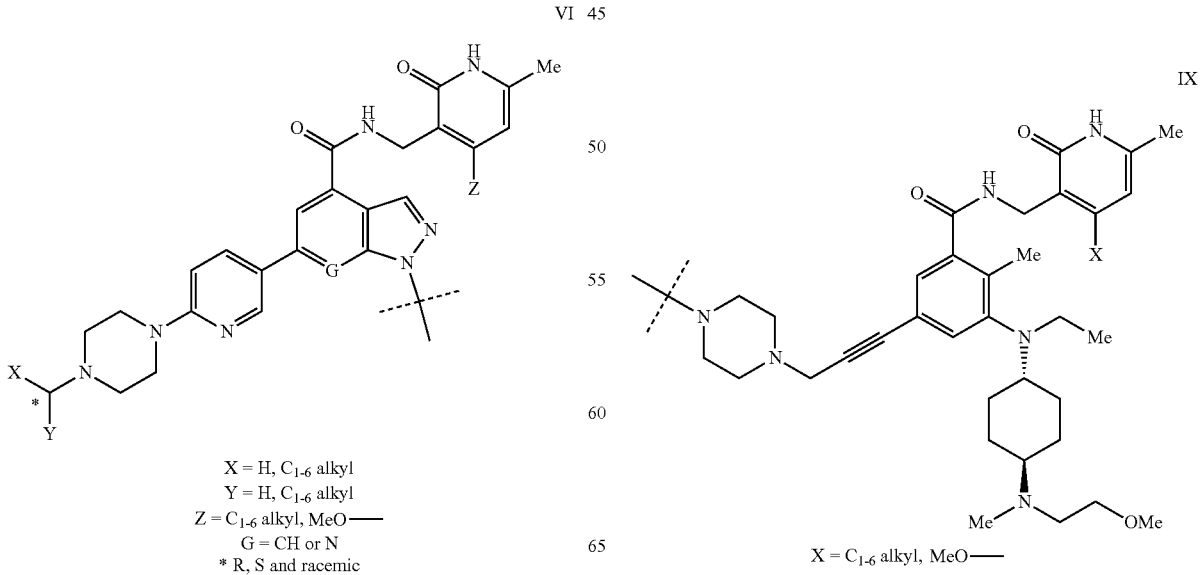
X = H, C$_{1-6}$ alkyl
Y = H, C$_{1-6}$ alkyl
Z = C$_{1-6}$ alkyl, MeO—
G = CH or N
* R, S and racemic
22
-continued
VII
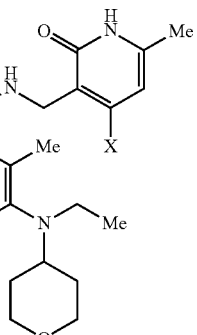
X = C$_{1-6}$ alkyl, MeO—
VIII
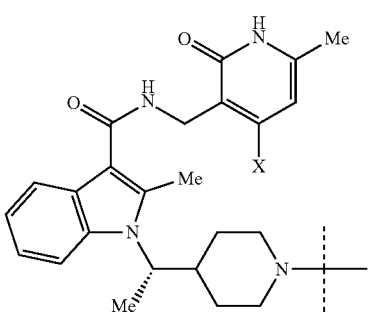
X = C$_{1-6}$ alkyl, MeO—
IX
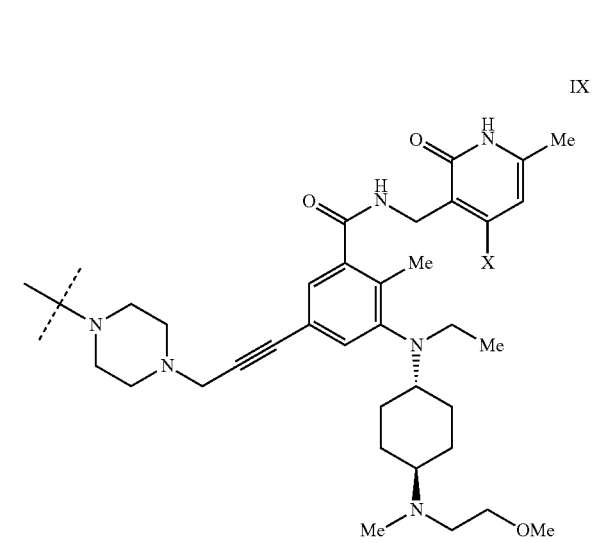
X = C$_{1-6}$ alkyl, MeO—

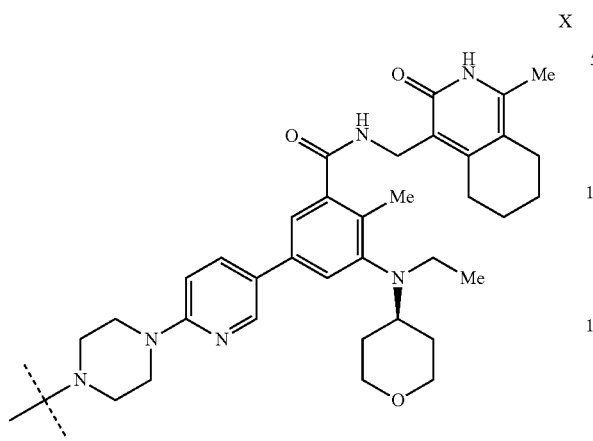

X

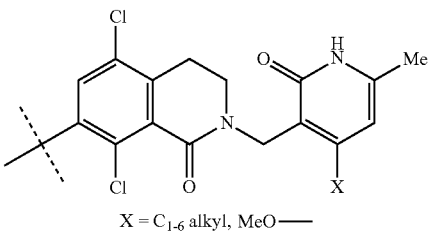

X = C$_{1-6}$ alkyl, MeO—

Novel EZH2 degraders/disruptors developed using the principles and methods described herein are shown in Table 1. Additional EZH2 degraders/disruptors can also be developed using the principles and methods disclosed herein. For example, other linkers, other degradation/disruptor tags, and/or other EZH2 ligands can be synthesized and tested. Some exemplary compounds are shown in the Figures following Table 1.

TABLE 1

| | Structure | Chemical Name |
|---|---|---|
| AM16-10A | 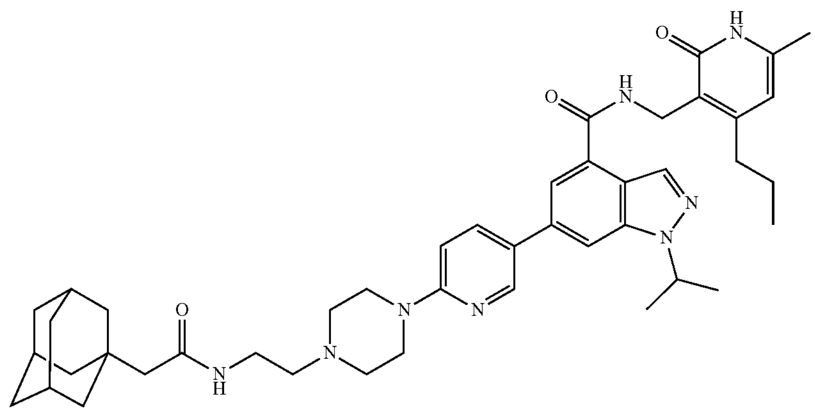 [SMILES: CCCc1cc(C)[nH]c(=O)c1CNC(=O)c1cc(-c2ccc(N3CCN(CCNC(=O)CC45CC6CC(CC(C6)C4)C5)CC3)nc2)cc2c1cnn2C(C)C] | 6-(6-(4-(2-(2-((3r,5r,7r)-adamantan-1-yl)acetamido)ethyl)piperazin-1-yl)pyridin-3-yl)-1-isopropyl-N-((6-methyl-2-oxo-4-propyl-1,2-dihydropyridin-3-yl)methyl)-1H-indazole-4-carboxamide |
| AM16-11A | 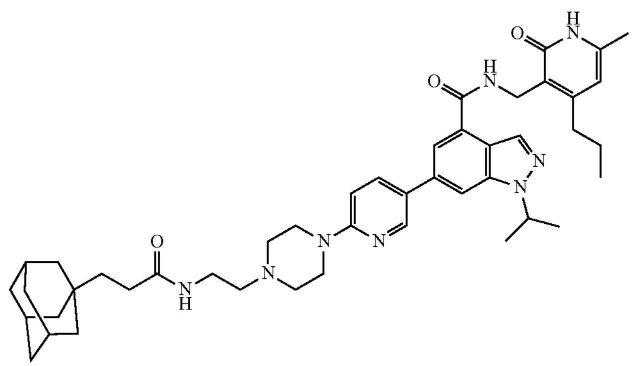 [SMILES: CCCc1cc(C)[nH]c(=O)c1CNC(=O)c1cc(-c2ccc(N3CCN(CCNC(=O)CCC45CC6CC(CC(C6)C4)C5)CC3)nc2)cc2c1cnn2C(C)C] | 6-(6-(4-(2-(3-((1r,3s)-adamantan-1-yl)propanamido)ethyl)piperazin-1-yl)pyridin-3-yl)-1-isopropyl-N-((6-methyl-2-oxo-4-propyl-1,2-dihydropyridin-3-yl)methyl)-1H-indazole-4-carboxamide |

TABLE 1-continued

| | Structure | Chemical Name |
|---|---|---|
| AM16-37A | 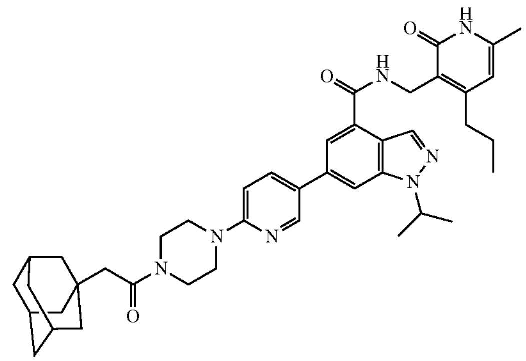 [SMILES: CCCc1cc(C)[nH]c(=O)c1CNC(=O)c1cc(-c2ccc(N3CCN(C(=O)CC45CC6CC(CC(C6)C4)C5)CC3)nc2)cc2c1cnn2C(C)C] | 6-(6-(4-(2-((1s,3s)-adamantan-1-yl)acetyl)piperazin-1-yl)pyridin-3-yl)-1-isopropyl-N-((6-methyl-2-oxo-4-propyl-1,2-dihydropyridin-3-yl)methyl)-1H-indazole-4-carboxamide |
| AM16-38A | 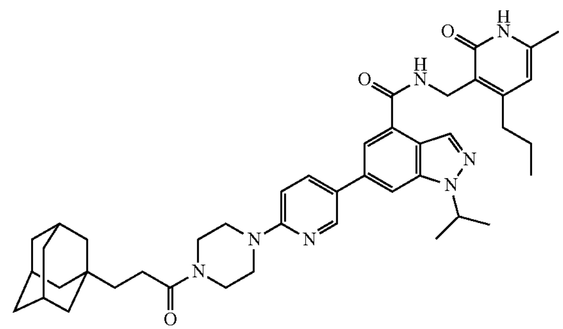 [SMILES: CCCc1cc(C)[nH]c(=O)c1CNC(=O)c1cc(-c2ccc(N3CCN(C(=O)CCC45CC6CC(CC(C6)C4)C5)CC3)nc2)cc2c1cnn2C(C)C] | 6-(6-(4-(3-((3r,5r,7r)-adamantan-1-yl)propanoyl)piperazin-1-yl)pyridin-3-yl)-1-isopropyl-N-((6-methyl-2-oxo-4-propyl-1,2-dihydropyridin-3-yl)methyl)-1H-indazole-4-carboxamide |
| XY019-43 | 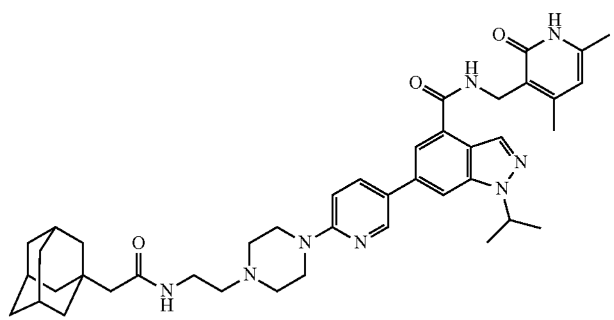 [SMILES: Cc1cc(C)c(CNC(=O)c2cc(-c3ccc(N4CCN(CCNC(=O)CC56CC7CC(CC(C7)C5)C6)CC4)nc3)cc3c2cnn3C(C)C)c(=O)[nH]1] | 6-(6-(4-(2-(2-((3r,5r,7r)-adamantan-1-yl)acetamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued

| | Structure | Chemical Name |
|---|---|---|
| XY019-44 | 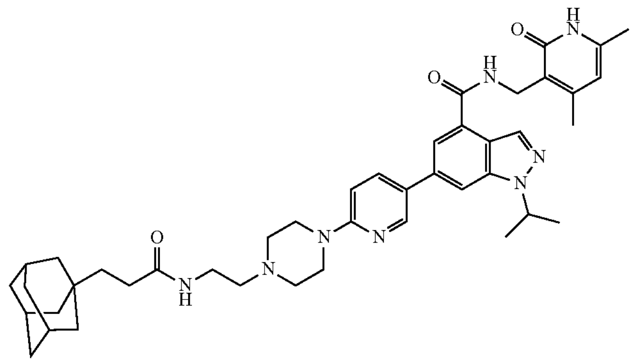 [SMILES: Cc1cc(C)c(CNC(=O)c2cc(-c3ccc(N4CCN(CCNC(=O)CCC56CC7CC(CC(C7)C5)C6)CC4)nc3)cc3c2cnn3C(C)C)c(=O)[nH]1] | 6-(6-(4-(2-(3-((3r,5r,7r)-adamantan-1-yl)propanamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| XY019-079 | 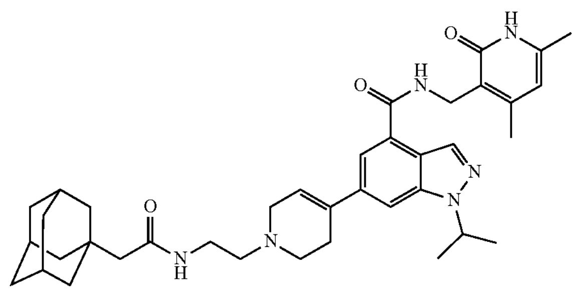 [SMILES: Cc1cc(C)c(CNC(=O)c2cc(C3=CCN(CCNC(=O)CC45CC6CC(CC(C6)C4)C5)CC3)cc3c2cnn3C(C)C)c(=O)[nH]1] | 6-(1-(2-(2-((3r,5r,7r)-adamantan-1-yl)acetamido)ethyl)-1,2,3,6-tetrahydropyridin-4-yl)-N-((4,6-dimethyl-2-oxo-1,2-dihydropyridin-3-yl)methyl)-1-isopropyl-1H-indazole-4-carboxamide |
| XY019-080 | 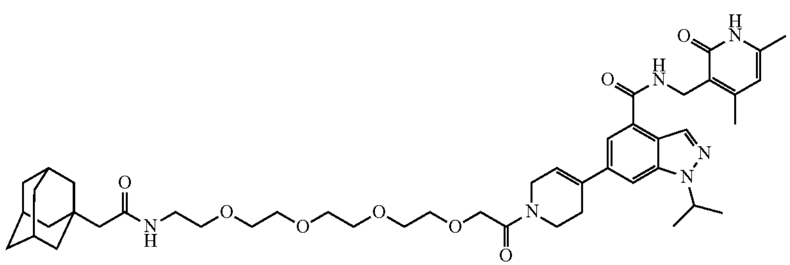 [SMILES: Cc1cc(C)c(CNC(=O)c2cc(C3=CCN(C(=O)COCCOCCOCCOCCNC(=O)CC45CC6CC(CC(C6)C4)C5)CC3)cc3c2cnn3C(C)C)c(=O)[nH]1] | 6-(1-(1-((3r,5r,7r)-adamantan-1-yl)-2-oxo-6,9,12,15-tetraoxa-3-azaheptadecan-17-oyl)-1,2,3,6-tetrahydropyridin-4-yl)-N-((4,6-dimethyl-2-oxo-1,2-dihydropyridin-3-yl)methyl)-1-isopropyl-1H-indazole-4-carboxamide |

TABLE 1-continued
| | Structure | Chemical Name |
|---|---|---|
| AM16-91A | 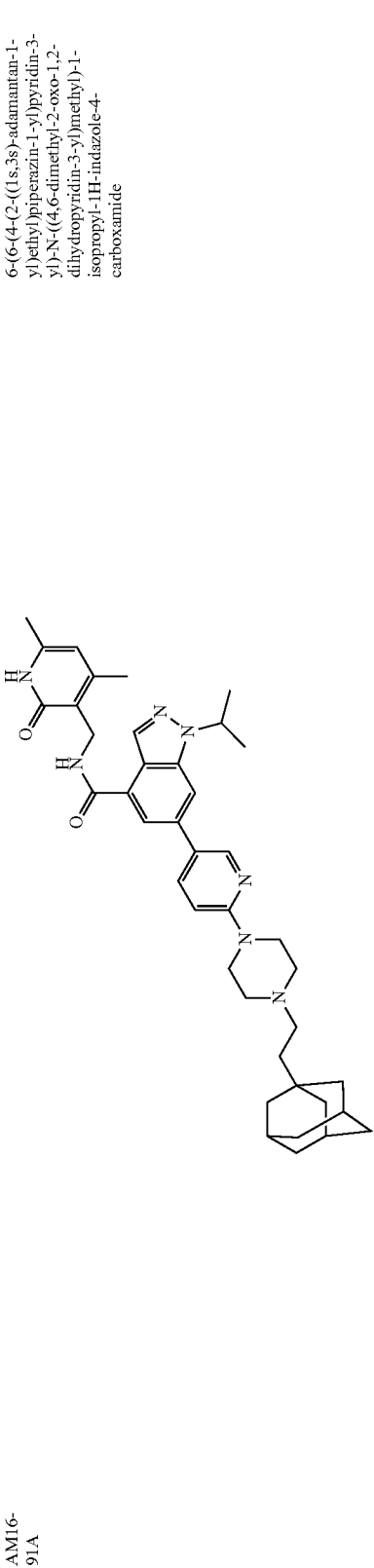 | 6-(6-(4-(2-((1s,3s)-adamantan-1-yl)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| AM16-92A | 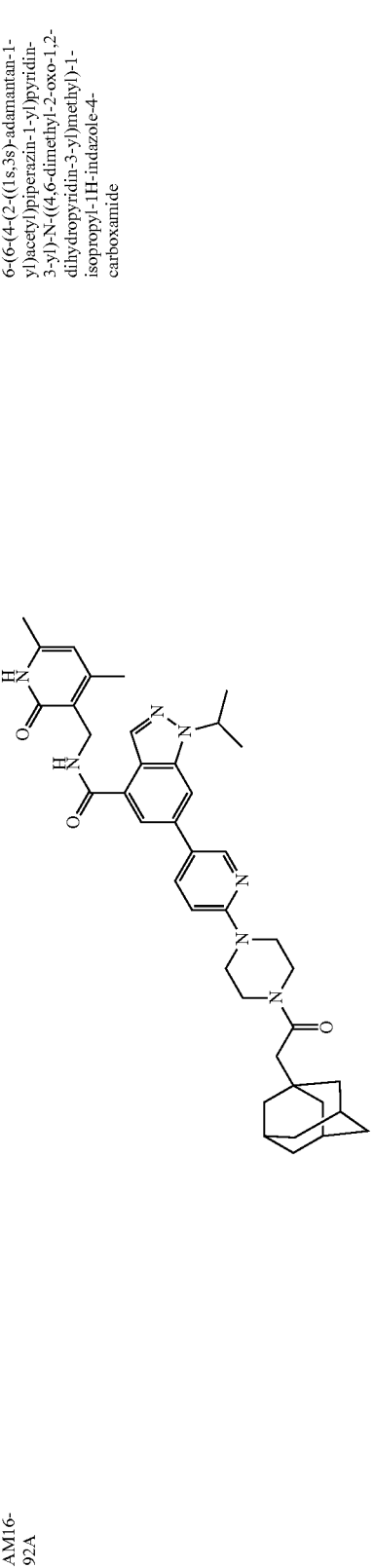 | 6-(6-(4-(2-((1s,3s)-adamantan-1-yl)acetyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued

| | Structure | Chemical Name |
|---|---|---|
| AM16-93A | 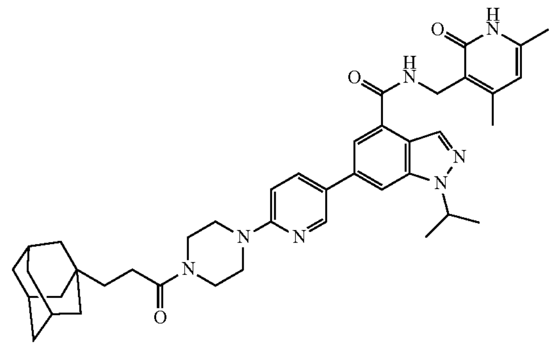 [SMILES: Cc1cc(C)c(CNC(=O)c2cc(-c3ccc(N4CCN(C(=O)CCC56CC7CC(CC(C7)C5)C6)CC4)nc3)cc3c2cnn3C(C)C)c(=O)[nH]1] | 6-(6-(4-(3-((1r,3s)-adamantan-1-yl)propanoyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| AM16-97A | 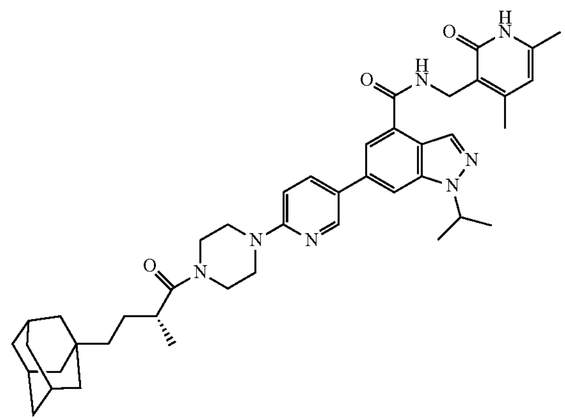 [SMILES: Cc1cc(C)c(CNC(=O)c2cc(-c3ccc(N4CCN(C(=O)[C@H](C)CCC56CC7CC(CC(C7)C5)C6)CC4)nc3)cc3c2cnn3C(C)C)c(=O)[nH]1] | 6-(6-(4-((2R)-4-((1r,3S)-adamantan-1-yl)-2-methylbutanoyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued
| | Structure | Chemical Name |
|---|---|---|
| AM16-100A | 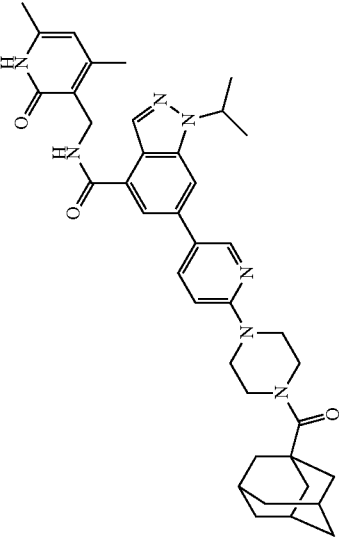 | 6-(6-(4-((3r,5r,7r)-adamantane-1-carbonyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| AM16-101A | 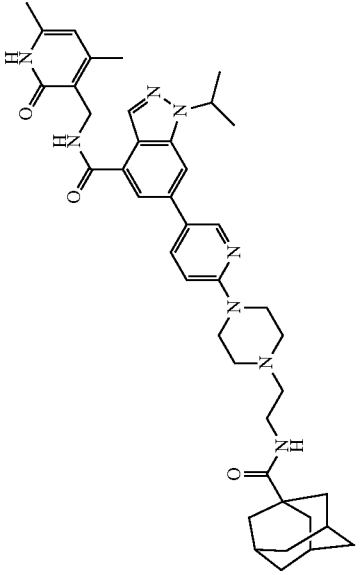 | 6-(6-(4-(2-((1s,3s)-adamantane-1-carboxamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued
| | Structure | Chemical Name |
|---|---|---|
| AM16-102A | 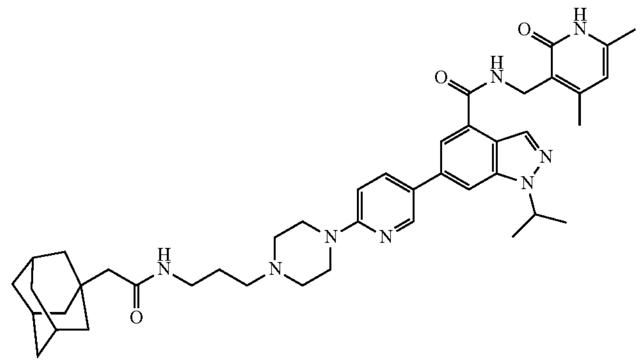 [SMILES: Cc1cc(C)c(CNC(=O)c2cc(-c3ccc(N4CCN(CCCNC(=O)CC56CC7CC(CC(C7)C5)C6)CC4)nc3)cc3c2cnn3C(C)C)c(=O)[nH]1] | 6-(6-(4-(3-(2-((1s,3s)-adamantan-1-yl)acetamido)propyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| AM16-105A | 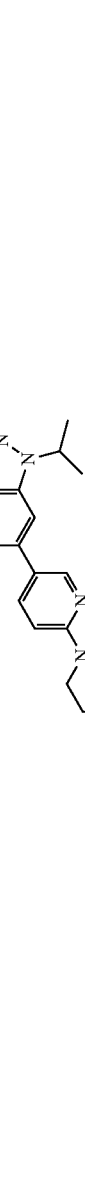 | 6-(6-(4-(2-((2R)-4-((1r,3S)-adamantan-1-yl)-2-methylbutanamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued
| | Structure | Chemical Name |
|---|---|---|
| AM16-106A | 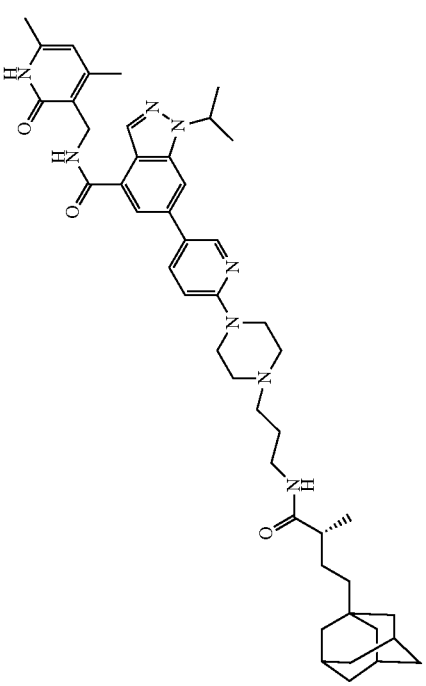 | 6-(6-(4-(3-((R)-4-((3R,5R,7R)-adamantan-1-yl)-2-methyl-butanamido)propyl)piperazin-1-yl)pyridin-3-yl)-N-((4,6-dimethyl-2-oxo-1,2-dihydro-pyridin-3-yl)methyl)-1-isopropyl-1H-indazole-4-carboxamide |
| XY012-120 | 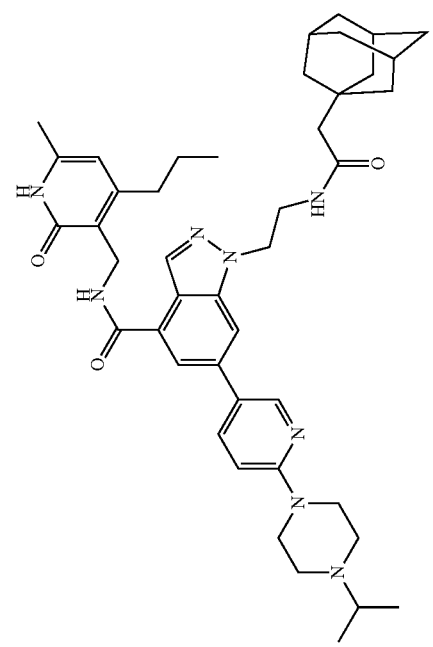 | 1-(2-(2-((1s,3s)-adamantan-1-yl)acetamido)ethyl)-6-(6-(4-isopropylpiperazin-1-yl)pyridin-3-yl)-N-((6-methyl-2-oxo-4-propyl-1,2-dihydropyridin-3-yl)methyl)-1H-indazole-4-carboxamide |

TABLE 1-continued
| | Structure | Chemical Name |
|---|---|---|
| AM29-21A | 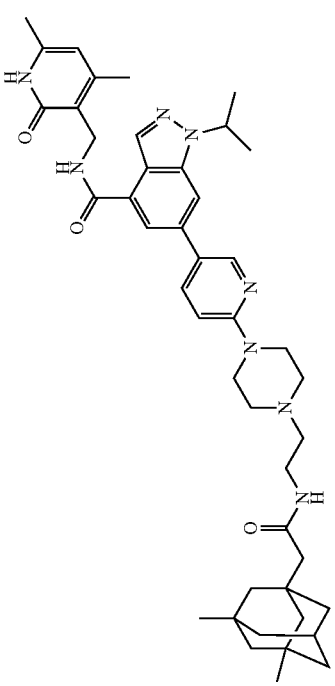 | N-((4,6-dimethyl-2-oxo-1,2-dihydropyridin-3-yl)methyl)-6-(6-(4-(2-((1r,3R,5S,7r)-3,5-dimethyladamantan-1-yl)acetamido)ethyl)piperazin-1-yl)pyridin-3-yl)-1-isopropyl-1H-indazole-4-carboxamide |
| AM29-22A | 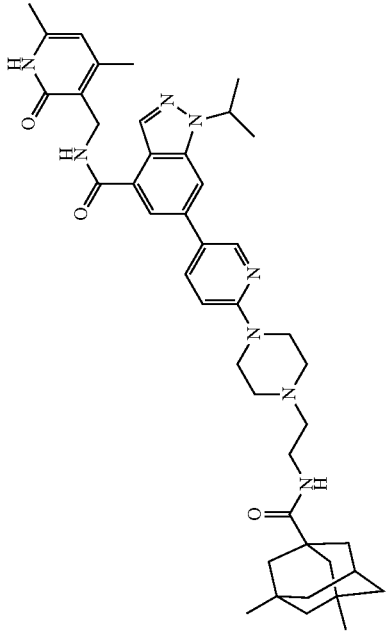 | N-((4,6-dimethyl-2-oxo-1,2-dihydropyridin-3-yl)methyl)-6-(6-(4-(2-((1R,3S)-3,5-dimethyladamantane-1-carboxamido)ethyl)piperazin-1-yl)pyridin-3-yl)-1-isopropyl-1H-indazole-4-carboxamide |

TABLE 1-continued
| | Structure | Chemical Name |
|---|---|---|
| AM29-32A | 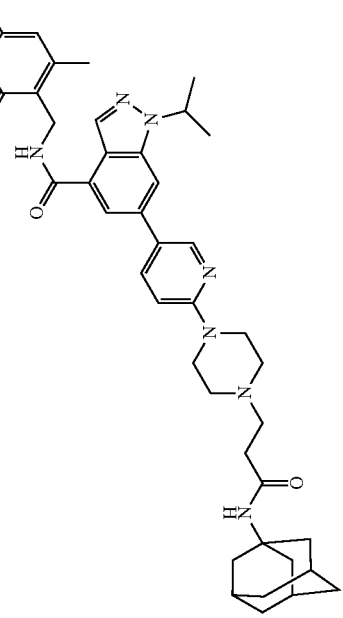 | 6-(6-(4-(3-(((1s,3s)-adamantan-1-yl)amino)-3-oxopropyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| AM29-33A | 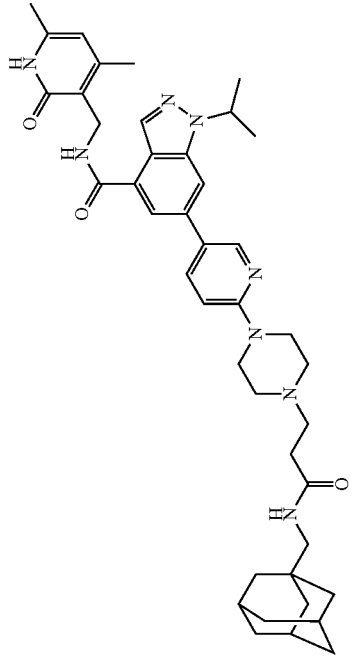 | 6-(6-(4-(3-((((3r,5r,7r)-adamantan-1-yl)methyl)amino)-3-oxopropyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued

| | Structure | Chemical Name |
|---|---|---|
| AM16-103A | 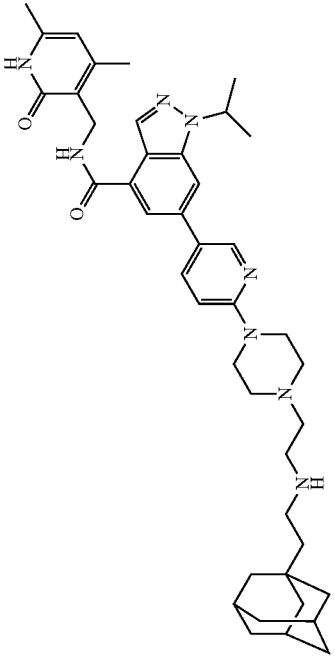 | 6-(6-(4-(2-(2-((3r,5r,7r)-adamantan-1-yl)ethyl)amino)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| AM29-182A | 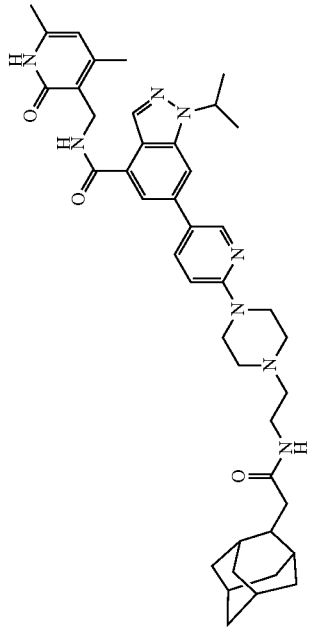 | 6-(6-(4-(2-(2-((1r,3r,5r,7r)-adamantan-2-yl)acetamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| AM29-55A | 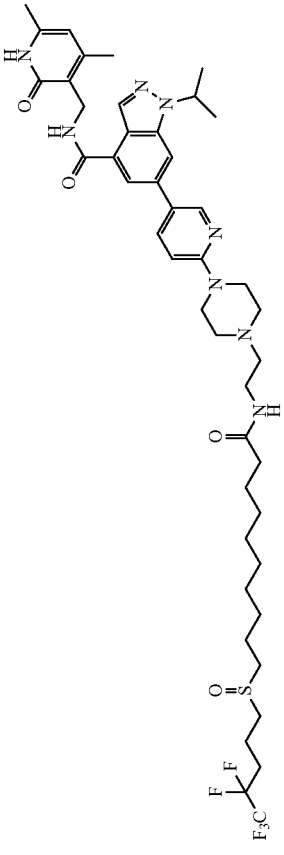 | N-((4,6-dimethyl-2-oxo-1,2-dihydropyridin-3-yl)methyl)-1-isopropyl-6-(6-(4-(2-(10-((4,4,5,5,5-pentafluoropentyl)sulfinyl)decanamido)ethyl)piperazin-1-yl)pyridin-3-yl)-1H-indazole-4-carboxamide |

TABLE 1-continued

| | Structure | Chemical Name |
|---|---|---|
| AM29-151A | 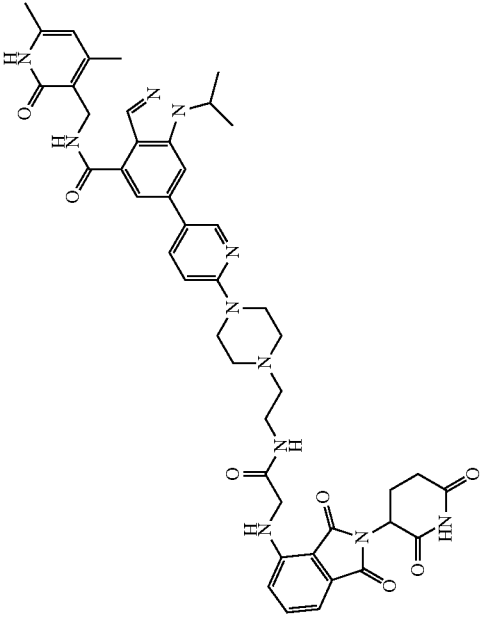 | N-((4,6-dimethyl-2-oxo-1,2-dihydropyridin-3-yl)methyl)-6-(6-(4-(2-(2-((2-(2,6-dioxopiperidin-3-yl)-1,3-dioxoisoindolin-4-yl)amino)acetamido)ethyl)piperazin-1-yl)pyridin-3-yl)-1-isopropyl-1H-indazole-4-carboxamide |
| AM29-152A | 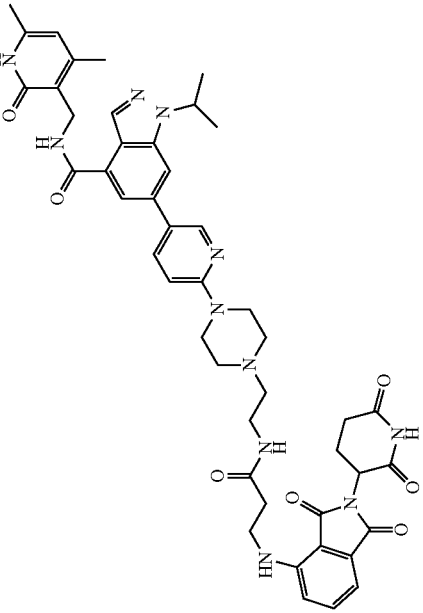 | N-((4,6-dimethyl-2-oxo-1,2-dihydropyridin-3-yl)methyl)-6-(6-(4-(2-(3-((2-(2,6-dioxopiperidin-3-yl)-1,3-dioxoisoindolin-4-yl)amino)propanamido)ethyl)piperazin-1-yl)pyridin-3-yl)-1-isopropyl-1H-indazole-4-carboxamide |

TABLE 1-continued

| | Structure | Chemical Name |
|---|---|---|
| AM29-137A | 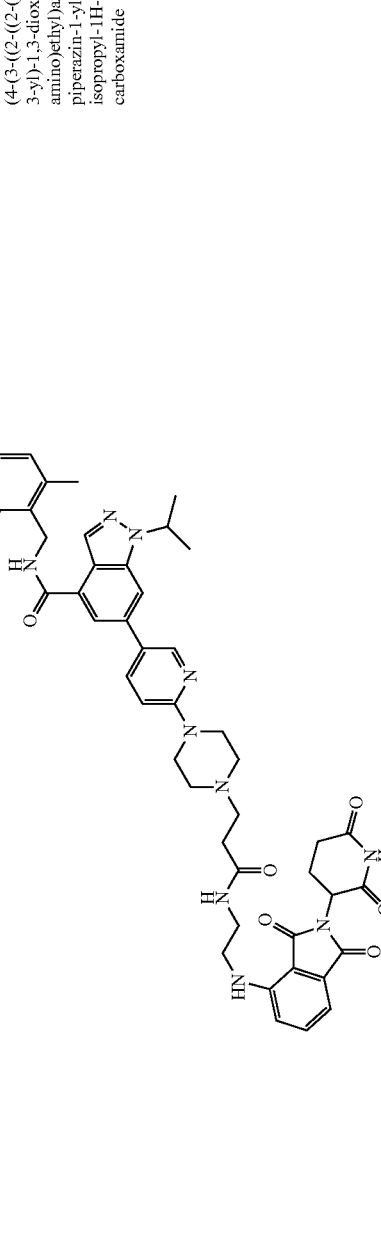 | N-((4,6-dimethyl-2-oxo-1,2-dihydropyridin-3-yl)methyl)-6-(6-(4-(3-((2-((2-(2,6-dioxopiperidin-3-yl)-1,3-dioxoisoindolin-4-yl)amino)ethyl)amino)-3-oxopropyl)piperazin-1-yl)pyridin-3-yl)-1-isopropyl-1H-indazole-4-carboxamide |
| AM29-153A | 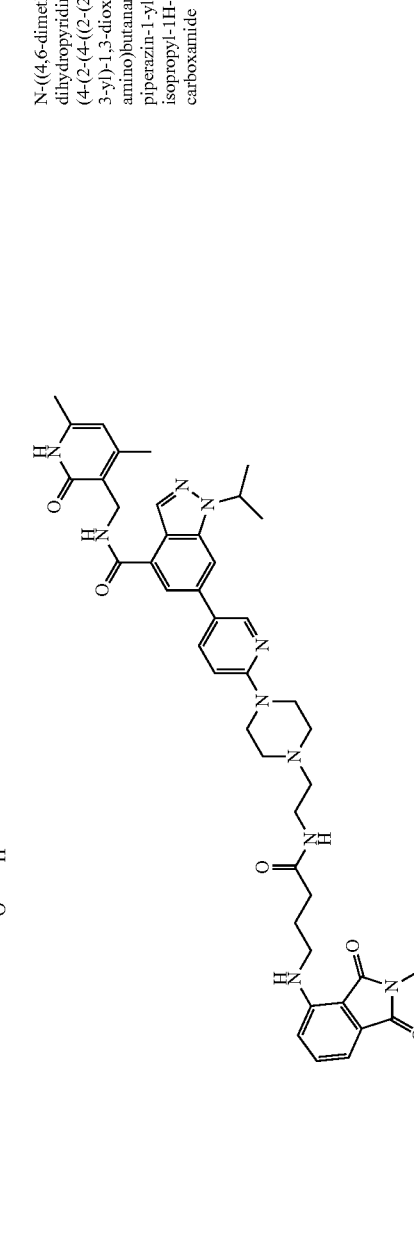 | N-((4,6-dimethyl-2-oxo-1,2-dihydropyridin-3-yl)methyl)-6-(6-(4-(2-(4-((2-(2,6-dioxopiperidin-3-yl)-1,3-dioxoisoindolin-4-yl)amino)butanamido)ethyl)piperazin-1-yl)pyridin-3-yl)-1-isopropyl-1H-indazole-4-carboxamide |

TABLE 1-continued

| | Structure | Chemical Name |
|---|---|---|
| AM29-138A | 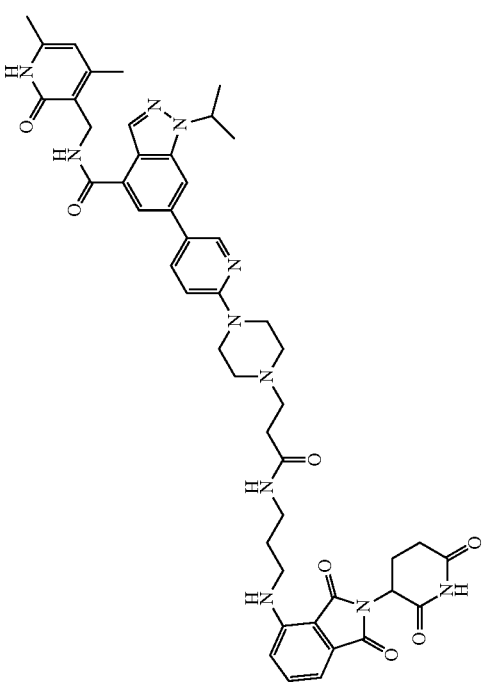 | N-((4,6-dimethyl-2-oxo-1,2-dihydropyridin-3-yl)methyl)-6-(6-(4-(3-((2-(2,6-dioxopiperidin-3-yl)-1,3-dioxoisoindolin-4-yl)amino)propyl)amino)-3-oxopropyl)piperazin-1-yl)pyridin-3-yl)-1-isopropyl-1H-indazole-4-carboxamide |
| AM29-154A | 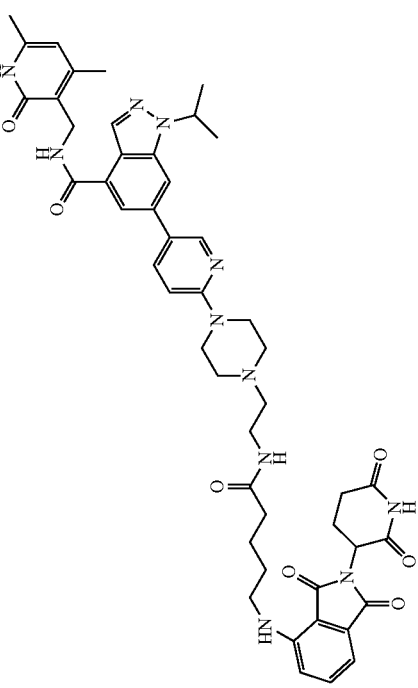 | N-((4,6-dimethyl-2-oxo-1,2-dihydropyridin-3-yl)methyl)-6-(6-(4-(2-(5-((2-(2,6-dioxopiperidin-3-yl)-1,3-dioxoisoindolin-4-yl)amino)pentanamido)ethyl)piperazin-1-yl)pyridin-3-yl)-1-isopropyl-1H-indazole-4-carboxamide |

TABLE 1-continued

| | Structure | Chemical Name |
|---|---|---|
| AM29-139A | 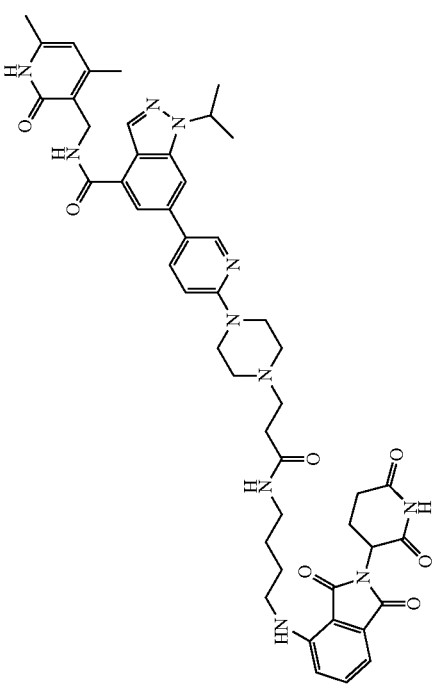 | N-((4,6-dimethyl-2-oxo-1,2-dihydropyridin-3-yl)methyl)-6-(6-(4-(3-((4-(2-(2,6-dioxopiperidin-3-yl)-1,3-dioxoisoindolin-4-yl)amino)butyl)amino)-3-oxopropyl)piperazin-1-yl)pyridin-3-yl)-1-isopropyl-1H-indazole-4-carboxamide |
| AM29-155A | 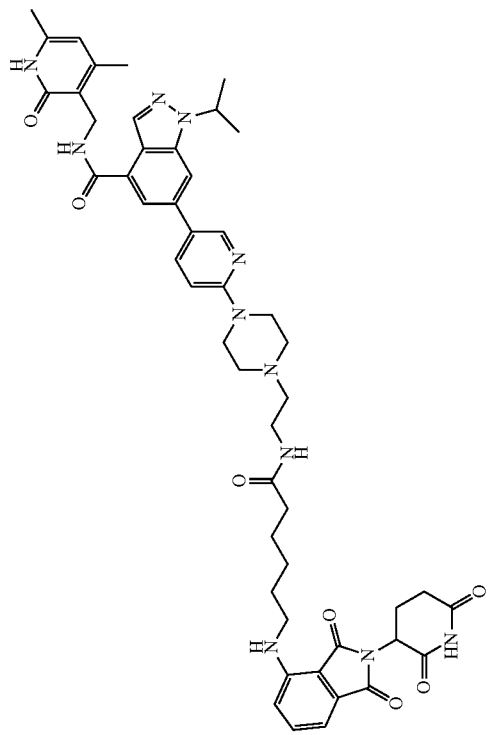 | N-((4,6-dimethyl-2-oxo-1,2-dihydropyridin-3-yl)methyl)-6-(6-(4-(2-(6-((2-(2,6-dioxopiperidin-3-yl)-1,3-dioxoisoindolin-4-yl)amino)hexanamido)ethyl)piperazin-1-yl)pyridin-3-yl)-1-isopropyl-1H-indazole-4-carboxamide |

TABLE 1-continued

| | Structure | Chemical Name |
|---|---|---|
| AM29-170A | 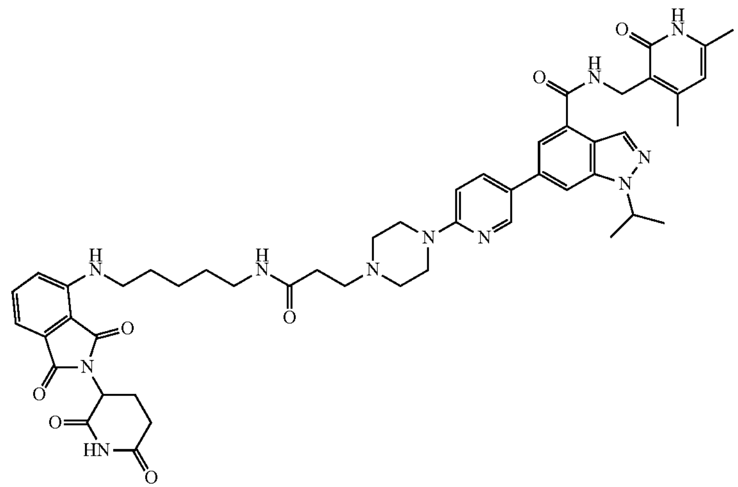 [SMILES: Cc1cc(C)c(CNC(=O)c2cc(-c3ccc(N4CCN(CCC(=O)NCCCCCNc5cccc6c5C(=O)N(C5CCC(=O)NC5=O)C6=O)CC4)nc3)cc3c2cnn3C(C)C)c(=O)[nH]1] | N-((4,6-dimethyl-2-oxo-1,2-dihydropyridin-3-yl)methyl)-6-(6-(4-(3-((5-((2-(2,6-dioxopiperidin-3-yl)-1,3-dioxoisoindolin-4-yl)amino)pentyl)amino)-3-oxopropyl)piperazin-1-yl)pyridin-3-yl)-1-isopropyl-1H-indazole-4-carboxamide |
| AM29-156A | 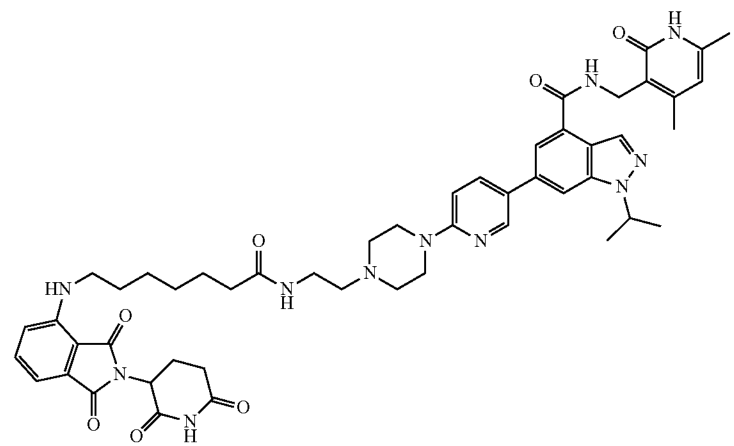 [SMILES: Cc1cc(C)c(CNC(=O)c2cc(-c3ccc(N4CCN(CCNC(=O)CCCCCCNc5cccc6c5C(=O)N(C5CCC(=O)NC5=O)C6=O)CC4)nc3)cc3c2cnn3C(C)C)c(=O)[nH]1] | N-((4,6-dimethyl-2-oxo-1,2-dihydropyridin-3-yl)methyl)-6-(6-(4-(2-(7-((2-(2,6-dioxopiperidin-3-yl)-1,3-dioxoisoindolin-4-yl)amino)heptanamido)ethyl)piperazin-1-yl)pyridin-3-yl)-1-isopropyl-1H-indazole-4-carboxamide |

TABLE 1-continued

| | Structure | Chemical Name |
|---|---|---|
| AM29-171A | 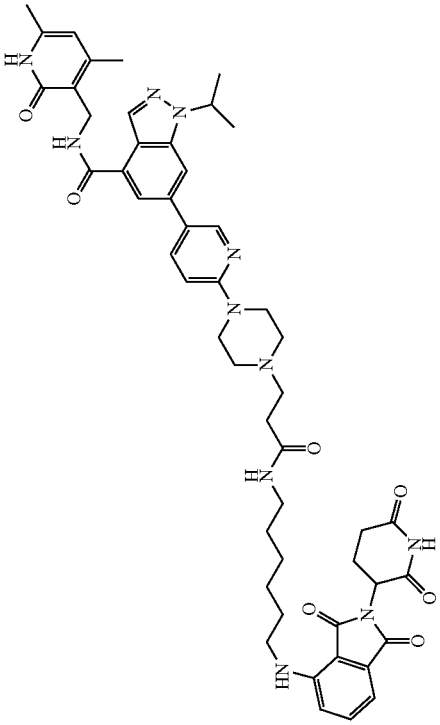 | N-((4,6-dimethyl-2-oxo-1,2-dihydropyridin-3-yl)methyl)-6-(6-(4-(3-((6-((2-(2,6-dioxopiperidin-3-yl)-1,3-dioxoisoindolin-4-yl)amino)hexyl)amino)-3-oxopropyl)piperazin-1-yl)pyridin-3-yl)-1-isopropyl-1H-indazole-4-carboxamide |
| AM29-157A | 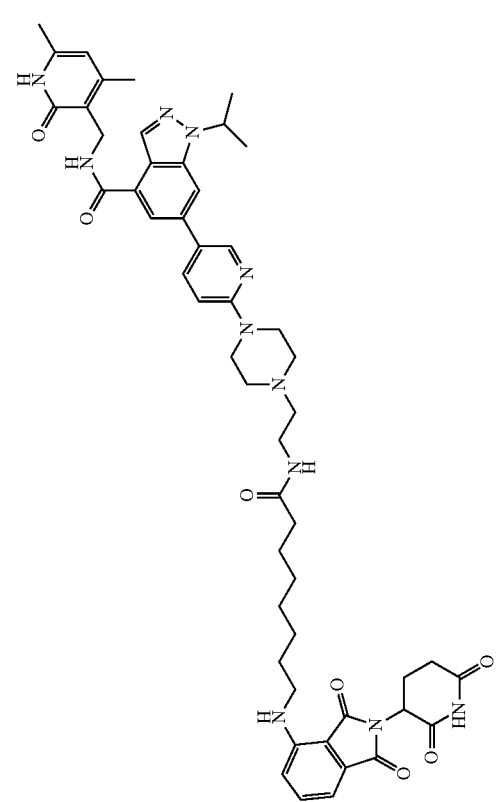 | N-((4,6-dimethyl-2-oxo-1,2-dihydropyridin-3-yl)methyl)-6-(6-(4-(2-(8-((2-(2,6-dioxopiperidin-3-yl)-1,3-dioxoisoindolin-4-yl)amino)octanamido)ethyl)piperazin-1-yl)pyridin-3-yl)-1-isopropyl-1H-indazole-4-carboxamide |

TABLE 1-continued

| | Structure | Chemical Name |
|---|---|---|
| AM29-172A | 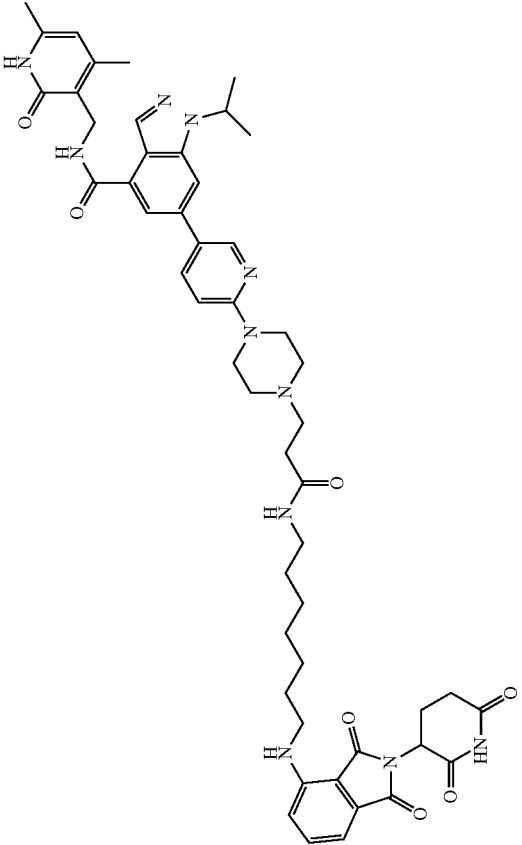 | N-((4,6-dimethyl-2-oxo-1,2-dihydropyridin-3-yl)methyl)-6-(6-(4-(3-((7-((2-(2,6-dioxopiperidin-3-yl)-1,3-dioxoisoindolin-4-yl)amino)heptyl)amino)-3-oxopropyl)piperazin-1-yl)pyridin-3-yl)-1-isopropyl-1H-indazole-4-carboxamide |
| AM29-173A | 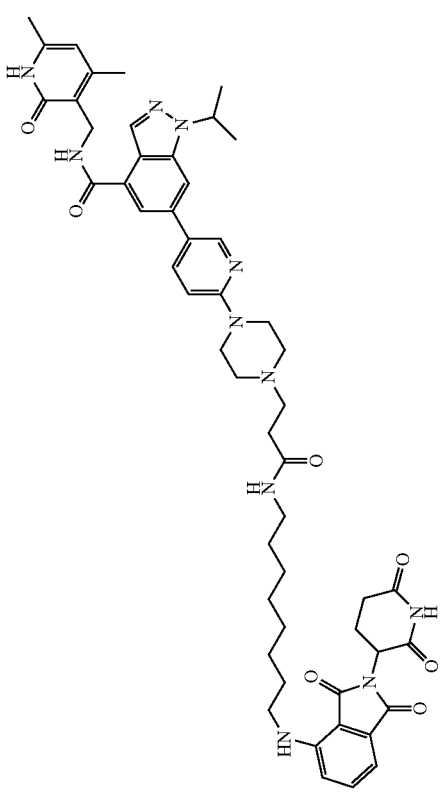 | N-((4,6-dimethyl-2-oxo-1,2-dihydropyridin-3-yl)methyl)-6-(6-(4-(3-((8-((2-(2,6-dioxopiperidin-3-yl)-1,3-dioxoisoindolin-4-yl)amino)octyl)amino)-3-oxopropyl)piperazin-1-yl)pyridin-3-yl)-1-isopropyl-1H-indazole-4-carboxamide |

TABLE 1-continued
| Structure | Chemical Name |
|---|---|
| 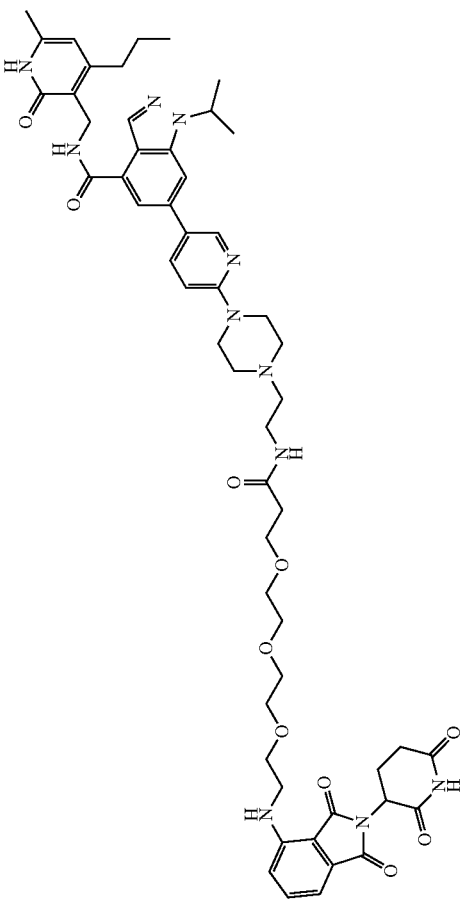 | 6-(6-(4-(1-((2-(2,6-dioxopiperidin-3-yl)-1,3-dioxoisoindolin-4-yl)amino)-12-oxo-3,6,9-trioxa-13-azapentadecan-15-yl)piperazin-1-yl)pyridin-3-yl)-1-isopropyl-N-((6-methyl-2-oxo-4-propyl-1,2-dihydropyridin-3-yl)methyl)-1H-indazole-4-carboxamide |
AM16-79A TABLE 1-continued
| | |
|---|---|
| | Chemical Name |
| Structure | |
| 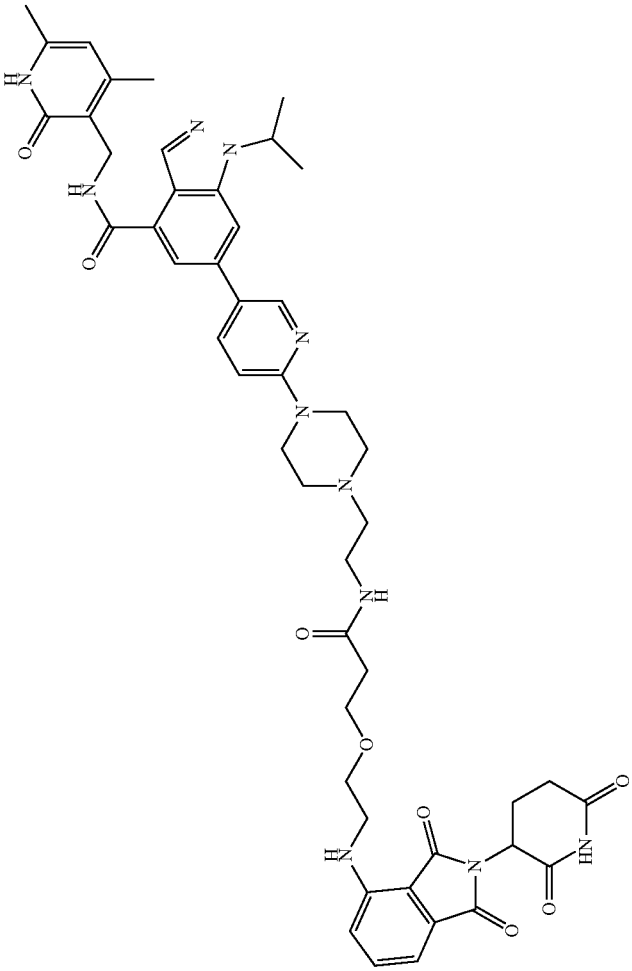 | N-((4,6-dimethyl-2-oxo-1,2-dihydropyridin-3-yl)methyl)-6-(6-(4-(2-(3-(2-((2-(2,6-dioxopiperidin-3-yl)-1,3-dioxoisoindolin-4-yl)amino)ethoxy)propanamido)ethyl)piperazin-1-yl)pyridin-3-yl)-1-isopropyl-1H-indazole-4-carboxamide |
| AM29-177A | |

| TABLE 1-continued | |
|---|---|
| Structure | Chemical Name |
| AM29-141A | N-((4,6-dimethyl-2-oxo-1,2-dihydropyridin-3-yl)methyl)-6-(6-(4-(3-((2-((2-(2,6-dioxopiperidin-3-yl)-1,3-dioxoisoindolin-4-yl)amino)ethoxy)ethyl)amino)-3-oxopropyl)piperazin-1-yl)pyridin-3-yl)-1-isopropyl-1H-indazole-4-carboxamide |

TABLE 1-continued
| Structure | Chemical Name |
|---|---|
| 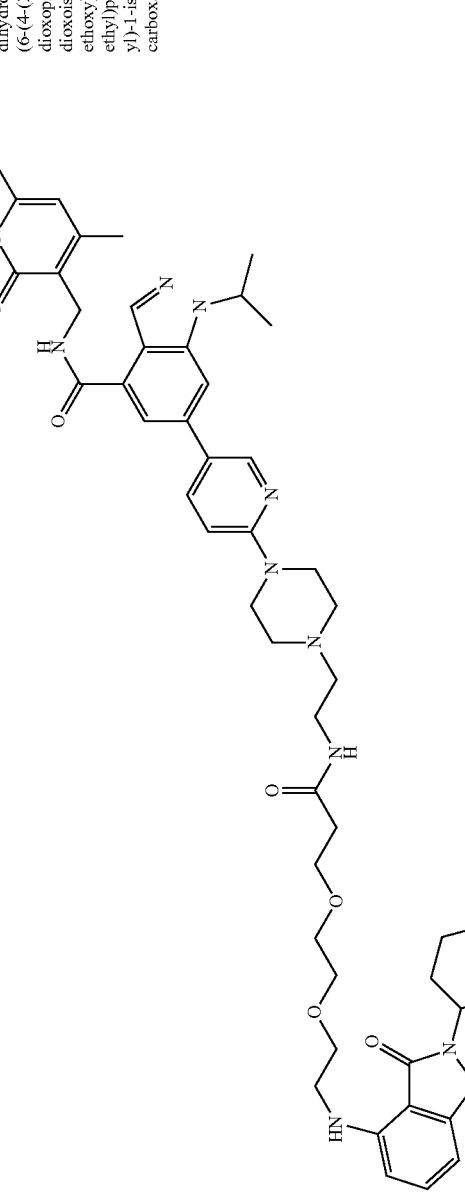 | N-((4,6-dimethyl-2-oxo-1,2-dihydropyridin-3-yl)methyl)-6-(6-(4-(2-(3-(2-(2-((2-(2,6-dioxopiperidin-3-yl)-1,3-dioxoisoindolin-4-yl)amino)ethoxy)ethoxy)propanamido)ethyl)piperazin-1-yl)pyridin-3-yl)-1-isopropyl-1H-indazole-4-carboxamide |
AM29-178A TABLE 1-continued

| Structure | Chemical Name |
|---|---|
| AM29-142A | N-((4,6-dimethyl-2-oxo-1,2-dihydropyridin-3-yl)methyl)-6-(6-(4-(3-((2-(2-(2-((2-(2,6-dioxopiperidin-3-yl)-1,3-dioxoisoindolin-4-yl)amino)ethoxy)ethoxy)ethyl)amino)-3-oxopropyl)piperazin-1-yl)pyridin-3-yl)-1-isopropyl-1H-indazole-4-carboxamide |

TABLE 1-continued
| Structure | Chemical Name |
|---|---|
| 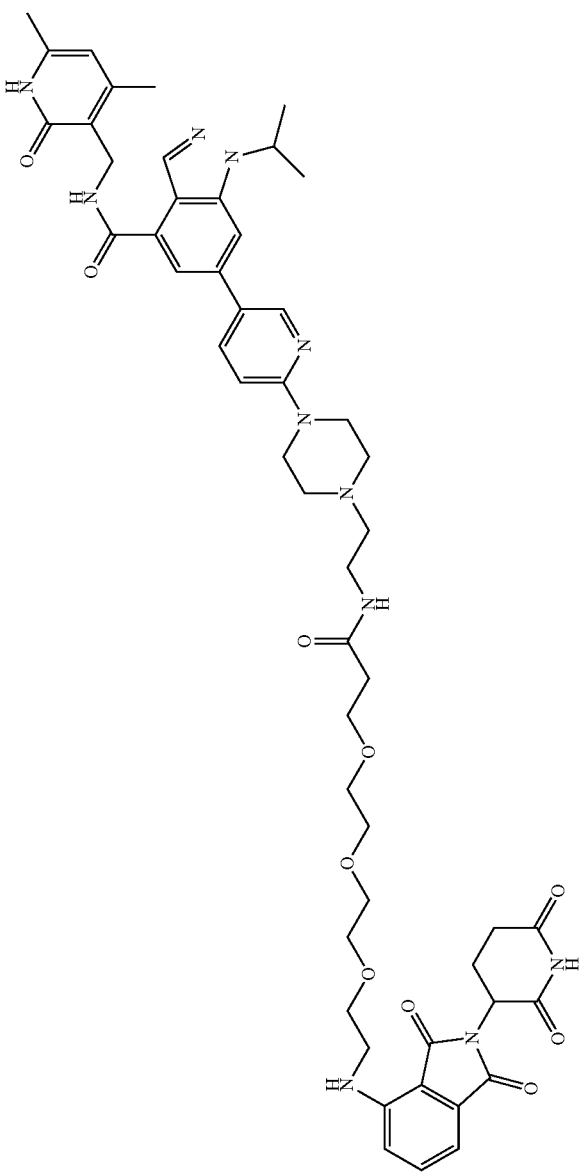 | N-((4,6-dimethyl-2-oxo-1,2-dihydropyridin-3-yl)methyl)-6-(6-(4-(1-((2-(2,6-dioxopiperidin-3-yl)-1,3-dioxoisoindolin-4-yl)amino)-12-oxo-3,6,9-trioxa-13-azapentadecan-15-yl)piperazin-1-yl)pyridin-3-yl)-1-isopropyl-1H-indazole-4-carboxamide |
AM29-179A TABLE 1-continued
| | Structure | Chemical Name |
|---|---|---|
| AM29-143A | 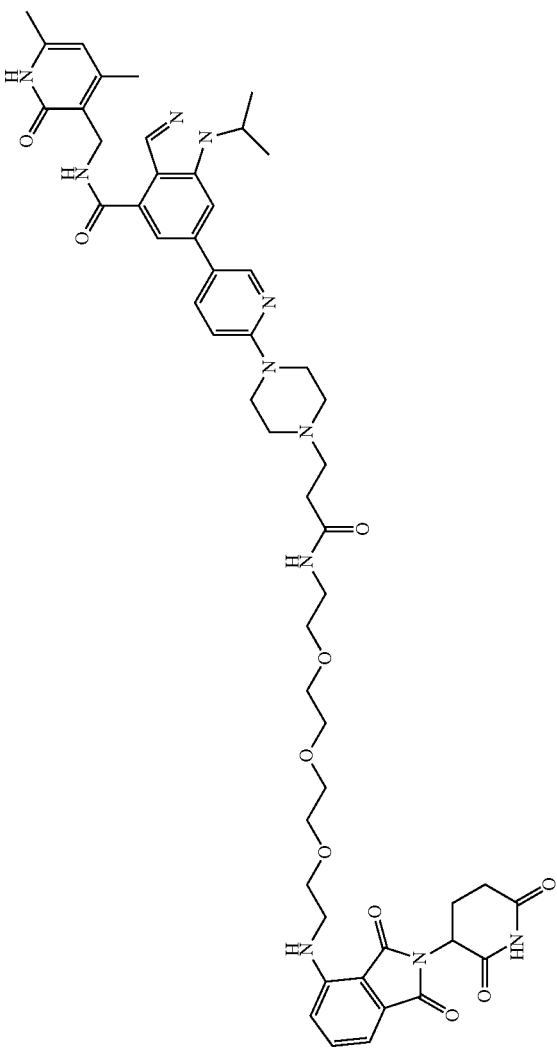 | N-((4,6-dimethyl-2-oxo-1,2-dihydropyridin-3-yl)methyl)-6-(6-(4-(1-((2-(2,6-dioxopiperidin-3-yl)-1,3-dioxoisoindolin-4-yl)amino)-13-oxo-3,6,9-trioxa-12-azapentadecan-15-yl)piperazin-1-yl)pyridin-3-yl)-1-isopropyl-1H-indazole-4-carboxamide |

TABLE 1-continued

| Structure | Chemical Name |
|---|---|
| 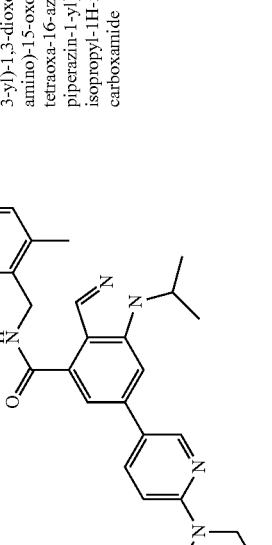 | N-((4,6-dimethyl-2-oxo-1,2-dihydropyridin-3-yl)methyl)-6-(6-(4-(1-((2-(2,6-dioxopiperidin-3-yl)-1,3-dioxoisoindolin-4-yl)amino)-15-oxo-3,6,9,12-tetraoxa-16-azaoctadecan-18-yl)piperazin-1-yl)pyridin-3-yl)-1-isopropyl-1H-indazole-4-carboxamide |
| 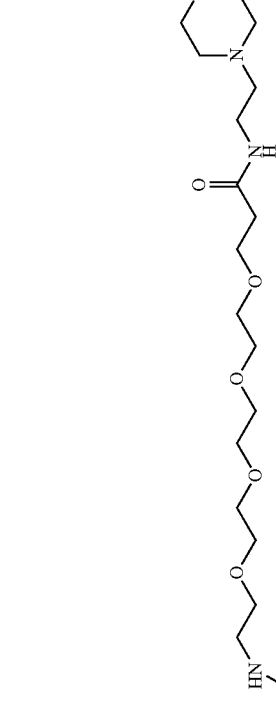 | N-((4,6-dimethyl-2-oxo-1,2-dihydropyridin-3-yl)methyl)-6-(6-(4-(1-((2-(2,6-dioxopiperidin-3-yl)-1,3-dioxoisoindolin-4-yl)amino)-16-oxo-3,6,9,12-tetraoxa-15-azaoctadecan-18-yl)piperazin-1-yl)pyridin-3-yl)-1-isopropyl-1H-indazole-4-carboxamide |

AM29-180A

AM29-144A

TABLE 1-continued

| Structure | Chemical Name |
|---|---|
| 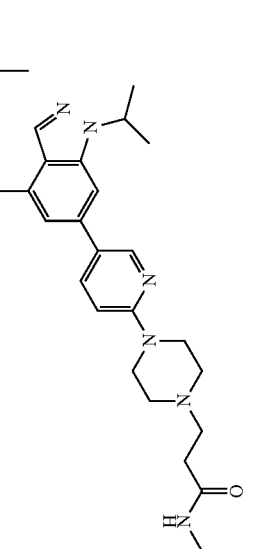 AM29-145A | N-((4,6-dimethyl-2-oxo-1,2-dihydropyridin-3-yl)methyl)-6-(6-(4-(1-((2-(2,6-dioxopiperidin-3-yl)-1,3-dioxoisoindolin-4-yl)amino)-19-oxo-3,6,9,12,15-pentaoxa-18-azahenicosan-21-yl)piperazin-1-yl)pyridin-3-yl)-1-isopropyl-1H-indazole-4-carboxamide |
| 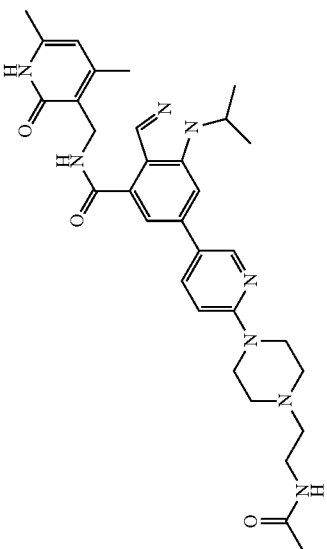 AM29-181A | N-((4,6-dimethyl-2-oxo-1,2-dihydropyridin-3-yl)methyl)-6-(6-(4-(1-((2-(2,6-dioxopiperidin-3-yl)-1,3-dioxoisoindolin-4-yl)amino)-18-oxo-3,6,9,12,15-pentaoxa-19-azahenicosan-21-yl)piperazin-1-yl)pyridin-3-yl)-1-isopropyl-1H-indazole-4-carboxamide |

TABLE 1-continued

| | Structure | Chemical Name |
|---|---|---|
| AM41-16A | 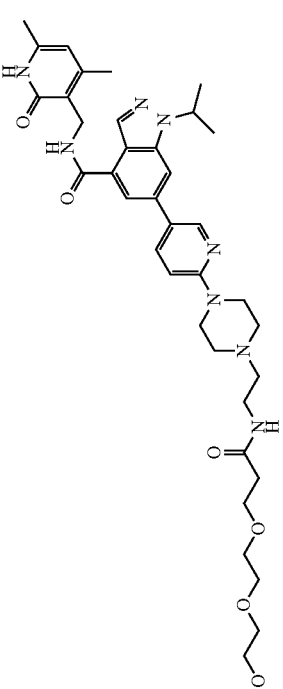 | N-((4,6-dimethyl-2-oxo-1,2-dihydropyridin-3-yl)methyl)-6-(6-(4-(1-((2-(2-(2,6-dioxopiperidin-3-yl)-1,3-dioxoisoindolin-4-yl)amino)-27-oxo-3,6,9,12,15,18,21,24-octaoxa-28-azatriacontan-30-yl)piperazin-1-yl)pyridin-3-yl)-1-isopropyl-1H-indazole-4-carboxamide |
| AM41-17A | 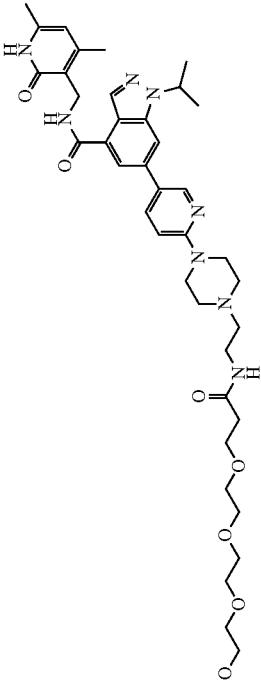 | N-((4,6-dimethyl-2-oxo-1,2-dihydropyridin-3-yl)methyl)-6-(6-(4-(1-((2-(2,6-dioxopiperidin-3-yl)-1,3-dioxoisoindolin-4-yl)amino)-33-oxo-3,6,9,12,15,18,21,24,27,30-decaoxa-34-azahexatriacontan-36-yl)piperazin-1-yl)pyridin-3-yl)-1-isopropyl-1H-indazole-4-carboxamide |

TABLE 1-continued

| | Structure | Chemical Name |
|---|---|---|
| AM41-18A | 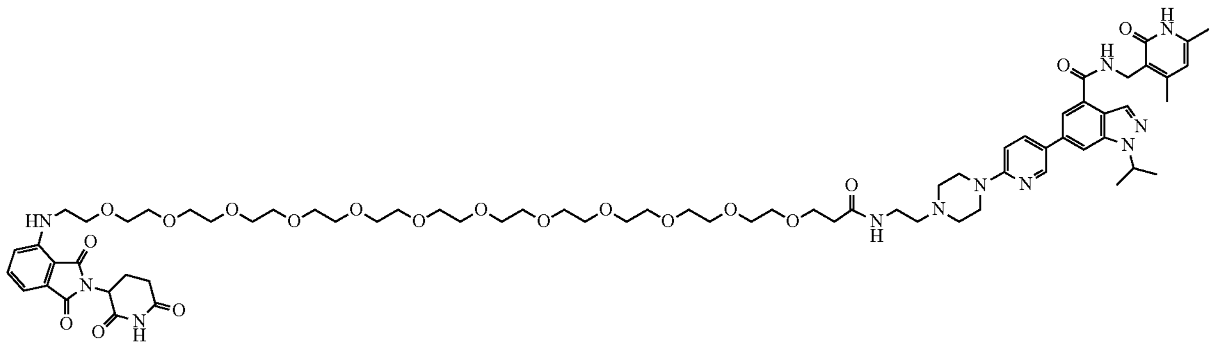 [SMILES: Cc1cc(C)c(CNC(=O)c2cc(-c3ccc(N4CCN(CCNC(=O)CCOCCOCCOCCOCCOCCOCCOCCOCCOCCOCCOCCOCCNc5cccc6c5C(=O)N(C5CCC(=O)NC5=O)C6=O)CC4)nc3)cc(NC(C)C)c2C=N)c(=O)[nH]1] | N-((4,6-dimethyl-2-oxo-1,2-dihydropyridin-3-yl)methyl)-6-(6-(4-(1-((2-(2,6-dioxopiperidin-3-yl)-1,3-dioxoisoindolin-4-yl)amino)-39-oxo-3,6,9,12,15,18,21,24,27,30,33,36-dodecaoxa-40-azadotetracontan-42-yl)piperazin-1-yl)pyridin-3-yl)-1-isopropyl-1H-indazole-4-carboxamide |
| XY012-157 | 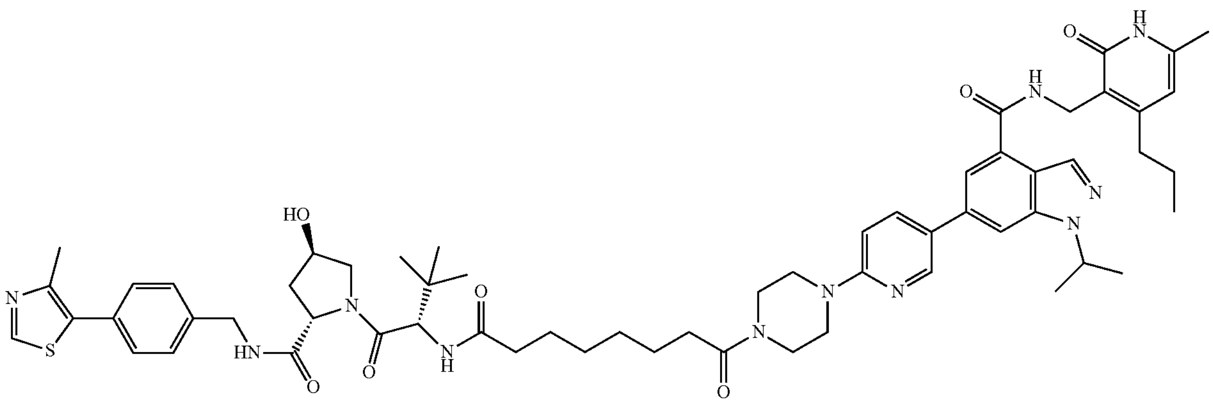 [SMILES: CCCc1cc(C)[nH]c(=O)c1CNC(=O)c1cc(-c2ccc(N3CCN(C(=O)CCCCCCC(=O)N[C@H](C(=O)N4C[C@H](O)C[C@H]4C(=O)NCc4ccc(-c5scnc5C)cc4)C(C)(C)C)CC3)nc2)cc(NC(C)C)c1C=N] | 6-(6-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)pyridin-3-yl)-1-isopropyl-N-((6-methyl-2-oxo-4-propyl-1,2-dihydropyridin-3-yl)methyl)-1H-indazole-4-carboxamide |

TABLE 1-continued

| | Structure | Chemical Name |
|---|---|---|
| XF034-164A | 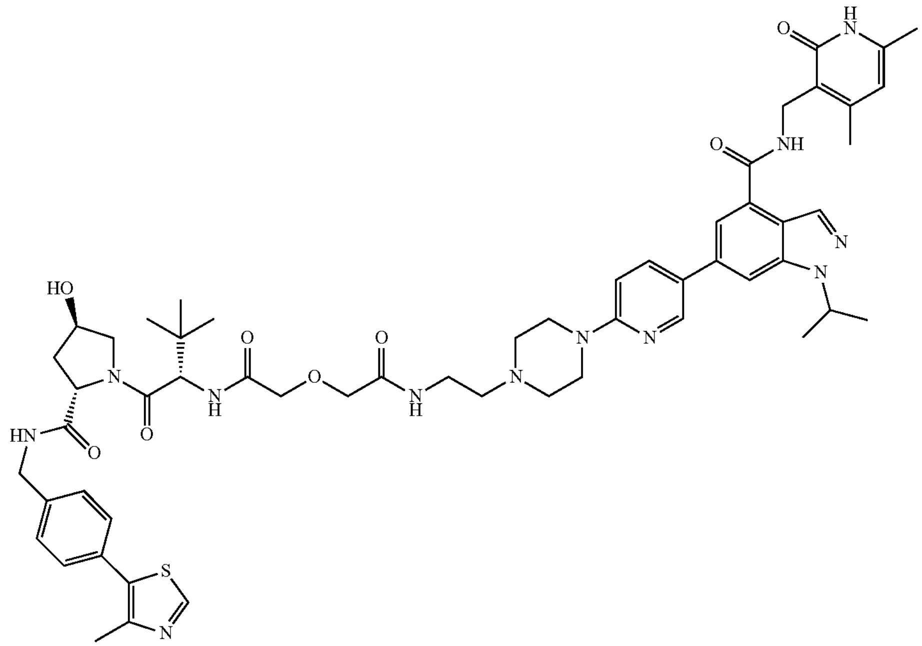 [SMILES: Cc1cc(C)c(CNC(=O)c2cc(-c3ccc(N4CCN(CCNC(=O)COCC(=O)N[C@H](C(=O)N5C[C@H](O)C[C@H]5C(=O)NCc5ccc(-c6scnc6C)cc5)C(C)(C)C)CC4)nc3)cc(NC(C)C)c2C=N)c(=O)[nH]1] | N-((4,6-dimethyl-2-oxo-1,2-dihydropyridin-3-yl)methyl)-6-(6-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetamido)ethyl)piperazin-1-yl)pyridin-3-yl)-1-isopropyl-1H-indazole-4-carboxamide |

TABLE 1-continued
| | Structure | Chemical Name |
|---|---|---|
| XF034-165A | 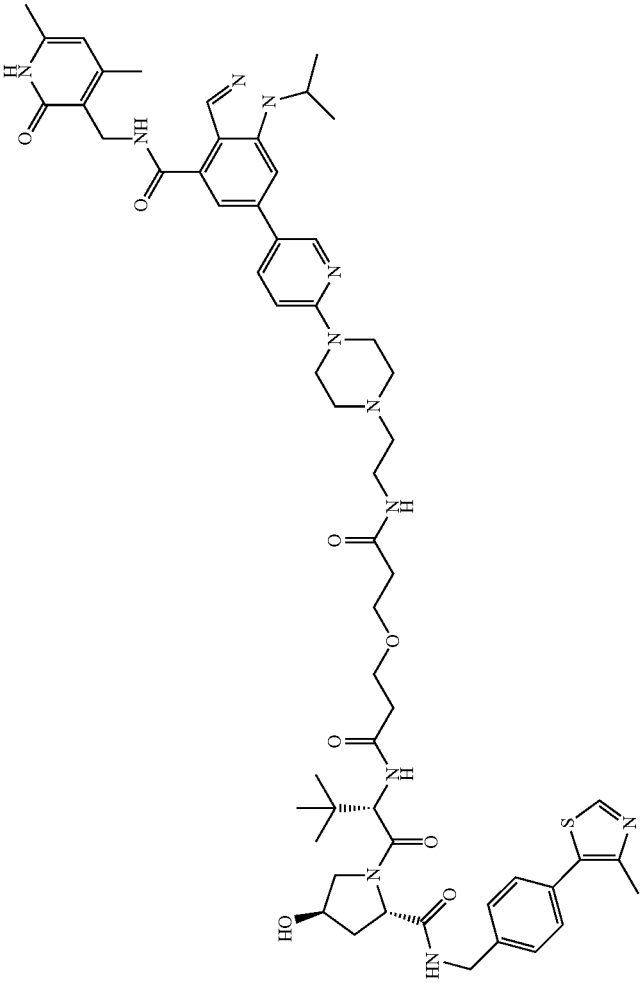 | N-((4,6-dimethyl-2-oxo-1,2-dihydropyridin-3-yl)methyl)-6-(6-(4-(2-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanamido)ethyl)piperazin-1-yl)pyridin-3-yl)-1-isopropyl-1H-indazole-4-carboxamide |

TABLE 1-continued
| Structure | Chemical Name |
|---|---|
| XF034-166A 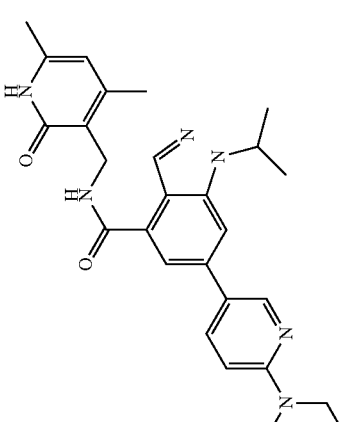 | N-((4,6-(dimethyl-2-oxo-1,2-dihydropyridin-3-yl)methyl)-6-(6-(4-((S)-13-((2S,4R)-4-hydroxy-2-((4-(4-methylthiazol-5-yl)benzyl)carbamoyl)pyrrolidine-1-carbonyl)-14,14-dimethyl-4,11-dioxo-6,9-dioxa-3,12-diazapentadecyl)piperazin-1-yl)pyridin-3-yl)-1-isopropyl-1H-indazole-4-carboxamide |

TABLE 1-continued
| Structure | Chemical Name |
|---|---|
| 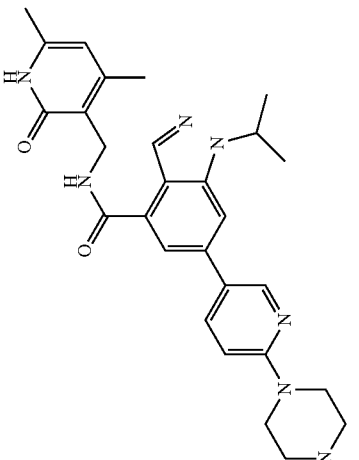 | N-((4,6-dimethyl-2-oxo-1,2-dihydropyridin-3-yl)methyl)-6-(6-(4-((S)-15-((2S,4R)-4-hydroxy-2-((4-(4-methylthiazol-5-yl)benzyl)carbamoyl)pyrrolidine-1-carbonyl)-16,16-dimethyl-4,13-dioxo-7,10-dioxa-3,14-diazaheptadecyl)piperazin-1-yl)pyridin-3-yl)-1-isopropyl-1H-indazole-4-carboxamide |
XF034-167A TABLE 1-continued

| | Structure | Chemical Name |
|---|---|---|
| XF034-168A | 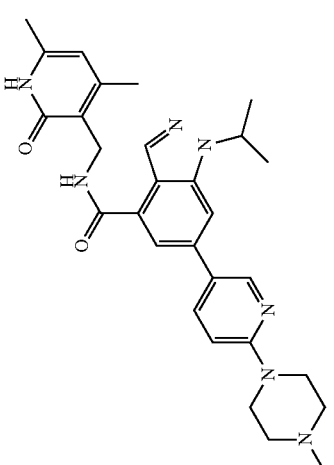 | N-((4,6-dimethyl-2-oxo-1,2-dihydropyridin-3-yl)methyl)-6-(6-(4-((S)-18-((2S,4R)-4-hydroxy-2-((4-(4-methylthiazol-5-yl)benzyl)carbamoyl)pyrrolidine-1-carbonyl)-19,19-dimethyl-4,16-dioxo-7,10,13-trioxa-3,17-diazaicosyl)piperazin-1-yl)pyridin-3-yl)-1-isopropyl-1H-indazole-4-carboxamide |
| XY019-041 | 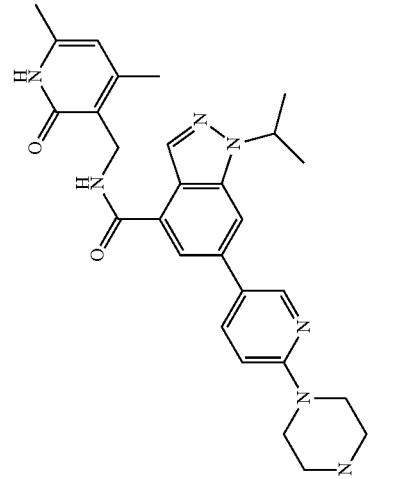 | N-((4,6-dimethyl-2-oxo-1,2-dihydropyridin-3-yl)methyl)-6-(6-(4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)piperazin-1-yl)pyridin-3-yl)-1-isopropyl-1H-indazole-4-carboxamide |

TABLE 1-continued

| Structure | Chemical Name |
|---|---|
| XF034-169A 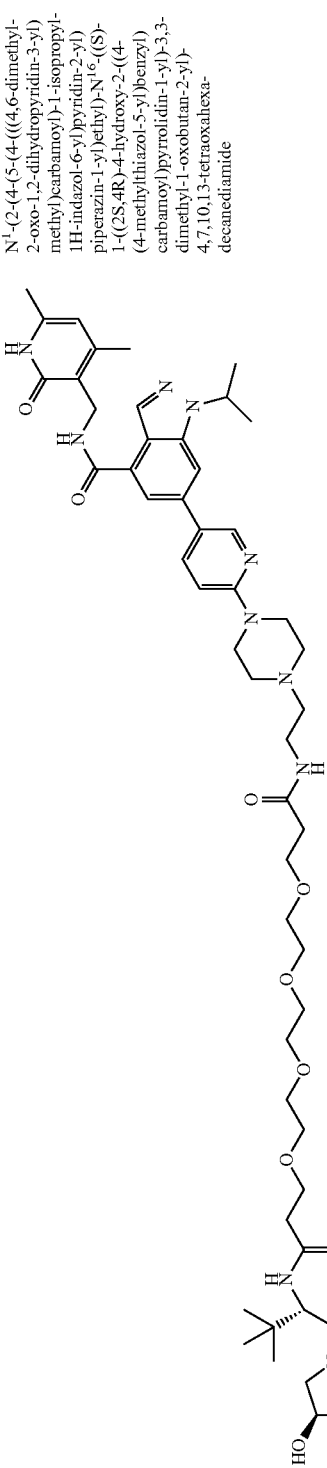 | N$^1$-(2-(4-(5-(4-(((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N$^{16}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide |
| XF034-170A 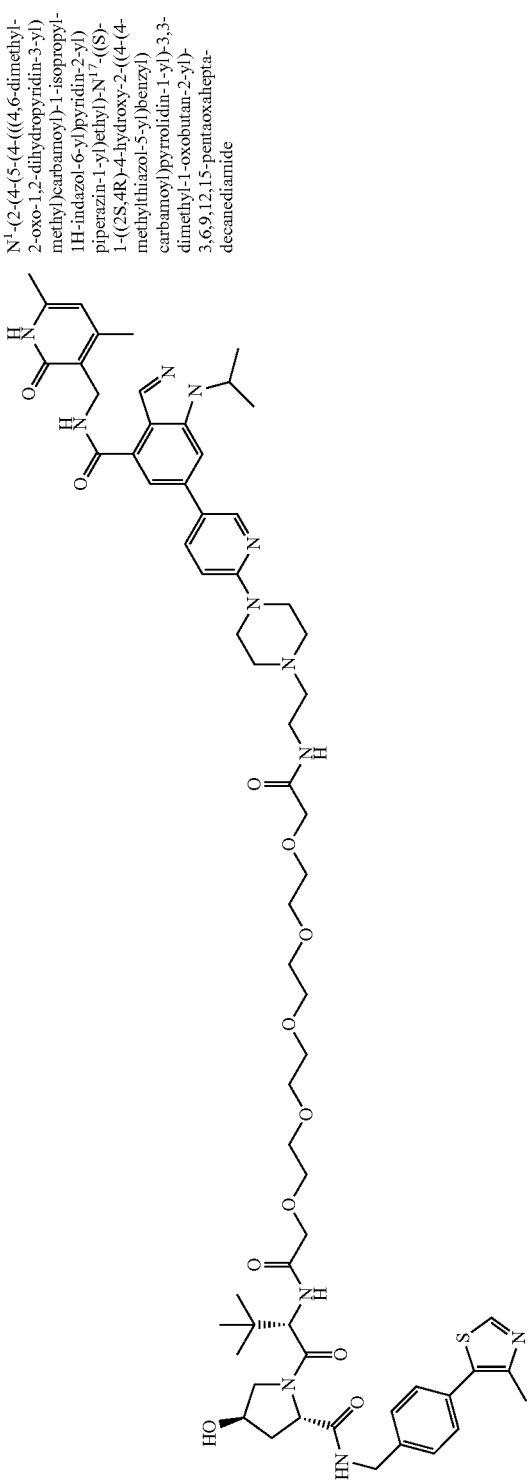 | N$^1$-(2-(4-(5-(4-(((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N$^{17}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide |

TABLE 1-continued

| Structure | Chemical Name |
|---|---|
| XF034-171A 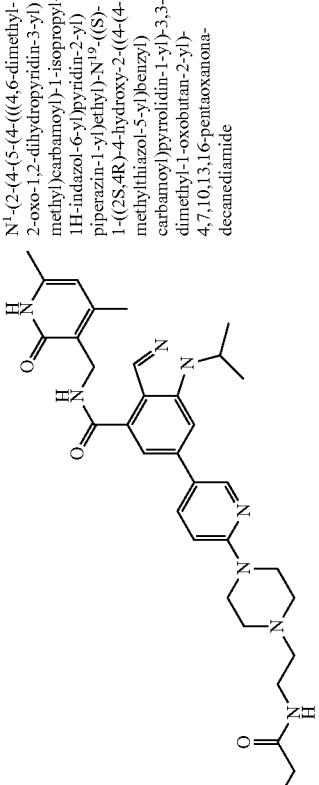 | N1-(2-(4-(5-(4-(((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N19-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| CZ40-10 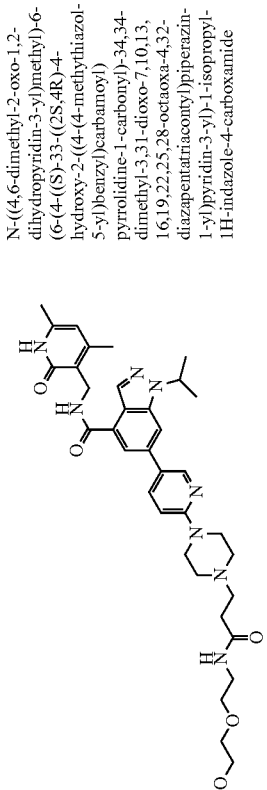 | N-((4,6-dimethyl-2-oxo-1,2-dihydropyridin-3-yl)methyl)-6-(6-(4-((S)-33-((2S,4R)-4-hydroxy-2-((4-(4-methylthiazol-5-yl)benzyl)carbamoyl)pyrrolidine-1-carbonyl)-34,34-dimethyl-3,31-dioxo-7,10,13,16,19,22,25,28-octaoxa-4,32-diazapentatriacontyl)piperazin-1-yl)pyridin-3-yl)-1-isopropyl-1H-indazole-4-carboxamide |
| CZ40-09 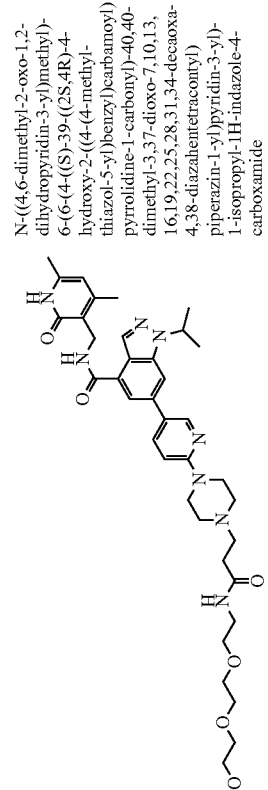 | N-((4,6-dimethyl-2-oxo-1,2-dihydropyridin-3-yl)methyl)-6-(6-(4-((S)-39-((2S,4R)-4-hydroxy-2-((4-(4-methylthiazol-5-yl)benzyl)carbamoyl)pyrrolidine-1-carbonyl)-40,40-dimethyl-3,37-dioxo-7,10,13,16,19,22,25,28,31,34-decaoxa-4,38-diazahentetracontyl)piperazin-1-yl)pyridin-3-yl)-1-isopropyl-1H-indazole-4-carboxamide |

TABLE 1-continued

| Structure | Chemical Name |
|---|---|
| 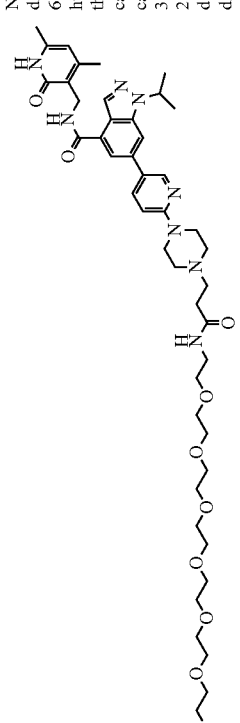 | CZ40-11: N-((4,6-dimethyl-2-oxo-1,2-dihydropyridin-3-yl)methyl)-6-(6-(4-((S)-45-((2S,4R)-4-hydroxy-2-((4-(4-methylthiazol-5-yl)benzyl)carbamoyl)pyrrolidine-1-carbonyl)-46,46-dimethyl-3,43-dioxo-7,10,13,16,19,22,25,28,31,34,37,40-dodecaoxa-4,44-diazaheptatetracontyl)piperazin-1-yl)pyridin-3-yl)-1-isopropyl-1H-indazole-4-carboxamide |
| 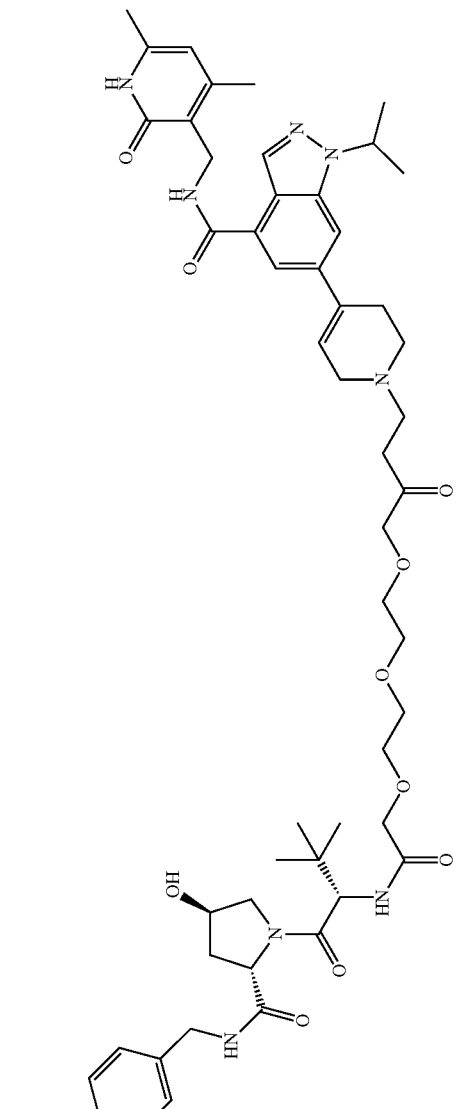 | XY019-077: N-((4,6-dimethyl-2-oxo-1,2-dihydropyridin-3-yl)methyl)-6-(1-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)-1,2,3,6-tetrahydropyridin-4-yl)-1-isopropyl-1H-indazole-4-carboxamide |

TABLE 1-continued

| | Structure | Chemical Name |
|---|---|---|
| XY019-083 | 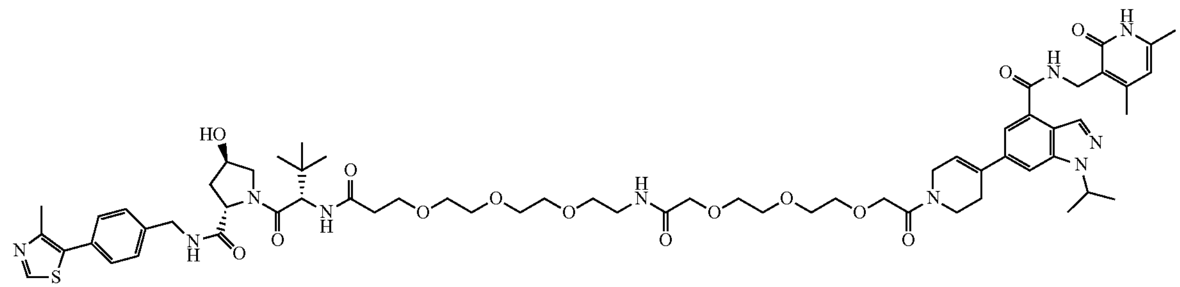 [SMILES: Cc1cc(C)c(CNC(=O)c2cc(C3=CCN(C(=O)COCCOCCOCC(=O)NCCOCCOCCOCCC(=O)N[C@H](C(=O)N4C[C@H](O)C[C@H]4C(=O)NCc4ccc(-c5scnc5C)cc4)C(C)(C)C)CC3)cc(NC(C)C)c2C=N)c(=O)[nH]1] | N-((4,6-dimethyl-2-oxo-1,2-dihydropyridin-3-yl)methyl)-6-(1-((S)-26-((2S,4R)-4-hydroxy-2-((4-(4-methylthiazol-5-yl)benzyl)carbamoyl)pyrrolidine-1-carbonyl)-27,27-dimethyl-11,24-dioxo-3,6,9,15,18,21-hexaoxa-12,25-diazaoctacosanoyl)-1,2,3,6-tetrahydropyridin-4-yl)-1-isopropyl-1H-indazole-4-carboxamide |
| XY019-084 | 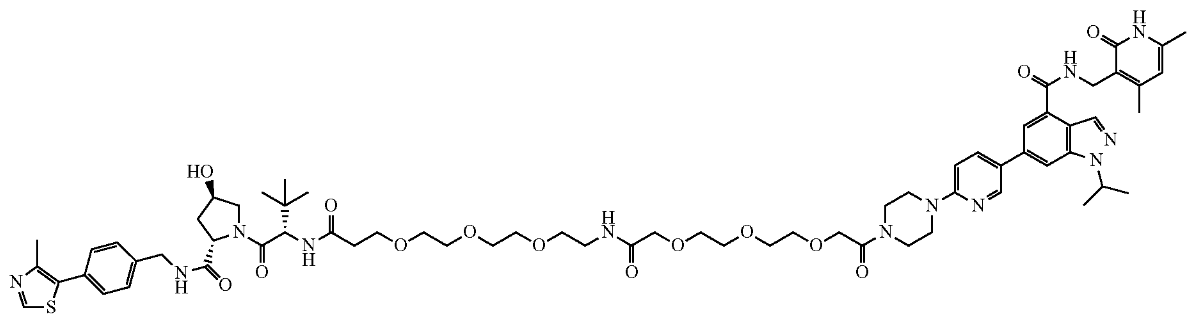 [SMILES: Cc1cc(C)c(CNC(=O)c2cc(-c3ccc(N4CCN(C(=O)COCCOCCOCC(=O)NCCOCCOCCOCCC(=O)N[C@H](C(=O)N5C[C@H](O)C[C@H]5C(=O)NCc5ccc(-c6scnc6C)cc5)C(C)(C)C)CC4)nc3)cc(NC(C)C)c2C=N)c(=O)[nH]1] | N-((4,6-dimethyl-2-oxo-1,2-dihydropyridin-3-yl)methyl)-6-(6-(4-((S)-26-((2S,4R)-4-hydroxy-2-((4-(4-methylthiazol-5-yl)benzyl)carbamoyl)pyrrolidine-1-carbonyl)-27,27-dimethyl-11,24-dioxo-3,6,9,15,18,21-hexaoxa-12,25-diazaoctacosanoyl)piperazin-1-yl)pyridin-3-yl)-1-isopropyl-1H-indazole-4-carboxamide |

TABLE 1-continued
| Structure | Chemical Name |
|---|---|
| 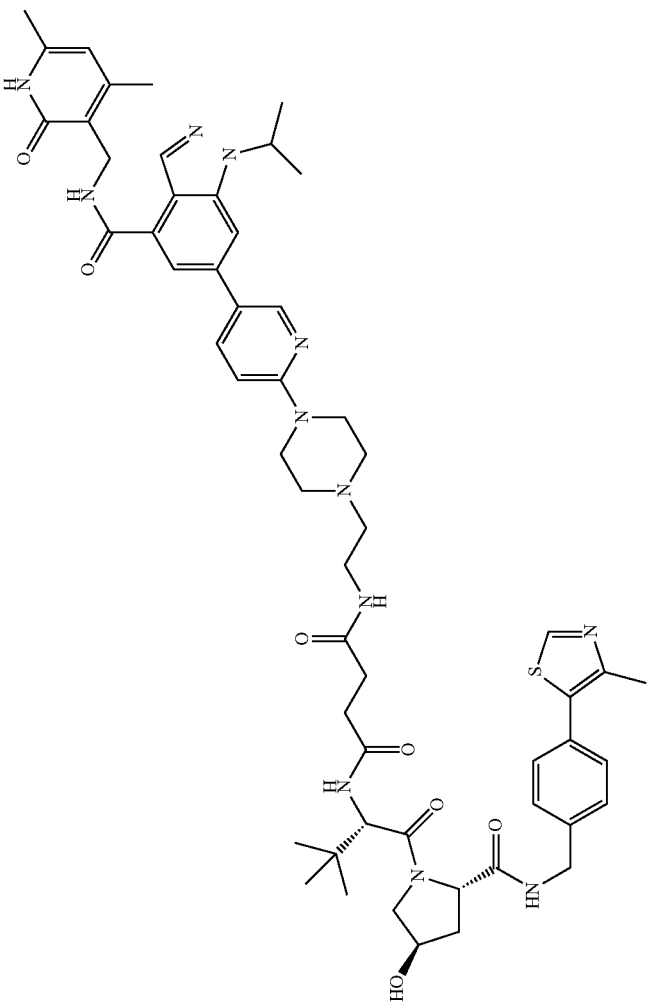 | N¹-(2-(4-(5-(4-(((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N⁴-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |
XF034-172A TABLE 1-continued

| | |
|---|---|
| Structure | Chemical Name |
| XF034-173A | N¹-(2-(4-(5-(4-((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N⁵-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |

TABLE 1-continued
| Structure | Chemical Name |
|---|---|
| 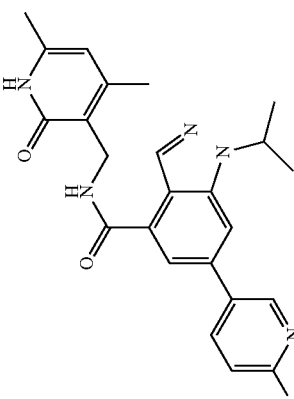 | N¹-(2-(4-(5-(4-(((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N⁶-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |
XF034-174A TABLE 1-continued
| Structure | Chemical Name |
|---|---|
| 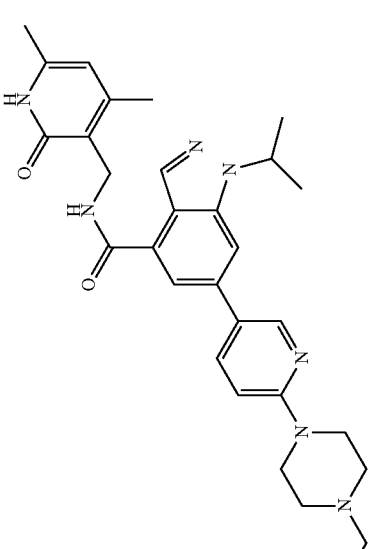 | N¹-(2-(4-(5-(4-(((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N⁷-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |
XF034-175A TABLE 1-continued
| Structure | Chemical Name |
|---|---|
| 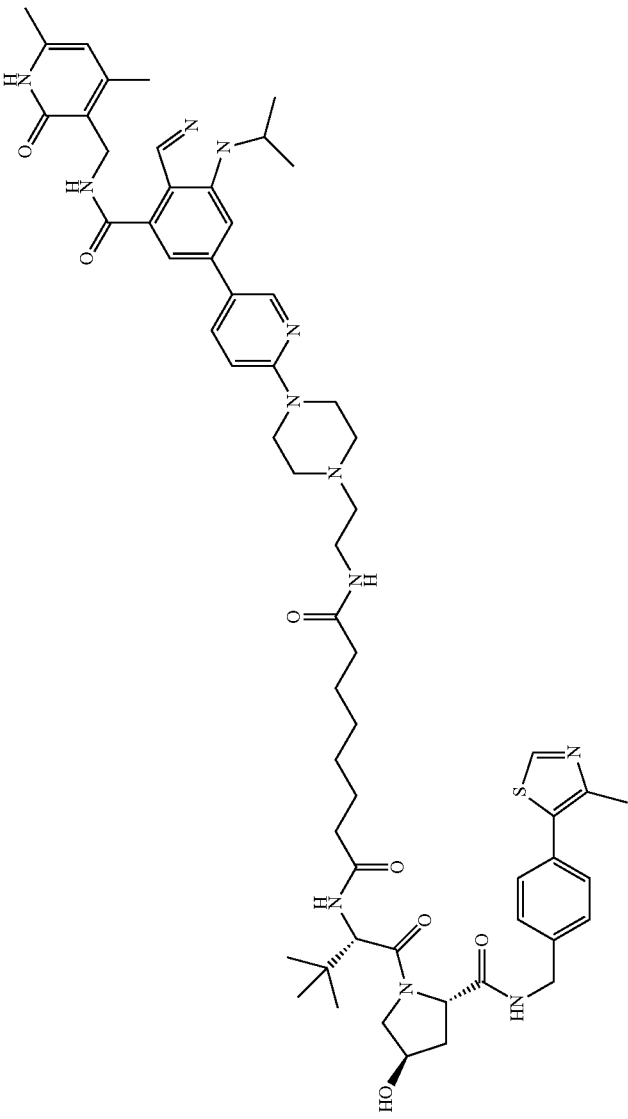 | XF034-176A N¹-(2-(4-(5-(4-(((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N⁸-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |

TABLE 1-continued

| | Structure | Chemical Name |
|---|---|---|
| XF034-177A | 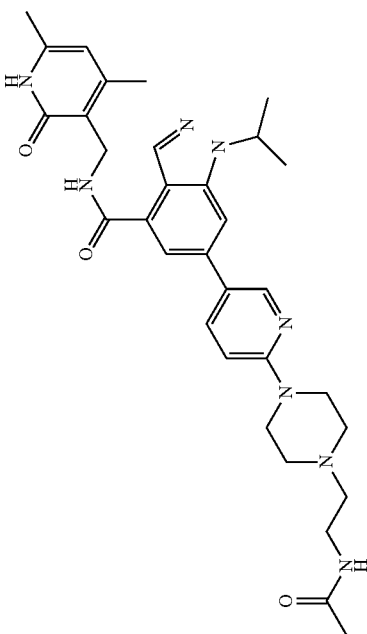 | N¹-(2-(4-(5-(4-((4,6-dimethyl-2-oxo-1,2-dihydropyridin-3-yl)methyl)carbamoyl)-1-isopropyl-1H-indazol-6-yl)pyridin-2-yl)piperazin-1-yl)ethyl)-N¹¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| YS36-48 | 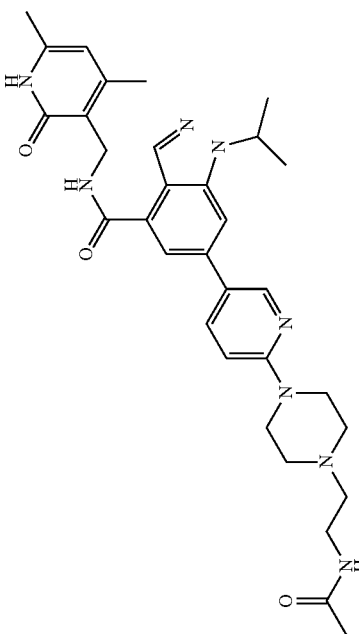 | 6-(6-(4-(20-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)-16-methyl-4,14-dioxo-7,10-dioxa-3,13,16-triazaicosyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued

| Structure | Chemical Name |
|---|---|
| YS36-49 | 6-(6-(4-(26-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)-22-methyl-4,20-dioxo-7,10,13,16-tetraoxa-3,19,22-triazahexacosyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| YS36-50 | 6-(6-(4-(29-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)-25-methyl-4,23-dioxo-7,10,13,16,19-pentaoxa-3,22,25-triazanonacosyl)piperazin-1-yl)pyridin-3-yl)-N-((4,6-dimethyl-2-oxo-1,2-dihydropyridin-3-yl)methyl)-1-isopropyl-1H-indazole-4-carboxamide |

| Structure | Chemical Name |
|---|---|
| YS36-51 | 6-(6-(4-(2-(2-(2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamido)acetamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued
| Structure | Chemical Name |
|---|---|
| 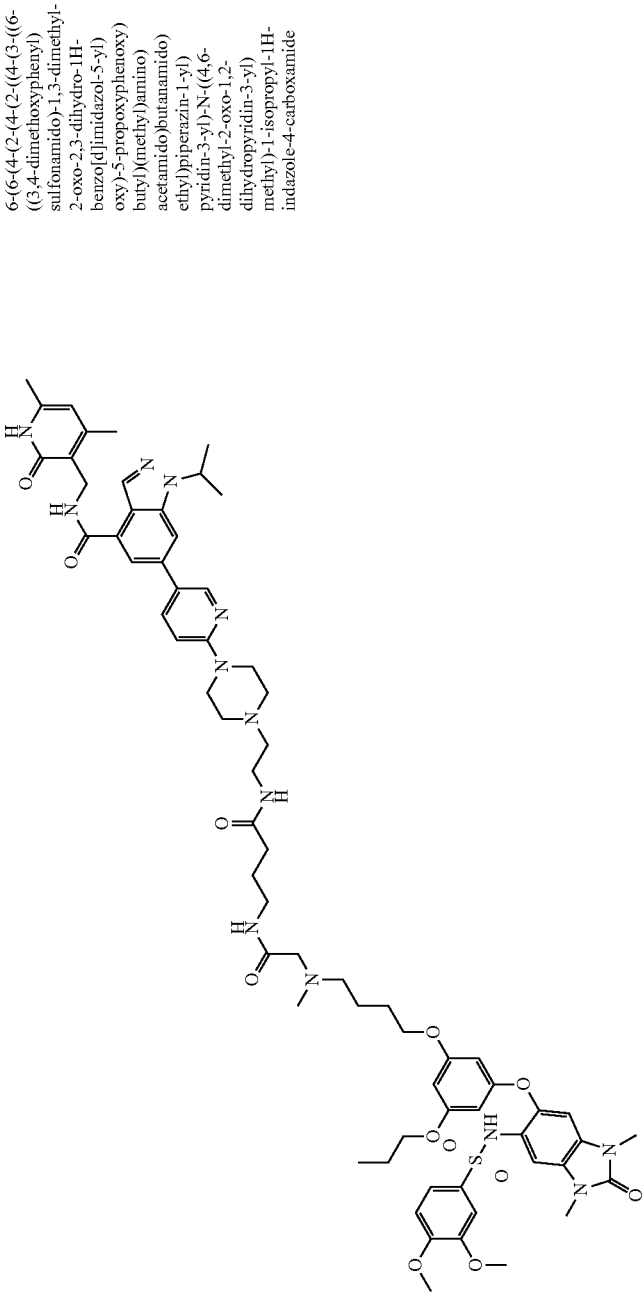 | YS36-52    6-(6-(4-(2-(4-(2-(4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamido)butanamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |

| Structure | Chemical Name |
|---|---|
| YS36-53 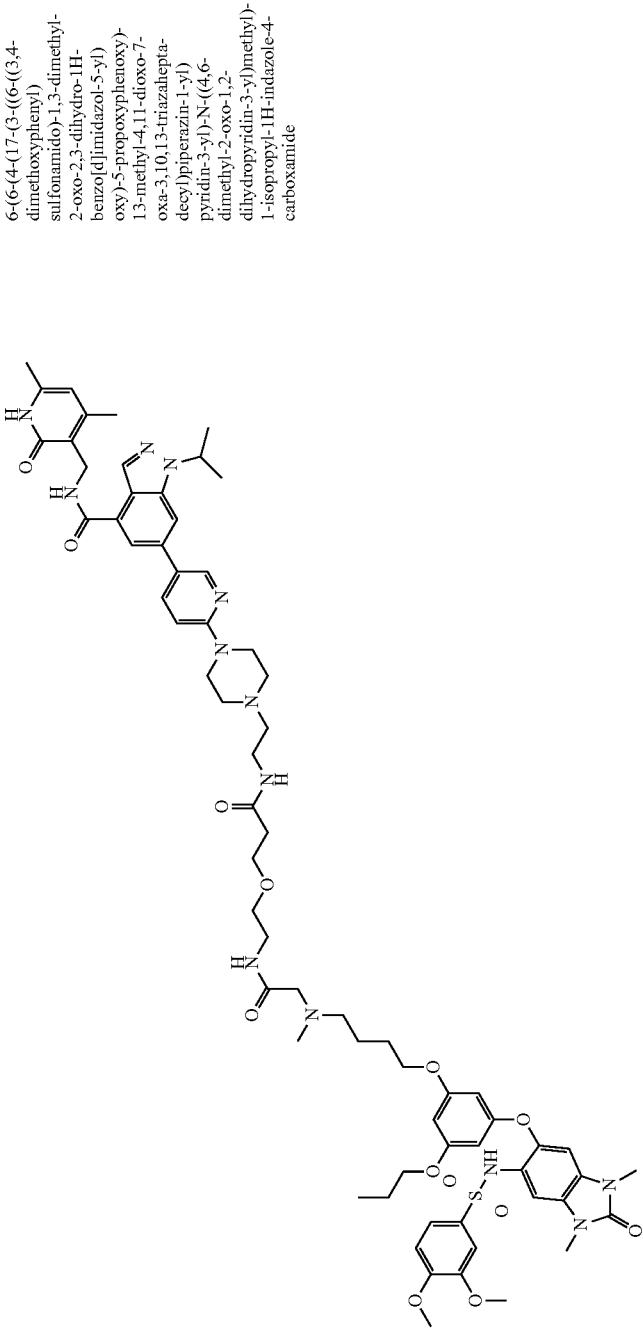 | 6-(6-(4-(17-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)-13-methyl-4,11-dioxo-7-oxa-3,10,13-triazaheptadecyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued

| | Structure | Chemical Name |
|---|---|---|
| YS36-54 | 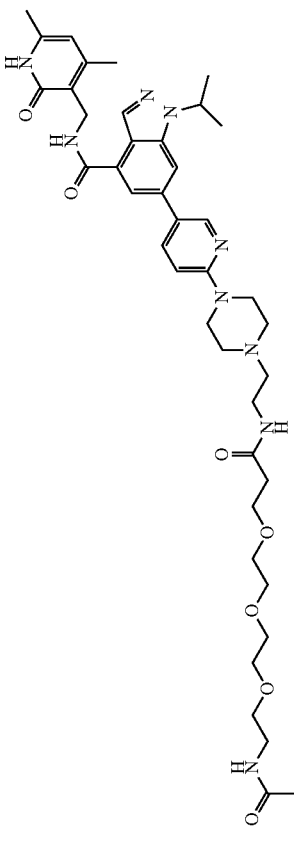 | 6-(6-(4-(23-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)-19-methyl-4,17-dioxo-7,10,13-trioxa-3,16,19-triazatricosyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| YS36-55 | 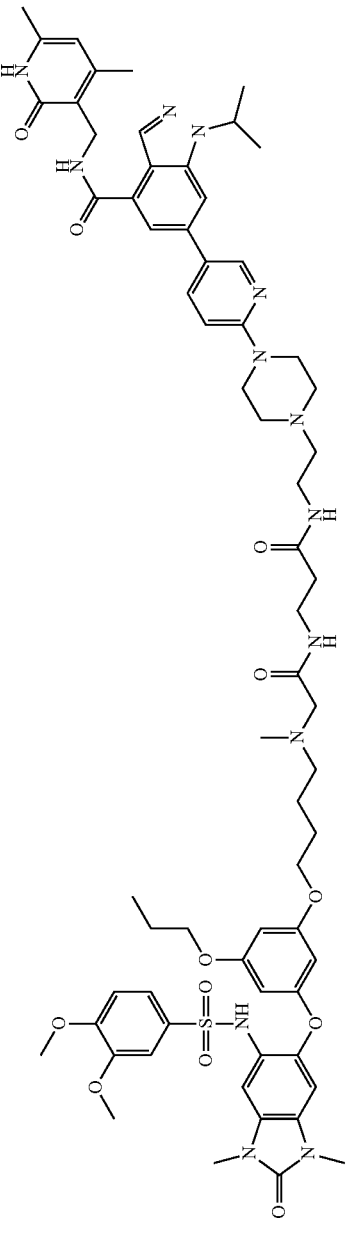 | 6-(6-(4-(2-(3-(2-(4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamido)propanamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued

| | Structure | Chemical Name |
|---|---|---|
| YS36-56 | 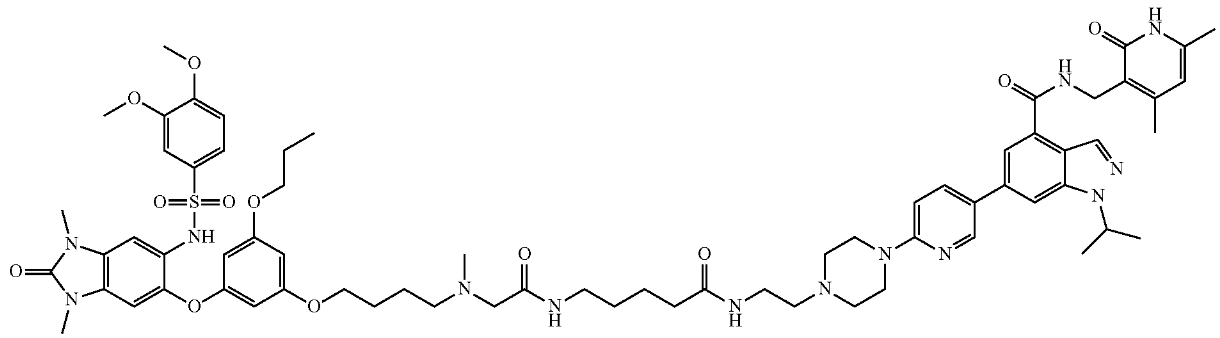 [SMILES: CCCOc1cc(OCCCCN(C)CC(=O)NCCCCC(=O)NCCN2CCN(c3ccc(-c4cc(NC(C)C)c(C=N)c(C(=O)NCc5c(C)cc(C)[nH]c5=O)c4)cn3)CC2)cc(Oc2cc3c(cc2NS(=O)(=O)c2ccc(OC)c(OC)c2)n(C)c(=O)n3C)c1] | 6-(6-(4-(2-(5-(2-((4-(3-((6-((3,4-dimethoxy-phenyl)sulfonamido)-1,3-dimethyl-2-oxo-2,3-dihydro-1H-benzo[d]imidazol-5-yl)oxy)-5-propoxyphenoxy)butyl)(methyl)amino)acetamido)pentanamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| YS36-57 | 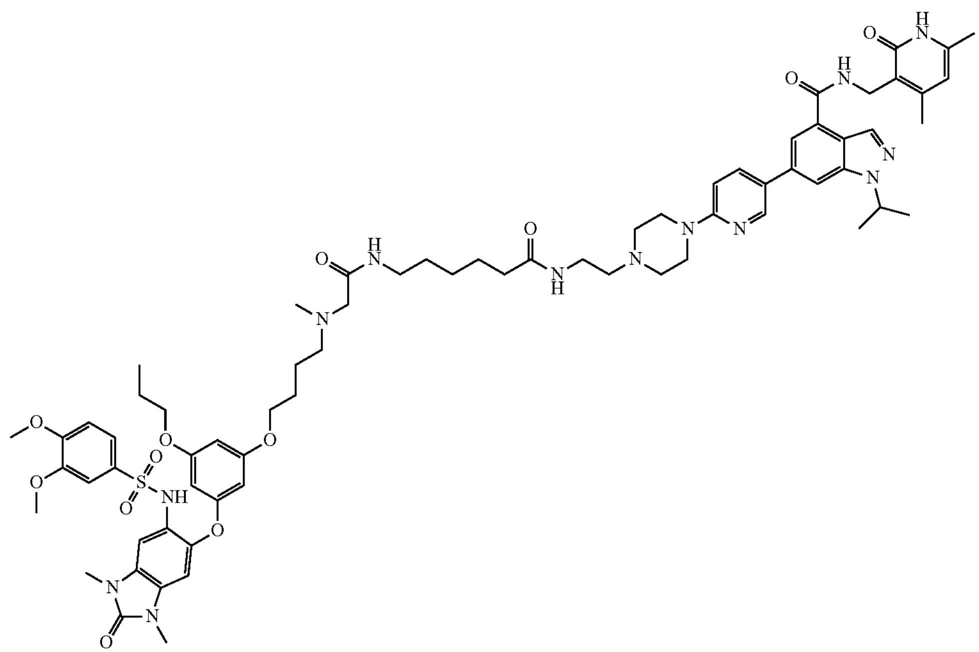 | 6-(6-(4-(2-(6-(2-((4-(3-((6-((3,4-dimethoxy-phenyl)sulfonamido)-1,3-dimethyl-2-oxo-2,3-dihydro-1H-benzo[d]imidazol-5-yl)oxy)-5-propoxyphenoxy)butyl)(methyl)amino)acetamido)hexanamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |

| Structure | Chemical Name |
|---|---|
| YS36-58 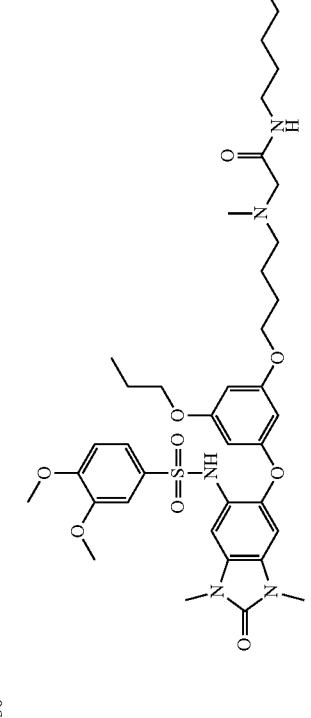 | 6-(6-(4-(2-(7-(2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamido)heptanamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |
| YS36-59 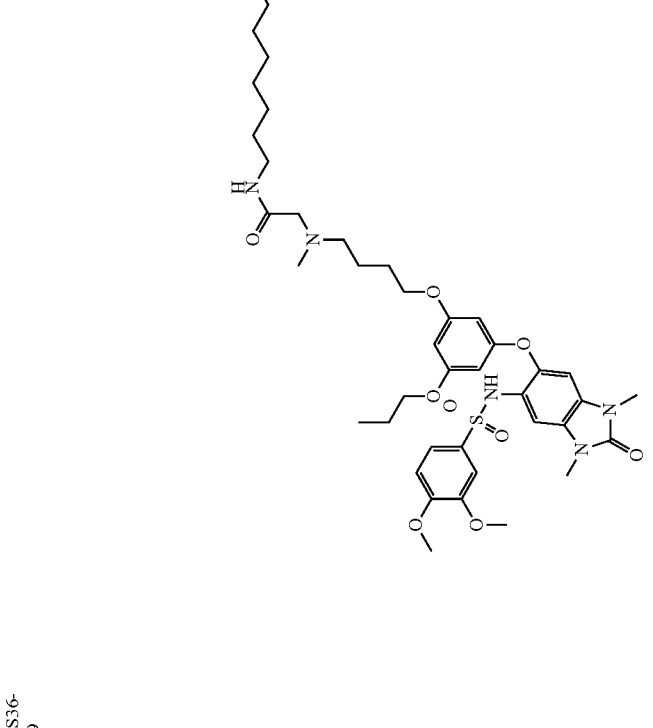 | 6-(6-(4-(2-(8-(2-((4-(3-((6-((3,4-dimethoxyphenyl)sulfonamido)-1,3-dimethyl-2-oxo-2,3-dihydro-1H-benzo[d]imidazol-5-yl)oxy)-5-propoxyphenoxy)butyl)(methyl)amino)acetamido)octanamido)ethyl)piperazin-1-yl)pyridin-3-yl)-N-((4,6-dimethyl-2-oxo-1,2-dihydropyridin-3-yl)methyl)-1-isopropyl-1H-indazole-4-carboxamide |

TABLE 1-continued
| Structure | Chemical Name |
|---|---|
| 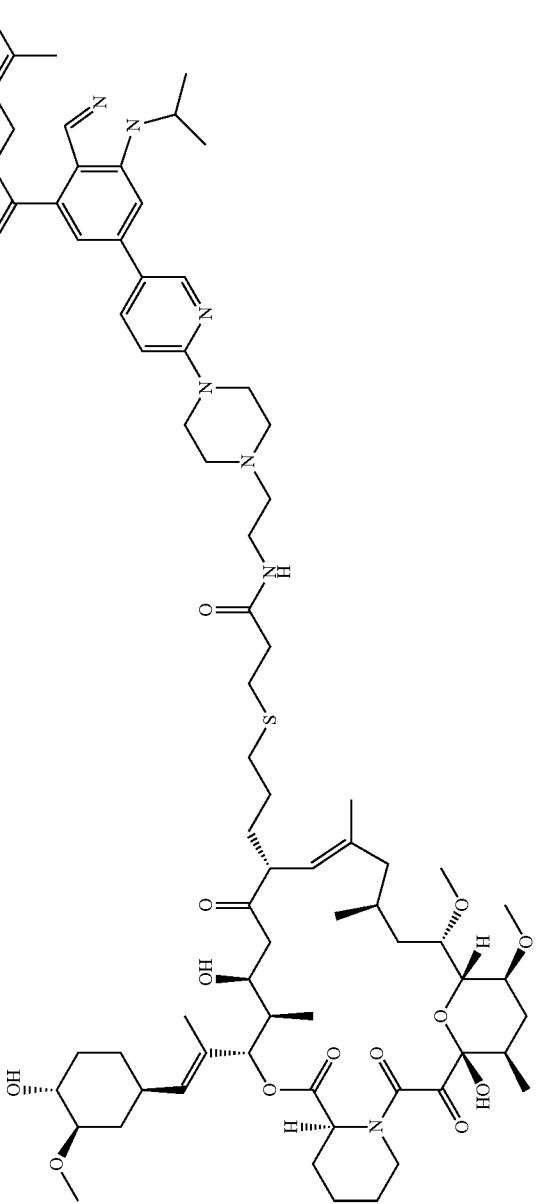 XY028-086 | FK506 adduct with N-((4,6-dimethyl-2-oxo-1,2-dihydropyridin-3-yl)methyl)-1-isopropyl-6-(6-(4-(2-(3-mercaptopropanamido)ethyl)piperazin-1-yl)pyridin-3-yl)-1H-indazole-4-carboxamide |
| 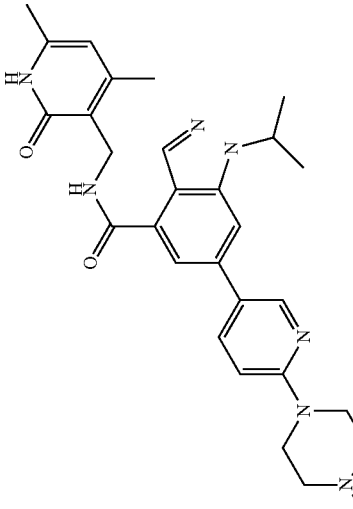 CZ40-72 | 4'-((4-(2-(2-((3r,5r,7r)-adamantan-1-yl)acetamido)ethyl)piperazin-1-yl)methyl)-N-((4,6-dimethyl-2-oxo-1,2-dihydropyridin-3-yl)methyl)-5-(ethyl(tetrahydro-2H-pyran-4-yl)amino)-4-methyl-[1,1'-biphenyl]-3-carboxamide |

TABLE 1-continued

| | Structure | Chemical Name |
|---|---|---|
| CZ40-73 | 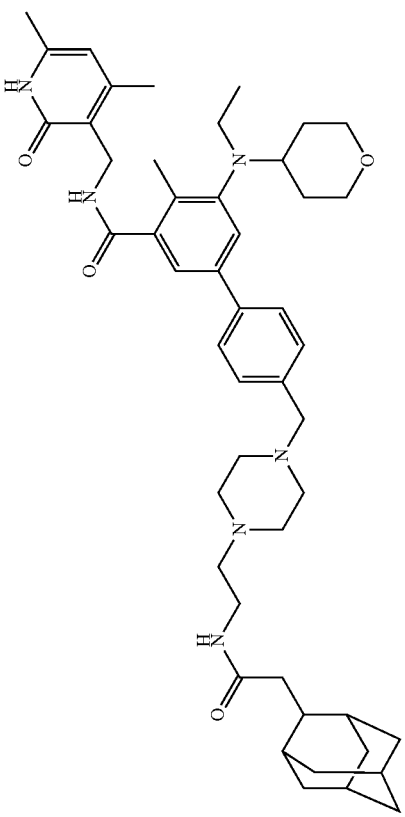 | 4'-((4-(2-(2-((1R,3S,5r,7r)-adamantan-2-yl)acetamido)ethyl)piperazin-1-yl)methyl)-N-((4,6-dimethyl-2-oxo-1,2-dihydropyridin-3-yl)methyl)-5-(ethyl(tetrahydro-2H-pyran-4-yl)amino)-4-methyl-[1,1'-biphenyl]-3-carboxamide |
| CZ40-75 | 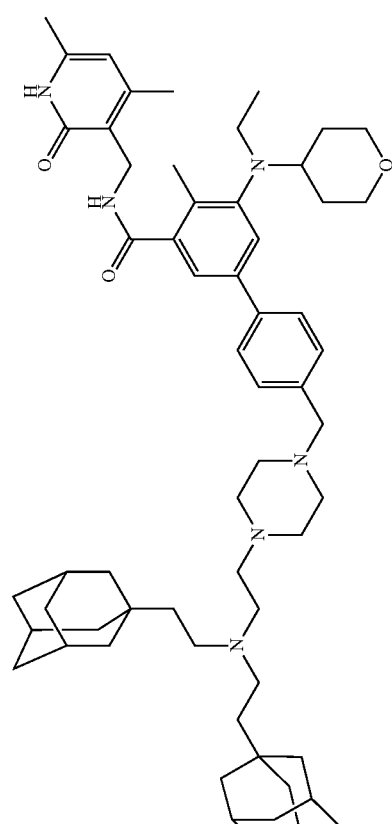 | 4'-((4-(2-(2-((1s,3S)-adamantan-1-yl)ethyl)(2-((3R,5R,7R)-adamantan-1-yl)ethyl)amino)ethyl)piperazin-1-yl)methyl)-N-((4,6-dimethyl-2-oxo-1,2-dihydropyridin-3-yl)methyl)-5-(ethyl((tetrahydro-2H-pyran-4-yl)amino)-4-methyl-[1,1'-biphenyl]-3-carboxamide |

TABLE 1-continued

| | Structure | Chemical Name |
|---|---|---|
| CZ40-149 | 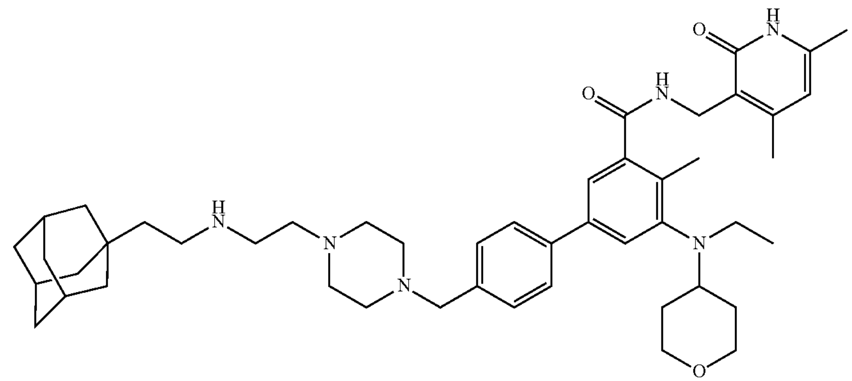 [SMILES: CCN(c1cc(-c2ccc(CN3CCN(CCNCCC45CC6CC(CC(C6)C4)C5)CC3)cc2)cc(C(=O)NCc2c(C)cc(C)[nH]c2=O)c1C)C1CCOCC1] | 4'-((4-(2-(2-((1s,3s)-adamantan-1-yl)ethyl)amino)ethyl)piperazin-1-yl)methyl)-N-((4,6-dimethyl-2-oxo-1,2-dihydropyridin-3-yl)methyl)-5-(ethyl(tetrahydro-2H-pyran-4-yl)amino)-4-methyl-[1,1'-biphenyl]-3-carboxamide |
| CZ40-74 | 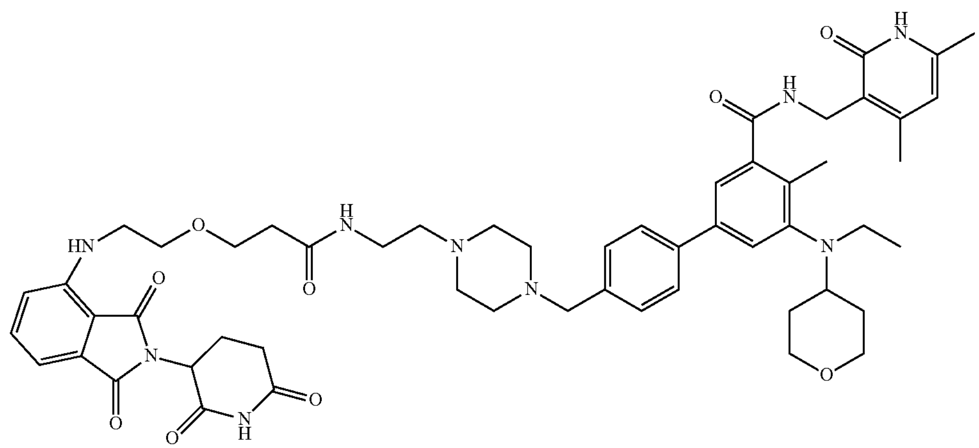 [SMILES: CCN(c1cc(-c2ccc(CN3CCN(CCNC(=O)CCOCCNc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydropyridin-3-yl)methyl)-4'-((4-(2-(3-(2-((2-(2,6-dioxopiperidin-3-yl)-1,3-dioxoisoindolin-4-yl)amino)ethoxy)propanamido)ethyl)piperazin-1-yl)methyl)-5-(ethyl(tetrahydro-2H-pyran-4-yl)amino)-4-methyl-[1,1'-biphenyl]-3-carboxamide |

TABLE 1-continued
| | Structure | Chemical Name |
|---|---|---|
| CZ40-131 | 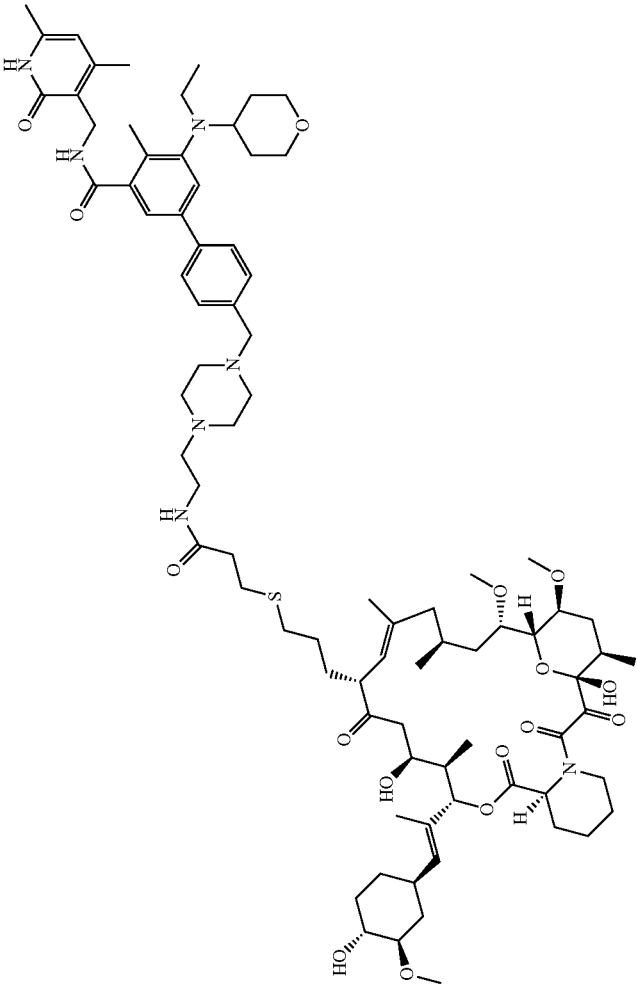 | FK506 adduct with N-((4,6-dimethyl-2-oxo-1,2-dihydropyridin-3-yl)methyl)-5-(ethyl(tetrahydro-2H-pyran-4-yl)amino)-4'-((4-(2-(3-mercaptopropanamido)ethyl)piperazin-1-yl)methyl)-4-methyl-[1,1'-biphenyl]-3-carboxamide |
| AM41-36A | 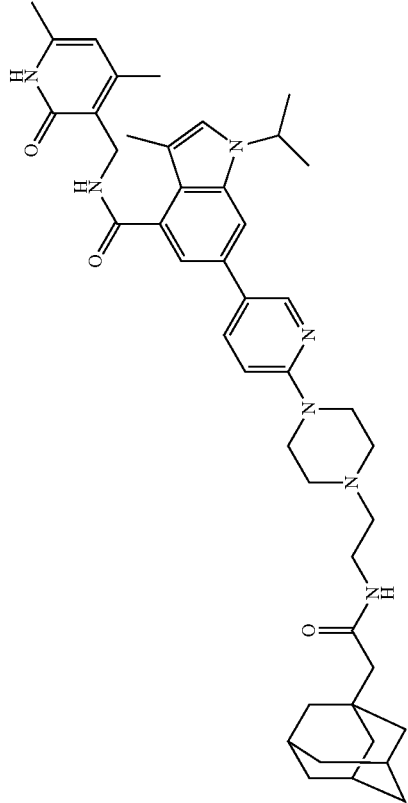 | 6-(6-(4-(2-(2-((3r,5r,7r)-adamantan-1-yl)acetamido)ethyl)piperazin-1-yl)pyridin-3-yl)-N-((4,6-dimethyl-2-oxo-1,2-dihydropyridin-3-yl)methyl)-1-isopropyl-3-methyl-1H-indole-4-carboxamide |

TABLE 1-continued

| | Structure | Chemical Name |
|---|---|---|
| AM41-37A | 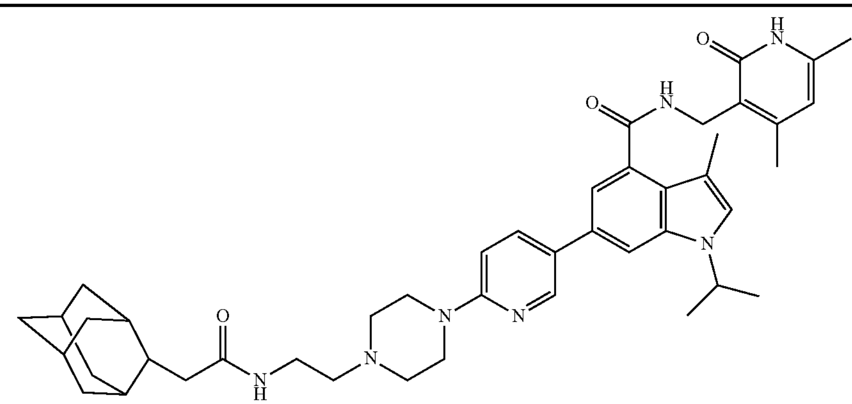 | 6-(6-(4-(2-(2-((1r,3r,5r,7r)-adamantan-2-yl)acetamido)ethyl)piperazin-1-yl)pyridin-3-yl)-N-((4,6-dimethyl-2-oxo-1,2-dihydropyridin-3-yl)methyl)-1-isopropyl-3-methyl-1H-indole-4-carboxamide |
| AM41-39A | 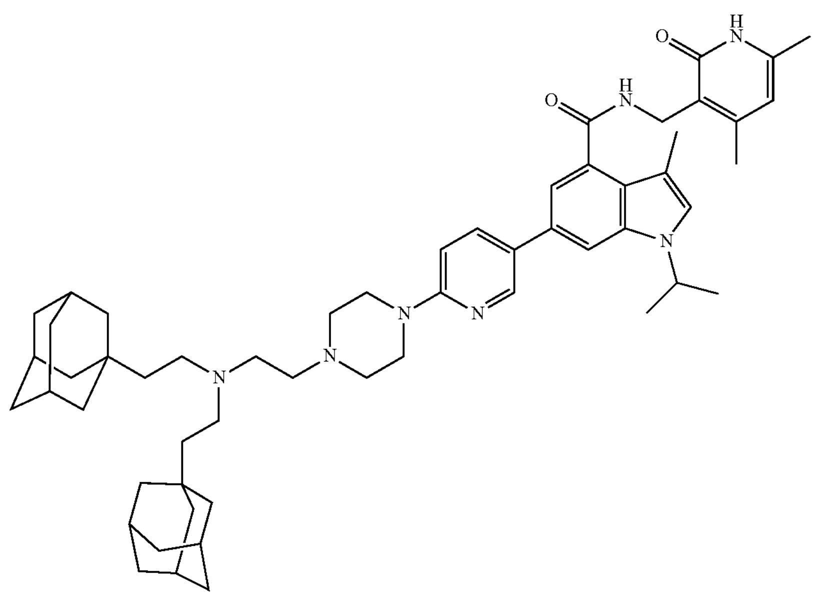 [SMILES: Cc1cc(C)c(CNC(=O)c2cc(-c3ccc(N4CCN(CCN(CCC56CC7CC(CC(C7)C5)C6)CCC56CC7CC(CC(C7)C5)C6)CC4)nc3)cc3c2c(C)cn3C(C)C)c(=O)[nH]1] | 6-(6-(4-(2-(bis(2-((3R,5R,7R)-adamantan-1-yl)ethyl)amino)ethyl)piperazin-1-yl)pyridin-3-yl)-N-((4,6-dimethyl-2-oxo-1,2-dihydropyridin-3-yl)methyl)-1-isopropyl-3-methyl-1H-indole-4-carboxamide |

TABLE 1-continued

| | Structure | Chemical Name |
|---|---|---|
| AM41-41A | 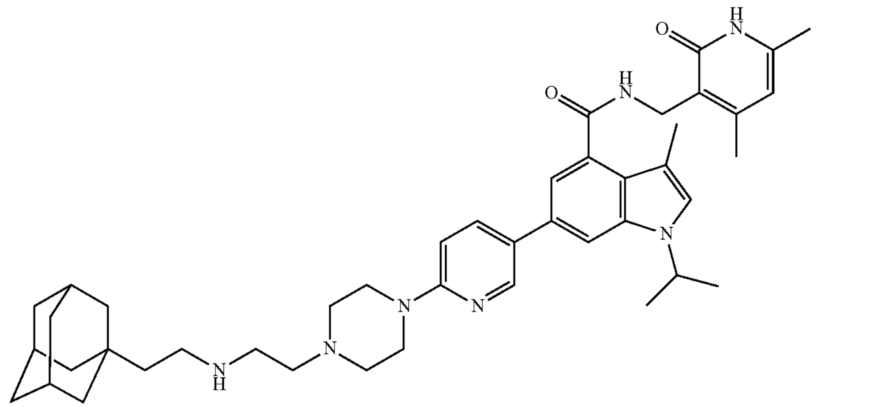 [SMILES: Cc1cc(C)c(CNC(=O)c2cc(-c3ccc(N4CCN(CCNCCC56CC7CC(CC(C7)C5)C6)CC4)nc3)cc3c2c(C)cn3C(C)C)c(=O)[nH]1] | 6-(6-(4-(2-((2-((3r,5r,7r)-adamantan-1-yl)ethyl)amino)ethyl)piperazin-1-yl)pyridin-3-yl)-N-((4,6-dimethyl-2-oxo-1,2-dihydropyridin-3-yl)methyl)-1-isopropyl-3-methyl-1H-indole-4-carboxamide |
| AM41-38A | 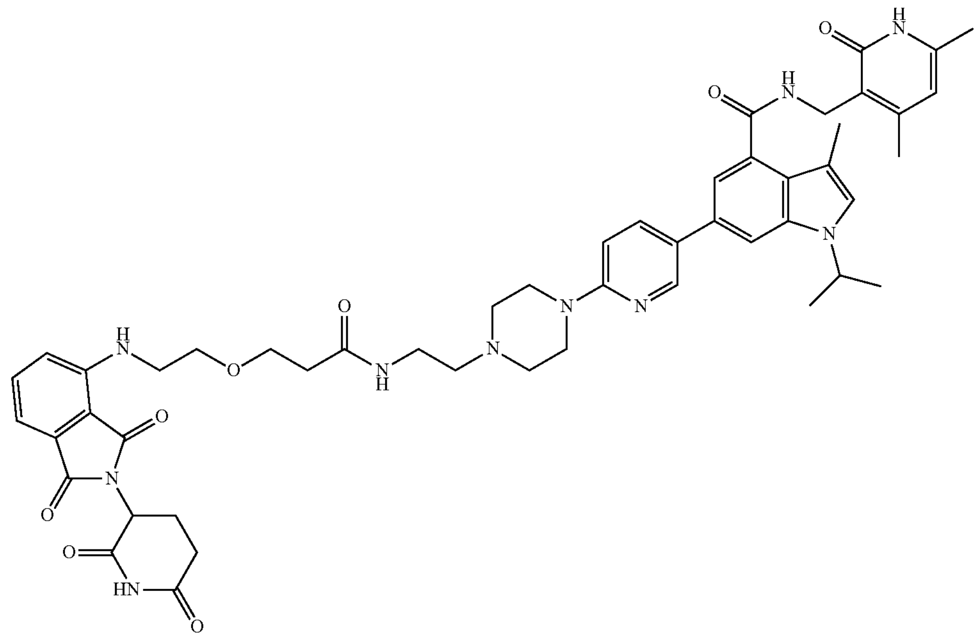 [SMILES: Cc1cc(C)c(CNC(=O)c2cc(-c3ccc(N4CCN(CCNC(=O)CCOCCNc5cccc6c5C(=O)N(C5CCC(=O)NC5=O)C6=O)CC4)nc3)cc3c2c(C)cn3C(C)C)c(=O)[nH]1] | N-((4,6-dimethyl-2-oxo-1,2-dihydropyridin-3-yl)methyl)-6-(6-(4-(2-(3-(2-(2-(2,6-dioxopiperidin-3-yl)-1,3-dioxoisoindolin-4-yl)amino)ethoxy)propanamido)ethyl)piperazin-1-yl)pyridin-3-yl)-1-isopropyl-3-methyl-1H-indole-4-carboxamide |

TABLE 1-continued
| | Structure | Chemical Name |
|---|---|---|
| AM41-40A | 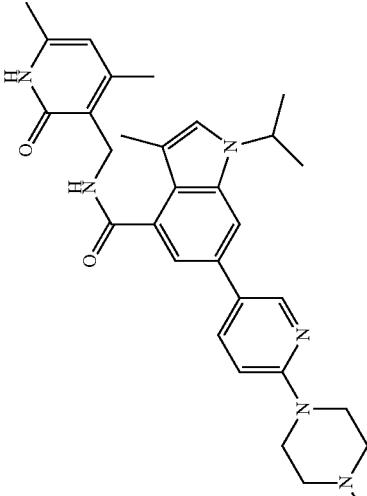 | FK506 adduct with N-((4,6-dimethyl-2-oxo-1,2-dihydropyridin-3-yl)methyl)-1-isopropyl-6-(6-(4-(2-(3-mercaptopropanamido)ethyl)piperazin-1-yl)pyridin-3-yl)-3-methyl-1H-indole-4-carboxamide |
| XF042-84 | 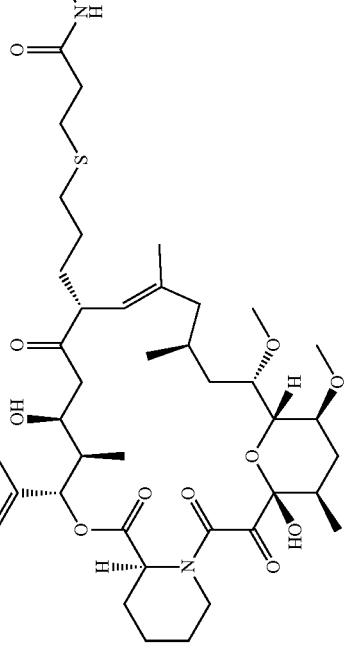 | 1-((R)-1-(1-(2-(2-((3R,5R,7R)-adamantan-1-yl)acetamido)ethyl)piperidin-4-yl)ethyl)-N-((4-methoxy-6-methyl-2-oxo-1,2-dihydropyridin-3-yl)methyl)-2-methyl-1H-indole-3-carboxamide |

TABLE 1-continued

| | Structure | Chemical Name |
|---|---|---|
| XF042-85 | 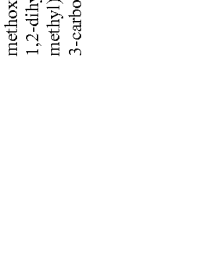 | 1-((R)-1-(1-(2-(2-((1R,3S,5R,7R)-adamantan-2-yl)acetamido)ethyl)piperidin-4-yl)ethyl)-N-((4-methoxy-6-methyl-2-oxo-1,2-dihydropyridin-3-yl)methyl)-2-methyl-1H-indole-3-carboxamide |
| XF042-95 | 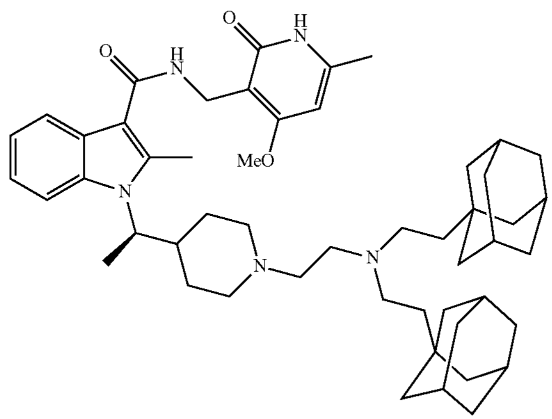 [SMILES: COc1cc(C)[nH]c(=O)c1CNC(=O)c1c(C)n([C@H](C)C2CCN(CCN(CCC34CC5CC(CC(C5)C3)C4)CCC34CC5CC(CC(C5)C3)C4)CC2)c2ccccc12] | 1-((R)-1-(1-(2-(bis(2-((3R,5R,7R)-adamantan-1-yl)ethyl)amino)ethyl)piperidin-4-yl)ethyl)-N-((4-methoxy-6-methyl-2-oxo-1,2-dihydropyridin-3-yl)methyl)-2-methyl-1H-indole-3-carboxamide |
| XF042-132 | 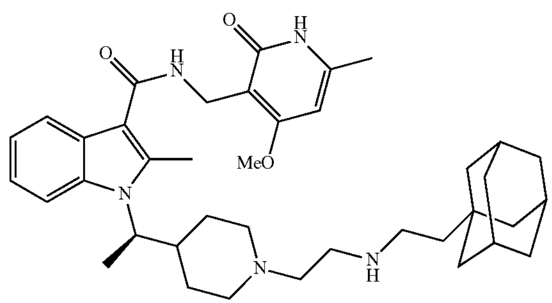 [SMILES: COc1cc(C)[nH]c(=O)c1CNC(=O)c1c(C)n([C@H](C)C2CCN(CCNCCC34CC5CC(CC(C5)C3)C4)CC2)c2ccccc12] | 1-((R)-1-(1-(2-((3R,5R,7R)-adamantan-1-yl)ethyl)amino)ethyl)piperidin-4-yl)ethyl)-N-((4-methoxy-6-methyl-2-oxo-1,2-dihydropyridin-3-yl)methyl)-2-methyl-1H-indole-3-carboxamide |

TABLE 1-continued
| Structure | Chemical Name |
|---|---|
| 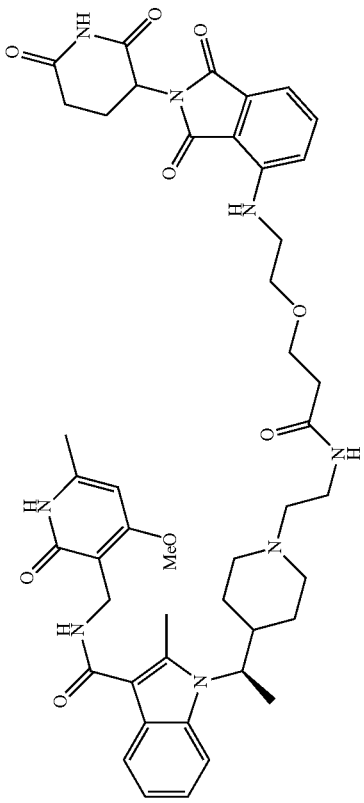 | XF042-86: 1-((1R)-1-(1-(2-(3-(2-((2,6-dioxopiperidin-3-yl)-1,3-dioxoisoindolin-4-yl)amino)ethoxy)propanamido)ethyl)piperidin-4-yl)ethyl)-N-((4-methoxy-6-methyl-2-oxo-1,2-dihydropyridin-3-yl)methyl)-2-methyl-1H-indole-3-carboxamide |
| 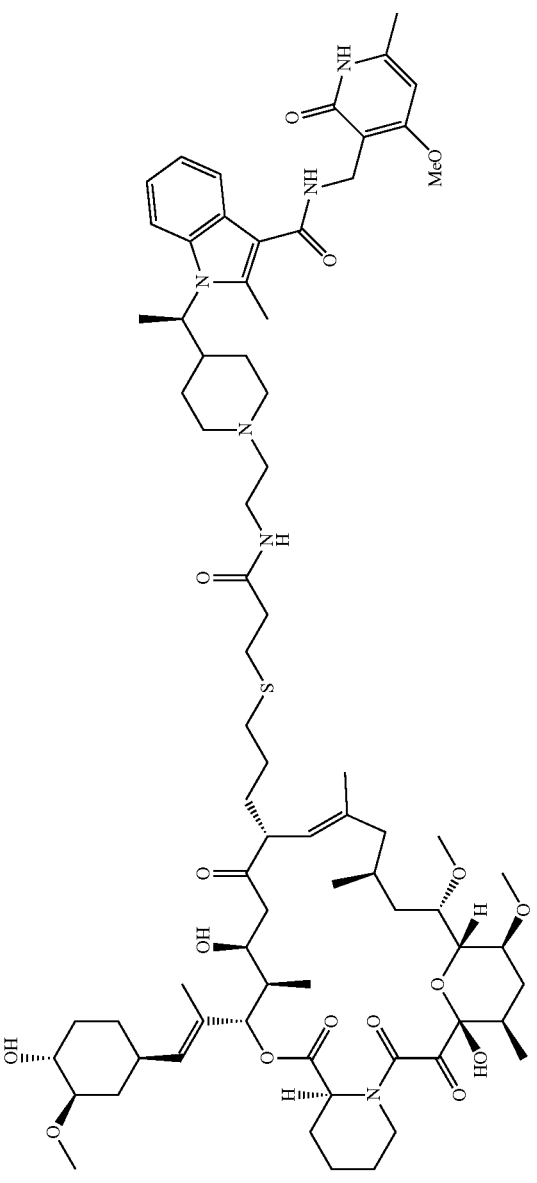 | XF042-94: FK506 adduct with (R)-1-(1-(2-(3-mercaptopropanamido)piperidin-4-yl)ethyl)-N-((4-methoxy-6-methyl-2-oxo-1,2-dihydropyridin-3-yl)methyl)-2-methyl-1H-indole-3-carboxamide |

TABLE 1-continued

| | Structure | Chemical Name |
|---|---|---|
| XF042-89 | 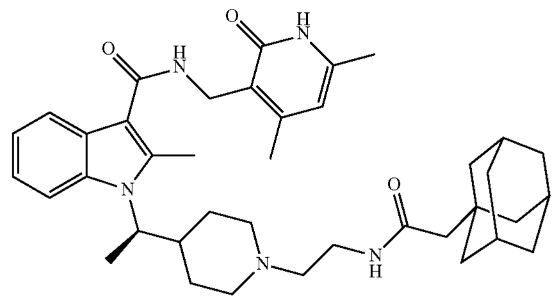 [SMILES: Cc1cc(C)c(CNC(=O)c2c(C)n([C@H](C)C3CCN(CCNC(=O)CC45CC6CC(CC(C6)C4)C5)CC3)c3ccccc23)c(=O)[nH]1] | 1-((R)-1-(1-(2-(2-(((3R,5R,7R)-adamantan-1-yl)acetamido)ethyl)piperidin-4-yl)ethyl)-N-((4,6-dimethyl-2-oxo-1,2-dihydropyridin-3-yl)methyl)-2-methyl-1H-indole-3-carboxamide |
| XF042-90 | 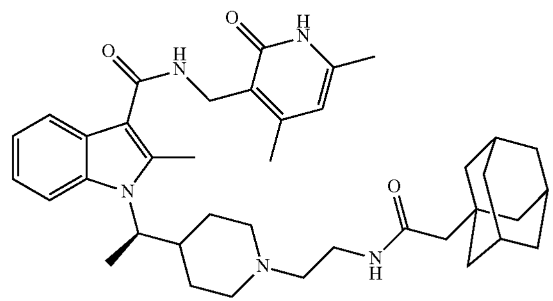 [SMILES: Cc1cc(C)c(CNC(=O)c2c(C)n([C@H](C)C3CCN(CCNC(=O)CC45CC6CC(CC(C6)C4)C5)CC3)c3ccccc23)c(=O)[nH]1] | 1-((R)-1-(1-(2-(2-(((1R,3S,5R,7R)-adamantan-2-yl)acetamido)ethyl)piperidin-4-yl)ethyl)-N-((4,6-dimethyl-2-oxo-1,2-dihydropyridin-3-yl)methyl)-2-methyl-1H-indole-3-carboxamide |
| XF042-93 | 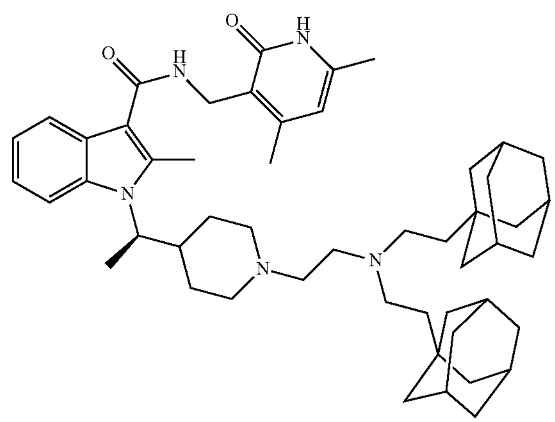 [SMILES: Cc1cc(C)c(CNC(=O)c2c(C)n([C@H](C)C3CCN(CCN(CCC45CC6CC(CC(C6)C4)C5)CCC45CC6CC(CC(C6)C4)C5)CC3)c3ccccc23)c(=O)[nH]1] | 1-((R)-1-(1-(2-(bis(2-((3R,5R,7R)-adamantan-1-yl)ethyl)amino)ethyl)piperidin-4-yl)ethyl)-N-((4,6-dimethyl-2-oxo-1,2-dihydropyridin-3-yl)methyl)-2-methyl-1H-indole-3-carboxamide |

TABLE 1-continued
| | Structure | Chemical Name |
|---|---|---|
| XF042-133 | 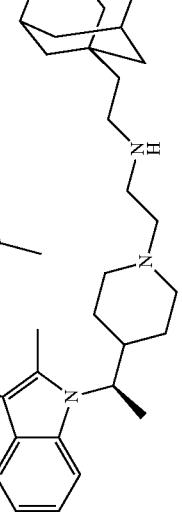 | 1-((R)-1-(1-(2-(2-((3R,5R,7R)-adamantan-1-yl)ethyl)amino)ethyl) piperidin-4-yl)ethyl)-N-((4,6-dimethyl-2-oxo-1,2-dihydropyridin-3-yl) methyl)-2-methyl-1H-indole-3-carboxamide |
| XF042-91 | 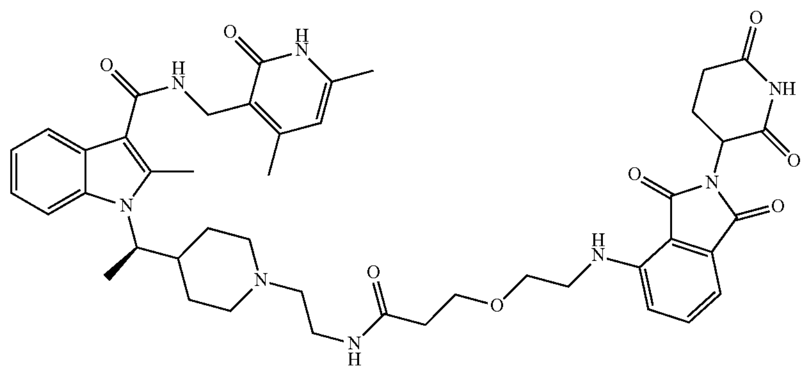 [SMILES: Cc1cc(C)c(CNC(=O)c2c(C)n([C@H](C)C3CCN(CCNC(=O)CCOCCNc4cccc5c4C(=O)N(C4CCC(=O)NC4=O)C5=O)CC3)c3ccccc23)c(=O)[nH]1] | N-((4,6-dimethyl-2-oxo-1,2-dihydropyridin-3-yl)methyl)-1-((1R)-1-(1-(2-(3-(2-((2,6-dioxopiperidin-3-yl)-1,3-dioxoisoindolin-4-yl) amino)ethoxy)propanamido) ethyl)piperidin-4-yl)ethyl)-2-methyl-1H-indole-3-carboxamide |

TABLE 1-continued
| Structure | Chemical Name |
|---|---|
| XF042-92 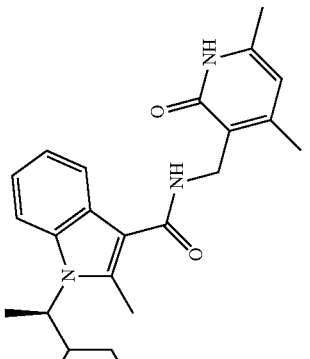 | FK506 adduct with (R)-N-((4,6-dimethyl-2-oxo-1,2-dihydropyridin-3-yl)methyl)-1-(1-(2-(3-mercaptopropanamido)ethyl)piperidin-4-yl)ethyl)-2-methyl-1H-indole-3-carboxamide |

Additional Exemplary Compounds (I)
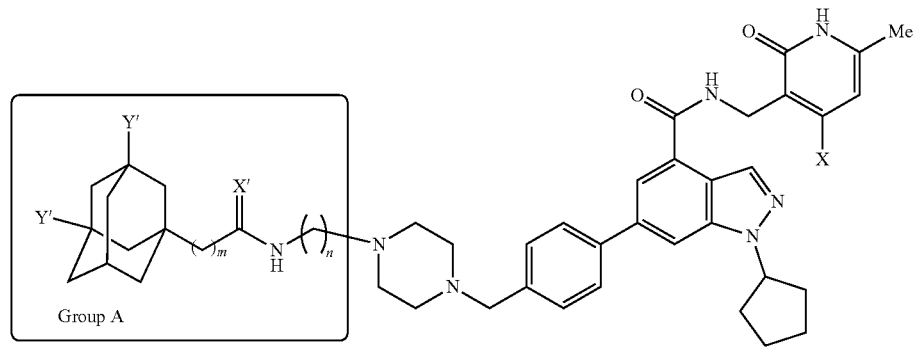
X = C$_{1-6}$ alkyl, MeO—
In Group A:
X' = O or H$_2$
Y' = H, C$_{1-6}$ alkyl
m = 0-15
n = 2-15
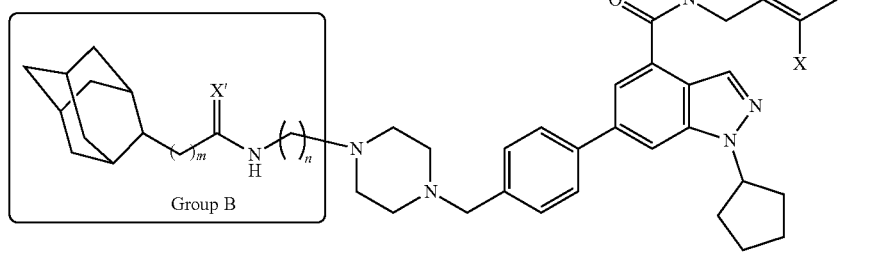
X = C$_{1-6}$ alkyl, MeO—
In Group B:
X' = O or H$_2$
m = 0-15
n = 2-15
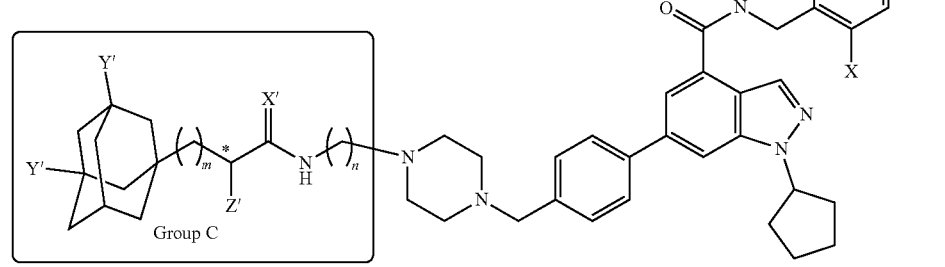
X = C$_{1-6}$ alkyl, MeO—
In Group C:
X' = O or H$_2$
Y' = H, C$_{1-6}$ alkyl
Z' = C$_{1-6}$ alkyl
m = 0-15
n = 2-15
* R, S and racemic -continued
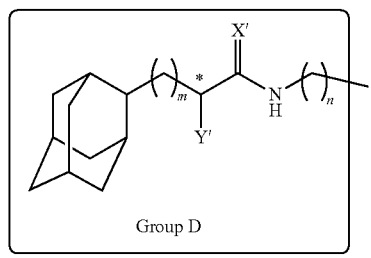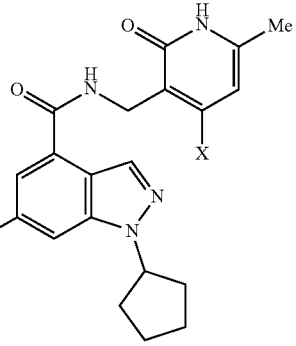
Group D
X = C$_{1-6}$ alkyl, MeO—
In Group D:
X' = O or H$_2$
Y' = H, C$_{1-6}$ alkyl
m = 0-15
n = 2-15
*R, S and racemic
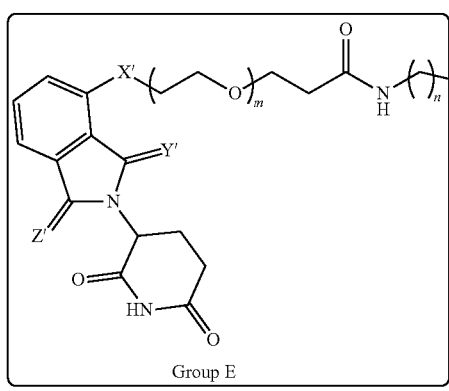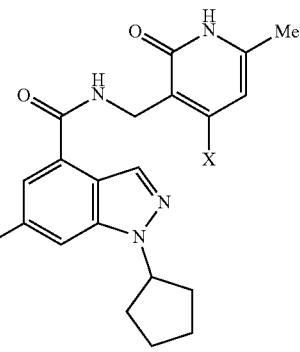
Group E
X = C$_{1-6}$ alkyl, MeO—
In Group E:
X' = NH, O or C$_{1-6}$ alkyl
Y' = O or H$_2$
Z' = O or H$_2$
m = 0-15
n = 2-15
*R, S and racemic

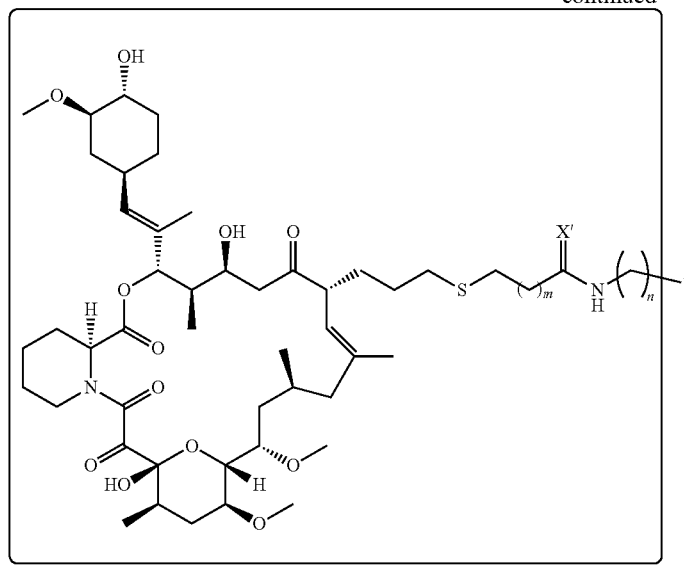

X = C$_{1-6}$ alkyl, MeO—

In Group F:
X' = O or H$_2$
m = 0-15
n = 2-15

Additional Exemplary Compounds (I)

Group=Group A, B, C, D, E, or F which appeared in the figure "Additional exemplary compounds (D)"

Each structure below represents the combination of variants of inhibitor and variants of each Group (as illustrated in the figure "Additional exemplary compounds (I)" and in the current figure "Additional exemplary compounds (II)")

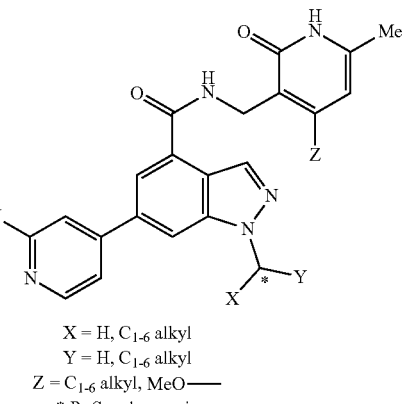

X = H, C$_{1-6}$ alkyl
Y = H, C$_{1-6}$ alkyl
Z = C$_{1-6}$ alkyl, MeO—
* R, S and racemic

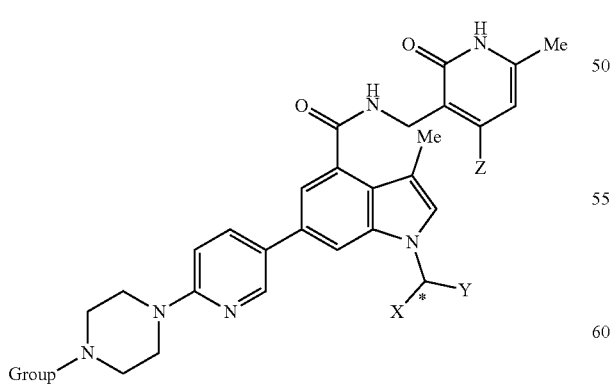

X = H, C$_{1-6}$ alkyl
Y = H, C$_{1-6}$ alkyl
Z = C$_{1-6}$ alkyl, MeO—
* R, S and racemic

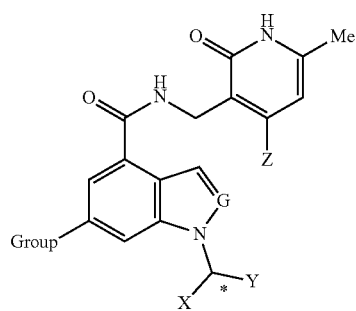

X = H, C$_{1-6}$ alkyl
Y = H, C$_{1-6}$ alkyl
Z = C$_{1-6}$ alkyl, MeO—
G = CH or N
* R, S and racemic

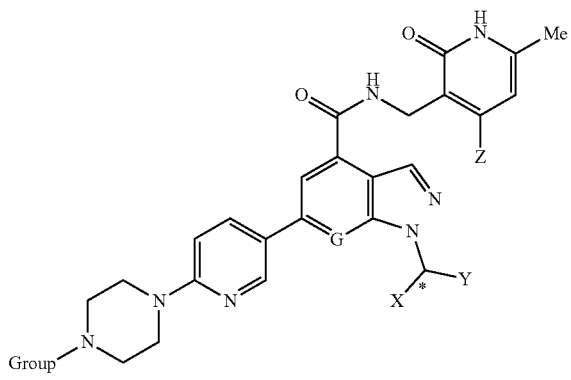

X = H, C$_{1-6}$ alkyl
Y = H, C$_{1-6}$ alkyl
Z = C$_{1-6}$ alkyl, MeO—
G = CH or N
* R, S and racemic

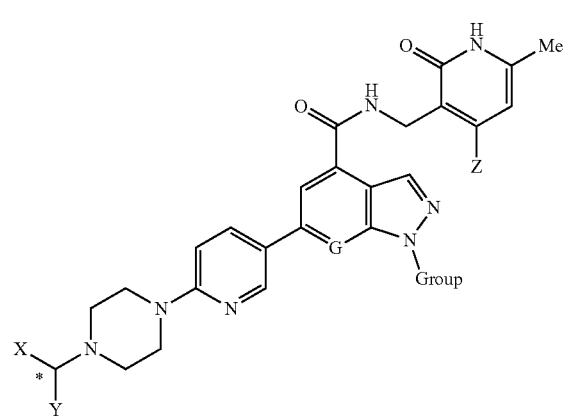

X = H, C$_{1-6}$ alkyl
Y = H, C$_{1-6}$ alkyl
Z = C$_{1-6}$ alkyl, MeO—
G = CH or N
* R, S and racemic

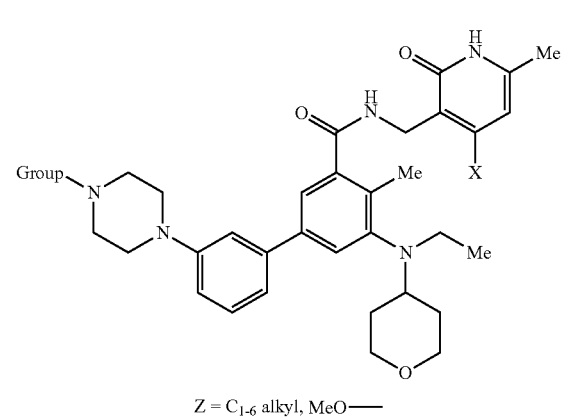

Z = C$_{1-6}$ alkyl, MeO—

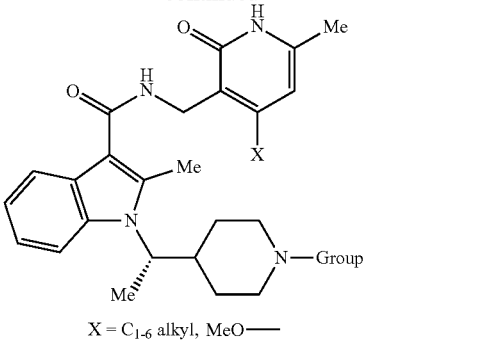

X = C$_{1-6}$ alkyl, MeO—

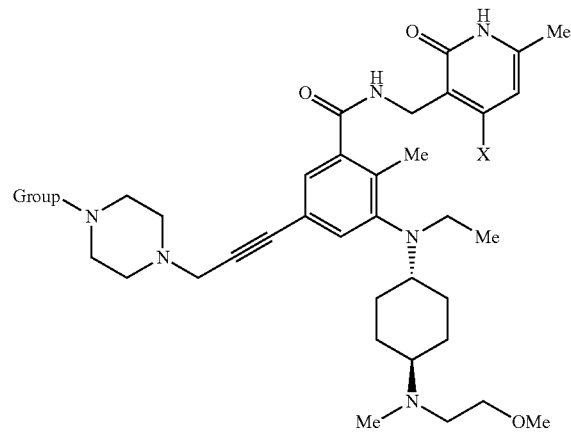

X = C$_{1-6}$ alkyl, MeO—

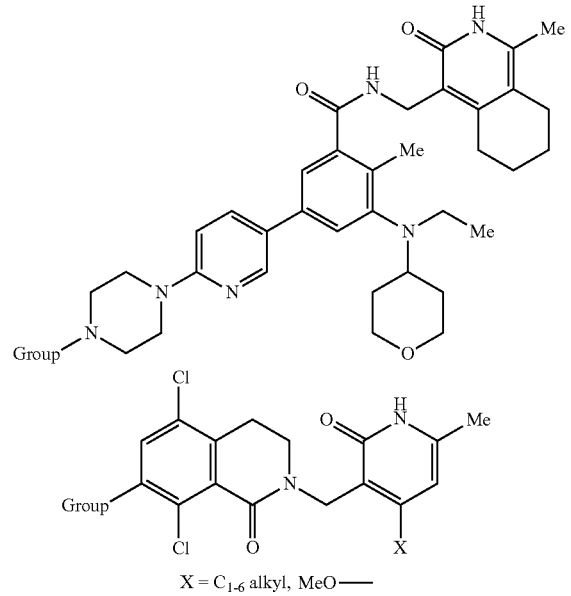

X = C$_{1-6}$ alkyl, MeO—

The inhibitory activity of EZH2 degraders/disruptors can be assessed by EZH2 biochemical assays known in the art (Konze et al., 2013: Yang et al., 2016): see, e.g., Example 115. Their binding affinity to EZH2 can be assessed using standard biophysical assays known in the art (e.g., ITC, SPR). Cellular assays (e.g., as depicted in Examples 113 and 114) can be used to assess the compounds' ability to induce EZH2 degradation/disruption, reduce the H3K27me3 mark, and/or inhibit cancer cell proliferation. Assay's suitable for use in any or all of these steps are known in the art, and include, e.g., Western blotting and MTT. Suitable cell lines for use in any or all of these steps are known in the art and include, e.g., HCC70, HCC1170, HCC1187, MDA-MB-468, MDA-MB-231, MCF-7, BT549, HCC1954, HeLa S3, HEK 293, U2OS, and HFF cells.

By way of non-limiting example, detailed synthesis protocols are shown in the Examples below for specific exemplary EZH2 degraders/disruptors.

In certain aspects, the compositions and methods described herein include the manufacture and use of pharmaceutical compositions and medicaments that include compounds identified by a method described herein as active ingredients. Also included are the pharmaceutical compositions themselves.

In some instances, the compositions disclosed herein can include other compounds, drugs, and/or agents used for the treatment of cancer. For example, in some instances, therapeutic compositions disclosed herein can be combined with one or more (e.g., one, two, three, four, five, or less than ten) compounds.

In some instances, the compositions disclosed herein can include EZH2 degraders/disruptors such as AM16-10A, XY019-43, AM29-182A, AM19-177A, AM16-103A, CZ40-75, CZ40-149, AM41-41A, XF042-95, XF042-93, XF042-133, XY028-086, CZ40-131, and XF042-92.

An EZH2 degrader/disruptor can selectively affect EZH2-mediated cancer cells (e.g., TNBC cells) compared to WT, normal or non-tumor cells (i.e., a degrader/disruptor able to kill or inhibit the growth of EZH2-mediated cancer cells while also having a relatively low ability to lyse or inhibit the growth of WT, normal or non-tumor cells), e.g., possess a $GI_{50}$ for one or more EZH2-mediated cancer cells more than 1.5-fold lower, more than 2-fold lower, more than 2.5-fold lower, more than 3-fold lower, more than 4-fold lower, more than 5-fold lower, more than 6-fold lower, more than 7-fold lower, more than 8-fold lower, more than 9-fold lower, more than 10-fold lower, more than 15-fold lower, or more than 20-fold lower than its $GI_{50}$ for one or more WT, normal or non-tumor cells, e.g., WT, normal or non-tumor cells of the same species and tissue type as the EZH2-mediated cancer cells.

One or more of the EZH2 degraders/disruptors disclosed herein can be formulated for use as or in pharmaceutical compositions. Such compositions can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/FormsSubmissionRequirements/ElectronicSubmissions/DataStandardsManualmonographs). The pharmaceutical compositions may be formulated for oral, parenteral, or transdermal delivery. The compound of the invention may also be combined with other pharmaceutical agents.

The pharmaceutical compositions disclosed herein can be administered, e.g., orally, parenterally, by inhalation spray or nebulizer, topically, rectally, nasally, buccally, vaginally, via an implanted reservoir, by injection (e.g., intravenously, intra-arterially, subdermally, intraperitoneally, intramuscularly, and/or subcutaneously), in an ophthalmic preparation, or via transmucosal administration. Suitable dosages may range from about 0.001 to about 100 mg/kg of body weight, or according to the requirements of the particular drug. The pharmaceutical compositions of this invention can contain any conventional non-toxic pharmaceutically-acceptable carriers, adjuvants or vehicles. In some cases, the pH of the formulation can be adjusted with pharmaceutically acceptable acids, bases, or buffers to enhance the stability of the formulated compound or its delivery form. The term "parenteral" as used herein includes subcutaneous, intracutaneous, intravenous, intramuscular, intraarticular, intra-arterial, intrasynovial, intrasternal, intrathecal, intralesional, and intracranial injection or infusion techniques. Alternatively or in addition, the present invention may be administered according to any of the methods as described in the FDA DSM.

Pharmaceutical compositions typically include a pharmaceutically acceptable carrier. The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound. As used herein the language "pharmaceutically acceptable carrier" includes saline, solvents, dispersion media, coatings, antibacterial and antifungal agents, isotonic and absorption delaying agents, and the like, compatible with pharmaceutical administration.

As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. As used herein, the term "pharmaceutically acceptable derivative" means any pharmaceutically acceptable salt, solvate or prodrug, e.g., ester, of an atovaquone-related compound described herein, which upon administration to the recipient is capable of providing (directly or indirectly) a compound described herein, or an active metabolite or residue thereof. Such derivatives are recognizable to those skilled in the art, without undue experimentation. Nevertheless, reference is made to the teaching of Burger's Medicinal Chemistry and Drug Discovery. 5th Edition. Vol 1: Principles and Practice, which is incorporated herein by reference to the extent of teaching such derivatives. Pharmaceutically acceptable derivatives include salts, solvates, esters, carbamates, and/or phosphate esters.

In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

As used herein, the EZH2 degraders/disruptors disclosed herein are defined to include pharmaceutically acceptable derivatives or prodrugs thereof. A "pharmaceutically acceptable derivative or prodrug" means any pharmaceutically acceptable salt, ester, salt of an ester, or other derivative of a compound or agent disclosed herein which, upon administration to a recipient, is capable of providing (directly or indirectly) a compound of this invention. Particularly favored derivatives and prodrugs are those that increase the bioavailability of the compounds disclosed herein when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein.

The EZH2 degraders/disruptors disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivative thereof.

In some instances, pharmaceutical compositions can include an effective amount of one or more EZH2 degraders/disruptors. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of cell growth, cell proliferation, or cancer).

In some aspects, the present disclosure provides methods for using a composition comprising an EZH2 degrader/disruptor, including pharmaceutical compositions (indicated below as 'X') disclosed herein in the following methods:

Substance X for use as a medicament in the treatment of one or more diseases or conditions disclosed herein (e.g., neurodegenerative disease, referred to in the following examples as 'Y'). Use of substance X for the manufacture of a medicament for the treatment of Y; and substance X for use in the treatment of Y.

In some instances, therapeutic compositions disclosed herein can be formulated for sale in the US, import into the US, and/or export from the US.

The pharmaceutical compositions can be included in a container, pack, or dispenser together with instructions for administration.

The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% 30) to about 95% active compound (w/w). Alternatively, such preparations can contain from about 20% to about 80% active compound.

In some aspects, an effective dose of an EZH2 degrader/disruptor can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day.

Pharmaceutical compositions of this invention can include one or more EZH2 degraders/disruptors and any pharmaceutically acceptable carrier and/or vehicle. In some instances, pharmaceuticals can further include one or more additional therapeutic agents in amounts effective for achieving a modulation of disease or disease symptoms.

Such additional therapeutic agents may include conventional chemotherapeutic agents known in the art. When co-administered, EZH2 degraders/disruptors disclosed herein can operate in conjunction with conventional chemotherapeutic agents to produce mechanistically additive or synergistic therapeutic effects.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tween®'s or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waves, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

Pharmaceutical compositions can be in the form of a solution or powder for injection. Such compositions may be formulated according to techniques known in the art using suitable dispersing or wetting agents (such as, for example. Tween®: 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tween®'s, Span™Ms, and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Pharmaceutically acceptable salts of the EZH2 degraders/disruptors of this disclosure include, e.g., those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include, e.g., alkali metal (e.g., sodium), alkaline earth metal (e.g., magnesium), ammonium and N-(alkyl) 4 salts. The invention also envisions the quaternization of any basic nitrogen-containing groups of the degraders disclosed herein. Water or oil-soluble or dispersible products can be obtained by such quaternization.

The methods described herein include methods for the treatment of disorders associated with EZH2-mediated cancer, the methods include administering a therapeutically effective amount of an EZH2 degrader/disruptor as described herein, to a subject (e.g., a mammalian subject, e.g., a human subject) who is in need of, or who has been determined to be in need of, such treatment.

In some instances, methods can include selection of a human subject who has or had a condition or disease. In some instances, suitable subjects include, for example, subjects who have or had a condition or disease but that resolved the disease or an aspect thereof, present reduced symptoms of disease (e.g., relative to other subjects (e.g., the majority of subjects) with the same condition or disease), and/or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease).

The terms "treat", "treating," or "treatment," as used herein, refer to partially or completely alleviating, inhibiting, ameliorating, and/or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the compositions and methods of the present invention. In some aspects, treatment can promote or result in, for example, a decrease in the number of tumor cells (e.g., in a subject) relative to the number of tumor cells prior to treatment: a decrease in the viability (e.g., the average/mean viability) of tumor cells (e.g., in a subject) relative to the viability of tumor cells prior to treatment; and/or reductions in one or more symptoms associated with one or more tumors in a subject relative to the subject's symptoms prior to treatment.

As used herein, the term "treating cancer" means causing a partial or complete decrease in the rate of growth of a tumor, and/or in the size of the tumor and/or in the rate of local or distant tumor metastasis, and/or the overall tumor burden in a subject, and/or any decrease in tumor survival, in the presence of a degrader/disruptor (e.g., an EZH2 degrader/disruptor) described herein.

As used herein, the term "preventing a disease" (e.g., preventing cancer) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

Exemplary EZH2-mediated cancers that can be treated with EZH2 degraders/disruptors include, for example, INI1-negative tumors, lymphoma (including diffuse large B-cell lymphoma (DLBCL), follicular lymphoma (FL), and non-Hodgkin's lymphoma (NHL)), malignant rhabdoid tumor, multiple myeloma, relapsed/refractory synovial sarcoma, breast cancers (including TNBC), prostate cancers, other solid tumors, acute lymphoblastic leukemia, acute myeloid leukemia, adrenocortical carcinoma, AIDS-related cancers, anal cancer, astrocytoma, childhood cerebellar cancer, basal cell carcinoma, skin cancer (non-melanoma), bile duct cancer, bladder cancer, bone cancer, osteosarcoma/malignant fibrous histiocytoma, brain stem glioma, brain tumor, cerebellar astrocytoma, cerebral astrocytoma/malignant glioma, ependymoma, medulloblastoma, supratentorial primitive neuroectodermal tumors, visual pathway and hypothalamic glioma, bronchial adenomas/carcinoids, Burkitt's lymphoma, carcinoid tumors, central nervous system lymphoma, cervical cancer, chronic lymphocytic leukemia, chronic myelogenous leukemia, chronic myeloproliferative disorder, colon cancer, colorectal cancer, cutaneous T-cell lymphoma, endometrial cancer, esophageal cancer, melanoma, retinoblastoma, gallbladder cancer, gastrointestinal carcinoid tumors, germ cell tumors, hairy cell leukemia, head and neck cancer, hepatocellular (liver) cancer, Hodgkin's lymphoma, hypopharyngeal cancer, islet cell carcinoma, Kaposi's sarcoma, kidney (renal cell) cancer, laryngeal cancer, lip and oral cavity cancer, lung cancer (small cell and non-small cell), Merkel cell carcinoma, mesothelioma, multiple endocrine neoplasia syndrome, multiple myeloma/plasma cell neoplasm mycosis fungoides, myelodysplastic syndrome, myeloid leukemia, myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, neuroectodermal tumors, pituitary tumors, pleuropulmonary blastoma, rectal cancer, rhabdomyosarcoma, salivary gland cancer. Ewing sarcoma, soft tissue sarcoma, uterine sarcoma, Sezary syndrome, small intestine cancer, squamous cell carcinoma, squamous neck cancer, stomach (gastric) cancer, testicular cancer, thymoma, thymic carcinoma, thyroid cancer, transitional cell cancer, trophoblastic tumors, urethral cancer, uterine cancer, vaginal cancer, vulvar cancer, Waldenstrom's macroglobulinemia, and Wilms' tumor.

The terms "prevent." "preventing." and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than that which would have occurred without the present invention.

The term "subject," as used herein, refers to any animal. In some instances, the subject is a mammal. In some instances, the term "subject," as used herein, refers to a human (e.g., a man, a woman, or a child).

In some instances, subject selection can include obtaining a sample from a subject (e.g., a candidate subject) and testing the sample for an indication that the subject is suitable for selection. In some instances, the subject can be confirmed or identified, e.g. by a health care professional, as having had or having a condition or disease. In some instances, exhibition of a positive immune response towards a condition or disease can be made from patient records, family history, and/or detecting an indication of a positive immune response. In some instances multiple parties can be included in subject selection. For example, a first party can obtain a sample from a candidate subject and a second party can test the sample. In some instances, subjects can be selected and/or referred by a medical practitioner (e.g., a general practitioner). In some instances, subject selection can include obtaining a sample from a selected subject and storing the sample and/or using the in the methods disclosed herein. Samples can include, for example, cells or populations of cells.

In general, methods include selecting a subject and administering to the subject an effective amount of one or more of the EZH2 degraders/disruptors described herein, e.g., in or as a pharmaceutical composition, and optionally repeating administration as required for the prophylaxis or treatment of cancer and can be administered, e.g., orally, intravenously or topically.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

In some instances, treatments methods can include a single administration, multiple administrations, and repeating administration as required for the prophylaxis or treatment of the disease or condition from which the subject is suffering (e.g., an EZH2-mediated cancer, e.g., breast cancers including TNBC). In some instances treatment methods can include assessing a level of disease in the subject prior to treatment, during treatment, and/or after treatment. In some instances, treatment can continue until a decrease in the level of disease in the subject is detected.

The terms "administer," "administering." or "administration," as used herein refers to implanting, absorbing, ingesting, injecting, or inhaling, the inventive drug, regardless of form. In some instances, one or more of the compounds disclosed herein can be administered to a subject topically (e.g., nasally) and/or orally. For example, the methods herein include administration of an effective amount of compound or compound composition to achieve the desired or stated effect. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician. Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week: including once every other day. The skilled artisan will appreciate that certain factors may influence the dosage and timing required to effectively treat a subject, including but not limited to the severity of the disease or disorder, previous treatments, the general health and/or age of the subject, and other diseases present.

Moreover, treatment of a subject with a therapeutically effective amount of the therapeutic compounds described herein can include a single treatment or a series of treatments. For example, effective amounts can be administered at least once. Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

EXAMPLES

Methods
HPLC: HPLC spectra for all compounds were acquired using an Agilent™ 1200 Series system with DAD detector.

Chromatography was performed on a 2.1×150 mm Zorbax™ 300SB-C18 5 μm column with water containing 0.1% formic acid as solvent A and acetonitrile containing 0.1% formic acid as solvent B at a flow rate of 0.4 ml/min. The gradient program was as follows: 1% B (0-1 min), 1-99% B (1-4 min), and 99% B (4-8 min). High-resolution mass spectra (HRMS) data were acquired in positive ion mode using an Agilent™ G1969A API-TOF with an electrospray ionization (ESI) source. Nuclear Magnetic Resonance (NMR) spectra were acquired on a Bruker®R: DRX-600 spectrometer with 600 MHz for proton ($^1$H NMR) and 150 MHz for carbon (13C NMR): chemical shifts are reported in (δ). Preparative HPLC was performed on Agilent™ Prep 1200 series with UV detector set to 254 nm. Samples were injected onto a Phenomenex™ LUNAR; 75×30 mm, 5 μm, C18 column at room temperature. The flow rate was 40 ml/min. A linear gradient was used with 10% (or 50%) of MeOH (A) in $H_2O$ (with 0.1% TFA) (B) to 100% of MeOH (A). HPLC was used to establish the purity of target compounds. All final compounds had >95% purity using the HPLC methods described above.

Example 1: Synthesis of AM16-10A

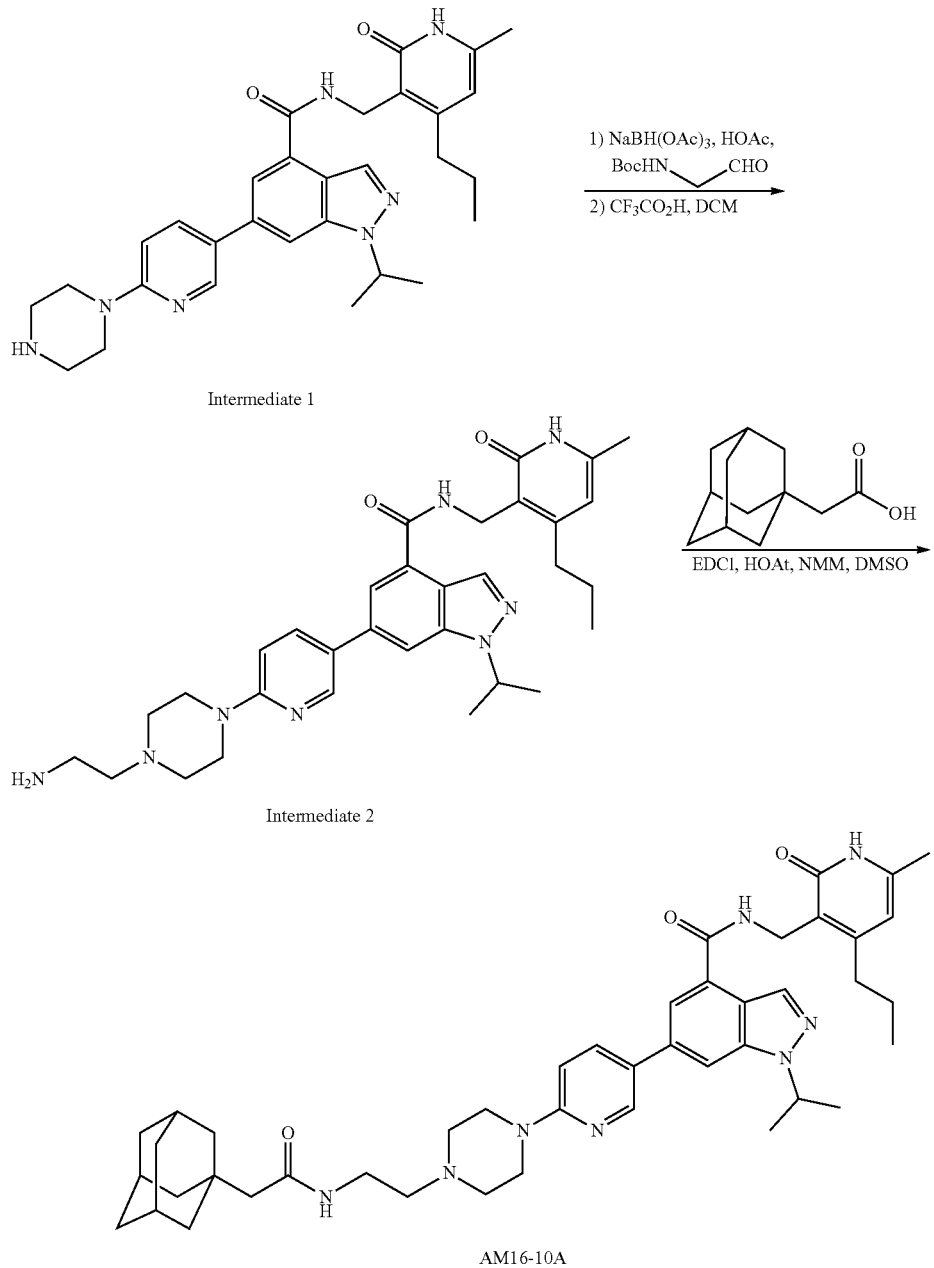

Intermediate 1 (385 mg, 0.60 mmol) and N-Boc-2-aminoacetaldehyde (191 mg, 1.2 mmol, Sigma®, #472654) were dissolved in DMF (5.0 mL) and acetic acid (0.5 mL). To the solution was added sodium triacetoxyborohydride (254 mg, 1.2 mmol) at 0° C. After being stirred overnight at room temperature, the mixture was filtered and purified by reverse-phase ISCO™ (10%-100% methanol/0.1% TFA in H₂O) to afford compound tert-butyl (2-(4-(5-(1-isopropyl-4-(((6-methyl-2-oxo-4-propyl-1,2-dihydropyridin-3-yl) methyl) carbamoyl)-1H-indazol-6-yl) pyridin-2-yl) piper-azin-1-yl)ethyl) carbamate 2,2,2-trifluoroacetate. The obtained intermediate was dissolved in DCM (30 mL) and treated with trifluoroacetic acid (5.0 mL) at room temperature. After being stirred overnight at room temperature, the mixture was concentrated and purified by reverse-phase ISCO™ to afford intermediate 2 (302 mg, 73% over 2 steps). Intermediate 2 (100 mg, 0.15 mmol), HOAt (1-hydroxy-7-azabenzo-triazole) (31 mg, 0.23 mmol) and 1-adamanta-neacetic acid (35 mg, 0.18 mmol, Sigma®, #127272) were dissolved in DMSO (2.0 mL). To the solution were added NMM (66 μL, 0.60 mmol), and EDCI (43 mg, 0.23 mmol) successively at room temperature. After being stirred overnight at room temperature, the mixture was concentrated under vacuum and purified by preparative HPLC (10%-100% methanol/0.1% TFA in H₂O) to afford AM16-10A as white solid in TFA salt form (75 mg, 58%). ¹H NMR (600 MHz, CDCl₃) δ 8.47 (s, 1H), 8.37 (s, 1H), 7.85 (d, J=7.8 Hz, 1H), 7.60 (brs, 4H), 6.75 (d, J=8.3 Hz, 1H), 6.38 (s, 1H), 4.95-4.84 (m, 1H), 4.67 (s, 2H), 4.28-3.54 (m, 7H), 3.50-2.97 (m, 6H), 2.88 (t, J=7.3 Hz, 2H), 2.40 (s, 3H), 1.92 (brs, 5H), 1.65-1.51 (m, 20H), 1.03 (t, J=7.2 Hz, 3H).

Example 2: Synthesis of AM16-11A

AM16-11A was synthesized according to the procedures for preparing AM16-10A from intermediate 2 (92 mg, 0.13 mmol), HOAt (27 mg, 0.20 mmol), 3-(1-adamantyl) pro-panoic acid (33 mg, 0.16 mmol, Matrix Scientific™, #038155), NMM (57 μL, 0.52 mmol), EDCI (39 mg, 0.20 mmol), and DMSO (2.0 mL). AM16-11A was obtained as white solid in TFA salt form (58 mg, 51%). ¹H NMR (600 MHz, CD₃OD) δ 8.57-8.49 (m, 1H), 8.37 (s, 1H), 8.08 (d, J=8.8 Hz, 1H), 7.94 (s, 1H), 7.76 (s, 1H), 7.06 (d, J=8.8 Hz, 1H), 6.17 (s, 1H), 5.12-5.05 (m, 1H), 4.60 (s, 2H), 4.25-3.60 (m, 6H), 3.60-3.33 (m, 6H), 2.77-2.69 (m, 2H), 2.27 (s, 3H), 2.23-2.16 (m, 2H), 1.93 (brs, 2H), 1.77-1.71 (m, 3H), 1.68-1.58 (m, 6H), 1.58-1.53 (m, 6H), 1.49 (brs, 6H), 1.41-1.32 (m, 2H), 1.02 (t, J=7.3 Hz, 3H).

Example 3: Synthesis of AM16-37A

AM16-37A was synthesized according to the procedures for preparing AM16-10A from intermediate 1 (100 mg, 0.16 mmol), HOAt (33 mg, 0.24 mmol), 1-adamantaneacetic acid (38 mg, 0.19 mmol), NMM (71 μL, 0.64 mmol), EDCI (46 mg, 0.24 mmol), and DMSO (2.0 mL). AM16-37A was obtained as yellow solid (73 mg, 65%). ¹H NMR (600 MHz, CDCl₃) δ 8.51 (s, 1H), 8.38 (s, 1H), 7.94-7.78 (m, 2H), 7.69 (s, 1H), 7.60 (s, 1H), 6.77 (d, J=8.7 Hz, 1H), 6.09 (brs, 1H), 4.96-4.82 (m, 1H), 4.65 (s, 2H), 3.81 (brs, 2H), 3.70 (s, 2H), 3.58 (brs, 2H), 3.47 (s, 2H), 2.77 (t, J=7.4 Hz, 2H), 2.27 (brs, 3H), 2.21 (s, 2H), 2.00-1.90 (m, 2H), 1.68-1.53 (m, 23H), 1.01 (t, J=7.2 Hz, 3H).

Example 4: Synthesis of AM16-38A

AM16-38A was synthesized according to the procedures for preparing AM16-10A from intermediate 1 (100 mg, 0.16 mmol), HOAt (33 mg, 0.24 mmol), 1-adamantaneacetic acid (38 mg, 0.19 mmol), NMM (71 μL, 0.64 mmol), EDCI (46 mg, 0.24 mmol), and DMSO (2.0 mL). AM16-38A was obtained as brown solid (69 mg, 60%). ¹H NMR (600 MHz, CDCl₃) δ 8.51 (s, 1H), 8.38 (s, 1H), 7.92-7.80 (m, 2H), 7.70 (s, 1H), 7.59 (s, 1H), 6.75 (d, J=8.6 Hz, 1H), 6.05 (s, 1H), 4.94-4.83 (m, 1H), 4.65 (s, 2H), 3.77 (brs, 2H), 3.71 (brs, 2H), 3.63 (brs, 2H), 3.56 (brs, 2H), 2.75 (t, J=7.4 Hz, 2H), 2.37-2.31 (m, 2H), 2.25 (s, 3H), 1.95 (d, J=17.0 Hz, 2H), 1.70 (t, J=12.9 Hz, 4H), 1.64-1.57 (m, 12H), 1.49 (s, 5H), 1.00 (t, J=7.3 Hz, 3H).

Example 5: Synthesis of the XY019-43

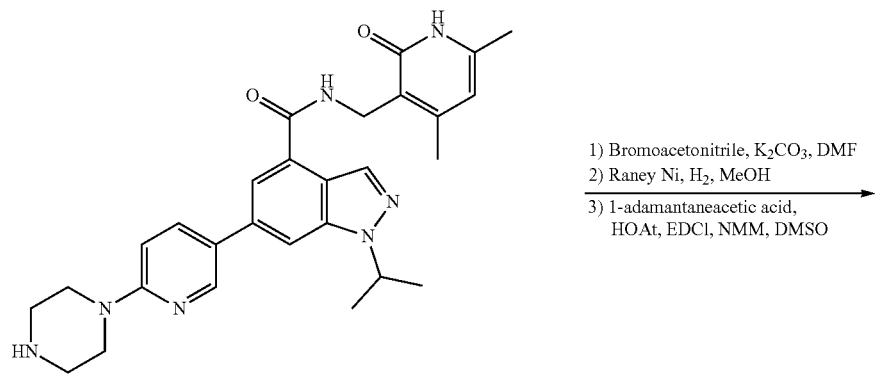

1) Bromoacetonitrile, K₂CO₃, DMF
2) Raney Ni, H₂, MeOH
3) 1-adamantaneacetic acid, HOAt, EDCl, NMM, DMSO Intermediate 3

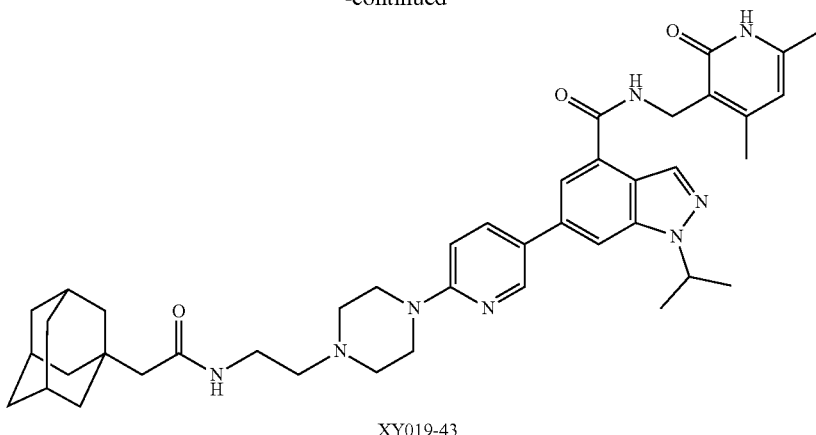

XY019-43

Intermediate 3 (80 mg, 0.16 mmol) was dissolved in DMF (10 mL). To the solution were added bromoacetonitrile (21 mg, 0.18 mmol) and potassium carbonate (66 mg, 0.48 mmol). After being stirred overnight at room temperature, the reaction mixture was filtered and concentrated. The residue was dissolved in methanol (30 mL) and ammonia solution (5.0 mL, 7 M in methanol). To the solution was added Raney® nickel (50 mg). The contents were purged and kept under hydrogen (balloon pressure) overnight before being filtered and concentrated under vacuum. Half of the residue was dissolved in DMSO (3.0 mL). To the solution were added NMM (24 mg, 0.24 mmol), 1-adamantaneacetic acid (19 mg, 0.10 mmol), HOAt (16 mg, 0.12 mmol), and EDCI (23 mg, 0.12 mmol). The mixture was allowed to stir at room temperature overnight. The progress of the reaction was monitored by LC-MS. The crude product was filtered and purified by preparative HPLC to yield XY019-43 as solid in TFA salt form (10 mg, 17%). $^1$H NMR (600 MHz, CD$_3$OD) δ 8.58 (d, J=2.4 Hz, 1H), 8.36 (s, 1H), 8.12 (dd, J=2.5, 8.9 Hz, 1H), 7.95 (s, 1H), 7.77 (s, 1H), 7.09 (d, J=8.9 Hz, 1H), 6.16 (s, 1H), 5.09 (p, J=6.6 Hz, 1H), 4.58 (s, 2H), 3.62 (t, J=6.1 Hz, 2H), 3.53 (brs, 8H), 3.34 (t, J=6.1 Hz, 2H), 2.43 (s, 3H), 2.26 (s, 3H), 2.00 (s, 2H), 1.96 (s, 3H), 1.76 (d, J=12.4 Hz, 3H), 1.71-1.61 (m, 9H), 1.57 (d, J=6.6 Hz, 6H). HRMS (m/z) for C$_{42}$H$_{55}$N$_8$O$_3^+$ [M+H]$^+$: calculated 719.4392, found 719.4396.

Example 6: Synthesis of XY019-44

XY019-44 (12 mg, 21%) was synthesized according to the procedures for preparing XY019-43. $^1$H NMR (600 MHz, CD$_3$OD) δ 8.58 (s, 1H), 8.37 (s, 1H), 8.13 (dd, J=2.5, 8.9 Hz, 1H), 7.95 (s, 1H), 7.78 (s, 1H), 7.10 (d, J=8.9 Hz, 1H), 6.17 (s, 1H), 5.09 (p, J=6.7 Hz, 1H), 4.58 (s, 2H), 3.61 (t, J=5.9 Hz, 2H), 3.48 (brs, 8H), 3.35 (t, J=5.9 Hz, 2H), 2.44 (s, 3H), 2.26 (s, 3H), 2.24-2.20 (m, 2H), 1.95 (s, 2H), 1.75 (d, J=12.4 Hz, 3H), 1.66 (d, J=12.0 Hz, 3H), 1.57 (d, J=6.5 Hz, 6H), 1.51 (s, 6H), 1.44-1.35 (m, 3H). HRMS (m/z) for C$_{43}$H$_{57}$N$_8$O$_3^+$ [M+H]$^+$: calculated 733.4548, found 733.4544.

Example 7: Synthesis of XY019-079

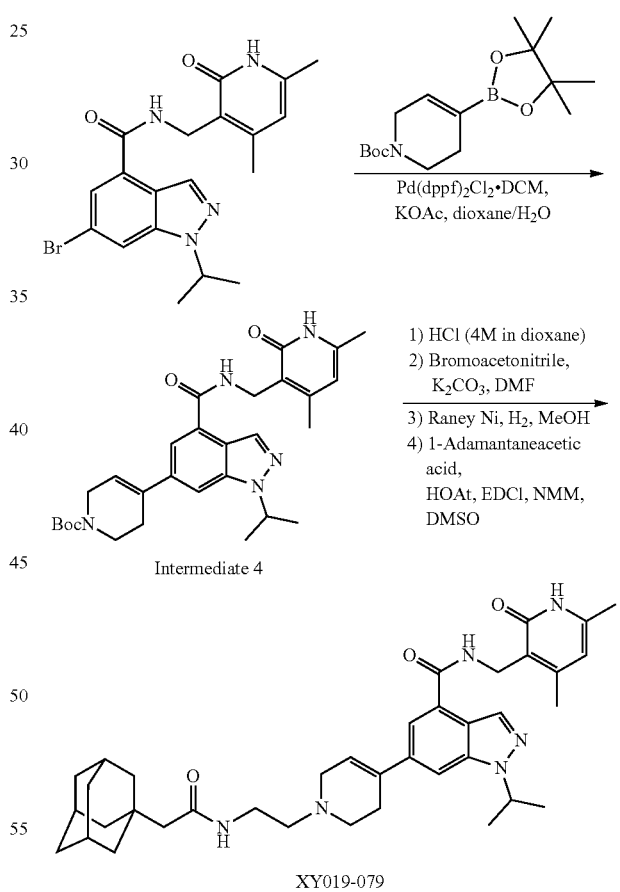

XY019-079

6-Bromo-N-((4,6-dimethyl-2-oxo-1,2-dihydropyridin-3-yl)methyl)-1-isopropyl-1H-indazole-4-carboxamide (294 mg, 0.707 mmol), tert-butyl 4-(4,4,5,5-tetramethyl-1,3,2-dioxaborolan-2-yl)-3,6-dihydropyridine-1 (2H)-carboxylate (262 mg, 0.85 mmol) and KOAc (207 mg, 2.1 mmol) were dissolved in 1,4-dioxane (30 mL) and water (5.0 mL) in a flask. To the solution was added Pd(dppf)Cl$_2$·DCM (30 mg, 10% wt) under argon atmosphere at room temperature. The mixture was heated at 80° C. overnight before being cooled to room temperature. The crude intermediate was filtered and purified by flash column chromatography (0-100% MeOH in DCM) to yield intermediate 4 (320 mg, 87%). MS (m/z) [M+H]+: 520.2. To the solution of intermediate 4 (60 mg, 0.12 mmol) in dioxane (5.0 mL), and methanol (5.0 mL) was added hydrogen chloride (1.0 mL, 4 M in dioxane) dropwise. The resulting solution was stirred at room temperature for 2 h before being concentrated under vacuum. The resulting residue was dissolved in DMF (10 mL). To the solution were added potassium carbonate (100 mg, 0.69 mmol) and bromoacetonitrile (30 mg, 0.25 mmol). After being stirred overnight at room temperature, the reaction mixture was filtered and concentrated. The crude intermediate obtained was dissolved in methanol (30 mL) and ammonia in methanol (7 M, 5.0 mL). To the solution was added Raney® nickel (20% wt) in catalytic amount. The reaction mixture was purged and stirred under hydrogen (balloon pressure) overnight. The reaction was monitored via LC-MS. Upon completion, the reaction mixture was filtered and concentrated under vacuum. The crude intermediate obtained was dissolved in DMSO (3.0 mL). To the solution were added NMM (35 mg, 0.35 mmol), 1-adamantaneacetic acid (27 mg, 0.14 mmol), HOAt (24 mg, 0.17 mmol), and EDCI (33 mg, 0.17 mmol). The mixture was allowed to stir at room temperature overnight. The progress of the reaction was monitored by LC-MS. The crude product was filtered and purified by preparative HPLC to yield XY019-079 as solid (15 mg, 20%). $^1$H NMR (600 MHz, CD$_3$OD) δ 8.34 (s, 1H), 7.82 (s, 1H), 7.70 (s, 1H), 6.35 (s, 1H), 6.18 (s, 1H), 5.05 (p, J=6.7 Hz, 1H), 4.56 (s, 2H), 4.29-4.17 (m, 1H), 4.00-3.88 (m, 2H), 3.71-3.61 (m, 2H), 3.47-3.38 (m, 3H), 3.08-3.00 (m, 2H), 2.43 (s, 3H), 2.26 (s, 3H), 2.00 (s, 2H), 1.99-1.90 (m, 3H), 1.75 (t, J=7.7 Hz, 3H), 1.70-1.59 (m, 9H), 1.55 (d, J=6.7 Hz, 6H). HRMS (m/z) for C$_{38}$H$_{51}$N$_6$O$_3$$^+$ [M+H]+: calculated 639.4017, found 639.4028.

Example 8: Synthesis of XY019-080

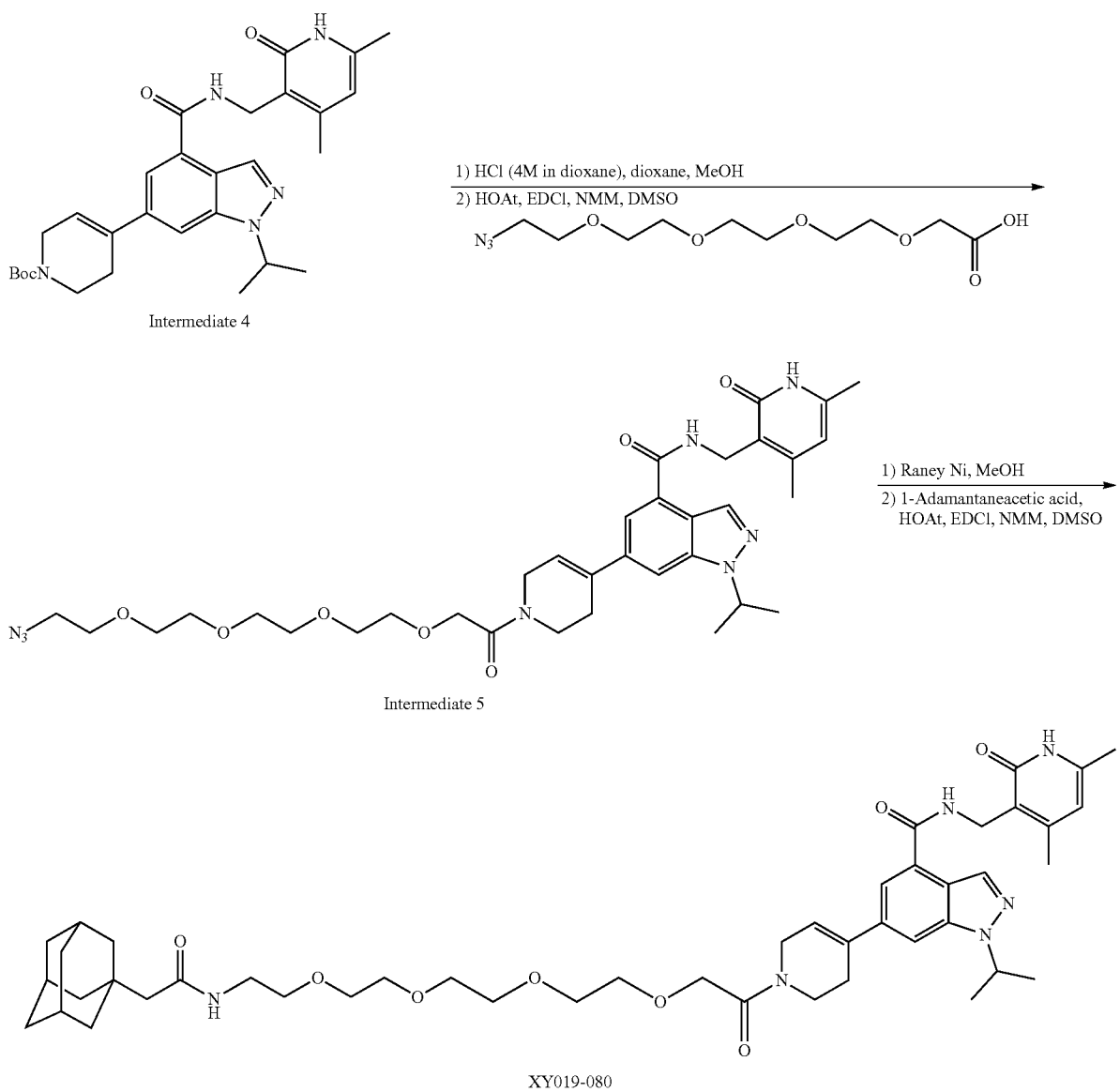

Intermediate 4

Intermediate 5

XY019-080

To the solution of intermediate 4 (60 mg, 0.12 mmol) in dioxane (5.0 mL), and methanol (5.0 mL) was added hydrogen chloride (1.0 mL, 4 M in dioxane) dropwise. The mixture was stirred at room temperature for 2 h before being concentrated under vacuum. The resulting residue was dissolved in DMSO (3.0 mL). To the solution were added NMM (70 mg, 0.70 mmol), 14-azido-3,6,9,12-tetraoxatetradecanoic acid (38 mg, 0.14 mmol), HOAt (24 mg, 0.17 mmol), and EDCI (33 mg, 0.17 mmol). The mixture was stirred overnight at room temperature. The progress of the reaction was monitored by LC-MS. The crude intermediate was filtered and purified by preparative HPLC to yield intermediate 5 (37 mg, 47%). $^1$H NMR (600 MHz, CD$_3$OD) δ 8.32 (d, J=2.1 Hz, 1H), 7.75 (s, 1H), 7.69 (s, 1H), 6.33 (d, J=14.0 Hz, 1H), 6.18 (s, 1H), 5.04 (p, J=6.6 Hz, 1H), 4.56 (s, 2H), 4.33 (d, J=19.0 Hz, 2H), 4.25 (d, J=8.7 Hz, 2H), 3.85 (t, J=5.7 Hz, 1H), 3.78 (t, J=5.6 Hz, 1H), 3.73-3.53 (m, 16H), 2.77 (s, 1H), 2.68 (s, 1H), 2.43 (s, 3H), 2.26 (s, 3H), 1.55 (d, J=6.6 Hz, 6H). MS (m/z) [M+H]$^+$: 679.3. Intermediate 5 (37 mg, 0.05 mmol) was dissolved in methanol (30 mL) and ammonia solution (5.0 mL, 7 M in methanol). To the solution was added Raney® nickel (20% wt) in catalytic amount. The reaction mixture was purged and stirred under hydrogen (balloon pressure) overnight. The reaction was monitored via LC-MS. Upon completion, the reaction mixture was filtered and concentrated under vacuum. The resulting residue was dissolved in DMSO (3.0 mL). To the solution were added NMM (15 mg, 0.15 mmol), 1-adamantaneacetic acid (12 mg, 0.06 mmol), HOAt (10 mg, 0.08 mmol), and EDCI (14 mg, 0.08 mmol). The reaction mixture was stirred at room temperature overnight. The progress of the reaction was monitored by LC-MS. The crude product was filtered and purified by preparative HPLC to yield XY019-080 as solid (4.5 mg, 20%). $^1$H NMR (600 MHz, CD$_3$OD) δ 8.32 (s, 1H), 7.74 (s, 1H), 7.69 (d, J=4.7 Hz, 1H), 6.33 (d, J=12.4 Hz, 1H), 6.16 (s, 1H), 5.04 (p, J=6.6 Hz, 1H), 4.57 (s, 2H), 4.34 (d, J=20.5 Hz, 2H), 4.25 (s, 2H), 3.86 (t, J=5.7 Hz, 1H), 3.77 (t, J=5.6 Hz, 1H), 3.73-3.45 (m, 12H), 2.77 (s, 1H), 2.68 (s, 1H), 2.42 (s, 3H), 2.26 (s, 3H), 2.02 (s, 1H), 1.95 (s, 1H), 1.92-1.85 (m, 4H), 1.80-1.56 (m, 15H), 1.55 (d, J=7.1 Hz, 6H). HRMS (m/z) for C$_{46}$H$_{65}$N$_6$O$_8$+ [M+H]$^+$: calculated 829.4858, found 829.4855.

Example 9: Synthesis of AM16-91A

1-Adamantaneethanol (1.0 gram, 5.6 mmol, Sigma®, #188115) was dissolved in DCM (15 mL). To the solution was added Dess-Martin periodinane (5.0 mL) at 0° C. After being stirred overnight at room temperature, the mixture was purified by ISCO™ to afford intermediate 6 (780 mg, 79%). $^1$H NMR (600 MHz, CDCl$_3$) δ 9.86 (t, J=3.2 Hz, 1H), 2.12 (d, J=3.2 Hz, 2H), 1.98 (brs, 3H), 1.67-1.64 (m, 12H). Intermediate 3 (100 mg, 0.16 mmol) and intermediate 6 (35 mg, 0.20 mmol) were dissolved in DCM (3.0 mL), and methanol (3.0 mL). To the solution was added sodium triacetoxyborohydride (55 mg, 0.26 mmol) at 0° C. After being stirred overnight at room temperature, the mixture was filtered and purified by preparative HPLC to afford AM16-91A as yellow solid in TFA salt form (99 mg, 80%). $^1$H NMR (600 MHz, CD$_3$OD) δ 8.53 (brs, 1H), 8.37 (s, 1H), 8.12-8.02 (m, 1H), 7.93 (s, 1H), 7.76 (s, 1H), 7.03 (d, J=8.7 Hz, 1H), 6.14 (s, 1H), 5.11-5.03 (m, 1H), 4.57 (s, 2H), 4.49 (brs, 2H), 3.69 (brs, 2H), 3.34-3.03 (m, 6H), 2.42 (s, 3H), 2.24 (s, 3H), 1.96 (brs, 3H), 1.79-1.73 (m, 3H), 1.70-1.65 (m, 3H), 1.59-1.54 (m, 14H).

Example 10: Synthesis of AM16-92A

AM16-92A was synthesized according to the procedures for preparing AM16-10A from intermediate 3 (100 mg, 0.16 mmol), HOAt (33 mg, 0.24 mmol), 1-adamantaneacetic acid (38 mg, 0.20 mmol), NMM (71 μL, 0.64 mmol), EDCI (46 mg, 0.24 mmol), and DMSO (2.0 mL). AM16-92A was obtained as white solid in TFA salt form (77 mg, 61%). $^1$H NMR (600 MHz, CD$_3$OD) δ 8.45-8.32 (m, 3H), 8.02 (s, 1H), 7.78 (s, 1H), 7.36-7.28 (m, 1H), 6.15 (s, 1H), 5.15-5.05 (m, 1H), 4.58 (s, 2H), 3.92-3.88 (m, 2H), 3.86-3.83 (m, 2H), 3.80-3.76 (m, 4H), 2.44 (s, 3H), 2.28 (s, 2H), 2.26 (s, 3H), 1.99-1.96 (m, 3H), 1.73-1.67 (m, 12H), 1.58 (s, 3H), 1.57 (s, 3H).

Example 11: Synthesis of AM16-93A

AM16-93A was synthesized according to the procedures for preparing AM16-10A from intermediate 3 (100 mg, 0.16 mmol), HOAt (33 mg, 0.24 mmol), 3-(1-adamantyl) propanoic acid (42 mg, 0.20 mmol), NMM (71 μL, 0.64 mmol),

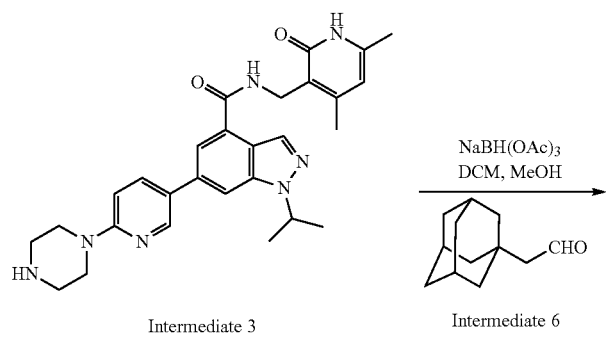

Intermediate 3  Intermediate 6

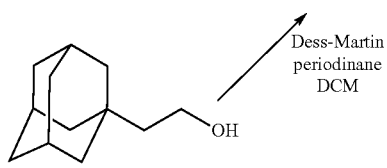

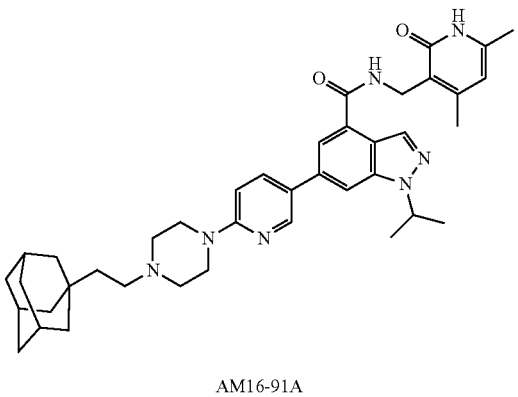

AM16-91A

EDCI (46 mg, 0.24 mmol), and DMSO (2.0 mL). AM16-93A was obtained green solid in TFA salt form (85 mg, 66%). $^1$H NMR (600 MHz, CD$_3$OD) δ 8.43-8.36 (m, 2H), 8.34-8.28 (m, 1H), 8.01 (s, 1H), 7.77 (s, 1H), 7.30-7.21 (m, 1H), 6.15 (s, 1H), 5.14-5.04 (m, 1H), 4.58 (s, 2H), 3.81 (brs, 6H), 3.76-3.70 (m, 2H), 2.45-2.38 (m, 5H), 2.25 (s, 3H), 1.99-1.94 (m, 3H), 1.73-1.69 (m, 3H), 1.60-1.54 (m, 12H), 1.49 (s, 3H), 1.41-1.37 (m, 2H).

Example 12: Synthesis of AM16-97A

AM16-97A was synthesized according to the procedures for preparing AM16-10A from intermediate 3 (67 mg, 0.11 mmol), HOAt (23 mg, 0.17 mmol), (2R)-4-((1r,3S)-adamantan-1-yl)-2-methylbutanoic acid (25 mg, 0.11 mmol), NMM (49 µL, 0.44 mmol), EDCI (33 mg, 0.17 mmol), and DMSO (2.0 mL). (2R)-4-((1r,3S)-Adamantan-1-yl)-2-methylbutanoic acid was synthesized according to the procedures reported previously (Neklesa et al., 2011). AM16-97A was obtained as brown solid in TFA salt form (58 mg, 63%). $^1$H NMR (600 MHz, CD$_3$OD) δ 8.43 (brs, 1H), 8.37 (s, 1H), 8.23 (brs, 1H), 7.98 (s, 1H), 7.77 (s, 1H), 7.17 (brs, 1H), 6.13 (s, 1H), 5.13-5.03 (m, 1H), 4.57 (s, 2H), 3.89-3.79 (m, 4H), 3.76 (brs, 2H), 3.70 (brs, 2H), 2.84-2.74 (m, 1H), 2.43 (s, 3H), 2.25 (s, 3H), 1.92 (brs, 3H), 1.77-1.70 (m, 3H), 1.67-1.63 (m, 3H), 1.59-1.54 (m, 6H), 1.50 (brs, 6H), 1.46-1.29 (m, 2H), 1.13 (d, J=6.6 Hz, 3H), 1.10-0.98 (m, 2H).

Example 13: Synthesis of AM16-100A

AM16-100A was synthesized according to the procedures for preparing AM16-10A from intermediate 3 (75 mg, 0.12 mmol), HOAt (25 mg, 0.18 mmol), 1-adamantanecarboxylic acid (27 mg, 0.15 mmol, Sigma®, #106399), NMM (53 µL, 0.48 mmol), EDCI (35 mg, 0.18 mmol), and DMSO (1.5 mL). AM16-100A was obtained as brown solid in TFA salt form (92 mg, 99%). $^1$H NMR (600 MHz, CD$_3$OD) δ 8.44-8.30 (m, 3H), 8.02 (s, 1H), 7.77 (s, 1H), 7.32 (d, J=9.3 Hz, 1H), 6.16 (s, 1H), 5.13-5.04 (m, 1H), 4.58 (s, 2H), 4.00-3.94 (m, 4H), 3.79-3.73 (m, 4H), 2.43 (s, 3H), 2.26 (s, 3H), 2.06-1.79 (m, 15H), 1.58 (s, 3H), 1.57 (s, 3H).

Example 14: Synthesis of AM16-101A

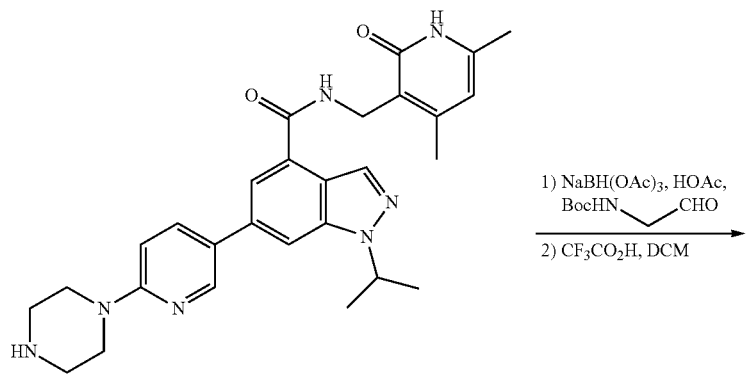

Intermediate 3

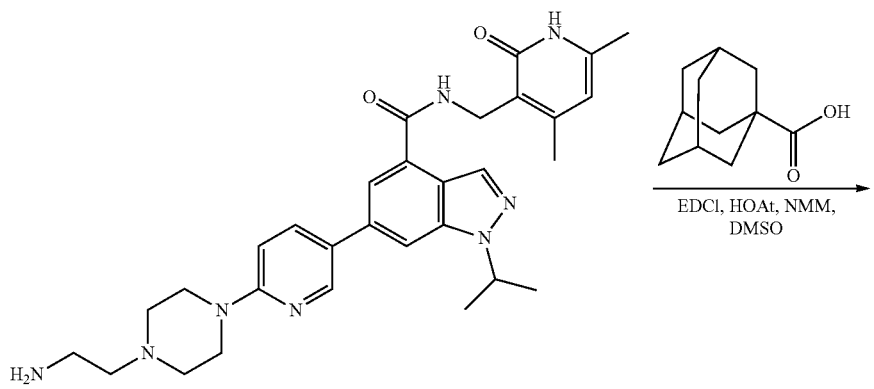

Intermediate 7

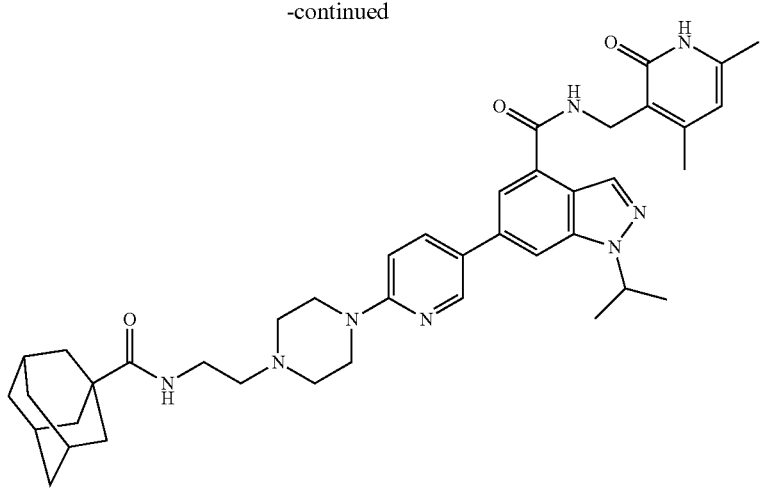

AM16-101A

Intermediate 3 (963 mg, 1.6 mmol) and N-Boc-2-amino-acetaldehyde (750 mg, 4.7 mmol) were dissolved in DCM (10 mL), and methanol (10 mL). To the solution was added sodium triacetoxy borohydride (1.3 gram, 6.3 mmol) at 0° C. After being stirred overnight at room temperature, the mixture was purified by reverse-phase ISCO™ (10%-100% methanol/0.1% TFA in H₂O) to afford compound tert-butyl (2-(4-(5-(4-(((4,6-dimethyl-2-oxo-1,2-dihydropyridin-3-yl) methyl) carbamoyl)-1-isopropyl-1H-indazol-6-yl) pyridin-2-yl) piperazin-1-yl)ethyl) carbamate (1.1 gram). The obtained intermediate was dissolved in DCM (30 mL) and treated with trifluoroacetic acid (5.0 mL) at room temperature. After being stirred overnight at room temperature, the mixture was purified by reverse-phase ISCO™ to afford intermediate 7 (750 mg, 72% over 2 steps). AM16-101A was synthesized according to the procedures for preparing AM16-10A from intermediate 7 (75 mg, 0.11 mmol), HOAt (23 mg, 0.17 mmol), 1-adamantanecarboxylic acid (25 mg, 0.14 mmol), NMM (51 µL, 0.46 mmol), EDCI (33 mg, 0.17 mmol), and DMSO (1.5 mL). AM16-101A was obtained as off-white solid in TFA salt form (80 mg, 86%). ¹H NMR (600 MHz, CD₃OD) δ 8.55 (brs, 1H), 8.37 (s, 1H), 8.14 (d, J=8.9 Hz, 1H), 7.96 (s, 1H), 7.77 (s, 1H), 7.11 (d, J=8.9 Hz, 1H), 6.18 (s, 1H), 5.13-5.04 (m, 1H), 4.58 (s, 2H), 4.34-3.40 (m, 10H), 3.39-3.34 (m, 2H), 2.44 (s, 3H), 2.26 (s, 3H), 2.03 (brs, 3H), 1.88 (s, 6H), 1.80 (d, J=12.3 Hz, 3H), 1.74 (d, J=12.0 Hz, 3H), 1.58 (s, 3H), 1.57 (s, 3H).

Example 15: Synthesis of AM16-102A

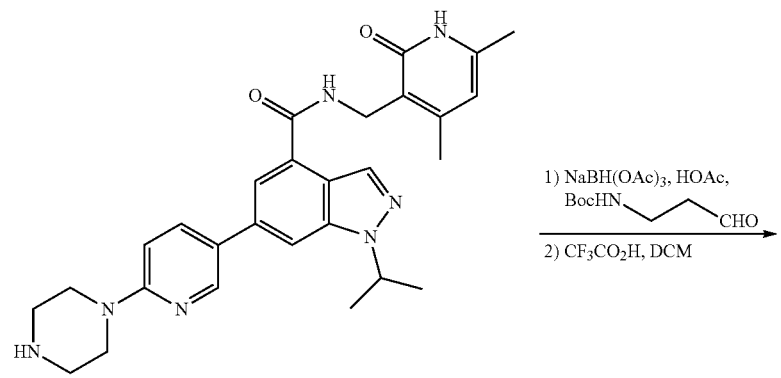

Intermediate 3

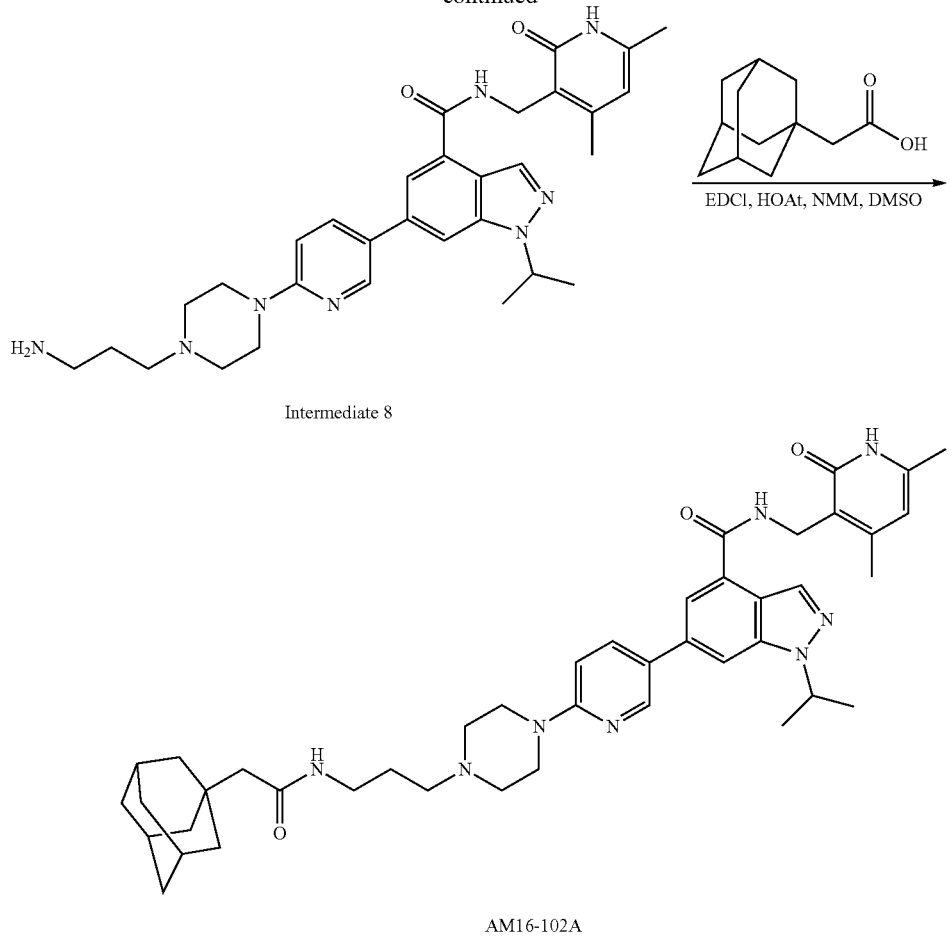

Intermediate 3 (250 mg, 0.41 mmol) and tert-butyl (3-oxopropyl) carbamate (106 mg, 0.61 mmol, AstaTech, #71690) were dissolved in DCM (2.0 mL), and methanol (2.0 mL). To the solution was added sodium triacetoxyborohydride (261 mg, 1.2 mmol) at 0° C. After being stirred overnight at room temperature, the mixture was purified by reverse-phase ISCO™ (10%-100% methanol/0.1% TFA in H$_2$O) to afford compound tert-butyl (2-(4-(5-(4-(((4,6-dimethyl-2-oxo-1,2-dihydropyridin-3-yl)methyl) carbamoyl)-1-isopropyl-1H-indazol-6-yl) pyridin-2-yl) piperazin-1-yl) ethyl) carbamate. The obtained intermediate was dissolved in DCM (10 mL) and treated with trifluoroacetic acid (1.7 mL) at room temperature. After being stirred overnight at room temperature, the mixture was purified by reverse-phase ISCO™ to afford intermediate 8 (233 mg, 85% over 2 steps). AM16-102A was synthesized according to the procedures for preparing AM16-10A from intermediate 8 (116 mg, 0.17 mmol), HOAt (35 mg, 0.26 mmol), 1-adamantaneacetic acid (41 mg, 0.21 mmol), NMM (75 µL, 0.68 mmol), EDCI (50 mg, 0.26 mmol), and DMSO (1.5 mL). AM16-102A was obtained as white solid in TFA salt form (101 mg, 70%). $^1$H NMR (600 MHz, CD$_3$OD) δ 8.55-8.46 (m, 1H), 8.37 (s, 1H), 8.16 (dd, J=8.9, 1.7 Hz, 1H), 7.96 (s, 1H), 7.76 (s, 1H), 7.13 (d, J=9.1 Hz, 1H), 6.20 (s, 1H), 5.14-5.02 (m, 1H), 4.58 (s, 2H), 3.87-3.31 (m, 8H), 3.27-3.22 (m, 2H), 2.43 (s, 3H), 2.26 (s, 3H), 2.07-1.99 (m, 2H), 1.98-1.86 (m, 5H), 1.78-1.60 (m, 14H), 1.57 (s, 3H), 1.56 (s, 3H).

Example 16: Synthesis of AM16-105A

AM16-105A was synthesized according to the procedures for preparing AM16-10A from intermediate 7 (100 mg, 0.15 mmol), HOAt (31 mg, 0.23 mmol), (2R)-4-((1r,3S)-adamantan-1-yl)-2-methylbutanoic acid (36 mg, 0.15 mmol), NMM (66 µL, 0.60 mmol), EDCI (44 mg, 0.23 mmol), and DMSO (1.5 mL). AM16-105A was obtained as white solid in TFA salt form (102 mg, 77%). $^1$H NMR (600 MHz, CD$_3$OD) δ 8.55 (d, J=1.8 Hz, 1H), 8.37 (s, 1H), 8.11 (dd, J=8.9, 2.0 Hz, 1H), 7.95 (s, 1H), 7.77 (s, 1H), 7.08 (d, J=8.9 Hz, 1H), 6.17 (s, 1H), 5.13-5.04 (m, 1H), 4.58 (s, 2H), 4.21-3.53 (m, 8H), 3.36 (t, J=6.3 Hz, 2H), 2.43 (s, 3H), 2.30-2.20 (m, 4H), 1.92 (s, 3H), 1.69 (dd, J=51.3, 11.9 Hz, 8H), 1.58 (s, 3H), 1.56 (s, 3H), 1.49 (s, 7H), 1.41-1.31 (m, 1H), 1.13 (d, J=6.8 Hz, 3H), 1.08 (td, J=13.0, 4.1 Hz, 1H), 0.98 (td, J=13.0, 4.3 Hz, 1H).

Example 17: Synthesis of AM16-106A

AM16-106A was synthesized according to the procedures for preparing AM16-10A from intermediate 8 (100 mg, 0.15 mmol), HOAt (31 mg, 0.23 mmol), (2R)-4-((1r,3S)-adamantan-1-yl)-2-methylbutanoic acid (36 mg, 0.15 mmol), NMM (66 µL, 0.60 mmol), EDCI (44 mg, 0.23 mmol), and DMSO (1.5 mL). AM16-106A was obtained as solid in TFA salt form (101 mg, 76%). $^1$H NMR (600 MHz, CD$_3$OD) δ 8.53 (s, 1H), 8.37 (s, 1H), 8.12 (dd, J=8.9, 2.0 Hz, 1H), 7.94 (s, 1H), 7.76 (s, 1H), 7.09 (d, J=9.0 Hz, 1H), 6.18 (s, 1H), 5.13-5.03 (m, 1H), 4.58 (s, 2H), 4.41-3.34 (m, 8H), 3.23 (t, J=7.5 Hz, 2H), 2.43 (s, 3H), 2.26 (s, 3H), 2.24-2.17 (m, 1H), 2.08-1.97 (m, 2H), 1.91 (brs, 3H), 1.78-1.58 (m, 8H), 1.57 (s, 3H), 1.56 (s, 3H), 1.48 (s, 7H), 1.39-1.30 (m, 1H), 1.13 (d, J=6.8 Hz, 3H), 1.07 (td, J=12.9, 4.0 Hz, 1H), 0.97 (td, J=13.0, 4.3 Hz, 1H).
Example 18: Synthesis of XY012-120
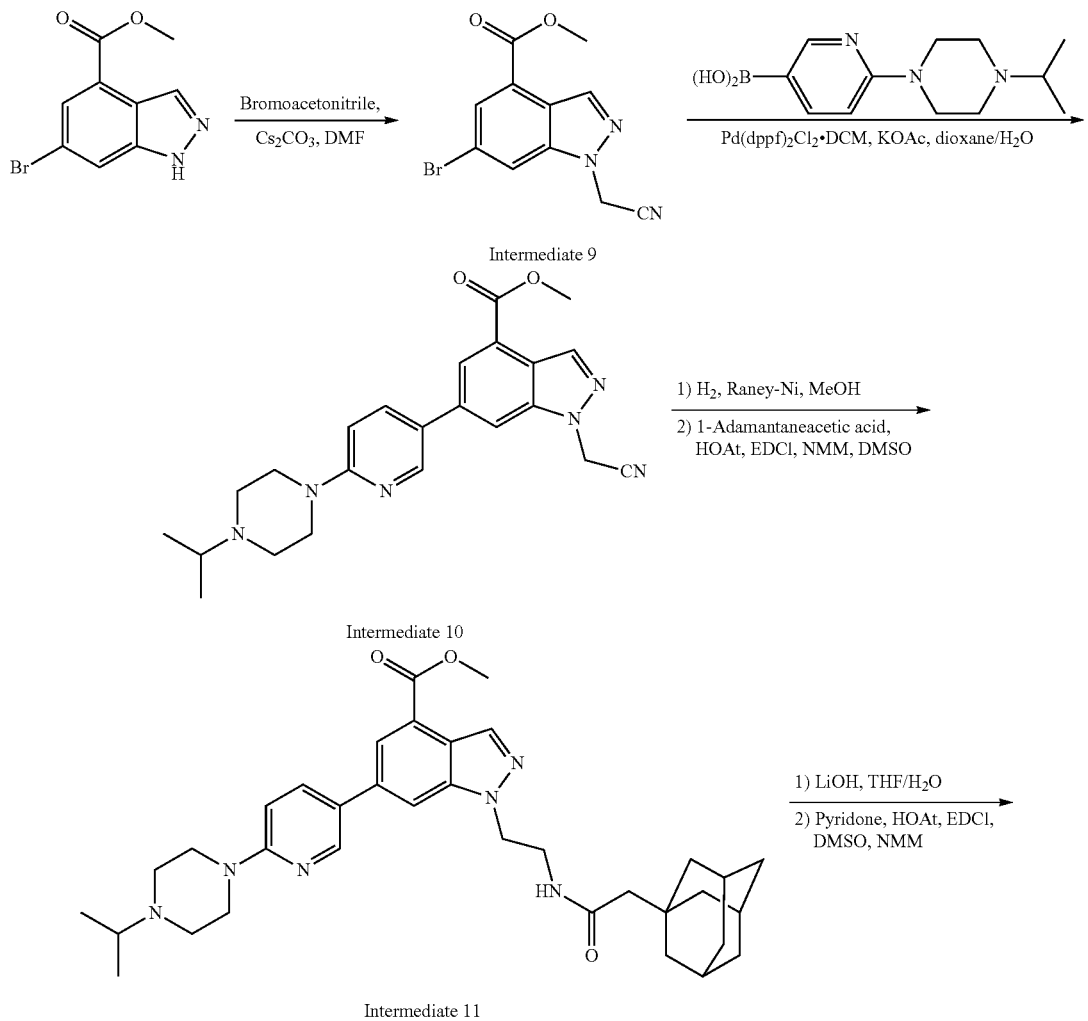
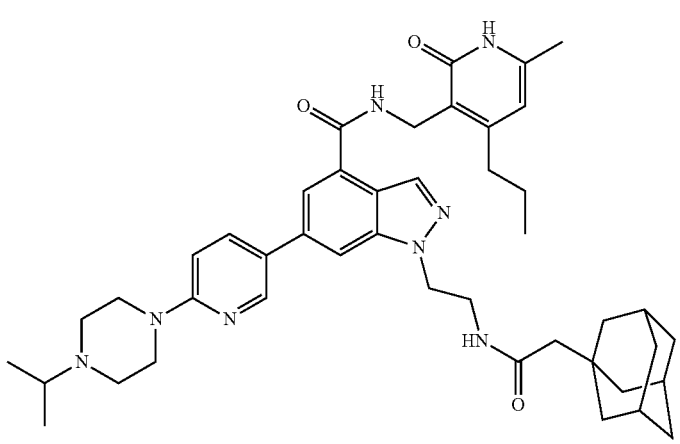
XY012-120

To the solution of methyl 6-bromo-1H-indazole-4-carboxylate (1.0 g, 3.9 mmol) in acetonitrile (100 mL) were added Cs$_2$CO$_3$ (2.6 g, 7.8 mmol) and bromoacetonitrile (0.71 g, 5.9 mmol) successively. And the reaction mixture was stirred at 60° C. for 30 min. Upon completion, the mixture was filtered, concentrated and purified by flash column chromatography (0-20% ethyl acetate in hexane) to yield intermediate 9 (0.24 g, 21%). 1H NMR (600 MHz, CDCl$_3$) δ 8.56 (s, 1H), 8.11 (s, 1H), 7.88 (s, 1H), 5.32 (s, 2H), 4.04 (s, 3H). MS (m/z) [M+H]$^+$: 293.9/295.9. Intermediate 9 (100 mg, 0.34 mmol), (6-(4-isopropylpiperazin-1-yl) pyridin-3-yl) boronic acid (94 mg, 0.37 mmol), and potassium acetate (100 mg, 1.0 mmol) were dissolved in 1,4-dioxane (30 mL) and water (5.0 mL). To the resulting solution was added Pd(dppf)Cl$_2$·DCM (20 mg, 20% wt) under argon atmosphere at room temperature. The mixture was heated at 80° C. overnight. After being cooled to room temperature, the mixture was purified by flash column chromatography (0-15% MeOH in DCM) to yield intermediate 10 (130 mg, 91%). $^1$H NMR (600 MHz, CD$_3$OD) δ 8.49-8.45 (m, 2H), 8.09-8.05 (m, 2H), 7.91 (dt, J=2.9, 8.9 Hz, 1H), 6.92 (dd, J=3.2, 8.8 Hz, 1H), 5.67 (s, 2H), 4.02 (s, 3H), 3.75 (t, J=5.2 Hz, 4H), 3.16-3.07 (m, 1H), 3.01 (t, J=5.0 Hz, 4H), 1.26 (dd, J=3.0, 6.5 Hz, 6H). MS (m/z) [M+H]$^+$: 419.2. To the solution of intermediate 10 (110 mg, 0.26 mmol) in methanol (30 mL) was added Raney® nickel (20% wt) in catalytic amount. The reaction mixture was purged and stirred under hydrogen (balloon pressure) overnight. The reaction was monitored via LC-MS. Upon completion, the reaction mixture was filtered and concentrated under vacuum. Half of the resulting residue was dissolved in DMSO (3.0 mL). To the solution were added NMM (40 mg, 0.39 mmol), 1-adamantaneacetic acid (28 mg, 0.14 mmol), HOAt (27 mg, 0.20 mmol), and EDCI (38 mg, 0.20 mmol). The mixture was stirred at room temperature overnight. The progress of the reaction was monitored by LC-MS. The crude intermediate was filtered and purified by preparative HPLC to yield intermediate 11 as solid (17 mg, 21%). $^1$H NMR (600 MHz, CD$_3$OD) δ 8.56 (d, J=2.6 Hz, 1H), 8.46 (d, J=2.2 Hz, 1H), 8.13 (dd, J=2.6, 8.9 Hz, 1H), 8.10 (s, 1H), 8.05 (s, 1H), 7.16 (d, J=8.9 Hz, 1H), 4.70-4.56 (m, 6H), 4.02 (s, 3H), 3.76 (t, J=5.9 Hz, 4H), 3.67-3.57 (m, 3H), 1.74 (s, 2H), 1.68 (s, 3H), 1.59-1.52 (m, 3H), 1.45-1.37 (m, 9H), 1.31 (s, 6H). MS (m/z) [M+H]$^+$: 599.3. To the solution of intermediate 11 (17 mg, 0.03 mmol) in THF/H$_2$O (8.0 mL/2.0 mL) was added LiOH (4.0 mg, 0.17 mmol). And the resulting mixture was stirred overnight at room temperature. The disappearance of starting material was confirmed by TLC. The reaction mixture was then concentrated under vacuum and the resulting residue was dissolved in DMSO (2.0 mL). To the solution were added 3-(aminomethyl)-4,6-dimethylpyridin-2 (1H)-one (7.0 mg, 0.032 mmol), NMM (9.0 mg, 0.085 mmol), HOAt (6.0 mg, 0.043 mmol), and EDCI (8.0 mg, 0.043 mmol). The mixture was allowed to stir overnight at room temperature. The progress of the reaction was monitored by LC-MS. The crude product was filtered and purified by preparative HPLC to yield XY012-120 as solid in TFA salt form (12 mg, 57%). $^1$H NMR (600 MHz, CD$_3$OD) δ 8.55 (d, J=2.4 Hz, 1H), 8.40 (s, 1H), 8.21 (dd, J=2.5, 9.0 Hz, 1H), 7.96 (s, 1H), 7.79 (d, J=1.3 Hz, 1H), 7.21 (d, J=9.1 Hz, 1H), 6.22 (s, 1H), 4.65-4.54 (m, 4H), 3.74 (t, J=5.9 Hz, 2H), 3.63 (p, J=6.6 Hz, 1H), 3.38 (brs, 8H), 2.78-2.73 (m, 2H), 2.28 (s, 3H), 1.72 (s, 2H), 1.68-1.62 (m, 5H), 1.53-1.49 (m, 3H), 1.43 (d, J=6.6 Hz, 6H), 1.40-1.34 (m, 3H), 1.30-1.26 (m, 6H), 1.02 (t, J=7.3 Hz, 3H). HRMS (m/z) for C$_{44}$H$_{59}$N$_8$O$_3$$^+$ [M+H]$^+$: calculated 747.4705, found 747.4704.

Example 19: Synthesis of AM29-21A

AM29-21A was synthesized according to the procedures for preparing AM16-10A from intermediate 5 (80 mg, 0.09 mmol), HOAt (19 mg, 0.14 mmol), 3,5-dimethyladamantane-1-acetic acid (25 mg, 0.11 mmol, Sigma®, #679976), NMM (40 μL, 0.36 mmol), EDCI (27 mg, 0.14 mmol), and DMSO (1.0 mL). AM29-21A was obtained as off-white solid in TFA salt form (58 mg. 74%). $^1$H NMR (600 MHz, CD$_3$OD) δ 8.50 (d, J=2.3 Hz, 1H), 8.37 (s, 1H), 8.19 (dd, J=9.1, 2.4 Hz, 1H), 7.96 (s, 1H), 7.76 (s, 1H), 7.16 (d, J=9.1 Hz, 1H), 6.22 (s, 1H), 5.13-5.04 (m, 1H), 4.58 (s, 2H), 3.98 (brs, 4H), 3.64 (t, J=6.0 Hz, 2H), 3.58 (brs, 4H), 3.38 (t, J=6.0 Hz, 2H), 2.44 (s, 3H), 2.28 (s, 3H), 2.08-1.96 (m, 3H), 1.57 (s, 3H), 1.56 (s, 3H), 1.45 (d, J=1.9 Hz, 2H), 1.36-1.17 (m, 9H), 1.16-1.11 (m, 1H), 1.07 (d, J=12.3 Hz, 1H), 0.80 (s, 6H).

Example 20: Synthesis of AM29-22A

AM29-22A was synthesized according to the procedures for preparing AM16-10A from intermediate 5 (80 mg, 0.09 mmol), HOAt (19 mg, 0.14 mmol), 3,5-dimethyladamantane-1-carboxylic acid (23 mg, 0.11 mmol, Sigma®, #679984), NMM (40 μL, 0.36 mmol), EDCI (27 mg, 0.14 mmol), and DMSO (1.0 mL). AM29-22A was obtained as off-white solid in TFA salt form (67 mg, 87%). $^1$H NMR (600 MHz, CD$_3$OD) δ 8.49 (d, J=2.3 Hz, 1H), 8.37 (s, 1H), 8.18 (dd, J=9.1, 2.4 Hz, 1H), 7.96 (s, 1H), 7.76 (s, 1H), 7.15 (d, J=9.1 Hz, 1H), 6.22 (s, 1H), 5.10-5.03 (m, 1H), 4.58 (s, 2H), 3.98 (brs, 4H), 3.64 (t, J=5.9 Hz, 2H), 3.56 (brs, 4H), 3.37 (t, J=5.9 Hz, 2H), 2.44 (s, 3H), 2.27 (s, 3H), 2.15-2.06 (m, 1H), 1.70 (d, J=2.0 Hz, 2H), 1.56 (d, J=6.6 Hz, 6H), 1.48 (dd, J=37.2, 12.5 Hz, 4H), 1.39-1.35 (m, 3H), 1.22-1.12 (m, 2H), 0.85 (s, 6H).

Example 21: Synthesis of AM29-32A

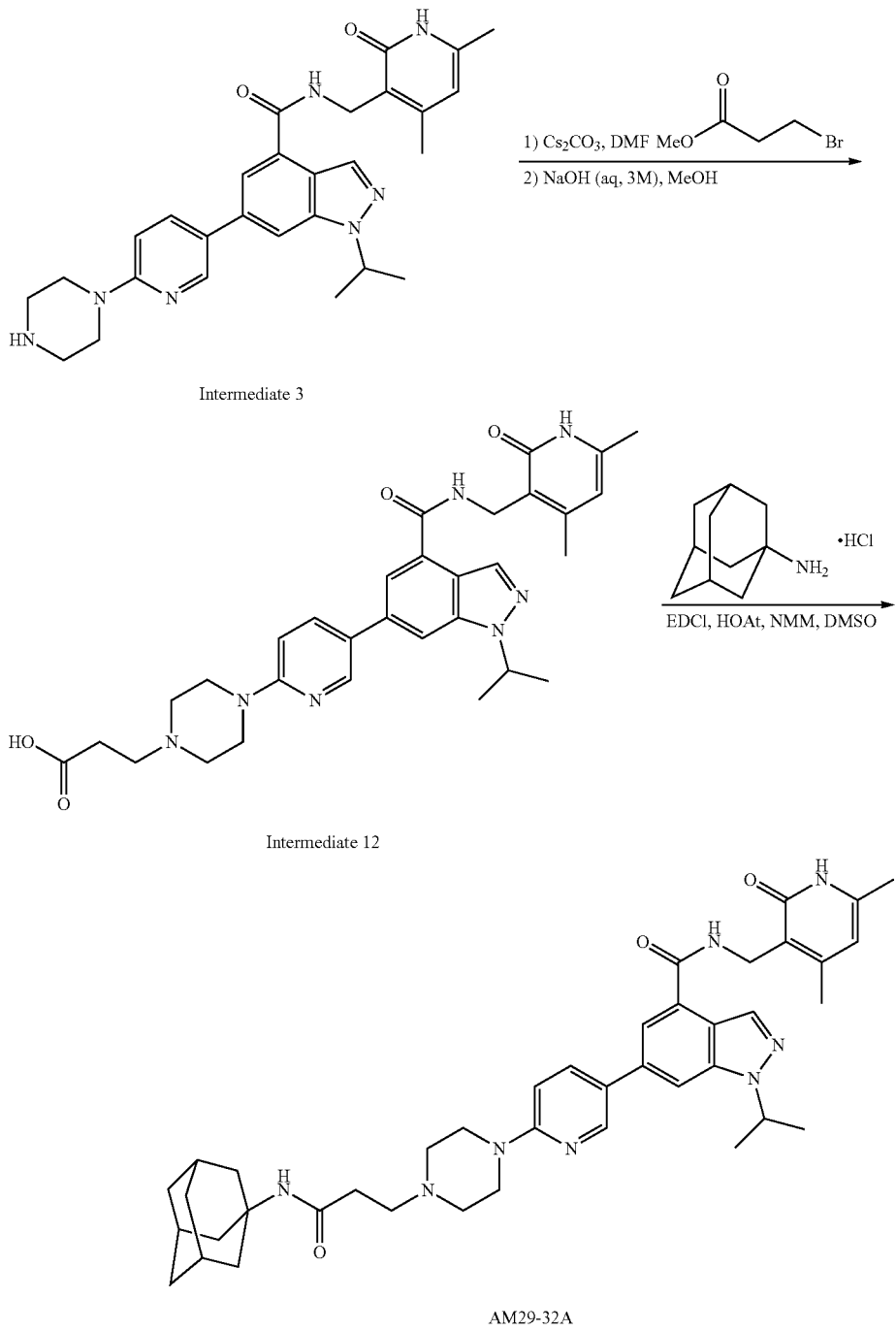

Intermediate 3 (100 mg, 0.16 mmol) and methyl 3-bromopropionate (41 mg, 0.25 mmol, Sigma®, #679984) were dissolved in DMF (1.0 mL). To the solution was added cesium carbonate (105 mg, 0.32 mmol) at room temperature. After being stirred overnight at room temperature, to the mixture were added sodium hydroxide solution (0.5 mL, 3M), and methanol (2.0 mL). After being stirred for additional 2 h at room temperature, the mixture was concentrated under vacuum and purified by preparative HPLC to afford intermediate 12 as a TFA salt (110 mg, 99%). AM29-32A was synthesized according to the procedures for preparing AM16-10A from intermediate 12 (55 mg, 0.08 mmol), HOAt (17 mg, 0.12 mmol), amantadine hydrochloride (19 mg, 0.10 mmol, Sigma®, #A1260), NMM (35 μL, 0.32 mmol), EDCI (23 mg, 0.12 mmol), and DMSO (1.0 mL). AM29-32A was obtained as off-white solid in TFA salt form (18 mg, 27%). $^1$H NMR (600 MHz, CD$_3$OD) δ 8.55 (d, J=2.3 Hz, 1H), 8.38 (s, 1H), 8.25 (dd, J=9.0, 2.4 Hz, 1H), 8.00 (s, 1H), 7.79 (s, 1H), 7.22 (d, J=9.1 Hz, 1H), 6.25 (s, 1H), 5.15-5.06 (m, 1H), 4.60 (s, 2H), 4.20-3.80 (m, 4H), 3.66-3.44 (m, 6H), 2.73 (t, J=6.8 Hz, 2H), 2.46 (s, 3H), 2.29 (s, 3H), 2.10-1.97 (m, 9H), 1.76-1.68 (m, 6H), 1.58 (s, 3H), 1.57 (s, 3H).

Example 22: Synthesis of AM29-33A

AM29-33A was synthesized according to the procedures for preparing AM16-10A from intermediate 12 (55 mg, 0.08 mmol), HOAt (17 mg, 0.12 mmol), 1-adamantanemethylamine (16 mg, 0.10 mmol, Acros Organics, #177420010), NMM (35 μL, 0.32 mmol), EDCI (23 mg. 0.12 mmol), and DMSO (1.0 mL). AM29-33A was obtained as off-white solid in TFA salt form (60 mg, 90%). $^1$H NMR (600 MHz, CD$_3$OD) δ 8.52 (s, 1H), 8.38 (s, 1H), 8.21 (dd, J=8.8, 1.7 Hz, 1H), 7.98 (s, 1H), 7.77 (s, 1H), 7.18 (d, J=8.8 Hz, 1H), 6.23 (s, 1H), 5.15-5.02 (m, 1H), 4.59 (s, 2H), 3.98 (brs, 4H), 3.62-3.44 (m, 6H), 2.91 (s, 2H), 2.85 (t, J=6.6 Hz, 2H), 2.45 (s, 3H), 2.28 (s, 3H), 1.96 (brs, 3H), 1.75 (d, J=11.9 Hz, 3H), 1.66 (d, J=11.8 Hz, 3H), 1.59-1.55 (m, 6H), 1.52 (brs, 6H).

Example 23: Synthesis of AM16-103A

Intermediate 7 (60 mg, 0.09 mmol) and intermediate 6 (48 mg, 0.27 mmol) were dissolved in DCM (1.5 mL), and methanol (1.5 mL). To the solution was added sodium triacetoxy borohydride (77 mg, 0.36 mmol) at 0° C. After being stirred overnight at room temperature, the mixture was purified by preparative HPLC to afford AM16-103A as yellow solid in TFA salt form (59 mg, 80%). $^1$H NMR (600 MHz, CD$_3$OD) δ 8.44 (d, J=2.3 Hz, 1H), 8.38 (s, 1H), 8.34 (dd, J=9.3, 2.3 Hz, 1H), 8.02 (s, 1H), 7.78 (d, J=0.9 Hz, 1H), 7.34 (d, J=9.3 Hz, 1H), 6.17 (s, 1H), 5.15-5.05 (m, 1H), 4.58 (s, 2H), 3.90-3.82 (m, 4H), 3.35 (t, J=6.1 Hz, 2H), 3.14-3.09 (m, 2H), 3.05-2.96 (m, 6H), 2.44 (s, 3H), 2.26 (s, 3H), 1.99 (brs, 3H), 1.79 (d, J=12.3 Hz, 3H), 1.70 (d, J=11.7 Hz, 3H), 1.61-1.57 (m, 12H), 1.53-1.47 (m, 2H).

Example 24: Synthesis of AM29-182A

AM29-182A was synthesized according to the procedures for preparing XY019-43 from intermediate 7 (30 mg, 0.05 mmol), HOAt (9 mg, 0.07 mmol), 2-(adamantan-2-yl) acetic acid (11 mg, 0.06 mmol), NMM (20 μL, 0.18 mmol), EDCI (14 mg, 0.07 mmol), and DMSO (1.0 mL). AM29-182 was obtained as white solid in TFA salt form (27 mg. 72%). $^1$H NMR (600 MHz, CD$_3$OD) δ 8.57 (d, J=2.4 Hz, 1H), 8.37 (s, 1H), 8.20 (dd, J=9.0, 2.5 Hz, 1H), 7.98 (s, 1H), 7.79 (s, 1H), 7.17 (d, J=9.0 Hz, 1H), 6.21 (s, 1H), 5.13-5.05 (m, 1H), 4.59 (s, 2H), 3.98 (brs, 4H), 3.63 (t, J=6.0 Hz, 2H), 3.55 (brs, 4H), 3.36 (t, J=5.8 Hz, 2H), 2.45 (s, 3H), 2.44 (d, J=7.6 Hz, 2H), 2.28 (s, 3H), 2.24 (t, J=7.6 Hz, 1H), 1.98-1.93 (m, 2H), 1.92-1.85 (m, 3H), 1.85-1.79 (m, 3H), 1.78 (brs, 2H), 1.69 (brs, 2H), 1.61 (brs, 2H), 1.58 (s, 3H), 1.57 (s, 3H).

Example 25: Synthesis of AM29-55A

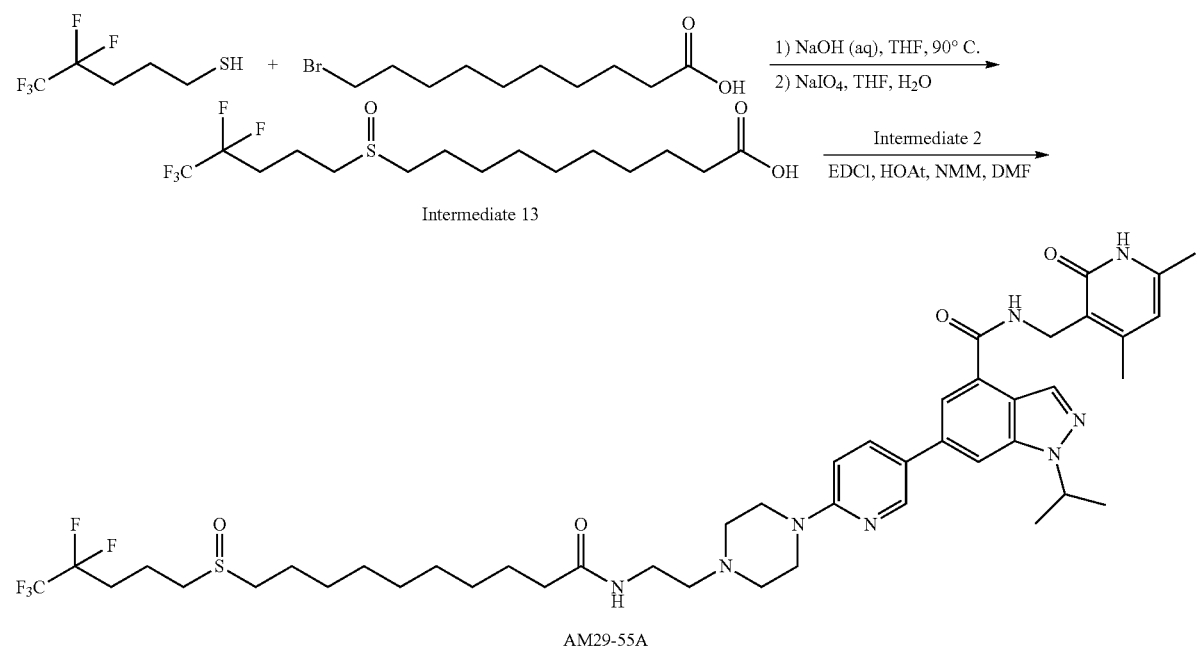

AM29-55A

To the solution of 4,4,5,5,5-pentafluoropentane-1-thiol (1.3 g, 6.8 mmol) and 10-bromodecanoic acid (1.4 g, 5.7 mmol) in THF (10 mL) was added sodium hydroxide aqueous solution (18%, 20 mL) dropwise. The reaction mixture was stirred at 90° C. for 4 hours. Upon completion, the pH value of reaction mixture was adjust to <6 using hydrochloric acid solution. After extraction with DCM, the organic layer was concentrated under vacuum. The residue was dissolved in THF (10 mL) and water (10 mL). To the resulting solution was added sodium periodate (0.5 g, 2.5 mmol) in portions at 0° C. After being stirred overnight at room temperature, the pH value of reaction mixture was adjusted to <5 using hydrochloric acid solution. After extraction with DCM and concentration under vacuum, crude intermediate 13 was obtained and used for the next step without further purification. AM29-55A was synthesized according to the procedures for preparing AM16-10A from intermediate 2 (60 mg, 0.08 mmol), HOAt (17 mg, 0.12 mmol), intermediate 13 (31 mg, 0.08 mmol), NMM (44 μL, 0.40 mmol), EDCI (23 mg, 0.12 mmol) and DMF (1.0 mL). AM29-55A was obtained as yellow solid in TFA salt form (22 mg, 27%). $^1$H NMR (600 MHz, CD$_3$OD) δ 8.57 (d, J=2.4 Hz, 1H), 8.37 (s, 1H), 8.16 (dd, J=9.0, 2.4 Hz, 1H), 7.96 (s, 1H), 7.78 (s, 1H), 7.13 (d, J=9.0 Hz, 1H), 6.19 (s, 1H), 5.14-5.04 (m, 1H), 4.59 (s, 2H), 3.97 (brs, 3H), 3.63 (t, J=5.9 Hz, 2H), 3.55 (brs, 3H), 3.36 (t, J=5.9 Hz, 2H), 2.94-2.87 (m, 1H), 2.86-2.75 (m, 3H), 2.45 (s, 3H), 2.39-2.28 (m, 2H), 2.27 (s, 3H), 2.12-2.01 (m, 2H), 1.82-1.71 (m, 2H), 1.69-1.60 (m, 2H), 1.58 (s, 3H), 1.57 (s, 3H), 1.54-1.22 (m, 14H).

Example 26: Synthesis of AM29-151A

Hz, 1H), 7.94 (s, 1H), 7.77 (s, 1H), 7.60 (t, J=7.7 Hz, 1H), 7.15 (d, J=7.0 Hz, 1H), 7.05 (d, J=8.8 Hz, 1H), 6.95 (d, J=8.4 Hz, 1H), 6.15 (s, 1H), 5.15-5.00 (m, 2H), 4.58 (s, 2H), 4.08 (s, 2H), 3.99-3.33 (m, 10H), 3.15-2.79 (m, 2H), 2.77-2.64 (m, 2H), 2.43 (s, 3H), 2.25 (s, 3H), 2.14-2.04 (m, 1H), 1.58 (s, 3H), 1.57 (s, 3H), 1.29 (brs, 1H).

Example 27: Synthesis of AM29-152A

AM29-152A was synthesized according to the procedures for preparing AM29-151A from intermediate 7 (10 mg, 0.02

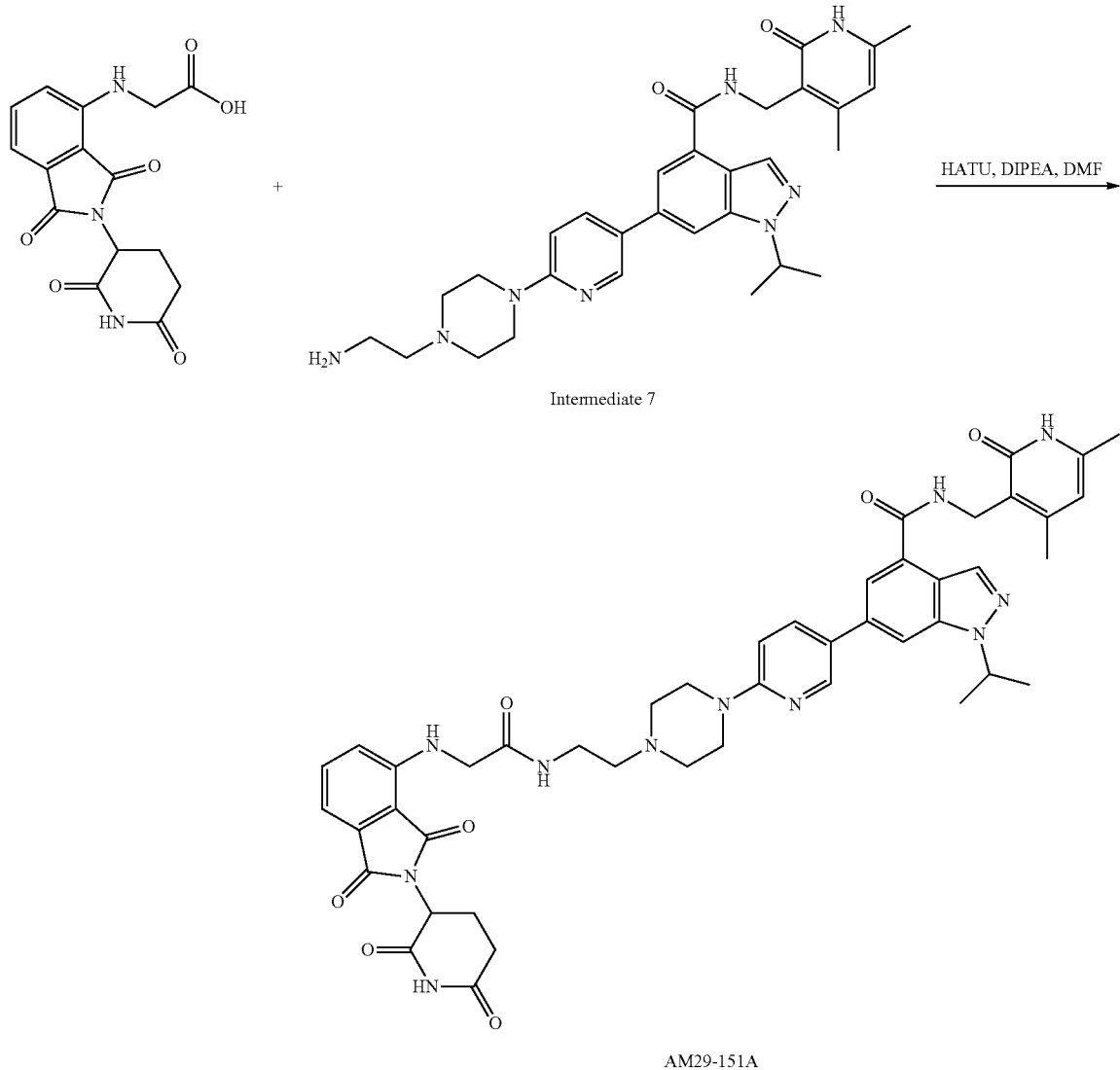

Intermediate 7 (10 mg, 0.02 mmol), HATU (1-[Bis(dimethylamino)methylene]-1H-1,2,3-triazolo[4,5-b]pyridinium 3-oxid hexafluorophosphate) (11 mg, 0.03 mmol) and (2-(2,6-dioxopiperidin-3-yl)-1,3-dioxoisoindolin-4-yl)glycine (6 mg, 0.02 mmol) were dissolved in DMF (1.0 mL). To the solution were added DIPEA (11 µL, 0.06 mmol) at room temperature. After being stirred overnight at room temperature, the mixture was purified by preparative HPLC (10%-100% methanol/0.1% TFA in H₂O) to afford AM29-151A as yellow solid in TFA salt form (11 mg, 73%). ¹H NMR (600 MHz, CD₃OD) δ 8.58 (s, 1H), 8.36 (s, 1H), 8.09 (d, J=8.6 mmol), HATU (11 mg, 0.03 mmol), 3-((2-(2,6-dioxopiperidin-3-yl)-1,3-dioxoisoindolin-4-yl)amino) propanoic acid (6 mg, 0.02 mmol), DIPEA (11 µL, 0.06 mmol), and DMF (1.0 mL). AM29-152A was obtained as yellow solid in TFA salt form (9.6 mg, 65%). ¹H NMR (600 MHz, CD₃OD) δ 8.58 (s, 1H), 8.37 (s, 1H), 8.08 (d, J=8.7 Hz, 1H), 7.96 (s, 1H), 7.78 (s, 1H), 7.59 (t, J=7.7 Hz, 1H), 7.15 (d, J=8.4 Hz, 1H), 7.06 (dd, J=16.8, 7.9 Hz, 2H), 6.16 (s, 1H), 5.14-5.06 (m, 1H), 5.03-4.94 (m, 1H), 4.59 (s, 2H), 4.24-3.34 (m, 12H), 2.85-2.53 (m, 6H), 2.44 (s, 3H), 2.26 (s, 3H), 2.11-1.99 (m, 1H), 1.59 (s, 3H), 1.58 (s, 3H), 1.29 (brs, 1H).

Example 28: Synthesis of AM29-137A

AM29-137A was synthesized according to the procedures for preparing AM29-151A from intermediate 12 (10 mg, 0.02 mmol), HATU (11 mg, 0.03 mmol), 4-((2-aminoethyl)amino)-2-(2,6-dioxopiperidin-3-yl) isoindoline-1,3-dione (8 mg, 0.02 mmol), DIPEA (11 µL, 0.06 mmol), and DMF (1.0 mL). AM29-137A was obtained as yellow solid in TFA salt form (11 mg, 75%). $^1$H NMR (600 MHz, CD$_3$OD) δ 8.56 (s, 1H), 8.38 (s, 1H), 8.11-8.03 (m, 1H), 7.94 (s, 1H), 7.77 (s, 1H), 7.57 (t, J=7.8 Hz, 1H), 7.12 (d, J=8.5 Hz, 1H), 7.08 (d, J=7.0 Hz, 1H), 7.03 (d, J=8.9 Hz, 1H), 6.15 (s, 1H), 5.14-5.07 (m, 1H), 5.06-4.99 (m, 1H), 4.58 (s, 2H), 4.35-3.39 (m, 13H), 2.87-2.75 (m, 3H), 2.74-2.65 (m, 2H), 2.43 (s, 3H), 2.25 (s, 3H), 2.14-2.04 (m, 1H), 1.58 (s, 3H), 1.57 (s, 3H), 1.45-1.23 (m, 1H).

Example 29: Synthesis of AM29-153A

AM29-153A was synthesized according to the procedures for preparing AM29-151A from intermediate 7 (10 mg, 0.02 mmol), HATU (11 mg, 0.03 mmol), 4-((2-(2,6-dioxopiperidin-3-yl)-1,3-dioxoisoindolin-4-yl)amino) butanoic acid (6 mg, 0.02 mmol), DIPEA (11 µL, 0.06 mmol), and DMF (1.0 mL). AM29-153A was obtained as yellow solid in TFA salt form (11 mg, 78%). $^1$H NMR (600 MHz, CD$_3$OD) δ 8.58 (d, J=2.1 Hz, 1H), 8.37 (s, 1H), 8.12 (dd, J=8.9, 2.3 Hz, 1H), 7.96 (s, 1H), 7.78 (s, 1H), 7.60-7.48 (m, 1H), 7.11-7.06 (m, 2H), 7.06-7.02 (m, 1H), 6.17 (s, 1H), 5.14-5.01 (m, 2H), 4.58 (s, 2H), 3.87-3.36 (m, 12H), 2.87-2.80 (m, 1H), 2.77-2.65 (m, 3H), 2.44 (s, 3H), 2.41-2.34 (m, 2H), 2.26 (s, 3H), 2.11-2.07 (m, 1H), 2.04-1.96 (m, 2H), 1.63-1.52 (m, 6H), 1.37-1.16 (m, 1H).

Example 30: Synthesis of AM29-138A

AM29-138A was synthesized according to the procedures for preparing AM29-151A from intermediate 12 (10 mg, 0.02 mmol), HATU (11 mg, 0.03 mmol), 4-((3-aminopropyl)amino)-2-(2,6-dioxopiperidin-3-yl) isoindoline-1,3-dione (8 mg, 0.02 mmol), DIPEA (11 µL, 0.06 mmol), and DMF (1.0 mL). AM29-138A was obtained as yellow solid in TFA salt form (14 mg, 96%). $^1$H NMR (600 MHz, CD$_3$OD) δ 8.55 (s, 1H), 8.37 (s, 1H), 8.10 (d, J=8.8 Hz, 1H), 7.94 (s, 1H), 7.77 (s, 1H), 7.54 (t, J=7.7 Hz, 1H), 7.14-6.97 (m, 3H), 6.16 (s, 1H), 5.13-5.01 (m, 2H), 4.58 (s, 2H), 4.28-3.34 (m, 13H), 2.90-2.75 (m, 3H), 2.75-2.63 (m, 2H), 2.43 (s, 3H), 2.25 (s, 3H), 2.13-2.05 (m, 1H), 1.90-1.79 (m, 2H), 1.57 (s, 3H), 1.56 (s, 3H), 1.29 (brs, 1H).

Example 31: Synthesis of AM29-154A

AM29-154A was synthesized according to the procedures for preparing AM29-151A from intermediate 7 (10 mg, 0.02 mmol), HATU (11 mg, 0.03 mmol), 5-((2-(2,6-dioxopiperidin-3-yl)-1,3-dioxoisoindolin-4-yl)amino) pentanoic acid (7 mg, 0.02 mmol), DIPEA (11 µL, 0.06 mmol), and DMF (1.0 mL). AM29-154A was obtained as yellow solid in TFA salt form (12 mg, 82%). $^1$H NMR (600 MHz, CD$_3$OD) δ 8.57 (s, 1H), 8.37 (s, 1H), 8.07 (dd, J=8.7, 2.1 Hz, 1H), 7.94 (s, 1H), 7.77 (s, 1H), 7.57-7.49 (m, 1H), 7.18-6.95 (m, 3H), 6.14 (s, 1H), 5.14-5.05 (m, 1H), 5.04-4.99 (m, 1H), 4.58 (s, 2H), 4.39-3.32 (m, 13H), 2.86-2.75 (m, 1H), 2.73-2.52 (m, 2H), 2.43 (s, 3H), 2.34 (t, J=7.1 Hz, 2H), 2.25 (s, 3H), 2.15-2.02 (m, 1H), 1.81-1.73 (m, 2H), 1.73-1.64 (m, 2H), 1.58 (s, 3H), 1.57 (s, 3H), 1.29 (brs, 1H).

Example 32: Synthesis of AM29-139A

AM29-139A was synthesized according to the procedures for preparing AM29-151A from intermediate 12 (10 mg, 0.02 mmol), HATU (11 mg, 0.03 mmol), 4-((4-aminobutyl)amino)-2-(2,6-dioxopiperidin-3-yl) isoindoline-1,3-dione (8 mg, 0.02 mmol), DIPEA (11 µL, 0.06 mmol), and DMF (1.0 mL). AM29-139A was obtained as yellow solid in TFA salt form (9.8 mg, 66%). $^1$H NMR (600 MHz, CD$_3$OD) δ 8.57 (s, 1H), 8.37 (s, 1H), 8.13-8.04 (m, 1H), 7.94 (s, 1H), 7.77 (s, 1H), 7.54 (t, J=7.8 Hz, 1H), 7.23-6.91 (m, 3H), 6.15 (s, 1H), 5.13-5.06 (m, 1H), 5.06-5.00 (m, 1H), 4.58 (s, 2H), 4.44-3.34 (m, 11H), 3.29-3.22 (m, 2H), 2.90-2.61 (m, 5H), 2.43 (s, 3H), 2.25 (s, 3H), 2.12-2.03 (m, 1H), 1.75-1.61 (m, 4H), 1.58 (s, 3H), 1.57 (s, 3H), 1.29 (brs, 1H).

Example 33: Synthesis of AM29-155A

AM29-155A was synthesized according to the procedures for preparing AM29-151A from intermediate 7 (10 mg, 0.02 mmol), HATU (11 mg, 0.03 mmol), 6-((2-(2,6-dioxopiperidin-3-yl)-1,3-dioxoisoindolin-4-yl)amino) hexanoic acid (7 mg, 0.02 mmol), DIPEA (11 µL, 0.06 mmol), and DMF (1.0 mL). AM29-155A was obtained as yellow solid in TFA salt form (12 mg, 76%). $^1$H NMR (600 MHz, CD$_3$OD) δ 8.57 (s, 1H), 8.37 (s, 1H), 8.16-8.06 (m, 1H), 7.95 (s, 1H), 7.78 (s, 1H), 7.57-7.48 (m, 1H), 7.08 (d, J=8.9 Hz, 1H), 7.02 (dd, J=13.8, 7.8 Hz, 2H), 6.17 (s, 1H), 5.14-5.06 (m, 1H), 5.06-4.99 (m, 1H), 4.58 (s, 2H), 4.21-3.32 (m, 13H), 2.88-2.77 (m, 1H), 2.76-2.62 (m, 2H), 2.44 (s, 3H), 2.30 (t, J=7.2 Hz, 2H), 2.26 (s, 3H), 2.14-2.05 (m, 1H), 1.75-1.63 (m, 4H), 1.58 (s, 3H), 1.57 (s, 3H), 1.51-1.40 (m, 2H), 1.36-1.19 (m, 1H).

Example 34: Synthesis of AM29-170A

AM29-170A was synthesized according to the procedures for preparing AM29-151A from intermediate 12 (20 mg, 0.02 mmol), HATU (22 mg. 0.06 mmol), 4-((5-aminopentyl)amino)-2-(2,6-dioxopiperidin-3-yl) isoindoline-1,3-dione (17 mg, 0.04 mmol), DIPEA (20 µL, 0.12 mmol), and DMF (1.0 mL). AM29-170A was obtained as yellow solid in TFA salt form (20 mg, 64%). $^1$H NMR (600 MHz, CD$_3$OD) δ 8.50 (s, 1H), 8.38 (s, 1H), 8.14 (d, J=6.6 Hz, 1H), 7.95 (s, 1H), 7.76 (s, 1H), 7.58-7.44 (m, 1H), 7.18-7.05 (m, 1H), 7.05-6.91 (m, 2H), 6.20 (s, 1H), 5.15-5.00 (m, 2H), 4.58 (s, 2H), 4.35-3.33 (m, 11H), 3.28-3.08 (m, 3H), 2.90-2.61 (m, 5H), 2.43 (s, 3H), 2.26 (s, 3H), 2.14-2.02 (m, 1H), 1.65 (s, 3H), 1.57-1.49 (m, 6H), 1.44 (s, 2H), 1.37-1.23 (m, 1H).

Example 35: Synthesis of AM29-156A

AM29-156A was synthesized according to the procedures for preparing AM29-151A from intermediate 7 (10 mg, 0.02 mmol), HATU (11 mg, 0.03 mmol), 7-((2-(2,6-dioxopiperidin-3-yl)-1,3-dioxoisoindolin-4-yl)amino) heptanoic acid (7 mg, 0.02 mmol), DIPEA (11 µL, 0.06 mmol), and DMF (1.0 mL). AM29-156A was obtained as yellow solid in TFA salt form (13 mg, 83%). $^1$H NMR (600 MHz, CD$_3$OD) δ 8.57 (d, J=2.4 Hz, 1H), 8.37 (s, 1H), 8.16-8.07 (m, 1H), 7.95 (s, 1H), 7.78 (s, 1H), 7.55-7.51 (m, 1H), 7.13-7.07 (m, 1H), 7.04-7.00 (m, 2H), 6.18 (s, 1H), 5.10-5.00 (m, 2H), 4.58 (s, 2H), 4.31-3.40 (m, 11H), 3.04 (t, J=2.8 Hz, 1H), 2.91 (t, J=2.7 Hz, 1H), 2.89-2.78 (m, 2H), 2.78-2.63 (m, 4H), 2.44 (t, J=2.6 Hz, 3H), 2.26 (s, 3H), 2.11-2.07 (m, 1H), 1.69-1.66 (m, 3H), 1.60-1.51 (m, 6H), 1.44-1.40 (m, 4H), 1.29 (brs, 1H).

Example 36: Synthesis of AM29-171A

AM29-171A was synthesized according to the procedures for preparing AM29-151A from intermediate 12 (20 mg, 0.02 mmol), HATU (22 mg, 0.06 mmol), 4-((6-aminohexyl)amino)-2-(2,6-dioxopiperidin-3-yl) isoindoline-1,3-dione (17 mg, 0.04 mmol), DIPEA (20 μL, 0.12 mmol), and DMF (1.0 mL). AM29-171A was obtained as yellow solid in TFA salt form (20 mg, 66%). $^1$H NMR (600 MHz, CD$_3$OD) δ 8.49 (s, 1H), 8.37 (s, 1H), 8.14 (d, J=8.2 Hz, 1H), 7.94 (s, 1H), 7.75 (s, 1H), 7.49 (t, J=7.7 Hz, 1H), 7.10 (d, J=9.0 Hz, 1H), 6.96 (d, J=7.7 Hz, 2H), 6.19 (s, 1H), 5.10-5.00 (m, 2H), 4.58 (s, 2H), 4.33-3.70 (m, 4H), 3.66-3.34 (m, 6H), 3.25 (t, J=6.5 Hz, 2H), 3.20 (t, J=6.7 Hz, 2H), 2.88-2.76 (m, 3H), 2.75-2.62 (m, 2H), 2.43 (s, 3H), 2.26 (s, 3H), 2.12-2.02 (m, 1H), 1.65-1.59 (m, 2H), 1.56 (s, 3H), 1.55 (s, 3H), 1.54-1.48 (m, 2H), 1.47-1.32 (m, 4H).

Example 37: Synthesis of AM29-157A

AM29-157A was synthesized according to the procedures for preparing AM29-151A from intermediate 7 (10 mg, 0.02 mmol), HATU (11 mg, 0.03 mmol), 8-((2-(2,6-dioxopiperidin-3-yl)-1,3-dioxoisoindolin-4-yl)amino) octanoic acid (8 mg, 0.02 mmol), DIPEA (11 μL, 0.06 mmol), and DMF (1.0 mL). AM29-157A was obtained as yellow solid in TFA salt form (11 mg, 67%). $^1$H NMR (600 MHz, CD$_3$OD) δ 8.58 (d, J=2.3 Hz, 1H), 8.37 (s, 1H), 8.11-8.02 (m, 1H), 7.94 (s, 1H), 7.77 (s, 1H), 7.57-7.46 (m, 1H), 7.21-6.94 (m, 3H), 6.14 (s, 1H), 5.13-5.01 (m, 2H), 4.58 (s, 2H), 4.36-3.32 (m, 12H), 3.07-2.78 (m, 2H), 2.76-2.65 (m, 2H), 2.48-2.35 (m, 3H), 2.30-2.19 (m, 5H), 2.12-2.05 (m, 1H), 1.75-1.60 (m, 4H), 1.60-1.51 (m, 6H), 1.41 (dd, J=19.6, 8.1 Hz, 7H).

Example 38: Synthesis of AM29-172A

AM29-172A was synthesized according to the procedures for preparing AM29-151A from intermediate 12 (20 mg, 0.02 mmol), HATU (22 mg, 0.06 mmol), 4-((7-aminoheptyl)amino)-2-(2,6-dioxopiperidin-3-yl) isoindoline-1,3-dione (18 mg, 0.04 mmol), DIPEA (20 μL, 0.12 mmol), and DMF (1.0 mL). AM29-172A was obtained as yellow solid in TFA salt form (23 mg, 73%). $^1$H NMR (600 MHz, CD$_3$OD) δ 8.50 (s, 1H), 8.38 (s, 1H), 8.13 (d, J=7.9 Hz, 1H), 7.94 (s, 1H), 7.75 (s, 1H), 7.49 (t, J=7.7 Hz, 1H), 7.09 (d, J=8.9 Hz, 1H), 6.96 (d, J=7.6 Hz, 2H), 6.19 (s, 1H), 5.11-5.00 (m, 2H), 4.58 (s, 2H), 3.98 (brs, 3H), 3.59-3.36 (m, 6H), 3.35 (s, 1H), 3.25 (t, J=6.6 Hz, 2H), 3.20 (t, J=6.8 Hz, 2H), 2.88-2.76 (m, 3H), 2.75-2.62 (m, 2H), 2.43 (s, 3H), 2.26 (s, 3H), 2.13-2.03 (m, 1H), 1.65-1.59 (m, 2H), 1.57 (s, 3H), 1.56 (s, 3H), 1.53-1.47 (m, 2H), 1.44-1.29 (m, 6H).

Example 39: Synthesis of AM29-173A

AM29-173A was synthesized according to the procedures for preparing AM29-151A from intermediate 12 (20 mg, 0.02 mmol), HATU (22 mg, 0.06 mmol), 4-((8-aminooctyl)amino)-2-(2,6-dioxopiperidin-3-yl) isoindoline-1,3-dione (18 mg, 0.04 mmol), DIPEA (20 μL, 0.12 mmol), and DMF (1.0 mL). AM29-173A was obtained as yellow solid in TFA salt form (26 mg, 82%). $^1$H NMR (600 MHz, CD$_3$OD) δ 8.53 (d, J=2.3 Hz, 1H), 8.38 (s, 1H), 8.13 (dd, J=8.9, 2.4 Hz, 1H), 7.95 (s, 1H), 7.77 (s, 1H), 7.54-7.45 (m, 1H), 7.10 (d, J=9.0 Hz, 1H), 6.99 (d, J=7.8 Hz, 2H), 6.19 (s, 1H), 5.13-5.07 (m, 1H), 5.06-5.00 (m, 1H), 4.58 (s, 2H), 4.21-3.73 (m, 3H), 3.61-3.39 (m, 6H), 3.27 (t, J=6.9 Hz, 2H), 3.20 (t, J=7.1 Hz, 2H), 2.89-2.64 (m, 5H), 2.44 (s, 3H), 2.26 (s, 3H), 2.12-2.05 (m, 1H), 1.67-1.59 (m, 2H), 1.57 (s, 3H), 1.56 (s, 3H), 1.54-1.47 (m, 2H), 1.45-1.21 (m, 9H).

Example 40: Synthesis of AM16-79A

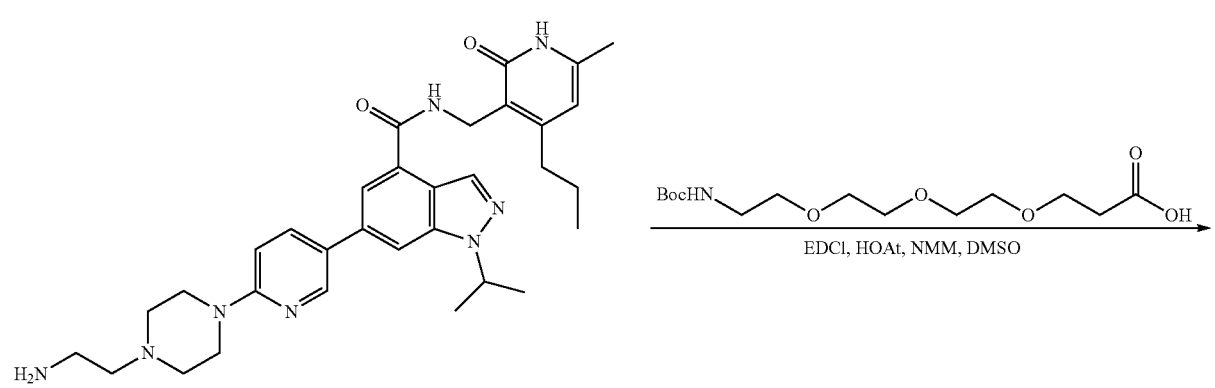

Intermediate 2

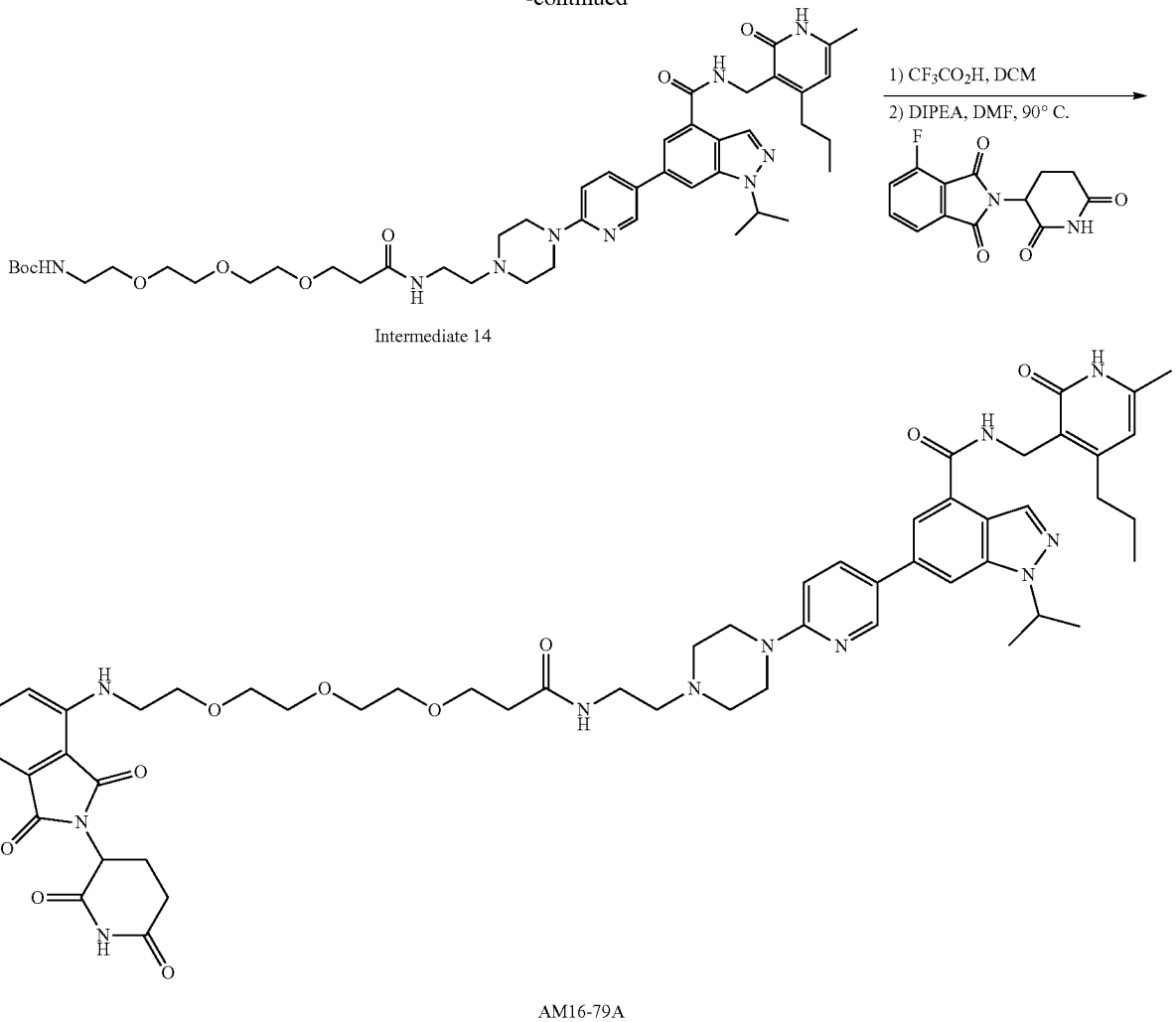

Intermediate 14 was synthesized according to the procedures for preparing AM16-10A from intermediate 2 (110 mg, 0.16 mmol), HOAt (33 mg, 0.24 mmol), 2,2-dimethyl-4-oxo-3,8,11,14-tetraoxa-5-azaheptadecan-17-oic acid (62 mg, 0.19 mmol, Broadpharm, BP-21656), NMM (71 µL, 0.64 mmol), EDCI (46 mg, 0.24 mmol), and DMSO (2.0 mL). Intermediate 14 was dissolved in DCM (2.0 mL) and to the solution was added trifluoroacetic acid (0.5 mL) at room temperature. After being stirred for 1 h at room temperature, the mixture was concentrated, basified with sodium bicarbonate solution and extracted with DCM. Organic phase was concentrated under vacuum and purified by ISCO™ silica gel column (0-20% MeOH in DCM) to afford compound 6-(6-(4-(1-amino-12-oxo-3,6,9-trioxa-13-azapentadecan-15-yl) piperazin-1-yl) pyridin-3-yl)-1-isopropyl-N-((6-methyl-2-oxo-4-propyl-1,2-dihydropyridin-3-yl)methyl)-1H-indazole-4-carboxamide. This compound was dissolved in anhydrous DMF (2.0 mL). To the resulting solution was added DIPEA (56 UL, 0.32 mmol). After being stirred overnight at 90° C., the mixture was concentrated under vacuum and purified by preparative HPLC to afford AM16-79A as yellow solid in TFA salt form (30 mg, 16% over 3 steps). $^1$H NMR (600 MHz, CD$_3$OD) δ 8.59-8.47 (m, 1H), 8.38 (s, 1H), 8.37-8.20 (m, 1H), 8.19-8.10 (m, 1H), 8.06-7.86 (m, 1H), 7.79-7.72 (m, 1H), 7.48-7.38 (m, 1H), 7.29-7.13 (m, 1H), 7.01-6.86 (m, 1H), 6.24 (s, 1H), 5.16-5.01 (m, 2H), 4.62 (s, 2H), 4.28-3.35 (m, 26H), 2.98-2.56 (m, 5H), 2.55-2.41 (m, 2H), 2.29 (s, 3H), 2.13-2.00 (m, 1H), 1.70-1.60 (m, 2H), 1.58 (d, J=6.4 Hz, 6H), 1.03 (t, J=7.2 Hz, 3H).

Example 41: Synthesis of AM29-177A

AM29-177A was synthesized according to the procedures for preparing AM29-151A from intermediate 7 (20 mg, 0.03 mmol), HATU (23 mg, 0.06 mmol), 3-(2-((2-(2,6-dioxopiperidin-3-yl)-1,3-dioxoisoindolin-4-yl)amino) ethoxy) propanoic acid (14 mg, 0.04 mmol), DIPEA (21 µL, 0.12 mmol), and DMF (1.0 mL). AM29-177A was obtained as yellow solid in TFA salt form (30 mg, 95%). $^1$H NMR (600 MHz, CD$_3$OD) δ 8.49 (s, 1H), 8.38 (s, 1H), 8.09 (d, J=8.8 Hz, 1H), 7.94 (s, 1H), 7.75 (s, 1H), 7.50 (t, J=7.7 Hz, 1H), 7.12-7.02 (m, 2H), 6.98 (d, J=6.9 Hz, 1H), 6.19 (s, 1H), 5.15-5.05 (m, 1H), 5.05-5.00 (m, 1H), 4.59 (s, 2H), 4.23-3.39 (m, 16H), 3.35 (s, 2H), 2.89-2.77 (m, 1H), 2.76-2.61 (m, 2H), 2.58-2.48 (m, 2H), 2.44 (s, 3H), 2.26 (s, 3H), 2.13-2.05 (m, 1H), 1.58 (s, 3H), 1.57 (s, 3H).

Example 42: Synthesis of AM29-141A

AM29-141A was synthesized according to the procedures for preparing AM29-151A from intermediate 12 (10 mg, 0.02 mmol), HATU (11 mg, 0.03 mmol), 4-((2-(2-aminoethoxy)ethyl)amino)-2-(2,6-dioxopiperidin-3-yl) isoindoline-1,3-dione (8 mg, 0.02 mmol), DIPEA (11 µL, 0.06 mmol), and DMF (1.0 mL). AM29-141A was obtained as yellow liquid in TFA salt form (4.8 mg, 32%). $^1$H NMR (600 MHz, CD$_3$OD) δ 8.56 (d, J=2.3 Hz, 1H), 8.37 (s, 1H), 8.02 (dd, J=8.8, 2.5 Hz, 1H), 7.92 (s, 1H), 7.76 (s, 1H), 7.59-7.51 (m, 1H), 7.10-7.03 (m, 2H), 6.98 (d, J=8.8 Hz, 1H), 6.14 (s, 1H), 5.11-5.04 (m, 2H), 4.58 (s, 2H), 4.07-3.37 (m, 20H), 2.86-2.81 (m, 1H), 2.74-2.70 (m, 2H), 2.44 (s, 3H), 2.25 (s, 3H), 2.14-2.09 (m, 1H), 1.59 (s, 3H), 1.58 (s, 3H).

Example 43: Synthesis of AM29-178A

AM29-178A was synthesized according to the procedures for preparing AM29-151A from intermediate 7 (20 mg, 0.03 mmol), HATU (23 mg, 0.06 mmol), 3-(2-(2-((2-(2,6-dioxopiperidin-3-yl)-1,3-dioxoisoindolin-4-yl)amino)ethoxy)ethoxy) propanoic acid (16 mg, 0.04 mmol), DIPEA (21 µL, 0.12 mmol), and DMF (1.0 mL). AM29-178A was obtained as yellow solid in TFA salt form (27 mg, 85%). $^1$H NMR (600 MHz, CD$_3$OD) δ 8.49 (s, 1H), 8.38 (s, 1H), 8.10 (d, J=9.0 Hz, 1H), 7.93 (s, 1H), 7.74 (s, 1H), 7.46 (t, J=7.8 Hz, 1H), 7.07 (d, J=9.0 Hz, 1H), 7.01 (d, J=8.5 Hz, 1H), 6.93 (d, J=7.0 Hz, 1H), 6.20 (s, 1H), 5.12-5.05 (m, 1H), 5.04-4.99 (m, 1H), 4.59 (s, 2H), 4.27-3.32 (m, 22H), 2.89-2.77 (m, 1H), 2.76-2.59 (m, 2H), 2.51 (t, J=5.5 Hz, 2H), 2.44 (s, 3H), 2.27 (s, 3H), 2.11-2.03 (m, 1H), 1.58 (s, 3H), 1.57 (s, 3H).

Example 44: Synthesis of AM29-142A

AM29-142A was synthesized according to the procedures for preparing AM29-151A from intermediate 12 (10 mg, 0.02 mmol), HATU (11 mg, 0.03 mmol), 4-((2-(2-(2-aminoethoxy)ethoxy)ethyl)amino)-2-(2,6-dioxopiperidin-3-yl) isoindoline-1,3-dione (8 mg, 0.02 mmol), DIPEA (11 µL, 0.06 mmol), and DMF (1.0 mL). AM29-142A was obtained as brown liquid in TFA salt form (4 mg, 25%). $^1$H NMR (600 MHz, CD$_3$OD) δ 8.58 (d, J=1.8 Hz, 1H), 8.37 (s, 1H), 8.05 (dd, J=8.7, 2.0 Hz, 1H), 7.93 (s, 1H), 7.77 (s, 1H), 7.56-7.51 (m, 1H), 7.10-7.06 (m, 1H), 7.05-7.00 (m, 2H), 6.14 (s, 1H), 5.11-5.03 (m, 2H), 4.58 (s, 2H), 3.79-3.40 (m, 23H), 2.87-2.80 (m, 1H), 2.77-2.72 (m, 3H), 2.43 (s, 3H), 2.25 (s, 3H), 2.12-2.06 (m, 1H), 1.58 (s, 3H), 1.57 (s, 3H).

Example 45: Synthesis of AM29-179A

AM29-179A was synthesized according to the procedures for preparing AM29-151A from intermediate 7 (20 mg, 0.03 mmol), HATU (23 mg, 0.06 mmol), 3-(2-(2-(2-((2-(2,6-dioxopiperidin-3-yl)-1,3-dioxoisoindolin-4-yl)amino) ethoxy) ethoxy) ethoxy) propanoic acid (18 mg, 0.04 mmol), DIPEA (21 µL, 0.12 mmol), and DMF (1.0 mL). AM29-179A was obtained as yellow solid in TFA salt form (26 mg, 78%). $^1$H NMR (600 MHz, CD$_3$OD) δ 8.50 (s, 1H), 8.38 (s, 1H), 8.13 (d, J=9.0 Hz, 1H), 7.94 (s, 1H), 7.75 (s, 1H), 7.46-7.39 (m, 1H), 7.12 (d, J=9.0 Hz, 1H), 6.98 (d, J=8.5 Hz, 1H), 6.93 (d, J=7.1 Hz, 1H), 6.22 (s, 1H), 5.11-5.06 (m, 1H), 5.06-5.00 (m, 1H), 4.59 (s, 2H), 3.97-3.37 (m, 26H), 2.88-2.78 (m, 1H), 2.77-2.61 (m, 2H), 2.50 (t, J=5.6 Hz, 2H), 2.45 (s, 3H), 2.27 (s, 3H), 2.13-2.02 (m, 1H), 1.58 (s, 3H), 1.57 (s, 3H).

Example 46: Synthesis of AM29-143A

AM29-143A was synthesized according to the procedures for preparing AM29-151A from intermediate 12 (10 mg, 0.02 mmol), HATU (11 mg, 0.03 mmol), 4-((2-(2-(2-(2-aminoethoxy) ethoxy) ethoxy)ethyl)amino)-2-(2,6-dioxopiperidin-3-yl) isoindoline-1,3-dione (9 mg, 0.02 mmol), DIPEA (11 µL, 0.06 mmol), and DMF (1.0 mL). AM29-143A was obtained as brown liquid in TFA salt form (11 mg, 67%). $^1$H NMR (600 MHz, CD$_3$OD) δ 8.57 (d, J=2.3 Hz, 1H), 8.37 (s, 1H), 8.05 (dd, J=8.8, 2.4 Hz, 1H), 7.93 (s, 1H), 7.76 (s, 1H), 7.51 (dd, J=8.4, 7.3 Hz, 1H), 7.06 (d, J=8.6 Hz, 1H), 7.01 (dd, J=7.9, 3.4 Hz, 2H), 6.14 (s, 1H), 5.12-5.02 (m, 2H), 4.58 (s, 2H), 3.97-3.31 (m, 26H), 2.89-2.80 (m, 1H), 2.79-2.64 (m, 4H), 2.43 (s, 3H), 2.25 (s, 3H), 2.13-2.06 (m, 1H), 1.58 (s, 3H), 1.57 (s, 3H).

Example 47: Synthesis of AM29-180A

AM29-180A was synthesized according to the procedures for preparing AM29-151A from intermediate 7 (20 mg, 0.03 mmol), HATU (23 mg, 0.06 mmol), 1-((2-(2,6-dioxopiperidin-3-yl)-1,3-dioxoisoindolin-4-yl)amino)-3,6,9,12-tetraoxapentadecan-15-oic acid (20 mg, 0.04 mmol), DIPEA (21 µL, 0.12 mmol), and DMF (1.0 mL). AM29-180A was obtained as yellow solid in TFA salt form (31 mg, 90%). $^1$H NMR (600 MHz, CD$_3$OD) δ 8.51 (s, 1H), 8.38 (s, 1H), 8.15 (d, J=9.0 Hz, 1H), 7.95 (s, 1H), 7.76 (s, 1H), 7.44 (t, J=7.8 Hz, 1H), 7.14 (d, J=9.0 Hz, 1H), 6.98 (d, J=8.5 Hz, 1H), 6.93 (d, J=7.0 Hz, 1H), 6.22 (s, 1H), 5.11-5.05 (m, 1H), 5.04-4.99 (m, 1H), 4.59 (s, 2H), 4.04-3.38 (m, 30H), 2.89-2.78 (m, 1H), 2.75-2.60 (m, 2H), 2.53-2.47 (m, 2H), 2.45 (s, 3H), 2.27 (s, 3H), 2.11-2.02 (m, 1H), 1.57 (s, 3H), 1.56 (s, 3H).

Example 48: Synthesis of AM29-144A

AM29-144A was synthesized according to the procedures for preparing AM29-151A from intermediate 12 (10 mg, 0.02 mmol), HATU (11 mg, 0.03 mmol), 4-((14-amino-3,6,9,12-tetraoxatetradecyl)amino)-2-(2,6-dioxopiperidin-3-yl) isoindoline-1,3-dione (10 mg, 0.02 mmol), DIPEA (11 µL, 0.06 mmol), and DMF (1.0 mL). AM29-144A was obtained as yellow solid in TFA salt form (9 mg, 53%). $^1$H NMR (600 MHz, CD$_3$OD) δ 8.55 (d, J=2.0 Hz, 1H), 8.37 (s, 1H), 8.09 (dd, J=8.9, 2.1 Hz, 1H), 7.94 (s, 1H), 7.77 (s, 1H), 7.58-7.45 (m, 1H), 7.16-7.02 (m, 2H), 7.01-6.93 (m, 1H), 6.16 (s, 1H), 5.13-5.06 (m, 1H), 5.06-5.01 (m, 1H), 4.58 (s, 2H), 4.18-3.36 (m, 30H), 2.79-2.76 (m, 1H), 2.75-2.63 (m, 2H), 2.44 (s, 3H), 2.36 (t, J=8.1 Hz, 1H), 2.26 (s, 3H), 2.13-2.07 (m, 1H), 2.06-1.97 (m, 1H), 1.58 (s, 3H), 1.57 (s, 3H).

Example 49: Synthesis of AM29-145A

AM29-145A was synthesized according to the procedures for preparing AM29-151A from intermediate 12 (10 mg, 0.02 mmol), HATU (11 mg, 0.03 mmol), 4-((17-amino-3,6,9,12,15-pentaoxaheptadecyl)amino)-2-(2,6-dioxopiperidin-3-yl) isoindoline-1,3-dione (11 mg, 0.02 mmol), DIPEA (11 µL, 0.06 mmol), and DMF (1.0 mL). AM29-145A was obtained as yellow liquid in TFA salt form (12 mg, 70%). $^1$H NMR (600 MHz, CD$_3$OD) δ 8.58 (d, J=2.4 Hz, 1H), 8.37 (s, 1H), 8.05 (dd, J=8.8, 2.5 Hz, 1H), 7.93 (s, 1H), 7.77 (d, J=0.9 Hz, 1H), 7.50 (dd, J=8.4, 7.3 Hz, 1H), 7.04 (dd, J=8.7, 6.5 Hz, 2H), 7.00 (d, J=7.1 Hz, 1H), 6.15 (s, 1H), 5.12-5.06 (m, 1H), 5.04 (dd, J=12.8, 5.5 Hz, 1H), 4.58 (s, 2H), 4.00-3.31 (m, 34H), 2.90-2.77 (m, 3H), 2.76-2.64 (m, 2H), 2.44 (s, 3H), 2.25 (s, 3H), 2.12-2.04 (m, 1H), 1.58 (s, 3H), 1.57 (s, 3H).

Example 50: Synthesis of AM29-181A

AM29-181A was synthesized according to the procedures for preparing AM29-151A from intermediate 7 (20 mg, 0.03 mmol), HATU (23 mg, 0.06 mmol), 1-((2-(2,6-dioxopiperidin-3-yl)-1,3-dioxoisoindolin-4-yl)amino)-3,6,9,12,15-pentaoxaoctadecan-18-oic acid (21 mg, 0.04 mmol), DIPEA (21 µL, 0.12 mmol), and DMF (1.0 mL). AM29-181A was obtained as yellow solid in TFA salt form (9 mg, 25%). $^1$H NMR (600 MHz, CD$_3$OD) δ 8.53 (s, 1H), 8.38 (d, J=2.7 Hz, 1H), 8.24-8.15 (m, 1H), 7.97 (s, 1H), 7.77 (s, 1H), 7.51-7.41 (m, 1H), 7.18 (dd, J=8.8, 3.0 Hz, 1H), 6.99 (dd, J=8.4, 3.3 Hz, 1H), 6.94 (dd, J=6.8, 3.5 Hz, 1H), 6.23 (s, 1H), 5.14-5.05 (m, 1H), 5.05-4.99 (m, 1H), 4.59 (s, 2H), 4.25-3.37 (m, 34H), 2.88-2.78 (m, 1H), 2.76-2.60 (m, 2H), 2.50 (d, J=3.3 Hz, 2H), 2.45 (d, J=3.1 Hz, 3H), 2.27 (d, J=2.8 Hz, 3H), 2.11-2.04 (m, 1H), 1.57 (s, 6H).

Example 51: Synthesis of AM41-16A

AM41-16A was synthesized according to the procedures for preparing AM29-151A from intermediate 7 (18 mg, 0.03 mmol), HATU (21 mg, 0.05 mmol), 1-((2-(2,6-dioxopiperidin-3-yl)-1,3-dioxoisoindolin-4-yl)amino)-3,6,9,12,15,18,21,24-octaoxaheptacosan-27-oic acid (19 mg, 0.03 mmol), DIPEA (19 µL, 0.11 mmol), and DMF (1.0 mL). AM41-16A was obtained as yellow liquid in TFA salt form (31 mg, 86%). $^1$H NMR (600 MHz, CD$_3$OD) δ 8.58 (d, J=2.4 Hz, 1H), 8.37 (s, 1H), 8.14 (dd, J=9.0, 2.4 Hz, 1H), 7.96 (s, 1H), 7.78 (s, 1H), 7.51-7.45 (m, 1H), 7.13 (d, J=9.0 Hz, 1H), 7.02 (d, J=8.6 Hz, 1H), 6.98 (d, J=7.0 Hz, 1H), 6.18 (s, 1H), 5.15-5.05 (m, 1H), 5.02 (dd, J=12.6, 5.5 Hz, 1H), 4.59 (s, 2H), 3.94-3.37 (m, 46H), 2.90-2.79 (m, 1H), 2.76-2.62 (m, 2H), 2.52 (t, J=5.6 Hz, 2H), 2.44 (s, 3H), 2.26 (s, 3H), 2.12-2.05 (m, 1H), 1.58 (s, 3H), 1.57 (s, 3H).

Example 52: Synthesis of AM41-17A

AM41-17A was synthesized according to the procedures for preparing AM29-151A from intermediate 7 (18 mg, 0.03 mmol), HATU (18 mg, 0.05 mmol), 1-((2-(2,6-dioxopiperidin-3-yl)-1,3-dioxoisoindolin-4-yl)amino)-3,6,9,12, 15,18,21,24,27,30-decaoxatritriacontan-33-oic acid (19 mg, 0.02 mmol), DIPEA (17 µL, 0.10 mmol), and DMF (1.0 mL). AM41-17A was obtained as yellow liquid in TFA salt form (27 mg, 79%). $^1$H NMR (600 MHz, CD$_3$OD) δ 8.57 (d, J=2.3 Hz, 1H), 8.38 (s, 1H), 8.21 (dd, J=9.0, 2.2 Hz, 1H), 7.99 (s, 1H), 7.79 (s, 1H), 7.49 (dd, J=8.3, 7.4 Hz, 1H), 7.20 (d, J=9.0 Hz, 1H), 7.02 (d, J=8.6 Hz, 1H), 6.99 (d, J=7.0 Hz, 1H), 6.21 (s, 1H), 5.14-5.06 (m, 1H), 5.05-5.00 (m, 1H), 4.59 (s, 2H), 4.23-3.37 (m, 54H), 2.89-2.79 (m, 1H), 2.76-2.62 (m, 2H), 2.52 (t, J=5.7 Hz, 2H), 2.45 (s, 3H), 2.27 (s, 3H), 2.13-2.05 (m, 1H), 1.58 (s, 3H), 1.57 (s, 3H).

Example 53: Synthesis of AM41-18A

AM41-18A was synthesized according to the procedures for preparing AM29-151A from intermediate 7 (18 mg, 0.03 mmol), HATU (14 mg, 0.04 mmol), 1-((2-(2,6-dioxopiperidin-3-yl)-1,3-dioxoisoindolin-4-yl)amino)-3,6,9,12,15,18,21,24,27,30,33,36-dodecaoxanonatriacontan-39-oic acid (16 mg, 0.02 mmol), DIPEA (13 µL, 0.07 mmol), and DMF (1.0 mL). AM41-18A was obtained as yellow liquid in TFA salt form (18 mg, 66%). 1H NMR (600 MHz, CD$_3$OD) δ 8.60 (d, J=2.4 Hz, 1H), 8.38 (s, 1H), 8.20 (dd, J=9.0, 2.4 Hz, 1H), 7.99 (s, 1H), 7.80 (d, J=0.9 Hz, 1H), 7.51 (dd, J=8.4, 7.2 Hz, 1H), 7.18 (d, J=9.0 Hz, 1H), 7.04 (d, J=8.6 Hz, 1H), 7.01 (d, J=7.1 Hz, 1H), 6.19 (s, 1H), 5.13-5.07 (m, 1H), 5.03 (dd, J=12.8, 5.5 Hz, 1H), 4.59 (s, 2H), 4.27-3.32 (m, 62H), 2.89-2.79 (m, 1H), 2.77-2.64 (m, 2H), 2.52 (t, J=5.7 Hz, 2H), 2.45 (s, 3H), 2.27 (s, 3H), 2.13-2.05 (m, 1H), 1.58 (s, 3H), 1.57 (s, 3H).

Example 54: Synthesis of XY012-157

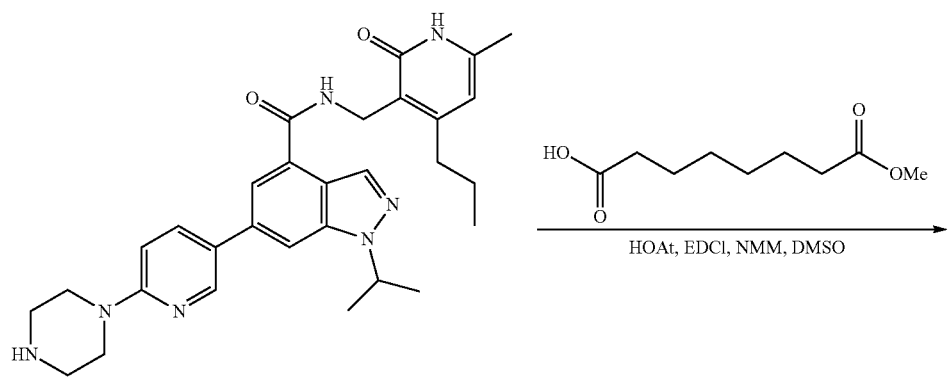

Intermediate 1

-continued

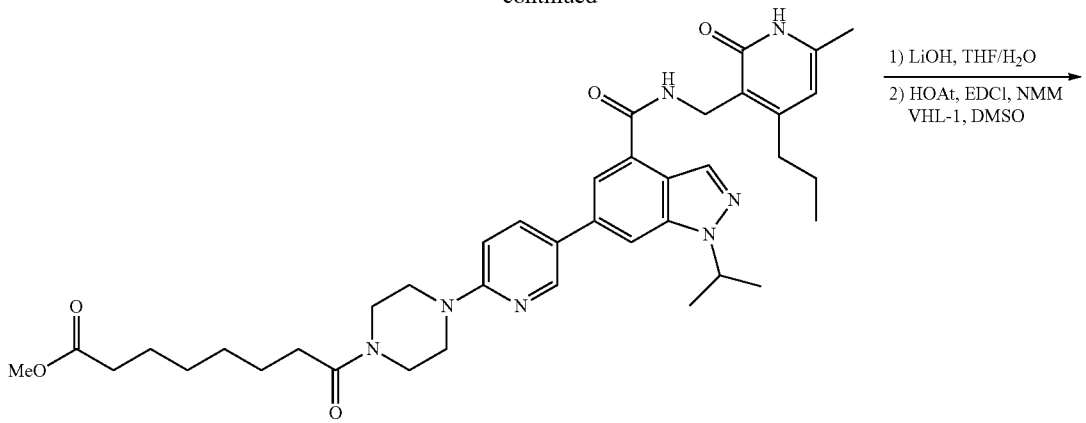

Intermediate 15

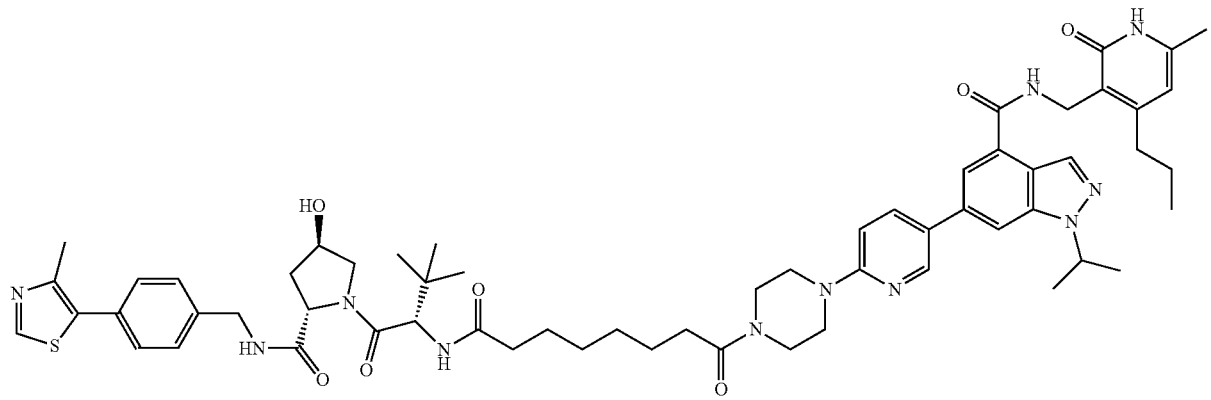

XY012-157

To the solution of intermediate 1 (45 mg, 0.09 mmol) in DMSO (2.0 mL) were added NMM (26 mg, 0.26 mmol), 8-methoxy-8-oxooctanoic acid (19 mg, 0.10 mmol), HOAt (17 mg, 0.13 mmol), and EDCI (25 mg, 0.13 mmol). The mixture was allowed to stir at room temperature overnight. The progress of the reaction was monitored by LC-MS. Upon completion, the mixture was concentrated under vacuum and purified by preparative HPLC to afford intermediate 15 (35 mg, 58%) as solid. MS (m/z) [M+H]$^+$: 698.3. To the stirring solution of intermediate 15 (35 mg, 0.05 mmol) in THF/H$_2$O (10 mL/5.0 mL) was added lithium hydroxide (6.0 mg, 0.22 mmol) and the resulting mixture was stirred overnight at room temperature. The progress of the reaction was monitored by LC-MS. Upon completion, the reaction mixture was concentrated under vacuum and the resulting residue was dissolved in DMSO (2.0 mL). To the solution were added NMM (23 mg, 0.23 mmol), VHL-1 (35 mg, 0.08 mmol), HOAt (10 mg, 0.08 mmol), and EDCI (14 mg, 0.08 mmol). The mixture was allowed to stir at room temperature overnight. The progress of the reaction was monitored by LC-MS. Upon completion, the mixture was concentrated under vacuum and purified by preparative HPLC to afford XY012-157 (11 mg, 20%) as solid. $^1$H NMR (600 MHz, CD$_3$OD) δ 8.99 (s, 1H), 8.49 (dd, J=9.5, 2.2 Hz, 1H), 8.39 (d, J=2.3 Hz, 2H), 8.07 (s, 1H), 7.78 (s, 1H), 7.47 (d, J=1.8 Hz, 1H), 7.46 (d, J=3.7 Hz, 2H), 7.41 (d, J=8.2 Hz, 2H), 6.18 (s, 1H), 5.11 (dt, J=13.2, 6.6 Hz, 1H), 4.64 (s, 1H), 4.60 (s, 2H), 4.58-4.47 (m, 3H), 4.36 (d, 1H), 3.91 (d, J=11.0 Hz, 1H), 3.88-3.77 (m, 9H), 2.77-2.74 (m, 2H), 2.50-2.43 (m, 5H), 2.35-2.18 (m, 6H), 2.11-2.04 (m, 1H), 1.70-1.60 (m, 6H), 1.58 (d, J=6.6 Hz, 6H), 1.44-1.35 (m, 4H), 1.05-0.99 (m, 12H). MS (m/z) [M+H]$^+$: 1096.2.

Example 55: Synthesis of XF034-164A

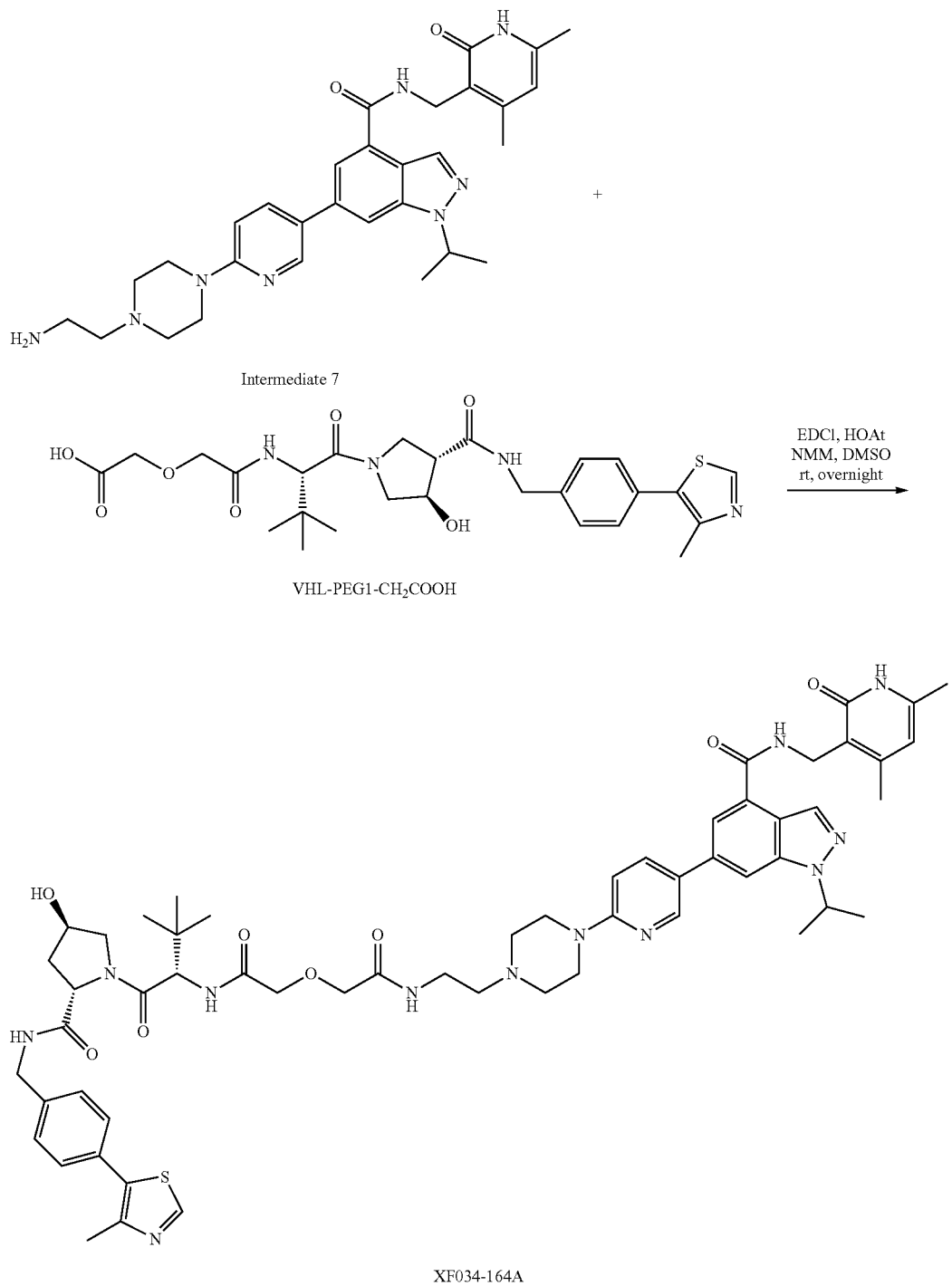

Intermediate 7 (10 mg, 0.02 mmol), HOAt (3.7 mg, 0.03 mmol), and VHL-PEG1-CH₂COOH (10 mg, 0.02 mmol) were dissolved in DMSO (1.0 mL). To the solution were added NMM (5.3 μL, 0.06 mmol), and EDCI (4.3 mg, 0.03 mmol) successively at room temperature. After being stirred overnight at room temperature, the mixture was purified by preparative HPLC (10%-100% methanol/0.1% TFA in H₂O) to afford XF034-164A as white solid in TFA salt form (14 mg, 72%). $^1$H NMR (600 MHz, CD₃OD) δ 9.00 (s, 1H), 8.56 (d, J=2.6 Hz, 1H), 8.37 (s, 1H), 8.17 (dd, J=9.3, 2.5 Hz, 1H), 7.96 (s, 1H), 7.78 (s, 1H), 7.46-7.38 (m, 4H), 7.15 (d, J=9.2 Hz, 1H), 6.21 (s, 1H), 5.11-5.06 (m, 1H), 4.71 (s, 1H), 4.62-4.53 (m, 4H), 4.53-4.43 (m, 2H), 4.43-4.33 (m, 2H), 4.23-4.10 (m, 5H), 3.90 (d, J=11.1 Hz, 2H), 3.84-3.79 (m, 2H), 3.76-3.68 (m, 2H), 3.64-3.49 (m, 3H), 3.42 (t, J=5.7 Hz, 2H), 2.47-2.42 (m, 6H), 2.29-2.21 (m, 4H), 2.13-2.05 (m, 1H), 1.57 (d, J=6.5 Hz, 6H), 1.06 (s, 9H).

Example 56: Synthesis of XF034-165A

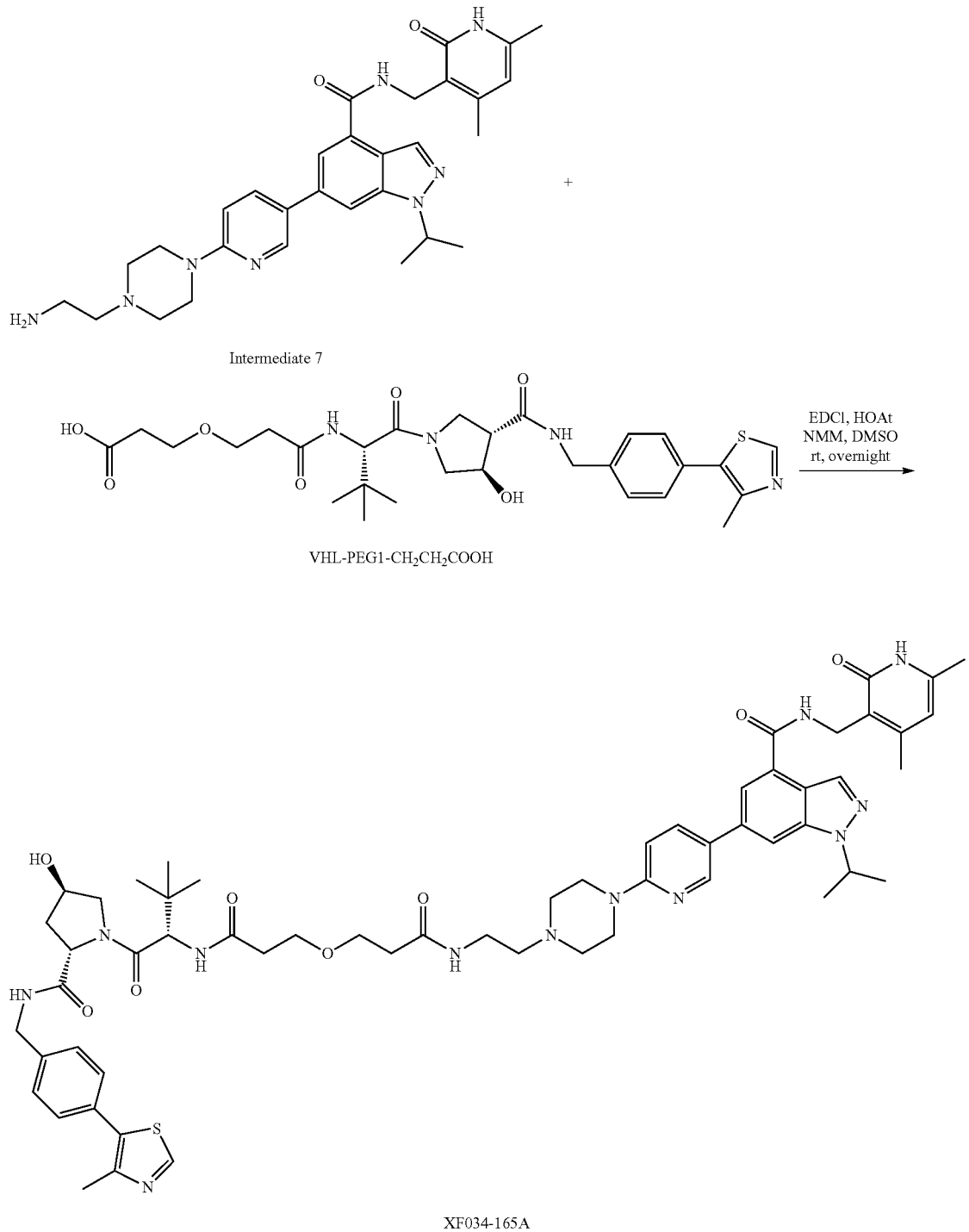

XF034-165A was synthesized according to the procedures for preparing XF034-164A from intermediate 7 (10 mg, 0.02 mmol), HOAt (3.7 mg, 0.03 mmol), VHL-PEG1-CH₂CH₂COOH (10.6 mg, 0.02 mmol), NMM (5.3 µL, 0.06 mmol), EDCI (4.3 mg, 0.03 mmol), and DMSO (1.0 mL). XF034-165A was obtained as white solid in TFA salt form (20 mg, 98%). $^1$H NMR (600 MHz, CD$_3$OD) δ 9.04 (s, 1H), 8.55 (d, J=2.4 Hz, 1H), 8.37 (s, 1H), 8.20 (dd, J=8.8, 2.5 Hz, 1H), 7.97 (s, 1H), 7.78 (s, 1H), 7.46-7.39 (m, 4H), 7.19 (d, J=9.1 Hz, 1H), 6.22 (s, 1H), 5.12-5.05 (m, 1H), 4.64 (s, 1H), 4.58 (s, 4H), 4.53-4.49 (m, 2H), 4.38 (d, J=15.3 Hz, 2H), 3.90 (d, J=10.9 Hz, 2H), 3.81 (dd, J=10.9, 3.7 Hz, 2H), 3.75-3.69 (m, 4H), 3.65 (t, J=5.2 Hz, 4H), 3.57 (s, 2H), 3.38 (t, J=5.7 Hz, 2H), 2.62-2.42 (m, 10H), 2.27 (s, 4H), 2.12-2.03 (m, 1H), 1.57 (d, J=6.5 Hz, 6H), 1.03 (d, J=10.3 Hz, 9H).

Example 57: Synthesis of XF034-166A

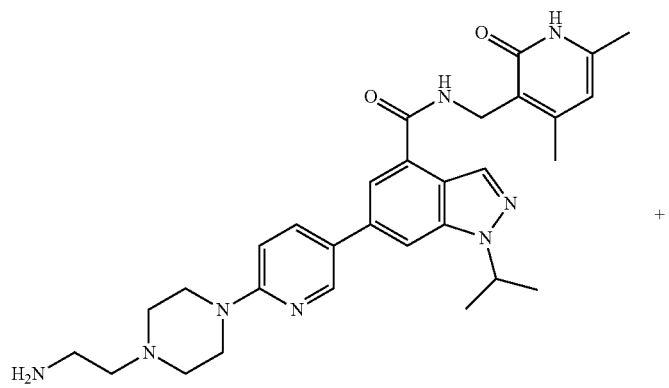

Intermediate 7

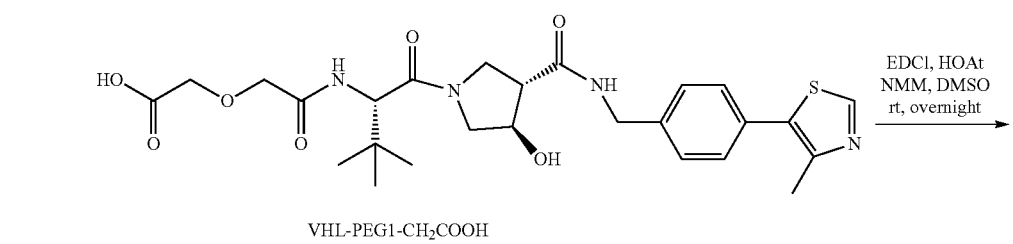

VHL-PEG1-CH₂COOH

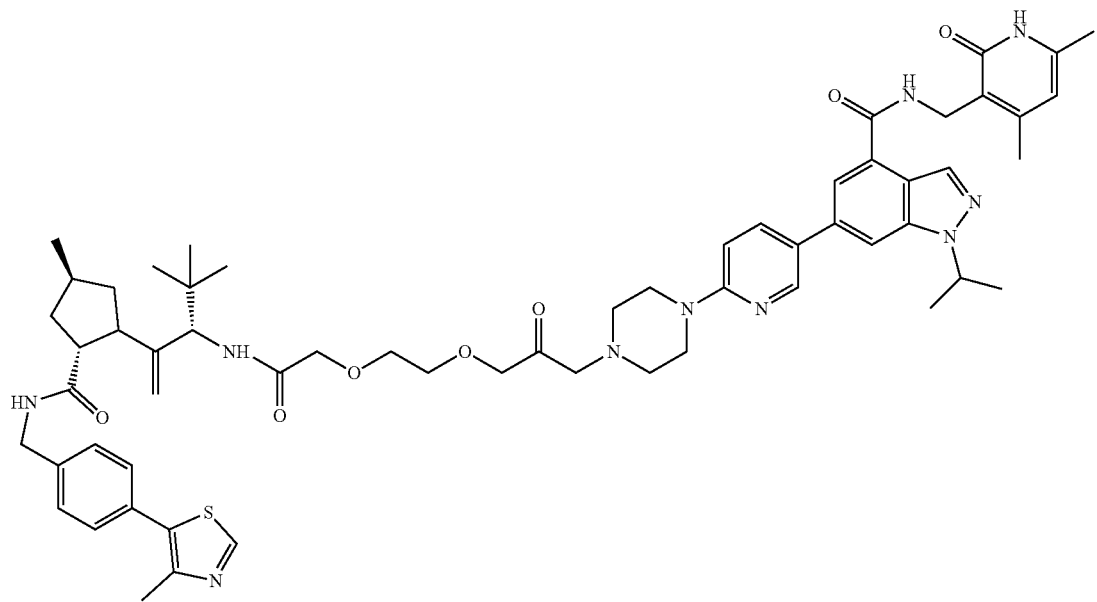

XF034-166A

XF034-166A was synthesized according to the procedures for preparing XF034-164A from intermediate 7 (10 mg, 0.02 mmol), HOAt (3.7 mg, 0.03 mmol), VHL-PEG2-CH₂COOH (10.9 mg, 0.02 mmol), NMM (5.3 µL, 0.06 mmol), EDCI (4.3 mg, 0.03 mmol), and DMSO (1.0 mL). XF034-166A was obtained as white solid in TFA salt form (16 mg, 77%). $^1$H NMR (600 MHz, CD$_3$OD) δ 9.02 (s, 1H), 8.55 (d, J=2.6 Hz, 1H), 8.37 (s, 1H), 8.17 (dd, J=9.1, 2.5 Hz, 1H), 7.96 (s, 1H), 7.81-7.75 (m, 1H), 7.73 (d, J=9.3 Hz, 1H), 7.48-7.41 (m, 3H), 7.15 (d, J=9.0 Hz, 1H), 6.21 (s, 1H), 5.08 (p, J=6.7 Hz, 1H), 4.71 (s, 1H), 4.58 (d, J=7.2 Hz, 3H), 4.51 (s, 1H), 4.49-4.40 (m, 2H), 4.21-3.48 (m, 19H), 3.46-3.35 (m, 2H), 2.45 (d, J=9.4 Hz, 6H), 2.27 (s, 4H), 2.12-2.05 (m, 1H), 1.57 (d, J=6.6 Hz, 7H), 1.05 (s, 9H).

Example 58: Synthesis of XF034-167A

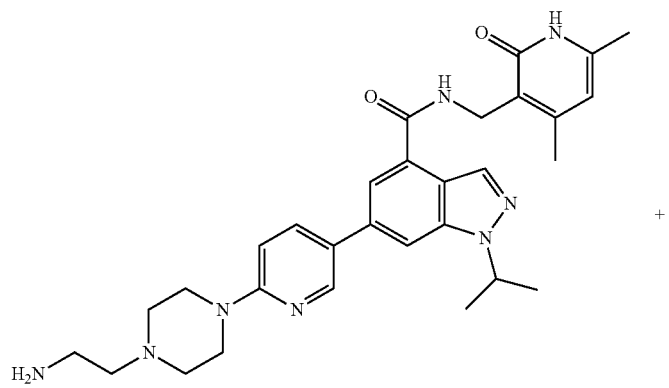

Intermediate 7

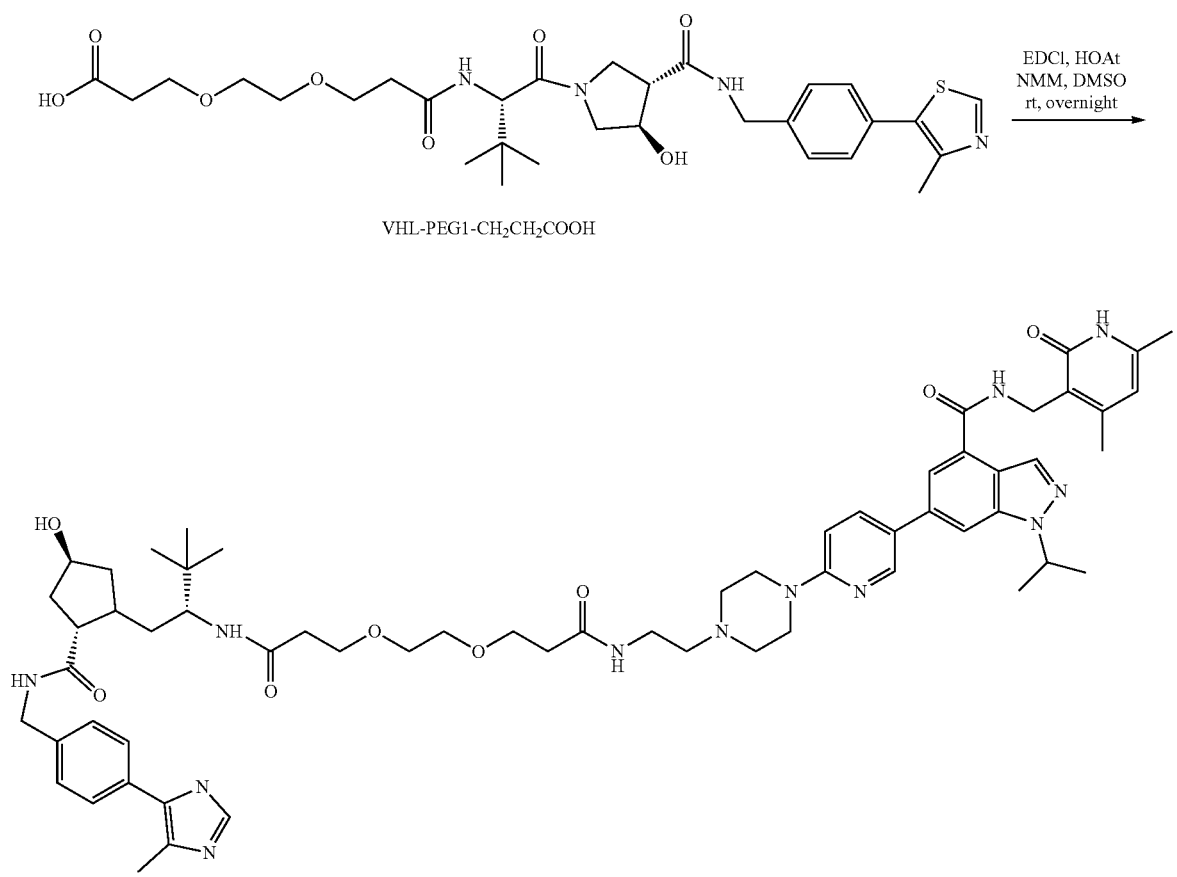

XF034-167A

XF034-167A was synthesized according to the procedures for preparing XF034-164A from intermediate 7 (10 mg, 0.02 mmol), HOAt (3.7 mg, 0.03 mmol), VHL-PEG2-CH$_2$CH$_2$COOH (11.4 mg, 0.02 mmol), NMM (5.3 µL, 0.06 mmol), EDCI (4.3 mg, 0.03 mmol), and DMSO (1.0 mL). XF034-167A was obtained as white solid in TFA salt form (16 mg, 74%). $^1$H NMR (600 MHz, CD$_3$OD) δ 8.96 (s, 1H), 8.58 (s, 1H), 8.37 (s, 1H), 8.14 (dt, J=8.9, 1.4 Hz, 1H), 7.99-7.93 (m, 1H), 7.78 (q, J=1.5 Hz, 1H), 7.48-7.40 (m, 4H), 7.13 (d, J=9.0 Hz, 1H), 6.17 (s, 1H), 5.08 (t, J=6.7 Hz, 1H), 4.64 (d, J=7.6 Hz, 1H), 4.60-4.44 (m, 5H), 4.35 (d, J=15.5 Hz, 1H), 3.88 (d, J=10.7 Hz, 2H), 3.82-3.51 (m, 18H), 3.37 (t, J=5.6 Hz, 2H), 2.56 (q, J=5.8 Hz, 2H), 2.53-2.48 (m, 2H), 2.45 (ddd, J=11.8, 2.8, 1.1 Hz, 6H), 2.29-2.19 (m, 4H), 2.07 (ddd, J=13.4, 9.2, 4.6 Hz, 1H), 1.57 (d, J=7.1 Hz, 6H), 1.03-1.00 (m, 9H).

Example 59: Synthesis of XF034-168A

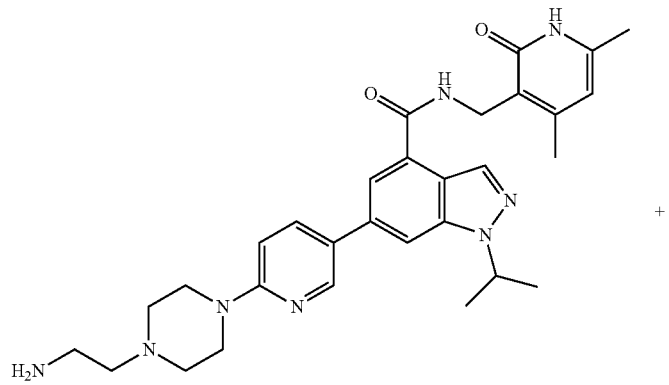

Intermediate 7

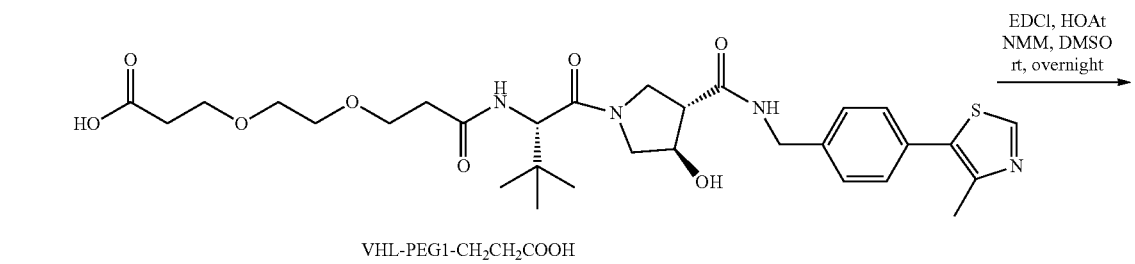

VHL-PEG1-CH₂CH₂COOH

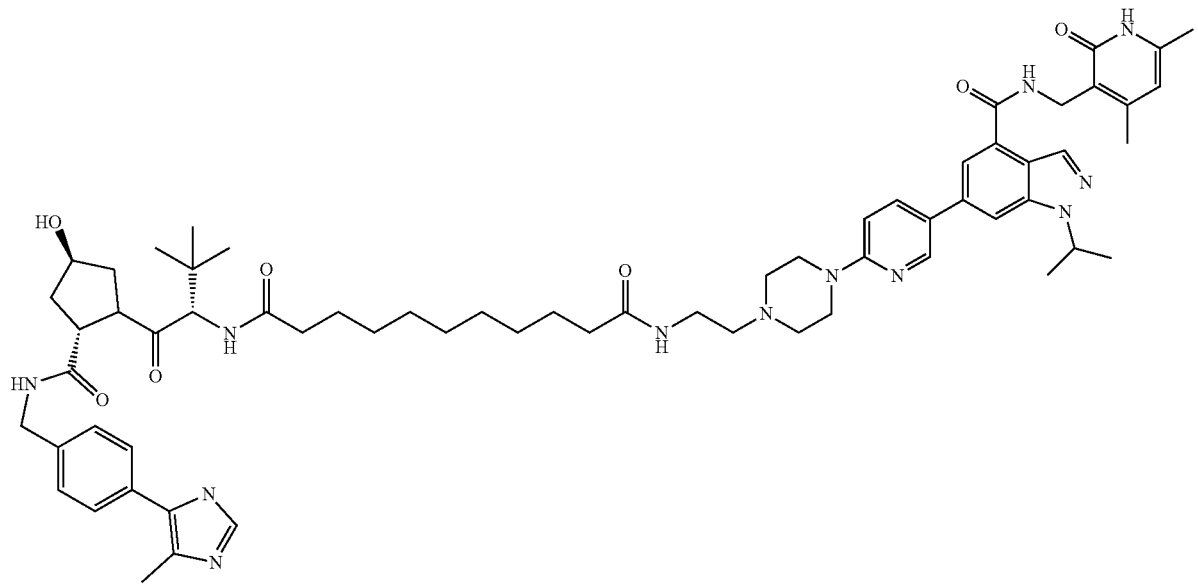

XF034-168A

XF034-168A was synthesized according to the procedures for preparing XF034-164A from intermediate 7 (10 mg, 0.02 mmol), HOAt (3.7 mg, 0.03 mmol), VHL-PEG3-CH₂CH₂COOH (12.2 mg, 0.02 mmol), NMM (5.3 μL, 0.05 mmol), EDCI (4.3 mg, 0.03 mmol), and DMSO (1.0 mL). XF034-168A was obtained as white solid in TFA salt form (13 mg, 58%). $^1$H NMR (600 MHz, CD$_3$OD) δ 8.96 (s, 1H), 8.58 (d, J=2.5 Hz, 1H), 8.37 (s, 1H), 8.14 (dd, J=9.1, 2.6 Hz, 1H), 7.95 (s, 1H), 7.82-7.74 (m, 1H), 7.43 (ddd, J=32.4, 21.2, 7.9 Hz, 4H), 7.13 (d, J=8.9 Hz, 1H), 6.17 (s, 1H), 5.11-5.02 (m, 1H), 4.64 (d, J=7.9 Hz, 1H), 4.60-4.46 (m, 5H), 4.36 (d, J=15.6 Hz, 1H), 3.88 (d, J=10.5 Hz, 2H), 3.83-3.49 (m, 22H), 3.37 (t, J=5.7 Hz, 2H), 2.62-2.40 (m, 10H), 2.28-2.17 (m, 4H), 2.10-2.03 (m, 1H), 1.57 (d, J=6.5 Hz, 6H), 1.03 (d, J=6.9 Hz, 9H).

Example 60: Synthesis of XY019-041

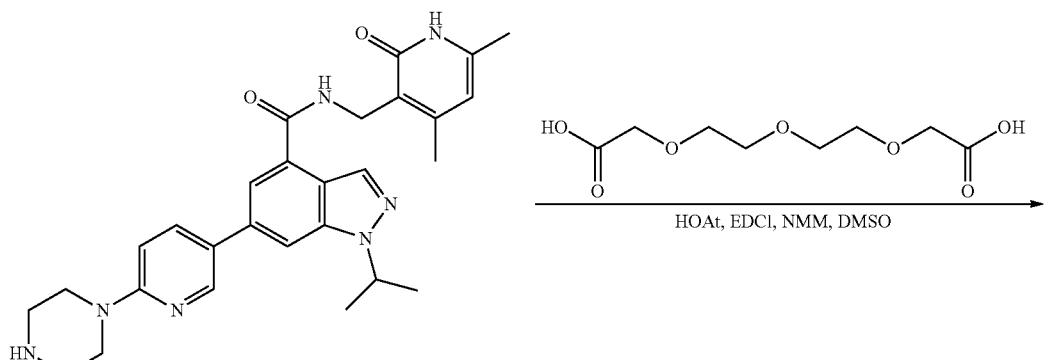
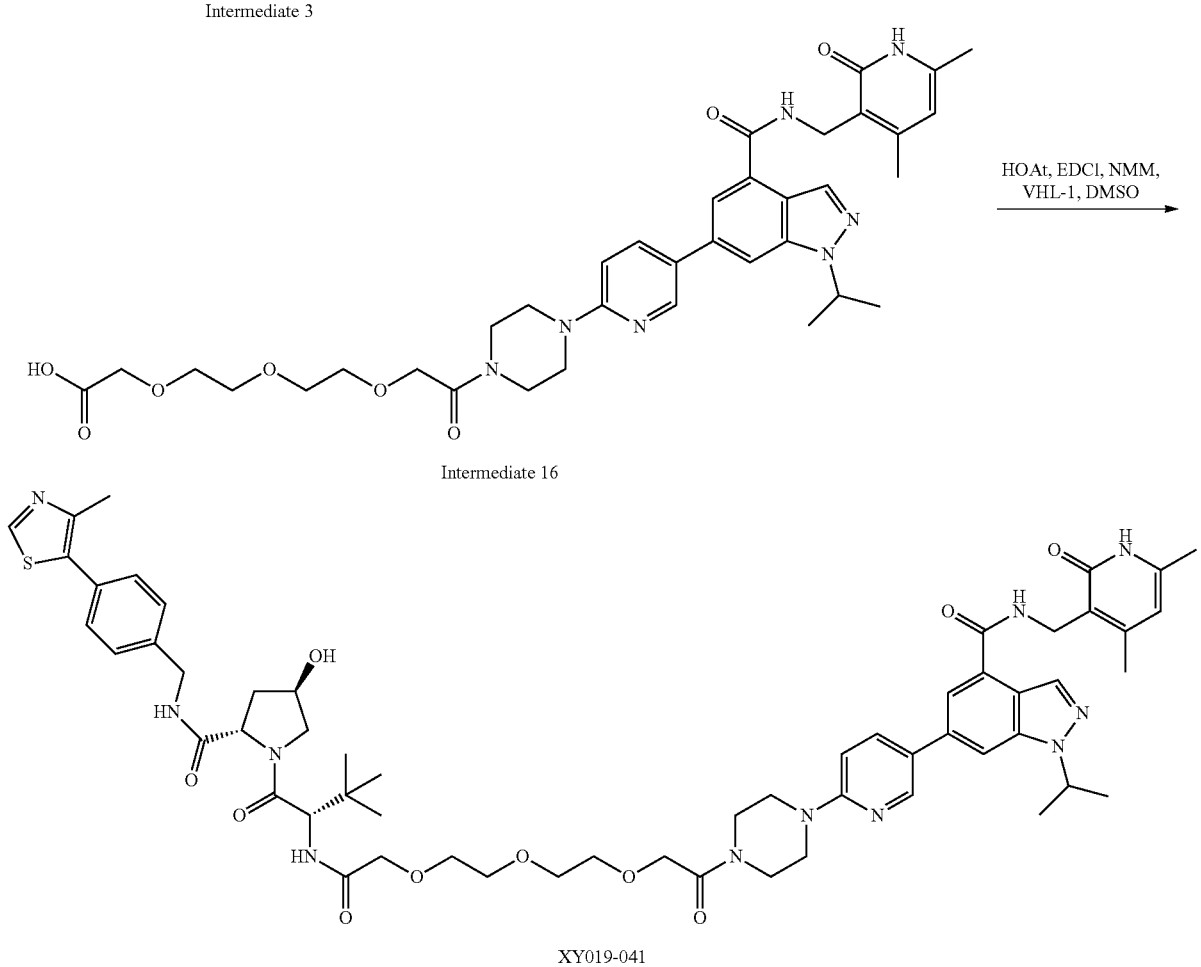

To the solution of intermediate 3 (80 mg, 0.16 mmol) in DMSO (5.0 mL) were added NMM (48 mg, 0.48 mmol), 2,2'-((oxybis(ethane-2,1-diyl))bis(oxy)) diacetic acid (76 mg, 0.24 mmol), HOAt (33 mg, 0.24 mmol), and EDCI (46 mg, 0.24 mmol). The mixture was allowed to stir at room temperature overnight. The progress of the reaction was monitored by LC-MS. Upon completion, the mixture was concentrated under vacuum and purified by preparative HPLC to afford intermediate 16 (76 mg, 67%). MS (m/z) [M+H]$^+$: 704.3. To the solution of intermediate 16 (50 mg, 0.07 mmol) in DMSO (2.0 mL) were added NMM (21 mg, 0.21 mmol), VHL-1 (40 mg, 0.09 mmol), HOAt (15 mg, 0.11 mmol), and EDCI (20 mg, 0.11 mmol). The resulting mixture was allowed to stir at room temperature overnight. The progress of the reaction was monitored by LC-MS. Upon completion, the mixture was concentrated under vacuum and purified by preparative HPLC to afford XY019-041 (40 mg, 50%) as solid. $^1$H NMR (600 MHz, CD$_3$OD) δ 9.08 (s, 1H), 8.48 (dd, J=9.5, 1.8 Hz, 1H), 8.39 (s, 1H), 8.35 (s, 1H), 8.07 (s, 1H), 7.79 (s, 1H), 7.50-7.38 (m, 5H), 6.21 (s, 1H), 5.15-5.06 (m, 1H), 4.66 (s, 1H), 4.57 (d, J=12.7 Hz, 2H), 4.56-4.44 (m, 2H), 4.38-4.23 (m, 2H), 4.04 (d, J=15.8 Hz, 1H), 3.94 (d, J=15.7 Hz, 1H), 3.91-3.60 (m, 20H), 2.48

(s, 3H), 2.44 (s, 3H), 2.30-2.19 (m, 4H), 2.10-2.04 (m, 1H), 1.57 (d, 6H), 1.04 (s, 9H). MS (m/z) [M+H]⁺: 1116.1.

Example 61: Synthesis of XF034-169A

XF034-169A was obtained as white solid in TFA salt form (20 mg, 90%). $^1$H NMR (600 MHz, CD$_3$OD) δ 9.07 (s, 1H), 8.57 (d, J=2.5 Hz, 1H), 8.37 (s, 1H), 8.22 (dd, J=9.0, 2.5 Hz, 1H), 7.98 (s, 1H), 7.79 (s, 1H), 7.44 (ddd, J=33.1, 20.3, 7.9

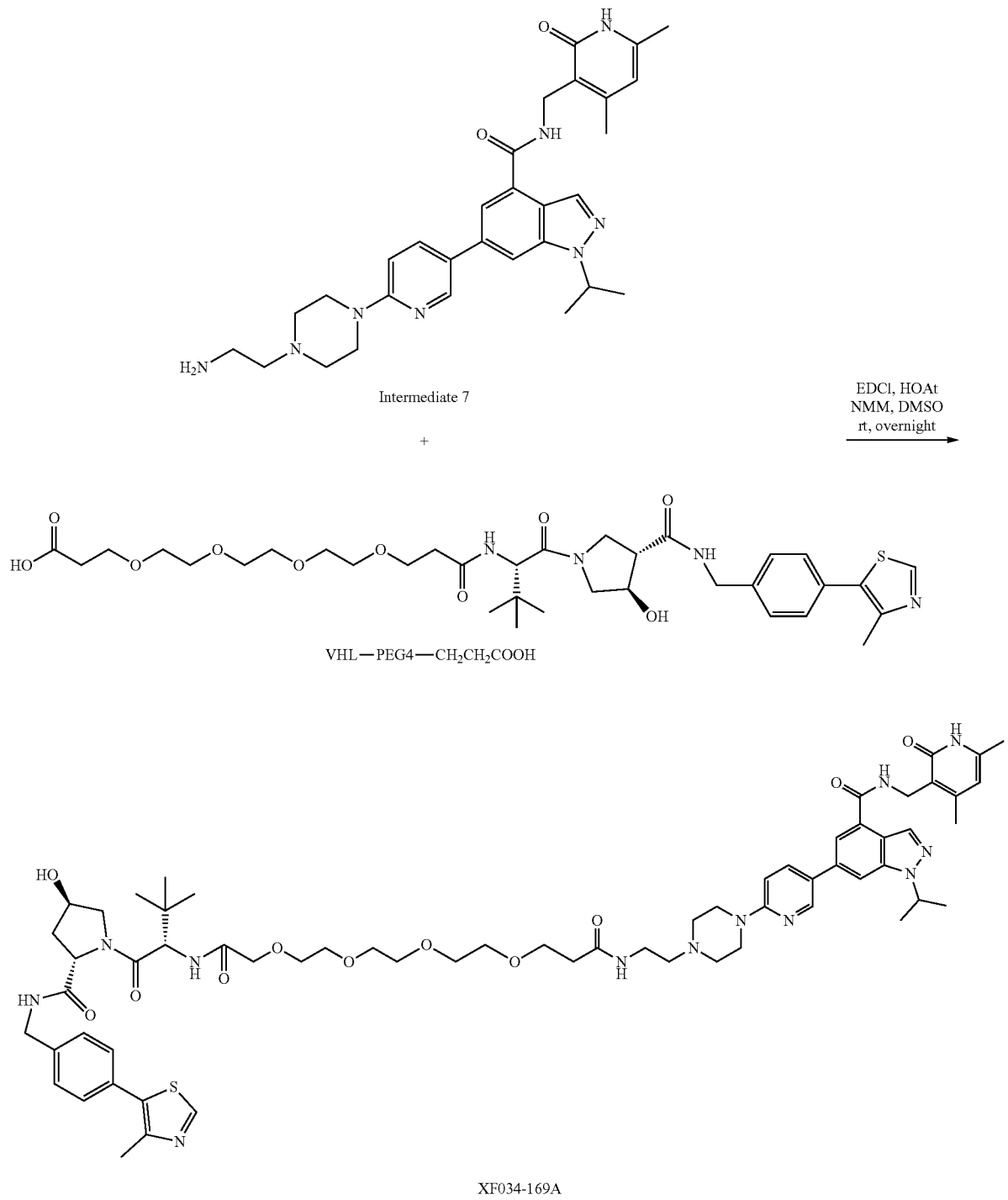

XF034-169A

XF034-169A was synthesized according to the procedures for preparing XF034-164A from intermediate 7 (10 mg, 0.02 mmol), HOAt (3.7 mg, 0.03 mmol), VHL-PEG4-CH$_2$CH$_2$COOH (13 mg, 0.02 mmol), NMM (5.3 μL, 0.06 mmol), EDCI (4.3 mg, 0.03 mmol), and DMSO (1.0 mL).

Hz, 4H), 7.20 (d, J=9.0 Hz, 1H), 6.22 (s, 1H), 5.17-5.07 (m, 1H), 4.66-4.45 (m, 6H), 4.36 (d, J=15.5 Hz, 1H), 3.88 (d, J=10.8 Hz, 2H), 3.83-3.50 (m, 25H), 3.39 (t, J=5.7 Hz, 2H), 2.60-2.42 (m, 10H), 2.27 (s, 4H), 2.25-2.19 (m, 1H), 2.07 (td, J=12.5, 10.8, 4.4 Hz, 1H), 1.57 (d, J=6.6 Hz, 6H), 1.02 (s, 9H).

Example 62: Synthesis of XF034-170A
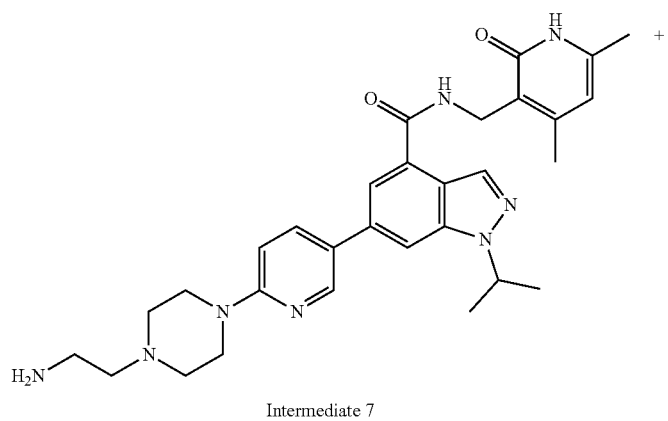
Intermediate 7
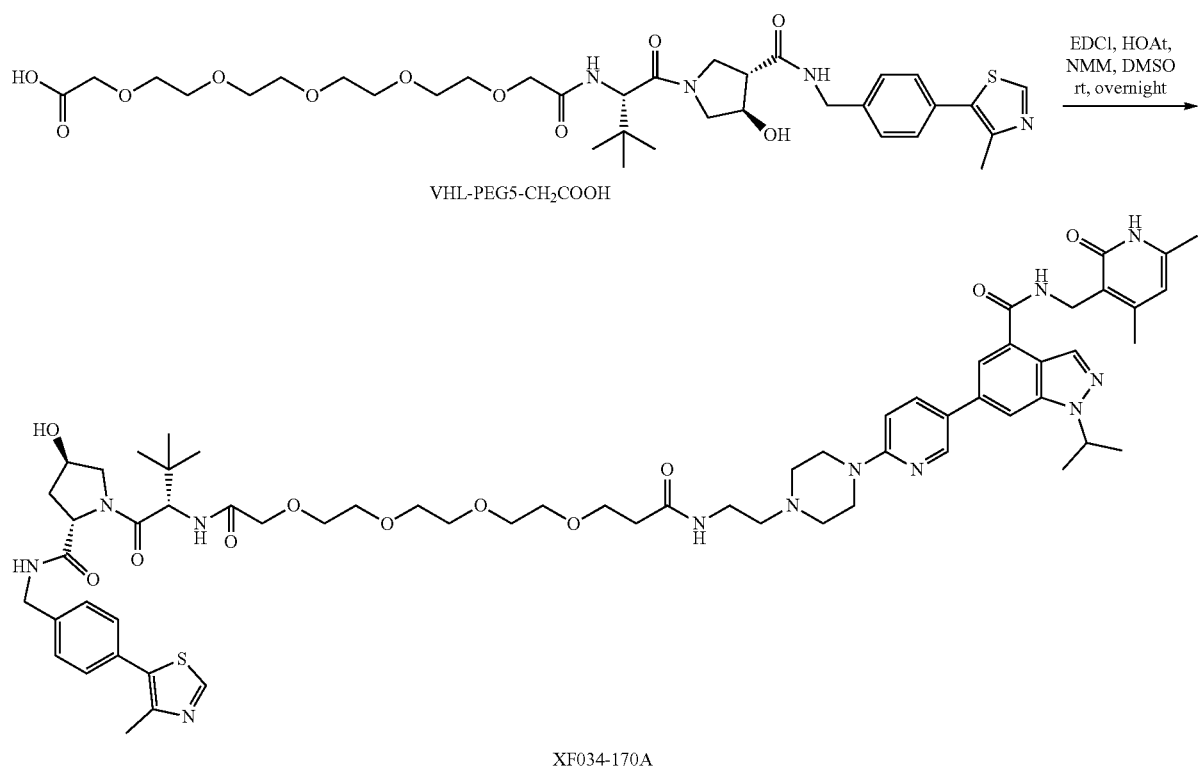
XF034-170A was synthesized according to the procedures for preparing XF034-164A from intermediate 7 (10 mg, 0.02 mmol), HOAt (3.7 mg, 0.03 mmol), VHL-PEG5-CH₂COOH (13 mg, 0.02 mmol), NMM (5.3 µL, 0.06 mmol), EDCI (4.3 mg, 0.03 mmol), and DMSO (1.0 mL). XF034-170A was obtained as white solid in TFA salt form (17 mg, 76%). ¹H NMR (600 MHz, CD₃OD) δ 9.04 (s, 1H), 8.56 (s, 1H), 8.37 (s, 1H), 8.20 (d, J=9.1 Hz, 1H), 7.98 (s, 1H), 7.78 (s, 1H), 7.50-7.35 (m, 4H), 7.18 (d, J=9.1 Hz, 1H), 6.22 (s, 1H), 5.08 (s, 1H), 4.58 (t, J=46.0 Hz, 6H), 4.37 (d, J=15.6 Hz, 1H), 4.18-3.50 (m, 32H), 3.42 (s, 2H), 2.53-2.35 (m, 6H), 2.25 (d, J=22.7 Hz, 4H), 2.08 (s, 1H), 1.57 (d, J=6.8 Hz, 6H), 1.03 (d, J=15.1 Hz, 9H).

Example 63: Synthesis of XF034-171A

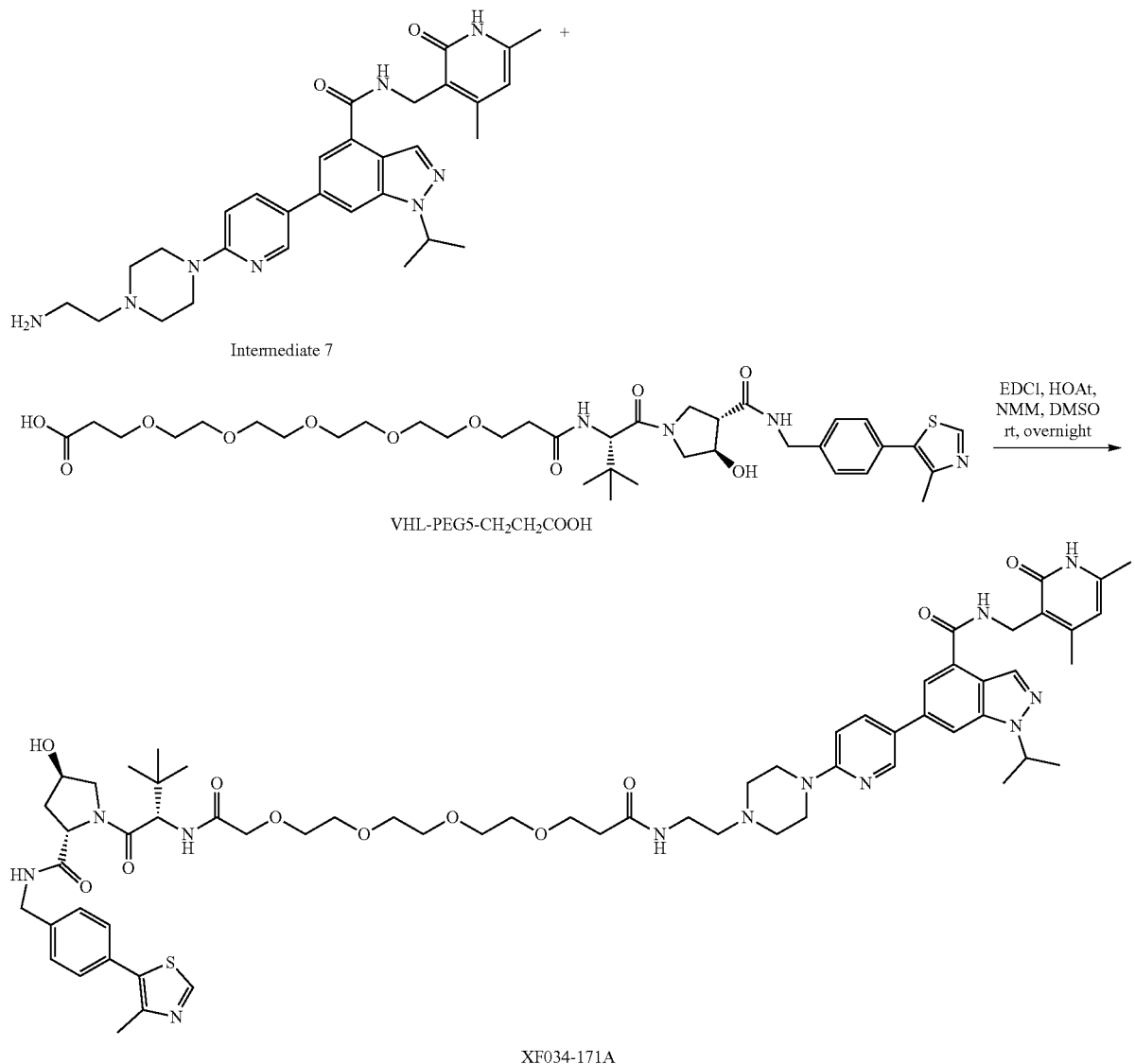

XF034-171A was synthesized according to the procedures for preparing XF034-164A from intermediate 3 (10 mg, 0.02 mmol), HOAt (3.7 mg, 0.03 mmol), VHL-PEG5-CH₂CH₂COOH (14 mg, 0.018 mmol), NMM (5.3 μL, 0.06 mmol), EDCI (4.3 mg, 0.03 mmol), and DMSO (1.0 mL). XF034-171A was obtained as white solid in TFA salt form (18 mg, 77%). $^1$H NMR (600 MHz, CD$_3$OD) δ 9.07 (s, 1H), 8.57 (d, J=2.6 Hz, 1H), 8.37 (s, 2H), 8.23 (dd, J=9.0, 2.5 Hz, 1H), 7.99 (s, 1H), 7.79 (s, 1H), 7.44 (dt, J=34.0, 9.0 Hz, 6H), 7.22 (d, J=9.0 Hz, 2H), 6.22 (s, 1H), 5.12-5.03 (m, 1H), 4.63 (s, 1H), 4.61-4.46 (m, 5H), 4.35 (d, J=15.5 Hz, 1H), 4.14-3.46 (m, 28H), 3.39 (t, J=5.6 Hz, 2H), 2.60-2.42 (m, 10H), 2.29-2.17 (m, 4H), 2.07 (td, J=13.0, 11.1, 4.4 Hz, 1H), 1.57 (d, J=6.5 Hz, 6H), 1.03 (d, J=7.3 Hz, 9H).

Example 64: Synthesis of CZ40-10

CZ40-10 was synthesized according to the procedures for preparing CZ40-09 by reaction with NH₂-PEG8-CH₂CH₂COO$^t$Bu. $^1$H NMR (600 MHz, CD$_3$OD) δ 9.07 (s, 1H), 8.52 (d, J=2.5 Hz, 1H), 8.37 (s, 1H), 8.20 (dd, J=9.0, 2.5 Hz, 1H), 7.97 (s, 1H), 7.77 (d, J=1.3 Hz, 1H), 7.46 (d, J=8.1 Hz, 2H), 7.40-7.38 (m, 2H), 7.17 (d, J=9.1 Hz, 1H), 6.19 (s, 1H), 5.09-5.05 (m, 1H), 4.64 (s, 1H), 4.58-4.49 (m, 5H), 4.35 (d, J=15.5 Hz, 1H), 3.88 (d, J=11.0 Hz, 2H), 3.79 (dd, J=10.9, 3.9 Hz, 2H), 3.69 (qdd, J=9.7, 6.9, 5.1 Hz, 4H), 3.63-3.53 (m, 36H), 3.40 (t, J=5.3 Hz, 2H), 2.83 (t, J=6.8 Hz, 2H), 2.56 (ddd, J=15.0, 7.5, 5.2 Hz, 1H), 2.48-2.44 (m, 4H), 2.42 (s, 3H), 2.25-2.20 (m, 4H), 2.07 (ddd, J=13.3, 9.2, 4.5 Hz, 1H), 1.55 (d, J=6.6 Hz, 6H), 1.03 (s, 9H). ESI m/z=1407.73 [M+H]$^+$.

Example 65: Synthesis of CZ40-09

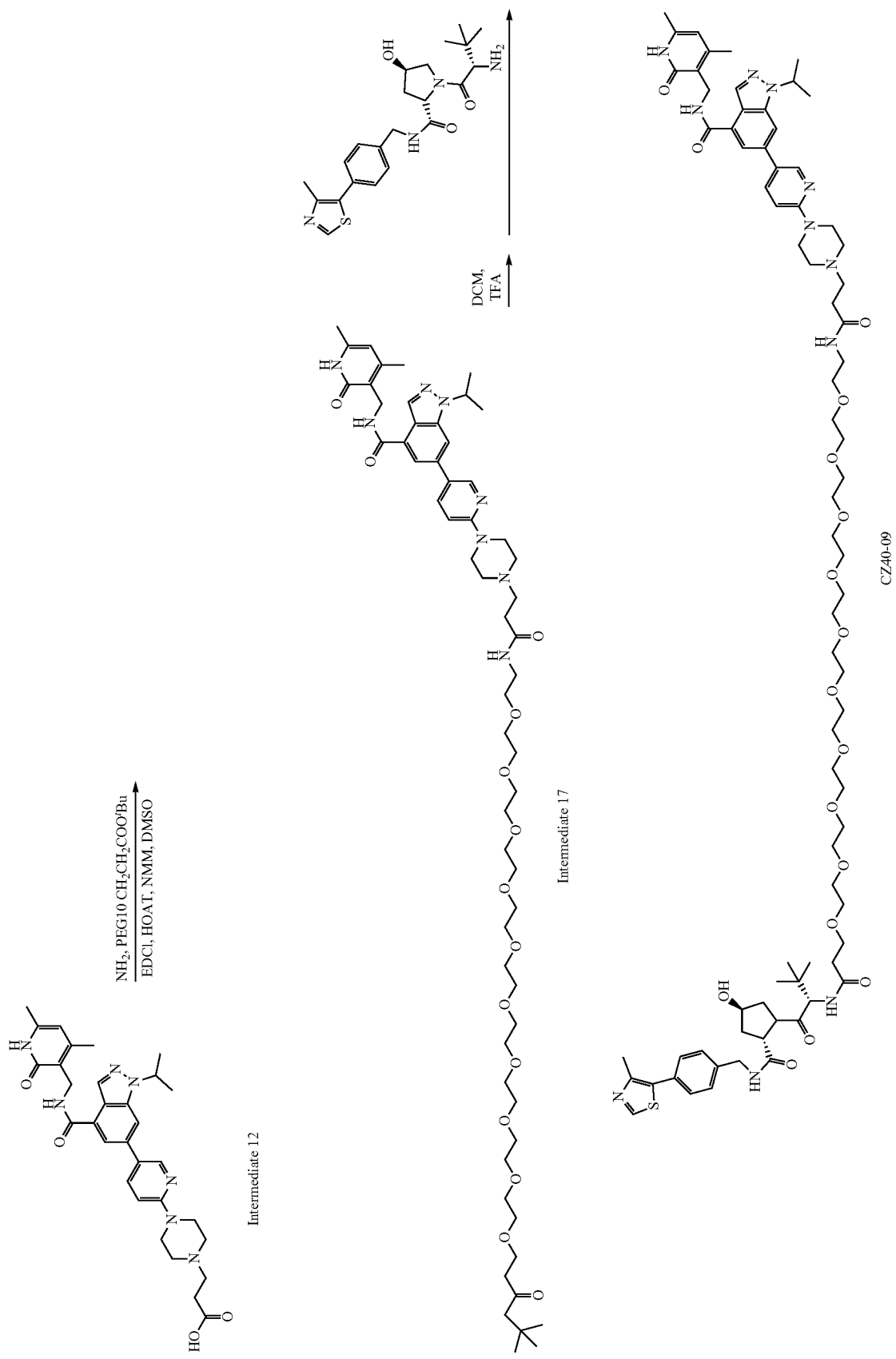

To the solution of NH$_2$-PEG10-CH$_2$CH$_2$COO$^t$Bu (58 mg, 0.10 mmol) and intermediate 12 (69 mg, 0.12 mmol) in DMSO (1.0 mL) were added HOAt (21 mg, 0.15 mmol), EDCI (29 mg, 0.15 mmol), and NMM (44 μL, 0.40 mmol) at room temperature. After being stirred overnight, the reaction mixture was purified by prepared HPLC to give intermediate 17 (110 mg, 99%) as yellow oil.

Intermediate 17 (110 mg, 0.10 mmol) was dissolved in dichloromethane (2.0 mL) and treated with trifluoroacetic acid (2.0 mL) at room temperature for 2 h. The mixture was concentrated and dried. The residue was dissolved in DMSO (1.0 mL). (2S,4R)-1-((S)-2-amino-3,3-dimethylbutanoyl)-4-hydroxy-N-(4-(4-methylthiazol-5-yl)benzyl) pyrrolidine-2-carboxamide (43 mg, 0.10 mmol), HOAt (21 mg, 0.15 mmol), EDCI (29 mg, 0.15 mmol), and NMM (88 μL, 0.80 mmol) were added to the solution subsequently at room temperature. After being stirred overnight, the reaction mixture was purified by prepared HPLC to afford CZ40-09 (120 mg, 80%) as white solid in TFA salt form. $^1$H NMR (600 MHz, CD$_3$OD) δ 8.98 (s, 1H), 8.54 (d, J=2.5 Hz, 1H), 8.37 (s, 1H), 8.14 (dd, J=9.0, 2.5 Hz, 1H), 7.95 (s, 1H), 7.77 (d, J=1.3 Hz, 1H), 7.46 (d, J=8.1 Hz, 2H), 7.40-7.38 (m, 2H), 7.11 (d, J=9.1 Hz, 1H), 6.16 (s, 1H), 5.09-5.05 (m, 1H), 4.64 (s, 1H), 4.58-4.49 (m, 5H), 4.34 (d, J=15.5 Hz, 1H), 3.88 (d, J=11.0 Hz, 2H), 3.79 (dd, J=10.9, 3.9 Hz, 2H), 3.69 (qdd, J=9.7, 6.9, 5.1 Hz, 4H), 3.63-3.53 (m, 44H), 3.41 (t, J=5.3 Hz, 2H), 2.82 (t, J=6.8 Hz, 2H), 2.56 (ddd, J=15.0, 7.5, 5.2 Hz, 1H), 2.48-2.44 (m, 4H), 2.41 (s, 3H), 2.24-2.18 (m, 4H), 2.07 (ddd, J=13.3, 9.2, 4.5 Hz, 1H), 1.56 (d, J=6.6 Hz, 6H), 1.03 (s, 9H). ESI m/z=1496.85 [M+H]$^+$.

Example 66: Synthesis of CZ40-11

CZ40-11 was synthesized according to the procedures for preparing CZ40-09 by reaction with NH$_2$-PEG12-CH$_2$CH$_2$COO$^t$Bu. $^1$H NMR (600 MHz, CD$_3$OD) δ 9.01 (s, 1H), 8.54 (d, J=2.5 Hz, 1H), 8.37 (s, 1H), 8.17 (dd, J=9.0, 2.5 Hz, 1H), 7.97 (s, 1H), 7.77 (d, J=1.3 Hz, 1H), 7.46 (d, J=8.1 Hz, 2H), 7.40-7.38 (m, 2H), 7.15 (d, J=9.1 Hz, 1H), 6.17 (s, 1H), 5.09-5.05 (m, 1H), 4.64 (s, 1H), 4.58-4.49 (m, 5H), 4.35 (d, J=15.5 Hz, 1H), 3.88 (d, J=11.0 Hz, 2H), 3.79 (dd, J=10.9, 3.9 Hz, 2H), 3.69 (qdd, J=9.7, 6.9, 5.1 Hz, 4H), 3.63-3.53 (m, 52H), 3.40 (t, J=5.3 Hz, 2H), 2.82 (t, J=6.8 Hz, 2H), 2.56 (ddd, J=15.0, 7.5, 5.2 Hz, 1H), 2.48-2.43 (m, 4H), 2.42 (s, 3H), 2.25-2.20 (m, 4H), 2.07 (ddd, J=13.3, 9.2, 4.5 Hz, 1H), 1.55 (d, J=6.6 Hz, 6H), 1.02 (s, 9H). ESI m/z=1583.83 [M+H]$^+$.

Example 67: Synthesis of XY019-077

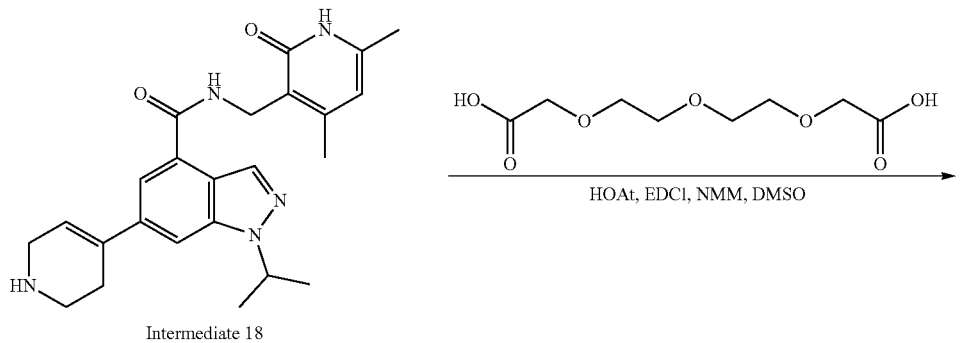

Intermediate 18

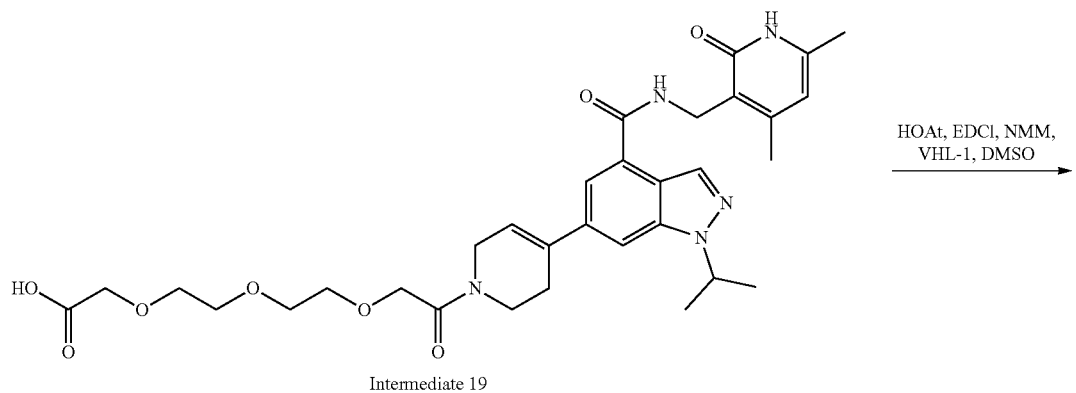

Intermediate 19

-continued
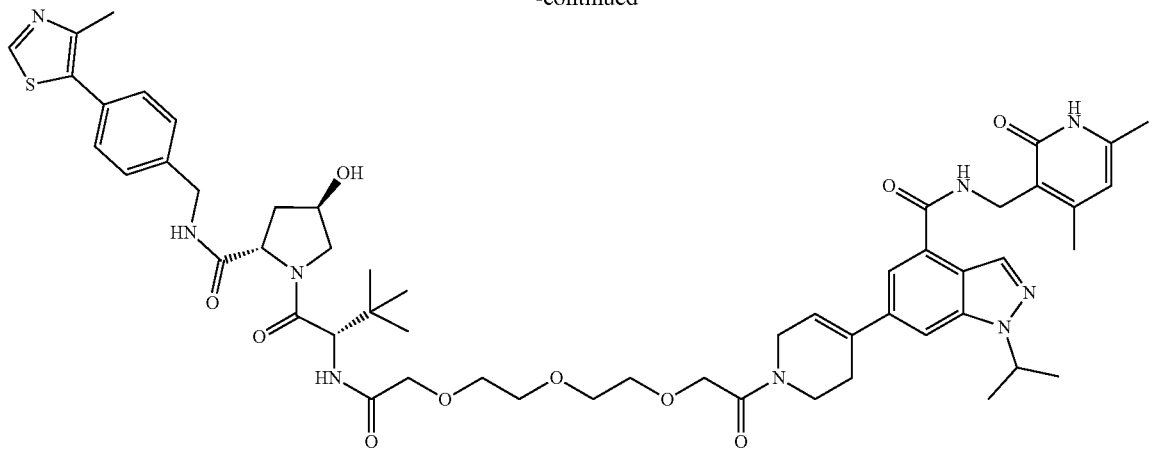
XY019-077
XY019-077 (20 mg, 43%) was synthesized according to the procedures for preparing XY019-041 from intermediate 18. $^1$H NMR (600 MHz, CD$_3$OD) δ 8.99 (s, 1H), 8.32 (s, 1H), 7.73 (s, 1H), 7.67 (d, J=6.3 Hz, 1H), 7.43 (d, J=7.3 Hz, 2H), 7.39 (d, J=8.0 Hz, 2H), 6.29 (d, J=21.0 Hz, 1H), 6.19 (s, 1H), 5.02 (dt, J=13.2, 6.5 Hz, 1H), 4.68 (s, 1H), 4.58-4.46 (m, 5H), 4.40-4.25 (m, 3H), 4.21 (s, 2H), 4.06-3.92 (m, 2H), 3.85 (d, J=11.4 Hz, 1H), 3.81-3.63 (m, 11H), 2.74-2.59 (m, 2H), 2.46 (s, 3H), 2.42 (s, 3H), 2.29-2.17 (m, 4H), 2.11-2.03 (m, 1H), 1.53 (d, J=6.6 Hz, 6H), 1.02 (s, 9H). MS (m/z) [M+H]$^+$: 1036.2.
Example 68: Synthesis of XY019-083

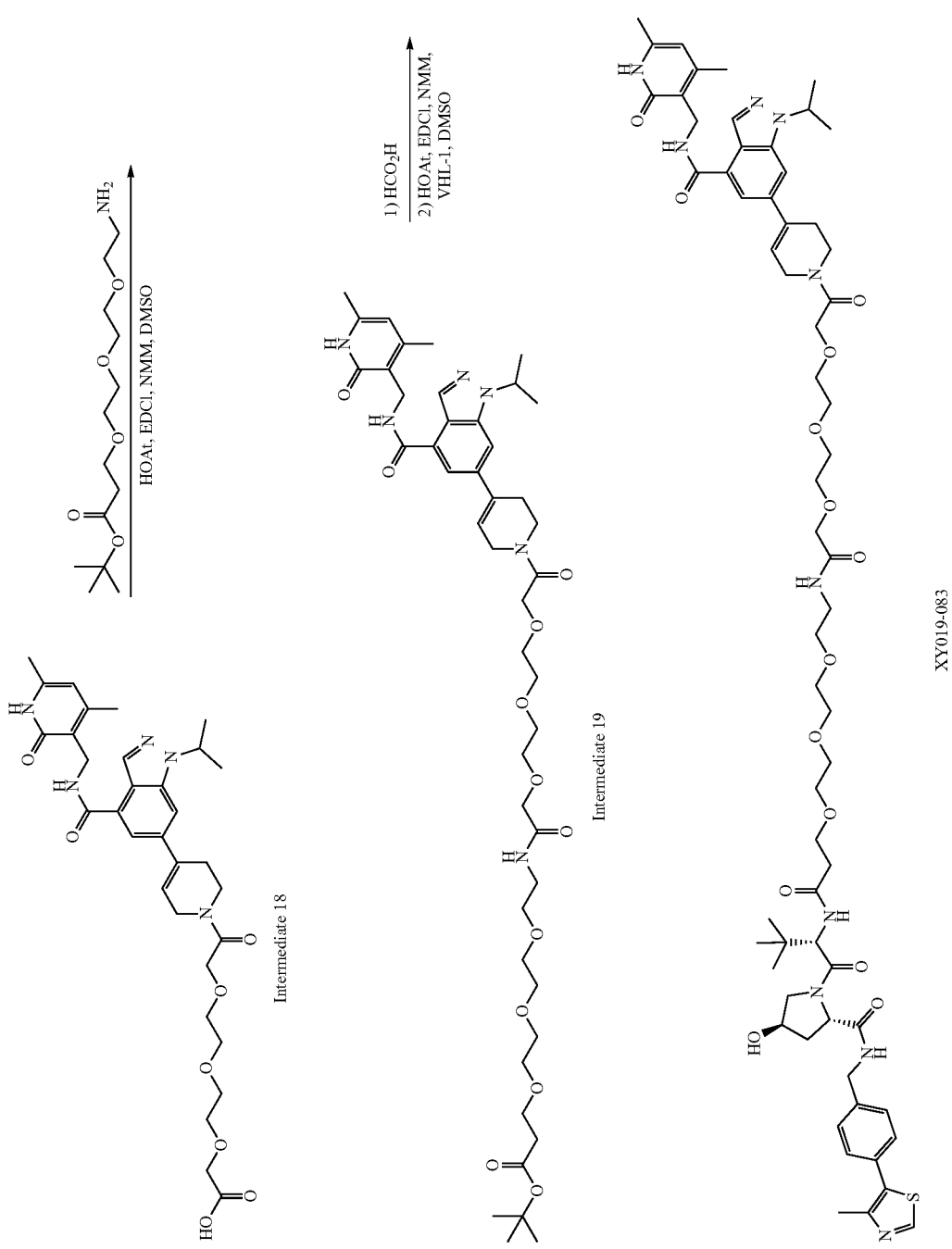

To the solution of intermediate 20 (22 mg, 0.03 mmol) in DMSO (3.0 mL) were added NMM (10 mg, 0.09 mmol), tert-butyl 3-(2-(2-(2-aminoethoxy) ethoxy) ethoxy) propanoate (13 mg, 0.04 mmol), HOAt (6.4 mg, 0.05 mmol), and EDCI (46 mg, 0.05 mmol). The mixture was allowed to stir at room temperature overnight. The progress of the reaction was monitored by LC-MS. Upon completion, the mixture was concentrated under vacuum and purified by preparative HPLC to afford intermediate 21 (21 mg, 70%). The solution of intermediate 21 (21 mg, 0.02 mmol) in formic acid (5.0 mL) was stirred overnight at room temperature. The progress of the reaction was monitored by LC-MS. Upon completion, the reaction was concentrated under vacuum and the resulting residue was dissolved in DMSO (2.0 mL). To the resulting solution were added VHL-1 (13 mg, 0.03 mmol), NMM (14 mg, 0.14 mmol), HOAt (4.6 mg, 0.03 mmol), and EDCI (6.5 mg, 0.03 mmol). The reaction mixture was allowed to stir at room temperature overnight. The progress of the reaction was monitored by LC-MS. Upon completion, the mixture was concentrated under vacuum and purified by preparative HPLC to afford XY019-083 (4.5 mg, 16%) as solid. $^1$H NMR (600 MHz, CD$_3$OD) δ 8.90 (s, 1H), 8.32 (s, 1H), 7.74 (s, 1H), 7.68 (s, 1H), 7.45 (d, J=8.1 Hz, 2H), 7.39 (d, J=8.0 Hz, 2H), 6.32 (d, J=21.1 Hz, 1H), 6.13 (s, 1H), 5.06-4.99 (m, 1H), 4.64 (d, J=8.9 Hz, 1H), 4.58-4.45 (m, 5H), 4.40-4.30 (m, 2H), 4.24 (s, 1H), 4.00-3.94 (m, 2H), 3.90-3.83 (m, 2H), 3.82-3.36 (m, 25H), 2.93-2.85 (m, 2H), 2.71 (d, J=45.0 Hz, 2H), 2.59-2.50 (m, 1H), 2.46 (s, 3H), 2.41 (s, 3H), 2.26-2.17 (m, 4H), 2.07 (d, J=8.8 Hz, 1H), 1.54 (d, J=6.5 Hz, 6H), 1.02 (s, 9H). MS (m/z) [M+H]$^+$: 1240.2.

Example 69: Synthesis of XY019-084

XY019-084 (20 mg, 49%) was synthesized according to the procedures for preparing XY019-083 from intermediate 16. $^1$H NMR (600 MHz, CD$_3$OD) δ 9.07 (s, 1H), 8.50 (d, J=9.4 Hz, 1H), 8.39 (s, 2H), 8.08 (s, 1H), 7.80 (s, 1H), 7.49 (d, J=9.5 Hz, 1H), 7.46 (d, J=8.0 Hz, 2H), 7.41 (d, J=8.0 Hz, 2H), 6.19 (s, 1H), 5.11 (dt, J=13.0, 6.5 Hz, 1H), 4.63 (s, 1H), 4.61-4.44 (m, 5H), 4.36 (s, 1H), 4.34 (s, 2H), 4.00 (s, 2H), 3.87 (M, 9H), 3.78 (dd, J=10.9, 3.5 Hz, 1H), 3.75-3.65 (m, 10H), 3.63-3.55 (m, 9H), 3.53 (t, J=5.5 Hz, 2H), 3.40 (t, J=5.3 Hz, 2H), 2.59-2.52 (m, 1H), 2.48 (s, 3H), 2.44 (s, 3H), 2.26 (s, 3H), 2.25-2.17 (m, 1H), 2.09-2.03 (m, 1H), 1.58 (d, J=6.6 Hz, 6H), 1.03 (s, 9H). HRMS (m/z) for C$_{67}$H$_{91}$N$_{12}$O$_{14}$S$^+$ [M+H]$^+$: calculated 1319.6493, found 1319.6483.

Example 70: Synthesis of XF034-172A

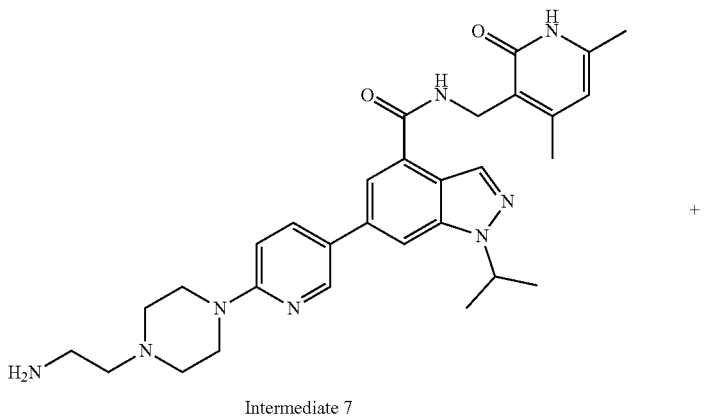

Intermediate 7

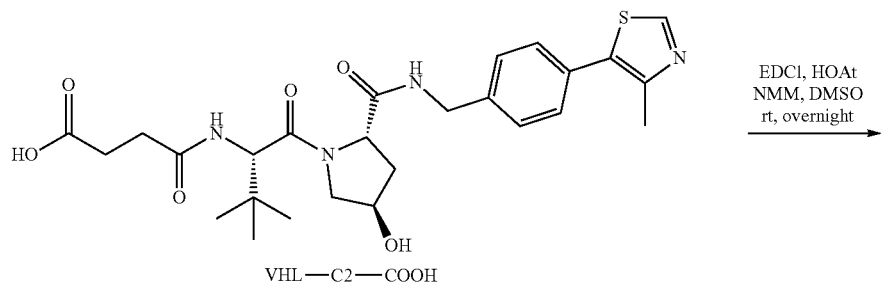

VHL—C2—COOH

EDCl, HOAt
NMM, DMSO
rt, overnight

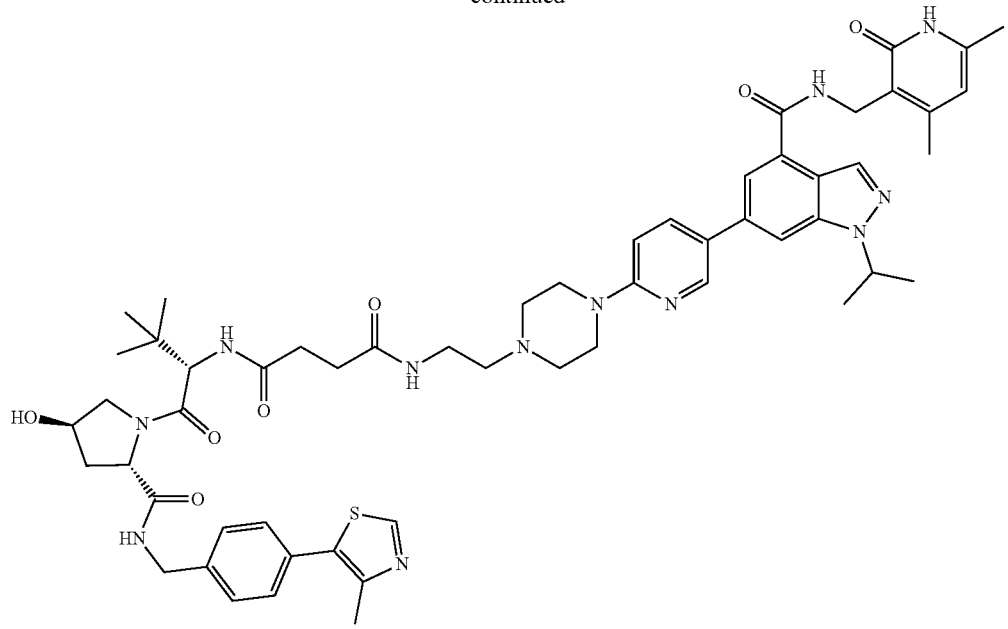

XF034-172A

XF034-172A was synthesized according to the procedures for preparing XF034-164A from intermediate 7 (10 mg, 0.02 mmol), HOAt (3.7 mg, 0.03 mmol), VHL-C2-COOH (9.8 mg, 0.02 mmol), NMM (5.3 μL, 0.06 mmol), EDCI (4.3 mg, 0.03 mmol), and DMSO (1.0 mL). XF034-172A was obtained as white solid in TFA salt form (10 mg, 51%). $^1$H NMR (600 MHz, CD$_3$OD) δ 8.98 (s, 1H), 8.58 (d, J=2.6 Hz, 1H), 8.37 (s, 1H), 8.15 (dd, J=9.2, 2.5 Hz, 1H), 7.95 (s, 1H), 7.77 (s, 1H), 7.49-7.36 (m, 5H), 7.14 (d, J=8.9 Hz, 2H), 6.19 (s, 1H), 5.08 (p, J=6.7 Hz, 1H), 4.61-4.49 (m, 5H), 4.45 (s, 1H), 4.35 (d, J=15.5 Hz, 1H), 3.81-3.51 (m, 10H), 3.39 (t, J=5.5 Hz, 2H), 2.68 (q, J=10.8, 8.5 Hz, 2H), 2.49-2.43 (m, 8H), 2.26 (s, 4H), 2.09-2.04 (m, 1H), 1.57 (d, J=6.5 Hz, 6H), 1.02 (s, 9H).

Example 71: Synthesis of XF034-173A

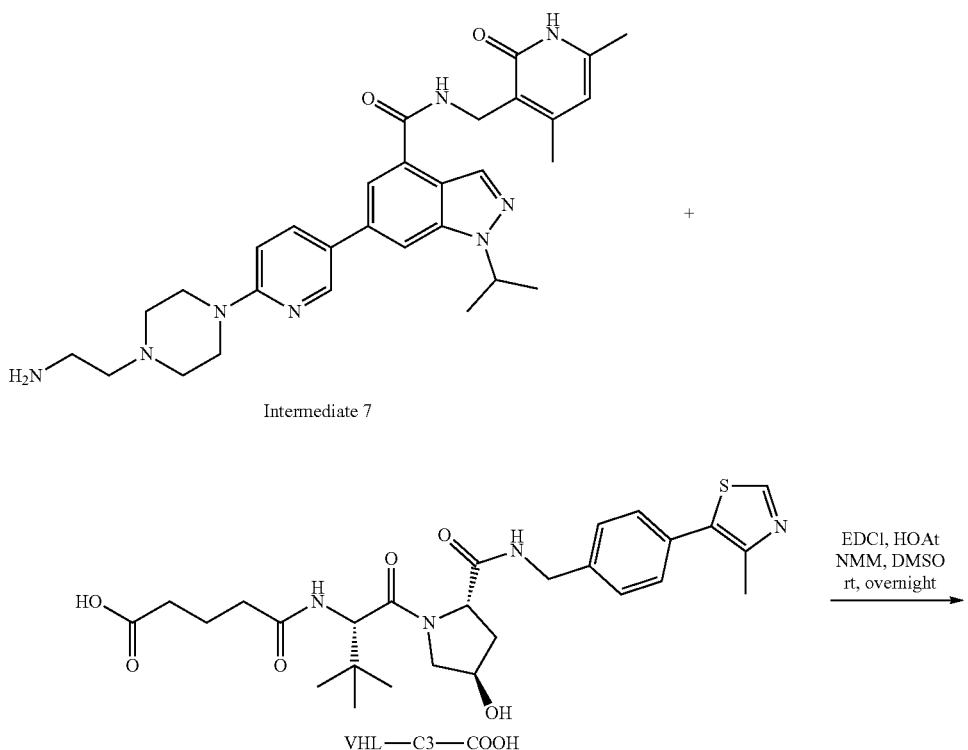

Intermediate 7

VHL—C3—COOH

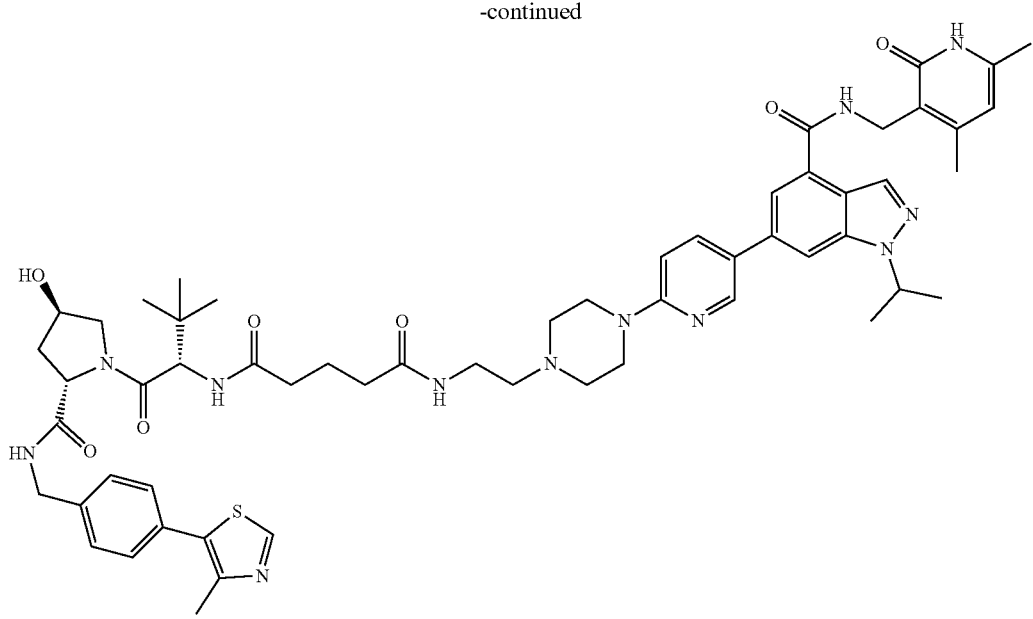

XF034-173A

XF034-173A was synthesized according to the procedures for preparing XF034-164A from intermediate 7 (10 mg, 0.02 mmol), HOAt (3.7 mg, 0.03 mmol), VHL-C3-COOH (10 mg, 0.02 mmol), NMM (5.3 μL, 0.06 mmol), EDCI (4.3 mg, 0.03 mmol), and DMSO (1.0 mL). XF034-173A was obtained as white solid in TFA salt form (14 mg, 70%). $^1$H NMR (600 MHz, CD$_3$OD) δ 9.00 (s, 1H), 8.56 (d, J=2.6 Hz, 1H), 8.37 (s, 1H), 8.16 (dd, J=9.2, 2.5 Hz, 1H), 7.96 (s, 1H), 7.77 (s, 1H), 7.51-7.36 (m, 4H), 7.15 (d, J=9.0 Hz, 1H), 6.20 (s, 1H), 5.15-5.06 (m, 1H), 4.60-4.48 (m, 6H), 4.36 (d, J=15.4 Hz, 1H), 3.92 (d, J=11.1 Hz, 2H), 3.81 (dd, J=11.0, 3.9 Hz, 2H), 3.76-3.43 (m, 8H), 3.37 (t, J=5.8 Hz, 2H), 2.45 (d, J=9.0 Hz, 6H), 2.39-2.19 (m, 8H), 2.09 (td, J=13.3, 11.3, 4.7 Hz, 1H), 1.98-1.89 (m, 2H), 1.57 (d, J=6.6 Hz, 6H), 1.05 (s, 9H).

Example 72: Synthesis of XF034-174A

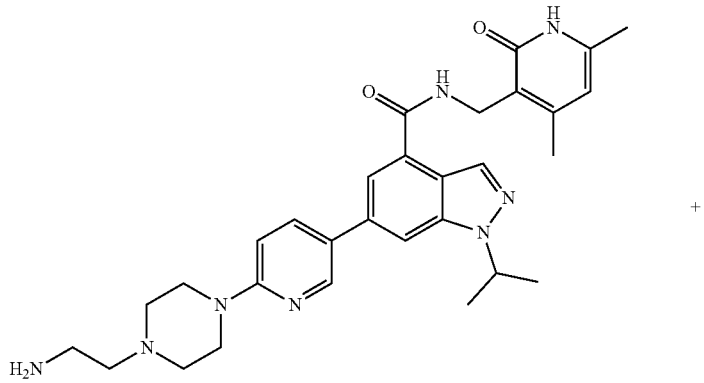

Intermediate 7

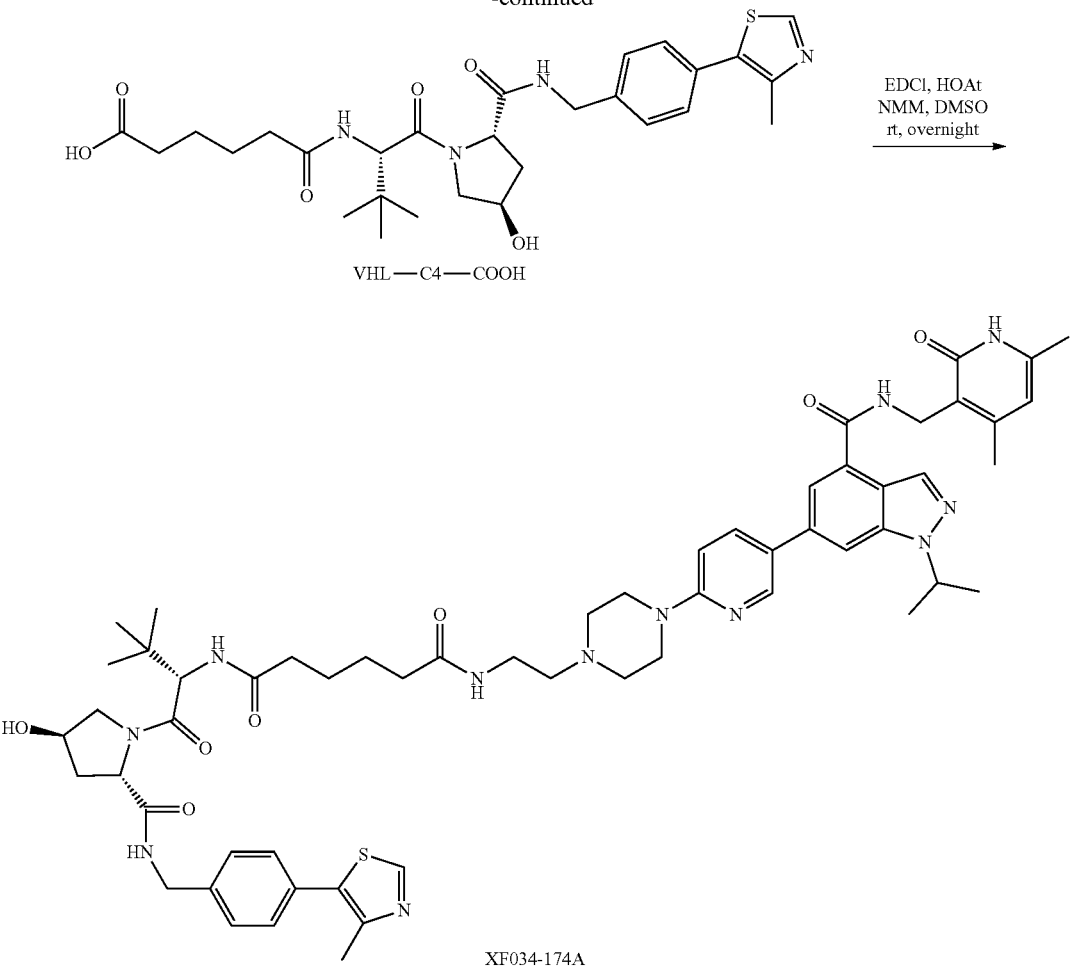

VHL—C4—COOH

XF034-174A

XF034-174A was synthesized according to the procedures for preparing XF034-164A from intermediate 7 (10 mg, 0.02 mmol), HOAt (3.7 mg, 0.03 mmol), VHL-C4-COOH (11 mg, 0.02 mmol), NMM (5.3 μL, 0.06 mmol), EDCI (4.3 mg, 0.03 mmol), and DMSO (1.0 mL). XF034-174A was obtained as white solid in TFA salt form (14 mg, 72%). $^1$H NMR (600 MHz, CD$_3$OD) δ 9.04 (s, 1H), 8.62-8.51 (m, 1H), 8.37 (d, J=3.3 Hz, 1H), 8.24-8.16 (m, 1H), 7.97 (d, J=3.6 Hz, 1H), 7.78 (d, J=3.4 Hz, 1H), 7.50-7.40 (m, 4H), 7.17 (dd, J=9.1, 3.5 Hz, 1H), 6.21 (s, 1H), 5.12-5.06 (m, 1H), 4.62-4.50 (m, 6H), 4.39-4.35 (m, 1H), 4.13-3.44 (m, 12H), 3.37 (t, J=5.7 Hz, 2H), 2.45 (dd, J=14.5, 3.5 Hz, 6H), 2.34-2.19 (m, 8H), 2.08 (td, J=9.6, 5.1 Hz, 1H), 1.67-1.61 (m, 4H), 1.57 (dd, J=6.7, 3.3 Hz, 6H), 1.03 (d, J=3.5 Hz, 9H).

Example 73: Synthesis of XF034-175A

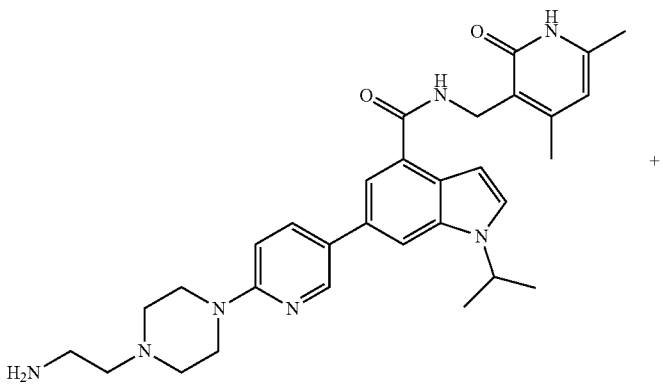

Intermediate 7

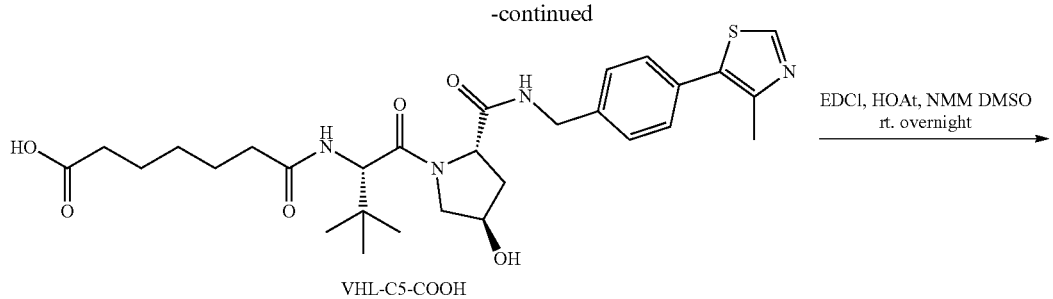
VHL-C5-COOH
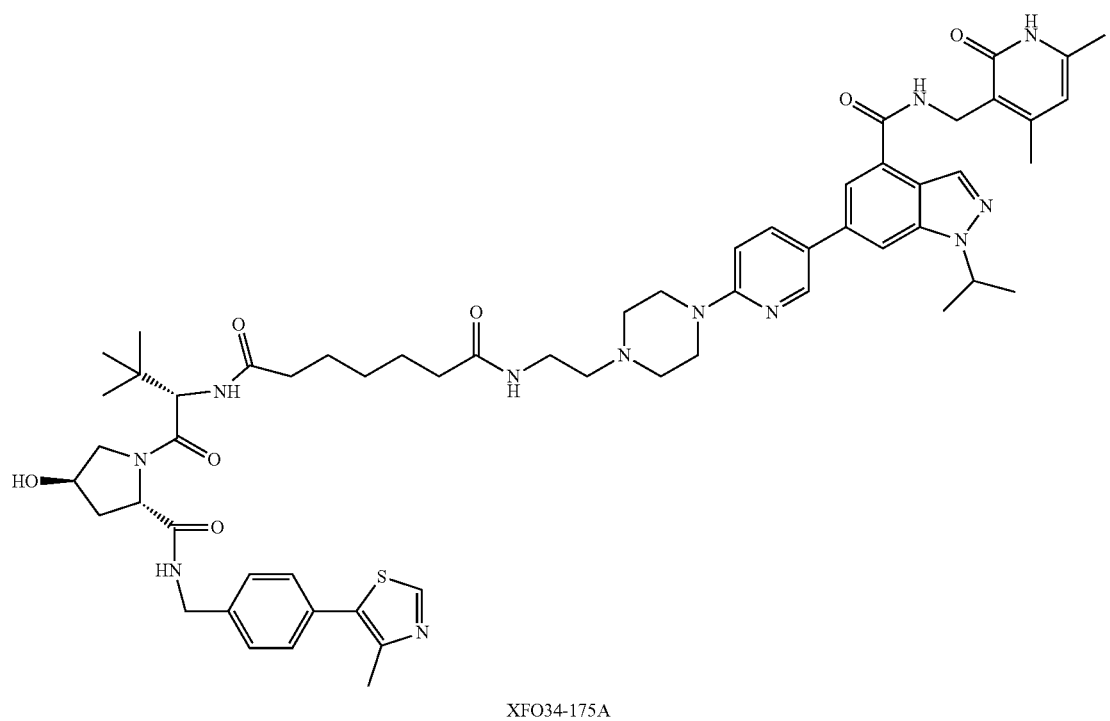
XFO34-175A
XF034-175A was synthesized according to the procedures for preparing XF034-164A from intermediate 7 (10 mg, 0.02 mmol), HOAt (3.7 mg, 0.03 mmol), VHL-C5-COOH (11 mg, 0.02 mmol), NMM (5.3 μL, 0.06 mmol), EDCI (4.3 mg, 0.03 mmol), and DMSO (1.0 mL). XF034-175A was obtained as white solid in TFA salt form (17 mg, 83%). $^1$H NMR (600 MHz, CD$_3$OD) δ 9.00 (s, 1H), 8.57 (d, J=2.6 Hz, 1H), 8.37 (s, 1H), 8.20-8.11 (m, 1H), 7.96 (s, 1H), 7.78 (s, 1H), 7.54-7.33 (m, 4H), 7.15 (d, J=9.0 Hz, 1H), 6.20 (s, 1H), 5.08 (p, J=6.7 Hz, 1H), 4.63 (s, 1H), 4.62-4.45 (m, 5H), 4.36 (d, J=15.4 Hz, 1H), 4.14-3.40 (m, 12H), 3.36 (t, J=6.0 Hz, 2H), 2.46 (d, J=16.3 Hz, 6H), 2.33-2.17 (m, 8H), 2.08 (td, J=12.7, 10.9, 4.4 Hz, 1H), 1.61 (dd, J=42.7, 7.3 Hz, 10H), 1.37 (q, J=7.8 Hz, 2H), 1.03 (s, 9H).

Example 74: Synthesis of XF034-176A
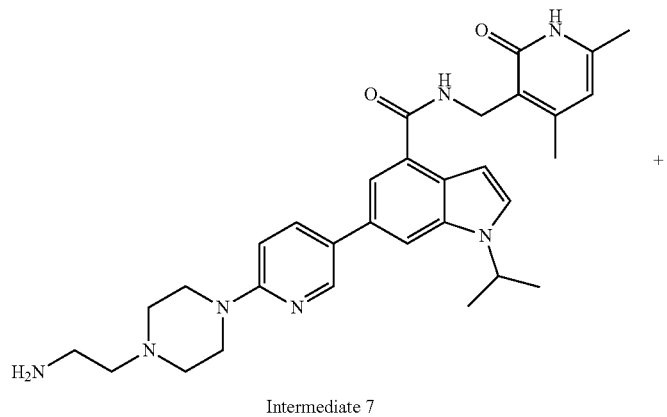
Intermediate 7
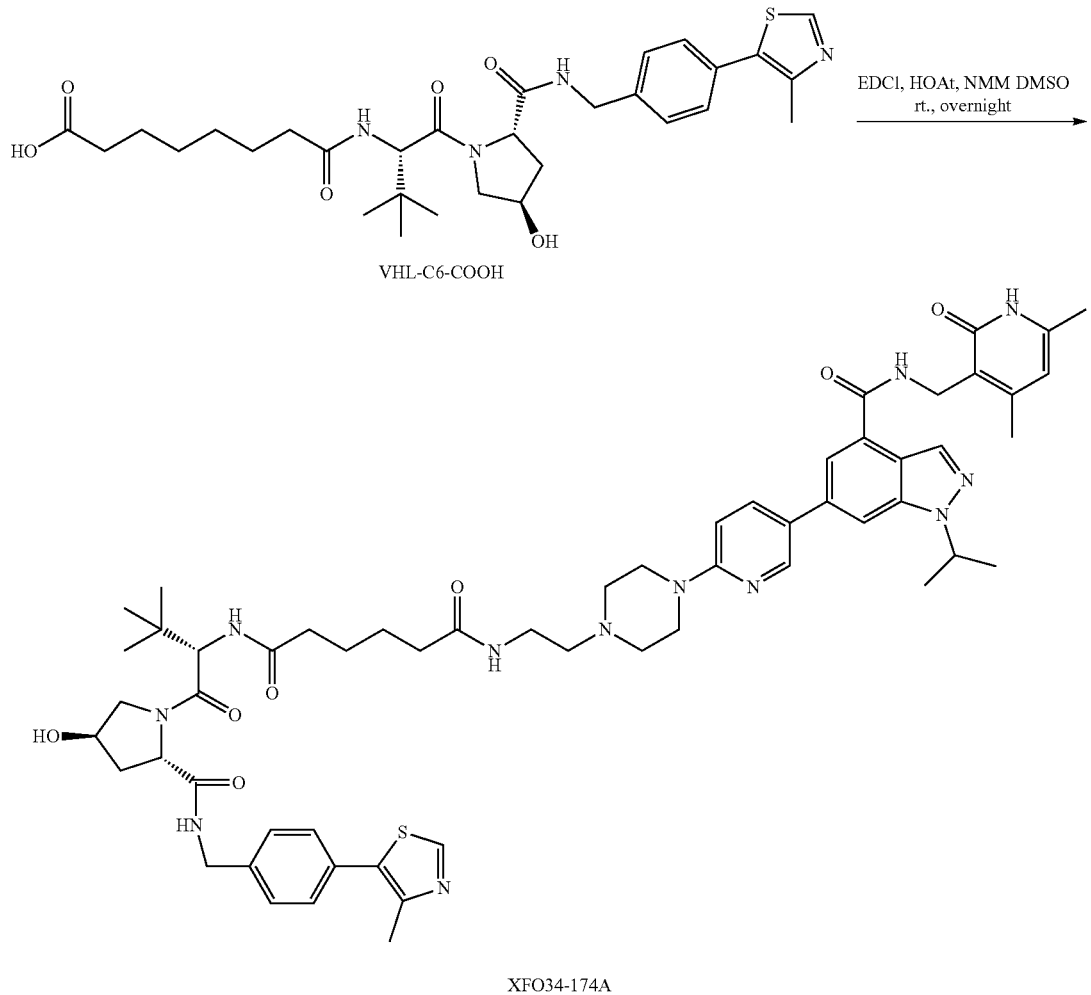
XF034-174A
XF034-176A was synthesized according to the procedures for preparing XF034-164A from intermediate 7 (10 mg, 0.02 mmol), HOAt (3.7 mg, 0.03 mmol), VHL-C6-COOH (11 mg, 0.02 mmol), NMM (5.3 μL, 0.06 mmol), EDCI (4.3 mg, 0.03 mmol), and DMSO (1.0 mL). XF034-176A was obtained as white solid in TFA salt form (12 mg, 61%). $^1$H NMR (600 MHz, CD$_3$OD) δ 9.03 (s, 1H), 8.58 (d, J=2.6 Hz, 1H), 8.37 (s, 1H), 8.19-8.11 (m, 1H), 7.97 (s, 1H), 7.78 (s, 1H), 7.54-7.27 (m, 4H), 7.15 (d, J=8.9 Hz, 1H), 6.19 (s, 1H), 5.09 (q, J=6.6 Hz, 1H), 4.63 (s, 1H), 4.62-4.46 (m, 5H), 4.36 (d, J=15.4 Hz, 1H), 4.15-3.44 (m, 12H), 3.35 (t, J=6.0 Hz, 2H), 2.46 (d, J=16.8 Hz, 6H), 2.25 (d, J=10.1 Hz, 8H), 2.11-2.03 (m, 1H), 1.65-1.52 (m, 10H), 1.35 (s, 4H), 1.03 (s, 9H).

Example 75: Synthesis of XF034-177A

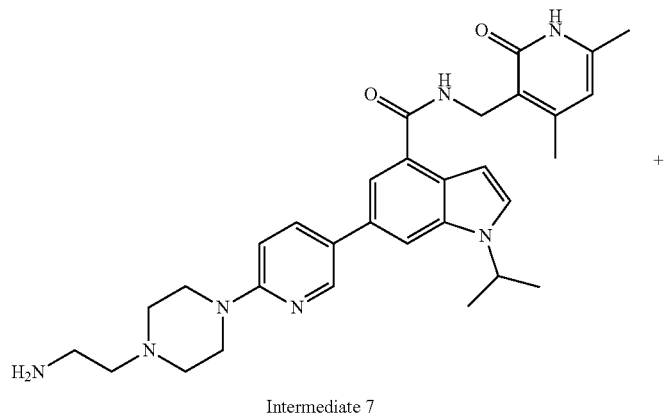

Intermediate 7

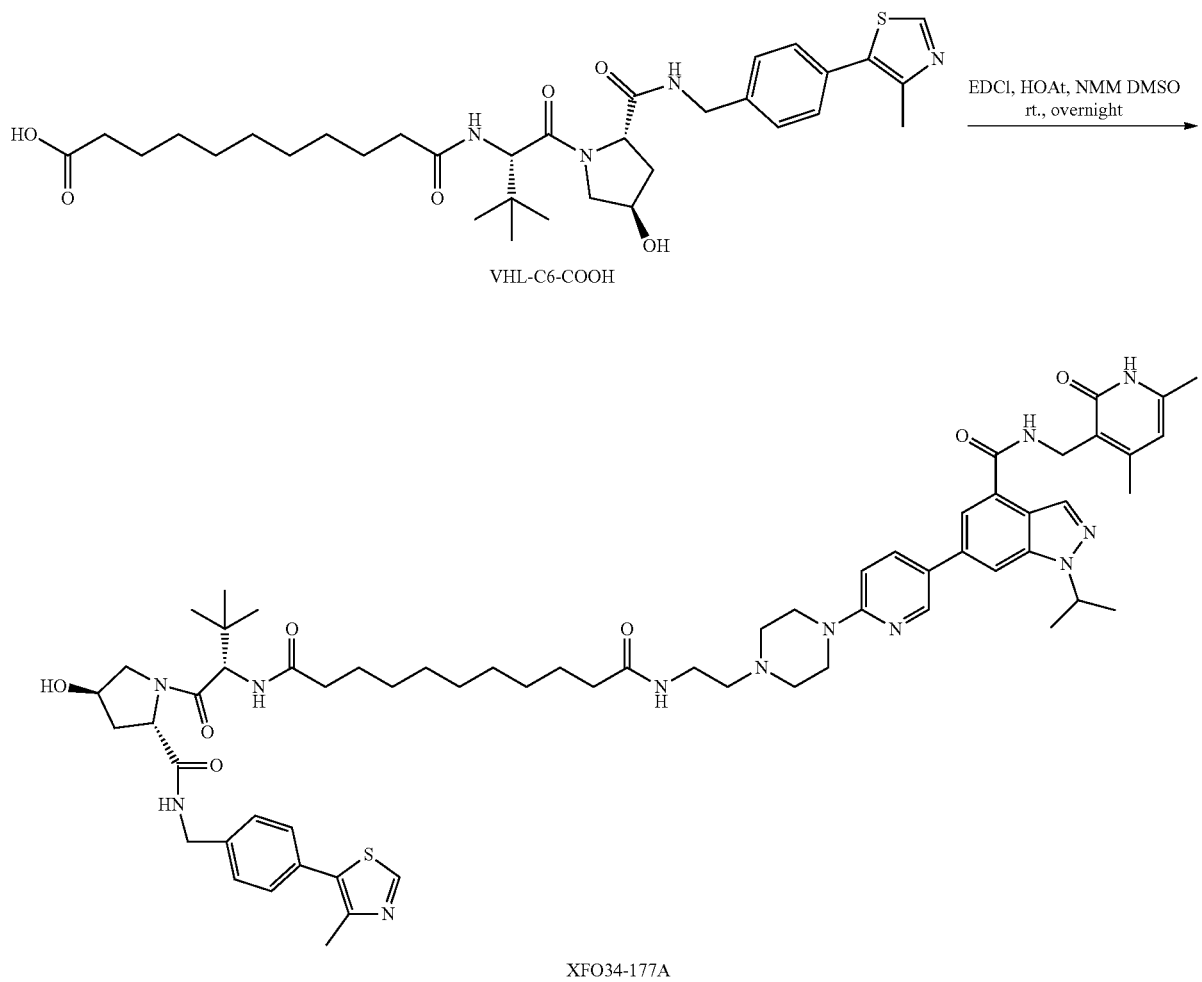

XF034-177A

XF034-177A was synthesized according to the procedures for preparing XF034-164A from intermediate 7 (10 mg, 0.02 mmol), HOAt (3.7 mg, 0.03 mmol), VHL-C9-COOH (12 mg, 0.02 mmol), NMM (5.3 μL, 0.06 mmol), EDCI (4.3 mg, 0.03 mmol), and DMSO (1.0 mL). XF034-177A was obtained as white solid in TFA salt form (9 mg, 41%). $^1$H NMR (600 MHz, CD$_3$OD) δ 8.99 (s, 1H), 8.59 (d, J=2.5 Hz, 1H), 8.37 (s, 1H), 8.16 (d, J=8.8 Hz, 1H), 7.96 (s, 1H), 7.79 (s, 1H), 7.60-7.22 (m, 4H), 7.14 (d, J=8.9 Hz, 1H), 6.19 (s, 1H), 5.08 (q, J=6.6 Hz, 1H), 4.63 (s, 1H), 4.60-4.44 (m, 5H), 4.35 (d, J=15.4 Hz, 1H), 3.99-3.43 (m, 12H), 3.35 (d, J=6.1 Hz, 2H), 2.46 (d, J=18.4 Hz, 6H), 2.33-2.16 (m, 8H), 2.08 (td, J=13.2, 11.1, 4.4 Hz, 1H), 1.66-1.52 (m, 10H), 1.32 (s, 10H), 1.03 (s, 9H).

Example 76: Synthesis of YS36-48

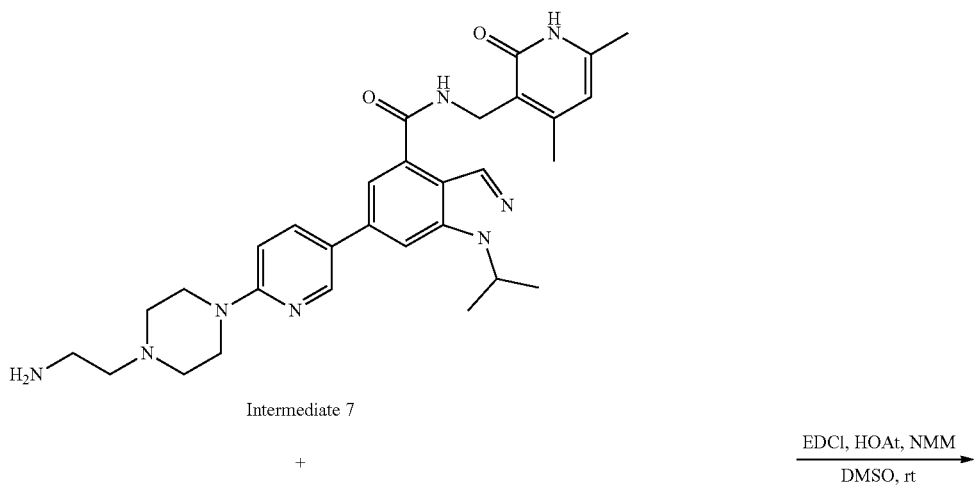

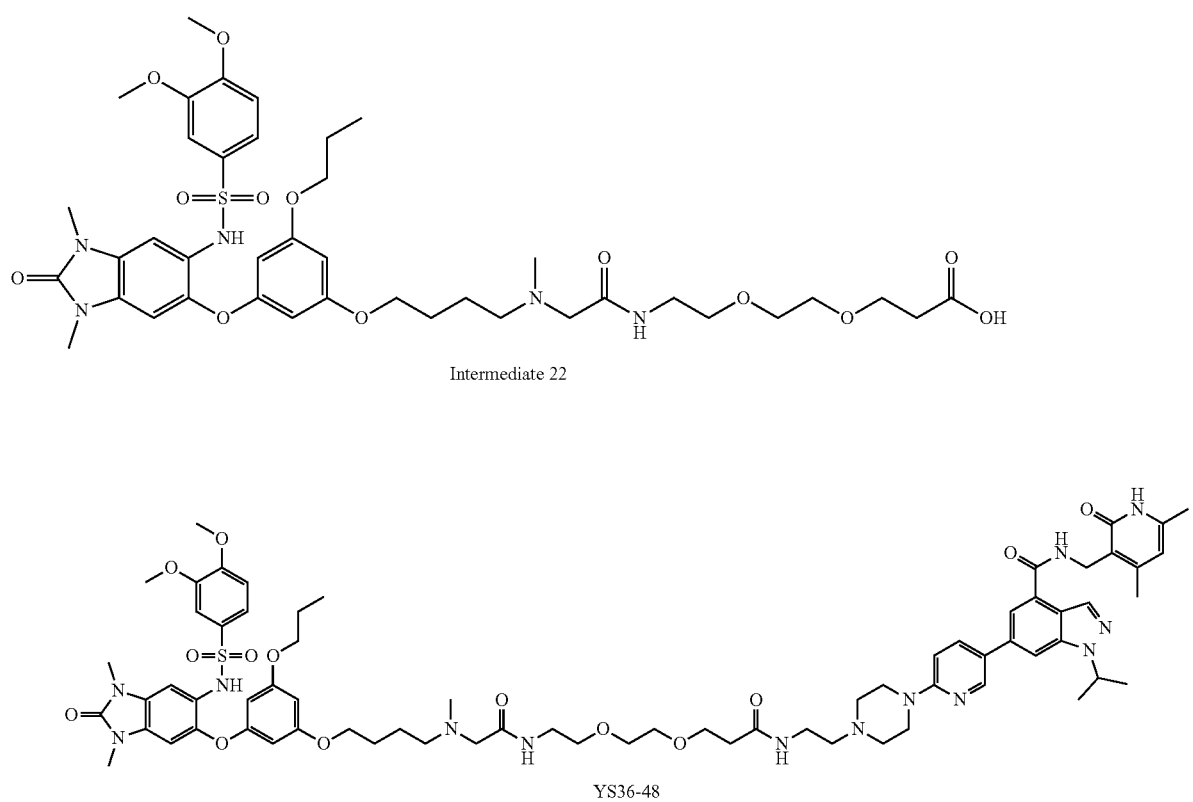

Intermediate 22 (10 mg, 0.01 mmol), HOAt (4.3 mg, 0.03 mmol), and intermediate 7 (10 mg, 0.01 mmol) were dissolved in DMSO (1.0 mL). To the solution were added NMM (14 μL, 0.13 mmol), and EDCI (6.1 mg, 0.03 mmol) successively at room temperature. After being stirred overnight at room temperature, the mixture was purified by preparative HPLC (10%-100% methanol/0.1% TFA in H$_2$O) to afford YS36-48 as white solid in TFA salt form (10 mg, 62%). $^1$H NMR (600 MHz, CD$_3$OD) δ 8.59 (d, J=2.5 Hz, 1H), 8.36 (s, 1H), 8.11 (dd, J=9.0, 2.5 Hz, 1H), 7.94 (s, 1H), 7.78 (s, 1H), 7.33 (s, 1H), 7.20 (dd, J=8.4, 2.1 Hz, 1H), 7.15 (d, J=2.1 Hz, 1H), 7.09 (d, J=8.9 Hz, 1H), 6.78 (d, J=8.5 Hz, 1H), 6.61 (s, 1H), 6.14 (d, J=16.1 Hz, 2H), 5.76 (d, J=2.4 Hz, 1H), 5.61 (d, J=2.4 Hz, 1H), 5.08 (p, J=6.5 Hz, 1H), 4.58 (s, 2H), 3.98 (bs, 8H), 3.84 (t, J=5.9 Hz, 2H), 3.79 (s, 3H), 3.75 (q, J=6.3 Hz, 4H), 3.65 (t, J=5.8 Hz, 2H), 3.60-3.59 (m, 9H), 3.54 (t, J=5.4 Hz, 4H), 3.43-3.40 (m, 5H), 3.36 (t, J=5.8 Hz, 2H), 3.24 (s, 3H), 2.94 (s, 3H), 2.51 (t, J=6.1 Hz, 2H), 2.43 (s, 3H), 2.25 (s, 3H), 1.90 (q, J=8.0 Hz, 2H), 1.80 (q, J=7.1, 6.7 Hz, 2H), 1.74 (p, J=6.9 Hz, 2H), 1.57 (d, J=6.6 Hz, 6H), 1.00 (t, J=7.4 Hz, 3H).

Example 77: Synthesis of YS36-49

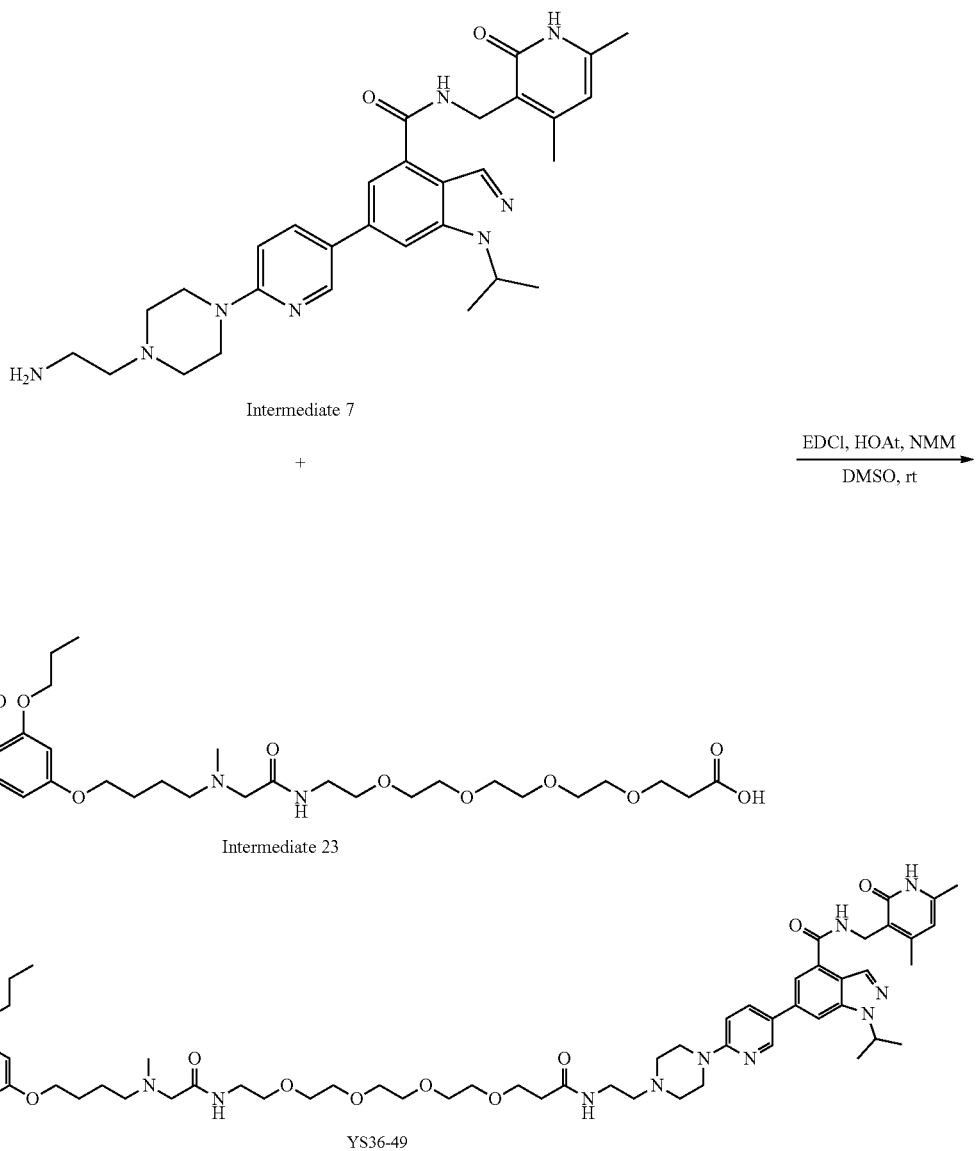

YS36-49 was synthesized according to the procedures for preparing YS36-48 from intermediate 23 (10 mg, 0.01 mmol), HOAt (4.3 mg, 0.03 mmol), intermediate 7 (10 mg, 0.01 mmol), NMM (14 µL, 0.13 mmol), EDCI (6.1 mg, 0.03 mmol), and DMSO (1.0 mL). YS36-49 was obtained as white solid in TFA salt form (11 mg, 65%). $^1$H NMR (600 MHz, CD$_3$OD) δ 8.58 (d, J=2.5 Hz, 1H), 8.36 (s, 1H), 8.17 (dd, J=9.0, 2.5 Hz, 1H), 7.97 (s, 1H), 7.78 (d, J=1.3 Hz, 1H), 7.33 (s, 1H), 7.24-7.09 (m, 3H), 6.78 (d, J=8.5 Hz, 1H), 6.61 (s, 1H), 6.19 (s, 1H), 6.13 (d, J=2.4 Hz, 1H), 5.75 (d, J=2.4 Hz, 1H), 5.61 (d, J=2.2 Hz, 1H), 5.08 (p, J=6.7 Hz, 1H), 4.58 (s, 2H), 3.98 (s, 8H), 3.84 (t, J=5.8 Hz, 2H), 3.80 (d, J=1.0 Hz, 3H), 3.76 (q, J=5.9 Hz, 4H), 3.65 (d, J=5.9 Hz, 2H), 3.63-3.48 (m, 21H), 3.43-3.35 (m, 7H), 3.24 (d, J=1.1 Hz, 3H), 2.94 (s, 3H), 2.51 (t, J=5.9 Hz, 2H), 2.44 (s, 3H), 2.26 (s, 3H), 1.93-1.89 (m, 2H), 1.81 (dt, J=14.2, 6.7 Hz, 2H), 1.75-1.71 (m, 2H), 1.57 (d, J=6.6 Hz, 6H), 1.00 (t, J=7.4 Hz, 3H).

Example 78: Synthesis of YS36-50

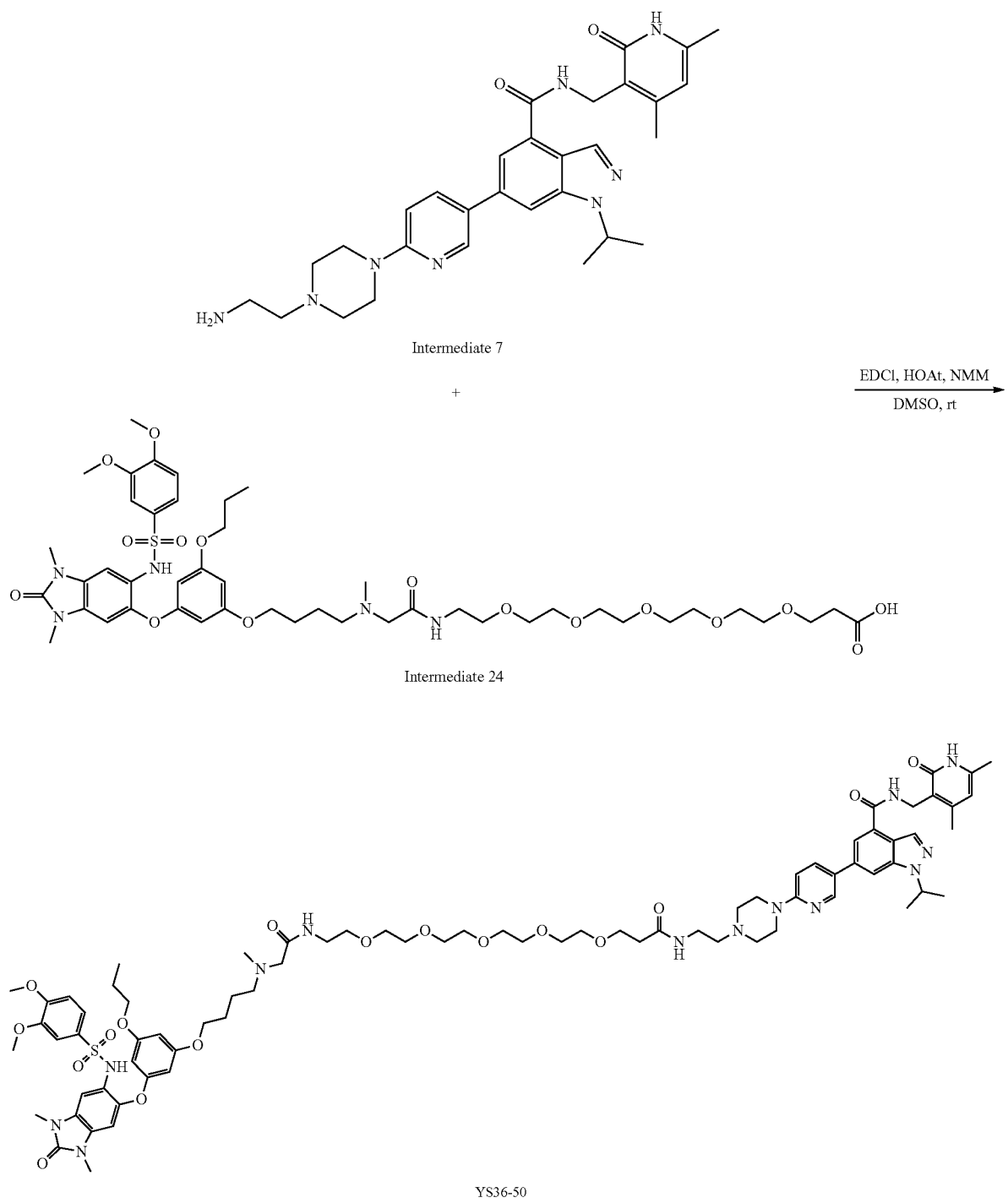

YS36-50 was synthesized according to the procedures for preparing YS36-48 from intermediate 24 (10 mg, 0.01 mmol), HOAt (4.3 mg, 0.03 mmol), intermediate 7 (10 mg, 0.01 mmol), NMM (14 μL, 0.13 mmol), EDCI (6.1 mg, 0.03 mmol), and DMSO (1.0 mL). YS36-50 was obtained as white solid in TFA salt form (8 mg, 46%). $^1$H NMR (600 MHz, CD$_3$OD) δ 8.59 (d, J=2.5 Hz, 1H), 8.36 (s, 1H), 8.13 (dd, J=8.9, 2.6 Hz, 1H), 7.96 (s, 1H), 7.78 (d, J=1.4 Hz, 1H), 7.33 (s, 1H), 7.22-7.07 (m, 3H), 6.78 (d, J=8.5 Hz, 1H), 6.61 (s, 1H), 6.17 (s, 1H), 6.14 (s, 1H), 5.76 (s, 1H), 5.61 (s, 1H), 5.08 (p, J=6.5 Hz, 1H), 4.57 (s, 2H), 4.10-3.87 (m, 8H), 3.84 (t, J=5.8 Hz, 2H), 3.80 (s, 3H), 3.77-3.75 (m, 4H), 3.66 (d, J=5.7 Hz, 2H), 3.62-3.47 (m, 25H), 3.39 (d, J=22.5 Hz, 7H), 3.24 (s, 3H), 2.94 (s, 3H), 2.51 (t, J=5.9 Hz, 2H), 2.43 (s, 3H), 2.26 (s, 3H), 1.93-1.89 (m, 2H), 1.82-1.78 (m, 2H), 1.74 (d, J=7.1 Hz, 2H), 1.57 (d, J=6.6 Hz, 6H), 1.00 (t, J=7.4 Hz, 3H).

Example 79: Synthesis of YS36-51

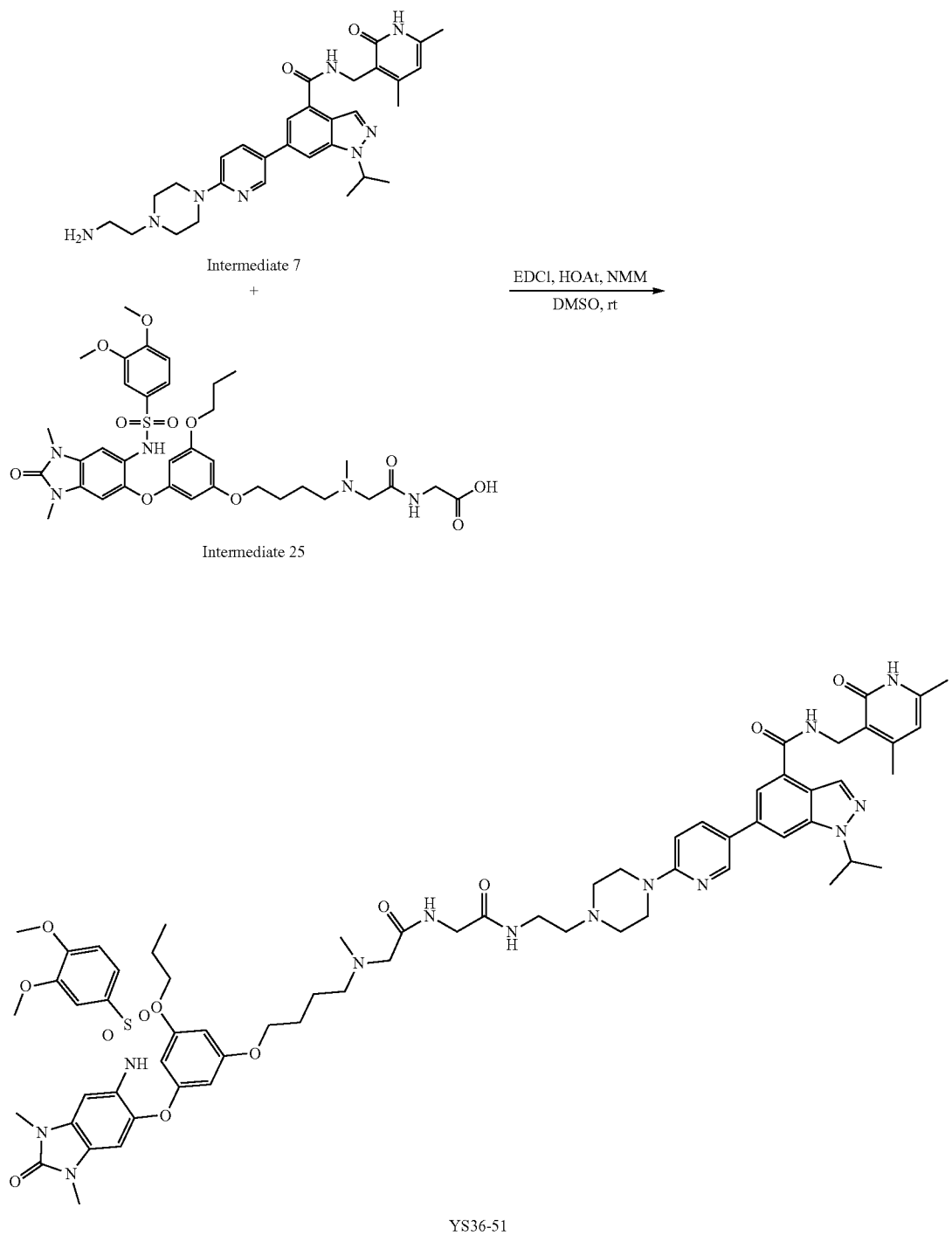

YS36-51 was synthesized according to the procedures for preparing YS36-48 from intermediate 25 (10 mg, 0.01 mmol), HOAt (4.3 mg, 0.03 mmol), intermediate 7 (10 mg, 0.01 mmol), NMM (14 μL, 0.13 mmol), EDCI (6.1 mg, 0.03 mmol), and DMSO (1.0 mL). YS36-51 was obtained as white solid in TFA salt form (9 mg, 60%). $^1$H NMR (600 MHz, CD$_3$OD) δ 8.56 (d, J=2.5 Hz, 1H), 8.36 (s, 1H), 8.12 (dd, J=8.9, 2.5 Hz, 1H), 7.94 (s, 1H), 7.77 (d, J=1.3 Hz, 1H), 7.31 (s, 1H), 7.23-7.00 (m, 3H), 6.77 (d, J=8.5 Hz, 1H), 6.60 (s, 1H), 6.21-6.08 (m, 2H), 5.74 (t, J=2.1 Hz, 1H), 5.63 (t, J=2.2 Hz, 1H), 5.08 (p, J=6.7 Hz, 1H), 4.58 (s, 2H), 4.06 (bs, 8H), 3.98 (s, 2H), 3.86 (t, J=5.9 Hz, 2H), 3.79 (s, 3H), 3.74 (t, J=6.5 Hz, 2H), 3.68 (t, J=6.0 Hz, 2H), 3.60 (s, 3H), 3.53 (bs, 4H), 3.38 (d, J=5.5 Hz, 5H), 3.23 (s, 3H), 2.97 (s, 3H), 2.44 (s, 3H), 2.25 (s, 3H), 1.93 (q, J=8.2, 7.4 Hz, 2H), 1.81 (p, J=6.3 Hz, 2H), 1.71 (q, J=7.0 Hz, 2H), 1.57 (d, J=6.6 Hz, 6H), 0.98 (t, J=7.4 Hz, 3H).

Example 80: Synthesis of YS36-52

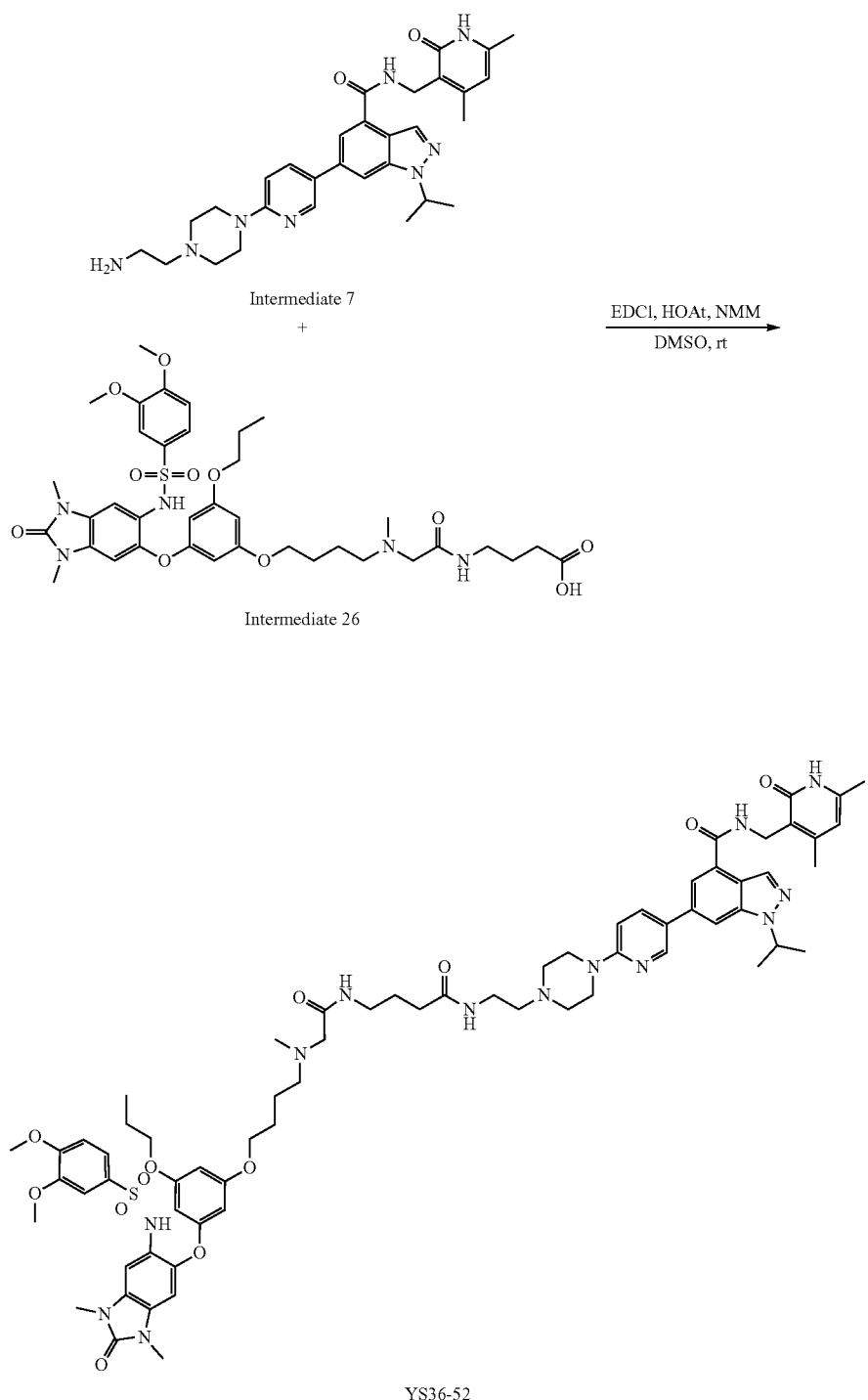

YS36-52 was synthesized according to the procedures for preparing YS36-48 from intermediate 26 (10 mg, 0.01 mmol), HOAt (4.3 mg, 0.03 mmol), intermediate 7 (10 mg, 0.01 mmol), NMM (14 μL, 0.13 mmol), EDCI (6.1 mg, 0.03 mmol), and DMSO (1.0 mL). YS36-52 was obtained as white solid in TFA salt form (13 mg, 85%). $^1$H NMR (600 MHz, CD$_3$OD) δ 8.56 (d, J=2.5 Hz, 1H), 8.37 (s, 1H), 8.18 (dd, J=9.0, 2.6 Hz, 1H), 7.97 (s, 1H), 7.78 (d, J=1.4 Hz, 1H), 7.32 (d, J=2.8 Hz, 1H), 7.26-7.09 (m, 3H), 6.77 (d, J=8.6 Hz, 1H), 6.61 (s, 1H), 6.21 (s, 1H), 6.13 (q, J=2.0 Hz, 1H), 5.75 (t, J=2.1 Hz, 1H), 5.66-5.56 (m, 1H), 5.09 (p, J=6.7 Hz, 1H), 4.58 (s, 2H), 3.96 (s, 8H), 3.85 (t, J=5.8 Hz, 2H), 3.80 (s, 3H), 3.75 (d, J=6.5 Hz, 2H), 3.60-3.62 (m, 9H), 3.38 (d, J=19.0 Hz, 5H), 3.27 (d, J=6.2 Hz, 2H), 3.24 (s, 3H), 2.95 (s, 3H), 2.45 (s, 3H), 2.28 (d, J=16.8 Hz, 5H), 1.94-1.90 (m, 2H), 1.86-1.80 (m, 4H), 1.73 (d, J=7.2 Hz, 2H), 1.57 (d, J=6.6 Hz, 6H), 1.00 (d, J=7.5 Hz, 3H).

Example 81: Synthesis of YS36-53

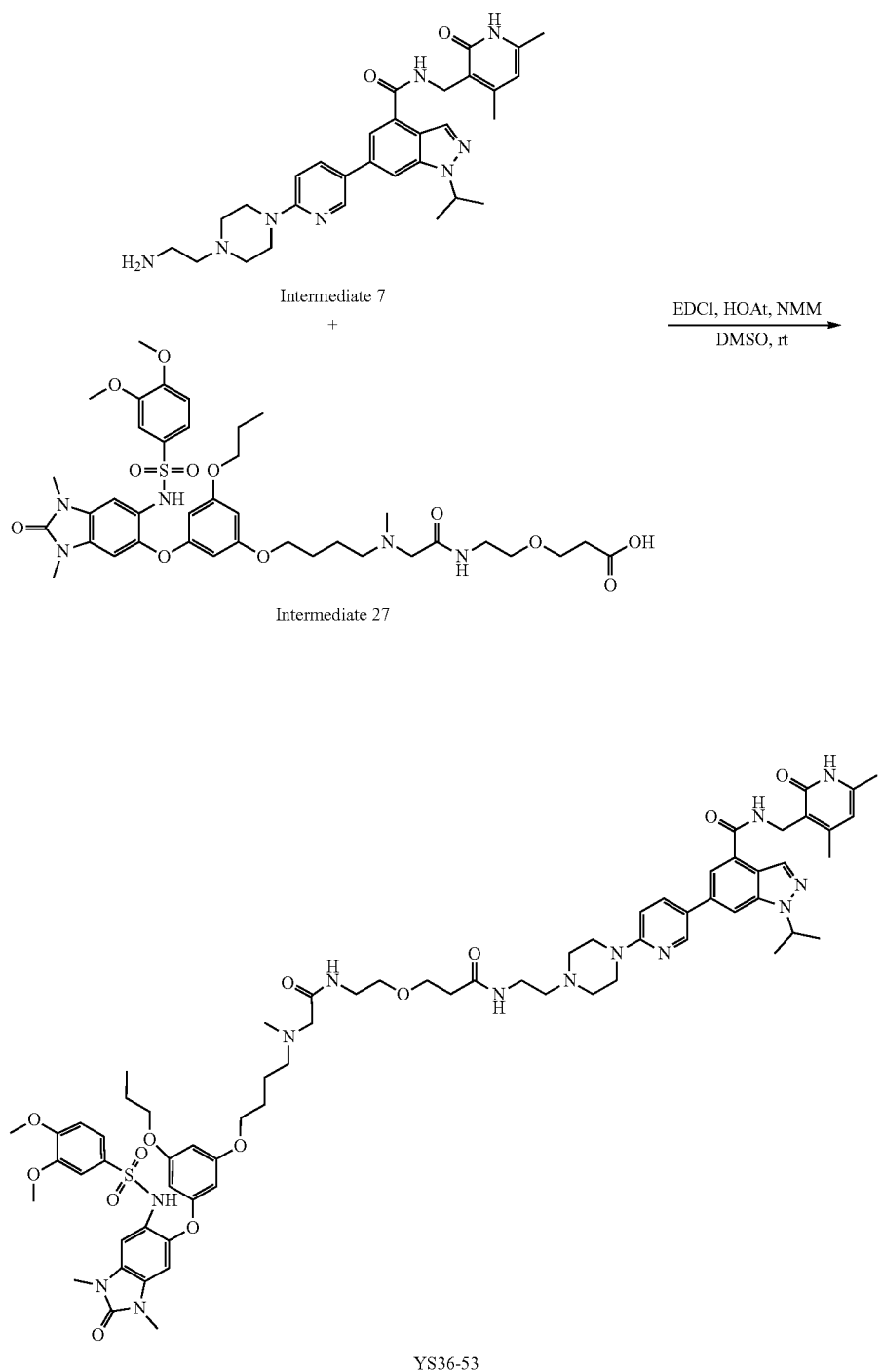

YS36-53 was synthesized according to the procedures for preparing YS36-48 from intermediate 27 (10 mg, 0.01 mmol), HOAt (4.3 mg, 0.03 mmol), intermediate 7 (10 mg, 0.01 mmol), NMM (14 µL, 0.13 mmol), EDCI (6.1 mg, 0.03 mmol), and DMSO (1.0 mL). YS36-53 was obtained as white solid in TFA salt form (15 mg, 96%). $^1$H NMR (600 MHz, CD$_3$OD) δ 8.57 (d, J=2.5 Hz, 1H), 8.37 (s, 1H), 8.19 (dd, J=9.0, 2.5 Hz, 1H), 7.97 (s, 1H), 7.79 (d, J=1.4 Hz, 1H), 7.32 (s, 1H), 7.21-7.09 (m, 3H), 6.78 (d, J=8.5 Hz, 1H), 6.61 (s, 1H), 6.22 (s, 1H), 6.13 (t, J=2.2 Hz, 1H), 5.75 (t, J=2.1 Hz, 1H), 5.62 (t, J=2.1 Hz, 1H), 5.10-5.07 (m, 1H), 4.58 (s, 2H), 3.98 (bs, 8H), 3.85 (t, J=5.9 Hz, 2H), 3.80 (s, 3H), 3.76 (d, J=6.5 Hz, 2H), 3.72 (d, J=6.1 Hz, 2H), 3.64 (d, J=5.9 Hz, 2H), 3.60 (s, 3H), 3.53 (t, J=5.5 Hz, 6H), 3.43 (d, J=5.6 Hz, 2H), 3.40 (s, 3H), 3.37 (d, J=5.8 Hz, 2H), 3.24 (s, 3H), 2.95 (s, 3H), 2.51 (d, J=6.1 Hz, 2H), 2.45 (s, 3H), 2.27 (s, 3H), 1.94-1.90 (m, 2H), 1.83-1.79 (m, 2H), 1.73 (q, J=7.0 Hz, 2H), 1.57 (d, J=6.6 Hz, 6H), 1.00 (t, J=7.4 Hz, 3H).

Example 82: Synthesis of YS36-54

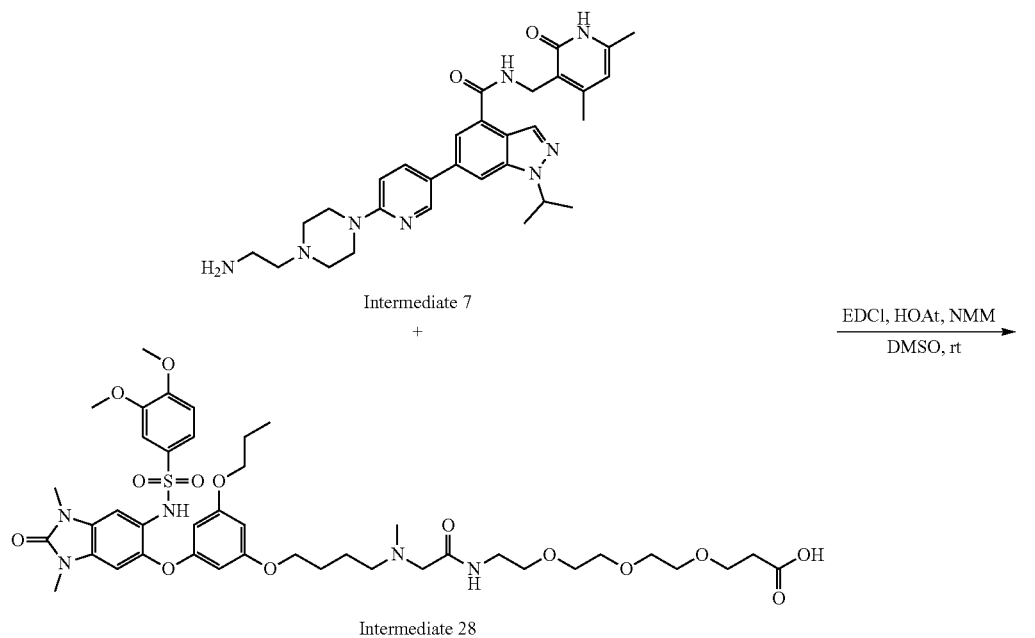

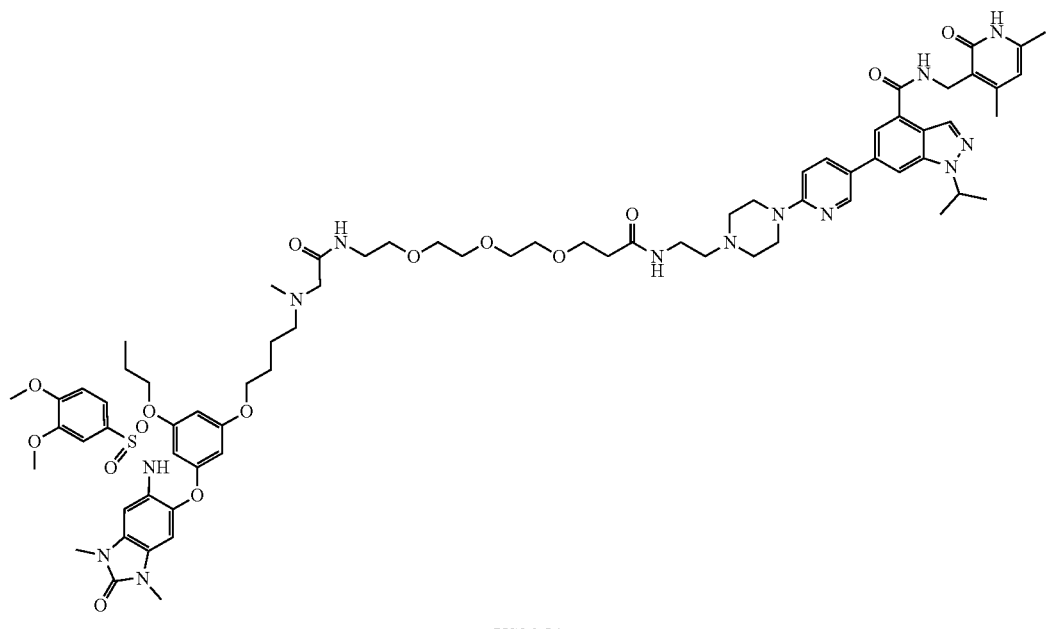

YS36-54 was synthesized according to the procedures for preparing YS36-48 from intermediate 28 (10 mg, 0.01 mmol), HOAt (4.3 mg, 0.03 mmol), intermediate 7 (10 mg, 0.01 mmol), NMM (14 μL, 0.13 mmol), EDCI (6.1 mg, 0.03 mmol), and DMSO (1.0 mL). YS36-54 was obtained as white solid in TFA salt form (10 mg, 60%). $^1$H NMR (600 MHz, CD$_3$OD) δ 8.59 (d, J=2.5 Hz, 1H), 8.36 (s, 1H), 8.10 (dd, J=8.9, 2.6 Hz, 1H), 7.94 (s, 1H), 7.77 (d, J=1.3 Hz, 1H), 7.33 (s, 1H), 7.26-7.07 (m, 3H), 6.78 (d, J=8.5 Hz, 1H), 6.61 (s, 1H), 6.22-6.04 (m, 2H), 5.76 (t, J=2.1 Hz, 1H), 5.61 (t, J=2.1 Hz, 1H), 5.12-5.06 (m, 1H), 4.57 (s, 2H), 3.91 (m, 8H), 3.84 (t, J=5.9 Hz, 2H), 3.79 (s, 3H), 3.77-3.74 (m, 4H), 3.65 (t, J=5.8 Hz, 2H), 3.62-3.47 (m, 17H), 3.40 (d, J=5.4 Hz, 5H), 3.37 (t, J=5.8 Hz, 2H), 3.23 (s, 3H), 2.94 (s, 3H), 2.51 (t, J=6.0 Hz, 2H), 2.43 (s, 3H), 2.25 (s, 3H), 1.91-1.87 (m, 2H), 1.81-1.76 (m, 2H), 1.74-1.71 (m, 2H), 1.57 (d, J=6.6 Hz, 6H), 1.00 (t, J=7.4 Hz, 3H).

Example 83: Synthesis of YS36-55

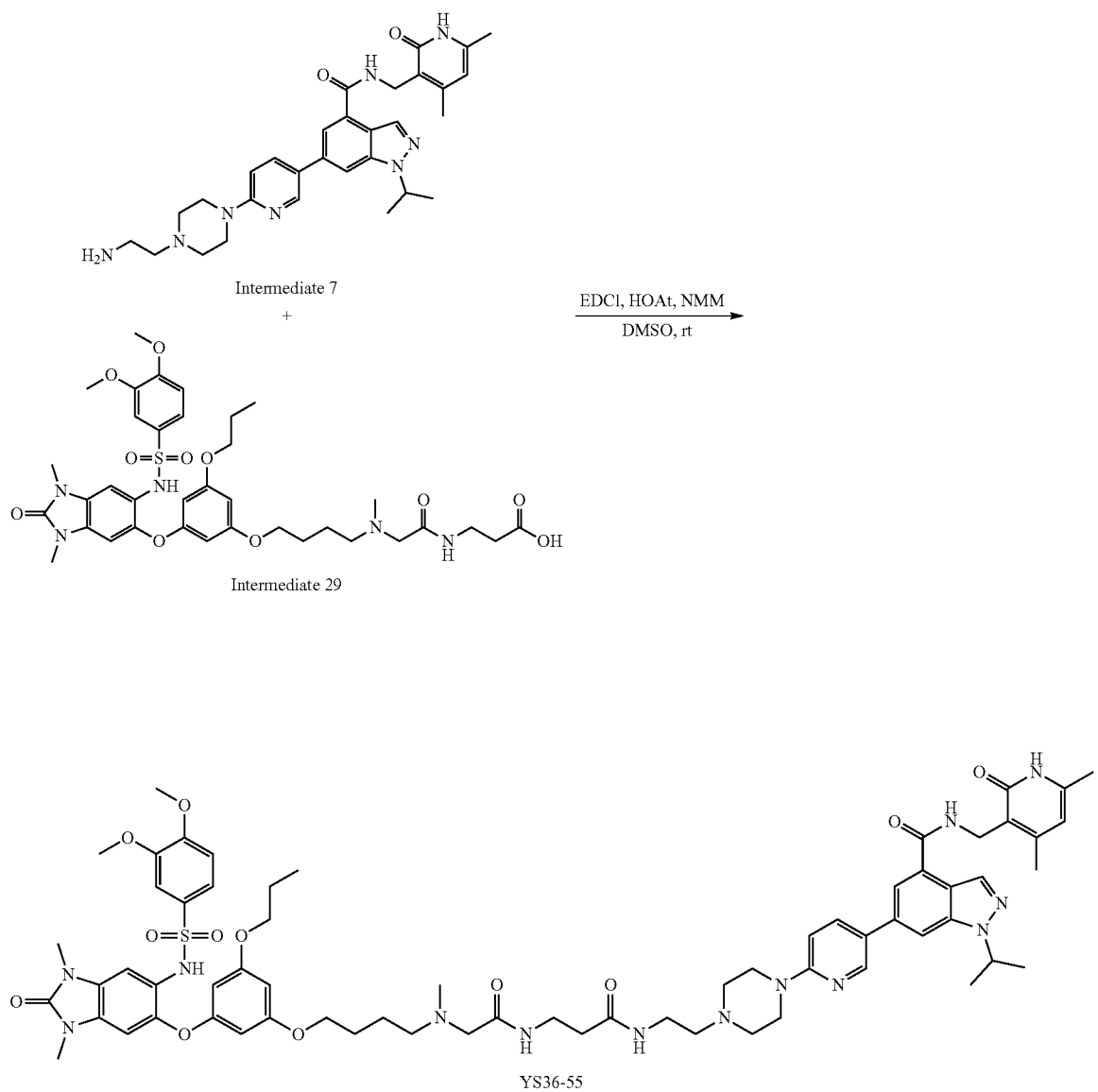

YS36-55 was synthesized according to the procedures for preparing YS36-48 from intermediate 29 (10 mg, 0.01 mmol), HOAt (4.3 mg, 0.03 mmol), intermediate 7 (10 mg, 0.01 mmol), NMM (14 μL, 0.13 mmol), EDCI (6.1 mg, 0.03 mmol), and DMSO (1.0 mL). YS36-55 was obtained as white solid in TFA salt form (9 mg, 59%). $^1$H NMR (600 MHz, CD$_3$OD) δ 8.57 (d, J=2.5 Hz, 1H), 8.37 (s, 1H), 8.13 (dd, J=9.0, 2.5 Hz, 1H), 7.95 (s, 1H), 7.78 (s, 1H), 7.32 (s, 1H), 7.20 (dd, J=8.5, 2.2 Hz, 1H), 7.15 (d, J=2.2 Hz, 1H), 7.10 (d, J=8.9 Hz, 1H), 6.78 (d, J=8.5 Hz, 1H), 6.61 (s, 1H), 6.18 (s, 1H), 6.14 (t, J=2.2 Hz, 1H), 5.75 (t, J=2.1 Hz, 1H), 5.63 (t, J=2.2 Hz, 1H), 5.09 (p, J=6.6 Hz, 1H), 4.58 (s, 2H), 3.99 (bs, 8H), 3.86 (t, J=5.9 Hz, 2H), 3.80 (s, 3H), 3.76 (t, J=6.5 Hz, 2H), 3.61-3.63 (m, 5H), 3.53-3.55 (m, 4H), 3.39 (s, 3H), 3.35 (t, J=5.9 Hz, 2H), 3.26 (s, 2H), 3.24 (s, 3H), 2.95 (s, 3H), 2.49 (t, J=6.7 Hz, 2H), 2.44 (s, 3H), 2.26 (s, 3H), 1.91 (dd, J=16.1, 8.0 Hz, 2H), 1.82 (q, J=7.3, 6.7 Hz, 2H), 1.72 (p, J=7.1 Hz, 2H), 1.57 (d, J=6.7 Hz, 6H), 1.00 (t, J=7.4 Hz, 3H).

Example 84: Synthesis of YS36-56

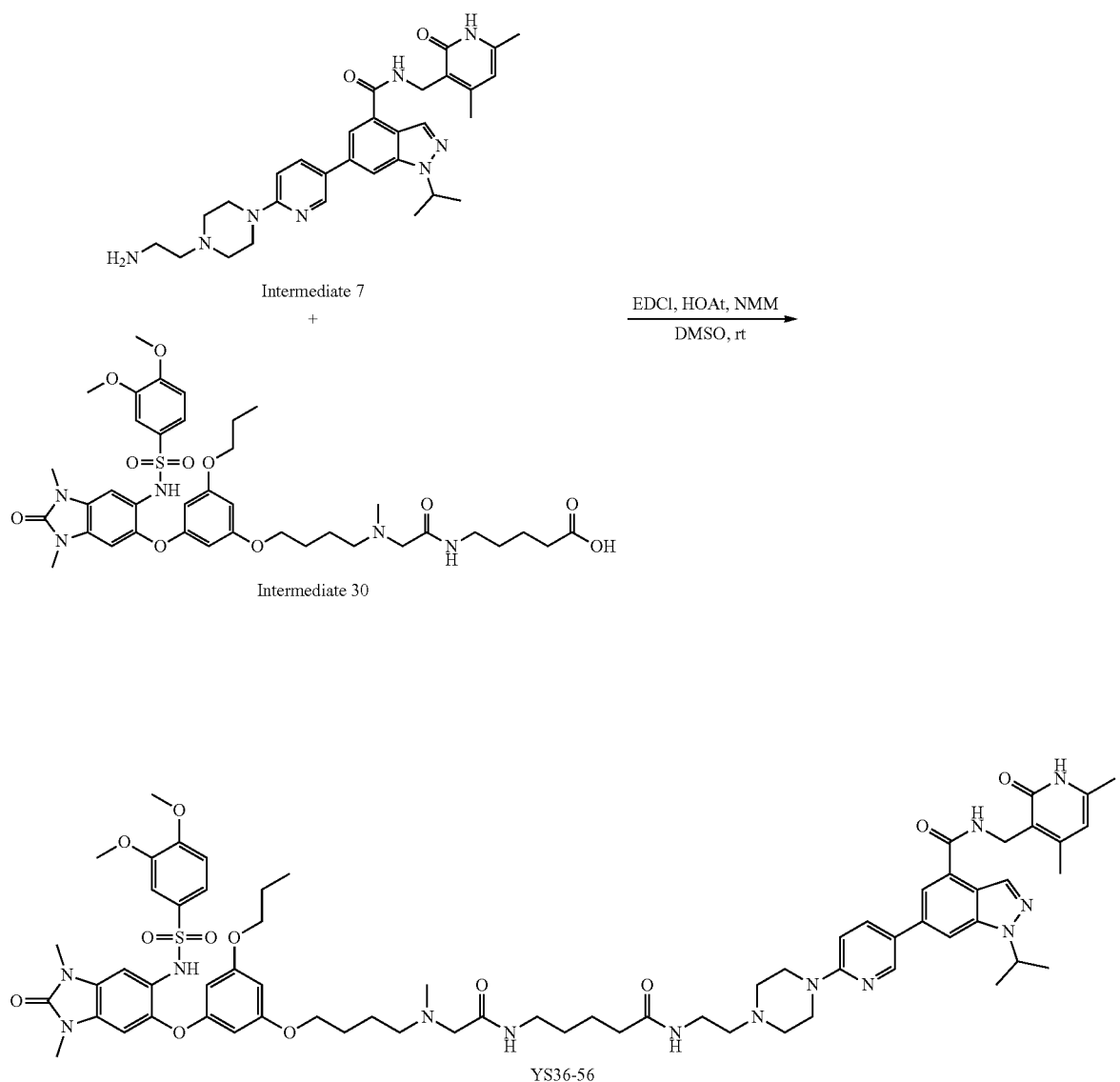

YS36-56 was synthesized according to the procedures for preparing YS36-48 from intermediate 30 (10 mg, 0.01 mmol), HOAt (4.3 mg, 0.03 mmol), intermediate 7 (10 mg, 0.01 mmol), NMM (14 µL, 0.13 mmol), EDCI (6.1 mg, 0.03 mmol), and DMSO (1.0 mL). YS36-56 was obtained as white solid in TFA salt form (9 mg, 58%). $^1$H NMR (600 MHz, CD$_3$OD) δ 8.58 (d, J=2.6 Hz, 1H), 8.36 (s, 1H), 8.14 (dd, J=8.9, 2.6 Hz, 1H), 7.96 (s, 1H), 7.78 (d, J=1.3 Hz, 1H), 7.33 (s, 1H), 7.20 (dd, J=8.4, 2.2 Hz, 1H), 7.15 (d, J=2.3 Hz, 1H), 7.12 (d, J=8.9 Hz, 1H), 6.78-6.77 (m, 1H), 6.61 (s, 1H), 6.18 (s, 1H), 6.14 (t, J=2.2 Hz, 1H), 5.77-5.75 (m, 1H), 5.64-5.60 (m, 1H), 5.09 (p, J=6.6 Hz, 1H), 4.58 (s, 2H), 3.91 (bs, 8H), 3.86 (d, J=5.8 Hz, 2H), 3.80 (s, 3H), 3.76 (t, J=6.5 Hz, 2H), 3.61-3.63 (m, 5H), 3.53 (bs, 4H), 3.40 (s, 3H), 3.35 (d, J=6.0 Hz, 2H), 3.26 (s, 2H), 3.24 (s, 3H), 2.95-2.92 (m, 3H), 2.44 (s, 3H), 2.26 (d, J=4.4 Hz, 5H), 1.91 (q, J=8.0 Hz, 2H), 1.82 (d, J=7.0 Hz, 2H), 1.73 (h, J=7.1 Hz, 2H), 1.63 (p, J=7.3 Hz, 2H), 1.57 (dd, J=7.5, 4.8 Hz, 8H), 1.02-0.97 (m, 3H).

Example 85: Synthesis of YS36-57

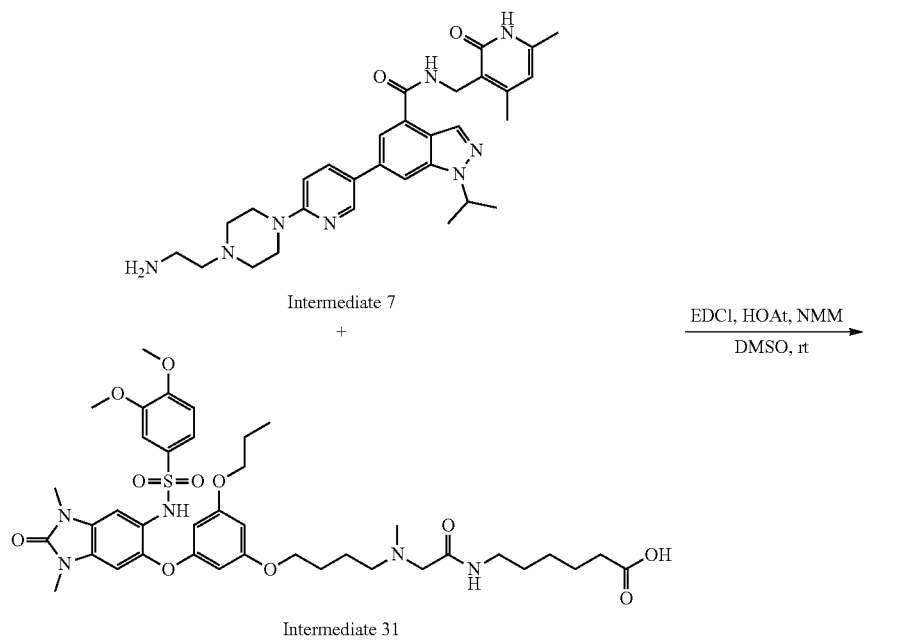

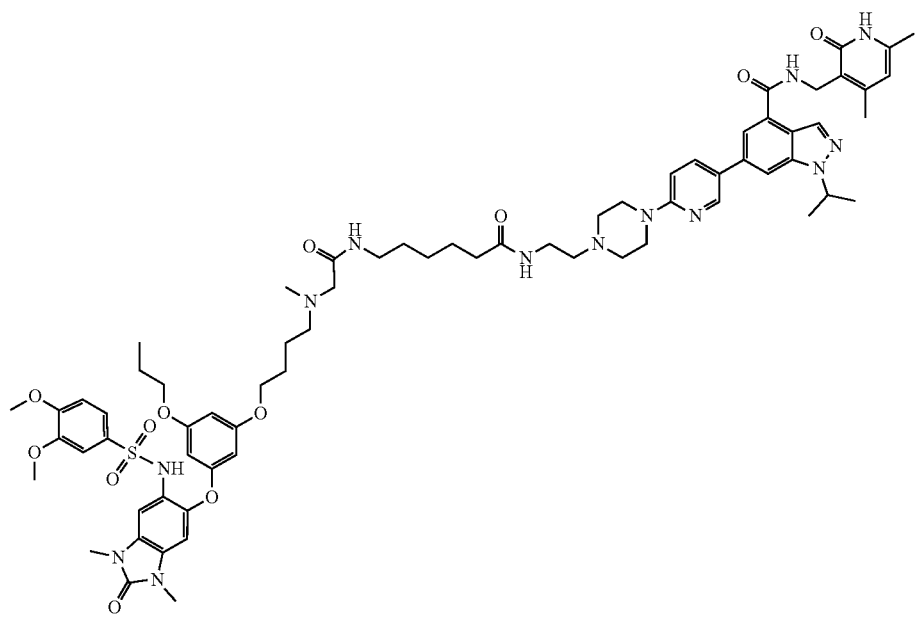

YS36-57 was synthesized according to the procedures for preparing YS36-48 from intermediate 31 (10 mg, 0.01 mmol), HOAt (4.3 mg, 0.03 mmol), intermediate 7 (10 mg, 0.01 mmol), NMM (14 μL, 0.13 mmol), EDCI (6.1 mg, 0.03 mmol), and DMSO (1.0 mL). YS36-57 was obtained as white solid in TFA salt form (9 mg, 58%). $^1$H NMR (600 MHz, CD$_3$OD) δ 8.58 (d, J=2.5 Hz, 1H), 8.36 (s, 1H), 8.15 (dd, J=9.0, 2.5 Hz, 1H), 7.96 (s, 1H), 7.78 (d, J=1.2 Hz, 1H), 7.33 (s, 1H), 7.22-7.09 (m, 3H), 6.78 (d, J=8.5 Hz, 1H), 6.61 (s, 1H), 6.18 (s, 1H), 6.14 (t, J=2.2 Hz, 1H), 5.76 (t, J=2.1 Hz, 1H), 5.60 (t, J=2.1 Hz, 1H), 5.09 (p, J=6.6 Hz, 1H), 4.58 (s, 2H), 3.91 (bs, 8H), 3.84 (d, J=5.9 Hz, 2H), 3.80 (s, 3H), 3.77 (t, J=6.5 Hz, 2H), 3.61-3.63 (m, 5H), 3.53 (bs, 4H), 3.41 (s, 3H), 3.35 (t, J=5.9 Hz, 2H), 3.24 (s, 5H), 2.94 (s, 3H), 2.44 (s, 3H), 2.26 (s, 3H), 2.23 (t, J=7.7 Hz, 2H), 1.91 (q, J=8.3 Hz, 2H), 1.81 (q, J=7.2, 6.6 Hz, 2H), 1.74 (h, J=7.1 Hz, 2H), 1.61 (t, J=7.7 Hz, 2H), 1.57 (d, J=6.6 Hz, 6H), 1.52 (d, J=7.7 Hz, 2H), 1.35 (q, J=8.1 Hz, 2H), 1.00 (t, J=7.4 Hz, 3H).

Example 86: Synthesis of YS36-58

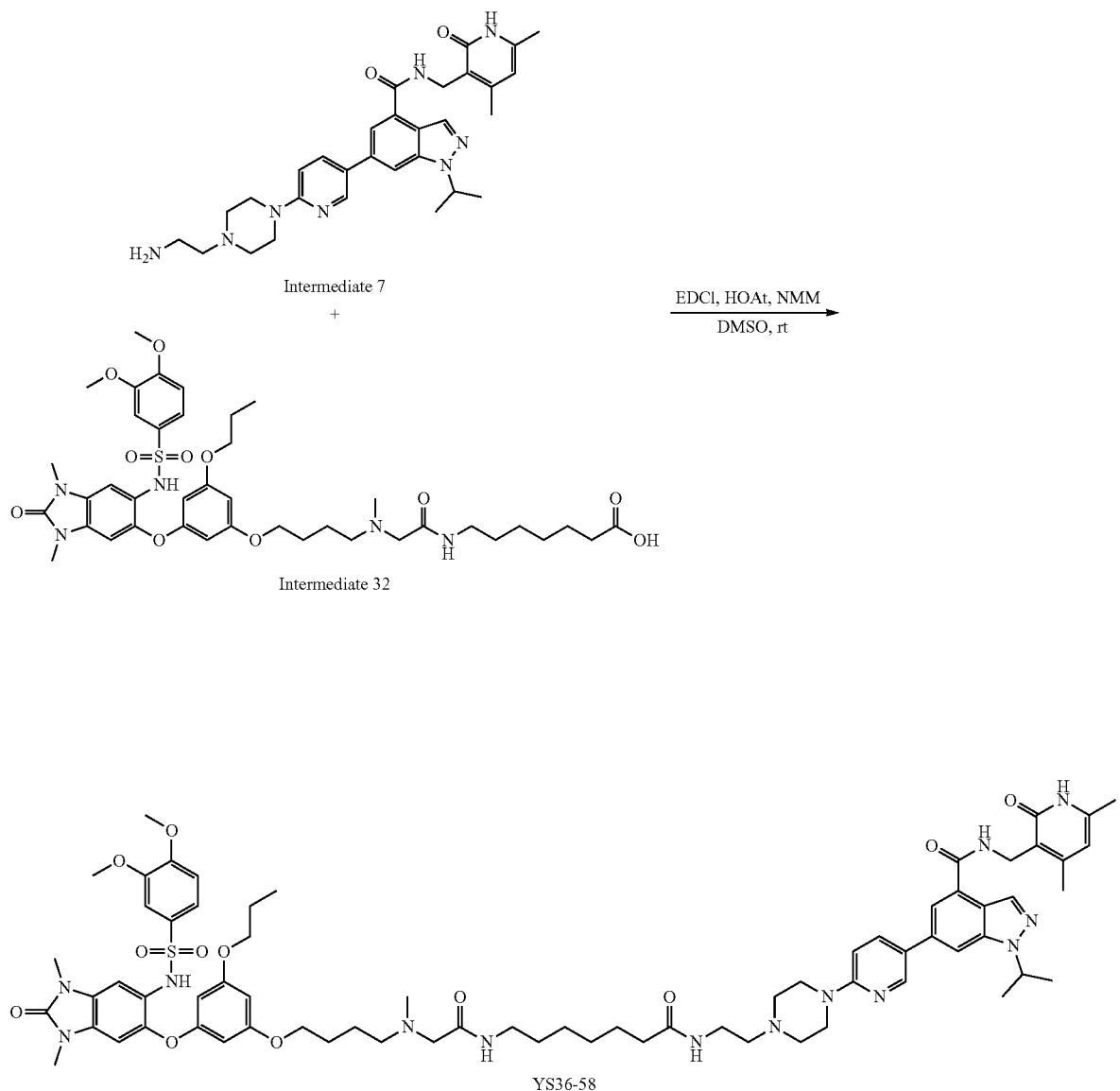

YS36-58 was synthesized according to the procedures for preparing YS36-48 from intermediate 32 (10 mg, 0.01 mmol), HOAt (4.3 mg, 0.03 mmol), intermediate 7 (10 mg, 0.01 mmol), NMM (14 μL, 0.13 mmol), EDCI (6.1 mg, 0.03 mmol), and DMSO (1.0 mL). YS36-58 was obtained as white solid in TFA salt form (11 mg, 70%). $^1$H NMR (600 MHz, CD$_3$OD) δ 8.61 (d, J=2.5 Hz, 1H), 8.35 (s, 1H), 8.11-8.08 (m, 1H), 7.94 (s, 1H), 7.77 (s, 1H), 7.34 (s, 1H), 7.21 (dd, J=8.5, 2.1 Hz, 1H), 7.16 (d, J=2.2 Hz, 1H), 7.07 (s, 1H), 6.79 (d, J=8.5 Hz, 1H), 6.61 (s, 1H), 6.14 (s, 2H), 5.79 (t, J=2.1 Hz, 1H), 5.59 (t, J=2.2 Hz, 1H), 5.09-5.07 (m, 1H), 4.57 (s, 2H), 3.98 (bs, 8H), 3.85 (t, J=5.9 Hz, 2H), 3.80 (s, 3H), 3.77 (t, J=6.5 Hz, 2H), 3.61-3.63 (m, 5H), 3.53 (bs, 4H), 3.41 (s, 3H), 3.34 (s, 2H), 3.19 (s, 5H), 2.93 (s, 3H), 2.44 (s, 2H), 2.25-2.21 (m, 5H), 1.94-1.90 (m, 3H), 1.81 (t, J=7.2 Hz, 2H), 1.74 (d, J=7.1 Hz, 2H), 1.57 (d, J=6.6 Hz, 8H), 1.51 (d, J=7.0 Hz, 2H), 1.34-1.31 (m, 4H), 1.01 (t, J=7.4 Hz, 3H).

Example 87: Synthesis of YS36-59

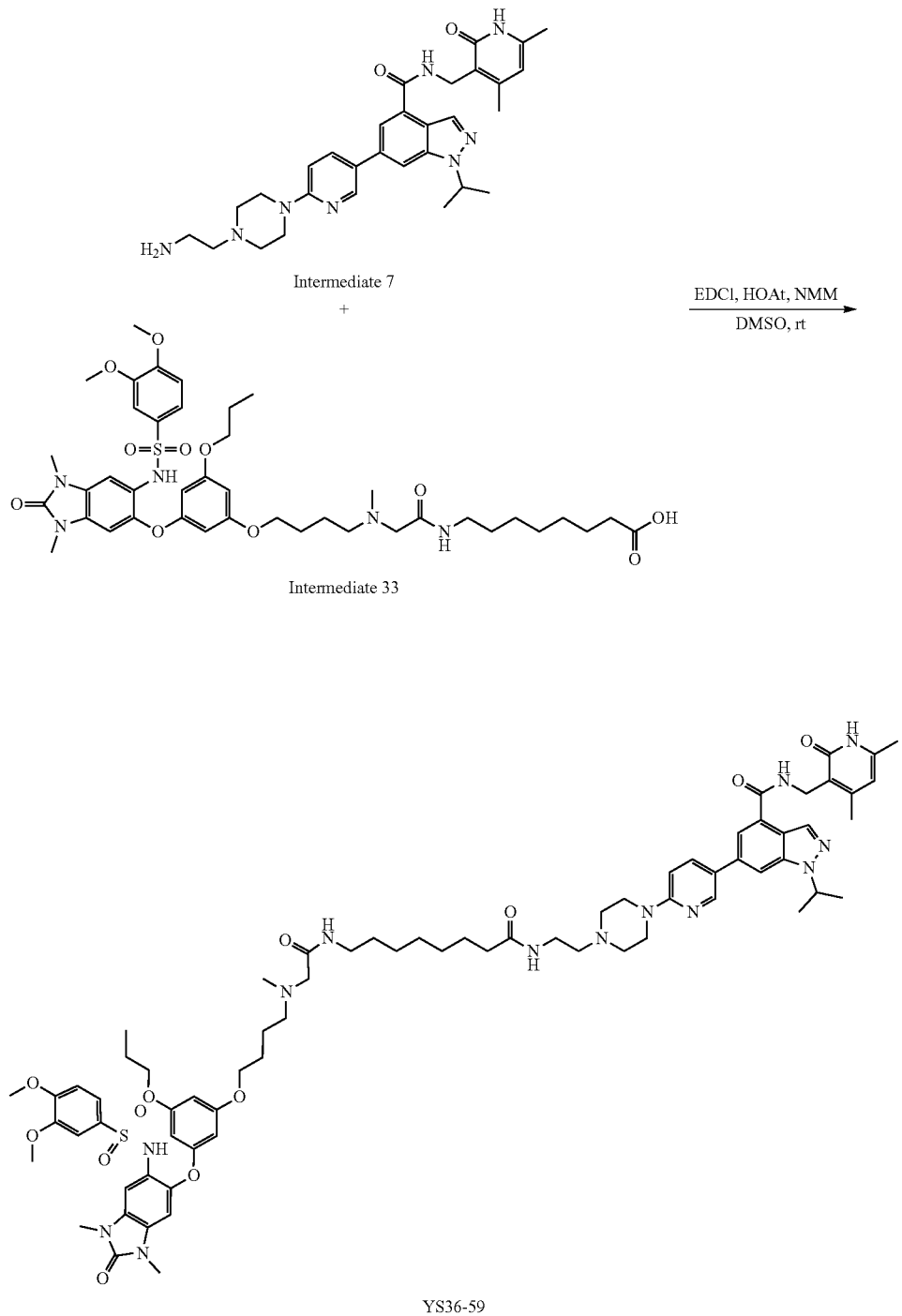

YS36-59 was synthesized according to the procedures for preparing YS36-48 from intermediate 33 (10 mg, 0.01 mmol), HOAt (4.3 mg, 0.03 mmol), intermediate 7 (10 mg, 0.01 mmol), NMM (14 µL, 0.13 mmol), EDCI (6.1 mg, 0.03 mmol), and DMSO (1.0 mL). YS36-59 was obtained as white solid in TFA salt form (12 mg, 76%). $^1$H NMR (600 MHz, CD$_3$OD) δ 8.59 (d, J=2.5 Hz, 1H), 8.36 (s, 1H), 8.13 (dd, J=8.9, 2.6 Hz, 1H), 7.95 (s, 1H), 7.78 (d, J=1.3 Hz, 1H), 7.34 (s, 1H), 7.23-7.08 (m, 3H), 6.78 (d, J=8.5 Hz, 1H), 6.61 (s, 1H), 6.19-6.13 (m, 2H), 5.77 (t, J=2.1 Hz, 1H), 5.59 (t, J=2.2 Hz, 1H), 5.11-5.06 (m, 1H), 4.58 (s, 2H), 3.90 (bs, 8H), 3.85 (t, J=5.9 Hz, 2H), 3.80 (s, 3H), 3.77 (t, J=6.5 Hz, 2H), 3.62-3.63 (m, 5H), 3.53 (m, 4H), 3.41 (s, 3H), 3.35 (t, J=5.9 Hz, 2H), 3.24 (s, 5H), 2.93 (s, 3H), 2.44 (s, 3H), 2.27-2.20 (m, 5H), 1.92 (p, J=7.7 Hz, 2H), 1.81 (p, J=6.2 Hz, 2H), 1.73 (p, J=7.0 Hz, 2H), 1.57 (d, J=6.6 Hz, 8H), 1.49 (d, J=7.0 Hz, 2H), 1.34-1.29 (m, 6H), 1.01 (t, J=7.4 Hz, 3H).

Example 88: Synthesis of XY028-086
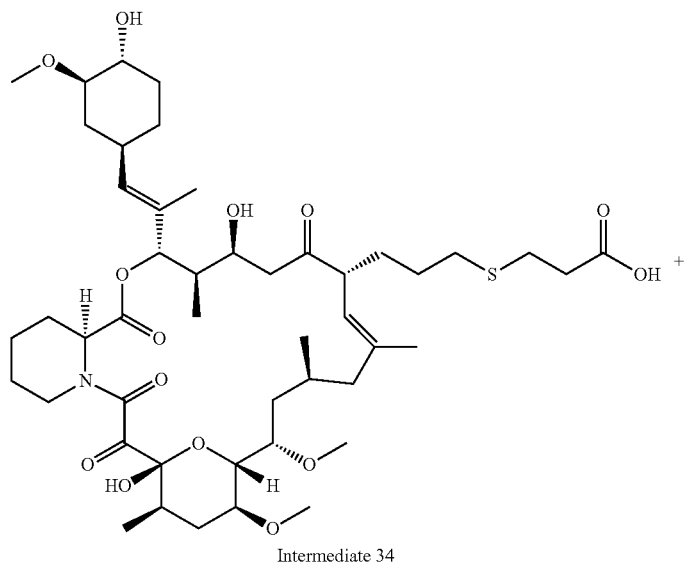
Intermediate 34
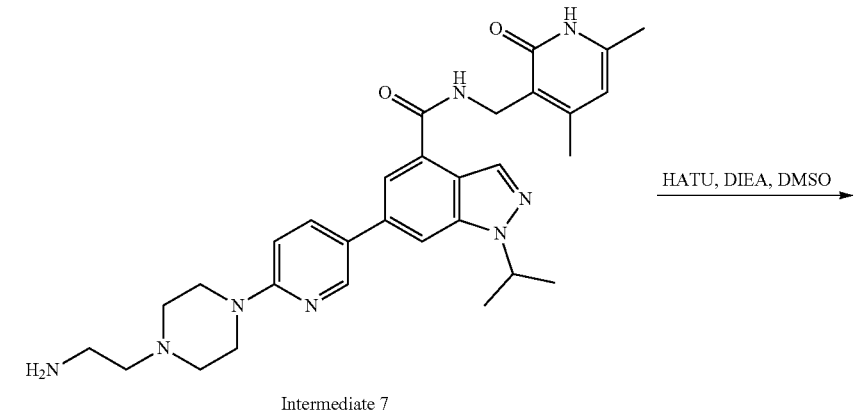
Intermediate 7
HATU, DIEA, DMSO
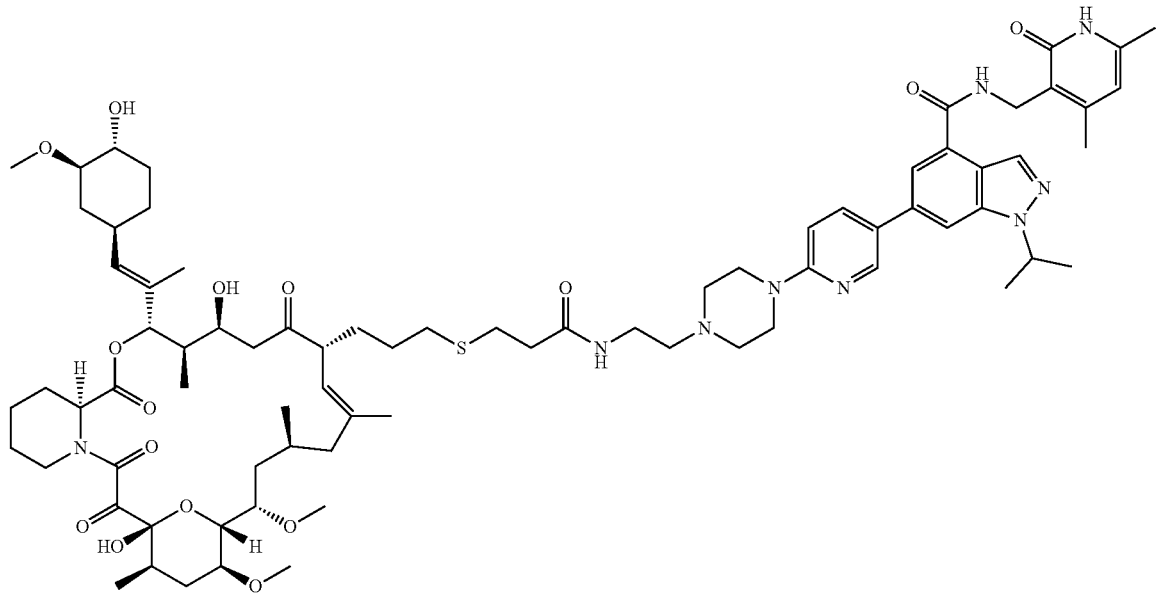
XY028-086
Intermediate 34 (20 mg, 0.02 mmol), intermediate 7 (15 mg, 0.02 mmol) and DIPEA (16 μL, 0.09 mmol) were dissolved in DMSO (1.0 mL). To the solution were added HATU (17 mg, 0.04 mmol) at room temperature. After being stirred overnight at room temperature, the mixture was purified by preparative HPLC (10%-100% methanol/0.1% TFA in H₂O) to afford XY028-086 as white solid in TFA salt form. ¹H NMR (600 MHz, CD₃OD) δ 8.58 (s, 1H), 8.38 (s, 1H), 8.22-8.13 (m, 1H), 7.98 (s, 1H), 7.80 (s, 1H), 7.18 (t, J=10.2 Hz, 1H), 6.21 (s, 1H), 5.28-5.20 (m, 1H), 5.18 (d, J=8.1 Hz, 1H), 5.14-5.02 (m, 2H), 4.59 (s, 2H), 4.32 (d, J=12.8 Hz, 1H), 4.21-3.83 (m, 4H), 3.80-3.46 (m, 10H), 3.45-3.33 (m, 10H), 3.07-2.66 (m, 5H), 2.62-2.50 (m, 4H), 2.45 (s, 3H), 2.37-2.24 (m, 5H), 2.21-0.70 (m, 51H).
Example 89: Synthesis of CZ40-72
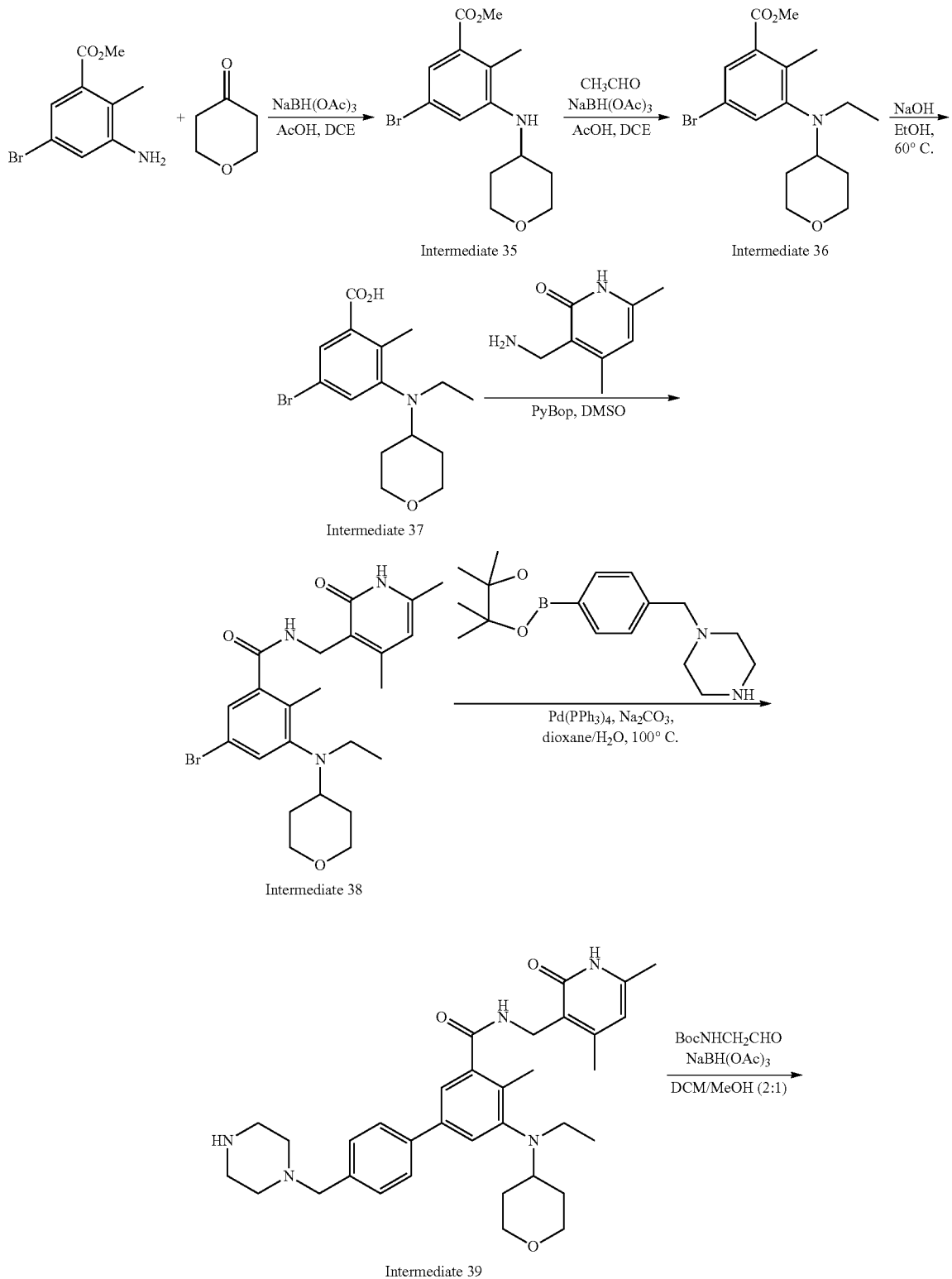

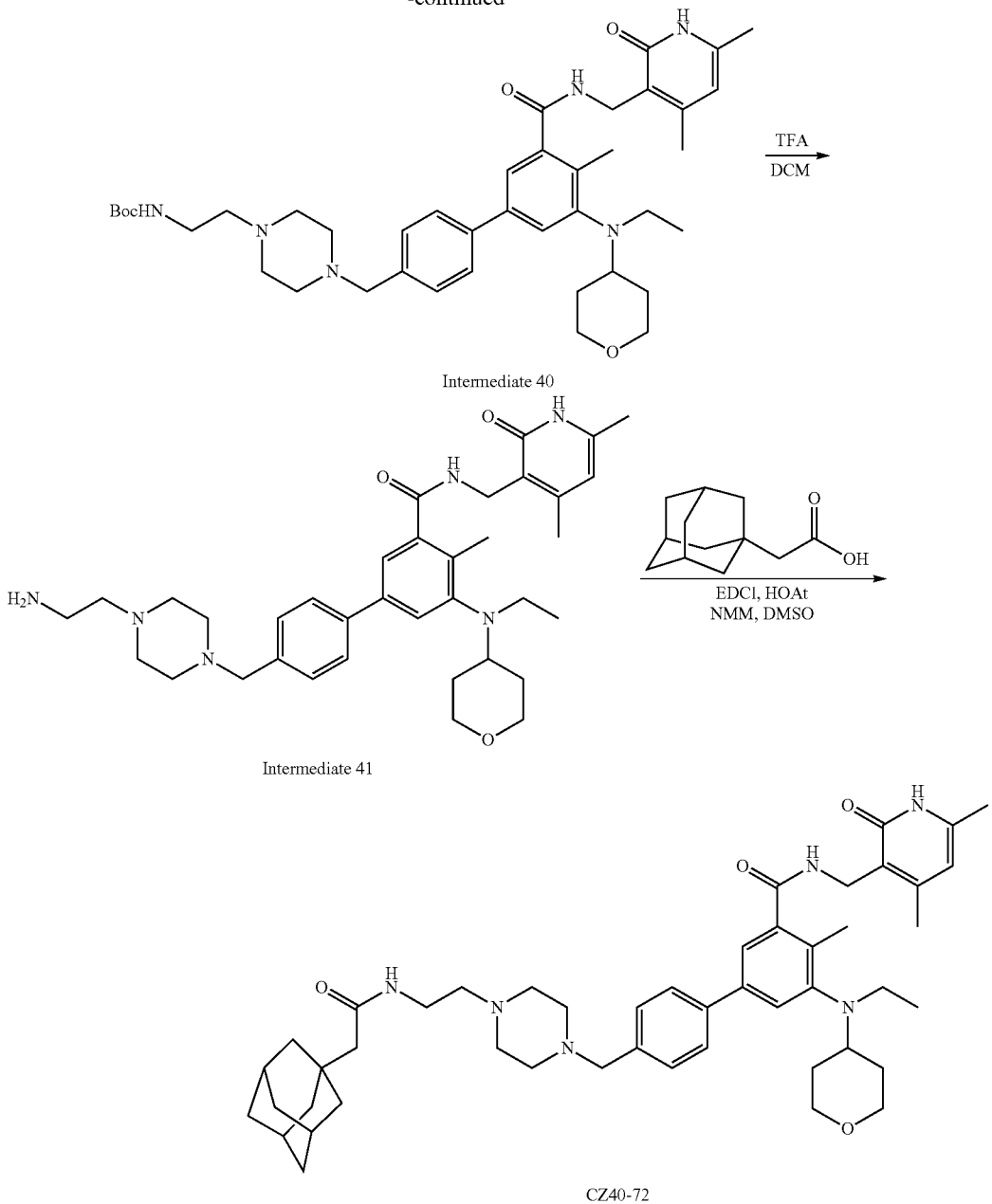

Intermediate 39 was synthesized from methyl 3-amino-5-bromo-2-methylbenzoate according to the Patent WO2012142504.

Intermediate 39 (228 mg, 0.40 mmol) and N-Boc-2-aminoacetaldehyde (96 mg, 0.60 mmol) were dissolved in DCM (4.0 mL), and methanol (2.0 mL). To the solution was added sodium triacetoxyborohydride (254 mg, 1.2 mmol) at 0° C. After being stirred overnight at room temperature, the mixture was quenched with water and extracted with DCM (10 mL for 3 times), dried and purified by ISCO™ (DCM/MeOH=20:1 to 10:1) to afford intermediate 40 (85 mg, 30%) as white solid.

Intermediate 40 (85 mg, 0.12 mmol) was dissolved in DCM (1.0 mL) and treated with trifluoroacetic acid (1.0 mL) at room temperature for 2 h. The mixture was concentrated and dried to give the crude intermediate 41 in TFA salt form. This product was used directly in the next step without further purification.

Intermediate 41 (14 mg, 0.02 mmol) was dissolved in DMSO (1.0 mL). 1-Adamantaneacetic acid (4 mg, 0.02 mmol), HOAt (4 mg, 0.03 mmol), EDCI (6 mg, 0.03 mmol), and NMM (11 μL, 0.09 mmol) were added to the solution subsequently at room temperature. After being stirred overnight, the reaction mixture was purified by prepared HPLC to afford CZ40-72 (11 mg, 75%) as white solid in TFA salt form. $^1$H NMR (600 MHz, CD$_3$OD) δ 7.86 (s, 1H), 7.77 (d, J=7.9 Hz, 2H), 7.70 (s, 1H), 7.56 (d, J=7.9 Hz, 2H), 6.14 (s, 1H), 4.50 (s, 2H), 4.12 (s, 2H), 3.99 (d, J=11.5 Hz, 2H), 3.70 (s, 2H), 3.46 (t, J=6.2 Hz, 2H), 3.38 (t, J=11.8 Hz, 2H), 3.24-3.14 (m, 9H), 3.01 (t, J=6.1 Hz, 2H), 2.43 (s, 3H), 2.40 (s, 3H), 2.25 (s, 3H), 1.94 (s, 2H), 1.93 (brs, 4H), 1.74-1.72 (m, 3H), 1.67-1.60 (m, 12H), 1.03 (t, J=7.0 Hz, 3H). ESI m/z=791.51 [M+H]$^+$.

Example 90: Synthesis of CZ40-73

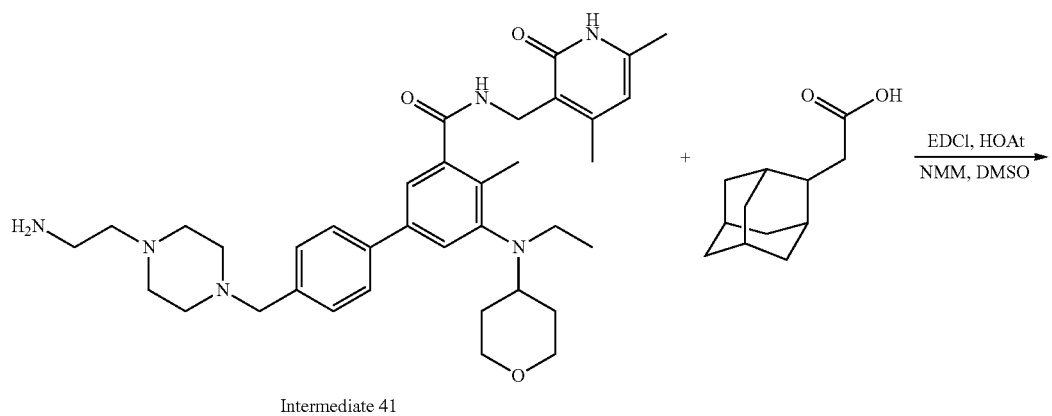

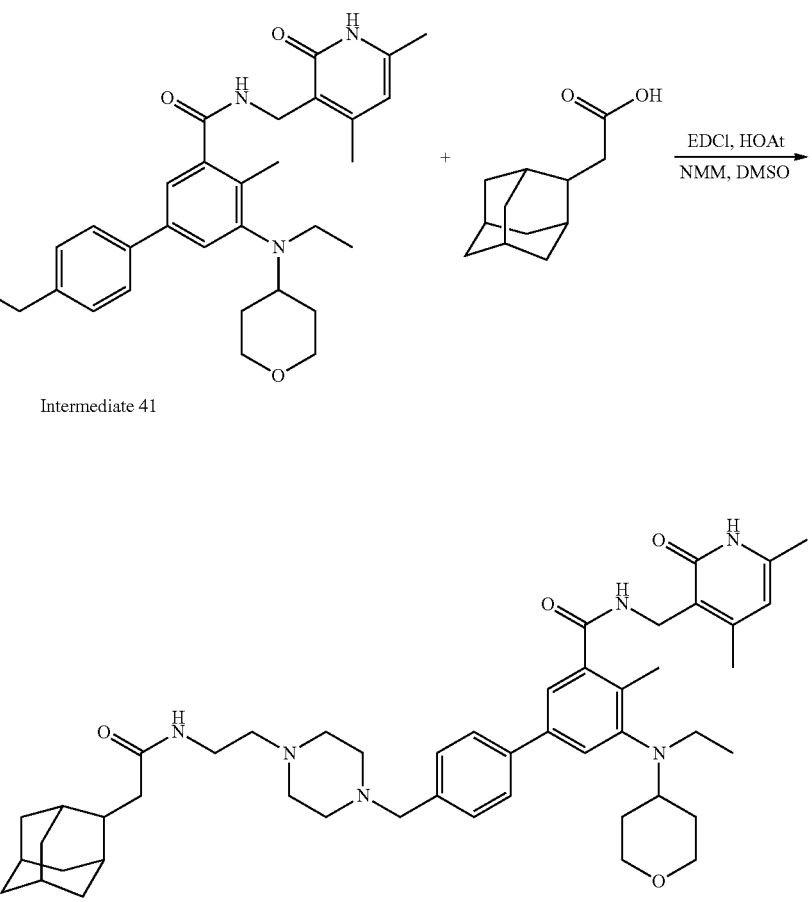

Intermediate 41 (14 mg, 0.02 mmol) was dissolved in DMSO (1.0 mL). 2-Adamantaneacetic acid (4 mg, 0.02 mmol), HOAt (4 mg, 0.03 mmol), EDCI (6 mg, 0.03 mmol), and NMM (11 μL, 0.09 mmol) were added to the solution subsequently at room temperature. After being stirred overnight, the reaction mixture was purified by prepared HPLC to afford CZ40-73 (10 mg, 68%) as white solid in TFA salt form. $^1$H NMR (600 MHz, CD$_3$OD) δ 7.86 (s, 1H), 7.77 (d, J=7.9 Hz, 2H), 7.70 (s, 1H), 7.57 (d, J=8.2 Hz, 2H), 6.14 (s, 1H), 4.50 (s, 2H), 4.13 (s, 2H), 3.99 (d, J=11.6 Hz, 2H), 3.69 (s, 2H), 3.46 (t, J=6.1 Hz, 2H), 3.38 (t, J=11.8 Hz, 2H), 3.23-3.15 (m, 9H), 3.01 (t, J=6.1 Hz, 2H), 2.43 (s, 3H), 2.39 (s, 3H), 2.37 (d, J=7.8 Hz, 2H), 2.25 (s, 3H), 2.20 (t, J=8.2 Hz, 1H), 1.93 (d, J=13.1 Hz, 2H), 1.86 (d, J=12.6 Hz, 4H), 1.81-1.73 (m, 8H), 1.66 (s, 2H), 1.56 (d, J=12.8 Hz, 2H), 1.02 (t, J=7.0 Hz, 3H). ESI m/z=791.51 [M+H]$^+$.

Example 91: Synthesis of CZ40-75

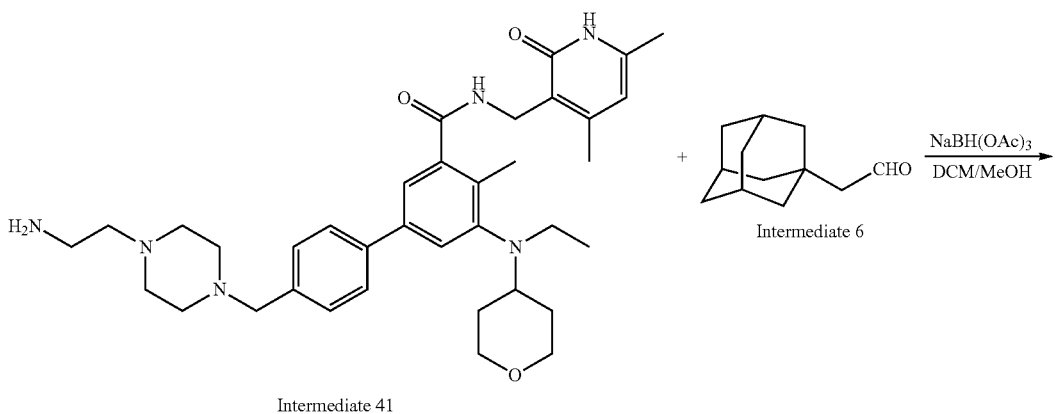

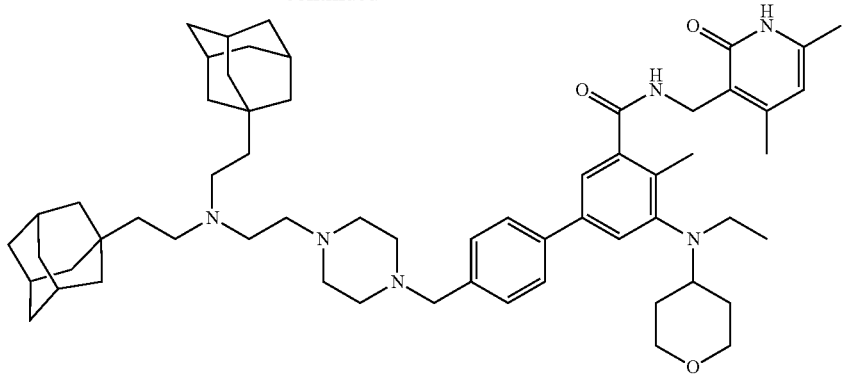

CZ40-75

Intermediate 41 (14 mg, 0.02 mmol) and intermediate 6 (12 mg, 0.06 mmol) were dissolved in DCM (4.0 mL), and methanol (2.0 mL). To the solution was added sodium triacetoxy borohydride (13 mg, 0.06 mmol) at 0° C. After being stirred overnight at room temperature, the mixture was quenched with water and extracted with DCM (10 mL for 3 times), dried and purified by prepared HPLC to afford CZ40-75 (12 mg, 77%) as white solid in TFA salt form. $^1$H NMR (600 MHz, CD$_3$OD) δ 7.57 (d, J=8.4 Hz, 2H), 7.46 (d, J=1.9 Hz, 1H), 7.40 (d, J=8.4 Hz, 2H), 7.32 (d, J=1.9 Hz, 1H), 6.13 (s, 1H), 4.49 (s, 2H), 3.95-3.89 (m, 2H), 3.74 (s, 2H), 3.37 (dd, J=11.7, 2.1 Hz, 2H), 3.27-3.09 (m, 9H), 2.72-2.66 (m, 10H), 2.39 (s, 3H), 2.32 (s, 3H), 2.25 (s 3H), 1.99-1.94 (m, 4H), 1.75 (d, J=12.4 Hz, 6H), 1.70-1.58 (m, 10H), 1.56 (d, J=2.8 Hz, 14H), 1.47-1.41 (m, 4H), 0.90 (t, J=7.0 Hz, 3H).

Example 92: Synthesis of CZ40-149

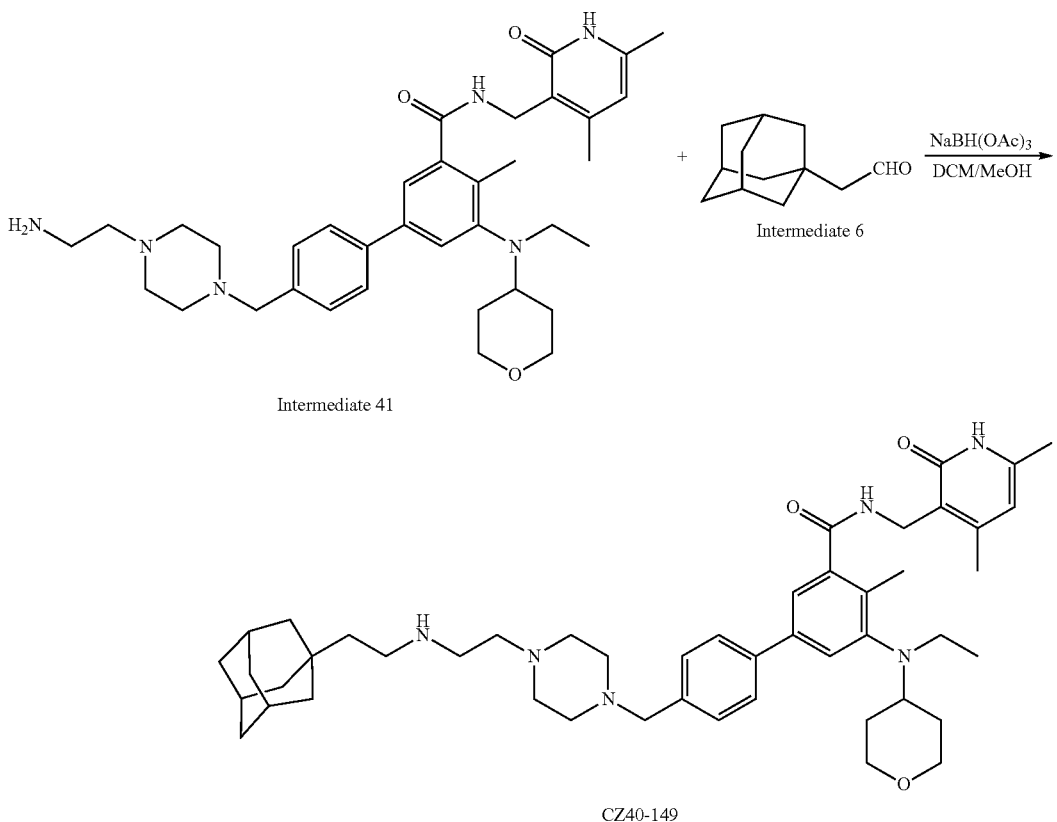

Intermediate 41

Intermediate 6

CZ40-149

Intermediate 41 (14 mg, 0.02 mmol) and intermediate 6 (4 mg, 0.02 mmol) were dissolved in DCM (2.0 mL), and methanol (1.0 mL). To the solution was added sodium triacetoxy borohydride (13 mg, 0.06 mmol) at room temperature. After being stirred overnight at room temperature, the mixture was quenched with water and extracted with DCM (10 mL for 3 times), dried and purified by prepared HPLC to afford CZ40-149 (8 mg, 51%) as white solid in TFA salt form. ¹H NMR (600 MHz, CD₃OD) δ 7.56 (d, J=7.9 Hz, 2H), 7.45 (d, J=1.7 Hz, 1H), 7.41 (d, J=7.9 Hz, 2H), 7.32 (d, J=1.8 Hz, 1H), 6.12 (s, 1H), 5.12 (s, 1H), 4.49 (s, 2H), 3.92 (d, J=11.6 Hz, 2H), 3.66 (s, 2H), 3.40-3.33 (m, 3H), 3.13 (ddt, J=23.6, 11.7, 5.4 Hz, 5H), 3.07-3.02 (m, 2H), 2.68-2.54 (m, 8H), 2.39 (s, 3H), 2.32 (s, 3H), 2.24 (s, 3H), 1.96 (s, 2H), 1.76 (d, J=12.2 Hz, 4H), 1.71-1.61 (m, 5H), 1.56 (d, J=2.8 Hz, 6H), 1.47-1.42 (m, 2H), 1.28 (s, 2H), 0.90 (t, J=7.0 Hz, 3H).

Example 93: Synthesis of CZ40-74

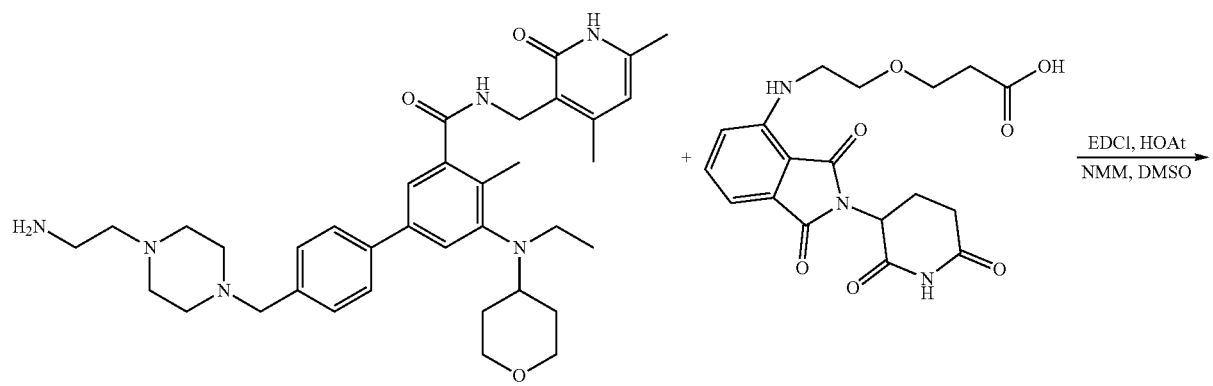

Intermediate 41

0.02 mmol), HOAt (4 mg, 0.03 mmol), EDCI (6 mg, 0.03 mmol), and NMM (11 µL, 0.09 mmol) were added to the solution subsequently at room temperature. After being stirred overnight, the reaction mixture was purified by prepared HPLC to afford CZ40-74 (5 mg, 28%) as yellow solid in TFA salt form. ¹H NMR (600 MHz, CD₃OD) δ 7.68-7.67 (m, 3H), 7.55-7.51 (m, 2H), 7.47 (d, J=8.0 Hz, 2H), 7.08 (d, J=8.4 Hz, 1H), 7.03 (d, J=7.2 Hz, 1H), 6.12 (s, 1H), 5.08-5.00 (m, 1H), 4.50 (s, 2H), 3.94 (brs, 6H), 3.76 (t, J=5.4 Hz, 2H), 3.68 (t, J=5.4 Hz, 2H), 3.48 (t, J=5.0 Hz, 2H), 3.44-3.33 (m, 6H), 3.09 (s, 4H), 2.93 (s, 6H), 2.83 (ddd, J=17.7, 14.0, 5.3 Hz, 2H), 2.76-2.63 (m, 2H), 2.50-2.43 (m, 2H), 2.39 (d, J=4.0 Hz, 6H), 2.24 (s, 3H), 2.11-2.07 (m, 1H), 1.74 (s, 2H), 0.97 (s, 3H). ESI m/z=986.50 [M+H]⁺.

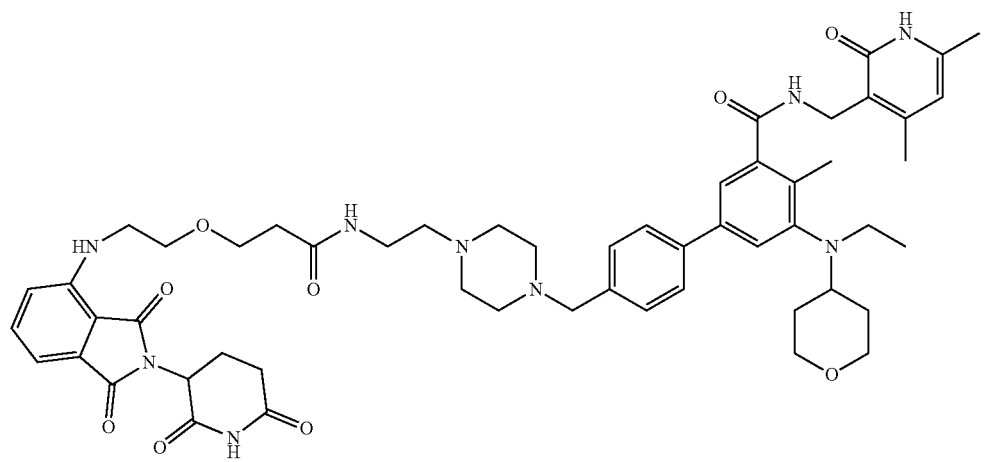

CZ40-74

Intermediate 41 (14 mg, 0.02 mmol) was dissolved in DMSO (1.0 mL). 3-(2-((2-(2,6-dioxopiperidin-3-yl)-1,3-dioxoisoindolin-4-yl)amino) ethoxy) propanoic acid (8 mg, Example 94: Synthesis of CZ40-131
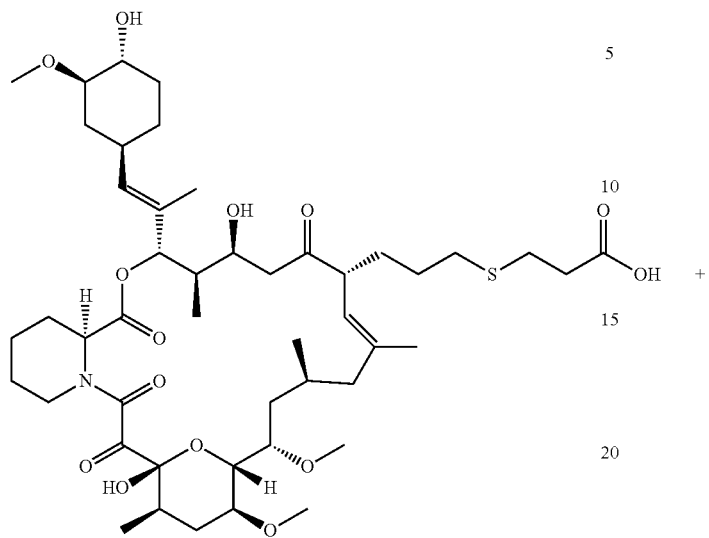
Intermediate 34
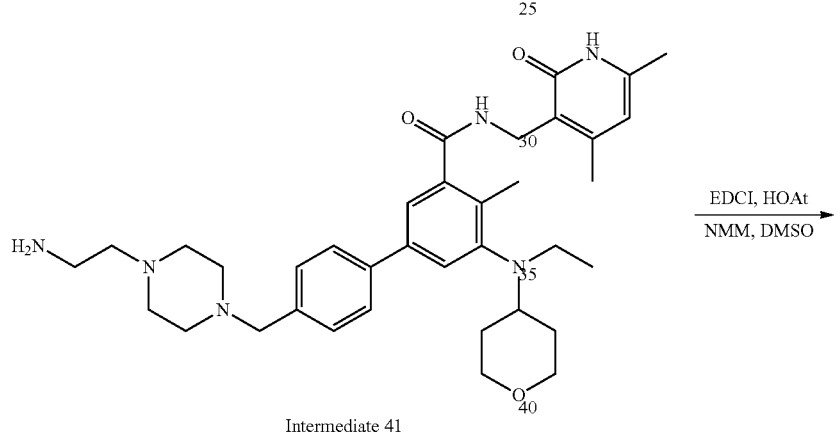
Intermediate 41
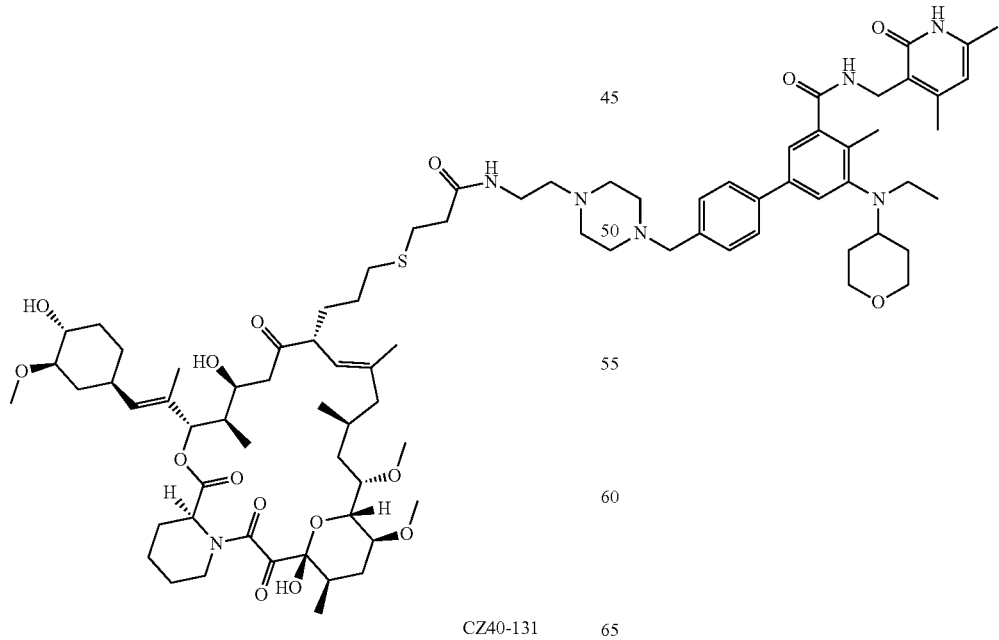
CZ40-131

Intermediate 41 (14 mg, 0.02 mmol) was dissolved in DMSO (1.0 mL). Intermediate 34 (16 mg, 0.02 mmol), HOAt (4 mg, 0.03 mmol), EDCI (6 mg, 0.03 mmol), and NMM (11 μL, 0.09 mmol) were added to the solution subsequently at room temperature. After being stirred overnight, the reaction mixture was purified by prepared HPLC to afford CZ40-31 (14 mg, 47%) as white solid in TFA salt form. $^1$H NMR (600 MHz, CD$_3$OD) δ 7.90 (s, 1H), 7.78 (d, J=7.9 Hz, 2H), 7.74 (s, 1H), 7.58 (dd, J=8.3, 3.2 Hz, 2H), 6.15 (s, 1H), 5.28-4.97 (m, 3H), 4.65 (s, 1H), 4.51 (s, 2H), 4.33 (d, J=13.4 Hz, 1H), 4.14 (d, J=8.4 Hz, 2H), 4.03-3.97 (m, 4H), 3.74 (dd, J=9.7, 2.9 Hz, 2H), 3.69-3.67 (m, 1H), 3.61 (dt, J=11.9, 5.6 Hz, 1H), 3.51 (q, J=6.0 Hz, 4H), 3.40-3.32 (m, 12H), 3.20 (brs, 4H), 3.10 (q, J=6.2 Hz, 2H), 3.06-2.92 (m, 2H), 2.82 (dd, J=14.4, 5.2 Hz, 1H), 2.80-2.69 (m, 2H), 2.57-2.45 (m, 4H), 2.44 (s, 3H), 2.40 (s, 3H), 2.37-2.28 (m, 3H), 2.25 (s, 3H), 2.21-1.17 (m, 34H), 1.14-1.01 (m, 4H), 0.98-0.84 (m, 12H). ESI m/z=1506.87 [M+H]$^+$.

Example 95: Synthesis of AM41-36A

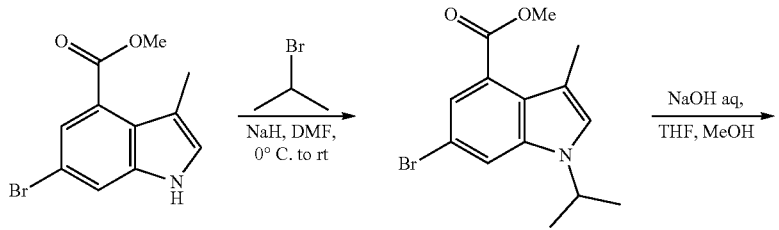

Intermediate 42

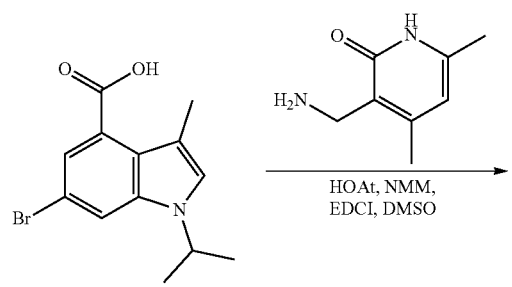

Intermediate 43

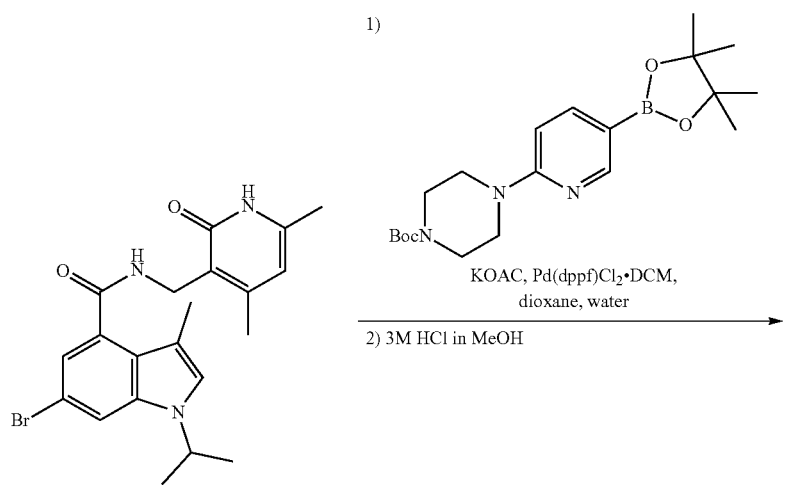

Intermediate 44

-continued
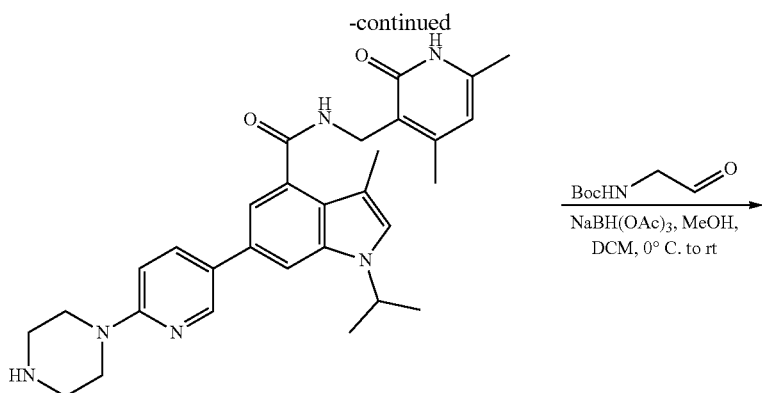
Intermediate 45
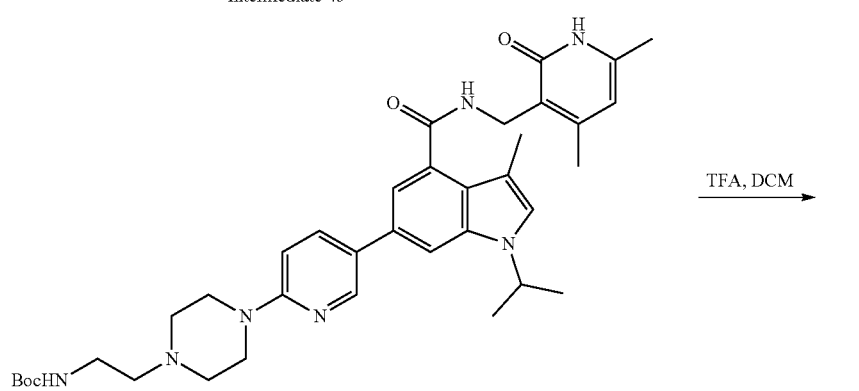
Intermediate 46
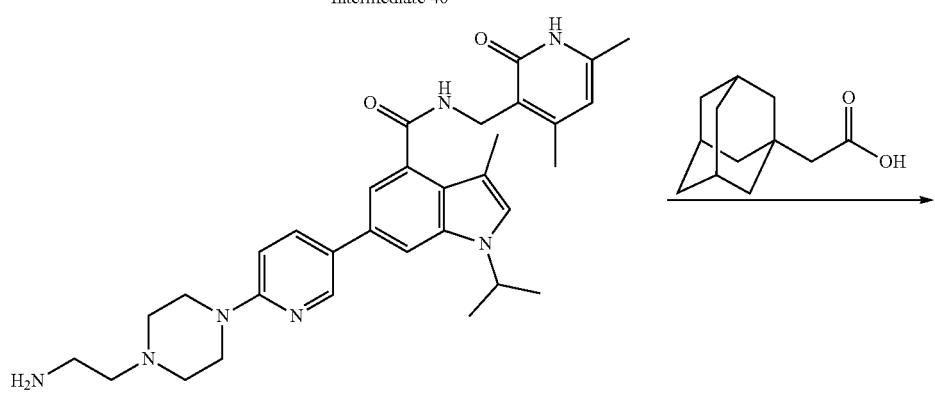
Intermediate 47
AM41-36A Intermediate 47 (20 mg, 0.03 mmol), HOAt (6 mg, 0.05 mmol), 1-adamantaneacetic acid (7 mg, 0.04 mmol), and EDCI (9 mg, 0.05 mmol) were dissolved in DMSO (1.0 mL). To the solution was added NMM (14 µL, 0.12 mmol) at room temperature. After being stirred overnight at room temperature, the mixture was purified by preparative HPLC (10%-100% methanol/0.1% TFA in $H_2O$) to afford AM41-36A as off-white solid in TFA salt form (25 mg, 100%). $^1H$ NMR (600 MHz, CD: OD) 8.44 (d, J=2.3 Hz, 1H), 8.30 (dd, J=9.1, 2.4 Hz, 1H), 7.74 (d, J=1.0 Hz, 1H), 7.34-7.29 (m, 2H), 7.27 (s, 1H), 6.22 (s, 1H), 4.86-4.80 (m, 1H), 4.57 (s, 2H), 3.98 (s, 4H), 3.61 (dd, J=18.9, 12.9 Hz, 6H), 3.37-3.35 (m, 2H), 2.45 (s, 3H), 2.28 (s, 3H), 2.22 (s, 3H), 2.01 (s, 2H), 1.97 (brs, 3H), 1.79-1.72 (m, 3H), 1.71-1.64 (m, 9H), 1.50 (s, 3H), 1.49 (s, 3H).

Example 96: Synthesis of AM41-37A

AM41-37A was synthesized according to the procedures for preparing AM41-36A from AM41-35A (20 mg, 0.03 mmol), HOAt (6 mg, 0.05 mmol), 2-(adamantan-2-yl) acetic acid (7 mg, 0.04 mmol), EDCI (9 mg, 0.05 mmol), NMM (14 µL, 0.12 mmol), and DMSO (1.0 mL). AM41-37A was obtained as off-white solid in TFA salt form (21 mg, 83%). $^1H$ NMR (600 MHz, $CD_3OD$) δ 8.43 (d, J=2.3 Hz, 1H), 8.29 (dd, J=9.1, 2.4 Hz, 1H), 7.74 (d, J=1.3 Hz, 1H), 7.33-7.25 (m, 3H), 6.21 (s, 1H), 4.86-4.78 (m, 1H), 4.57 (s, 2H), 3.98 (brs, 4H), 3.62 (t, J=5.9 Hz, 2H), 3.56 (brs, 4H), 3.38-3.33 (m, 2H), 2.46-2.40 (m, 5H), 2.27 (s, 3H), 2.26-2.23 (m, 1H), 2.22 (s, 3H), 1.98-1.92 (m, 2H), 1.92-1.85 (m, 3H), 1.84-1.74 (m, 5H), 1.69 (brs, 2H), 1.61 (brs, 1H), 1.59 (brs, 1H), 1.50 (s, 3H), 1.49 (s, 3H).

Example 97: Synthesis of AM41-39A

AM41-39A was synthesized according to the procedures for preparing AM16-103A from AM41-35A (20 mg, 0.03 mmol), intermediate 6 (16 mg, 0.09 mmol), sodium triacetoxy borohydride (26 mg, 0.12 mmol), DCM (0.5 mL), and methanol (0.5 mL). AM41-39A was obtained as white solid (6 mg, 24%). $^1H$ NMR (600 MHz, $CD_3OD$) δ 8.44 (d, J=2.5 Hz, 1H), 7.92 (dd, J=8.9, 2.5 Hz, 1H), 7.64 (d, J=1.3 Hz, 1H), 7.27 (d, J=1.1 Hz, 1H), 7.20 (s, 1H), 6.91 (d, J=8.8 Hz, 1H), 6.12 (s, 1H), 4.82-4.76 (m, 1H), 4.56 (s, 2H), 3.64-3.52 (m, 4H), 3.30-3.27 (m, 2H), 3.25-3.19 (m, 4H), 2.75 (t, J=5.7 Hz, 2H), 2.70-2.60 (m, 4H), 2.43 (s, 3H), 2.24 (s, 3H), 2.22 (s, 3H), 1.98 (brs, 7H), 1.81-1.75 (m, 6H), 1.72-1.68 (m, 6H), 1.60-1.58 (m, 11H), 1.50 (s, 3H), 1.49 (s, 3H), 1.48-1.44 (m, 4H).

Example 98: Synthesis of AM41-41A

AM41-41A was synthesized according to the procedures for preparing AM16-103A from AM41-35A (20 mg, 0.03 mmol), intermediate 6 (5 mg, 0.03 mmol), sodium triacetoxy borohydride (26 mg, 0.12 mmol), DCM (0.5 mL), and methanol (0.5 mL). AM41-41A was obtained as white solid (10 mg, 46%). $^1H$ NMR (600 MHz, MeOD) δ 8.42 (d, J=2.2 Hz, 1H), 7.92 (dd, J=8.9, 2.4 Hz, 1H), 7.63 (s, 1H), 7.27 (s, 1H), 7.20 (s, 1H), 6.92 (d, J=8.9 Hz, 1H), 6.13 (s, 1H), 4.83-4.75 (m, 1H), 4.56 (s, 2H), 3.62-3.54 (m, 4H), 3.19 (t, J=5.7 Hz, 2H), 3.12-3.03 (m, 2H), 2.70 (t, J=5.7 Hz, 2H), 2.67-2.59 (m, 4H), 2.43 (s, 3H), 2.24 (s, 3H), 2.21 (s, 3H), 1.98 (brs, 5H), 1.78 (d, J=12.1 Hz, 2H), 1.70 (d, J=11.7 Hz, 2H), 1.58 (s, 6H), 1.50 (s, 3H), 1.49 (s, 3H), 1.40-1.34 (m, 2H).

Example 99: Synthesis of AM41-38A

AM41-38A was synthesized according to the procedures for preparing AM29-151A from AM41-35A (20 mg, 0.03 mmol), HATU (23 mg, 0.06 mmol), 3-(2-((2-(2,6-dioxopiperidin-3-yl)-1,3-dioxoisoindolin-4-yl)amino) ethoxy) propanoic acid (14 mg, 0.04 mmol), DIPEA (21 µL, 0.12 mmol), and DMF (1.0 mL). AM41-38A was obtained as yellow solid in TFA salt form (16 mg, 51%). $^1H$ NMR (600 MHz, $CD_3OD$) δ 8.38 (d, J=2.1 Hz, 1H), 8.20 (dd, J=9.1, 2.2 Hz, 1H), 7.72 (s, 1H), 7.51 (dd, J=8.4, 7.2 Hz, 1H), 7.30 (d, J=1.0 Hz, 1H), 7.27 (s, 1H), 7.20 (d, J=9.2 Hz, 1H), 7.07 (d, J=8.6 Hz, 1H), 6.98 (d, J=7.0 Hz, 1H), 6.21 (s, 1H), 5.04 (dd, J=12.7, 5.5 Hz, 1H), 4.86-4.80 (m, 1H), 4.57 (s, 2H), 3.92 (brs, 4H), 3.80 (t, J=5.7 Hz, 2H), 3.71 (t, J=4.9 Hz, 2H), 3.65-3.41 (m, 9H), 3.37-3.31 (m, 2H), 2.88-2.77 (m, 1H), 2.75-2.61 (m, 2H), 2.53 (t, J=5.6 Hz, 2H), 2.45 (s, 3H), 2.27 (s, 3H), 2.22 (s, 3H), 2.11-2.04 (m, 1H), 1.51 (s, 3H), 1.49 (s, 3H).

Example 100: Synthesis of AM41-40A

AM41-40A was synthesized according to the procedures for preparing XY028-086. AM41-40A was obtained as off-white solid in TFA salt form (15 mg, 44%). $^1H$ NMR (600 MHz, $CD_3OD$) δ 8.48 (dd, J=6.7, 2.2 Hz, 1H), 8.17 (td, J=8.7, 2.3 Hz, 1H), 7.73-7.66 (m, 1H), 7.31 (d, J=0.8 Hz, 1H), 7.25 (s, 1H), 7.23-7.16 (m, 1H), 6.17 (s, 1H), 5.24 (dd, J=27.8, 4.2 Hz, 1H), 5.17 (d, J=8.9 Hz, 1H), 5.10-4.97 (m, 1H), 4.82 (dd, J=13.6, 6.9 Hz, 1H), 4.61 (d, J=54.1 Hz, 3H), 4.32 (d, J=11.0 Hz, 1H), 4.21-3.79 (m, 5H), 3.70-3.48 (m, 10H), 3.41-3.35 (m, 10H), 3.09-2.69 (m, 6H), 2.55 (dt, J=10.4, 6.6 Hz, 4H), 2.45 (s, 3H), 2.38-2.27 (m, 2H), 2.26 (s, 3H), 2.21 (s, 3H), 2.10 (ddd, J=30.0, 21.7, 14.0 Hz, 4H), 1.86 (ddd, J=23.7, 15.8, 9.8 Hz, 4H), 1.75 (s, 3H), 1.66 (d, J=9.6 Hz, 3H), 1.62-1.56 (m, 5H), 1.50 (s, 3H), 1.50 (s, 3H), 1.49 (s, 3H), 1.49 (s, 3H), 1.40-1.27 (m, 4H), 1.23-1.15 (m, 1H), 1.10-1.04 (m, 1H), 0.95-0.87 (m, 10H).

Example 101: Synthesis of XF042-84

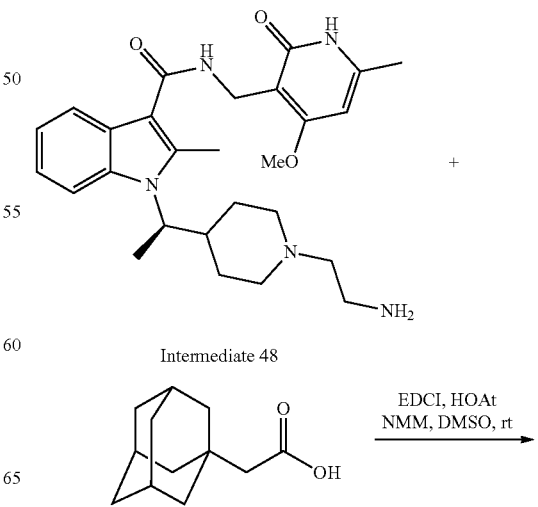

-continued

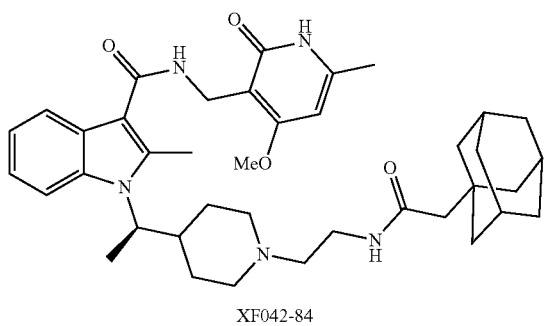

XF042-84

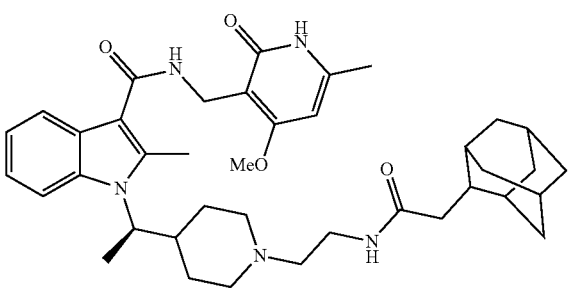

XF042-85

Intermediate 48 was synthesized according to the procedures published in J. Med. Chem. 2016, 59, 9928-9941. Intermediate 48 (20 mg, 0.04 mmol), HOAt (8.6 mg, 0.06 mmol), and 1-adamantaneacetic acid (8.1 mg, 0.04 mmol) were dissolved in DMSO (1.0 mL). To the solution were added NMM (14 µL, 0.13 mmol), and EDCI (12 mg, 0.06 mmol) successively at room temperature. After being stirred overnight at room temperature, the mixture was purified by preparative HPLC (10%-100% methanol/0.1% TFA in $H_2O$) to afford XF042-84 as white solid in TFA salt form (28 mg, 98%). $H^1$ NMR (600 MHz, $CD_3OD$) δ 7.77-7.73 (m, 1H), 7.66-7.59 (m, 1H), 7.16 (pd, J=7.2, 1.4 Hz, 2H), 6.70 (s, 1H), 4.57 (s, 2H), 4.27 (dq, J=14.0, 7.1 Hz, 1H), 4.06 (s, 3H), 3.77 (d, J=12.4 Hz, 1H), 3.51 (t, J=6.1 Hz, 2H), 3.46 (d, J=12.7 Hz, 1H), 3.18 (dp, J=25.1, 6.9, 6.4 Hz, 2H), 3.09-3.02 (m, 1H), 2.79-2.73 (m, 1H), 2.69-2.60 (m, 4H), 2.46 (s, 3H), 2.31 (d, J=14.4 Hz, 1H), 1.94 (d, J=13.8 Hz, 5H), 1.73 (d, J=12.3 Hz, 4H), 1.68-1.58 (m, 12H), 1.45-1.36 (m, 1H), 1.06 (d, J=14.4 Hz, 1H).

Example 102: Synthesis of XF042-85

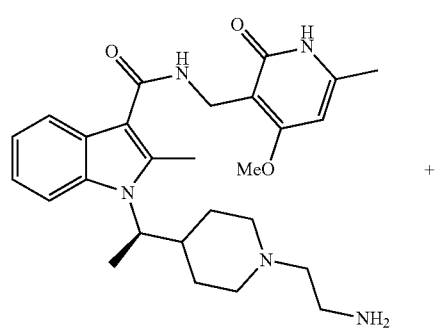

Intermediate 48

XF042-85 was synthesized according to the procedures for preparing XF042-84 from intermediate 48 (20 mg, 0.04 mmol), HOAt (8.6 mg, 0.06 mmol), 2-adamantaneacetic acid (8.1 mg, 0.04 mmol), NMM (14 µL, 0.13 mmol), EDCI (12 mg, 0.06 mmol), and DMSO (1.0 mL). XF042-85 was obtained as white solid in TFA salt form (24 mg, 85%). $^1H$ NMR (600 MHz, $CD_3OD$) δ 7.74 (d, J=7.4 Hz, 1H), 7.62 (d, J=7.7 Hz, 1H), 7.14 (p, J=6.9 Hz, 2H), 6.55 (s, 1H), 4.57 (s, 2H), 4.25 (t, J=8.8 Hz, 1H), 4.02 (d, J=1.9 Hz, 3H), 3.76 (d, J=12.3 Hz, 1H), 3.52 (t, J=5.9 Hz, 2H), 3.44 (d, J=12.5 Hz, 1H), 3.22-3.12 (m, 2H), 3.05 (t, J=12.9 Hz, 1H), 2.77-2.70 (m, 1H), 2.68-2.60 (m, 4H), 2.43-2.35 (m, 5H), 2.30 (d, J=14.3 Hz, 1H), 2.19 (s, 1H), 1.93-1.83 (m, 5H), 1.77 (d, J=18.3 Hz, 5H), 1.73-1.62 (m, 6H), 1.55 (d, J=13.0 Hz, 2H), 1.39 (q, J=13.8 Hz, 1H), 1.05 (d, J=14.5 Hz, 1H).

Example 103: Synthesis of XF042-95

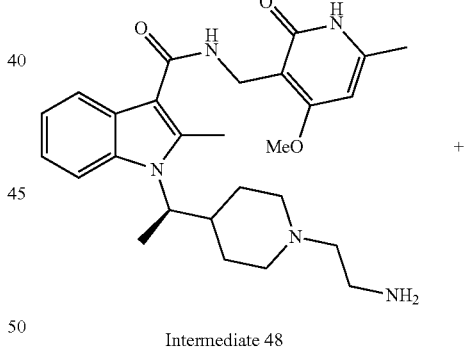

Intermediate 48

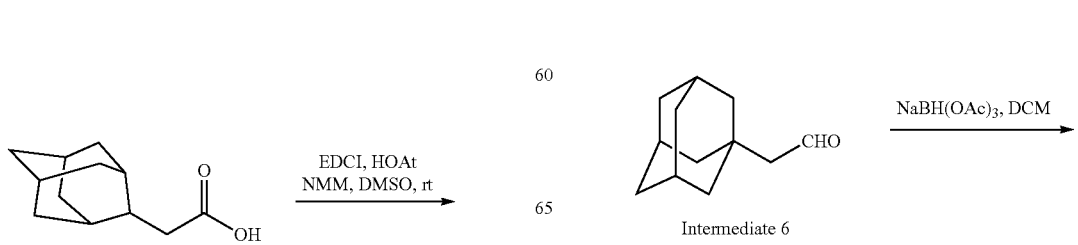

Intermediate 6

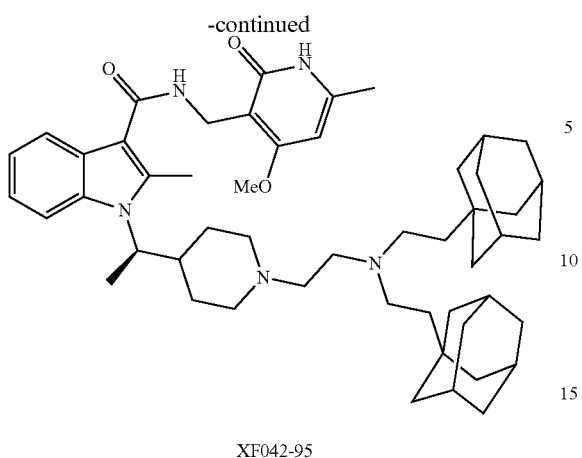

XF042-95

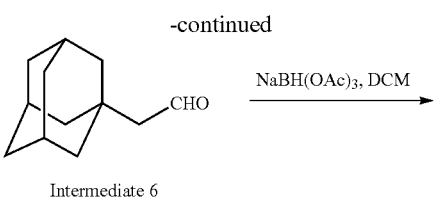

Intermediate 6

Intermediate 48 (25 mg, 0.05 mmol) and intermediate 6 (28 mg, 0.16 mmol) were dissolved in DCM (2 mL). To the solution was added the sodium triacetoxyborohydride (34 mg, 0.02 mmol) at 0° C. After being stirred overnight at room temperature, the mixture was evaporated and purified by ISCO™ to afford XF042-95 as white solid (8.9 mg, 27%). ¹H NMR (600 MHz, CD$_3$OD) δ 7.71 (d, J=8.0 Hz, 1H), 7.58 (d, J=8.3 Hz, 1H), 7.09 (d, J=8.6 Hz, 2H), 6.31 (s, 1H), 4.53 (s, 2H), 4.17 (s, 1H), 3.97 (d, J=2.3 Hz, 3H), 3.09 (s, 4H), 2.80 (d, J=11.7 Hz, 1H), 2.67 (s, 1H), 2.60 (s, 3H), 2.33 (s, 3H), 2.18 (d, J=11.5 Hz, 1H), 2.07 (s, 1H), 1.97 (s, 6H), 1.86 (d, J=11.2 Hz, 1H), 1.80-1.49 (m, 31H), 1.39 (d, J=9.1 Hz, 5H), 1.29 (s, 1H), 1.12 (s, 1H), 0.89 (d, J=13.5 Hz, 1H).

Example 104: Synthesis of XF042-132

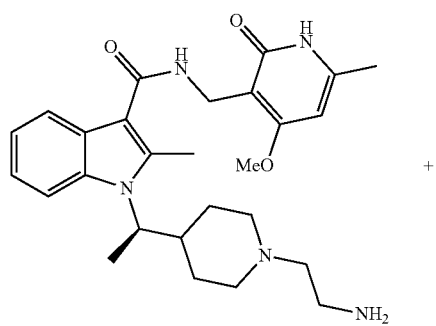

Intermediate 48

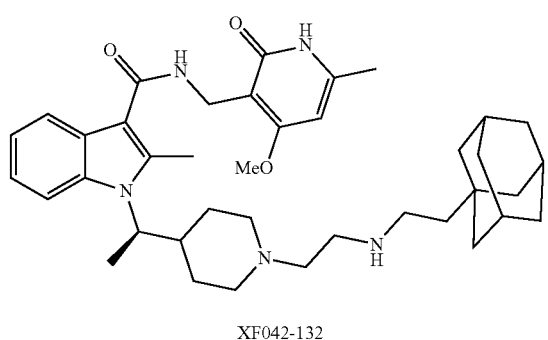

XF042-132

XF042-132 was synthesized according to the procedures for preparing XF042-95 from intermediate 48 (15 mg, 0.03 mmol) and intermediate 6 (5.8 mg, 0.03 mmol). XF042-132 was obtained as white solid (8.2 mg, 98%). ¹H NMR (600 MHz, CD$_3$OD) δ 7.70 (d, J=7.8 Hz, 1H), 7.57 (d, J=8.0 Hz, 1H), 7.10 (dt, J=18.5, 7.3 Hz, 2H), 6.33 (s, 1H), 4.52 (s, 2H), 4.18 (dq, J=13.9, 7.1 Hz, 1H), 3.98 (d, J=3.8 Hz, 3H), 3.06 (s, 2H), 3.05-2.97 (m, 3H), 2.74 (d, J=15.4 Hz, 1H), 2.60 (s, 3H), 2.55 (dq, J=13.0, 7.1, 6.0 Hz, 2H), 2.34 (s, 3H), 2.30 (d, J=10.6 Hz, 1H), 2.16-2.09 (m, 1H), 2.04 (d, J=13.1 Hz, 1H), 1.96 (s, 2H), 1.93 (s, 1H), 1.84-1.74 (m, 3H), 1.68 (d, J=12.3 Hz, 2H), 1.64-1.50 (m, 10H), 1.46-1.40 (m, 3H), 1.28 (s, 3H), 1.16-1.08 (m, 1H), 0.86 (s, 1H).

Example 105: Synthesis of XF042-86

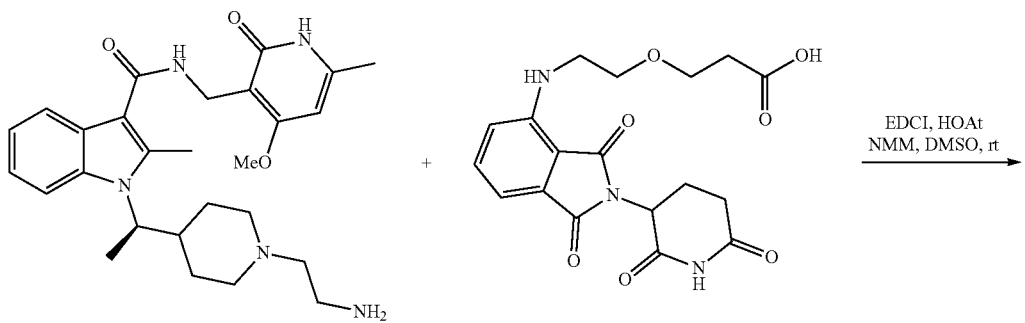

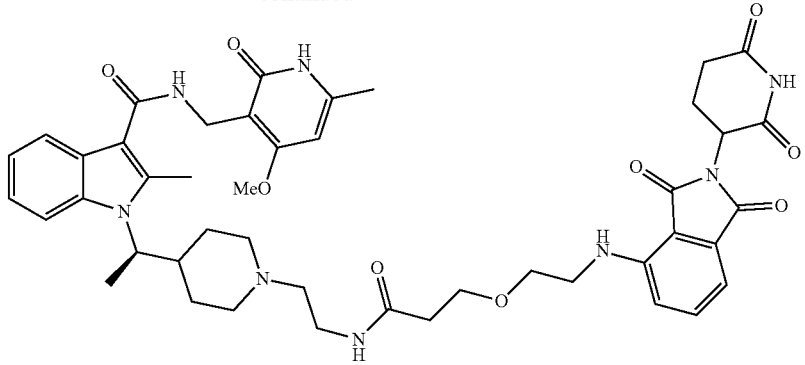

XF042-86

XF042-86 was synthesized according to the procedures for preparing XF042-84 from intermediate 48 (20 mg, 0.04 mmol), HOAt (8.6 mg, 0.06 mmol), 3-(2-((2-(2,6-dioxopiperidin-3-yl)-1,3-dioxoisoindolin-4-yl)amino) ethoxy) propanoic acid (16.2 mg, 0.04 mmol), NMM (14 μL, 0.13 mmol), EDCI (12 mg, 0.06 mmol), and DMSO (1.0 mL). XF042-86 was obtained as yellow solid in TFA salt form (29 mg, 82%). $^1$H NMR (600 MHz, CD$_3$OD) δ 7.73 (d, J=7.3 Hz, 1H), 7.58 (t, J=8.4 Hz, 1H), 7.55-7.41 (m, 1H), 7.19-7.10 (m, 2H), 7.08-6.93 (m, 2H), 6.66 (s, 1H), 5.02 (tdd, J=17.0, 10.6, 5.5 Hz, 1H), 4.57 (d, J=4.7 Hz, 2H), 4.22 (q, J=7.8 Hz, 1H), 4.04 (s, 3H), 3.74 (td, J=6.2, 2.6 Hz, 2H), 3.70-3.65 (m, 2H), 3.65-3.61 (m, 2H), 3.48 (tt, J=11.3, 6.2 Hz, 2H), 3.40 (t, J=5.1 Hz, 2H), 3.11 (ddq, J=25.8, 14.0, 7.0, 6.3 Hz, 2H), 2.98 (d, J=13.5 Hz, 1H), 2.85-2.78 (m, 1H), 2.71-2.63 (m, 3H), 2.60-2.54 (m, 4H), 2.46 (d, J=19.0 Hz, 5H), 2.23 (t, J=16.1 Hz, 1H), 2.07 (d, J=13.8 Hz, 1H), 1.60 (dd, J=14.2, 6.9 Hz, 4H), 1.32 (q, J=13.5 Hz, 1H), 0.97 (t, J=13.7 Hz, 1H).

Example 106: Synthesis of XF042-94

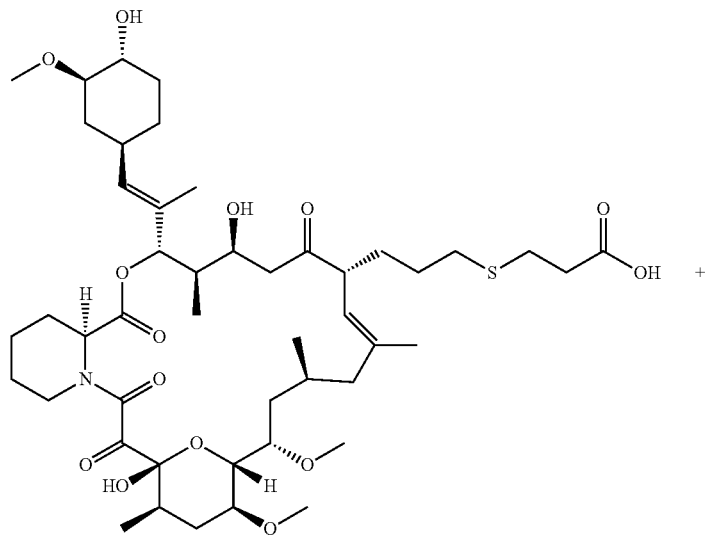

Intermediate 34

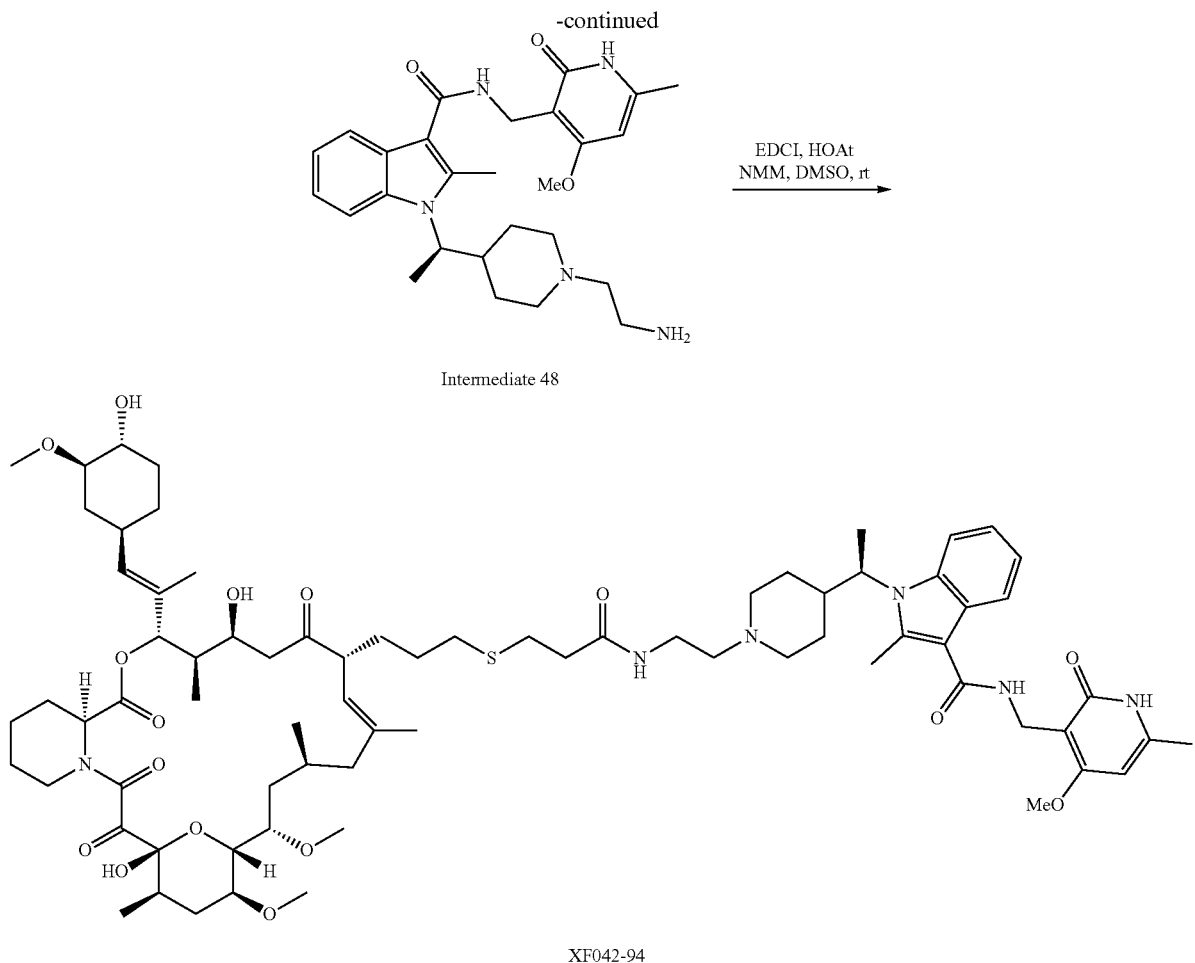

Intermediate 48

XF042-94

XF042-94 was synthesized according to the procedures for preparing XF042-84 from intermediate 48 (10 mg, 0.02 mmol), HOAt (4.1 mg, 0.03 mmol), intermediate 34 (19 mg, 0.02 mmol), NMM (6.5 μL, 0.06 mmol), EDCI (5.8 mg, 0.03 mmol), and DMSO (1.0 mL). XF042-94 was obtained as white solid in TFA salt form (22 mg, 81%). $^1$H NMR (600 MHz, CD$_3$OD) δ 7.74 (d, J=7.5 Hz, 1H), 7.62 (d, J=7.8 Hz, 1H), 7.17-7.09 (m, 2H), 6.53 (s, 1H), 5.28-5.13 (m, 2H), 4.97 (ddtt, J=9.8, 6.2, 2.5, 1.2 Hz, 1H), 4.67-4.63 (m, 1H), 4.57 (s, 2H), 4.43-4.25 (m, 2H), 4.01-4.03 (m, 4H), 3.80 (d, J=12.3 Hz, 1H), 3.75-3.13 (m, 21H), 3.13-2.85 (m, 3H), 2.85-2.24 (m, 16H), 2.23-1.16 (m, 35H), 1.10-0.60 (m, 11H).

Example 107: Synthesis of XF042-89

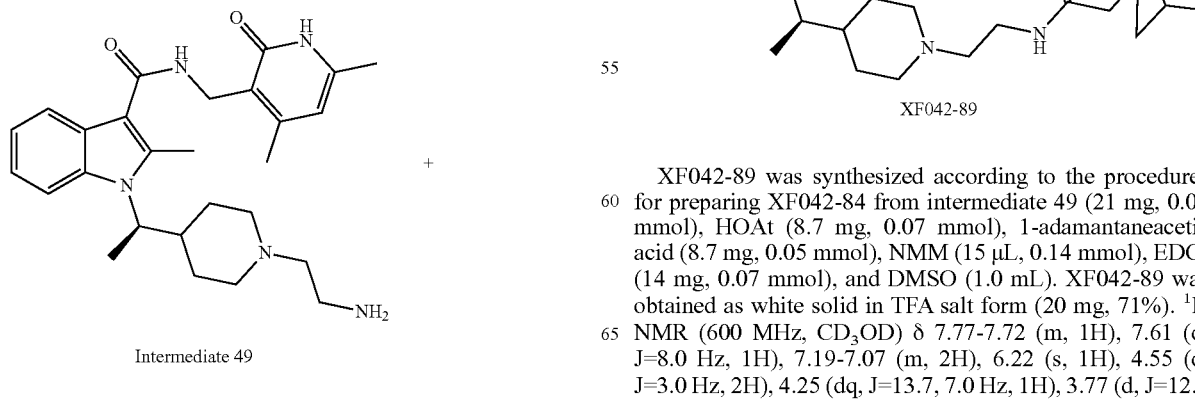

Intermediate 49

XF042-89

XF042-89 was synthesized according to the procedures for preparing XF042-84 from intermediate 49 (21 mg, 0.05 mmol), HOAt (8.7 mg, 0.07 mmol), 1-adamantaneacetic acid (8.7 mg, 0.05 mmol), NMM (15 μL, 0.14 mmol), EDCI (14 mg, 0.07 mmol), and DMSO (1.0 mL). XF042-89 was obtained as white solid in TFA salt form (20 mg, 71%). $^1$H NMR (600 MHz, CD$_3$OD) δ 7.77-7.72 (m, 1H), 7.61 (d, J=8.0 Hz, 1H), 7.19-7.07 (m, 2H), 6.22 (s, 1H), 4.55 (d, J=3.0 Hz, 2H), 4.25 (dq, J=13.7, 7.0 Hz, 1H), 3.77 (d, J=12.4

Hz, 1H), 3.53-3.49 (m, 2H), 3.45 (d, J=12.6 Hz, 1H), 3.23-3.13 (m, 2H), 3.10-3.01 (m, 1H), 2.75 (dd, J=9.2, 4.2 Hz, 1H), 2.61 (s, 4H), 2.44 (s, 3H), 2.28 (s, 4H), 1.94 (d, J=14.4 Hz, 5H), 1.75-1.60 (m, 16H), 1.38 (d, J=13.4 Hz, 1H), 1.07 (d, J=14.6 Hz, 1H).

Example 108: Synthesis of XF042-90

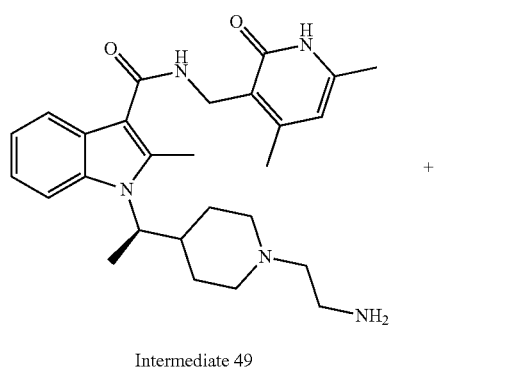

Intermediate 49

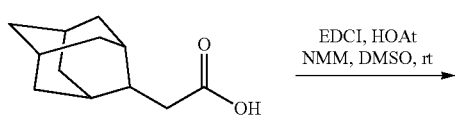

EDCI, HOAt
NMM, DMSO, rt

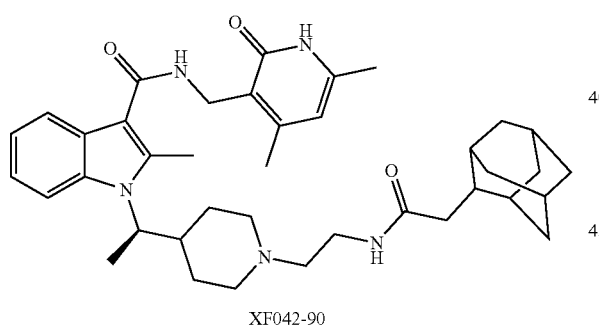

XF042-90

XF042-90 was synthesized according to the procedures for preparing XF042-84 from intermediate 2 (21 mg, 0.05 mmol), HOAt (8.7 mg, 0.07 mmol), 2-adamantaneacetic acid (8.7 mg, 0.05 mmol), NMM (15 μL, 0.14 mmol), EDCI (13.5 mg, 0.07 mmol), and DMSO (1.0 mL). XF042-90 was obtained as white solid in TFA salt form (24 mg, 83%). $^1$H NMR (600 MHz, CD$_3$OD) δ 7.74 (d, J=7.7 Hz, 1H), 7.61 (d, J=8.2 Hz, 1H), 7.18-7.09 (m, 2H), 6.26 (s, 1H), 4.55 (d, J=2.4 Hz, 2H), 4.25 (dq, J=14.0, 7.1 Hz, 1H), 3.76 (d, J=12.4 Hz, 1H), 3.51 (t, J=5.8 Hz, 2H), 3.44 (d, J=12.5 Hz, 1H), 3.23-3.10 (m, 2H), 3.05 (t, J=12.6 Hz, 1H), 2.78-2.71 (m, 1H), 2.67-2.62 (m, 1H), 2.61 (s, 3H), 2.45 (s, 3H), 2.38 (d, J=7.6 Hz, 2H), 2.29 (s, 4H), 2.19 (s, 1H), 1.91 (d, J=13.0 Hz, 2H), 1.89-1.83 (m, 3H), 1.80-1.74 (m, 5H), 1.71-1.60 (m, 6H), 1.56 (d, J=12.8 Hz, 2H), 1.37 (q, J=13.5 Hz, 1H), 1.07 (d, J=14.6 Hz, 1H).

Example 109: Synthesis of XF042-93

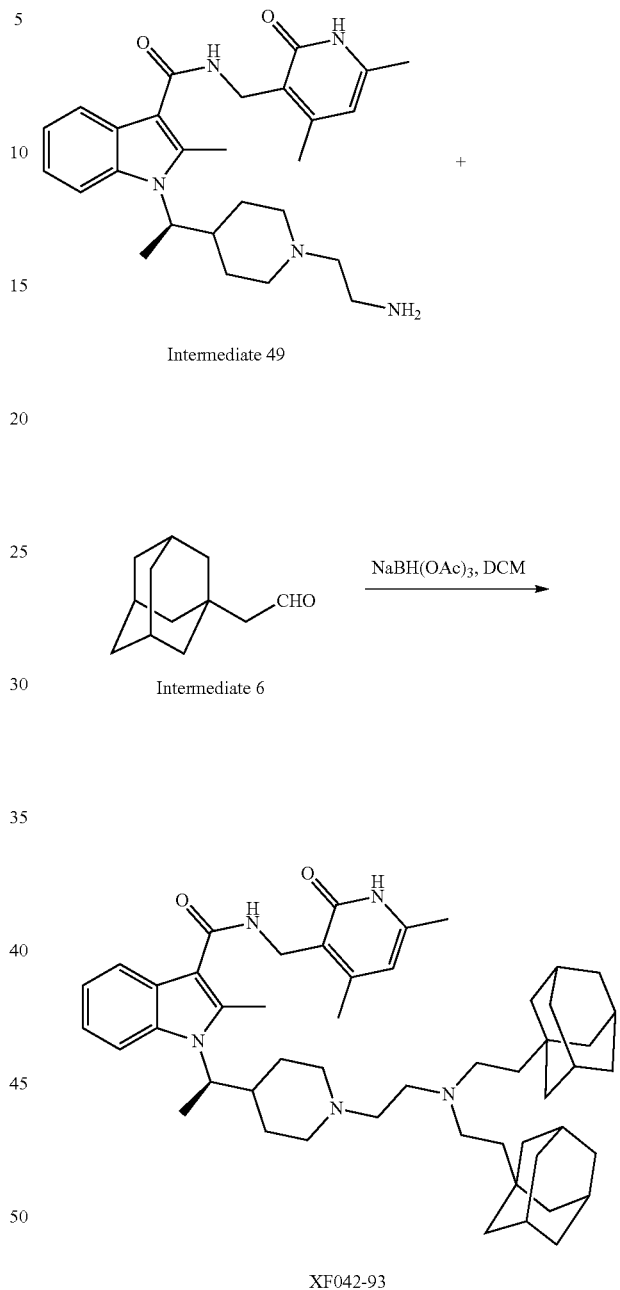

XF042-93 was synthesized according to the procedures for preparing XF042-95 from intermediate 49 (29 mg, 0.06 mmol) and intermediate 6 (33 mg, 0.19 mmol). XF042-93 was obtained as white solid (10 mg, 26%). $^1$H NMR (600 MHz, CD$_3$OD) δ 7.72 (d, J=7.6 Hz, 1H), 7.58 (d, J=8.0 Hz, 1H), 7.14-7.07 (m, 2H), 6.13 (s, 1H), 4.53 (s, 2H), 4.17 (dt, J=13.6, 6.9 Hz, 1H), 3.09 (d, J=11.6 Hz, 4H), 2.79 (d, J=11.7 Hz, 1H), 2.67-2.52 (m, 5H), 2.42 (s, 3H), 2.38-2.28 (m, 1H), 2.25 (s, 3H), 2.18 (t, J=11.8 Hz, 1H), 2.08 (d, J=12.8 Hz, 1H), 1.96 (s, 6H), 1.85 (t, J=11.6 Hz, 1H), 1.76 (d, J=12.4 Hz, 6H), 1.72-1.49 (m, 21H), 1.48-1.21 (m, 8H), 1.13 (tt, J=14.2, 7.2 Hz, 1H), 0.89 (dd, J=13.9, 8.7 Hz, 1H).

Example 110: Synthesis of XF042-133

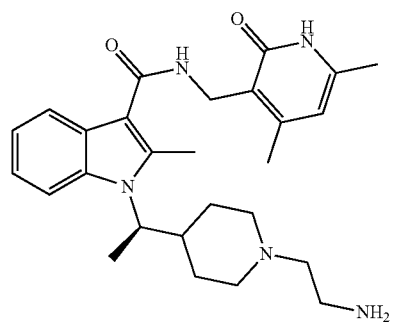

Intermediate 49

+

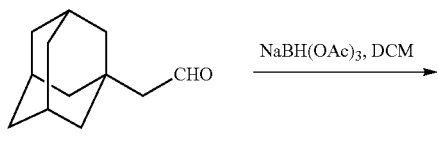

Intermediate 6

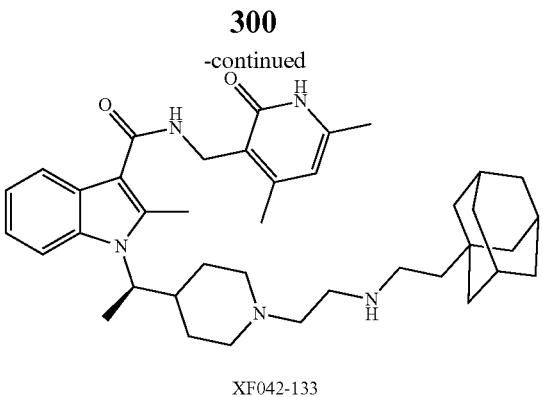

XF042-133

XF042-133 was synthesized according to the procedures for preparing XF042-95 from intermediate 49 (15 mg, 0.03 mmol) and intermediate 6 (5.8 mg, 0.03 mmol). XF042-133 was obtained as white solid (16.3 mg, 87%). $^1$H NMR (600 MHz, CD$_3$OD) δ 7.70 (d, J=7.8 Hz, 1H), 7.58 (d, J=8.1 Hz, 1H), 7.10 (dt, J=21.6, 7.4 Hz, 2H), 6.17 (s, 1H), 4.55 (s, 2H), 4.19 (dq, J=13.9, 7.1 Hz, 1H), 3.64 (d, J=11.8 Hz, 1H), 3.19 (dt, J=21.5, 7.1 Hz, 3H), 3.07-3.00 (m, 2H), 2.89 (d, J=11.4 Hz, 1H), 2.78 (d, J=22.0 Hz, 2H), 2.59 (s, 3H), 2.42 (s, 3H), 2.37 (h, J=8.6, 7.7 Hz, 2H), 2.26 (s, 3H), 2.02 (d, J=75.9 Hz, 5H), 1.76 (d, J=12.4 Hz, 3H), 1.70-1.50 (m, 11H), 1.48-1.39 (m, 3H), 1.38-1.17 (m, 4H), 0.91-0.88 (m, 1H).

Example 111: Synthesis of XF042-91

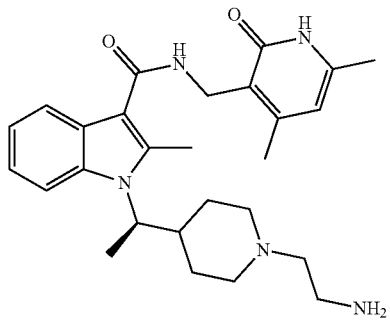

Intermediate 49

+

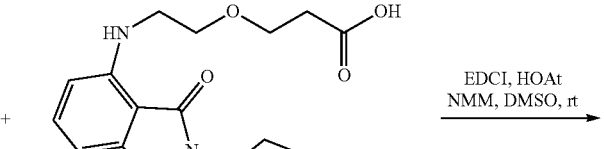

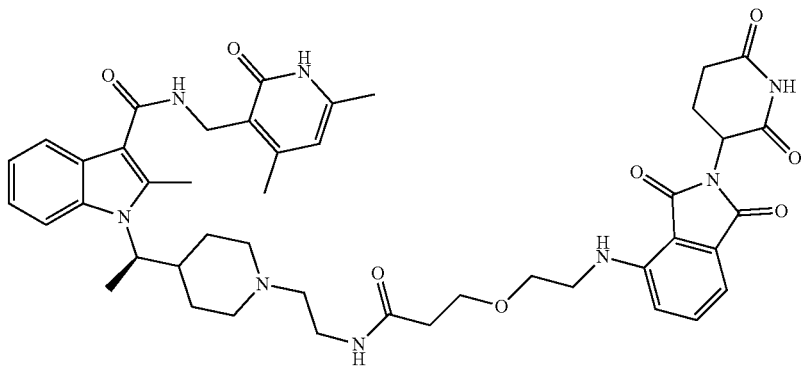

XF042-91

XF042-91 was synthesized according to the procedures for preparing XF042-84 from intermediate 49 (21 mg, 0.05 mmol), HOAt (9.2 mg, 0.07 mmol), 3-(2-((2-(2,6-dioxopiperidin-3-yl)-1,3-dioxoisoindolin-4-yl)amino) ethoxy) propanoic acid (18 mg, 0.05 mmol), NMM (15 μL, 0.14 mmol), EDCI (14 mg, 0.06 mmol), and DMSO (1.0 mL). XF042-91 was obtained as yellow solid in TFA salt form (33 mg, 89%). $^1$H NMR (600 MHz, CD$_3$OD) δ 7.74 (s, 1H), 7.56 (t, J=6.6 Hz, 1H), 7.49 (ddd, J=10.4, 8.4, 7.0 Hz, 1H), 7.18-7.09 (m, 2H), 7.04-6.95 (m, 2H), 6.34 (s, 1H), 5.01 (ddd, J=18.6, 12.6, 5.3 Hz, 1H), 4.61-4.55 (m, 2H), 4.21 (dt, J=11.4, 6.2 Hz, 1H), 3.74 (t, J=5.6 Hz, 2H), 3.68 (d, J=13.4 Hz, 1H), 3.62 (t, J=5.1 Hz, 2H), 3.48 (dq, J=11.2, 5.5 Hz, 2H), 3.44 (d, J=5.6 Hz, 1H), 3.40 (t, J=5.0 Hz, 3H), 3.35 (d, J=12.1 Hz, 2H), 3.17-3.06 (m, 2H), 2.98 (d, J=12.9 Hz, 1H), 2.87-2.78 (m, 1H), 2.74-2.67 (m, 3H), 2.59 (d, J=4.4 Hz, 3H), 2.51-2.44 (m, 3H), 2.31 (s, 3H), 2.23 (t, J=16.6 Hz, 1H), 2.10-2.04 (m, 1H), 1.60 (dd, J=14.9, 6.9 Hz, 4H), 1.31 (s, 1H), 0.98 (t, J=13.8 Hz, 1H).

Example 112: Synthesis of XF042-92

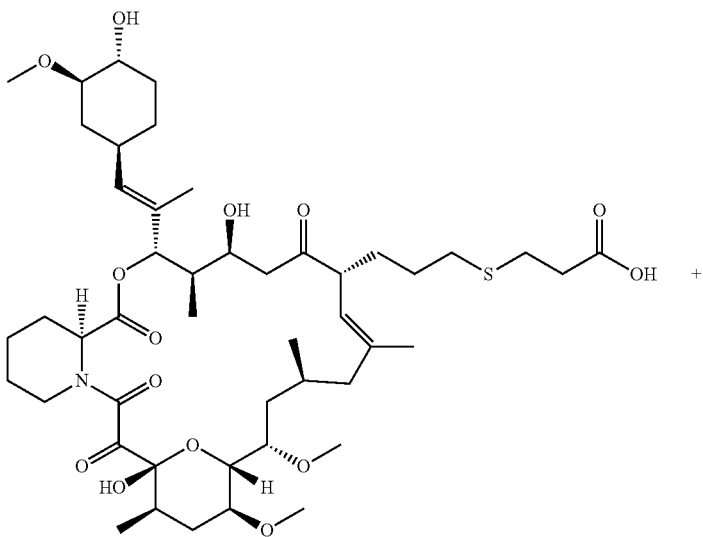

Intermediate 34

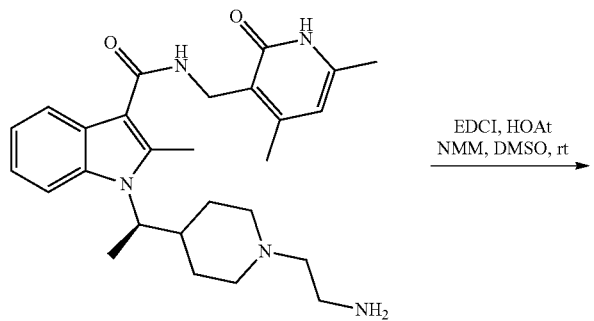

Intermediate 49

-continued

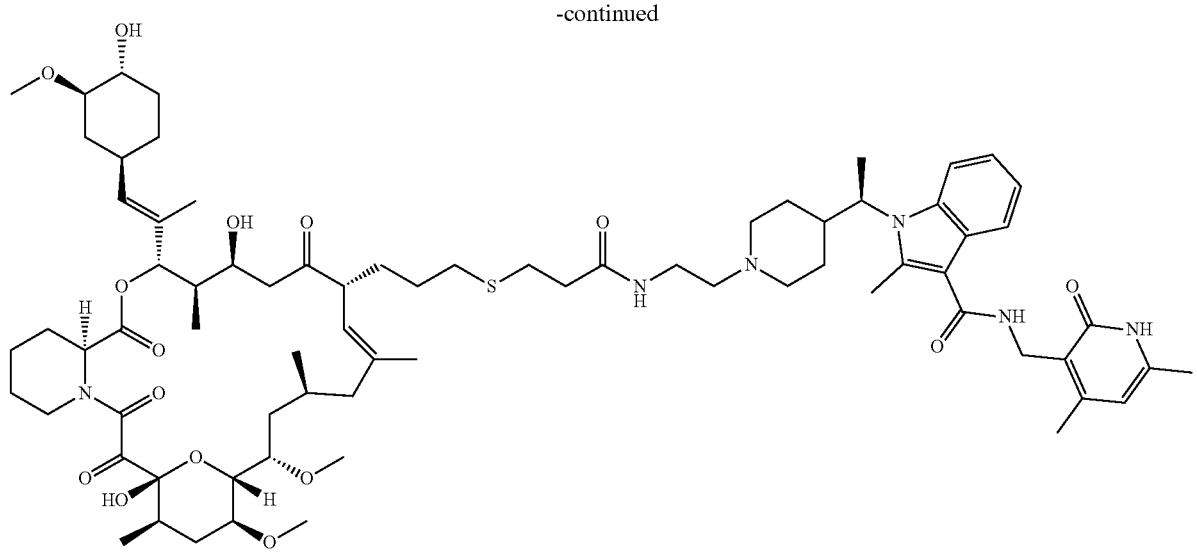

XF042-92

XF042-92 was synthesized according to the procedures for preparing XF042-84 from intermediate 49 (11 mg, 0.02 mmol), HOAt (4.5 mg, 0.03 mmol), intermediate 34 (21 mg, 0.02 mmol), NMM (7.2 μL, 0.07 mmol), EDCI (6.3 mg, 0.03 mmol), and DMSO (1.0 mL). XF042-92 was obtained as white solid in TFA salt form (19 mg, 60%). $^1$H NMR (600 MHz, CD$_3$OD) δ 7.75 (s, 1H), 7.62 (d, J=7.9 Hz, 1H), 7.16-7.07 (m, 2H), 6.25 (s, 1H), 5.30-5.16 (m, 2H), 4.96 (ddtt, J=11.1, 7.4, 2.5, 1.2 Hz, 1H), 4.65 (t, J=3.7 Hz, 1H), 4.56 (s, 2H), 4.35-4.21 (m, 1H), 4.06-3.94 (m, 1H), 3.85-2.85 (m, 25H), 2.85-2.58 (m, 7H), 2.57-1.97 (m, 18H), 1.95-0.72 (m, 41H).

Example 113: Proliferation Assays 1-3×10$^3$ cells were seeded in 96-well plates in duplicates and treated at the indicated compound concentrations. Cells were monitored using the IncuCyte® live cell imaging system (Essen BioScience™, Ann Arbor, MI) which was placed in a cell culture incubator operated at 37° C. and 5% CO$_2$. Cell confluence was determined using calculations derived from phase-contrast images. The concentration for 50% of maximal inhibition of cell proliferation (GI$_{50}$) values were determined by fitting to a standard four-parameter logistic using GraphPad Prism® v5. Results are provided in Tables 2 and 3. Graphs depicting the GI$_{50}$s of select EZH2 degraders/disruptors described here for various cancer cell lines are shown in FIGS. 4-49.

TABLE 2
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| AM16-10A | 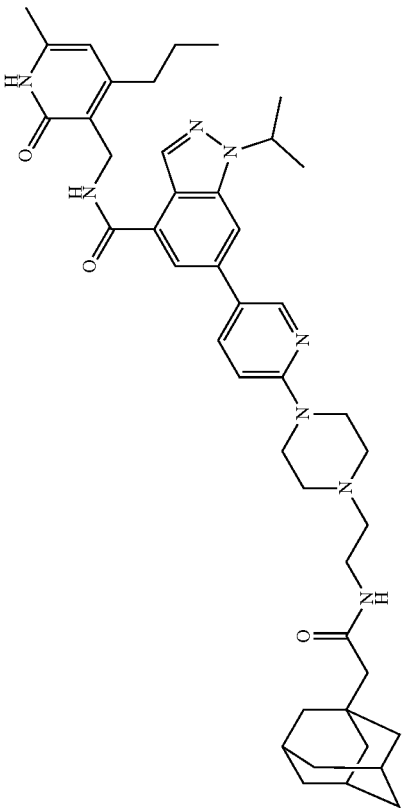 | 1.2 | 1.4 | 0.57 | 1.2 |
| AM16-11A | 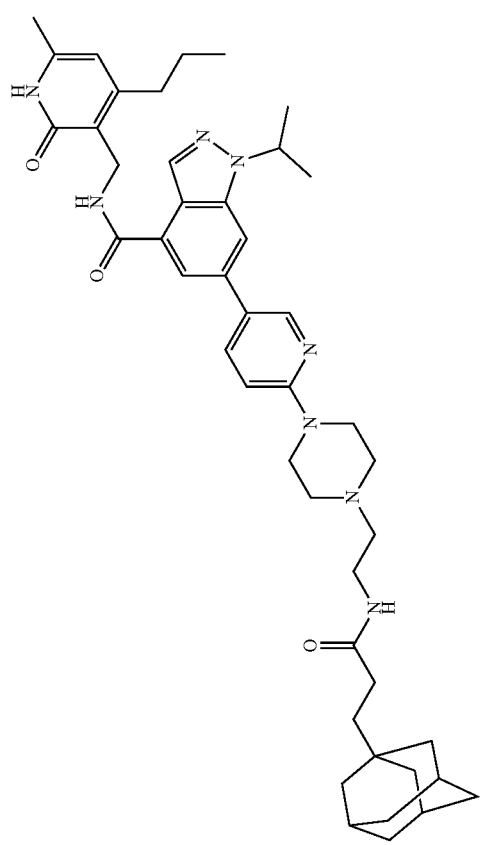 | N/A | N/A | 2.6 | N/A |

TABLE 2-continued
| Cmpd # | Structure | GI$_{50}$ (µM) MCF-7 | GI$_{50}$ (µM) MDA-MB-468 | GI$_{50}$ (µM) HCC1187 | GI$_{50}$ (µM) HCC1170 |
|---|---|---|---|---|---|
| AM16-37A | 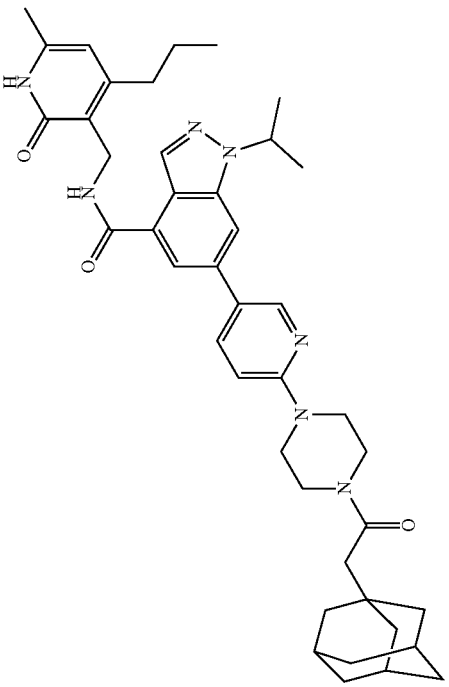 | N/A | N/A | 2.1 | N/A |
| AM16-38A | 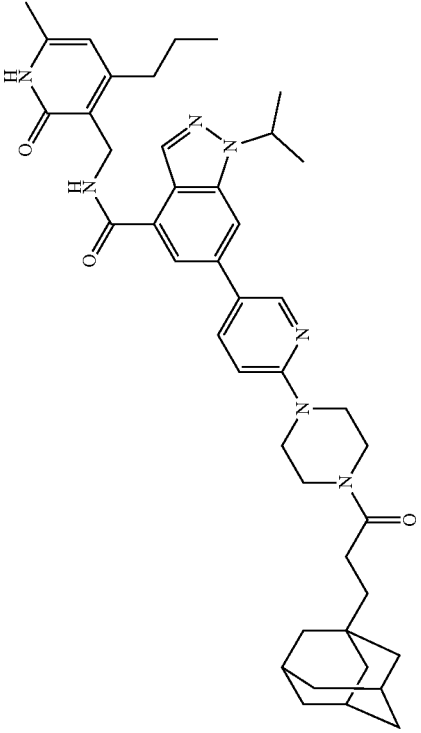 | N/A | N/A | 2.0 | N/A |

TABLE 2-continued

| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| XY019-43 | 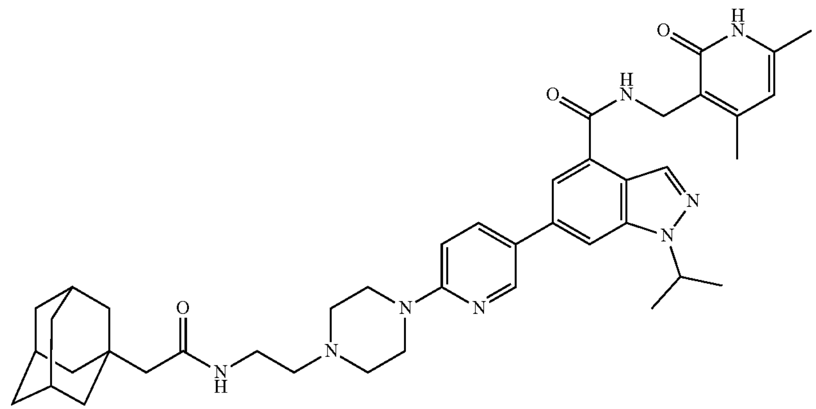 [SMILES: Cc1cc(C)c(CNC(=O)c2cc(-c3ccc(N4CCN(CCNC(=O)CC56CC7CC(CC(C7)C5)C6)CC4)nc3)cc3c2cnn3C(C)C)c(=O)[nH]1] | 0.35 | 0.54 | 0.65 | N/A |
| XY019-44 | 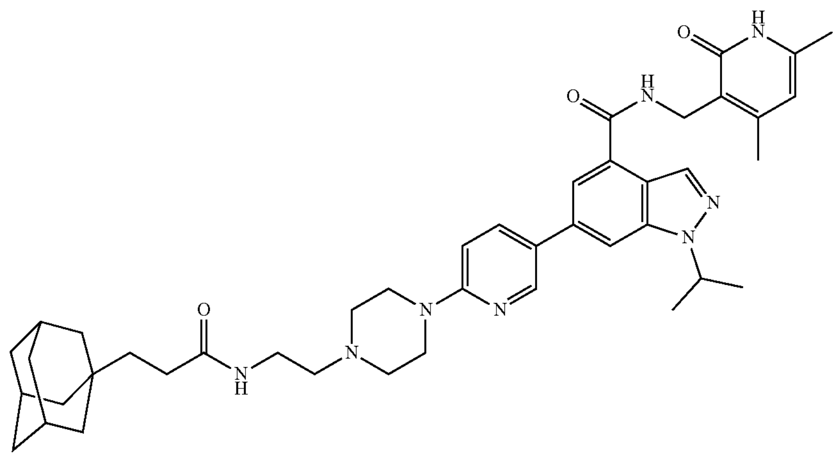 [SMILES: Cc1cc(C)c(CNC(=O)c2cc(-c3ccc(N4CCN(CCNC(=O)CCC56CC7CC(CC(C7)C5)C6)CC4)nc3)cc3c2cnn3C(C)C)c(=O)[nH]1] | N/A | N/A | 2.2 | N/A |

TABLE 2-continued

| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| AM16-92A | 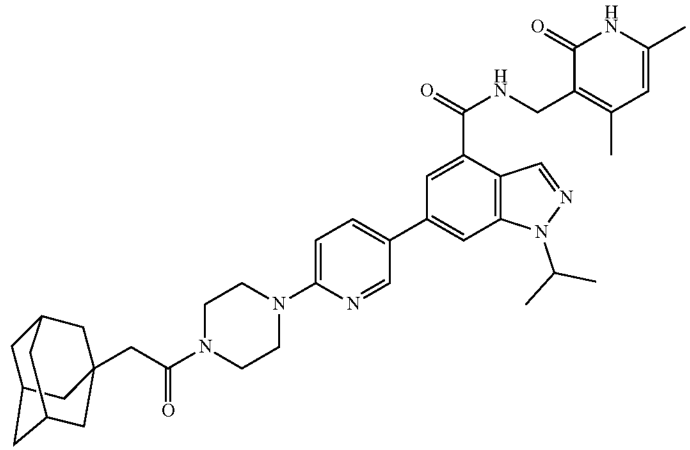 [SMILES: Cc1cc(C)c(CNC(=O)c2cc(-c3ccc(N4CCN(C(=O)CC56CC7CC(CC(C7)C5)C6)CC4)nc3)cc3c2cnn3C(C)C)c(=O)[nH]1] | 1.0 | N/A | 1.1 | N/A |
| AM16-93A | 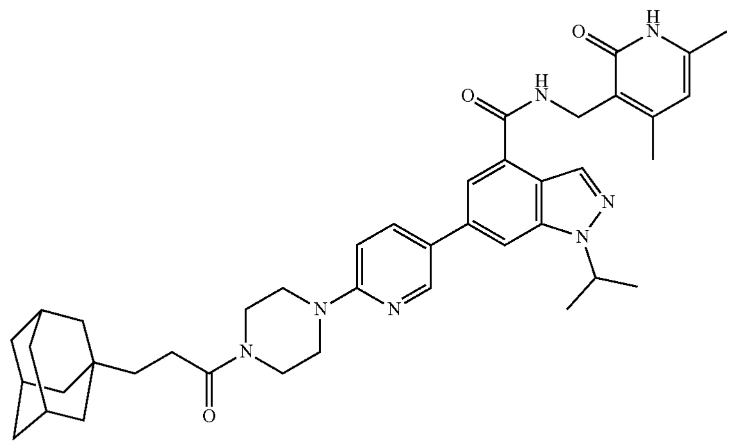 [SMILES: Cc1cc(C)c(CNC(=O)c2cc(-c3ccc(N4CCN(C(=O)CCC56CC7CC(CC(C7)C5)C6)CC4)nc3)cc3c2cnn3C(C)C)c(=O)[nH]1] | N/A | N/A | 1.5 | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| AM16-97A | 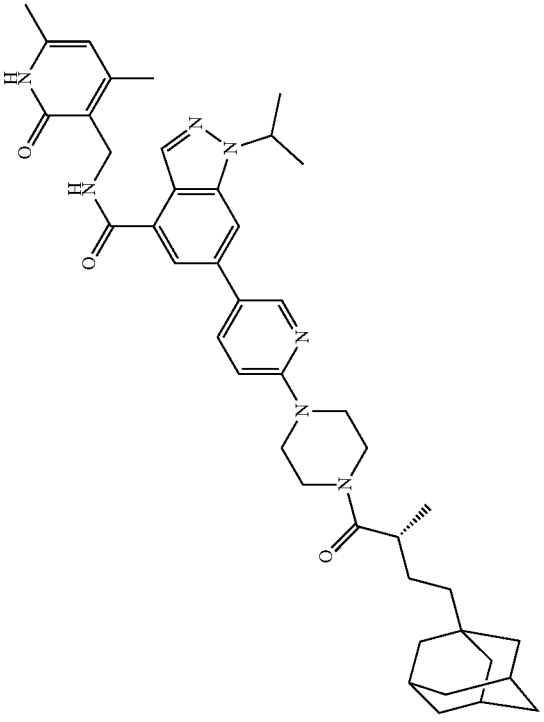 | N/A | N/A | 1.2 | N/A |
| AM16-101A | 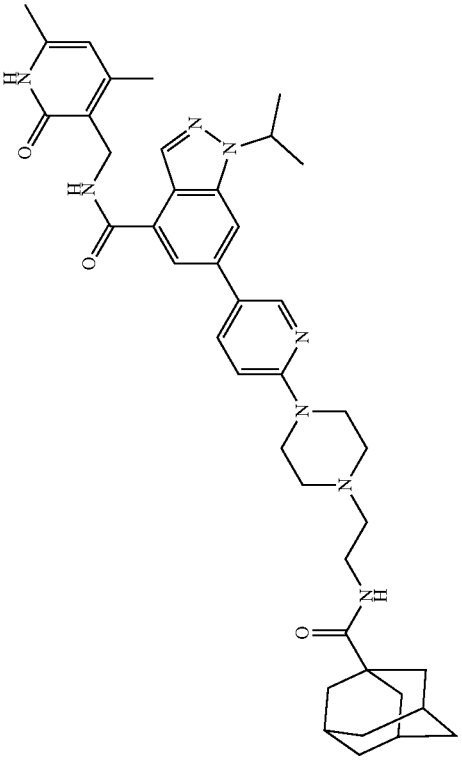 | 0.69 | 1.1 | N/A | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| AM16-105A | 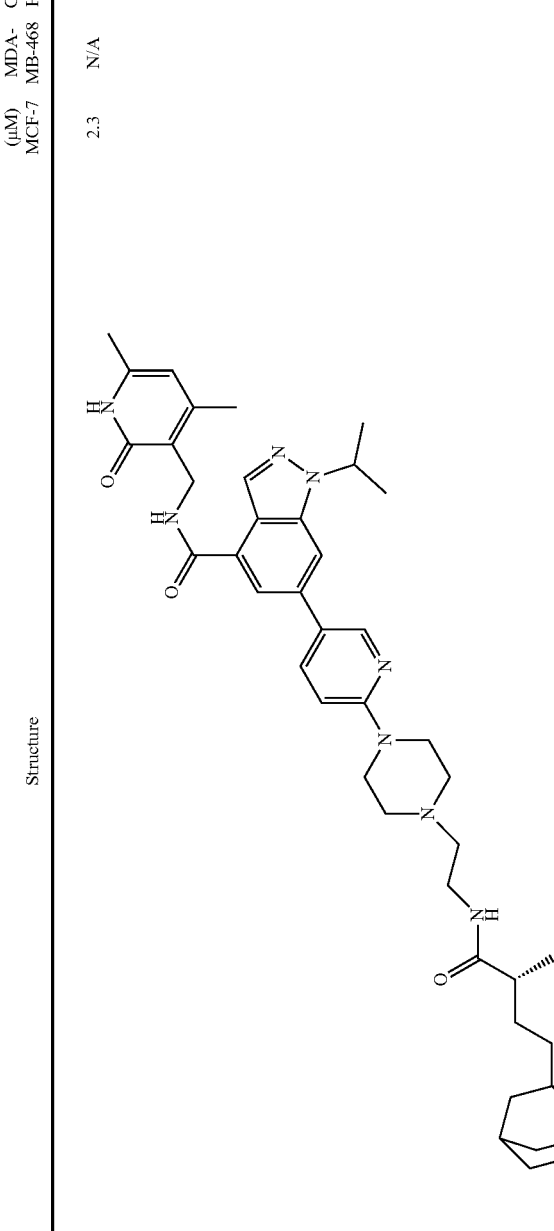 | 2.3 | N/A | 1.2 | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| AM16-106A | 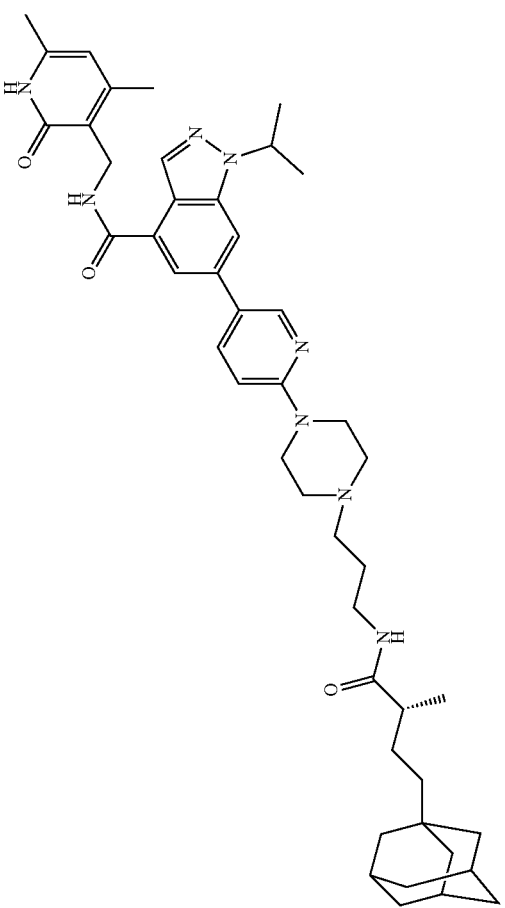 | N/A | N/A | 4.3 | N/A |
| AM29-21A | 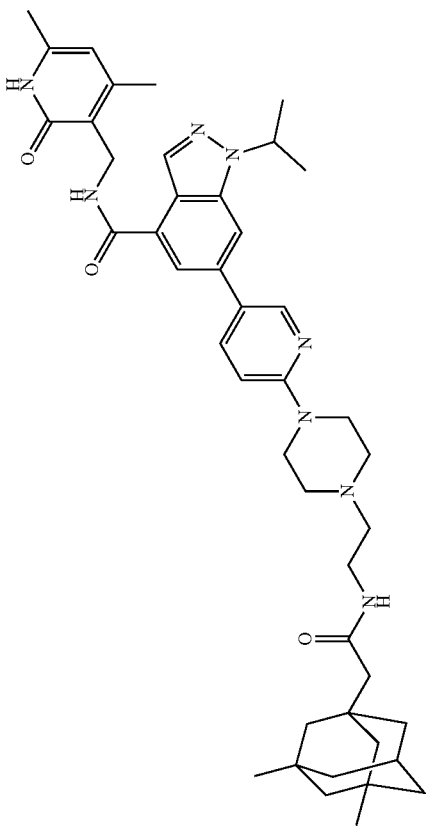 | 0.28 | 0.20 | N/A | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| AM29-22A | 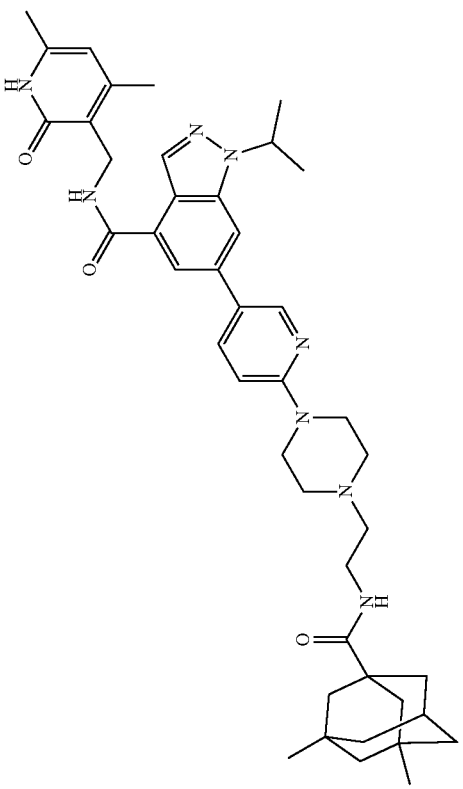 | 0.69 | 0.87 | N/A | N/A |
| AM29-33A | 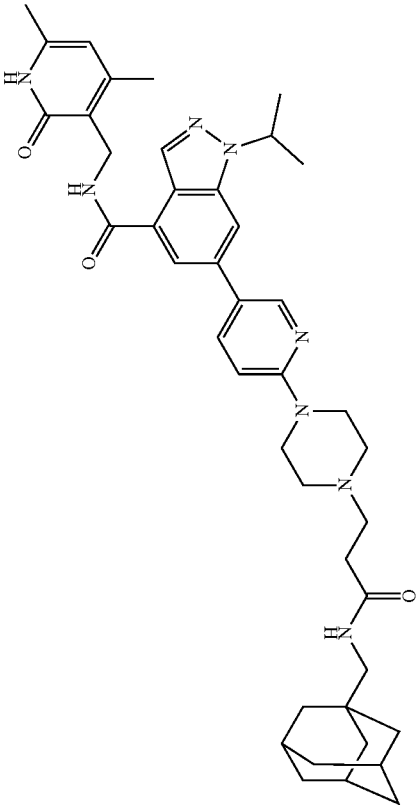 | 0.70 | 0.71 | N/A | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| AM16-103A | 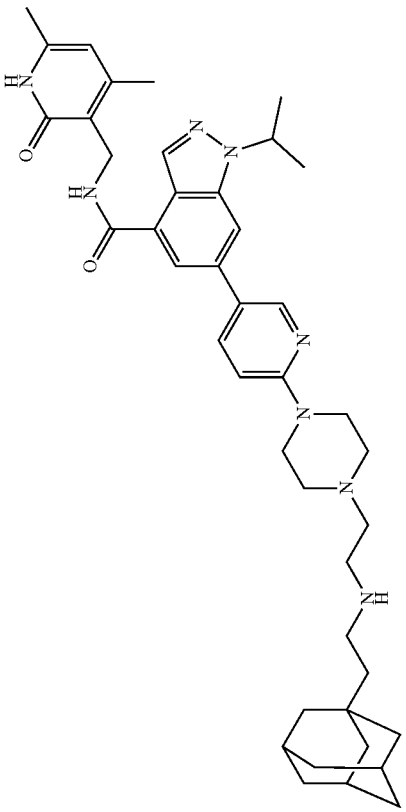 | N/A | 1.2 | N/A | N/A |
| AM29-182A | 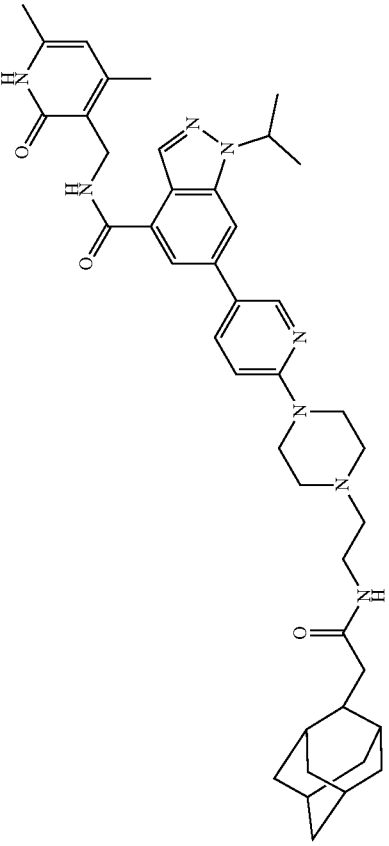 | N/A | 1.8 | N/A | N/A |

TABLE 2-continued
| Cmpd # | Structure | GI$_{50}$ (µM) MCF-7 | GI$_{50}$ (µM) MDA-MB-468 | GI$_{50}$ (µM) HCC1187 | GI$_{50}$ (µM) HCC1170 |
|---|---|---|---|---|---|
| AM29-177A | 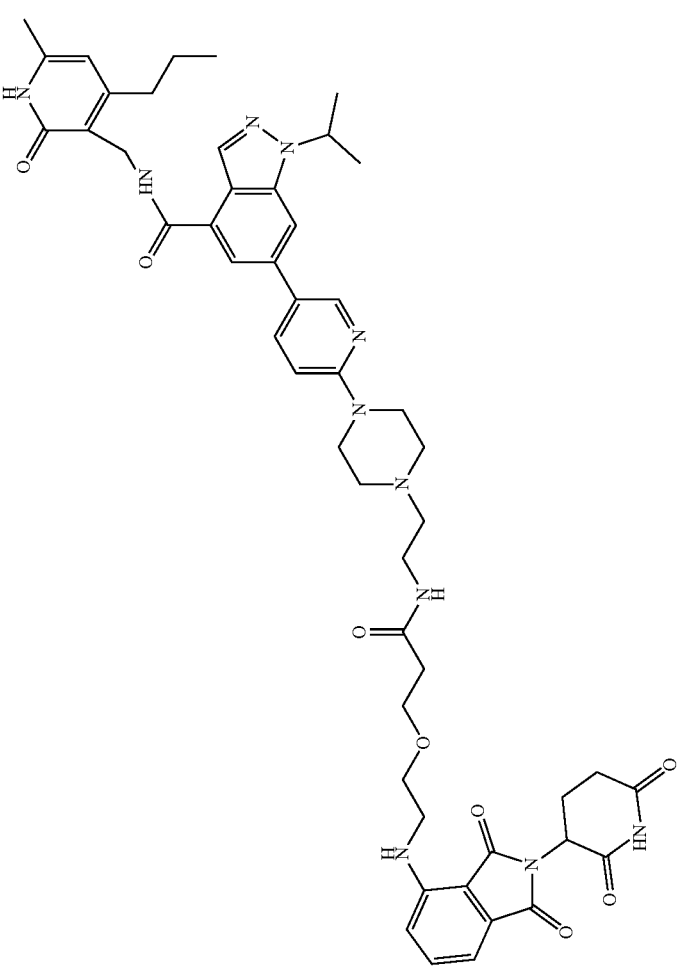 | N/A | 2.5 | N/A | N/A |

TABLE 2-continued
| Cmpd # | Structure | GI$_{50}$ (µM) MCF-7 | GI$_{50}$ (µM) MDA-MB-468 | GI$_{50}$ (µM) HCC1187 | GI$_{50}$ (µM) HCC1170 |
|---|---|---|---|---|---|
| XY028-086 | 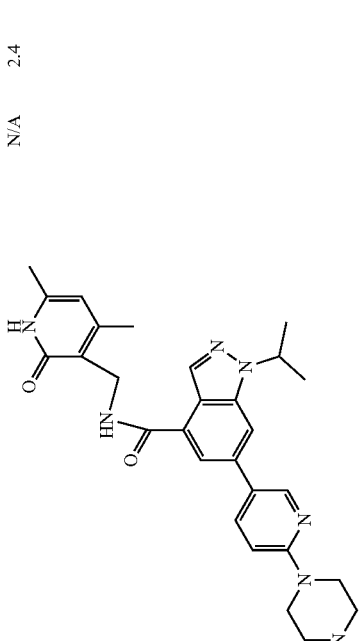 | N/A | 2.4 | N/A | N/A |
| CZ40-75 | 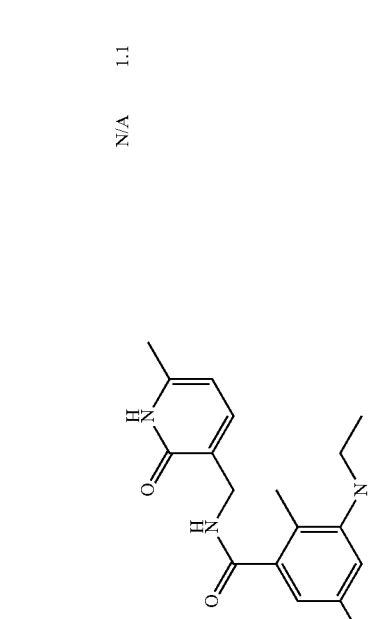 | N/A | 1.1 | N/A | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| CZ40-149 | 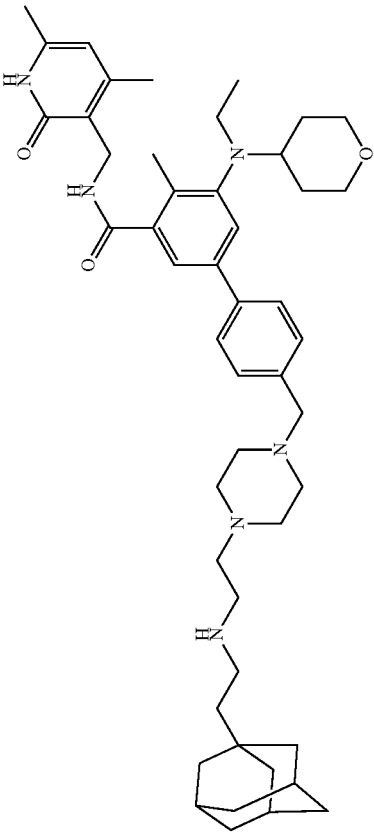 | N/A | 1.8 | N/A | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| CZ40-131 | 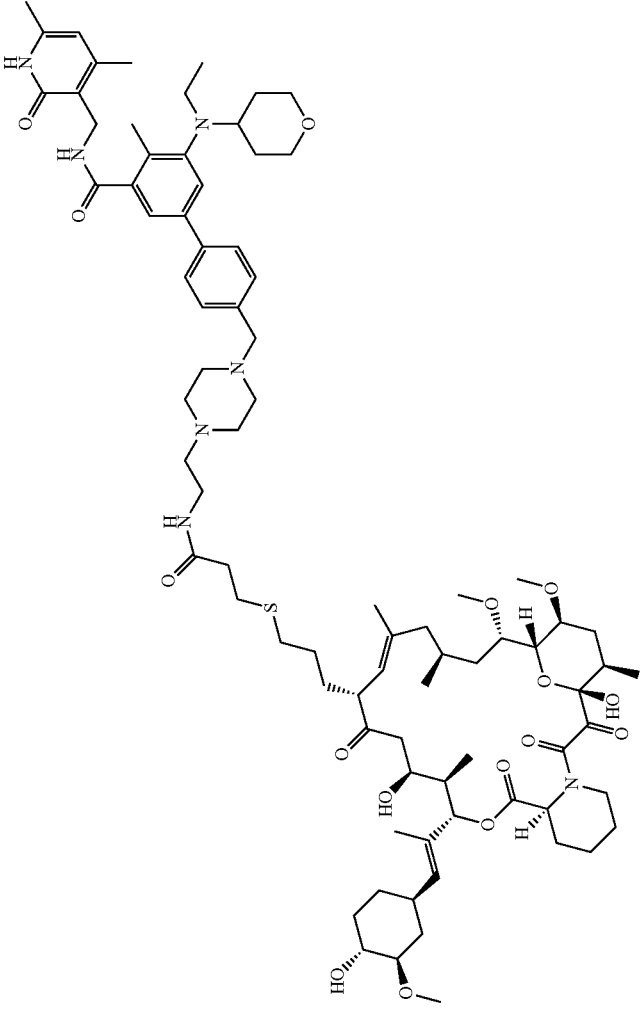 | N/A | 1.5 | N/A | N/A |

TABLE 2-continued
| Cmpd # | Structure | GI$_{50}$ (µM) MCF-7 | GI$_{50}$ (µM) MDA-MB-468 | GI$_{50}$ (µM) HCC1187 | GI$_{50}$ (µM) HCC1170 |
|---|---|---|---|---|---|
| AM41-41A | 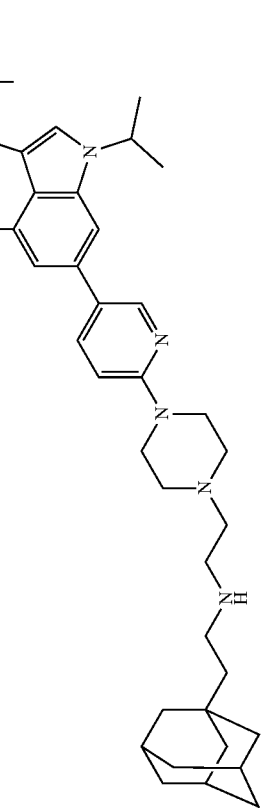 | N/A | 2.3 | N/A | N/A |
| XF042-95 | 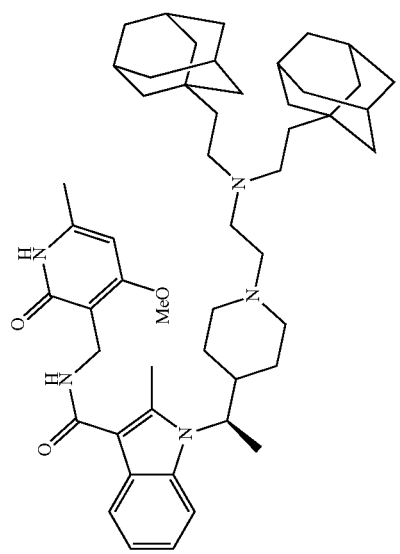 | N/A | 2.5 | N/A | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| XF042-90 | 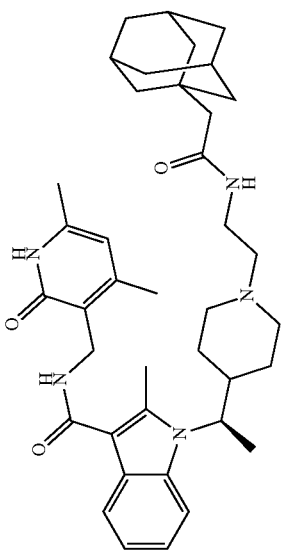 | N/A | 7.2 | N/A | N/A |
| XF042-93 | 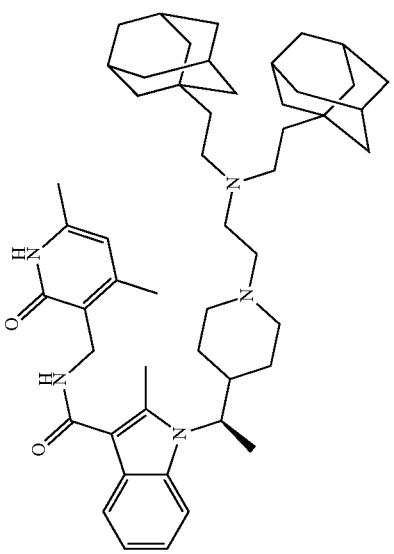 | N/A | 2.2 | N/A | N/A |
| XF042-133 | 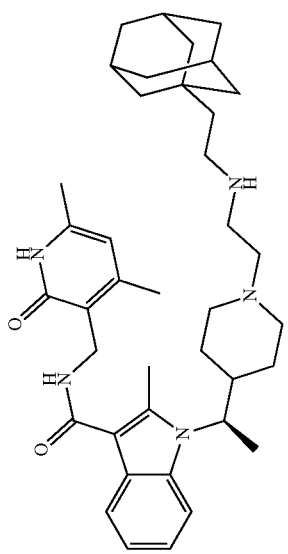 | N/A | 4.9 | N/A | N/A |

TABLE 2-continued
| Cmpd # | Structure | GI$_{50}$ (μM) MCF-7 | GI$_{50}$ (μM) MDA-MB-468 | GI$_{50}$ (μM) HCC1187 | GI$_{50}$ (μM) HCC1170 |
|---|---|---|---|---|---|
| XF042-92 | 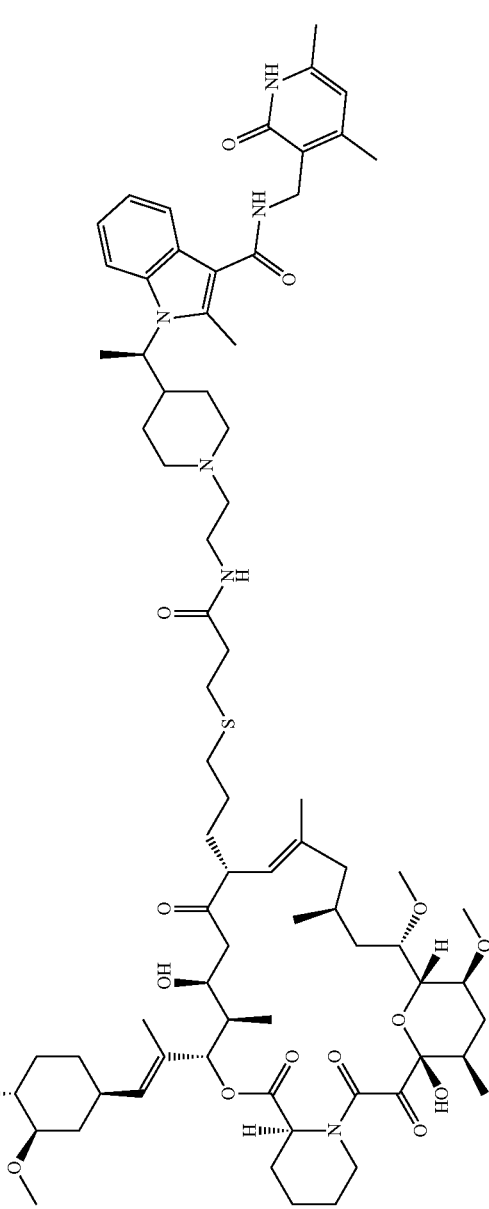 | N/A | 2.6 | N/A | N/A |

TABLE 3

| Cmpd # | Structure | GI$_{50}$ (μM) BT549 | GI$_{50}$ (μM) HCC1954 |
|---|---|---|---|
| XY019-43 | 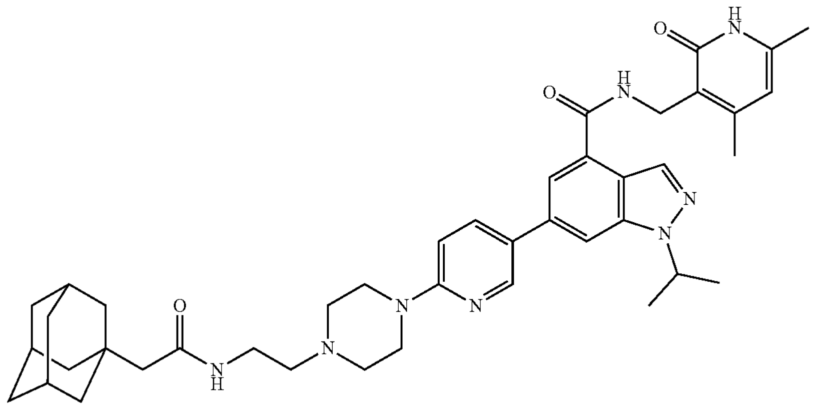 [SMILES: Cc1cc(C)c(CNC(=O)c2cc(-c3ccc(N4CCN(CCNC(=O)CC56CC7CC(CC(C7)C5)C6)CC4)nc3)cc3c2cnn3C(C)C)c(=O)[nH]1] | 2.2 | 2.7 |
| AM16-103A | 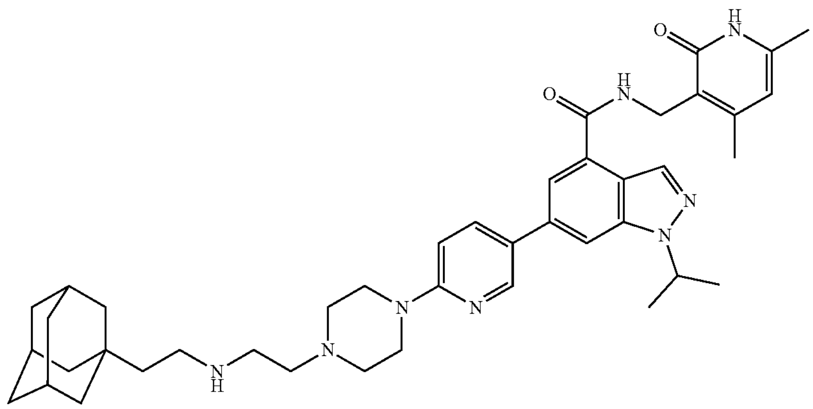 [SMILES: Cc1cc(C)c(CNC(=O)c2cc(-c3ccc(N4CCN(CCNCCC56CC7CC(CC(C7)C5)C6)CC4)nc3)cc3c2cnn3C(C)C)c(=O)[nH]1] | 1.4 | 2.1 |
| AM29-182A | 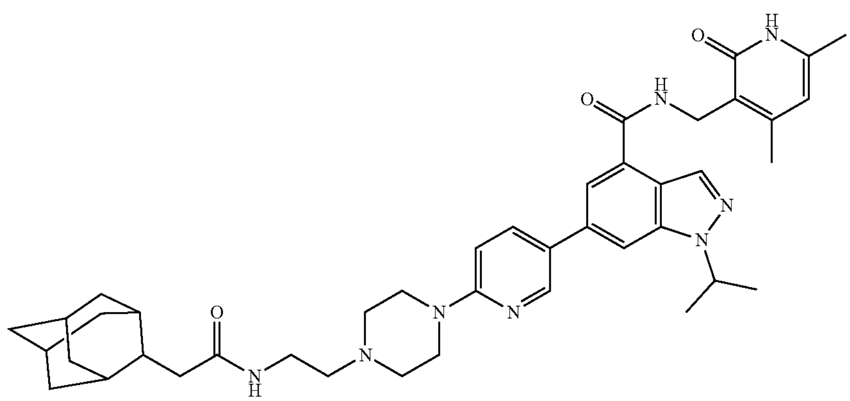 [SMILES: Cc1cc(C)c(CNC(=O)c2cc(-c3ccc(N4CCN(CCNC(=O)CC5C6CC7CC(C6)CC5C7)CC4)nc3)cc3c2cnn3C(C)C)c(=O)[nH]1] | 2.5 | 3.9 |

Example 114: Western Blot Assays

Approximately 1×10$^4$ cells were plated into 6-well plates and treated with compound at indicated concentration and for the indicated time. Protein lysates were prepared using Laemmli buffer and the concentration of protein lysates were determined using Bradford assay. An average of 10-20 μg of protein per sample were analyzed on a 4-20% tris-glycine polyacrylamide gel or a NuPAGE™ 4-12% Bis-Tris protein gel. EZH2 (Cell Signaling®) #5246), H3K27me3 (Millipore™ #07-449), Vinculin (Sigma® #V9131), H$_3$ (Cell Signaling® #4499S) or β-actin (Sigma® #A4700) primary antibodies were used according to the manufacturer's instructions.

Figure 50:
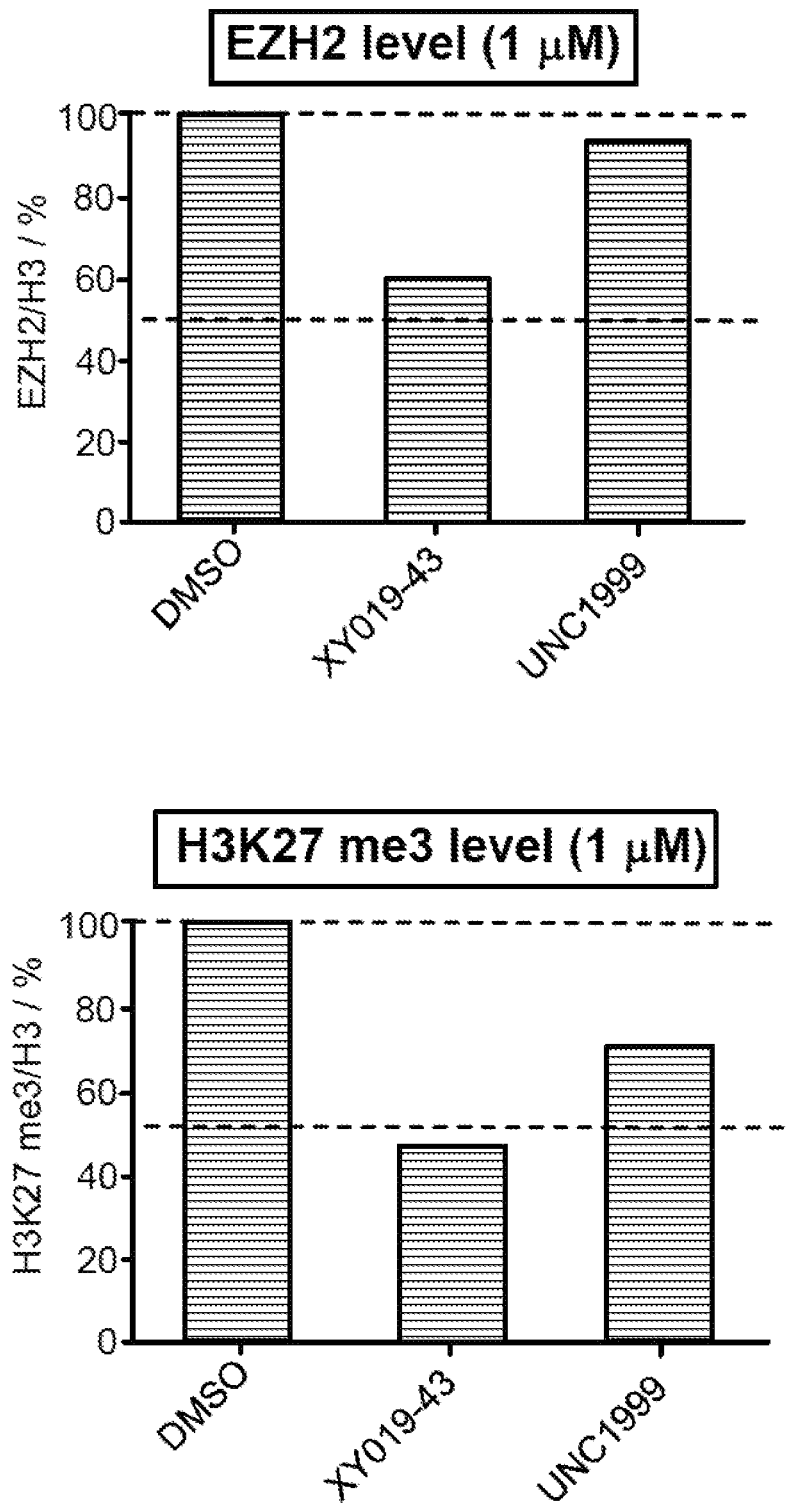
FIG. 50 is a graph depicting Western blot results showing EZH2 (2-day treatment) and H3K27me3 (1-day treatment) levels in MCF-7 cells treated with 1 μM AM16-10A, UNC1999 (negative control), or DMSO.
Figure 51:
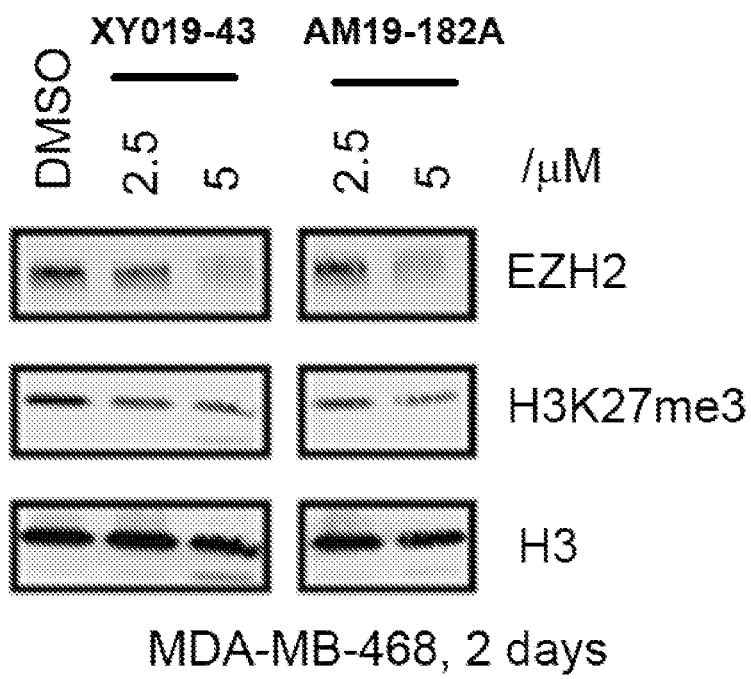
FIG. 51 is a Western blot showing EZH2 and H3K27me3 levels in MDA-MB-468 cells treated for 2 days with 2.5 or 5 μM XY019-43, AM29-182A, or DMSO.
Figure 52:
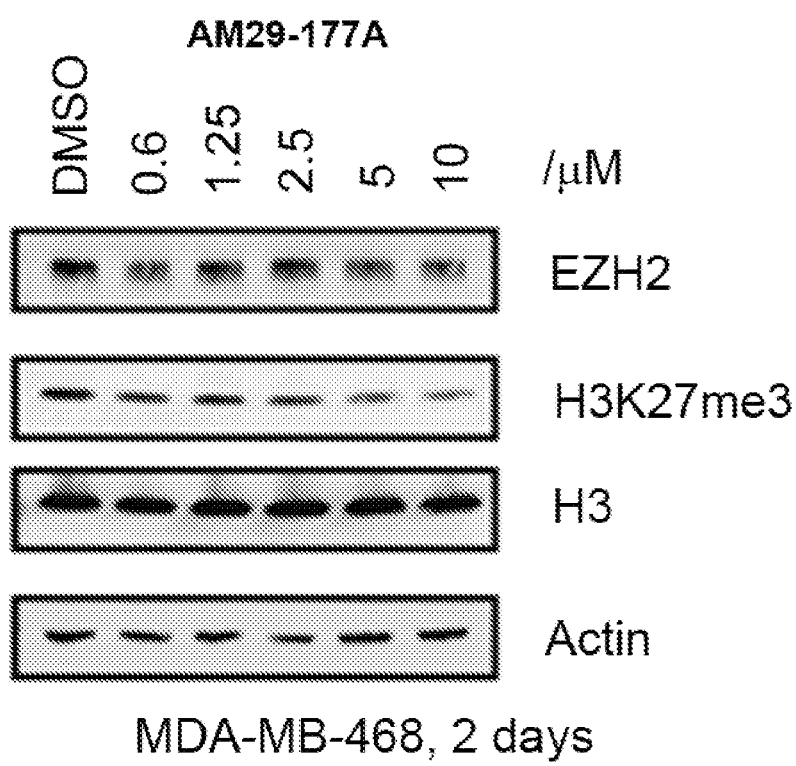
FIG. 52 is a Western blot showing EZH2 and H3K27me3 levels in MDA-MB-468 cells treated for 2 days with various concentrations of AM29-177A or DMSO.
Figure 53:
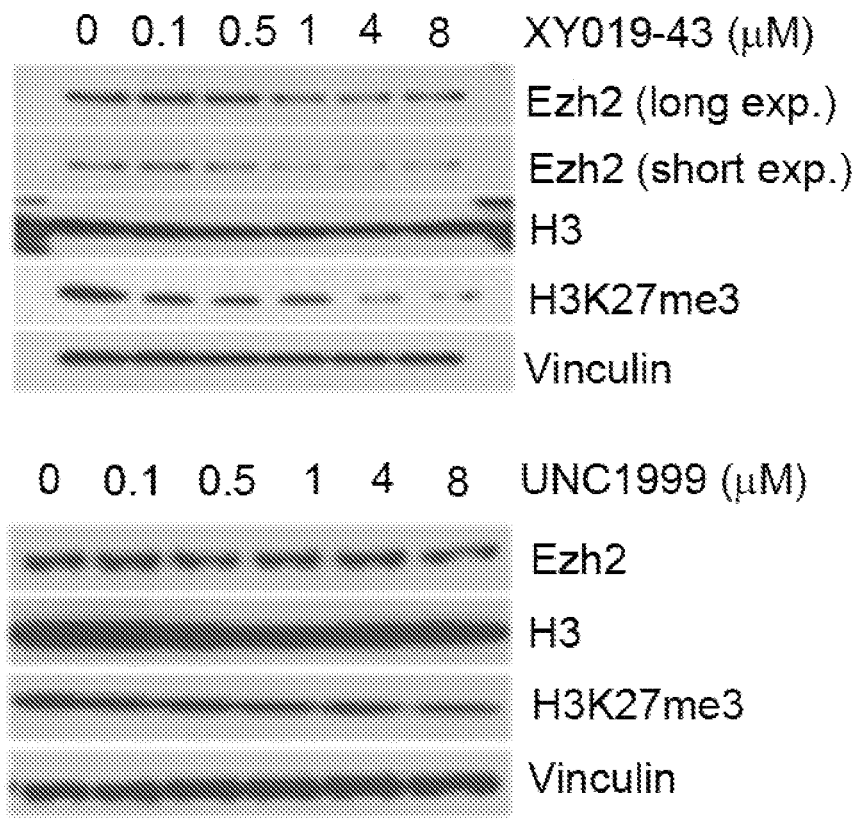
FIG. 53 is a Western blot showing EZH2 and H3K27me3 levels in MDA-MB-468 cells treated for 1 day with various concentrations of XY019-43, UNC1999 (negative control), or DMSO.
Figure 54:
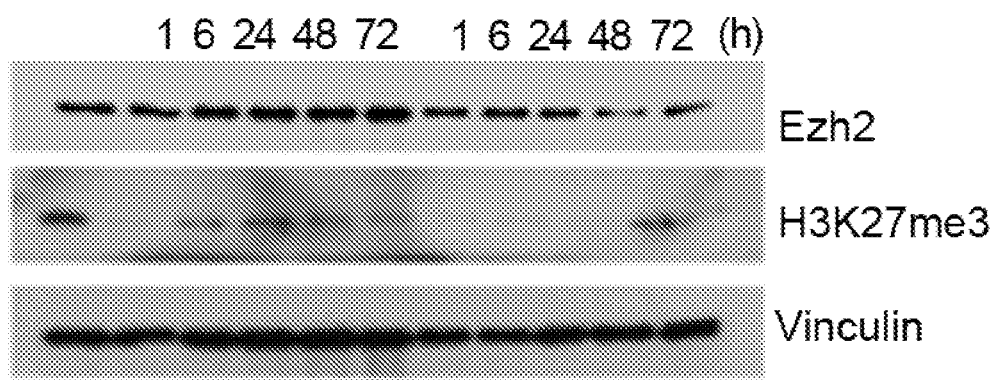
FIG. 54 is a Western blot showing EZH2 and H3K27me3 levels in HCC1187 cells treated for various times (h) with 1 μM AM16-10A, UNC1999 (negative control), or DMSO.

Cellular EZH2 and H3K27me3 levels in MCF-7 cells treated with XY019-43 or UNC1999 (negative control) at 1 μM are shown in FIG. 50. Cellular EZH2 and H3K27me3 levels in MDA-MB-468 cells treated with XY019-43, AM19-182A, AM29-177, or UNC1999 (negative control) at various concentrations for various time points are shown in FIGS. 51-53. In addition, cellular EZH2 and H3K27me3 levels in HCC1187 cells treated with 1 M AM16-10A or UNC1999 (negative control) for various time points are shown in FIG. 54.

Example 115: Biochemical Assays

Figure 55:
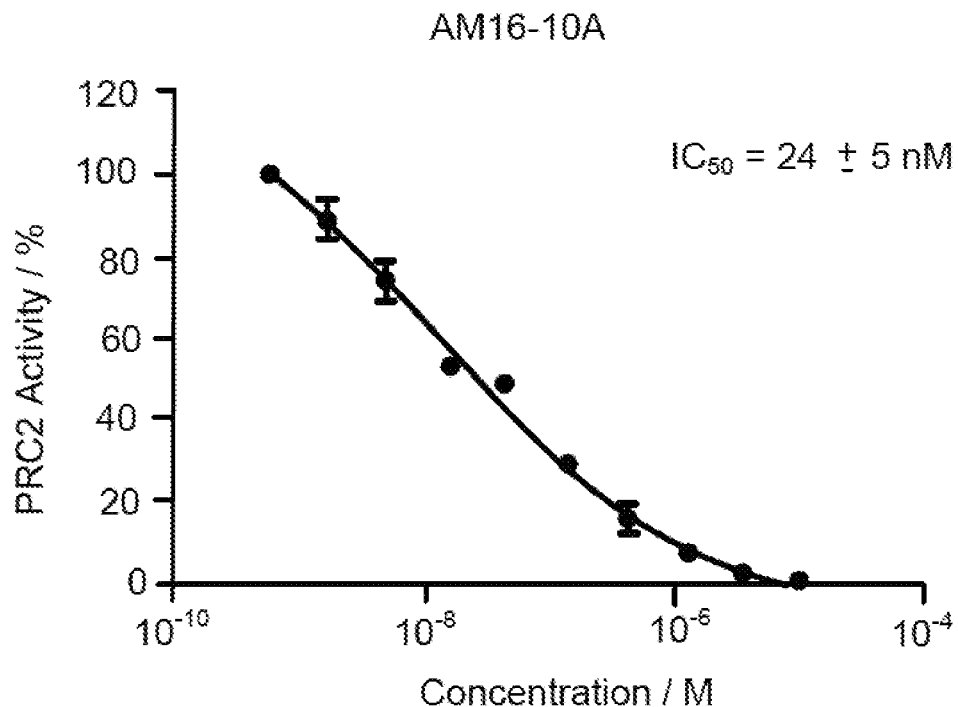
FIG. 55 is a graph depicting the in vitro $IC_{50}$ of AM16-10A for PRC2-EZH2.
Figure 56:
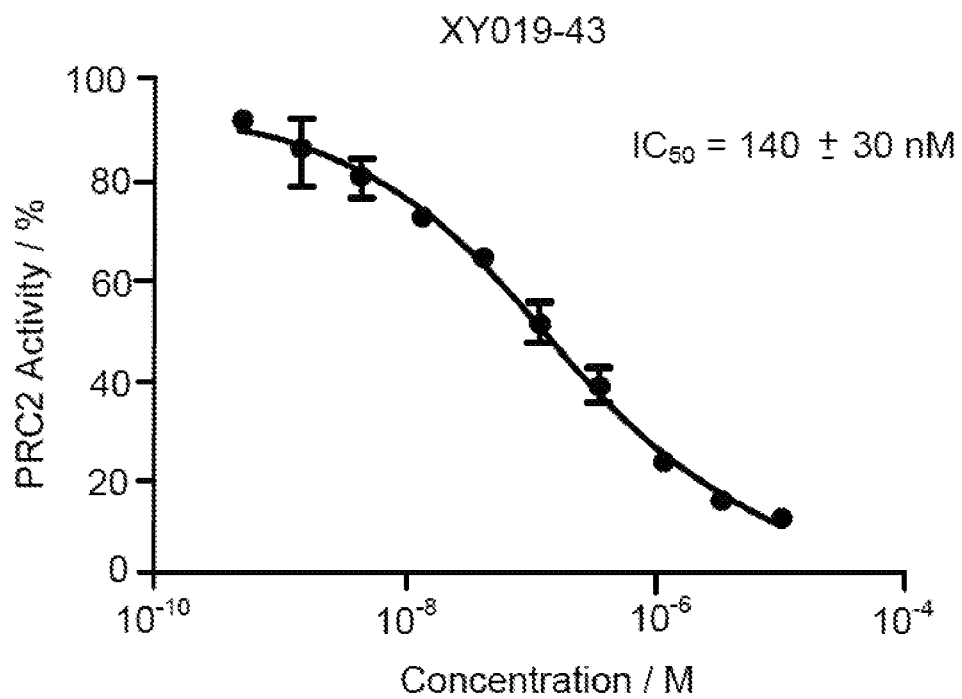
FIG. 56 is a graph depicting the in vitro $IC_{50}$ of XY019-43 for PRC2-EZH2.
Figure 57:
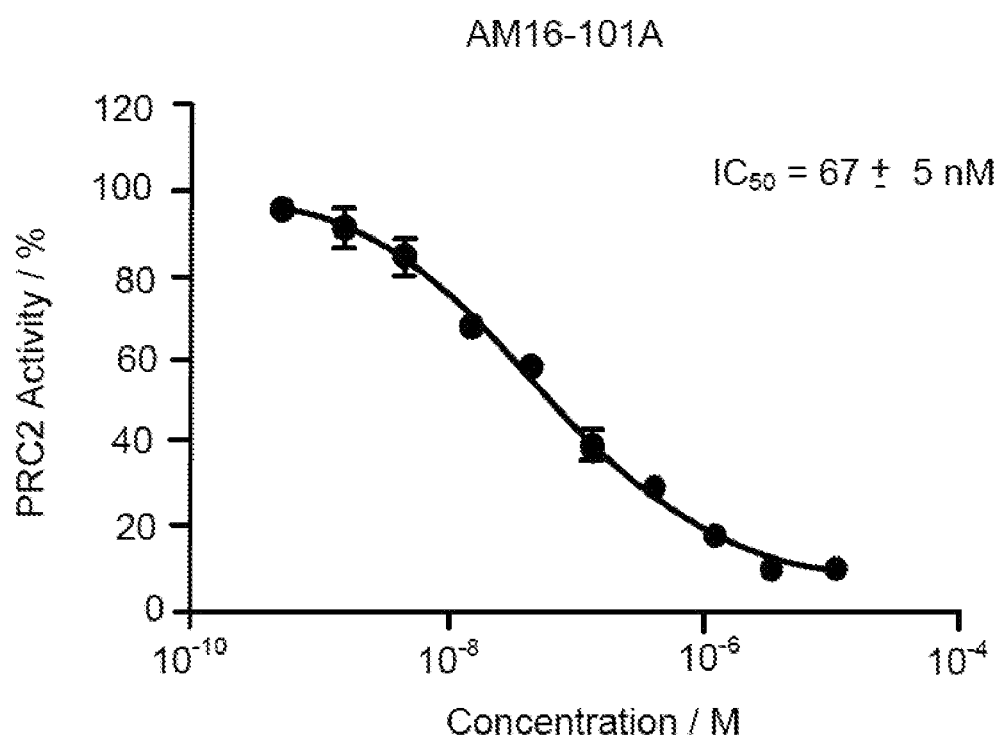
FIG. 57 is a graph depicting the in vitro $IC_{50}$ of AM16-101A for PRC2-EZH2.

Methyltransferase activity assays were performed by monitoring the incorporation of tritiumlabeled methyl group from S-adenosylmethionine ($^3$H-SAM) to biotinylated peptide substrates using Scintillation Proximity Assay (SPA) for EZH2/PRC2 5-component complex. Compounds were dissolved in DMSO to a stock concentration of 10 mM. Compounds were tested in a 10-dose $IC_{50}$ mode with 3-fold serial dilution, in duplicate, at 10 µM. Reactions were carried out at 1 µM SAM and 5 µM Histone H3. Results for AM16-10A, XY019-43 and AM16-101A are shown in FIGS. 55-57.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Bachmann, I. M., Halvorsen, O. J., Collett, K., Stefansson, I. M., Straume, O., Haukaas, S. A., Salvesen, H. B., Otte, A. P., and Akslen, L. A. (2006). EZH2 expression is associated with high proliferation rate and aggressive tumor subgroups in cutaneous melanoma and cancers of the endometrium, prostate, and breast. J Clin Oncol 24, 268-273.

Bodor, C., O'Riain, C., Wrench, D., Matthews, J., Iyengar, S., Tayyib, H., Calaminici, M., Clear, A., Iqbal, S., Quentmeier, H . . . et al. (2011). EZH2 Y641 mutations in follicular lymphoma. Leukemia 25, 726-729.

Bondeson, D. P., Mares, A., Smith, I. E., Ko, E., Campos, S., Miah, A. H., Mulholland, K. E., Routly, N., Buckley, D. L., Gustafson, J. L., et al. (2015). Catalytic in vivo protein knockdown by small-molecule PROTACs. Nat Chem Biol 11, 611-617.

Bracken, A. P., Pasini, D., Capra, M., Prosperini, E., Colli, E., and Helin, K. (2003). EZH2 is downstream of the pRB-E2F pathway, essential for proliferation and amplified in cancer. EMBO J 22, 5323-5335.

Bradley, W. D., Arora, S., Busby, J., Balasubramanian, S., Gehling, V. S., Nasveschuk, C. G., Vaswani, R. G., Yuan, C. C., Hatton, C., Zhao, F . . . et al. (2014). EZH2 inhibitor efficacy in non-Hodgkin's lymphoma does not require suppression of H3K27 monomethylation. Chem Biol 21, 1463-1475.

Broun, A., Gajiwala, K. S., Deng, Y. L., Liu, W., Bolanos, B., Bingham, P., He, Y. A., Diehl, W., Grable, N., Kung, P. P . . . et al. (2016). Polycomb repressive complex 2 structure with inhibitor reveals a mechanism of activation and drug resistance. Nat Commun 7, 11384.

Buckley, D. L., and Crews, C. M. (2014). Small-molecule control of intracellular protein levels through modulation of the ubiquitin proteasome system. Angew Chem 53, 2312-2330.

Buckley, D. L., Gustafson, J. L., Van Molle, I., Roth, A. G., Tae, H. S., Gareiss, P. C., Jorgensen, W. L., Ciulli, A., and Crews, C. M. (2012a). Small-molecule inhibitors of the interaction between the E3 ligase VHL and HIFIalpha. Angew Chem 57, 11463-11467.

Buckley, D. L., Van Molle, I., Gareiss, P. C., Tae, H. S., Michel, J., Noblin, D. J., Jorgensen, W. L., Ciulli, A., and Crews, C. M. (2012b). Targeting the von Hippel-Lindau E3 ubiquitin ligase using small molecules to disrupt the VHL/HIF-1 alpha interaction. J Am Chem Soc 134, 4465-4468.

Campbell, J. E., Kuntz, K. W., Knutson, S. K., Warholic, N. M., Keilhack, H., Wigle, T. J., Raimondi, A., Klaus, C. R., Rioux, N., Yokoi, A . . . et al. (2015). EPZ011989, A Potent, Orally-Available EZH2 Inhibitor with Robust in Vivo Activity. ACS Med Chem Lett 6, 491-495.

Cao, R., Wang, L., Wang, H., Xia, L., Erdjument-Bromage, H., Tempst, P., Jones, R. S., and Zhang, Y. (2002). Role of histone $H_3$ lysine 27 methylation in Polycomb-group silencing. Science 298, 1039-1043.

Chamberlain, P. P., Lopez-Girona, A., Miller, K., Carmel, G., Pagarigan, B., Chie-Leon, B., Rychak, E., Corral, L. G., Ren, Y. J., Wang, M . . . et al. (2014). Structure of the human Cereblon-DDB1-lenalidomide complex reveals basis for responsiveness to thalidomide analogs. Nat Struct Mol Biol 21, 803-809.

Chang, C. J., Yang, J. Y., Xia, W., Chen, C. T., Xie, X., Chao, C. H., Woodward, W. A., Hsu, J. M., Hortobagyi, G. N., and Hung, M. C. (2011). EZH2 promotes expansion of breast tumor initiating cells through activation of RAF1-beta-catenin signaling. Cancer Cell 19, 86-100.

Czermin, B., Melfi, R., McCabe, D., Seitz, V., Imhof, A., and Pirrotta, V. (2002). *Drosophila* enhancer of Zeste/ESC complexes have a histone $H_3$ methyltransferase activity that marks chromosomal Polycomb sites. Cell 111, 185-196.

Du, J., Li, L., Ou, Z., Kong, C., Zhang, Y., Dong, Z., Zhu, S., Jiang, H., Shao, Z., Huang, B . . . et al. (2012). FOXC1, a target of polycomb, inhibits metastasis of breast cancer cells. Breast Cancer Res Treat 131, 65-73.

Fischer, E. S., Bohm, K., Lydeard, J. R., Yang, H., Stadler, M. B., Cavadini, S., Nagel, J., Serluca, F., Acker, V., Lingaraju, G. M., et al. (2014). Structure of the DDB1-CRBN E3 ubiquitin ligase in complex with thalidomide. Nature 512, 49-53.

Fujii, S., Ito, K., Ito, Y., and Ochiai, A. (2008). Enhancer of Zeste Homologue 2 (EZH2) Down-regulates RUNX3 by Increasing Histone H3 Methylation. J Biol Chem 283, 17324-17332.

Fujii, S., Tokita, K., Wada, N., Ito, K., Yamauchi, C., Ito, Y., and Ochiai, A. (2011). MEK-ERK pathway regulates EZH2 overexpression in association with aggressive breast cancer subtypes. Oncogene 30, 4118-4128.

Galdeano, C., Gadd, M. S., Soares, P., Scaffidi, S., Van Molle, I., Birced, I., Hewitt, S., Dias, D. M., and Ciulli, A. (2014). Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem 57, 8657-8663.

Gao, T. T., Zhang, L. D., Zhu, Y. X., Song, X. J., Feng, Q., Lei, Q., Shi, S. X., Deng, H. X., Xiong, M. H., You, X. Y . . . et al. (2016). ZLD1122, a novel EZH2 and EZH1 small molecular inhibitor, blocks H3K27 methylation and diffuse large B cell lymphoma cell growth. Rsc Adv 6, 28512-28521.

Garapaty-Rao, S., Nasveschuk, C., Gagnon, A., Chan, E. Y., Sandy, P., Busby, J., Balasubramanian, S., Campbell, R., Zhao, F., Bergeron, L . . . et al. (2013). Identification of EZH2 and EZH1 small molecule inhibitors with selective impact on diffuse large B cell lymphoma cell growth. Chem Biol 20, 1329-1339.

Gehling, V. S., Vaswani, R. G., Nasveschuk, C. G., Duplessis, M., Iyer, P., Balasubramanian, S., Zhao, F., Good, A.

C., Campbell, R., Lee, C . . . et al. (2015). Discovery, design, and synthesis of indole-based EZH2 inhibitors. Bioorg Med Chem Lett 25, 3644-3649.

Gluz, O., Liedtke, C., Gottschalk, N., Pusztai, L., Nitz, U., and Harbeck, N. (2009). Triple-negative breast cancer-current status and future directions. Ann Oncol 20, 1913-1927.

Gonzalez, M. E., Li, X., Toy, K., DuPrie, M., Ventura, A. C., Banerjee, M., Ljungman, M., Merajver, S. D., and Kleer, C. G. (2008). Downregulation of EZH2 decreases growth of estrogen receptor-negative invasive breast carcinoma and requires BRCA1. Oncogene 28, 843-853.

Gonzalez, M. E., Moore, H. M., Li, X., Toy, K. A., Huang, W., Sabel, M. S., Kidwell, K. M., and Kleer, C. G. (2014). EZH2 expands breast stem cells through activation of NOTCH1 signaling. Proc Natl Acad Sci USA 111, 3098-3103.

Holm, K., Grabau, D., Lovgren, K., Aradottir, S., Gruvberger-Saal, S., Howlin, J., Saal, L. H., Ethier, S. P., Bendahl, P. O., Stal, O . . . et al. (2012). Global H3K27 trimethylation and EZH2 abundance in breast tumor subtypes. Mol Oncol 6, 494-506.

Ito, T., Ando, H., Suzuki, T., Ogura, T., Hotta, K., Imamura, Y., Yamaguchi, Y., and Handa, H. (2010). Identification of a primary target of thalidomide teratogenicity. Science 327, 1345-1350.

Jiao, L., and Liu, X. (2015). Structural basis of histone H3K27 trimethylation by an active polycomb repressive complex 2. Science 350, aac4383.

Justin, N., Zhang, Y., Tarricone, C., Martin, S. R., Chen, S., Underwood, E., De Marco, V., Haire, L. F., Walker, P. A., Reinberg, D., et al. (2016). Structural basis of oncogenic histone H3K27M inhibition of human polycomb repressive complex 2. Nat Commun 7, 11316.

Kaniskan, H. U., Martini, M. L., and Jin, J. (2017). Inhibitors of Protein Methyltransferases and Demethylases. Chem Rev, DOI: 10.1021/acs.chemrev. 1026b00801.

Kim, K. H., and Roberts, C. W. (2016). Targeting EZH2 in cancer. Nat Med 22, 128-134.

Kleer, C. G., Cao, Q., Varambally, S., Shen, R., Ota, I., Tomlins, S. A., Ghosh, D., Sewalt, R. G. A. B., Otte, A. P., Hayes, D. F . . . et al. (2003). EZH2 is a marker of aggressive breast cancer and promotes neoplastic transformation of breast epithelial cells. Proc Natl Acad Sci USA 100, 11606-11611.

Knutson, S. K., Warholic, N. M., Wigle, T. J., Klaus, C. R., Allain, C. J., Raimondi, A., Porter Scott. M., Chesworth, R., Moyer, M. P., Copeland, R. A., et al. (2013). Durable tumor regression in genetically altered malignant rhabdoid tumors by inhibition of methyltransferase EZH2. Proc Natl Acad Sci USA 110, 7922-7927.

Knutson, S. K., Wigle, T. J., Warholic, N. M., Sneeringer, C. J., Allain, C. J., Klaus, C. R., Sacks, J. D., Raimondi, A., Majer, C. R., Song. J., et al. (2012). A selective inhibitor of EZH2 blocks H3K27 methylation and kills mutant lymphoma cells. Nat Chem Biol 8, 890-896.

Konze, K. D., Ma. A., Li, F., Barsyte-Lovejoy, D., Parton, T., MacNevin, C. J., Liu, F., Gao, C., Huang. X. P., Kuznetsova, E . . . et al. (2013). An Orally Bioavailable Chemical Probe of the Lysine Methyltransferases EZH2 and EZH1. ACS Chem Biol 8, 1324-1334.

Kung. P. P., Rui, E., Bergqvist, S., Bingham, P., Braganza, J., Collins, M., Cui, M., Diehl, W., Dinh. D., Fan, C . . . et al. (2016). Design and Synthesis of Pyridone-Containing 3,4-Dihydroisoquinoline-1 (2H)-ones as a Novel Class of Enhancer of Zeste Homolog 2 (EZH2) Inhibitors. J Med Chem 59. 8306-8325.

Kuzmichev, A., Nishioka, K., Erdjument-Bromage, H., Tempst. P., and Reinberg, D. (2002). Histone methyltransferase activity associated with a human multiprotein complex containing the Enhancer of Zeste protein. Genes Dev 16, 2893-2905.

Lin, N. U., Vanderplas, A., Hughes, M. E., Theriault, R. L., Edge, S. B., Wong. Y.-N., Blayney, D. W., Niland, J. C., Winer, E. P., and Weeks, J. C. (2012). Clinicopathologic features, patterns of recurrence, and survival among women with triple-negative breast cancer in the National Comprehensive Cancer Network. Cancer 118, 5463-5472.

Mahara. S., Lee, P. L., Feng. M., Tergaonkar, V., Chng. W. J., and Yu, Q. (2016). HIFI-α activation underlies a functional switch in the paradoxical role of Ezh2/PRC2 in breast cancer. Proc Natl Acad Sci USA 113, E3735-E3744.

Majer, C. R., Jin, L., Scott, M. P., Knutson, S. K., Kuntz, K. W., Keilhack, H., Smith, J. J., Moyer, M. P., Richon, V. M., Copeland, R. A., et al. (2012). A687V EZH2 is a gain-of-function mutation found in lymphoma patients. FEBS Lett 586. 3448-3451.

McCabe, M. T., Graves, A. P., Ganji, G., Diaz, E., Halsey, W. S., Jiang. Y., Smitheman, K. N., Ott, H. M., Pappalardi, M. B., Allen, K. E., et al. (2012a). Mutation of A677 in histone methyltransferase EZH2 in human B-cell lymphoma promotes hypertrimethylation of histone $H_3$ on lysine 27 (H3K27). Proc Natl Acad Sci USA 109, 2989-2994.

McCabe. M. T., Ott, H. M., Ganji, G., Korenchuk, S., Thompson, C., Van Aller, G. S., Liu, Y., Graves, A. P., Iii. A. D., Diaz, E . . . et al. (2012b). EZH2 inhibition as a therapeutic strategy for lymphoma with EZH2-activating mutations. Nature 492, 108-112.

Morin, R. D., Johnson, N. A., Severson, T. M., Mungall, A. J., An, J., Goya, R., Paul, J. E., Boyle, M., Woolcock, B. W., Kuchenbauer, F . . . et al. (2010). Somatic mutations altering EZH2 (Tyr641) in follicular and diffuse large B-cell lymphomas of germinal-center origin. Nat Genet 42, 181-185.

Muller, J., Hart, C. M., Francis, N. J., Vargas, M. L., Sengupta, A., Wild, B., Miller, E. L., O'Connor, M. B., Kingston, R. E., and Simon, J. A. (2002). Histone methyltransferase activity of a *Drosophila* Polycomb group repressor complex. Cell 111, 197-208.

Neklesa, T. K., Tae, H. S., Schneekloth, A. R., Stulberg, M. J., Corson, T. W., Sundberg, T. B., Raina, K., Holley, S. A., and Crews, C. M. (2011). Small-molecule hydrophobic tagging-induced degradation of HaloTag fusion proteins. Nat Chem Biol 7, 538-543.

Qi, W., Chan, H., Teng. L., Li, L., Chuai, S., Zhang, R., Zeng. J., Li. M., Fan, H., Lin, Y . . . et al. (2012). Selective inhibition of Ezh2 by a small molecule inhibitor blocks tumor cells proliferation. Proc Natl Acad Sci USA 109, 21360-21365.

Ren, G., Baritaki, S., Marathe, H., Feng, J., Park, S., Beach, S., Bazeley, P. S., Beshir, A. B., Fenteany, G., Mehra, R . . . et al. (2012). Polycomb protein EZH2 regulates tumor invasion via the transcriptional repression of the metastasis suppressor RKIP in breast and prostate cancer. Cancer Res 72, 3091-3104.

Sauvageau, M., and Sauvageau, G. (2010). Polycomb group proteins: multi-faceted regulators of somatic stem cells and cancer. Cell Stem Cell 7, 299-313.

Sneeringer, C. J., Scott, M. P., Kuntz, K. W., Knutson, S. K., Pollock, R. M., Richon, V. M., and Copeland, R. A. (2010). Coordinated activities of wild-type plus mutant EZH2 drive tumor-associated hypertrimethylation of lysine 27 on histone H₃ (H3K27) in human B-cell lymphomas. Proc Natl Acad Sci USA 107, 20980-20985.

Song. X., Gao, T., Wang, N., Feng, Q., You, X., Ye, T., Lei, Q., Zhu, Y., Xiong, M., Xia, Y . . . et al. (2016). Selective inhibition of EZH2 by ZLD1039 blocks H3K27methylation and leads to potent anti-tumor activity in breast cancer. Sci Rep 6, 20864.

Stewart. B. W., and Wild, C. P. (2014). World Cancer Rep 2014 (Lyon, FRA: International Agency for Research on Cancer).

Taniguchi, H., Jacinto, F. V., Villanueva, A., Fernandez, A. F., Yamamoto, H., Carmona, F. J., Puertas, S., Marquez, V. E., Shinomura, Y., Imai, K . . . et al. (2012). Silencing of Kruppel-like factor 2 by the histone methyltransferase EZH2 in human cancer. Oncogene 31, 1988-1994.

Varambally, S., Dhanasekaran, S. M., Zhou, M., Barrette, T. R., Kumar-Sinha, C., Sanda, M. G., Ghosh, D., Pienta, K. J., Sewalt, R. G., Otte, A. P., et al. (2002). The polycomb group protein EZH2 is involved in progression of prostate cancer. Nature 419, 624-629.

Verma, S. K., Tian, X., LaFrance, L. V., Duquenne, C., Suarez, D. P., Newlander, K. A., Romeril, S. P., Burgess, J. L., Grant, S. W., Brackley, J. A., et al. (2012). Identification of Potent, Selective, Cell-Active Inhibitors of the Histone Lysine Methyltransferase EZH2. ACS Med Chem Lett 3, 1091-1096.

Wang, G. G., Konze, K. D., and Tao, J. (2015). Polycomb genes, miRNA, and their deregulation in B-cell malignancies. Blood 125, 1217-1225.

Winter, G. E., Buckley, D. L., Paulk, J., Roberts, J. M., Souza, A., Dhe-Paganon, S., and Bradner, J. E. (2015). Phthalimide conjugation as a strategy for in vivo target protein degradation. Science 348, 1376-1381.

Xu, B., Konze, K. D., Jin, J., and Wang, G. G. (2015). Targeting EZH2 and PRC2 dependence as novel anticancer therapy. Exp Hematol 43, 698-712.

Yang, X., Li, F., Konze, K. D., Meslamani, J., Ma, A., Brown, P. J., Zhou, M. M., Arrowsmith, C. H., Kaniskan, H. U., Vedadi, M., et al. (2016). Structure-Activity Relationship Studies for Enhancer of Zeste Homologue 2 (EZH2) and Enhancer of Zeste Homologue 1 (EZH1) Inhibitors. J Med Chem 59, 7617-7633.

Zengerle, M., Chan, K. H., and Ciulli, A. (2015). Selective Small Molecule Induced Degradation of the BET Bromodomain Protein BRD4. ACS Chem Biol 10, 1770-1777.

What is claimed is:

1. A bivalent compound comprising a degrader/disruption tag X" conjugated to an enhancer of zeste homologue 2 (EZH2) ligand Y" via a Linker:

X"-Linker-Y", and enantiomers and pharmaceutically acceptable salts thereof, wherein:

X" comprises a degrader/disruption tag selected from the group consisting of adamantane, 1-((4,4,5,5,5-pentafluoropentyl) sulfinyl) nonane, pomalidomide, thalidomide and VHL-1;

Y'" comprises an EZH2 ligand selected from the group consisting of:

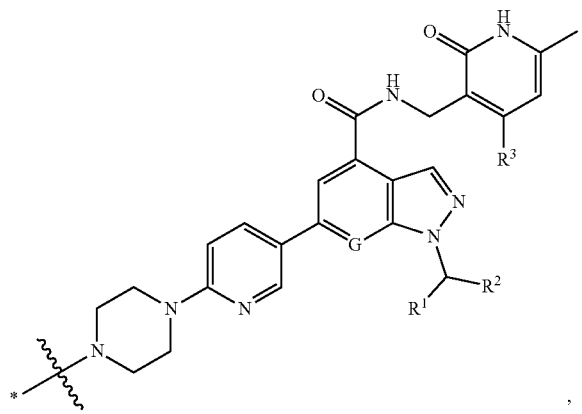

wherein the waved bond with * indicates the linker attachment position;

$R^1$ is hydrogen or $C_{1-6}$ alkyl;

$R^2$ is hydrogen or $C_{1-6}$ alkyl;

$R^3$ is $C_{1-6}$ alkyl or methoxy (MeO—); and

G is CH or N; and the linker is selected from the group consisting of

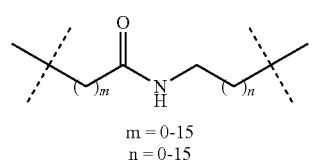

Formula I m = 0-15
n = 0-15

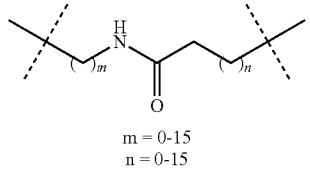

Formula II m = 0-15
n = 0-15

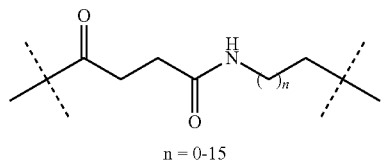

Formula III n = 0-15

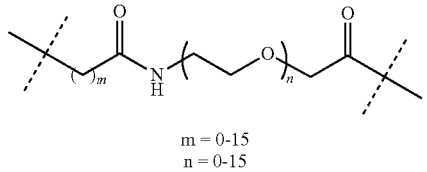

Formula IV m = 0-15
n = 0-15

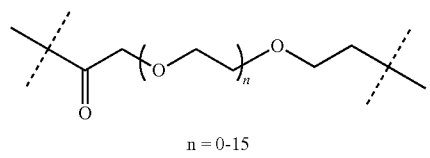

Formula V n = 0-15

-continued

Formula VI n = 0-15

Formula VII n = 0-15

Formula VIII n = 0-15

Formula IX n = 0-15

Formula X

X = O, NR
R = H, C$_{1-6}$ alkyl
m = 0-15
n = 0-15

Formula XI

R = H, C$_{1-6}$ alkyl
m = 0-15
n = 0-15
* R, S and racemic

Formula XII

X = O or H$_2$
Y = O or H$_2$
n = 0-15

Formula XIII

X = O or H$_2$
Y = O or H$_2$
m = 0-15
n = 0-6
o = 0-15

-continued

Formula XIV

X = O or H$_2$
Y = O or H$_2$
m = 0-15
n = 0-15 wherein R is independently —CH$_2$—; —CF$_2$; —CH(C$_{1-3}$ alkyl)-; —C(C$_{1-3}$ alkyl)(C$_{1-3}$ alkyl)-; —CH=CH—; —C(C$_{1-3}$ alkyl)=C(C$_{1-3}$ alkyl)-; —C≡C—; —O—; —NH—; —N(C$_{1-3}$ alkyl); —C(O)NH—; —C(O)N(C$_{1-3}$ alkyl)-; or a 3-13 membered ring, a fused ring, a bridged ring, or a spiro ring with or without one or more heteroatoms selected from the group consisting of —NH—, —N(C$_{1-3}$ alkyl)-, and —O—;
X and Y are independently O or H$_2$; and
m and n are independently 0-15; and wherein X'=NH, O or C$_{1-6}$ alkyl
m=0-15 and
n"=2-15.

2. A method of treating an enhancer of zeste homologue 2 (EZH2)-mediated cancer, comprising administering to a subject in need thereof having an EZH2-mediated cancer selected from the group consisting of breast cancer, glioblastoma, prostate cancer, uterine cancer, ovarian cancer, pancreatic cancer, melanoma, renal cell carcinoma, bladder cancer, colorectal cancer, lymphoma, leukemia, malignant rhabdoid tumor, and oropharyngeal cancer a bivalent compound according to claim 1.

3. The method of claim 2, wherein the EZH2-mediated cancer overexpresses EZH2 relative to a wild-type tissue of the same species and tissue type.

4. The method of claim 2, wherein the EZH2-mediated cancer comprises hyper-trimethylated H3K27.

5. The method of claim 2, wherein the at least one bivalent compound is administered orally, parenterally, intradermally, subcutaneously, topically, or rectally.

6. The method of claim 2, further comprising treating the subject with one or more additional therapeutic regimens for treating cancer selected from the group consisting of surgery, chemotherapy, radiation therapy, hormone therapy, and immunotherapy.

7. The method of claim 2, wherein the breast cancer is triple-negative breast cancer (TNBC).

8. The method of claim 2, wherein the EZH2-mediated cancer is a relapsed cancer.

9. The bivalent compound of claim 1, wherein Y″ comprises an EZH2 ligand selected from the group consisting of:

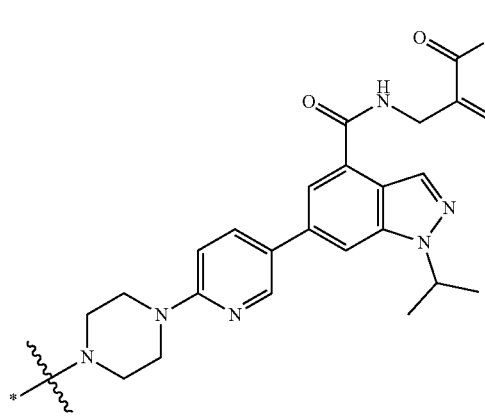

and

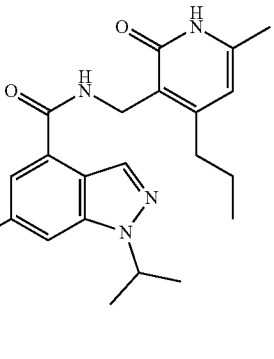

10. A bivalent compound (AM29-177A) having the following structure:

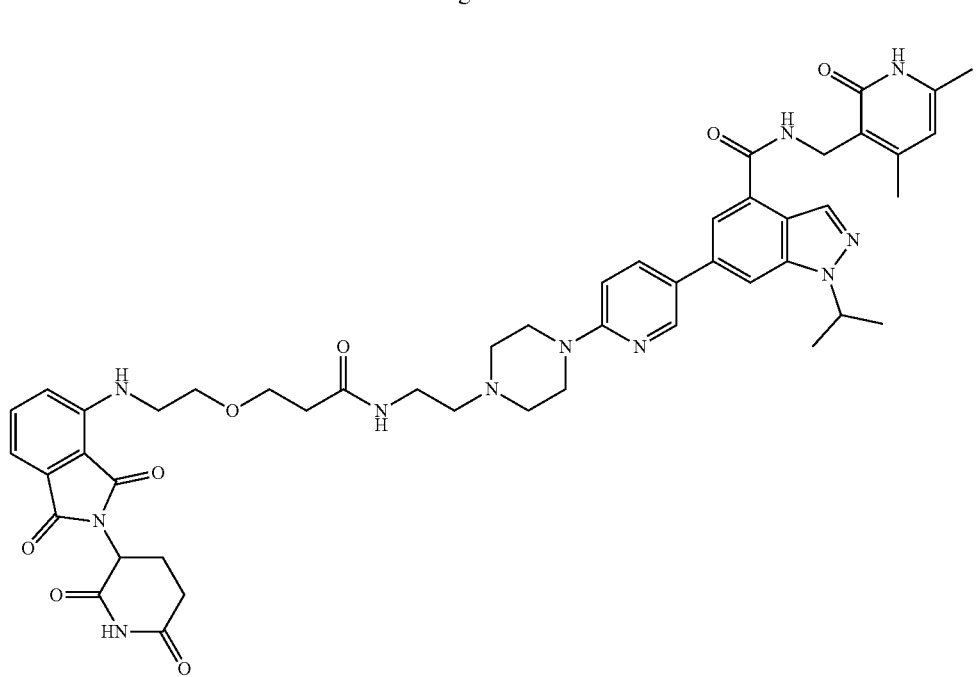

and enantiomers and pharmaceutically acceptable salts thereof.

11. A pharmaceutical composition comprising a bivalent compound according to claim 1, and a pharmaceutically acceptable carrier.

12. A pharmaceutical composition comprising the bivalent compound according to claim 10, and a pharmaceutically acceptable carrier.

* * * * *